United States Patent
Deretic et al.

(10) Patent No.: US 10,610,564 B2
(45) Date of Patent: Apr. 7, 2020

(54) IRGM AND PRECISION AUTOPHAGY CONTROLS FOR ANTIMICROBIAL AND INFLAMMATORY DISEASE STATES AND METHODS OF DETECTION OF AUTOPHAGY

(71) Applicant: STC.UNM, Albuqerque, NM (US)

(72) Inventors: Vojo P. Deretic, Placitas, NM (US); Tomonori Kimura, Minoh (JP)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 15/553,786

(22) PCT Filed: Feb. 25, 2016

(86) PCT No.: PCT/US2016/019599
§ 371 (c)(1),
(2) Date: Aug. 25, 2017

(87) PCT Pub. No.: WO2016/138286
PCT Pub. Date: Sep. 1, 2016

(65) Prior Publication Data
US 2018/0236024 A1    Aug. 23, 2018

Related U.S. Application Data

(60) Provisional application No. 62/121,232, filed on Feb. 26, 2015, provisional application No. 62/165,357, filed on May 22, 2015.

(51) Int. Cl.
| | |
|---|---|
| *A61K 38/05* | (2006.01) |
| *A61K 38/17* | (2006.01) |
| *A61K 31/713* | (2006.01) |
| *A61K 45/06* | (2006.01) |
| *A61P 1/00* | (2006.01) |
| *A61P 29/00* | (2006.01) |

(52) U.S. Cl.
CPC ............ *A61K 38/05* (2013.01); *A61K 31/713* (2013.01); *A61K 38/17* (2013.01); *A61K 45/06* (2013.01); *A61P 1/00* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 4,082,735 | A | 4/1978 | Jones et al. |
| 4,082,736 | A | 4/1978 | Jones et al. |
| 4,101,536 | A | 7/1978 | Yamamura et al. |
| 4,101,649 | A | 7/1978 | Anvar |
| 4,153,684 | A | 5/1979 | Anvar |
| 4,158,052 | A | 6/1979 | Anvar |
| 4,185,089 | A | 1/1980 | Anvar |
| 4,186,184 | A | 1/1980 | Anvar |
| 4,220,637 | A | 9/1980 | Anvar |
| 4,235,771 | A | 11/1980 | Adam et al. |
| 4,317,771 | A | 3/1982 | Shiba et al. |
| 4,396,607 | A | 8/1983 | Anvar |
| 4,406,890 | A | 9/1983 | Tarcsay et al. |
| 4,430,265 | A | 2/1984 | Yuichi et al. |
| 4,461,761 | A | 7/1984 | Anvar |

FOREIGN PATENT DOCUMENTS

| | | |
|---|---|---|
| FR | 2355505 A1 | 1/1978 |
| GB | 2020665 A | 11/1979 |
| GB | 1570625 A | 7/1980 |
| WO | 9601645 A1 | 1/1996 |
| WO | 2011133879 A2 | 10/2011 |
| WO | 2014200705 A1 | 12/2014 |
| WO | WO 2014/20075 A1 * | 12/2014 |

OTHER PUBLICATIONS

Nys et al. "Autophagy: a new target or an old strategy for the treatment of Crohn's disease?" Nat. Rev. Gastroenterol. Hepatol. 10, 395-401 (2013) (Year: 2013).*
Rubino et al. "Identification of a synthetic muramyl peptide derivative with enhanced Nod2 stimulatory capacity," Innate Immunity, 19(5) 493-503 (2013) (Year: 2013).*
Jounai, N., F. Takeshita, K. Kobiyama, A. Sawano, A. Miyawaki, K.Q. Xin, K.J. Ishii, T. Kawai, S. Akira, K Suzuki, and K. Okuda. 2007. The Atg5 Atg12 conjugate associates with innate antiviral immune responses. Proc Natl Acad Sci U S A. 104:14050-14055.
Kabeya, Y., N. Mizushima, T. Ueno, A. Yamamoto, T. Kirisako, T. Noda, E. Kominami, Y. Ohsumi, and T. Yoshimori. 2000. LC3, a mammalian homologue of yeast Apg8p, is localized in autophagosome membranes after processing. The EMBO journal. 19:5720-5728.

(Continued)

*Primary Examiner* — Christina Bradley
(74) *Attorney, Agent, or Firm* — Henry D. Coleman; R. Neil Sudol

(57) ABSTRACT

The present invention relates to the discovery that IRGM, encoded by a uniquely human gene which confers risk for inflammatory diseases, affects autoophagy through a hitherto unknown mechanism. The present invention shows that IRGM controls autophagy and that IRGM modulators, in particular, double-stranded RNA, including poly I:C, poly-UG (polyUGUGU) and polyICLC and muramyldipeptide and related analogs of same, including N-acetyl muramyl-L-alanyl-D-isoglutamine (Muramyl dipeptide or MDP) and numerous other compounds as identified herein, which may be used alone, in combination, or in combination with alternative autophagy modulators and additional bioactive agents to provide effective therapies for a number of diseases, including cancer, bacterial infections and inflammatory diseases, especially including tuberculosis infections and Crohn's disease, among others. The present invention is also directed to compositions and methods for treating inflammatory or autophagy-related diseases including diseases which cause excessive inflammation in patients.

3 Claims, 67 Drawing Sheets
Specification includes a Sequence Listing.

(56) References Cited

OTHER PUBLICATIONS

Kanayama, A., R.B. Seth, L. Sun, C.K. Ea, M. Hong, A. Shaito, Y.H. Chiu, L. Deng, and Z.J. Chen. 2004. TAB2 and TAB3 activate the NF-kappaB pathway through binding to polyubiquitin chains. Molecular cell. 15:535-548.

Kawai, T., and S. Akira. 2011. Regulation of innate immune signalling pathways by the tripartite motif (TRIM) family proteins. EMBO molecular medicine. 3:513-527.

Kenific, C.M., and J. Debnath. 2015. Cellular and metabolic functions for autophagy in cancer cells. Trends Cell Biol. 25:37-45.

Khan, M.M., S. Strack, F. Wild, A. Hanashima, A. Gasch, K. Brohm, M. Reischl, S. Carnio, D. Labeit, M. Sandri, S. Labeit, and R. Rudolf. 2014. Role of autophagy, SQSTMI, SH3GLB1, and TRIM63 in the turnover of nicotinic acetylcholine receptors. Autophagy. 10:123-136.

Kim, J., Kim, Y.C., Fang, C., Russell, R.C., Kim, J.H., Fan, W., Liu, R., Zhong, Q., and Guan, K.L. (2013). Differential regulation of distinct Vps34 complexes by AMPK in nutrient stress and autophagy. Cell 152, 290-303.

Kim, J., Kundu, M., Viollet, B., and Guan, K.L. (2011). AMPK and mTOR regulate autophagy through direct phosphorylation of Ulk1. Nature cell biology 13, 132-141.

Kimura, T., A. Takahashi, Y. Takabatake, T. Namba, T. Yamamoto, J.Y. Kaimori, I. Matsui, H. Kitamura, F. Niimura, T. Matsusaka, T. Soga, H. Rakugi, and Y. Isaka. 2013. Autophagy protects kidney proximal tubule epithelial cells from mitochondrial metabolic stress. Autophagy. 9:1876-1886.

Konno, H., K. Konno, and G.N. Barber. 2013. Cyclic Dinucleotides Trigger ULK1 (ATG1) Phosphorylation of STING to Prevent Sustained Innate Immune Signaling. Cell.

Kramer, R.M., E.F. Roberts, S.L. Um, A.G. Borsch-Haubold, S.P. Watson, M.J. Fisher, and J.A. Jakubowski. 1996. p38 mitogen-activated protein kinase phosphorylates cytosolic phospholipase A2 (cPLA2) in thrombin-stimulated platelets. Evidence that proline-directed phosphorylation is not required for mobilization of arachidonic acid by cPLA2. J Biol Chem. 271:27723-27729.

Kroemer, G. 2015. Autophagy: a druggable process that is deregulated in aging and human disease. The Journal of Clinical Investigation. 125:1-4.

Kyei, G.B., C. Dinkins, A.S. Davis, E. Roberts, S.B. Singh, C. Dong, L. Wu, E. Kominami, T. Ueno, A. Yamamoto, M. Federico, A. Panganiban, I. Vergne, and V. Deretic. 2009. Autophagy pathway intersects with HIV-1 biosynthesis and regulates viral yields in macrophages. J Cell Biol. 186:255-268.

Lapaquette, P., A.L. Glasser, A. Huett, R.J. Xavier, and A. Darfeuille-Michaud. 2010. Crohn's disease-associated adherent-invasive E. coli are selectively favoured by impaired autophagy to replicate intracellularly. Cellular microbiology. 12:99-113.

Levine, B., Mizushima, N., and Virgin, H.W. (2011). Autophagy in immunity and inflammation. Nature 469, 323-335.

Li, Q., J. Yan, A.P. Mao, C. Li, Y. Ran, H.B. Shu, and Y.Y. Wang. 2011. Tripartite motif 8 (TRIM8) modulates TNFalpha- and IL-1beta-triggered NF-kappaB activation by targeting TAK1 for K63-linked polyubiquitination. Proc Natl Acad Sci U S A. 108:19341-19346.

Liang, Q., G.J. Seo, Y.J. Choi, M.J. Kwak, J. Ge, M.A. Rodgers, M. Shi, B.J. Leslie, K.P. Hopfner, T. Ha, B.H. Oh, and J.U. Jung. 2014. Crosstalk between the cGAS DNA sensor and Beclin-1 autophagy protein shapes innate antimicrobial immune responses. Cell Host Microbe. 15:228-238.

Liang, X.H., S. Jackson, M. Seaman, K. Brown, B. Kempkes, H. Hibshoosh, and B. Levine. 1999. Induction of autophagy and inhibition of tumorigenesis by beclin 1. Nature. 402:672-676.

Ma, Y., L Galluzzi, L. Zitvogel, and G. Kroemer. 2013. Autophagy and cellular immune responses. Immunity. 39:211-227.

Maejima, I., A. Takahashi, H. Omori, T. Kimura, Y. Takabatake, T. Saitoh, A. Yamamoto, M. Hamasaki, T. Noda, Y. Isaka, and T. Yoshimori. 2013. Autophagy sequesters damaged lysosomes to control lysosomal biogenesis and kidney injury. The Embo journal. 32:2336-2347.

Mandell, M.A., A. Jain, J. Arko-Mensah, S. Chauhan, T. Kimura, C. Dinkins, G. Silvestri, J. Munch, F. Kirchhoff, A. Simonsen, Y. Wei, B. Levine, T. Johansen, and V. Deretic. 2014. TRIM proteins regulate autophagy and can target autophagic substrates by direct recognition. Dev Cell. 30:394-409.

Masters, S.L., A. Simon, I. Aksentijevich, and D.L. Kastner. 2009. Horror autoinflammaticus: the molecular pathophysiology of autoinflammatory disease. Annual review of immunology. 27:621-668.

Mathew, R., S. Khor, S.R. Hackett, J.D. Rabinowitz, D.H. Perlman, and E. White. 2014. Functional Role of Autophagy-Mediated Proteome Remodeling in Cell Survival Signaling and Innate Immunity. Molecular cell.

Matsunaga, K., Saitoh, T., Tabata, K., Omori, H., Satoh, T., Kurotori, N., Maejima, I., Shirahama-Noda, K, Ichimura, T., Isobe, T., et al. (2009). Two Beclin 1-binding proteins, Atg14L and Rubicon, reciprocally regulate autophagy at different stages. Nat Cell Biol 11, 385-396.

McCarroll, S.A., Huett, A., Kuballa, P., Chilewski, S.D., Landry, A., Goyette, P., Zody, M.C., Hall, J.L., Brant, S.R., Cho, J.H., et al. (2008). Deletion polymorphism upstream of IRGM associated with altered IRGM expression and Crohn's disease. Nat Genet 40, 1107-1112.

McEwan, W.A., J.C. Tam, R.E. Watkinson, S.R. Bidgood, D.L Mallery, and L.C. James. 2013. Intracellular antibody-bound pathogens stimulate immune signaling via the Fc receptor TRIM21. Nature immunology. 14:327-336.

Meinzer, U., P. Quartier, J.F. Alexandra, V. Hentgen, F. Retornaz, and I. Kone-Paut. 2011. Interleukin-1 targeting drugs in familial Mediterranean fever: a case series and a review of the literature. Seminars in arthritis and rheumatism. 41:265-271.

Mihaylova, M.M., and Shaw, R.J. (2011). The AMPK signalling pathway coordinates cell growth, autophagy and metabolism. Nature cell biology 13, 1016-1023.

Minguela, A., S. Pastor, W. Mi, J.A. Richardson, and E.S. Ward. 2007. Feedback regulation of murine autoimmunity via dominant anti-inflammatory effects of interferon gamma. J Immunol. 178:134-144.

Mishra, B.B., V.A. Rathinam, G.W. Martens, A.J. Martinot, H. Komfeld, K.A. Fitzgerald, and C.M. Sassetti. 2013. Nitric oxide controls the immunopathology of tuberculosis by inhibiting NLRP3 inflammasome-dependent processing of IL-1beta. Nature immunology. 14:52-60.

Mizushima, N., A. Kuma, Y. Kobayashi, A. Yamamoto, M. Matsubae, T. Takao, T. Natsume, Y. Ohsumi, and T. Yoshimori. 2003. Mouse Apg16L, a novel WD-repeat protein, targets to the autophagic isolation membrane with the Apg12-Apg5 conjugate. Journal of cell science. 116:1679-1688.

Mizushima, N., Levine, B., Cuervo, A.M., and Klionsky, D.J. (2008). Autophagy fights disease through cellular self-digestion. Nature 451, 1069-1075.

Mizushima, N., T. Yoshimori, and B. Levine. 2010. Methods in mammalian autophagy research. Cell. 140:313-326.

Mizushima, N., T. Yoshimori, and Y. Ohsumi. 2011. The role of atg proteins in autophagosome formation. Annual review of cell and developmental biology. 27:107-132.

Nakahira, K., J.A. Haspel, V.A. Rathinam, S.J. Lee, T. Dolinay, H.C. Lam, J.A. Englert, M. Rabinovitch, M. Cernadas, H.P. Kim, K.A. Fitzgerald, S.W. Ryter, and A.M. Choi. 2011. Autophagy proteins regulate innate immune responses by inhibiting the release of mitochondrial DNA mediated by the NALP3 inflammasome. Nature immunology. 12:222-230.

Nandi, B., and S.M. Behar. 2011. Regulation of neutrophils by interferon-gamma limits lung inflammation during tuberculosis infection. J Exp Med. 208:2251-2262.

Nazio, F., F. Strappazzon, M. Antonioli, P. Bielli, V. Cianfanelli, M. Bordi, C. Gretzmeier, J. Dengjel, M. Piacentini, G.M. Fimia, and F. Cecconi. 2013. mTOR inhibits autophagy by controlling ULK1 ubiquitylation, self-association and function through AMBRA1 and TRAF6. Nat Cell Biol. 15:406-416.

(56) References Cited

OTHER PUBLICATIONS

Niida, M., M. Tanaka, and T. Kamitani. 2010. Downregulation of active IKK beta by Ro52-mediated autophagy. Mol Immunol. 47:2378-2387.
Nishimura, T., T. Kaizuka, K. Cadwell, M.H. Sahani, T. Saitoh, S. Akira, H.W. Virgin, and N. Mizushima. 2013. FIP200 regulates targeting of Atg16L1 to the isolation membrane. EMBO Rep. 14:284-291.
Ogura, Y., Bonen, D.K., Inohara, N., Nicolae, D.L., Chen, F.F., Ramos, R., Britton, H., Moran, T., Karaliuskas, R., Duerr, R.H., et al. (2001). A frameshift mutation in NOD2 associated with susceptibility to Crohn's disease. Nature 411, 603-606.
Omenetti, A., S. Carta, L. Delfino, A. Martini, M. Gattorno, and A. Rubartelli. 2014. Increased NLRP3-dependent interleukin 1beta secretion in patients with familial Mediterranean fever: correlation with MEFV genotype. Annals of the rheumatic diseases. 73:462-469.
Pankiv, S., T.H. Clausen, T. Lamark, A. Brech, J.A. Bruun, H. Outzen, A. Overvatn, G. Bjorkoy, and T. Johansen. 2007. p62/SQSTM1 binds directly to Atg8/LC3 to facilitate degradation of ubiquitinated protein aggregates by autophagy. J Biol Chem. 282:24131-24145.
Papin, S., S. Cuenin, L. Agostini, F. Martinon, S. Werner, H.D. Beer, C. Gruffer, M. Gruffer, and J. Tschopp. 2007. The SPRY domain of Pyrin, mutated in familial Mediterranean fever patients, interacts with inflammasome components and inhibits proIL-1beta processing. Cell Death Differ. 14:1457-1466.
Pineda, C.T., S. Ramanathan, K. Fon Tacer, J.L. Weon, M.B. Potts, Y.H. Ou, M.A. White, and P.R. Potts. 2015. Degradation of AMPK by a Cancer-Specific Ubiquitin Ligase. Cell. 160:715-728.
Pizon, V., S. Rybina, F. Gerbal, F. Delort, P. Vicart, G. Baldacci, and E. Karsenti. 2013. MURF2B, a novel LC3-binding protein, participates with MURF2A in the switch between autophagy and ubiquitin proteasome system during differentiation of C2C12 muscle cells. PLoS One. 8:e76140.
Rabinowitz, J.D., and E. White. 2010. Autophagy and metabolism. Science. 330:1344-1348.
Randow, F., and R.J. Youle. 2014. Self and Nonself: How Autophagy Targets Mitochondria and Bacteria. Cell Host Microbe. 15:403-411.
Reymond, A., G. Meroni, A. Fantozzi, G. Merla, S. Cairo, L. Luzi, D. Riganelli, E. Zanaria, S. Messali, S. Cainarca, A. Guffanti, S. Minucci, P.G. Pelicci, and A. Ballabio. 2001. The tripartite motif family identifies cell compartments. The EMBO journal. 20:2140-2151.
Rogov, V., V. Dotsch, T. Johansen, and V. Kirkin. 2014. Interactions between autophagy receptors and ubiquitin-like proteins form the molecular basis for selective autophagy. Molecular cell. 53:167-178.
Romanello, V., Guadagnin, E., Gomes, L., Roder, I., Sandri, C., Petersen, Y., Milan, G., Masiero, E, Del Piccolo, P., Foretz, M., et al. (2010). Mitochondrial fission and remodelling contributes to muscle atrophy. EMBO J 29, 1774-1785.
Abbott, D.W., Yang, Y., Huh, J.E., Madhavarapu, S., Kelliher, M.A., and Cantley, L.C. (2007). Coordinated regulation of Toll-like receptor and NOD2 signaling by K63-linked polyubiquitin chains. Mol Cell Biol 27, 6012-6025.
Axe, E.L., S.A. Walker, M. Manifava, P. Chandra, H.L. Roderick, A. Habermann, G. Griffiths, and N.T. Ktistakis. 2008. Autophagosome formation from membrane compartments enriched in phosphatidylinositol 3-phosphate and dynamically connected to the endoplasmic reticulum. J Cell Biol. 182:685-701.
Banchereau, J., and V. Pascual. 2006. Type I interferon in systemic lupus erythematosus and other autoimmune diseases. Immunity. 25:383-392.
Barde, I., B. Rauwel, R.M. Marin-Florez, A. Corsinotti, E. Laurenti, S. Verp, S. Offner, J. Marquis, A. Kapopoulou, J. Vanicek, and D. Trono. 2013. A KRAB/KAP1-miRNA cascade regulates erythropoiesis through stage-specific control of mitophagy. Science. 340:350-353.
Bauemfeind, F.G., G. Horvath, A. Stutz, E.S. Alnemri, K. MacDonald, D. Speert, T. Fernandes-Alnemri, J. Wu, B.G. Monks, K.A. Fitzgerald,
V. Hornung, and E. Latz. 2009. Cutting edge: NF-kappaB activating pattern recognition and cytokine receptors license NLRP3 inflammasome activation by regulating NLRP3 expression. J Immunol. 183:787-791.
Bekpen, C., Marques-Bonet, T., Alkan, C., Antonacci, F., Leogrande, M.B., Ventura, M., Kidd, J.M., Siswara, P., Howard, J.C., and Eichler, E.E. (2009). Death and resurrection of the human IRGM gene. PLoS Genet 5, e1000403.
Bell, J.L., A. Malyukova, J.K. Holien, J. Koach, M.W. Parker, M. Kavallaris, G.M. Marshall, and B.B. Cheung. 2012. TRIM16 acts as an E3 ubiquitin ligase and can heterodimerize with other TRIM family members. PLoS One. 7:e37470.
Birgisdottir, A.B., T. Lamark, and T. Johansen. 2013. The LIR motif—crucial for selective autophagy. Journal of cell science. 126:3237-3247.
Bodemann, B.O., A. Orvedahl, T. Cheng, R.R. Ram, Y.H. Ou, E. Formstecher, M. Maiti, C.C. Hazelett, E.M. Wauson, M. Balakireva, J.H. Camonis, C. Yeaman, B. Levine, and M.A. White. 2011. RalB and the Exocyst Mediate the Cellular Starvation Response by Direct Activation of Autophagosome Assembly. Cell. 144:253-267.
Brest, P., Lapaquette, P., Souidi, M., Lebrigand, K., Cesaro, A., Vouret-Craviari, V., Mari, B., Barbry, P., Mosnier, J.F., Hebuterne, X., et al. (2011). A synonymous variant in IRGM alters a binding site for miR-196 and causes deregulation of IRGM-dependent xenophagy in Crohn's disease. Nat Genet 43, 242-245.
Broz, P., J. von Moltke, J.W. Jones, R.E. Vance, and D.M. Monack. 2010. Differential requirement for Caspase-1 autoproteolysis in pathogen-induced cell death and cytokine processing. Cell Host Microbe. 8:471-483.
Carthagena, L., A. Bergamaschi, J.M. Luna, A. David, P.D. Uchil, F. Margottin-Goguet, W. Mothes, U. Hazan, C. Transy, G. Pancino, and S. Nisole. 2009. Human TRIM gene expression in response to interferons. PLoS One. 4: e4894.
Chae, J.J., G. Wood, S.L. Masters, K. Richard, G. Park, B.J. Smith, and D.L. Kastner. 2006. The B30.2 domain of pyrin, the familial Mediterranean fever protein, interacts directly with caspase-1 to modulate IL-1beta production. Proc Natl Acad Sci U S A. 103:9982-9987.
Chae, J.J., Y.H. Cho, G.S. Lee, J. Cheng, P.P. Liu, L. Feigenbaum, S.I. Katz, and D.L Kastner. 2011. Gain-of-function Pyrin mutations induce NLRP3 protein-independent interleukin-1beta activation and severe autoinflammation in mice. Immunity. 34:755-768.
Chan, E.Y., and S.A. Tooze. 2009. Evolution of Atg1 function and regulation. Autophagy. 5:758-765.
Chan, W.M., Mak, M.C., Fung, T.K, Lau, A., Siu, W.Y., and Poon, R.Y. (2006). Ubiquitination of p53 at multiple sites in the DNA-binding domain. Mol Cancer Res 4, 15-25.
Chauhan, S., Goodwin, J.G., Manyam, G., Wang, J., Kamat, A.M., and Boyd, D.D. (2013). ZKSCAN3 is a master transcriptional repressor of autophagy. Molecular cell 50, 16-28.
Chauhan, S., M.A. Mandell, and V. Deretic. 2015. IRGM Governs the Core Autophagy Machinery to Conduct Antimicrobial Defense. Molecular cell. 58:507-521.
Choi, J., Park, S., Biering, S.B., Selleck, E, Liu, C.Y., Zhang, X., Fujita, N., Saitoh, T., Akira, S., Yoshimori, T., et al. (2014). The parasitophorous vacuole membrane of Toxoplasma gondii is targeted for disruption by ubiquitin-like conjugation systems of autophagy. Immunity 40, 924-935.
Consortium (2007). Genome-wide association study of 14,000 cases of seven common diseases and 3,000 shared controls. Nature 447, 661-678.
Cooney, R., Baker, J., Brain, O., Danis, B., Pichulik, T., Allan, P., Ferguson, D.J., Campbell, B.J., Jewell, D., and Simmons, A. (2010). NOD2 stimulation induces autophagy in dendritic cells influencing bacterial handling and antigen presentation. Nat Med 16, 90-97.
Craddock, N., Hurles, M.E, Cardin, N., Pearson, R.D., Plagnol, V., Robson, S., Vukcevic, D., Barnes, C., Conrad, D. F., Giannoulatou, E., et al. (2010). Genome-wide association study of CNVs in 16,000 cases of eight common Diseases and 3,000 shared controls. Nature 464, 713-720.
Criollo, A., M. Niso-Santano, S.A. Malik, M. Michaud, E. Morselli, G. Marino, S. Lachkar, A.V. Arkhipenko, F. Harper, G. Pierron, J.C. Rain, J. Ninomiya-Tsuji, J.M. Fuentes, S. Lavandero, L. Galluzzi,

(56) References Cited

OTHER PUBLICATIONS

M.C. Maiuri, and G. Kroemer. 2011. Inhibition of autophagy by TAB2 and TAB3. The EMBO journal. 30:4908-4920.
Deretic, V., Kimura, T., Timmins, G., Moseley, P., Chauhan, S., and Mandell, M. (2015). Immunologic manifestations of autophagy. The Journal of Clinical Investigation 125, 75-84.
Deretic, V., T. Saitoh, and S. Akira. 2013. Autophagy in infection, inflammation and immunity. Nat Rev Immunol. 13:722-737.
Dooley, H.C., Razi, M., Poison, H.E., Girardin, S.E., Wilson, M.I., and Tooze, S.A. (2014). WIPI2 Links LC3 Conjugation with PI3P, Autophagosome Formation, and Pathogen Clearance by Recruiting Atg12-5-16L1. Molecular cell 55, 238-252.
Egan, D.F., D.B. Shackelford, M.M. Mihaylova, S. Gelino, R.A. Kohnz, W. Mair, D.S. Vasquez, A. Joshi, D.M. Gwinn, R. Taylor, J.M. Asara, J. Fitzpatrick, A. Dillin, B. Viollet, M. Kundu, M. Hansen, and R.J. Shaw. 2011. Phosphorylation of ULK1 (hATG1) by AMP-activated protein kinase connects energy sensing to mitophagy. Science. 331:456-461.
Espinosa, A., V. Dardalhon, S. Brauner, A. Ambrosi, R. Higgs, F.J. Quintana, M. Sjostrand, M.L. Eloranta, J. Ni Gabhann, O. Winqvist, B. Sundelin, C.A. Jefferies, B. Rozell, V.K. Kuchroo, and M. Wahren-Herleni. 2009. Loss of the lupus autoantigen Ro52/Trim21 induces tissue inflammation and systemic autoimmunity by disregulating the IL-23-Th17 pathway. J Exp Med. 206:1661-1671.
Fabri, M., S. Stenger, D.M. Shin, J.M. Yuk, P.T. Liu, S. Realegeno, H.M. Lee, S.R. Krutzik, M. Schenk, P.A. Sieling, R. Teles, D. Montoya, S.S. Iyer, H. Bruns, D.M. Lewinsohn, B.W. Hollis, M. Hewison, J.S. Adams, a. Steinmeyer, U. lugel, G. Cheng, E.K. Jo, B.R. Bloom, and R.L. Modlin. 2011. Vitamin D is required for IFN-gamma-mediated antimicrobial activity of human macrophages. Science translational medicine. 3:104ra102.
Fimia, G.M., Stoykova, A., Romagnoli, A., Giunta, L., Di Bartolomeo, S., Nardacci, R., Corazzari, M., Fuoco, C., Ucar, A., Schwartz, R, et al. (2007). Ambra1 regulates autophagy and development of the nervous system. Nature 447, 1121-1125.
Frake, R.A., T. Ricketts, F.M. Menzies, and D.C. Rubinsztein. 2015. Autophagy and neurodegeneration. The Journal of Clinical Investigation. 125:65-74.
French_FMF_Consortium. 1997. A candidate gene for familial Mediterranean fever. Nature genetics. 17:25-31.
Fung, T.K., Yam, C.H., and Poon, R.Y. (2005). The N-terminal regulatory domain of cyclin A contains redundant ubiquitination targeting sequences and acceptor sites. Cell Cycle 4, 1411-1420.
Gammoh, N., Florey, O., Overholtzer, M., and Jiang, X. (2013). Interaction between FIP200 and ATG16L1 distinguishes ULK1 complex-dependent and -independent autophagy. Nat Struct Mol Biol 20, 144-149.
Gao, D., J. Wu, Y.T. Wu, F. Du, C. Aroh, N. Yan, L. Sun, and Z.J. Chen. 2013. Cyclic GMP-AMP synthase is an innate Immune sensor of HIV and other retroviruses. Science. 341:903-906.
Ghezzi, P., and C.A. Dinarello. 1988. IL-1 induces IL-1. III. Specific inhibition of IL-1 production by IFN-gamma. J Immunol. 140:4238-4244.
Gomes, L.C., and I. Dikic. 2014. Autophagy in antimicrobial immunity. Molecular cell. 54:224-233.
Gregoire, I.P., Richetta, C., Meyniel-Schicklin, L., Borel, S., Pradezynski, F., Diaz, O., Deloire, A., Azocar, O., Baguet, J., Le Breton, M., et al. (2011). IRGM is a common target of RNA viruses that subvert the autophagy network. PLoS pathogens 7, e1002422.

Gutierrez, M.G., Master, S.S., Singh, S.B., Taylor, G.A., Colombo, M.I., and Deretic, V. (2004). Autophagy is a defense mechanism inhibiting BCG and *Mycobacterium tuberculosis* survival in infected macrophages. Cell 119, 753-766.
Hasegawa, M., Fujimoto, Y., Lucas, P.C., Nakano, H., Fukase, K., Nunez, G., and Inohara, N. (2008). A critical role of RICK/RIP2 polyubiquitination in Nod-induced NF-kappaB activation. EMBO J 27, 373-383.
He, C., and B. Levine. 2010. The Beclin 1 interactome. Current opinion in cell biology. 22:140-149.
Herrero-Martin, G., M. Hoyer-Hansen, C. Garcia-Garcia, C. Fumarola, T. Farkas, A. Lopez-Rivas, and M. Jaattela. 2009. TAK1 activates AMPK-dependent cytoprotective autophagy in TRAIL-treated epithelial cells. The EMBO journal. 28:677-685.
Higgs, R., E. Lazzari, C. Wynne, J. Ni Gabhann, A. Espinosa, M. Wahren-Herlenius, and C.A. Jefferies. 2010. Self Protection from anti-viral responses—Ro52 promotes degradation of the transcription factor IRF7 downstream of the rival Toll-Like receptors. PLoS One. 5:e11776.
Higgs, R., J. Ni Gabhann, N. Ben Larbi, E.P. Breen, K.A. Fitzgerald, and C.A. Jefferies. 2008. The E3 ubiquitin ligase Ro52 negatively regulates IFN-beta production post-pathogen recognition by polyubiquitin-mediated degradation of RF3. J Immunol. 181:1780-1786.
Hoyer-Hansen, M., Bastholm, L., Szyniarowski, P., Campanella, M., Szabadkai, G., Farkas, T., Bianchi, K., Fehrenbacher, N., Elling, F., Rizzuto, R., et al. (2007). Control of macroautophagy by calcium, calmodulin-dependent kinase kinase-beta, and Bcl-2. Molecular cell 25, 193-205.
Hugot, J.P., Chamaillard, M., Zouali, H., Lesage, S., Cezard, J.P., Belaiche, J., Almer, S., Tysk, C., O'Morain, C.A., Gassull, M., et al. (2001). Association of NOD2 leucine-rich repeat variants with susceptibility to Crohn's disease. Nature 411, 599-603.
Inbal, B., S. Bialik, I. Sabanay, G. Shani, and A. Kimchi. 2002. DAP kinase and DRP-1 mediate membrane blebbing and the formation of autophagic vesicles during programmed cell death. J Cell Biol. 157:455-468.
Intemann, C.D., Thye, T., Niemann, S., Browne, E.N., Amanua Chinbuah, M., Enimil, A., Gyapong, J., Osei, I., Owusu-Dabo, E., Helm, S., et al. (2009). Autophagy gene variant IRGM -261T contributes to protection from tuberculosis caused by *Mycobacterium tuberculosis* but not by *M. africanum* strains. PLoS Pathog 5, e1000577.
Itakura, E., Kishi, C., Inoue, K., and Mizushima, N. (2008). Beclin 1 forms two distinct phosphatidylinositol 3-kinase complexes with mammalian Atg14 and UVRAG. Mol Biol Cell 19, 5360-5372.
Johansen, T., and T. Lamark. 2011. Selective autophagy mediated by autophagic adapter proteins. Autophagy. 7:279-296.
Lu X.C. et al.; "Association between variants of the autophagy related gene-IRGM and susceptibility to Crohn's disease and ulcerative colitis: a meta-analysis" PLOS ONE, Nov. 13, 2013; vol. 8, No. 11:e80602, p. 1-13. doi: 10.1371/journal.pone.0080602.
Mandell M.A. et al.; "TRIM proteins regulate autophagy: TRIM5 is a selective autophagy receptor mediating HIV-1 restriction"; Autophagy, 2014; 10(12):2387-2388 . doi: 10.4161/15548627.2014.984278.
Mandell M.A. et al.; "TRIM proteins regulate autophagy and can target autophagic substrates by direct recognition", Dev. Cell. Aug. 25, 2014; 30(4):394-409. doi: 10.1016/j devcel.2014.06.013, pp. 1-13.

\* cited by examiner

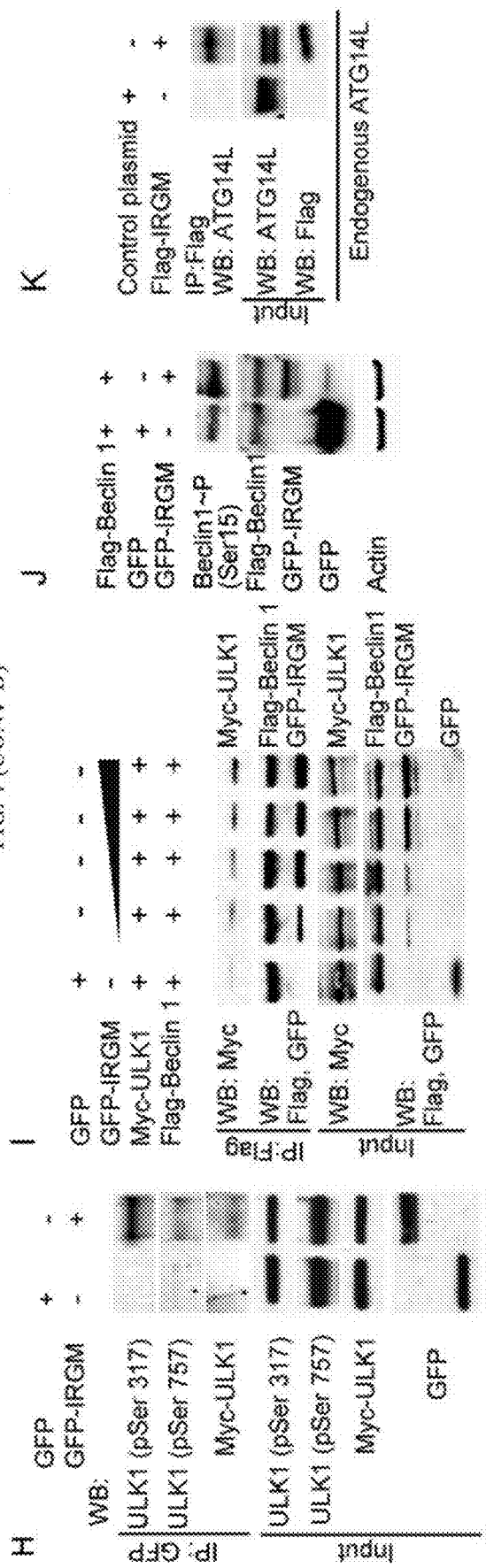

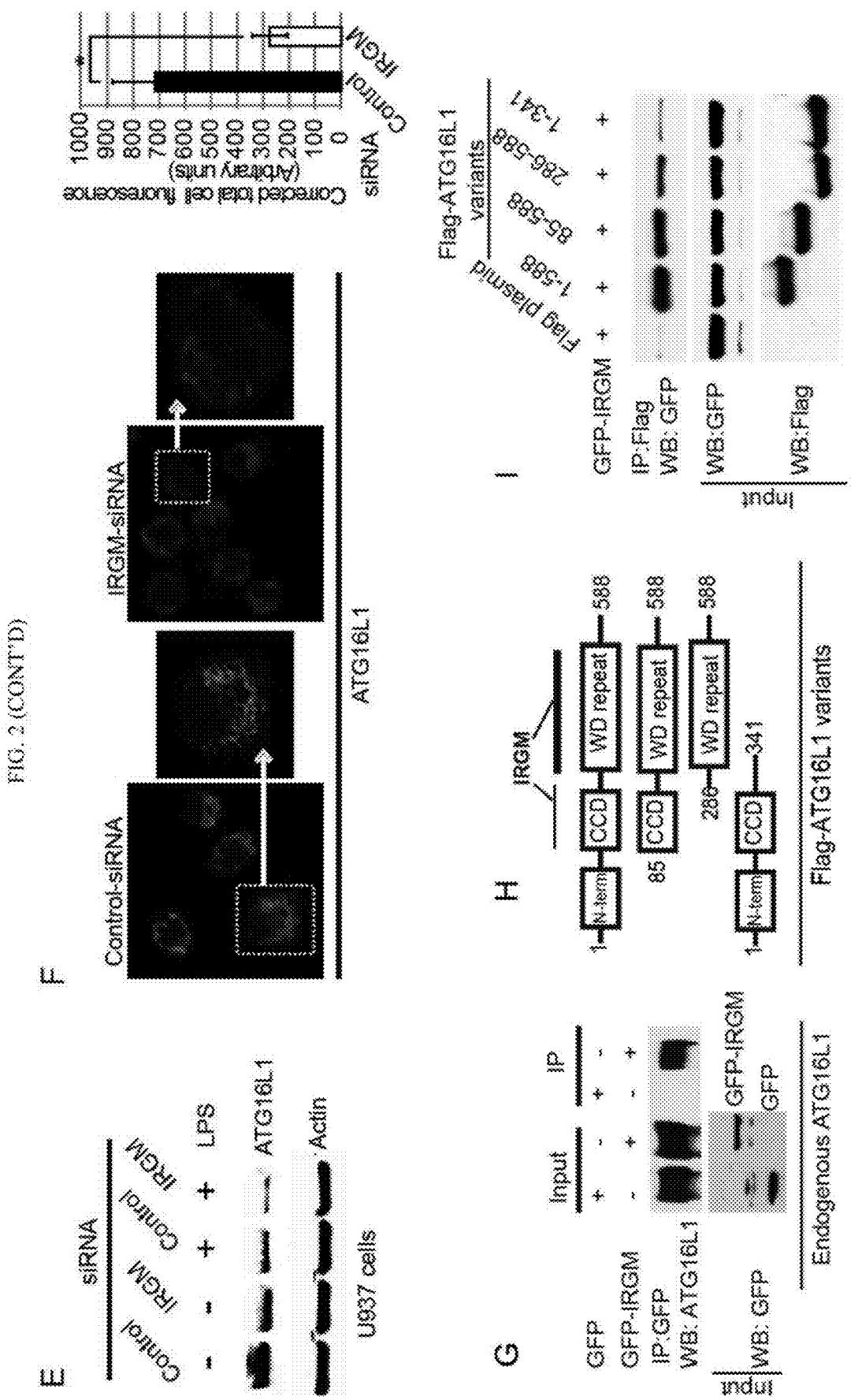

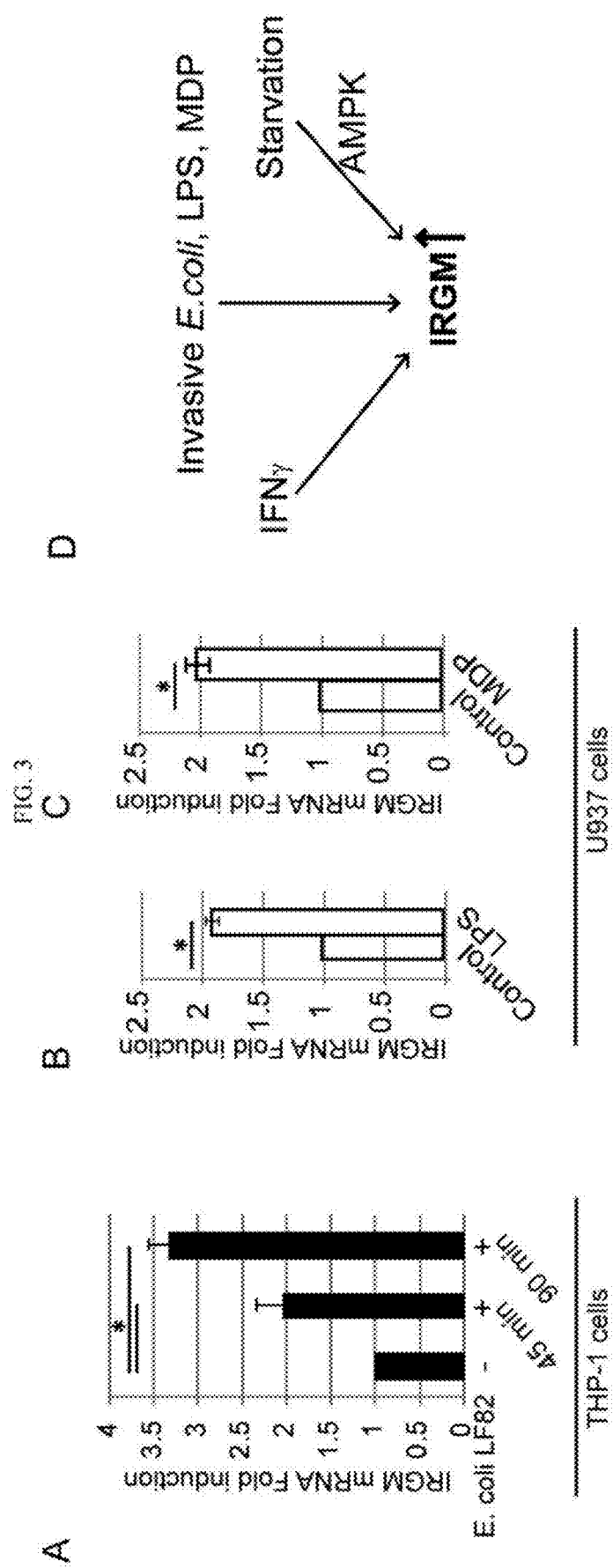

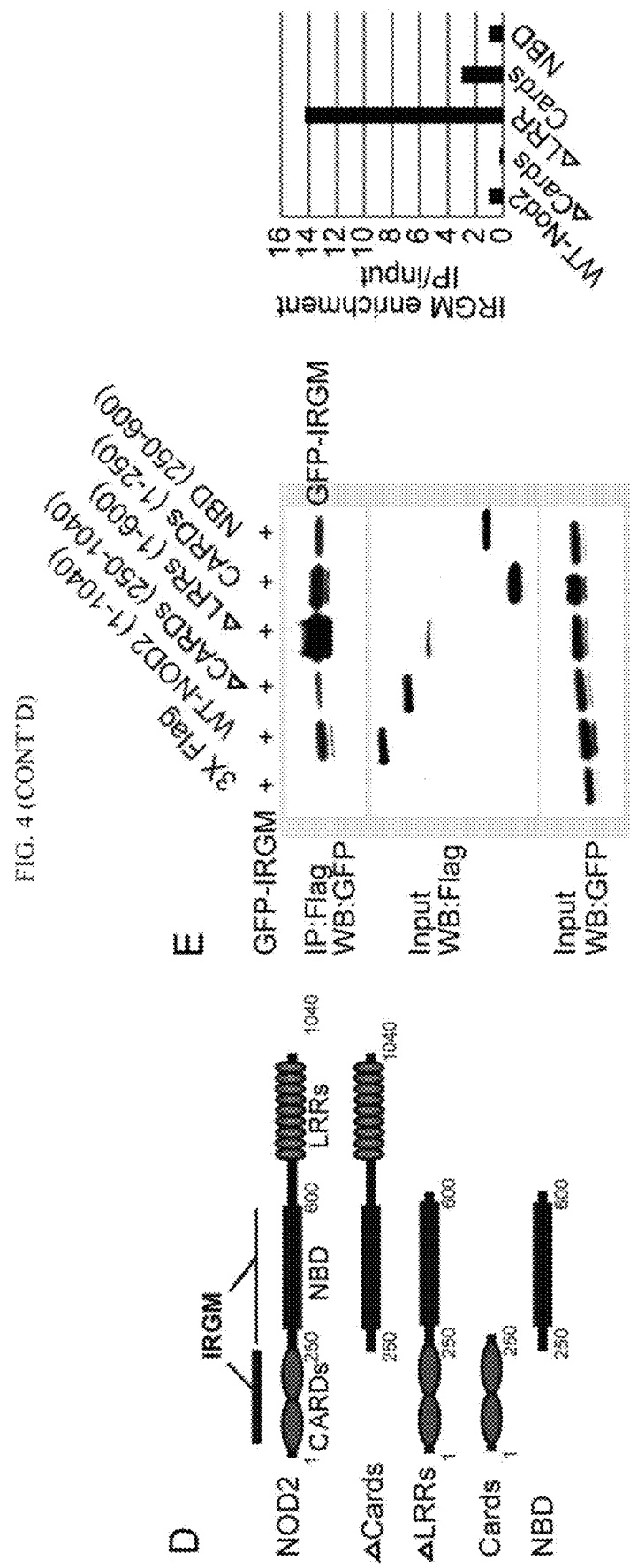

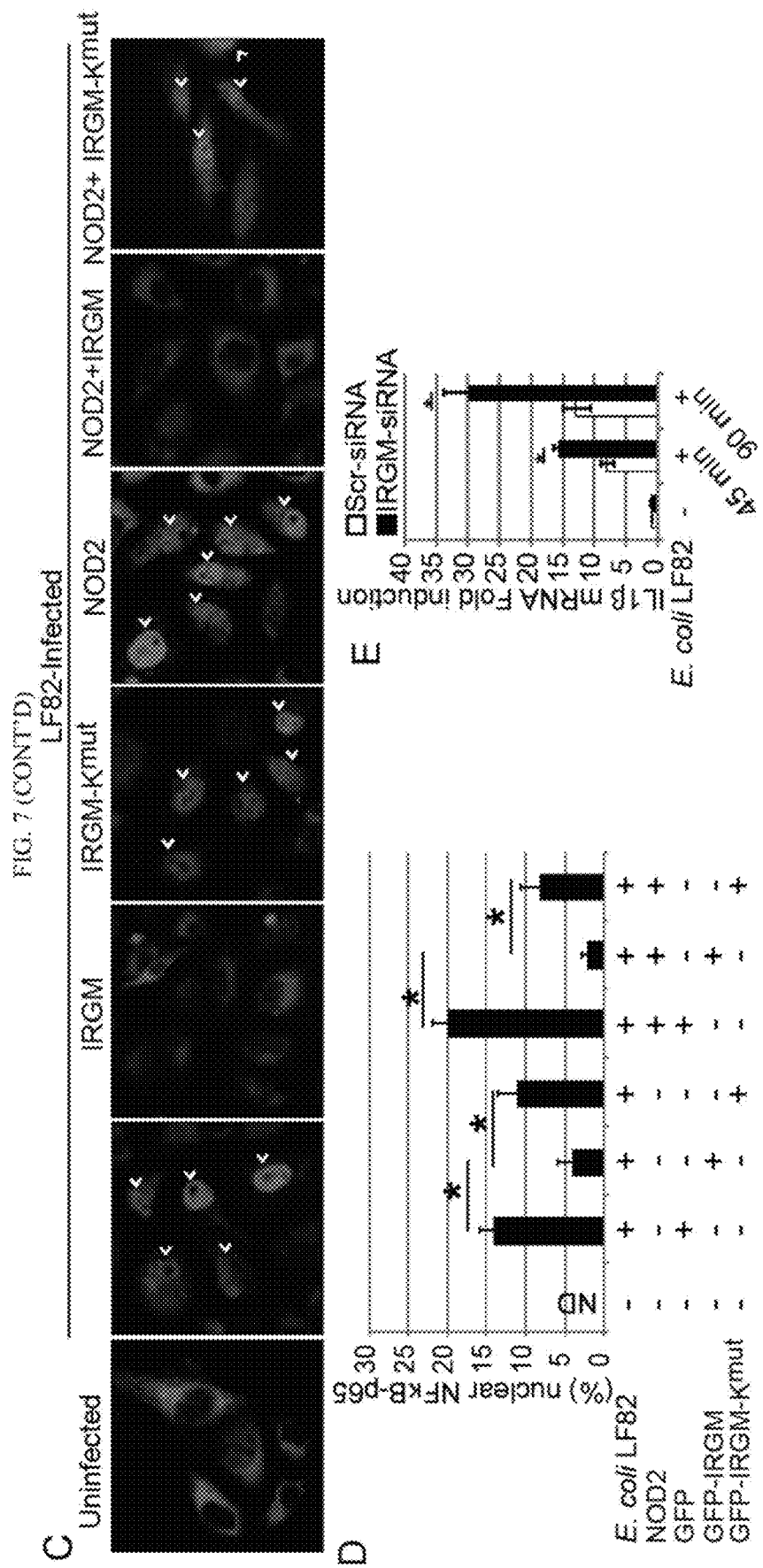

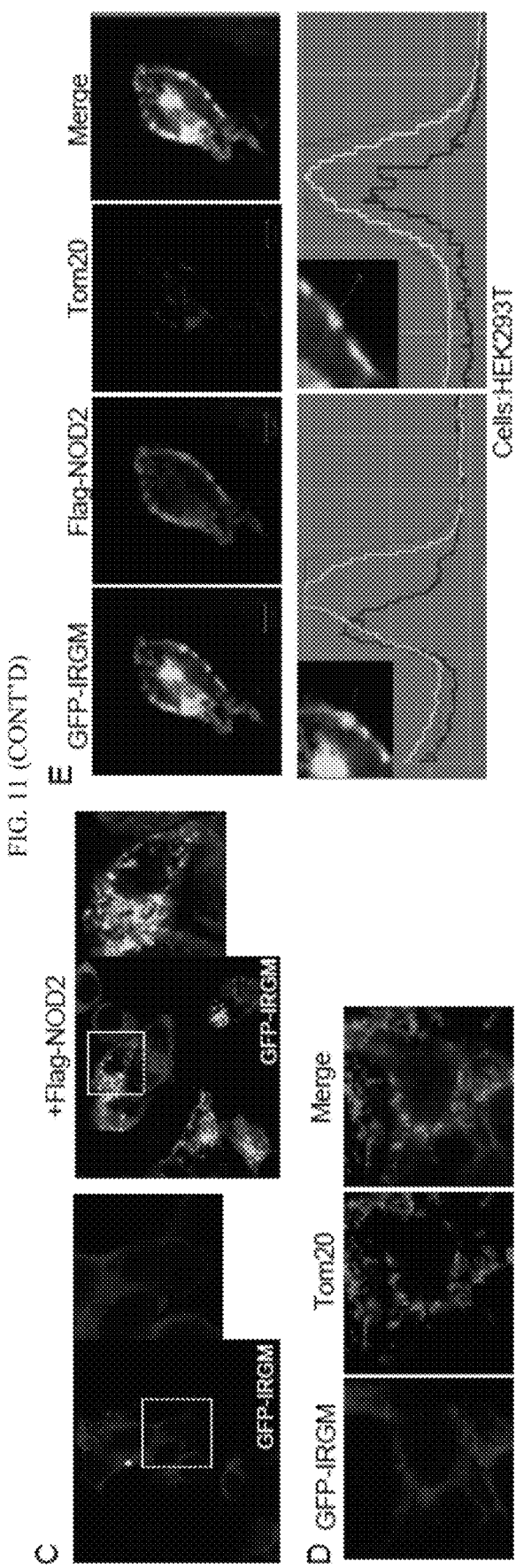

FIG. 12

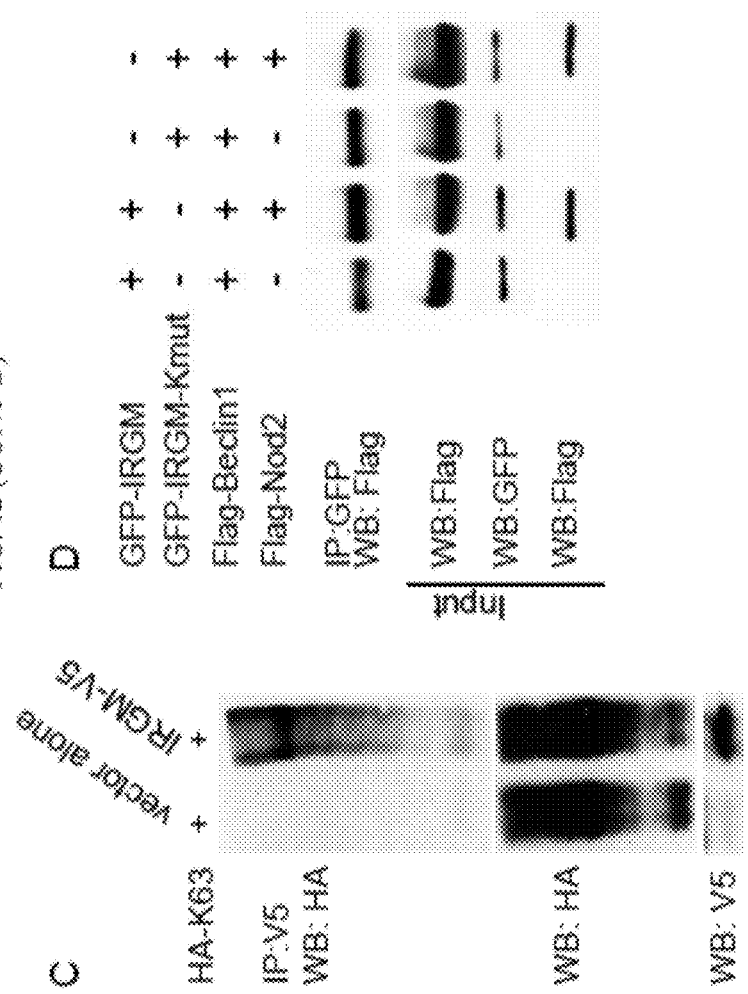

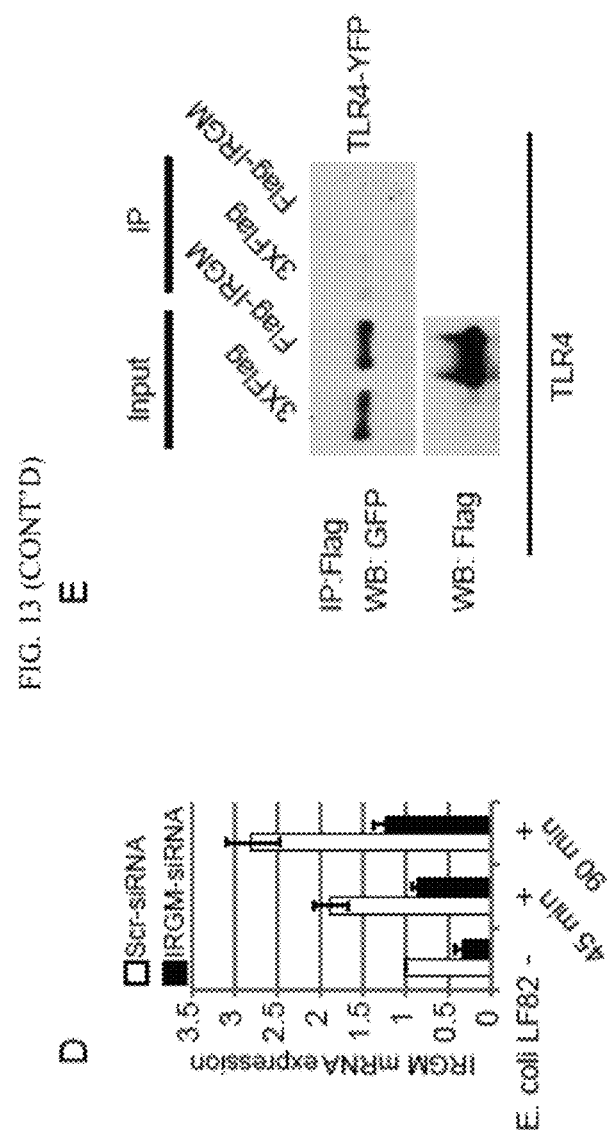

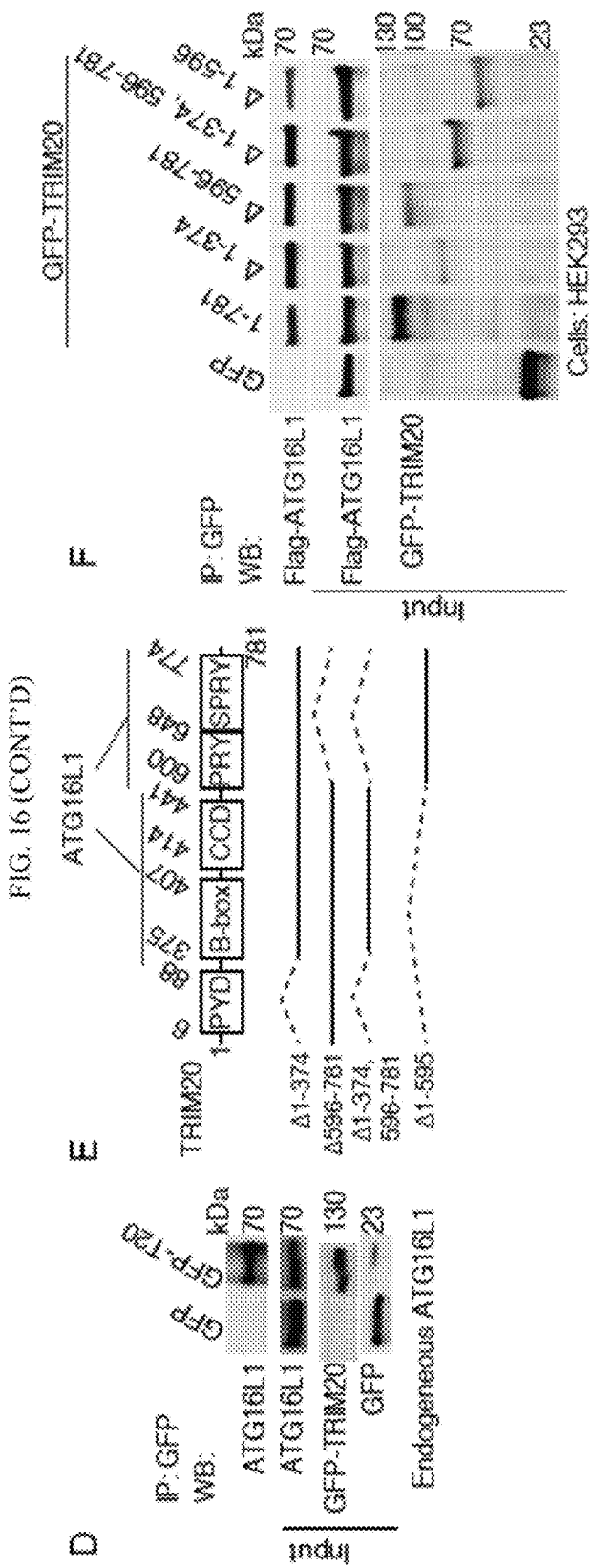

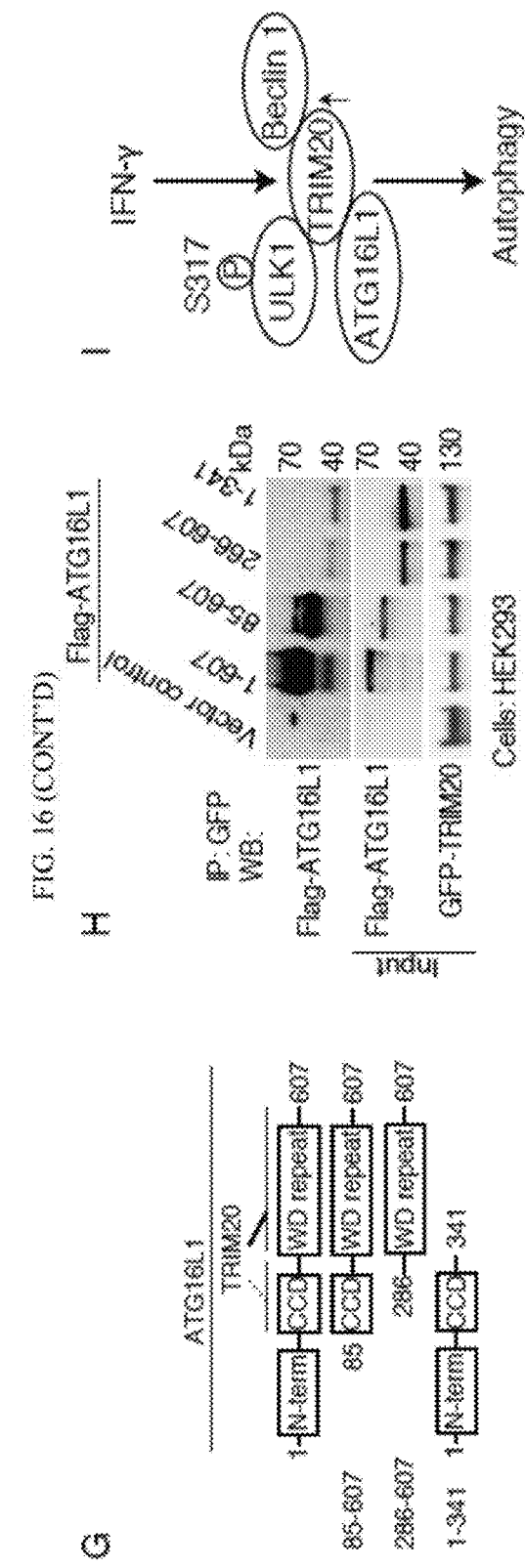

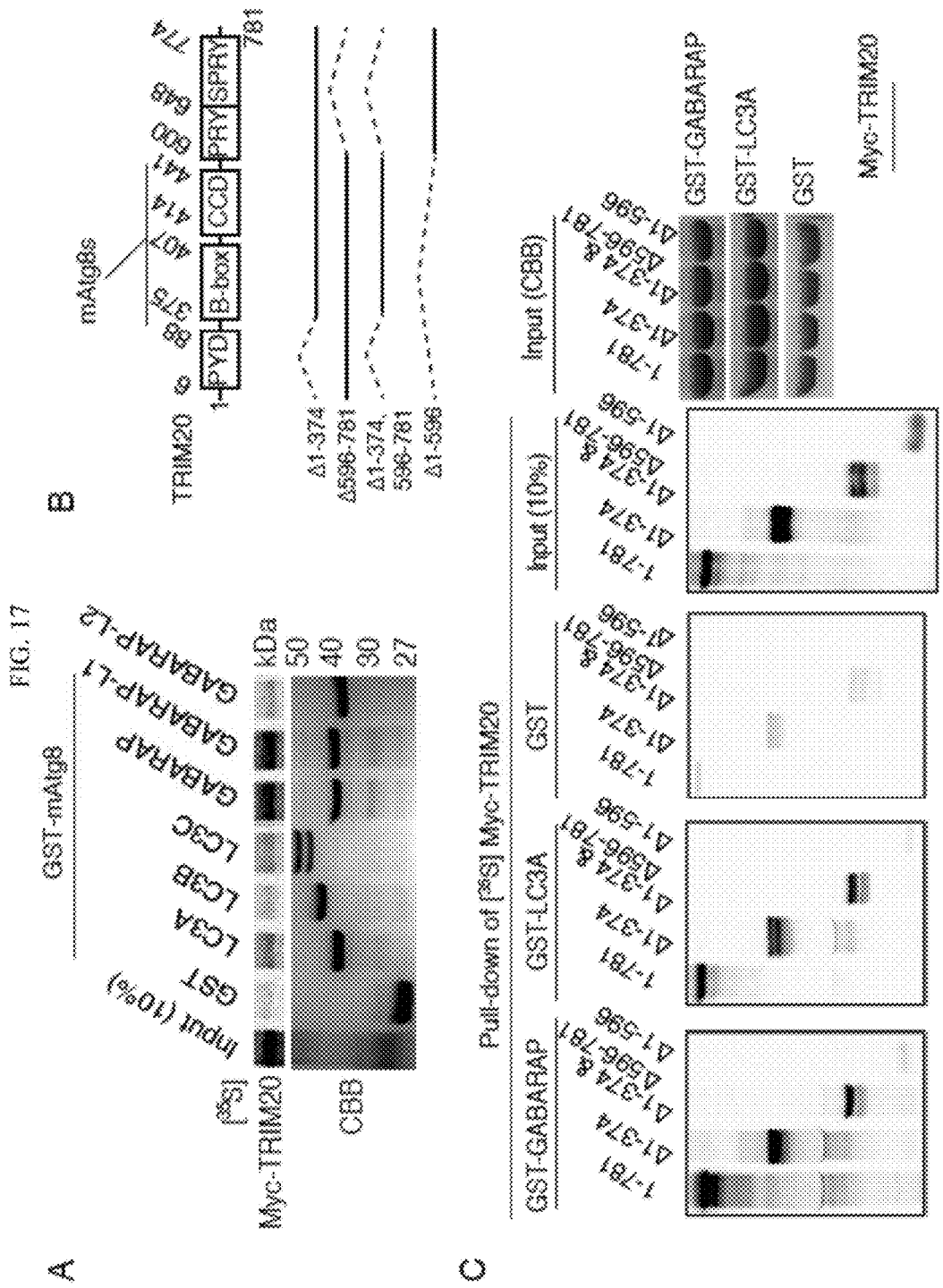

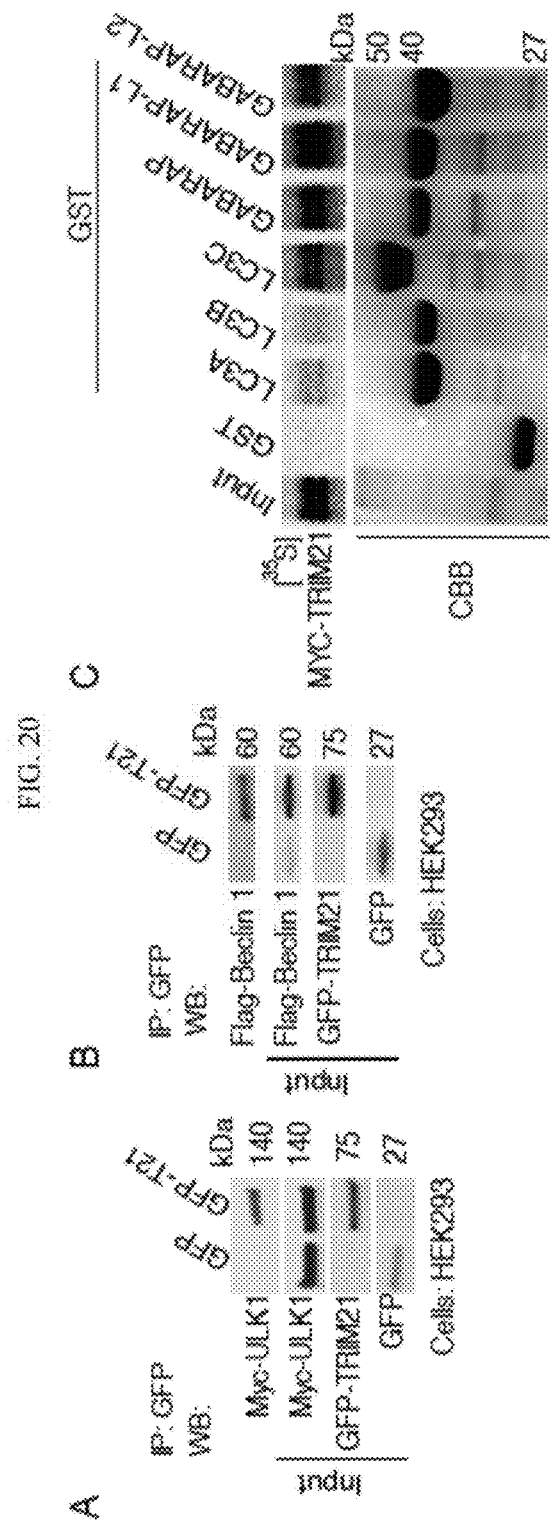

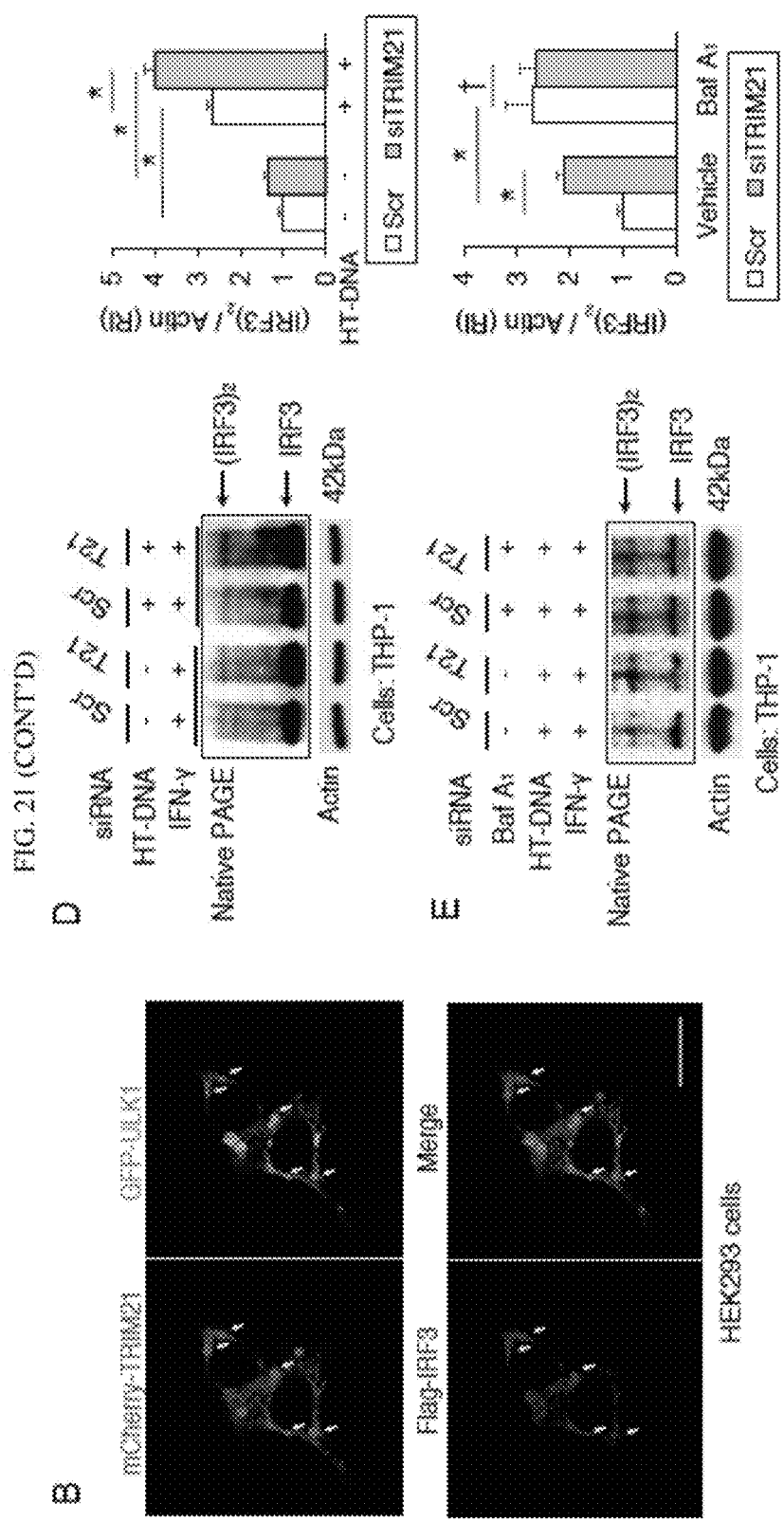

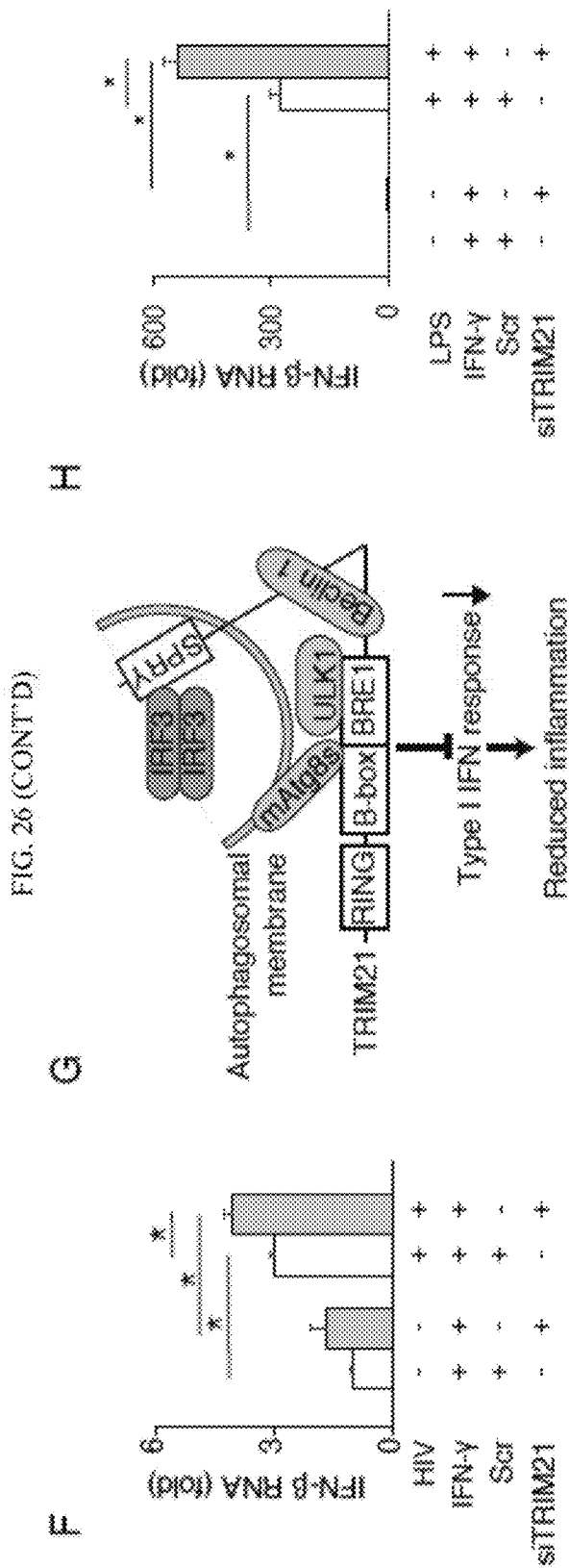

SEQUENCE LISTING

<160> NUMBER OF SEQ ID NOS: 348

<210> SEQ ID NO 1
<211> LENGTH: 734
<212> TYPE: PRT
<213> ORGANISM: Homo Sapiens

<400> SEQUENCE: 1

```
Met Gly Glu Ser Pro Ala Ser Val Val Leu Asn Ala Ser Gly Gly Leu
1               5                   10                  15

Phe Ser Leu Lys Met Glu Thr Leu Glu Ser Glu Leu Thr Cys Pro Ile
                20                  25                  30

Cys Leu Glu Leu Phe Glu Asp Pro Leu Leu Leu Pro Cys Ala His Ser
            35                  40                  45

Leu Cys Phe Ser Cys Ala His Arg Ile Leu Val Ser Ser Cys Ser Ser
    50                  55                  60

Gly Glu Ser Ile Glu Pro Ile Thr Ala Phe Gln Cys Pro Thr Cys Arg
65                  70                  75                  80

Tyr Val Ile Ser Leu Asn His Arg Gly Leu Asp Gly Leu Lys Arg Asn
                85                  90                  95

Val Thr Leu Gln Asn Ile Asp Arg Phe Gln Lys Ala Ser Val Ser Gly
            100                 105                 110

Pro Asn Ser Pro Ser Glu Ser Arg Arg Glu Arg Thr Tyr Arg Pro Thr
        115                 120                 125

Thr Ala Met Ser Ser Glu Arg Ile Ala Cys Gln Phe Cys Glu Gln Asp
    130                 135                 140

Pro Pro Arg Asp Ala Val Lys Thr Cys Ile Thr Cys Glu Val Ser Tyr
145                 150                 155                 160

Cys Asp Arg Cys Leu Arg Ala Thr His Pro Asn Lys Lys Pro Phe Thr
                165                 170                 175

Ser His Arg Leu Val Glu Pro Val Pro Asp Thr His Leu Arg Gly Ile
            180                 185                 190

Thr Cys Leu Asp His Glu Asn Glu Lys Val Asn Met Tyr Cys Val Ser
        195                 200                 205

Asp Asp Gln Leu Ile Cys Ala Leu Cys Lys Leu Val Gly Arg His Arg
    210                 215                 220

Asp His Gln Val Ala Ser Leu Asn Asp Arg Phe Glu Lys Leu Lys Gln
225                 230                 235                 240

Thr Leu Glu Met Asn Leu Thr Asn Leu Val Lys Arg Asn Ser Glu Leu
                245                 250                 255

Glu Asn Gln Met Ala Lys Leu Ile Gln Ile Cys Gln Gln Val Glu Val
            260                 265                 270

Asn Thr Ala Met His Glu Ala Lys Leu Met Glu Glu Cys Asp Glu Leu
        275                 280                 285

Val Glu Ile Ile Gln Gln Arg Lys Gln Met Ile Ala Val Lys Ile Lys
    290                 295                 300

Glu Thr Lys Val Met Lys Leu Arg Lys Leu Ala Gln Gln Val Ala Asn
305                 310                 315                 320

Cys Arg Gln Cys Leu Glu Arg Ser Thr Val Leu Ile Asn Gln Ala Glu
                325                 330                 335

His Ile Leu Lys Glu Asn Asp Gln Ala Arg Phe Leu Gln Ser Ala Lys
            340                 345                 350

Asn Ile Ala Glu Arg Val Ala Met Ala Thr Ala Ser Ser Gln Val Leu
        355                 360                 365
```

```
Ile Pro Asp Ile Asn Phe Asn Asp Ala Phe Glu Asn Phe Ala Leu Asp
    370                 375                 380
Phe Ser Arg Glu Lys Lys Leu Leu Glu Gly Leu Asp Tyr Leu Thr Ala
385                 390                 395                 400
Pro Asn Pro Ser Ile Arg Glu Glu Leu Cys Thr Ala Ser His Asp
                405                 410                 415
Thr Ile Thr Val His Trp Ile Ser Asp Glu Phe Ser Ile Ser Ser
            420                 425                 430
Tyr Glu Leu Gln Tyr Thr Ile Phe Thr Gly Gln Ala Asn Phe Ile Ser
            435                 440                 445
Lys Ser Trp Cys Ser Trp Gly Leu Trp Pro Glu Ile Arg Lys Cys Lys
450                 455                 460
Glu Ala Val Ser Cys Ser Arg Leu Ala Gly Ala Pro Arg Gly Leu Tyr
465                 470                 475                 480
Asn Ser Val Asp Ser Trp Met Ile Val Pro Asn Ile Lys Gln Asn His
                485                 490                 495
Tyr Thr Val His Gly Leu Gln Ser Gly Thr Arg Tyr Ile Phe Ile Val
            500                 505                 510
Lys Ala Ile Asn Gln Ala Gly Ser Arg Asn Ser Glu Pro Thr Arg Leu
            515                 520                 525
Lys Thr Asn Ser Gln Pro Phe Lys Leu Asp Pro Lys Met Thr His Lys
            530                 535                 540
Lys Leu Lys Ile Ser Asn Asp Gly Leu Gln Met Glu Lys Asp Glu Ser
545                 550                 555                 560
Ser Leu Lys Lys Ser His Thr Pro Glu Arg Phe Ser Gly Thr Gly Cys
                565                 570                 575
Tyr Gly Ala Ala Gly Asn Ile Phe Ile Asp Ser Gly Cys His Tyr Trp
            580                 585                 590
Glu Val Val Met Gly Ser Ser Thr Trp Tyr Ala Ile Gly Ile Ala Tyr
            595                 600                 605
Lys Ser Ala Pro Lys Asn Glu Trp Ile Gly Lys Asn Ala Ser Ser Trp
610                 615                 620
Val Phe Ser Arg Cys Asn Ser Asn Phe Val Val Arg His Asn Asn Lys
625                 630                 635                 640
Glu Met Leu Val Asp Val Pro Pro His Leu Lys Arg Leu Gly Val Leu
                645                 650                 655
Leu Asp Tyr Asp Asn Asn Met Leu Ser Phe Tyr Asp Pro Ala Asn Ser
            660                 665                 670
Leu His Leu His Thr Phe Asp Val Thr Phe Ile Leu Pro Val Cys Pro
            675                 680                 685
Thr Phe Thr Ile Trp Asn Lys Ser Leu Met Ile Leu Ser Gly Leu Pro
690                 695                 700
Ala Pro Asp Phe Ile Asp Tyr Pro Glu Arg Gln Glu Cys Asn Cys Arg
705                 710                 715                 720
Pro Gln Glu Ser Pro Tyr Val Ser Gly Met Lys Thr Cys His
                725                 730
```

<210> SEQ ID NO 2
<211> LENGTH: 19
<212> TYPE: RNA
<213> ORGANISM: Homo Sapiens

<400> SEQUENCE: 2
gaugaaagcu cucuaaaga                                                 19

```
<210> SEQ ID NO 3
<211> LENGTH: 19
<212> TYPE: RNA
<213> ORGANISM: Homo Sapiens

<400> SEQUENCE: 3
gaacaaaucc cuaaugauc                                                       19

<210> SEQ ID NO 4
<211> LENGTH: 19
<212> TYPE: RNA
<213> ORGANISM: Homo Sapiens

<400> SEQUENCE: 4
guagacagcu ggaugauug                                                       19

<210> SEQ ID NO 5
<211> LENGTH: 19
<212> TYPE: RNA
<213> ORGANISM: Homo Sapiens

<400> SEQUENCE: 5
caaaucagcu ccaaagaau                                                       19

<210> SEQ ID NO 6
<211> LENGTH: 771
<212> TYPE: PRT
<213> ORGANISM: Homo Sapiens

<400> SEQUENCE: 6

Met His Arg Ser Gly Arg Tyr Gly Thr Gln Gln Gln Arg Ala Gly Ser
1               5                   10                  15

Lys Thr Ala Gly Pro Pro Cys Gln Trp Ser Arg Met Ala Ser Glu Gly
            20                  25                  30

Thr Asn Ile Pro Ser Pro Val Val Arg Gln Ile Asp Lys Gln Phe Leu
        35                  40                  45

Ile Cys Ser Ile Cys Leu Glu Arg Tyr Lys Asn Pro Lys Val Leu Pro
    50                  55                  60

Cys Leu His Thr Phe Cys Glu Arg Cys Leu Gln Asn Tyr Ile Pro Ala
65                  70                  75                  80

His Ser Leu Thr Leu Ser Cys Pro Val Cys Arg Gln Thr Ser Ile Leu
                85                  90                  95

Pro Glu Lys Gly Val Ala Ala Leu Gln Asn Asn Phe Phe Ile Thr Asn
            100                 105                 110

Leu Met Asp Val Leu Gln Arg Thr Pro Gly Ser Asn Ala Glu Glu Ser
        115                 120                 125

Ser Ile Leu Glu Thr Val Thr Ala Val Ala Ala Gly Lys Pro Leu Ser
    130                 135                 140

Cys Pro Asn His Asp Gly Asn Val Met Glu Phe Tyr Cys Gln Ser Cys
145                 150                 155                 160

Glu Thr Ala Met Cys Arg Glu Cys Thr Glu Gly Glu His Ala Glu His
                165                 170                 175

Pro Thr Val Pro Leu Lys Asp Val Val Glu Gln His Lys Ala Ser Leu
            180                 185                 190

Gln Val Gln Leu Asp Ala Val Asn Lys Arg Leu Pro Glu Ile Asp Ser
        195                 200                 205

Ala Leu Gln Phe Ile Ser Glu Ile Ile His Gln Leu Thr Asn Gln Lys
    210                 215                 220
```

```
Ala Ser Ile Val Asp Asp Ile His Ser Thr Phe Asp Glu Leu Gln Lys
225                 230                 235                 240

Thr Leu Asn Val Arg Lys Ser Val Leu Leu Met Glu Leu Glu Val Asn
            245                 250                 255

Tyr Gly Leu Lys His Lys Val Leu Gln Ser Gln Leu Asp Thr Leu Leu
        260                 265                 270

Gln Gly Gln Glu Ser Ile Lys Ser Cys Ser Asn Phe Thr Ala Gln Ala
    275                 280                 285

Leu Asn His Gly Thr Glu Thr Glu Val Leu Leu Val Lys Lys Gln Met
290                 295                 300

Ser Glu Lys Leu Asn Glu Leu Ala Asp Gln Asp Phe Pro Leu His Pro
305                 310                 315                 320

Arg Glu Asn Asp Gln Leu Asp Phe Ile Val Glu Thr Glu Gly Leu Lys
                325                 330                 335

Lys Ser Ile His Asn Leu Gly Thr Ile Leu Thr Thr Asn Ala Val Ala
            340                 345                 350

Ser Glu Thr Val Ala Thr Gly Glu Gly Leu Arg Gln Thr Ile Ile Gly
        355                 360                 365

Gln Pro Met Ser Val Thr Ile Thr Thr Lys Asp Lys Asp Gly Glu Leu
370                 375                 380

Cys Lys Thr Gly Asn Ala Tyr Leu Thr Ala Glu Leu Ser Thr Pro Asp
385                 390                 395                 400

Gly Ser Val Ala Asp Gly Glu Ile Leu Asp Asn Lys Asn Gly Thr Tyr
                405                 410                 415

Glu Phe Leu Tyr Thr Val Gln Lys Gly Asp Phe Thr Leu Ser Leu
            420                 425                 430

Arg Leu Tyr Asp Gln His Ile Arg Gly Ser Pro Phe Lys Leu Lys Val
            435                 440                 445

Ile Arg Ser Ala Asp Val Ser Pro Thr Thr Glu Gly Val Lys Arg Arg
450                 455                 460

Val Lys Ser Pro Gly Ser Gly His Val Lys Gln Lys Ala Val Lys Arg
465                 470                 475                 480

Pro Ala Ser Met Tyr Ser Thr Gly Lys Arg Lys Glu Asn Pro Ile Glu
                485                 490                 495

Asp Asp Leu Ile Phe Arg Val Gly Thr Lys Gly Arg Asn Lys Gly Glu
            500                 505                 510

Phe Thr Asn Leu Gln Gly Val Ala Ala Ser Thr Asn Gly Lys Ile Leu
            515                 520                 525

Ile Ala Asp Ser Asn Asn Gln Cys Val Gln Ile Phe Ser Asn Asp Gly
            530                 535                 540

Gln Phe Lys Ser Arg Phe Gly Ile Arg Gly Arg Ser Pro Gly Gln Leu
545                 550                 555                 560

Gln Arg Pro Thr Gly Val Ala Val His Pro Ser Gly Asp Ile Ile Ile
                565                 570                 575

Ala Asp Tyr Asp Asn Lys Trp Val Ser Ile Phe Ser Ser Asp Gly Lys
            580                 585                 590

Phe Lys Thr Lys Ile Gly Ser Gly Lys Leu Met Gly Pro Lys Gly Val
            595                 600                 605

Ser Val Asp Arg Asn Gly His Ile Ile Val Asp Asn Lys Ala Cys
            610                 615                 620

Cys Val Phe Ile Phe Gln Pro Asn Gly Lys Ile Val Thr Arg Phe Gly
625                 630                 635                 640
```

-continued

```
Ser Arg Gly Asn Gly Asp Arg Gln Phe Ala Gly Pro His Phe Ala Ala
            645                 650                 655

Val Asn Ser Asn Glu Ile Ile Ile Thr Asp Phe His Asn His Ser
        660                 665                 670

Val Lys Val Phe Asn Gln Glu Gly Glu Phe Met Leu Lys Phe Gly Ser
    675                 680                 685

Asn Gly Glu Gly Asn Gly Gln Phe Asn Ala Pro Thr Gly Val Ala Val
    690                 695                 700

Asp Ser Asn Gly Asn Ile Ile Val Ala Asp Trp Gly Asn Ser Arg Ile
705                 710                 715                 720

Gln Val Phe Asp Gly Ser Gly Ser Phe Leu Ser Tyr Ile Asn Thr Ser
                725                 730                 735

Ala Asp Pro Leu Tyr Gly Pro Gln Gly Leu Ala Leu Thr Ser Asp Gly
            740                 745                 750

His Val Val Ala Asp Ser Gly Asn His Cys Phe Lys Val Tyr Arg
        755                 760                 765

Tyr Leu Gln
    770

<210> SEQ ID NO 7
<211> LENGTH: 19
<212> TYPE: RNA
<213> ORGANISM: Homo Sapiens

<400> SEQUENCE: 7
gaacggcacc uaugaguuu                                                  19

<210> SEQ ID NO 8
<211> LENGTH: 19
<212> TYPE: RNA
<213> ORGANISM: Homo Sapiens

<400> SEQUENCE: 8
ggaaggagaa uucauguug                                                  19

<210> SEQ ID NO 9
<211> LENGTH: 19
<212> TYPE: RNA
<213> ORGANISM: Homo Sapiens

<400> SEQUENCE: 9
ggaaugugau ggaauuuua                                                  19

<210> SEQ ID NO 10
<211> LENGTH: 19
<212> TYPE: RNA
<213> ORGANISM: Homo Sapiens

<400> SEQUENCE: 10
caaccaaugu gugcagaua                                                  19

<210> SEQ ID NO 11
<211> LENGTH: 744
<212> TYPE: PRT
<213> ORGANISM: Homo Sapiens

<400> SEQUENCE: 11

Met Ala Lys Arg Glu Asp Ser Pro Gly Pro Glu Val Gln Pro Met Asp
1               5                   10                  15

Lys Gln Phe Leu Val Cys Ser Ile Cys Leu Asp Arg Tyr Gln Cys Pro
```

-continued

```
                20                  25                  30
Lys Val Leu Pro Cys Leu His Thr Phe Cys Glu Arg Cys Leu Gln Asn
            35                  40                  45
Tyr Ile Pro Ala Gln Ser Leu Thr Leu Ser Cys Pro Val Cys Arg Gln
50                  55                  60
Thr Ser Ile Leu Pro Glu Gln Gly Val Ser Ala Leu Gln Asn Asn Phe
65                  70                  75                  80
Phe Ile Ser Ser Leu Met Glu Ala Met Gln Gln Ala Pro Asp Gly Ala
                85                  90                  95
His Asp Pro Glu Asp Pro His Pro Leu Ser Val Val Ala Gly Arg Pro
                100                 105                 110
Leu Ser Cys Pro Asn His Glu Gly Lys Thr Met Glu Phe Tyr Cys Glu
                115                 120                 125
Ala Cys Glu Thr Ala Met Cys Gly Glu Cys Arg Ala Gly Glu His Arg
                130                 135                 140
Glu His Gly Thr Val Leu Leu Arg Asp Val Val Glu Gln His Lys Ala
145                 150                 155                 160
Ala Leu Gln Arg Gln Leu Glu Ala Val Arg Gly Arg Leu Pro Gln Leu
                165                 170                 175
Ser Ala Ala Ile Ala Leu Val Gly Gly Ile Ser Gln Gln Leu Gln Glu
                180                 185                 190
Arg Lys Ala Glu Ala Leu Ala Gln Ile Ser Ala Ala Phe Glu Asp Leu
                195                 200                 205
Glu Gln Ala Leu Gln Gln Arg Lys Gln Ala Leu Val Ser Asp Leu Glu
                210                 215                 220
Thr Ile Cys Gly Ala Lys Gln Lys Val Leu Gln Ser Gln Leu Asp Thr
225                 230                 235                 240
Leu Arg Gln Gly Gln Glu His Ile Gly Ser Ser Cys Ser Phe Ala Glu
                245                 250                 255
Gln Ala Leu Arg Leu Gly Ser Ala Pro Glu Val Leu Leu Val Arg Lys
                260                 265                 270
His Met Arg Glu Arg Leu Ala Ala Leu Ala Ala Gln Ala Phe Pro Glu
                275                 280                 285
Arg Pro His Glu Asn Ala Gln Leu Glu Leu Val Leu Glu Val Asp Gly
                290                 295                 300
Leu Arg Arg Ser Val Leu Asn Leu Gly Ala Leu Leu Thr Thr Ser Ala
305                 310                 315                 320
Thr Ala His Glu Thr Val Ala Thr Gly Glu Gly Leu Arg Gln Ala Leu
                325                 330                 335
Val Gly Gln Pro Ala Ser Leu Thr Val Thr Thr Lys Asp Lys Asp Gly
                340                 345                 350
Arg Leu Val Arg Thr Gly Ser Ala Glu Leu Arg Ala Glu Ile Thr Gly
                355                 360                 365
Pro Asp Gly Thr Arg Leu Pro Val Pro Val Val Asp His Lys Asn Gly
                370                 375                 380
Thr Tyr Glu Leu Val Tyr Thr Ala Arg Thr Glu Gly Glu Leu Leu Leu
385                 390                 395                 400
Ser Val Leu Leu Tyr Gly Gln Pro Val Arg Gly Ser Pro Phe Arg Val
                405                 410                 415
Arg Ala Leu Arg Pro Gly Asp Leu Pro Pro Ser Pro Asp Asp Val Lys
                420                 425                 430
Arg Arg Val Lys Ser Pro Gly Gly Pro Gly Ser His Val Arg Gln Lys
                435                 440                 445
```

Ala Val Arg Arg Pro Ser Ser Met Tyr Ser Thr Gly Lys Arg Lys
450                     455                     460

Asp Asn Pro Ile Glu Asp Glu Leu Val Phe Arg Val Gly Ser Arg Gly
465                     470                     475                     480

Arg Glu Lys Gly Glu Phe Thr Asn Leu Gln Gly Val Ser Ala Ala Ser
                    485                     490                     495

Ser Gly Arg Ile Val Val Ala Asp Ser Asn Asn Gln Cys Ile Gln Val
                500                     505                     510

Phe Ser Asn Glu Gly Gln Phe Lys Phe Arg Phe Gly Val Arg Gly Arg
            515                     520                     525

Ser Pro Gly Gln Leu Gln Arg Pro Thr Gly Val Ala Val Asp Thr Asn
530                     535                     540

Gly Asp Ile Ile Val Ala Asp Tyr Asp Asn Arg Trp Val Ser Ile Phe
545                     550                     555                     560

Ser Pro Glu Gly Lys Phe Lys Thr Lys Ile Gly Ala Gly Arg Leu Met
                565                     570                     575

Gly Pro Lys Gly Val Ala Val Asp Arg Asn Gly His Ile Ile Val Val
            580                     585                     590

Asp Asn Lys Ser Cys Cys Val Phe Thr Phe Gln Pro Asn Gly Lys Leu
        595                     600                     605

Val Gly Arg Phe Gly Gly Arg Gly Ala Thr Asp Arg His Phe Ala Gly
610                     615                     620

Pro His Phe Val Ala Val Asn Asn Lys Asn Glu Ile Val Val Thr Asp
625                     630                     635                     640

Phe His Asn His Ser Val Lys Val Tyr Ser Ala Asp Gly Glu Phe Leu
                645                     650                     655

Phe Lys Phe Gly Ser His Gly Glu Gly Asn Gly Gln Phe Asn Ala Pro
            660                     665                     670

Thr Gly Val Ala Val Asp Ser Asn Gly Asn Ile Ile Val Ala Asp Trp
        675                     680                     685

Gly Asn Ser Arg Ile Gln Val Phe Asp Ser Ser Gly Ser Phe Leu Ser
690                     695                     700

Tyr Ile Asn Thr Ser Ala Glu Pro Leu Tyr Gly Pro Gln Gly Leu Ala
705                     710                     715                     720

Leu Thr Ser Asp Gly His Val Val Val Ala Asp Ala Gly Asn His Cys
                725                     730                     735

Phe Lys Ala Tyr Arg Tyr Leu Gln
            740

<210> SEQ ID NO 12
<211> LENGTH: 19
<212> TYPE: RNA
<213> ORGANISM: Homo Sapiens

<400> SEQUENCE: 12
gcaagacgau ggaguuuua                                                  19

<210> SEQ ID NO 13
<211> LENGTH: 19
<212> TYPE: RNA
<213> ORGANISM: Homo Sapiens

<400> SEQUENCE: 13
gaaaggacaa cccaauuga                                                  19

```
<210> SEQ ID NO 14
<211> LENGTH: 19
<212> TYPE: RNA
<213> ORGANISM: Homo Sapiens

<400> SEQUENCE: 14
ccacaagaau ggcacauau                                                    19

<210> SEQ ID NO 15
<211> LENGTH: 19
<212> TYPE: RNA
<213> ORGANISM: Homo Sapiens

<400> SEQUENCE: 15
gagagcggcu ggcugcauu                                                    19

<210> SEQ ID NO 16
<211> LENGTH: 500
<212> TYPE: PRT
<213> ORGANISM: Homo Sapiens

<400> SEQUENCE: 16
```

| | | | | | | | | | | | | | | |
|---|---|---|---|---|---|---|---|---|---|---|---|---|---|---|
| Met | Glu | Ala | Glu | Asp | Ile | Gln | Glu | Glu | Leu | Thr | Cys | Pro | Ile | Cys | Leu |
| 1 | | | | 5 | | | | | 10 | | | | | 15 | |
| Asp | Tyr | Phe | Gln | Asp | Pro | Val | Ser | Ile | Glu | Cys | Gly | His | Asn | Phe | Cys |
| | | | 20 | | | | | 25 | | | | | 30 | | |
| Arg | Gly | Cys | Leu | His | Arg | Asn | Trp | Ala | Pro | Gly | Gly | Pro | Phe | Pro | |
| | | 35 | | | | | 40 | | | | | 45 | | | |
| Cys | Pro | Glu | Cys | Arg | His | Pro | Ser | Ala | Pro | Ala | Ala | Leu | Arg | Pro | Asn |
| 50 | | | | | 55 | | | | | 60 | | | | | |
| Trp | Ala | Leu | Ala | Arg | Leu | Thr | Glu | Lys | Thr | Gln | Arg | Arg | Leu | Gly | |
| 65 | | | | | 70 | | | | | 75 | | | | | 80 |
| Pro | Val | Pro | Pro | Gly | Leu | Cys | Gly | Arg | His | Trp | Glu | Pro | Leu | Arg | Leu |
| | | | | 85 | | | | | 90 | | | | | 95 | |
| Phe | Cys | Glu | Asp | Asp | Gln | Arg | Pro | Val | Cys | Leu | Val | Cys | Arg | Glu | Ser |
| | | | | 100 | | | | | 105 | | | | | 110 | |
| Gln | Glu | His | Gln | Thr | His | Ala | Met | Ala | Pro | Ile | Asp | Glu | Ala | Phe | Glu |
| | | | 115 | | | | | 120 | | | | | 125 | | |
| Ser | Tyr | Arg | Thr | Gly | Asn | Phe | Asp | Ile | His | Val | Asp | Glu | Trp | Lys | Arg |
| | | 130 | | | | | 135 | | | | | 140 | | | |
| Arg | Leu | Ile | Arg | Leu | Leu | Leu | Tyr | His | Phe | Lys | Gln | Glu | Glu | Lys | Leu |
| 145 | | | | | 150 | | | | | 155 | | | | | 160 |
| Leu | Lys | Ser | Gln | Arg | Asn | Leu | Val | Ala | Lys | Met | Lys | Lys | Val | Met | His |
| | | | | 165 | | | | | 170 | | | | | 175 | |
| Leu | Gln | Asp | Val | Glu | Val | Lys | Asn | Ala | Thr | Gln | Trp | Lys | Asp | Lys | Ile |
| | | | 180 | | | | | 185 | | | | | 190 | | |
| Lys | Ser | Gln | Arg | Met | Arg | Ile | Ser | Thr | Glu | Phe | Ser | Lys | Leu | His | Asn |
| | | 195 | | | | | 200 | | | | | 205 | | | |
| Phe | Leu | Val | Glu | Glu | Asp | Leu | Phe | Leu | Gln | Arg | Leu | Asn | Lys | Glu | |
| | | 210 | | | | | 215 | | | | | 220 | | | |
| Glu | Glu | Glu | Thr | Lys | Lys | Lys | Leu | Asn | Glu | Asn | Thr | Leu | Lys | Leu | Asn |
| 225 | | | | | 230 | | | | | 235 | | | | | 240 |
| Gln | Thr | Ile | Ala | Ser | Leu | Lys | Lys | Leu | Ile | Leu | Glu | Val | Gly | Glu | Lys |
| | | | | 245 | | | | | 250 | | | | | 255 | |
| Ser | Gln | Ala | Pro | Thr | Leu | Glu | Leu | Leu | Gln | Asn | Pro | Lys | Glu | Val | Leu |
| | | | 260 | | | | | 265 | | | | | 270 | | |
| Thr | Arg | Ser | Glu | Ile | Gln | Asp | Val | Asn | Tyr | Ser | Leu | Glu | Ala | Val | Lys |

-continued

```
              275                 280                 285
Val Lys Thr Val Cys Gln Ile Pro Leu Met Lys Glu Met Leu Lys Arg
    290                 295                 300

Phe Gln Val Ala Val Asn Leu Ala Glu Asp Thr Ala His Pro Lys Leu
305                 310                 315                 320

Val Phe Ser Gln Glu Gly Arg Tyr Val Lys Asn Thr Ala Ser Ala Ser
                325                 330                 335

Ser Trp Pro Val Phe Ser Ser Ala Trp Asn Tyr Phe Ala Gly Trp Arg
            340                 345                 350

Asn Pro Gln Lys Thr Ala Phe Val Glu Arg Phe Gln His Leu Pro Cys
        355                 360                 365

Val Leu Gly Lys Asn Val Phe Thr Ser Gly Lys His Tyr Trp Glu Val
    370                 375                 380

Glu Ser Arg Asp Ser Leu Glu Val Ala Val Gly Val Cys Arg Glu Asp
385                 390                 395                 400

Val Met Gly Ile Thr Asp Arg Ser Lys Met Ser Pro Asp Val Gly Ile
                405                 410                 415

Trp Ala Ile Tyr Trp Ser Ala Ala Gly Tyr Trp Pro Leu Ile Gly Phe
            420                 425                 430

Pro Gly Thr Pro Thr Gln Gln Glu Pro Ala Leu His Arg Val Gly Val
        435                 440                 445

Tyr Leu Asp Arg Gly Thr Gly Asn Val Ser Phe Tyr Ser Ala Val Asp
    450                 455                 460

Gly Val His Leu His Thr Phe Ser Cys Ser Ser Val Ser Arg Leu Arg
465                 470                 475                 480

Pro Phe Phe Trp Leu Ser Pro Leu Ala Ser Leu Val Ile Pro Pro Val
                485                 490                 495

Thr Asp Arg Lys
            500

<210> SEQ ID NO 17
<211> LENGTH: 19
<212> TYPE: RNA
<213> ORGANISM: Homo Sapiens

<400> SEQUENCE: 17
ccaaguggcu guaaaccua                                               19

<210> SEQ ID NO 18
<211> LENGTH: 19
<212> TYPE: RNA
<213> ORGANISM: Homo Sapiens

<400> SEQUENCE: 18
gaagacagug ugccagaua                                               19

<210> SEQ ID NO 19
<211> LENGTH: 19
<212> TYPE: RNA
<213> ORGANISM: Homo Sapiens

<400> SEQUENCE: 19
gaaguugaga guagagaua                                               19

<210> SEQ ID NO 20
<211> LENGTH: 19
<212> TYPE: RNA
<213> ORGANISM: Homo Sapiens
```

<400> SEQUENCE: 20
caaacuaucg cuucauuga                                                                19

<210> SEQ ID NO 21
<211> LENGTH: 493
<212> TYPE: PRT
<213> ORGANISM: Homo Sapiens

<400> SEQUENCE: 21

Met Ala Ser Gly Ile Leu Val Asn Val Lys Glu Val Thr Cys Pro
1               5                   10                  15

Ile Cys Leu Glu Leu Leu Thr Gln Pro Leu Ser Leu Asp Cys Gly His
                20                  25                  30

Ser Phe Cys Gln Ala Cys Leu Thr Ala Asn His Lys Lys Ser Met Leu
            35                  40                  45

Asp Lys Gly Glu Ser Ser Cys Pro Val Cys Arg Ile Ser Tyr Gln Pro
        50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

```
Ser Ile Thr Ser Gly Lys His Tyr Trp Glu Val Asp Val Ser Lys Lys
            355                 360                 365

Thr Ala Trp Ile Leu Gly Val Cys Ala Gly Phe Gln Pro Asp Ala Met
370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
                435                 440                 445

Val Ser Phe Phe Asn Ile Thr Asn His Gly Phe Leu Ile Tyr Lys Phe
450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490

<210> SEQ ID NO 22
<211> LENGTH: 19
<212> TYPE: RNA
<213> ORGANISM: Homo Sapiens

<400> SEQUENCE: 22
gcagaaaguu gaucauugu                                              19

<210> SEQ ID NO 23
<211> LENGTH: 19
<212> TYPE: RNA
<213> ORGANISM: Homo Sapiens

<400> SEQUENCE: 23
gagaguagcu gcccugugu                                              19

<210> SEQ ID NO 24
<211> LENGTH: 19
<212> TYPE: RNA
<213> ORGANISM: Homo Sapiens

<400> SEQUENCE: 24
ggaauccugg uuaauguaa                                              19

<210> SEQ ID NO 25
<211> LENGTH: 19
<212> TYPE: RNA
<213> ORGANISM: Homo Sapiens

<400> SEQUENCE: 25
uuaccagccu gagaacaua                                              19

<210> SEQ ID NO 26
<211> LENGTH: 488
<212> TYPE: PRT
<213> ORGANISM: Homo Sapiens

<400> SEQUENCE: 26

Met Thr Ser Pro Val Leu Val Asp Ile Arg Glu Glu Val Thr Cys Pro
1               5                   10                  15

Ile Cys Leu Glu Leu Leu Thr Glu Pro Leu Ser Ile Asp Cys Gly His
```

-continued

```
                20                  25                  30
Ser Phe Cys Gln Ala Cys Ile Thr Pro Asn Gly Arg Glu Ser Val Ile
            35                  40                  45
Gly Gln Glu Gly Glu Arg Ser Cys Pro Val Cys Gln Thr Ser Tyr Gln
        50                  55                  60
Pro Gly Asn Leu Arg Pro Asn Arg His Leu Ala Asn Ile Val Arg Arg
65                  70                  75                  80
Leu Arg Glu Val Val Leu Gly Pro Gly Lys Gln Leu Lys Ala Val Leu
                85                  90                  95
Cys Ala Asp His Gly Glu Lys Leu Gln Leu Phe Cys Gln Glu Asp Gly
            100                 105                 110
Lys Val Ile Cys Trp Leu Cys Glu Arg Ser Gln Glu His Arg Gly His
        115                 120                 125
His Thr Phe Leu Val Glu Val Ala Gln Glu Tyr Gln Glu Lys Phe
            130                 135                 140
Gln Glu Ser Leu Lys Lys Leu Lys Asn Glu Glu Gln Glu Ala Glu Lys
145                 150                 155                 160
Leu Thr Ala Phe Ile Arg Glu Lys Lys Thr Ser Trp Lys Asn Gln Met
                165                 170                 175
Glu Pro Glu Arg Cys Arg Ile Gln Thr Glu Phe Asn Gln Leu Arg Asn
            180                 185                 190
Ile Leu Asp Arg Val Glu Gln Arg Glu Leu Lys Lys Leu Glu Gln Glu
        195                 200                 205
Glu Lys Lys Gly Leu Arg Ile Ile Glu Glu Ala Glu Asn Asp Leu Val
        210                 215                 220
His Gln Thr Gln Ser Leu Arg Glu Leu Ile Ser Asp Leu Glu Arg Arg
225                 230                 235                 240
Cys Gln Gly Ser Thr Met Glu Leu Leu Gln Asp Val Ser Asp Val Thr
                245                 250                 255
Glu Arg Ser Glu Phe Trp Thr Leu Arg Lys Pro Glu Ala Leu Pro Thr
            260                 265                 270
Lys Leu Arg Ser Met Phe Arg Ala Pro Asp Leu Lys Arg Met Leu Arg
        275                 280                 285
Val Cys Arg Glu Leu Thr Asp Val Gln Ser Tyr Trp Val Asp Val Thr
        290                 295                 300
Leu Asn Pro His Thr Ala Asn Leu Asn Leu Val Leu Ala Lys Asn Arg
305                 310                 315                 320
Arg Gln Val Arg Phe Val Gly Ala Lys Val Ser Gly Pro Ser Cys Leu
                325                 330                 335
Glu Lys His Tyr Asp Cys Ser Val Leu Gly Ser Gln His Phe Ser Ser
            340                 345                 350
Gly Lys His Tyr Trp Glu Val Asp Val Ala Lys Lys Thr Ala Trp Ile
        355                 360                 365
Leu Gly Val Cys Ser Asn Ser Leu Gly Pro Thr Phe Ser Phe Asn His
        370                 375                 380
Phe Ala Gln Asn His Ser Ala Tyr Ser Arg Tyr Gln Pro Gln Ser Gly
385                 390                 395                 400
Tyr Trp Val Ile Gly Leu Gln His Asn His Glu Tyr Arg Ala Tyr Glu
                405                 410                 415
Asp Ser Ser Pro Ser Leu Leu Leu Ser Met Thr Val Pro Pro Arg Arg
            420                 425                 430
Val Gly Val Phe Leu Asp Tyr Glu Ala Gly Thr Val Ser Phe Tyr Asn
        435                 440                 445
```

```
Val Thr Asn His Gly Phe Pro Ile Tyr Thr Phe Ser Lys Tyr Tyr Phe
    450                 455                 460

Pro Thr Thr Leu Cys Pro Tyr Phe Asn Pro Cys Asn Cys Val Ile Pro
465                 470                 475                 480

Met Thr Leu Arg Arg Pro Ser Ser
                485

<210> SEQ ID NO 27
<211> LENGTH: 19
<212> TYPE: RNA
<213> ORGANISM: Homo Sapiens

<400> SEQUENCE: 27
uaaagaagcu gaagaacga                                                       19

<210> SEQ ID NO 28
<211> LENGTH: 19
<212> TYPE: RNA
<213> ORGANISM: Homo Sapiens

<400> SEQUENCE: 28
cuacaaagcu gagaaguau                                                       19

<210> SEQ ID NO 29
<211> LENGTH: 19
<212> TYPE: RNA
<213> ORGANISM: Homo Sapiens

<400> SEQUENCE: 29
ggaccuacau ucucuuuca                                                       19

<210> SEQ ID NO 30
<211> LENGTH: 19
<212> TYPE: RNA
<213> ORGANISM: Homo Sapiens

<400> SEQUENCE: 30
ccacuacucu uuguccaua                                                       19

<210> SEQ ID NO 31
<211> LENGTH: 303
<212> TYPE: PRT
<213> ORGANISM: Homo Sapiens

<400> SEQUENCE: 31

Met Ala Ala Glu Gln Glu Lys Val Gly Ala Glu Phe Gln Ala Leu Arg
1               5                   10                  15

Ala Phe Leu Val Glu Gln Glu Gly Arg Leu Leu Gly Arg Leu Glu Glu
                20                  25                  30

Leu Ser Arg Glu Val Ala Gln Lys Gln Asn Glu Asn Leu Ala Gln Leu
            35                  40                  45

Gly Val Glu Ile Thr Gln Leu Ser Lys Leu Ser Ser Gln Ile Gln Glu
        50                  55                  60

Thr Ala Gln Lys Pro Asp Leu Asp Phe Leu Gln Glu Phe Lys Ser Thr
65                  70                  75                  80

Leu Ser Arg Cys Ser Asn Val Pro Gly Pro Lys Pro Thr Thr Val Ser
                85                  90                  95

Ser Glu Met Lys Asn Lys Val Trp Asn Val Ser Leu Lys Thr Phe Val
                100                 105                 110
```

```
Leu Lys Gly Met Leu Lys Lys Phe Lys Glu Asp Leu Arg Gly Glu Leu
            115                 120                 125

Glu Lys Glu Glu Lys Val Glu Leu Thr Leu Asp Pro Asp Thr Ala Asn
        130                 135                 140

Pro Arg Leu Ile Leu Ser Leu Asp Leu Lys Gly Val Arg Leu Gly Glu
145                 150                 155                 160

Arg Ala Gln Asp Leu Pro Asn His Pro Cys Arg Phe Asp Thr Asn Thr
                165                 170                 175

Arg Val Leu Ala Ser Cys Gly Phe Ser Ser Gly Arg His His Trp Glu
            180                 185                 190

Val Glu Val Gly Ser Lys Asp Gly Trp Ala Phe Gly Val Ala Arg Glu
        195                 200                 205

Ser Val Arg Arg Lys Gly Leu Thr Pro Phe Thr Pro Glu Glu Gly Val
    210                 215                 220

Trp Ala Leu Gln Leu Asn Gly Gly Gln Tyr Trp Ala Val Thr Ser Pro
225                 230                 235                 240

Glu Arg Ser Pro Leu Ser Cys Gly His Leu Ser Arg Val Arg Val Ala
                245                 250                 255

Leu Asp Leu Glu Val Gly Ala Val Ser Phe Tyr Ala Val Glu Asp Met
            260                 265                 270

Arg His Leu Tyr Thr Phe Arg Val Asn Phe Gln Glu Arg Val Phe Pro
        275                 280                 285

Leu Phe Ser Val Cys Ser Thr Gly Thr Tyr Leu Arg Ile Trp Pro
    290                 295                 300

<210> SEQ ID NO 32
<211> LENGTH: 19
<212> TYPE: RNA
<213> ORGANISM: Homo Sapiens

<400> SEQUENCE: 32 gaagguggc agugggcua                                                     19

<210> SEQ ID NO 33
<211> LENGTH: 19
<212> TYPE: RNA
<213> ORGANISM: Homo Sapiens

<400> SEQUENCE: 33
gcucuaaaca acacacaga                                                    19

<210> SEQ ID NO 34
<211> LENGTH: 19
<212> TYPE: RNA
<213> ORGANISM: Homo Sapiens

<400> SEQUENCE: 34
caaauaugcu ccugacgga                                                    19

<210> SEQ ID NO 35
<211> LENGTH: 19
<212> TYPE: RNA
<213> ORGANISM: Homo Sapiens

<400> SEQUENCE: 35
cauccugacc aaugcgaca                                                    19

<210> SEQ ID NO 36
<211> LENGTH: 551
```

<212> TYPE: PRT
<213> ORGANISM: Homo Sapiens

<400> SEQUENCE: 36

```
Met Ala Glu Asn Trp Lys Asn Cys Phe Glu Glu Leu Ile Cys Pro
1               5                   10                  15

Ile Cys Leu His Val Phe Val Glu Pro Val Gln Leu Pro Cys Lys His
                20                  25                  30

Asn Phe Cys Arg Gly Cys Ile Gly Glu Ala Trp Ala Lys Asp Ser Gly
            35                  40                  45

Leu Val Arg Cys Pro Glu Cys Asn Gln Ala Tyr Asn Gln Lys Pro Gly
        50                  55                  60

Leu Glu Lys Asn Leu Lys Leu Thr Asn Ile Val Glu Lys Phe Asn Ala
65                  70                  75                  80

Leu His Val Glu Lys Pro Ala Ala Leu His Cys Val Phe Cys Arg
                85                  90                  95

Arg Gly Pro Pro Leu Pro Ala Gln Lys Val Cys Leu Arg Cys Glu Ala
                100                 105                 110

Pro Cys Cys Gln Ser His Val Gln Thr His Leu Gln Gln Pro Ser Thr
        115                 120                 125

Ala Arg Gly His Leu Leu Val Glu Ala Asp Asp Val Arg Ala Trp Ser
        130                 135                 140

Cys Pro Gln His Asn Ala Tyr Arg Leu Tyr His Cys Glu Ala Glu Gln
145                 150                 155                 160

Val Ala Val Cys Gln Tyr Cys Tyr Tyr Ser Gly Ala His Gln Gly
                165                 170                 175

His Ser Val Cys Asp Val Glu Ile Arg Arg Asn Glu Ile Arg Lys Met
            180                 185                 190

Leu Met Lys Gln Gln Asp Arg Leu Glu Arg Glu Gln Asp Ile Glu
                195                 200                 205

Asp Gln Leu Tyr Lys Leu Glu Ser Asp Lys Arg Leu Val Glu Glu Lys
        210                 215                 220

Val Asn Gln Leu Lys Glu Glu Val Arg Leu Gln Tyr Glu Lys Leu His
225                 230                 235                 240

Gln Leu Leu Asp Glu Asp Leu Arg Gln Thr Val Glu Val Leu Asp Lys
                245                 250                 255

Ala Gln Ala Lys Phe Cys Ser Glu Asn Ala Gln Ala Leu His Leu
                260                 265                 270

Gly Glu Arg Met Gln Glu Ala Lys Lys Leu Leu Gly Ser Leu Gln Leu
        275                 280                 285

Leu Phe Asp Lys Thr Glu Asp Val Ser Phe Met Lys Asn Thr Lys Ser
    290                 295                 300

Val Lys Ile Leu Met Asp Arg Thr Gln Thr Cys Thr Ser Ser Ser Leu
305                 310                 315                 320

Ser Pro Thr Lys Ile Gly His Leu Asn Ser Lys Leu Phe Leu Asn Glu
                325                 330                 335

Val Ala Lys Lys Glu Lys Gln Leu Arg Lys Met Leu Glu Gly Pro Phe
                340                 345                 350

Ser Thr Pro Val Pro Phe Leu Gln Ser Val Pro Leu Tyr Pro Cys Gly
                355                 360                 365

Val Ser Ser Ser Gly Ala Glu Lys Arg Lys His Ser Thr Ala Phe Pro
    370                 375                 380

Glu Ala Ser Phe Leu Glu Thr Ser Ser Gly Pro Val Gly Gly Gln Tyr
385                 390                 395                 400
```

-continued

```
Gly Ala Ala Gly Thr Ala Ser Gly Glu Gly Gln Ser Gly Gln Pro Leu
                405                 410                 415
Gly Pro Cys Ser Ser Thr Gln His Leu Val Ala Leu Pro Gly Gly Ala
            420                 425                 430
Gln Pro Val His Ser Ser Pro Val Phe Pro Pro Ser Gln Tyr Pro Asn
        435                 440                 445
Gly Ser Ala Ala Gln Gln Pro Met Leu Pro Gln Tyr Gly Gly Arg Lys
    450                 455                 460
Ile Leu Val Cys Ser Val Asp Asn Cys Tyr Cys Ser Val Ala Asn
465                 470                 475                 480
His Gly Gly His Gln Pro Tyr Pro Arg Ser Gly His Phe Pro Trp Thr
                485                 490                 495
Val Pro Ser Gln Glu Tyr Ser His Pro Leu Pro Thr Pro Ser Val
            500                 505                 510
Pro Gln Ser Leu Pro Ser Leu Ala Val Arg Asp Trp Leu Asp Ala Ser
        515                 520                 525
Gln Gln Pro Gly His Gln Asp Phe Tyr Arg Val Tyr Gly Gln Pro Ser
    530                 535                 540
Thr Lys His Tyr Val Thr Ser
545                 550

<210> SEQ ID NO 37
<211> LENGTH: 19
<212> TYPE: RNA
<213> ORGANISM: Homo Sapiens

<400> SEQUENCE: 37
gcaagauucu cgucuguuc                                                    19

<210> SEQ ID NO 38
<211> LENGTH: 19
<212> TYPE: RNA
<213> ORGANISM: Homo Sapiens

<400> SEQUENCE: 38
ggaaugaaau ccggaagau                                                    19

<210> SEQ ID NO 39
<211> LENGTH: 19
<212> TYPE: RNA
<213> ORGANISM: Homo Sapiens

<400> SEQUENCE: 39
ggacaacugu uacuguucu                                                    19

<210> SEQ ID NO 40
<211> LENGTH: 19
<212> TYPE: RNA
<213> ORGANISM: Homo Sapiens

<400> SEQUENCE: 40
gaacaccaag ucugugaaa                                                    19

<210> SEQ ID NO 41
<211> LENGTH: 710
<212> TYPE: PRT
<213> ORGANISM: Homo Sapiens

<400> SEQUENCE: 41
```

-continued

```
Met Glu Glu Met Glu Glu Leu Lys Cys Pro Val Cys Gly Ser Phe
1               5                   10                  15

Tyr Arg Glu Pro Ile Ile Leu Pro Cys Ser His Asn Leu Cys Gln Ala
            20                  25                  30

Cys Ala Arg Asn Ile Leu Val Gln Thr Pro Glu Ser Glu Ser Pro Gln
            35                  40                  45

Ser His Arg Ala Ala Gly Ser Gly Val Ser Asp Tyr Asp Tyr Leu Asp
        50                  55                  60

Leu Asp Lys Met Ser Leu Tyr Ser Glu Ala Asp Ser Gly Tyr Gly Ser
65                  70                  75                  80

Tyr Gly Gly Phe Ala Ser Ala Pro Thr Thr Pro Cys Gln Lys Ser Pro
                85                  90                  95

Asn Gly Val Arg Val Phe Pro Pro Ala Met Pro Pro Ala Thr His
            100                 105                 110

Leu Ser Pro Ala Leu Ala Pro Val Pro Arg Asn Ser Cys Ile Thr Cys
            115                 120                 125

Pro Gln Cys His Arg Ser Leu Ile Leu Asp Asp Arg Gly Leu Arg Gly
            130                 135                 140

Phe Pro Lys Asn Arg Val Leu Glu Gly Val Ile Asp Arg Tyr Gln Gln
145                 150                 155                 160

Ser Lys Ala Ala Ala Leu Lys Cys Gln Leu Cys Glu Lys Ala Pro Lys
                165                 170                 175

Glu Ala Thr Val Met Cys Glu Gln Cys Asp Val Phe Tyr Cys Asp Pro
            180                 185                 190

Cys Arg Leu Arg Cys His Pro Pro Arg Gly Pro Leu Ala Lys His Arg
            195                 200                 205

Leu Val Pro Pro Ala Gln Gly Arg Val Ser Arg Leu Ser Pro Arg
            210                 215                 220

Lys Val Ser Thr Cys Thr Asp His Glu Leu Glu Asn His Ser Met Tyr
225                 230                 235                 240

Cys Val Gln Cys Lys Met Pro Val Cys Tyr Gln Cys Leu Glu Glu Gly
                245                 250                 255

Lys His Ser Ser His Glu Val Lys Ala Leu Gly Ala Met Trp Lys Leu
            260                 265                 270

His Lys Ser Gln Leu Ser Gln Ala Leu Asn Gly Leu Ser Asp Arg Ala
            275                 280                 285

Lys Glu Ala Lys Glu Phe Leu Val Gln Leu Arg Asn Met Val Gln Gln
            290                 295                 300

Ile Gln Glu Asn Ser Val Glu Phe Glu Ala Cys Leu Val Ala Gln Cys
305                 310                 315                 320

Asp Ala Leu Ile Asp Ala Leu Asn Arg Arg Lys Ala Gln Leu Leu Ala
                325                 330                 335

Arg Val Asn Lys Glu His Glu His Lys Leu Lys Val Val Arg Asp Gln
            340                 345                 350

Ile Ser His Cys Thr Val Lys Leu Arg Gln Thr Thr Gly Leu Met Glu
            355                 360                 365

Tyr Cys Leu Glu Val Ile Lys Glu Asn Asp Pro Ser Gly Phe Leu Gln
            370                 375                 380

Ile Ser Asp Ala Leu Ile Arg Arg Val His Leu Thr Glu Asp Gln Trp
385                 390                 395                 400

Gly Lys Gly Thr Leu Thr Pro Arg Met Thr Thr Asp Phe Asp Leu Ser
                405                 410                 415

Leu Asp Asn Ser Pro Leu Leu Gln Ser Ile His Gln Leu Asp Phe Val
```

```
                420             425             430
    Gln Val Lys Ala Ser Ser Pro Val Pro Ala Thr Pro Ile Leu Gln Leu
            435                 440                 445

Glu Glu Cys Cys Thr His Asn Asn Ser Ala Thr Leu Ser Trp Lys Gln
    450                 455                 460

Pro Pro Leu Ser Thr Val Pro Ala Asp Gly Tyr Ile Leu Glu Leu Asp
    465                 470                 475                 480

Asp Gly Asn Gly Gly Gln Phe Arg Glu Val Tyr Val Gly Lys Glu Thr
                    485                 490                 495

Met Cys Thr Val Asp Gly Leu His Phe Asn Ser Thr Tyr Asn Ala Arg
                500                 505                 510

Val Lys Ala Phe Asn Lys Thr Gly Val Ser Pro Tyr Ser Lys Thr Leu
            515                 520                 525

Val Leu Gln Thr Ser Glu Val Ala Trp Phe Ala Phe Asp Pro Gly Ser
        530                 535                 540

Ala His Ser Asp Ile Ile Leu Ser Asn Asp Asn Leu Thr Val Thr Cys
    545                 550                 555                 560

Ser Ser Tyr Asp Asp Arg Val Val Leu Gly Lys Thr Gly Phe Ser Lys
                    565                 570                 575

Gly Ile His Tyr Trp Glu Leu Thr Val Asp Arg Tyr Asp Asn His Pro
                580                 585                 590

Asp Pro Ala Phe Gly Val Ala Arg Met Asp Val Met Lys Asp Val Met
                595                 600                 605

Leu Gly Lys Asp Asp Lys Ala Trp Ala Met Tyr Val Asp Asn Asn Arg
        610                 615                 620

Ser Trp Phe Met His Asn Asn Ser His Thr Asn Arg Thr Glu Gly Gly
    625                 630                 635                 640

Ile Thr Lys Gly Ala Thr Ile Gly Val Leu Leu Asp Leu Asn Arg Lys
                    645                 650                 655

Asn Leu Thr Phe Phe Ile Asn Asp Glu Gln Gln Gly Pro Ile Ala Phe
                660                 665                 670

Asp Asn Val Glu Gly Leu Phe Phe Pro Ala Val Ser Leu Asn Arg Asn
                675                 680                 685

Val Gln Val Thr Leu His Thr Gly Leu Pro Val Pro Asp Phe Tyr Ser
        690                 695                 700

Ser Arg Ala Ser Ile Ala
    705                 710

<210> SEQ ID NO 42
<211> LENGTH: 19
<212> TYPE: RNA
<213> ORGANISM: Homo Sapiens

<400> SEQUENCE: 42
ccacaggucu cauggagua                                                19

<210> SEQ ID NO 43
<211> LENGTH: 19
<212> TYPE: RNA
<213> ORGANISM: Homo Sapiens

<400> SEQUENCE: 43 gcuggaggu gauuaagga                                                 19

<210> SEQ ID NO 44
<211> LENGTH: 19
```

```
<212> TYPE: RNA
<213> ORGANISM: Homo Sapiens

<400> SEQUENCE: 44
caacggcguc cgcguguuu                                                        19

<210> SEQ ID NO 45
<211> LENGTH: 19
<212> TYPE: RNA
<213> ORGANISM: Homo Sapiens

<400> SEQUENCE: 45
aaacaggagu cagcccgua                                                        19

<210> SEQ ID NO 46
<211> LENGTH: 395
<212> TYPE: PRT
<213> ORGANISM: Homo Sapiens

<400> SEQUENCE: 46
```

| Met | Ala | Ser | Ala | Ala | Ser | Val | Thr | Ser | Leu | Ala | Asp | Glu | Val | Asn | Cys |
|---|---|---|---|---|---|---|---|---|---|---|---|---|---|---|---|
| 1 | | | | 5 | | | | | 10 | | | | | 15 | |

| Pro | Ile | Cys | Gln | Gly | Thr | Leu | Arg | Glu | Pro | Val | Thr | Ile | Asp | Cys | Gly |
|---|---|---|---|---|---|---|---|---|---|---|---|---|---|---|---|
| | | | 20 | | | | | 25 | | | | | 30 | | |

| His | Asn | Phe | Cys | Arg | Ala | Cys | Leu | Thr | Arg | Tyr | Cys | Glu | Ile | Pro | Gly |
|---|---|---|---|---|---|---|---|---|---|---|---|---|---|---|---|
| | | 35 | | | | | 40 | | | | | 45 | | | |

| Pro | Asp | Leu | Glu | Glu | Ser | Pro | Thr | Cys | Pro | Leu | Cys | Lys | Glu | Pro | Phe |
|---|---|---|---|---|---|---|---|---|---|---|---|---|---|---|---|
| | 50 | | | | | 55 | | | | | 60 | | | | |

| Arg | Pro | Gly | Ser | Phe | Arg | Pro | Asn | Trp | Gln | Leu | Ala | Asn | Val | Val | Glu |
|---|---|---|---|---|---|---|---|---|---|---|---|---|---|---|---|
| 65 | | | | | 70 | | | | | 75 | | | | | 80 |

| Asn | Ile | Glu | Arg | Leu | Gln | Leu | Val | Ser | Thr | Leu | Gly | Leu | Gly | Glu | Glu |
|---|---|---|---|---|---|---|---|---|---|---|---|---|---|---|---|
| | | | | 85 | | | | | 90 | | | | | 95 | |

| Asp | Val | Cys | Gln | Glu | His | Gly | Glu | Lys | Ile | Tyr | Phe | Phe | Cys | Glu | Asp |
|---|---|---|---|---|---|---|---|---|---|---|---|---|---|---|---|
| | | | 100 | | | | | 105 | | | | | 110 | | |

| Asp | Glu | Met | Gln | Leu | Cys | Val | Val | Cys | Arg | Glu | Ala | Gly | Glu | His | Ala |
|---|---|---|---|---|---|---|---|---|---|---|---|---|---|---|---|
| | | 115 | | | | | 120 | | | | | 125 | | | |

| Thr | His | Thr | Met | Arg | Phe | Leu | Glu | Asp | Ala | Ala | Ala | Pro | Tyr | Arg | Glu |
|---|---|---|---|---|---|---|---|---|---|---|---|---|---|---|---|
| | 130 | | | | | 135 | | | | | 140 | | | | |

| Gln | Ile | His | Lys | Cys | Leu | Lys | Cys | Leu | Arg | Lys | Glu | Arg | Glu | Ile | |
|---|---|---|---|---|---|---|---|---|---|---|---|---|---|---|---|
| 145 | | | | | 150 | | | | | 155 | | | | | 160 |

| Gln | Glu | Ile | Gln | Ser | Arg | Glu | Asn | Lys | Arg | Met | Gln | Val | Leu | Leu | Thr |
|---|---|---|---|---|---|---|---|---|---|---|---|---|---|---|---|
| | | | | 165 | | | | | 170 | | | | | 175 | |

| Gln | Val | Ser | Thr | Lys | Arg | Gln | Gln | Val | Ile | Ser | Glu | Phe | Ala | His | Leu |
|---|---|---|---|---|---|---|---|---|---|---|---|---|---|---|---|
| | | | 180 | | | | | 185 | | | | | 190 | | |

| Arg | Lys | Phe | Leu | Glu | Glu | Gln | Gln | Ser | Ile | Leu | Leu | Ala | Gln | Leu | Glu |
|---|---|---|---|---|---|---|---|---|---|---|---|---|---|---|---|
| | | 195 | | | | | 200 | | | | | 205 | | | |

| Ser | Gln | Asp | Gly | Asp | Ile | Leu | Arg | Gln | Arg | Asp | Glu | Phe | Asp | Leu | Leu |
|---|---|---|---|---|---|---|---|---|---|---|---|---|---|---|---|
| | 210 | | | | | 215 | | | | | 220 | | | | |

| Val | Ala | Gly | Glu | Ile | Cys | Arg | Phe | Ser | Ala | Leu | Ile | Glu | Glu | Leu | Glu |
|---|---|---|---|---|---|---|---|---|---|---|---|---|---|---|---|
| 225 | | | | | 230 | | | | | 235 | | | | | 240 |

| Glu | Lys | Asn | Glu | Arg | Pro | Ala | Arg | Glu | Leu | Leu | Thr | Asp | Ile | Arg | Ser |
|---|---|---|---|---|---|---|---|---|---|---|---|---|---|---|---|
| | | | | 245 | | | | | 250 | | | | | 255 | |

| Thr | Leu | Ile | Arg | Cys | Glu | Thr | Arg | Lys | Cys | Arg | Lys | Pro | Val | Ala | Val |
|---|---|---|---|---|---|---|---|---|---|---|---|---|---|---|---|
| | | | 260 | | | | | 265 | | | | | 270 | | |

| Ser | Pro | Glu | Leu | Gly | Gln | Arg | Ile | Arg | Asp | Phe | Pro | Gln | Gln | Ala | Leu |
|---|---|---|---|---|---|---|---|---|---|---|---|---|---|---|---|
| | | 275 | | | | | 280 | | | | | 285 | | | |

```
Pro Leu Gln Arg Glu Met Lys Met Phe Leu Glu Lys Leu Cys Phe Glu
    290                 295                 300
Leu Asp Tyr Glu Pro Ala His Ile Ser Leu Asp Pro Gln Thr Ser His
305                 310                 315                 320
Pro Lys Leu Leu Leu Ser Glu Asp His Gln Arg Ala Gln Phe Ser Tyr
                325                 330                 335
Lys Trp Gln Asn Ser Pro Asp Asn Pro Gln Arg Phe Asp Arg Ala Thr
            340                 345                 350
Cys Val Leu Ala His Thr Gly Ile Thr Gly Gly Arg His Thr Trp Val
        355                 360                 365
Trp Met Ala Arg Val Pro Gly Asp Ser Gly Cys Cys Gln Phe Cys Ser
    370                 375                 380
Pro Pro Ser Val Leu Gly Thr Glu Val Ala Ala
385                 390                 395

<210> SEQ ID NO 47
<211> LENGTH: 19
<212> TYPE: RNA
<213> ORGANISM: Homo Sapiens

<400> SEQUENCE: 47
gagaggagau ucaagaaau                                                       19

<210> SEQ ID NO 48
<211> LENGTH: 19
<212> TYPE: RNA
<213> ORGANISM: Homo Sapiens

<400> SEQUENCE: 48
cagaagcacu cuauaaga                                                        19

<210> SEQ ID NO 49
<211> LENGTH: 19
<212> TYPE: RNA
<213> ORGANISM: Homo Sapiens

<400> SEQUENCE: 49
gggaacaaau ccauaagug                                                       19

<210> SEQ ID NO 50
<211> LENGTH: 19
<212> TYPE: RNA
<213> ORGANISM: Homo Sapiens

<400> SEQUENCE: 50
gcuuugaguu ggacuauga                                                       19

<210> SEQ ID NO 51
<211> LENGTH: 468
<212> TYPE: PRT
<213> ORGANISM: Homo Sapiens

<400> SEQUENCE: 51

Met Ala Ala Pro Asp Leu Ser Thr Asn Leu Gln Glu Glu Ala Thr Cys
1               5                   10                  15
Ala Ile Cys Leu Asp Tyr Phe Thr Asp Pro Val Met Thr Asp Cys Gly
                20                  25                  30
His Asn Phe Cys Arg Glu Cys Ile Arg Arg Cys Trp Gly Gln Pro Glu
            35                  40                  45
Gly Pro Tyr Ala Cys Pro Glu Cys Arg Glu Leu Ser Pro Gln Arg Asn
```

```
            50                  55                  60
Leu Arg Pro Asn Arg Pro Leu Ala Lys Met Ala Glu Met Ala Arg Arg
 65                  70                  75                  80

Leu His Pro Pro Ser Pro Val Pro Gln Gly Val Cys Pro Ala His Arg
                 85                  90                  95

Glu Pro Leu Ala Ala Phe Cys Gly Asp Glu Leu Arg Leu Leu Cys Ala
                100                 105                 110

Ala Cys Glu Arg Ser Gly Glu His Trp Ala His Arg Val Arg Pro Leu
            115                 120                 125

Gln Asp Ala Ala Glu Asp Leu Lys Ala Lys Leu Glu Lys Ser Leu Glu
        130                 135                 140

His Leu Arg Lys Gln Met Gln Asp Ala Leu Leu Phe Gln Ala Gln Ala
145                 150                 155                 160

Asp Glu Thr Cys Val Leu Trp Gln Lys Met Val Glu Ser Gln Arg Gln
                165                 170                 175

Asn Val Leu Gly Glu Phe Glu Arg Leu Arg Arg Leu Leu Ala Glu Glu
            180                 185                 190

Glu Gln Gln Leu Leu Gln Arg Leu Glu Glu Glu Leu Glu Val Leu
        195                 200                 205

Pro Arg Leu Arg Glu Gly Ala Ala His Leu Gly Gln Gln Ser Ala His
210                 215                 220

Leu Ala Glu Leu Ile Ala Glu Leu Glu Gly Arg Cys Gln Leu Pro Ala
225                 230                 235                 240

Leu Gly Leu Leu Gln Asp Ile Lys Asp Ala Leu Arg Arg Val Gln Asp
                245                 250                 255

Val Lys Leu Gln Pro Pro Glu Val Val Pro Met Glu Leu Arg Thr Val
            260                 265                 270

Cys Arg Val Pro Gly Leu Val Glu Thr Leu Arg Arg Phe Arg Gly Asp
        275                 280                 285

Val Thr Leu Asp Pro Asp Thr Ala Asn Pro Glu Leu Ile Leu Ser Glu
    290                 295                 300

Asp Arg Arg Ser Val Gln Arg Gly Asp Leu Arg Gln Ala Leu Pro Asp
305                 310                 315                 320

Ser Pro Glu Arg Phe Asp Pro Gly Pro Cys Val Leu Gly Gln Glu Arg
                325                 330                 335

Phe Thr Ser Gly Arg His Tyr Trp Glu Val Glu Val Gly Asp Arg Thr
            340                 345                 350

Ser Trp Ala Leu Gly Val Cys Arg Glu Asn Val Asn Arg Lys Glu Lys
        355                 360                 365

Gly Glu Leu Ser Ala Gly Asn Gly Phe Trp Ile Leu Val Phe Leu Gly
    370                 375                 380

Ser Tyr Tyr Asn Ser Ser Glu Arg Ala Leu Ala Pro Leu Arg Asp Pro
385                 390                 395                 400

Pro Arg Arg Val Gly Ile Phe Leu Asp Tyr Glu Ala Gly His Leu Ser
                405                 410                 415

Phe Tyr Ser Ala Thr Asp Gly Ser Leu Leu Phe Ile Phe Pro Glu Ile
            420                 425                 430

Pro Phe Ser Gly Thr Leu Arg Pro Leu Phe Ser Pro Leu Ser Ser Ser
        435                 440                 445

Pro Thr Pro Met Thr Ile Cys Arg Pro Lys Gly Gly Ser Gly Asp Thr
    450                 455                 460

Leu Ala Pro Gln
465
```

```
<210> SEQ ID NO 52
<211> LENGTH: 19
<212> TYPE: RNA
<213> ORGANISM: Homo Sapiens

<400> SEQUENCE: 52
ggacaucucu cuuucuaca                                              19

<210> SEQ ID NO 53
<211> LENGTH: 19
<212> TYPE: RNA
<213> ORGANISM: Homo Sapiens

<400> SEQUENCE: 53
gggagaacgu gaacaggaa                                              19

<210> SEQ ID NO 54
<211> LENGTH: 19
<212> TYPE: RNA
<213> ORGANISM: Homo Sapiens

<400> SEQUENCE: 54
gagcugaucc ugucugaag                                              19

<210> SEQ ID NO 55
<211> LENGTH: 19
<212> TYPE: RNA
<213> ORGANISM: Homo Sapiens

<400> SEQUENCE: 55
ucacugcuau ucaucuuuc                                              19

<210> SEQ ID NO 56
<211> LENGTH: 407
<212> TYPE: PRT
<213> ORGANISM: Homo Sapiens

<400> SEQUENCE: 56

Met Glu Leu Leu Glu Glu Asp Leu Thr Cys Pro Ile Cys Cys Ser Leu
1               5                   10                  15

Phe Asp Asp Pro Arg Val Leu Pro Cys Ser His Asn Phe Cys Lys Lys
                20                  25                  30

Cys Leu Glu Gly Ile Leu Glu Gly Ser Val Arg Asn Ser Leu Trp Arg
            35                  40                  45

Pro Ala Pro Phe Lys Cys Pro Thr Cys Arg Lys Glu Thr Ser Ala Thr
        50                  55                  60

Gly Ile Asn Ser Leu Gln Val Asn Tyr Ser Leu Lys Gly Ile Val Glu
65                  70                  75                  80

Lys Tyr Asn Lys Ile Lys Ile Ser Pro Lys Met Pro Val Cys Lys Gly
                85                  90                  95

His Leu Gly Gln Pro Leu Asn Ile Phe Cys Leu Thr Asp Met Gln Leu
            100                 105                 110

Ile Cys Gly Ile Cys Ala Thr Arg Gly Glu His Thr Lys His Val Phe
        115                 120                 125

Cys Ser Ile Glu Asp Ala Tyr Ala Gln Glu Arg Asp Ala Phe Glu Ser
    130                 135                 140

Leu Phe Gln Ser Phe Glu Thr Trp Arg Arg Gly Asp Ala Leu Ser Arg
145                 150                 155                 160
```

```
Leu Asp Thr Leu Glu Thr Ser Lys Arg Lys Ser Leu Gln Leu Leu Thr
                165                 170                 175

Lys Asp Ser Asp Lys Val Lys Glu Phe Phe Glu Lys Leu Gln His Thr
            180                 185                 190

Leu Asp Gln Lys Lys Asn Glu Ile Leu Ser Asp Phe Glu Thr Met Lys
        195                 200                 205

Leu Ala Val Met Gln Ala Tyr Asp Pro Glu Ile Asn Lys Leu Asn Thr
    210                 215                 220

Ile Leu Gln Glu Gln Arg Met Ala Phe Asn Ile Ala Glu Ala Phe Lys
225                 230                 235                 240

Asp Val Ser Glu Pro Ile Val Phe Leu Gln Gln Met Gln Glu Phe Arg
                245                 250                 255

Glu Lys Ile Lys Val Ile Lys Glu Thr Pro Leu Pro Ser Asn Leu
            260                 265                 270

Pro Ala Ser Pro Leu Met Lys Asn Phe Asp Thr Ser Gln Trp Glu Asp
        275                 280                 285

Ile Lys Leu Val Asp Val Asp Lys Leu Ser Leu Pro Gln Asp Thr Gly
    290                 295                 300

Thr Phe Ile Ser Lys Ile Pro Trp Ser Phe Tyr Lys Leu Phe Leu Leu
305                 310                 315                 320

Ile Leu Leu Leu Gly Leu Val Ile Val Phe Gly Pro Thr Met Phe Leu
                325                 330                 335

Glu Trp Ser Leu Phe Asp Asp Leu Ala Thr Trp Lys Gly Cys Leu Ser
            340                 345                 350

Asn Phe Ser Ser Tyr Leu Thr Lys Thr Ala Asp Phe Ile Glu Gln Ser
        355                 360                 365

Val Phe Tyr Trp Glu Gln Val Thr Asp Gly Phe Phe Ile Phe Asn Glu
    370                 375                 380

Arg Phe Lys Asn Phe Thr Leu Val Val Leu Asn Asn Val Ala Glu Phe
385                 390                 395                 400

Val Cys Lys Tyr Lys Leu Leu
                405

<210> SEQ ID NO 57
<211> LENGTH: 19
<212> TYPE: RNA
<213> ORGANISM: Homo Sapiens

<400> SEQUENCE: 57
gaggaaaucc cuacaguua                                             19

<210> SEQ ID NO 58
<211> LENGTH: 19
<212> TYPE: RNA
<213> ORGANISM: Homo Sapiens

<400> SEQUENCE: 58
ugaacaaugu ggcagaauu                                             19

<210> SEQ ID NO 59
<211> LENGTH: 19
<212> TYPE: RNA
<213> ORGANISM: Homo Sapiens

<400> SEQUENCE: 59
gacacuggca cauucauua                                             19
```

-continued

```
<210> SEQ ID NO 60
<211> LENGTH: 19
<212> TYPE: RNA
<213> ORGANISM: Homo Sapiens

<400> SEQUENCE: 60
uaacauugcu gaggcuuuc                                                        19

<210> SEQ ID NO 61
<211> LENGTH: 442
<212> TYPE: PRT
<213> ORGANISM: Homo Sapiens

<400> SEQUENCE: 61
```

Met Ala Gly Ala Ala Thr Gly Ser Arg Thr Pro Gly Arg Ser Glu Leu
1               5                   10                  15

Val Glu Gly Cys Gly Trp Arg Cys Pro Glu His Gly Asp Arg Val Ala
            20                  25                  30

Glu Leu Phe Cys Arg Arg Cys Arg Arg Cys Val Cys Ala Leu Cys Pro
        35                  40                  45

Val Leu Gly Ala His Arg Gly His Pro Val Gly Leu Ala Leu Glu Ala
    50                  55                  60

Ala Val His Val Gln Lys Leu Ser Gln Glu Cys Leu Lys Gln Leu Ala
65                  70                  75                  80

Ile Lys Lys Gln Gln His Ile Asp Asn Ile Thr Gln Ile Glu Asp Ala
                85                  90                  95

Thr Glu Lys Leu Lys Ala Asn Ala Glu Ser Ser Lys Thr Trp Leu Lys
            100                 105                 110

Gly Lys Phe Thr Glu Leu Arg Leu Leu Leu Asp Glu Glu Glu Ala Leu
        115                 120                 125

Ala Lys Lys Phe Ile Asp Lys Asn Thr Gln Leu Thr Leu Gln Val Tyr
    130                 135                 140

Arg Glu Gln Ala Asp Ser Cys Arg Gln Leu Asp Ile Met Asn Asp
145                 150                 155                 160

Leu Ser Asn Arg Val Trp Ser Ile Ser Gln Glu Pro Asp Pro Val Gln
                165                 170                 175

Arg Leu Gln Ala Tyr Thr Ala Thr Glu Gln Glu Met Gln Gln Met
            180                 185                 190

Ser Leu Gly Glu Leu Cys His Pro Val Pro Leu Ser Phe Glu Pro Val
        195                 200                 205

Lys Ser Phe Phe Lys Gly Leu Val Glu Ala Val Glu Ser Thr Leu Gln
    210                 215                 220

Thr Pro Leu Asp Ile Arg Leu Lys Glu Ser Ile Asn Cys Gln Leu Ser
225                 230                 235                 240

Asp Pro Ser Ser Thr Lys Pro Gly Thr Leu Leu Lys Thr Ser Pro Ser
                245                 250                 255

Pro Glu Arg Ser Leu Leu Leu Lys Tyr Ala Arg Thr Pro Thr Leu Asp
            260                 265                 270

Pro Asp Thr Met His Ala Arg Leu Arg Leu Ser Ala Asp Arg Leu Thr
        275                 280                 285

Val Arg Cys Gly Leu Leu Gly Ser Leu Gly Pro Val Pro Val Leu Arg
    290                 295                 300

Phe Asp Ala Leu Trp Gln Val Leu Ala Arg Asp Cys Phe Ala Thr Gly
305                 310                 315                 320

Arg His Tyr Trp Glu Val Asp Val Gln Glu Ala Gly Ala Gly Trp Trp
                325                 330                 335

```
Val Gly Ala Ala Tyr Ala Ser Leu Arg Arg Gly Ala Ser Ala Ala
            340                 345                 350

Ala Arg Leu Gly Cys Asn Arg Gln Ser Trp Cys Leu Lys Arg Tyr Asp
        355                 360                 365

Leu Glu Tyr Trp Ala Phe His Asp Gly Gln Arg Ser Arg Leu Arg Pro
370                 375                 380

Arg Asp Asp Leu Asp Arg Leu Gly Val Phe Leu Asp Tyr Glu Ala Gly
385                 390                 395                 400

Val Leu Ala Phe Tyr Asp Val Thr Gly Gly Met Ser His Leu His Thr
            405                 410                 415

Phe Arg Ala Thr Phe Gln Glu Pro Leu Tyr Pro Ala Leu Arg Leu Trp
        420                 425                 430

Glu Gly Ala Ile Ser Ile Pro Arg Leu Pro
            435                 440

<210> SEQ ID NO 62
<211> LENGTH: 19
<212> TYPE: RNA
<213> ORGANISM: Homo Sapiens

<400> SEQUENCE: 62
caacauaacc cagauagaa                                                  19

<210> SEQ ID NO 63
<211> LENGTH: 19
<212> TYPE: RNA
<213> ORGANISM: Homo Sapiens

<400> SEQUENCE: 63
uccagaggcu ucaggcaua                                                  19

<210> SEQ ID NO 64
<211> LENGTH: 19
<212> TYPE: RNA
<213> ORGANISM: Homo Sapiens

<400> SEQUENCE: 64
gcuaaugcag agucaagua                                                  19

<210> SEQ ID NO 65
<211> LENGTH: 19
<212> TYPE: RNA
<213> ORGANISM: Homo Sapiens

<400> SEQUENCE: 65
cagauuacua cuugacgaa                                                  19

<210> SEQ ID NO 66
<211> LENGTH: 465
<212> TYPE: PRT
<213> ORGANISM: Homo Sapiens

<400> SEQUENCE: 66

Met Pro Ala Thr Pro Ser Leu Lys Val Val His Glu Leu Pro Ala Cys
1               5                   10                  15

Thr Leu Cys Ala Gly Pro Leu Glu Asp Ala Val Thr Ile Pro Cys Gly
            20                  25                  30

His Thr Phe Cys Arg Leu Cys Leu Pro Ala Leu Ser Gln Met Gly Ala
        35                  40                  45
```

-continued

```
Gln Ser Ser Gly Lys Ile Leu Leu Cys Pro Leu Cys Gln Glu Glu
    50              55              60
Gln Ala Glu Thr Pro Met Ala Pro Val Pro Leu Gly Pro Leu Gly Glu
65              70              75              80
Thr Tyr Cys Glu Glu His Gly Glu Lys Ile Tyr Phe Cys Glu Asn
                85              90              95
Asp Ala Glu Phe Leu Cys Val Phe Cys Arg Glu Gly Pro Thr His Gln
            100             105             110
Ala His Thr Val Gly Phe Leu Asp Glu Ala Ile Gln Pro Tyr Arg Asp
        115             120             125
Arg Leu Arg Ser Arg Leu Glu Ala Leu Ser Thr Glu Arg Asp Glu Ile
    130             135             140
Glu Asp Val Lys Cys Gln Glu Asp Gln Lys Leu Gln Val Leu Leu Thr
145             150             155             160
Gln Ile Glu Ser Lys Lys His Gln Val Glu Thr Ala Phe Glu Arg Leu
                165             170             175
Gln Gln Glu Leu Glu Gln Arg Cys Leu Leu Leu Ala Arg Leu Arg
            180             185             190
Glu Leu Glu Gln Gln Ile Trp Lys Glu Arg Asp Glu Tyr Ile Thr Lys
        195             200             205
Val Ser Glu Glu Val Thr Arg Leu Gly Ala Gln Val Lys Glu Leu Glu
    210             215             220
Glu Lys Cys Gln Gln Pro Ala Ser Glu Leu Leu Gln Asp Val Arg Val
225             230             235             240
Asn Gln Ser Arg Cys Glu Met Lys Thr Phe Val Ser Pro Glu Ala Ile
                245             250             255
Ser Pro Asp Leu Val Lys Lys Ile Arg Asp Phe His Arg Lys Ile Leu
            260             265             270
Thr Leu Pro Glu Met Met Arg Met Phe Ser Glu Asn Leu Ala His His
        275             280             285
Leu Glu Ile Asp Ser Gly Val Ile Thr Leu Asp Pro Gln Thr Ala Ser
    290             295             300
Arg Ser Leu Val Leu Ser Glu Asp Arg Lys Ser Val Arg Tyr Thr Arg
305             310             315             320
Gln Lys Lys Ser Leu Pro Asp Ser Pro Leu Arg Phe Asp Gly Leu Pro
                325             330             335
Ala Val Leu Gly Phe Pro Gly Phe Ser Ser Gly Arg His Arg Trp Gln
            340             345             350
Val Asp Leu Gln Leu Gly Asp Gly Gly Cys Thr Val Gly Val Ala
        355             360             365
Gly Glu Gly Val Arg Arg Lys Gly Glu Met Gly Leu Ser Ala Glu Asp
    370             375             380
Gly Val Trp Ala Val Ile Ile Ser His Gln Gln Cys Trp Ala Ser Thr
385             390             395             400
Ser Pro Gly Thr Asp Leu Pro Leu Ser Glu Ile Pro Arg Gly Val Arg
                405             410             415
Val Ala Leu Asp Tyr Glu Ala Gly Gln Val Thr Leu His Asn Ala Gln
            420             425             430
Thr Gln Glu Pro Ile Phe Thr Phe Thr Ala Ser Phe Ser Gly Lys Val
        435             440             445
Phe Pro Phe Phe Ala Val Trp Lys Lys Gly Ser Cys Leu Thr Leu Lys
450             455             460

Gly
```

```
<210> SEQ ID NO 67
<211> LENGTH: 19
<212> TYPE: RNA
<213> ORGANISM: Homo Sapiens

<400> SEQUENCE: 67
cagcagauuu ggaaggaga                                                      19

<210> SEQ ID NO 68
<211> LENGTH: 19
<212> TYPE: RNA
<213> ORGANISM: Homo Sapiens

<400> SEQUENCE: 68
cggagagaga ugagauuga                                                      19

<210> SEQ ID NO 69
<211> LENGTH: 19
<212> TYPE: RNA
<213> ORGANISM: Homo Sapiens

<400> SEQUENCE: 69
gggaugaaua uaucacaaa                                                      19

<210> SEQ ID NO 70
<211> LENGTH: 19
<212> TYPE: RNA
<213> ORGANISM: Homo Sapiens

<400> SEQUENCE: 70
ggugugagau gaagacuuu                                                      19

<210> SEQ ID NO 71
<211> LENGTH: 564
<212> TYPE: PRT
<213> ORGANISM: Homo Sapiens

<400> SEQUENCE: 71
```

| | | | | | | | | | | | | | | | |
|---|---|---|---|---|---|---|---|---|---|---|---|---|---|---|---|
| Met | Ala | Glu | Leu | Asp | Leu | Met | Ala | Pro | Gly | Pro | Leu | Pro | Arg | Ala | Thr |
| 1 | | | | 5 | | | | | 10 | | | | | 15 | |
| Ala | Gln | Pro | Pro | Ala | Pro | Leu | Ser | Pro | Asp | Ser | Gly | Ser | Pro | Ser | Pro |
| | | | 20 | | | | | 25 | | | | | 30 | | |
| Asp | Ser | Gly | Ser | Ala | Ser | Pro | Val | Glu | Glu | Asp | Val | Gly | Ser | Ser | |
| | | 35 | | | | | 40 | | | | | 45 | | | |
| Glu | Lys | Leu | Gly | Arg | Glu | Thr | Glu | Glu | Gln | Asp | Ser | Asp | Ser | Ala | Glu |
| | 50 | | | | | 55 | | | | | 60 | | | | |
| Gln | Gly | Asp | Pro | Ala | Gly | Gly | Lys | Glu | Val | Leu | Cys | Asp | Phe | Cys | |
| 65 | | | | | 70 | | | | | 75 | | | | | 80 |
| Leu | Asp | Asp | Thr | Arg | Arg | Val | Lys | Ala | Val | Lys | Ser | Cys | Leu | Thr | Cys |
| | | | | 85 | | | | | 90 | | | | | 95 | |
| Met | Val | Asn | Tyr | Cys | Glu | Glu | His | Leu | Gln | Pro | His | Gln | Val | Asn | Ile |
| | | | | 100 | | | | | 105 | | | | | 110 | |
| Lys | Leu | Gln | Ser | His | Leu | Leu | Thr | Glu | Pro | Val | Lys | Asp | His | Asn | Trp |
| | | | 115 | | | | | 120 | | | | | 125 | | |
| Arg | Tyr | Cys | Pro | Ala | His | His | Ser | Pro | Leu | Ser | Ala | Phe | Cys | Cys | Pro |
| | | 130 | | | | | 135 | | | | | 140 | | | |
| Asp | Gln | Gln | Cys | Ile | Cys | Gln | Asp | Cys | Cys | Gln | Glu | His | Ser | Gly | His |
| 145 | | | | | 150 | | | | | 155 | | | | | 160 |

```
Thr Ile Val Ser Leu Asp Ala Ala Arg Arg Asp Lys Glu Ala Glu Leu
                165                 170                 175

Gln Cys Thr Gln Leu Asp Leu Glu Arg Lys Leu Lys Leu Asn Glu Asn
            180                 185                 190

Ala Ile Ser Arg Leu Gln Ala Asn Gln Lys Ser Val Leu Val Ser Val
        195                 200                 205

Ser Glu Val Lys Ala Val Ala Glu Met Gln Phe Gly Glu Leu Leu Ala
    210                 215                 220

Ala Val Arg Lys Ala Gln Ala Asn Val Met Leu Phe Leu Glu Glu Lys
225                 230                 235                 240

Glu Gln Ala Ala Leu Ser Gln Ala Asn Gly Ile Lys Ala His Leu Glu
                245                 250                 255

Tyr Arg Ser Ala Glu Met Glu Lys Ser Lys Gln Glu Leu Glu Arg Met
            260                 265                 270

Ala Ala Ile Ser Asn Thr Val Gln Phe Leu Glu Glu Tyr Cys Lys Phe
        275                 280                 285

Lys Asn Thr Glu Asp Ile Thr Phe Pro Ser Val Tyr Val Gly Leu Lys
    290                 295                 300

Asp Lys Leu Ser Gly Ile Arg Lys Val Ile Thr Glu Ser Thr Val His
305                 310                 315                 320

Leu Ile Gln Leu Leu Glu Asn Tyr Lys Lys Leu Gln Glu Phe Ser
                325                 330                 335

Lys Glu Glu Glu Tyr Asp Ile Arg Thr Gln Val Ser Ala Val Val Gln
            340                 345                 350

Arg Lys Tyr Trp Thr Ser Lys Pro Glu Pro Ser Thr Arg Glu Gln Phe
        355                 360                 365

Leu Gln Tyr Ala Tyr Asp Ile Thr Phe Asp Pro Asp Thr Ala His Lys
    370                 375                 380

Tyr Leu Arg Leu Gln Glu Glu Asn Arg Lys Val Thr Asn Thr Thr Pro
385                 390                 395                 400

Trp Glu His Pro Tyr Pro Asp Leu Pro Ser Arg Phe Leu His Trp Arg
                405                 410                 415

Gln Val Leu Ser Gln Gln Ser Leu Tyr Leu His Arg Tyr Tyr Phe Glu
            420                 425                 430

Val Glu Ile Phe Gly Ala Gly Thr Tyr Val Gly Leu Thr Cys Lys Gly
        435                 440                 445

Ile Asp Arg Lys Gly Glu Glu Arg Asn Ser Cys Ile Ser Gly Asn Asn
    450                 455                 460

Phe Ser Trp Ser Leu Gln Trp Asn Gly Lys Glu Phe Thr Ala Trp Tyr
465                 470                 475                 480

Ser Asp Met Glu Thr Pro Leu Lys Ala Gly Pro Phe Arg Arg Leu Gly
                485                 490                 495

Val Tyr Ile Asp Phe Pro Gly Gly Ile Leu Ser Phe Tyr Gly Val Glu
            500                 505                 510

Tyr Asp Thr Met Thr Leu Val His Lys Phe Ala Cys Lys Phe Ser Glu
        515                 520                 525

Pro Val Tyr Ala Ala Phe Trp Leu Ser Lys Lys Glu Asn Ala Ile Arg
    530                 535                 540

Ile Val Asp Leu Gly Glu Glu Pro Glu Lys Pro Ala Pro Ser Leu Val
545                 550                 555                 560

Gly Thr Ala Pro
```

```
<210> SEQ ID NO 72
<211> LENGTH: 19
<212> TYPE: RNA
<213> ORGANISM: Homo Sapiens

<400> SEQUENCE: 72
gaccacaacu ggcgauacu                                                      19

<210> SEQ ID NO 73
<211> LENGTH: 19
<212> TYPE: RNA
<213> ORGANISM: Homo Sapiens

<400> SEQUENCE: 73
gcagugaagu ccugucuaa                                                      19

<210> SEQ ID NO 74
<211> LENGTH: 19
<212> TYPE: RNA
<213> ORGANISM: Homo Sapiens

<400> SEQUENCE: 74
ggaacaggac agcgacucu                                                      19

<210> SEQ ID NO 75
<211> LENGTH: 19
<212> TYPE: RNA
<213> ORGANISM: Homo Sapiens

<400> SEQUENCE: 75
ccgcaucagg ugaacauca                                                      19

<210> SEQ ID NO 76
<211> LENGTH: 348
<212> TYPE: PRT
<213> ORGANISM: Homo Sapiens

<400> SEQUENCE: 76
```

Met Gln Phe Gly Glu Leu Leu Ala Ala Val Arg Lys Ala Gln Ala Asn
1               5                   10                  15

Val Met Leu Phe Leu Glu Glu Lys Glu Gln Ala Ala Leu Ser Gln Ala
            20                  25                  30

Asn Gly Ile Lys Ala His Leu Glu Tyr Arg Ser Ala Glu Met Glu Lys
        35                  40                  45

Ser Lys Gln Glu Leu Glu Thr Met Ala Ala Ile Ser Asn Thr Val Gln
    50                  55                  60

Phe Leu Glu Glu Tyr Cys Lys Phe Lys Asn Thr Glu Asp Ile Thr Phe
65                  70                  75                  80

Pro Ser Val Tyr Ile Gly Leu Lys Asp Lys Leu Ser Gly Ile Arg Lys
                85                  90                  95

Val Ile Thr Glu Ser Thr Val His Leu Ile Gln Leu Leu Glu Asn Tyr
            100                 105                 110

Lys Lys Lys Leu Gln Glu Phe Ser Lys Glu Glu Tyr Asp Ile Arg
        115                 120                 125

Thr Gln Val Ser Ala Ile Val Gln Arg Lys Tyr Trp Thr Ser Lys Pro
    130                 135                 140

Glu Pro Ser Thr Arg Glu Gln Phe Leu Gln Tyr Val His Asp Ile Thr
145                 150                 155                 160

Phe Asp Pro Asp Thr Ala His Lys Tyr Leu Arg Leu Gln Glu Glu Asn
                165                 170                 175

-continued

```
Arg Lys Val Thr Asn Thr Thr Pro Trp Glu His Pro Tyr Pro Asp Leu
            180                 185                 190

Pro Ser Arg Phe Leu His Trp Arg Gln Val Leu Ser Gln Gln Ser Leu
        195                 200                 205

Tyr Leu His Arg Tyr Tyr Phe Glu Val Glu Ile Phe Gly Ala Gly Thr
    210                 215                 220

Tyr Val Gly Leu Thr Cys Lys Gly Ile Asp Gln Lys Gly Glu Arg
225                 230                 235                 240

Ser Ser Cys Ile Ser Gly Asn Asn Phe Ser Trp Ser Leu Gln Trp Asn
                245                 250                 255

Gly Lys Glu Phe Thr Ala Trp Tyr Ser Asp Met Glu Thr Pro Leu Lys
            260                 265                 270

Ala Gly Pro Phe Trp Arg Leu Gly Val Tyr Ile Asp Phe Pro Gly Gly
        275                 280                 285

Ile Leu Ser Phe Tyr Gly Val Glu Tyr Asp Ser Met Thr Leu Val His
    290                 295                 300

Lys Phe Ala Cys Lys Phe Ser Glu Pro Val Tyr Ala Ala Phe Trp Leu
305                 310                 315                 320

Ser Lys Lys Glu Asn Ala Ile Arg Ile Val Asp Leu Gly Glu Glu Pro
                325                 330                 335

Glu Lys Pro Ala Pro Ser Leu Val Gly Thr Ala Pro
            340                 345
```

<210> SEQ ID NO 77
<211> LENGTH: 19
<212> TYPE: RNA
<213> ORGANISM: Homo Sapiens

<400> SEQUENCE: 77
gaggaguacu gcaaguuua                                               19

<210> SEQ ID NO 78
<211> LENGTH: 19
<212> TYPE: RNA
<213> ORGANISM: Homo Sapiens

<400> SEQUENCE: 78
gcaaaggcau cgaccagaa                                               19

<210> SEQ ID NO 79
<211> LENGTH: 19
<212> TYPE: RNA
<213> ORGANISM: Homo Sapiens

<400> SEQUENCE: 79
gcaaaguuau cacggaauc                                               19

<210> SEQ ID NO 80
<211> LENGTH: 19
<212> TYPE: RNA
<213> ORGANISM: Homo Sapiens

<400> SEQUENCE: 80
aggauaaacu cucgggcau                                               19

<210> SEQ ID NO 81
<211> LENGTH: 477
<212> TYPE: PRT
<213> ORGANISM: Homo Sapiens

<400> SEQUENCE: 81

| | | | | | | | | | | | | | | |
|---|---|---|---|---|---|---|---|---|---|---|---|---|---|---|
| Met | Glu | Ala | Val | Glu | Leu | Ala | Arg | Lys | Leu | Gln | Glu | Glu | Ala | Thr | Cys |
| 1 | | | | 5 | | | | | 10 | | | | | 15 | |
| Ser | Ile | Cys | Leu | Asp | Tyr | Phe | Thr | Asp | Pro | Val | Met | Thr | Thr | Cys | Gly |
| | | | 20 | | | | | 25 | | | | | 30 | | |
| His | Asn | Phe | Cys | Arg | Ala | Cys | Ile | Gln | Leu | Ser | Trp | Glu | Lys | Ala | Arg |
| | | 35 | | | | | 40 | | | | | 45 | | | |
| Gly | Lys | Lys | Gly | Arg | Arg | Lys | Arg | Gly | Ser | Phe | Pro | Cys | Pro | Glu |
| | 50 | | | | | 55 | | | | | 60 | | | | |
| Cys | Arg | Glu | Met | Ser | Pro | Gln | Arg | Asn | Leu | Leu | Pro | Asn | Arg | Leu | Leu |
| 65 | | | | | 70 | | | | | 75 | | | | | 80 |
| Thr | Lys | Val | Ala | Glu | Met | Ala | Gln | Gln | His | Pro | Gly | Leu | Gln | Lys | Gln |
| | | | | 85 | | | | | 90 | | | | | 95 | |
| Asp | Leu | Cys | Gln | Glu | His | His | Glu | Pro | Leu | Lys | Leu | Phe | Cys | Gln | Lys |
| | | | 100 | | | | | 105 | | | | | 110 | | |
| Asp | Gln | Ser | Pro | Ile | Cys | Val | Val | Cys | Arg | Glu | Ser | Arg | Glu | His | Arg |
| | | | 115 | | | | | 120 | | | | | 125 | | |
| Leu | His | Arg | Val | Leu | Pro | Ala | Glu | Glu | Ala | Val | Gln | Gly | Tyr | Lys | Leu |
| | 130 | | | | | 135 | | | | | 140 | | | | |
| Lys | Leu | Glu | Glu | Asp | Met | Glu | Tyr | Leu | Arg | Glu | Gln | Ile | Thr | Arg | Thr |
| 145 | | | | | 150 | | | | | 155 | | | | | 160 |
| Gly | Asn | Leu | Gln | Ala | Arg | Glu | Glu | Gln | Ser | Leu | Ala | Glu | Trp | Gln | Gly |
| | | | | 165 | | | | | 170 | | | | | 175 | |
| Lys | Val | Lys | Glu | Arg | Arg | Glu | Arg | Ile | Val | Leu | Glu | Phe | Glu | Lys | Met |
| | | | 180 | | | | | 185 | | | | | 190 | | |
| Asn | Leu | Tyr | Leu | Val | Glu | Glu | Gln | Arg | Leu | Leu | Gln | Ala | Leu | Glu |
| | | 195 | | | | | 200 | | | | | 205 | | | |
| Thr | Glu | Glu | Glu | Glu | Thr | Ala | Ser | Arg | Leu | Arg | Glu | Ser | Val | Ala | Cys |
| | 210 | | | | | 215 | | | | | 220 | | | | |
| Leu | Asp | Arg | Gln | Gly | His | Ser | Leu | Glu | Leu | Leu | Leu | Gln | Leu | Glu |
| 225 | | | | | 230 | | | | | 235 | | | | | 240 |
| Glu | Arg | Ser | Thr | Gln | Gly | Pro | Leu | Gln | Met | Leu | Gln | Asp | Met | Lys | Glu |
| | | | | 245 | | | | | 250 | | | | | 255 | |
| Pro | Leu | Ser | Arg | Lys | Asn | Asn | Val | Ser | Val | Gln | Cys | Pro | Glu | Val | Ala |
| | | | 260 | | | | | 265 | | | | | 270 | | |
| Pro | Pro | Thr | Arg | Pro | Arg | Thr | Val | Cys | Arg | Val | Pro | Gly | Gln | Ile | Glu |
| | | 275 | | | | | 280 | | | | | 285 | | | |
| Val | Leu | Arg | Gly | Phe | Leu | Glu | Asp | Val | Val | Pro | Asp | Ala | Thr | Ser | Ala |
| | 290 | | | | | 295 | | | | | 300 | | | | |
| Tyr | Pro | Tyr | Leu | Leu | Leu | Tyr | Glu | Ser | Arg | Gln | Arg | Arg | Tyr | Leu | Gly |
| 305 | | | | | 310 | | | | | 315 | | | | | 320 |
| Ser | Ser | Pro | Glu | Gly | Ser | Gly | Phe | Cys | Ser | Lys | Asp | Arg | Phe | Val | Ala |
| | | | | 325 | | | | | 330 | | | | | 335 | |
| Tyr | Pro | Cys | Ala | Val | Gly | Gln | Thr | Ala | Phe | Ser | Ser | Gly | Arg | His | Tyr |
| | | | 340 | | | | | 345 | | | | | 350 | | |
| Trp | Glu | Val | Gly | Met | Asn | Ile | Thr | Gly | Asp | Ala | Leu | Trp | Ala | Leu | Gly |
| | | 355 | | | | | 360 | | | | | 365 | | | |
| Val | Cys | Arg | Asp | Asn | Val | Ser | Arg | Lys | Asp | Arg | Val | Pro | Lys | Cys | Pro |
| | 370 | | | | | 375 | | | | | 380 | | | | |
| Glu | Asn | Gly | Phe | Trp | Val | Val | Gln | Leu | Ser | Lys | Gly | Thr | Lys | Tyr | Leu |
| 385 | | | | | 390 | | | | | 395 | | | | | 400 |
| Ser | Thr | Phe | Ser | Ala | Leu | Thr | Pro | Val | Met | Leu | Met | Glu | Pro | Pro | Ser |

```
                    405                 410                 415
His Met Gly Ile Phe Leu Asp Phe Glu Ala Gly Glu Val Ser Phe Tyr
            420                 425                 430

Ser Val Ser Asp Gly Ser His Leu His Thr Tyr Ser Gln Ala Thr Phe
        435                 440                 445

Pro Gly Pro Leu Gln Pro Phe Phe Cys Leu Gly Ala Pro Lys Ser Gly
    450                 455                 460

Gln Met Val Ile Ser Thr Val Thr Met Trp Val Lys Gly
465                 470                 475
```

<210> SEQ ID NO 82
<211> LENGTH: 19
<212> TYPE: RNA
<213> ORGANISM: Homo Sapiens

<400> SEQUENCE: 82
gcuaagaggc uuucuagag                                               19

<210> SEQ ID NO 83
<211> LENGTH: 19
<212> TYPE: RNA
<213> ORGANISM: Homo Sapiens

<400> SEQUENCE: 83
ggaagaacaa cgugagugu                                               19

<210> SEQ ID NO 84
<211> LENGTH: 19
<212> TYPE: RNA
<213> ORGANISM: Homo Sapiens

<400> SEQUENCE: 84
ggucccaccu gcacaccua                                               19

<210> SEQ ID NO 85
<211> LENGTH: 19
<212> TYPE: RNA
<213> ORGANISM: Homo Sapiens

<400> SEQUENCE: 85
gagcggagag aacgcauug                                               19

<210> SEQ ID NO 86
<211> LENGTH: 667
<212> TYPE: PRT
<213> ORGANISM: Homo Sapiens

<400> SEQUENCE: 86

```
Met Glu Thr Leu Glu Ser Glu Leu Thr Cys Pro Ile Cys Leu Glu Leu
1               5                   10                  15

Phe Glu Asp Pro Leu Leu Leu Pro Cys Ala His Ser Leu Cys Phe Asn
            20                  25                  30

Cys Ala His Arg Ile Leu Val Ser His Cys Ala Thr Asn Glu Ser Val
        35                  40                  45

Glu Ser Ile Thr Ala Phe Gln Cys Pro Thr Cys Arg His Val Ile Thr
    50                  55                  60

Leu Ser Gln Arg Gly Leu Asp Gly Leu Lys Arg Asn Val Thr Leu Gln
65                  70                  75                  80

Asn Ile Ile Asp Arg Phe Gln Lys Ala Ser Val Ser Gly Pro Asn Ser
                85                  90                  95
```

```
Pro Ser Glu Thr Arg Arg Glu Arg Ala Phe Asp Ala Asn Thr Met Thr
            100                 105                 110
Ser Ala Glu Lys Val Leu Cys Gln Phe Cys Asp Gln Asp Pro Ala Gln
            115                 120                 125
Asp Ala Val Lys Thr Cys Val Thr Cys Glu Val Ser Tyr Cys Asp Glu
            130                 135                 140
Cys Leu Lys Ala Thr His Pro Asn Lys Pro Phe Thr Gly His Arg
145                 150                 155                 160
Leu Ile Glu Pro Ile Pro Asp Ser His Ile Arg Gly Leu Met Cys Leu
                    165                 170                 175
Glu His Glu Asp Glu Lys Val Asn Met Tyr Cys Val Thr Asp Asp Gln
                    180                 185                 190
Leu Ile Cys Ala Leu Cys Lys Leu Val Gly Arg His Arg Asp His Gln
                    195                 200                 205
Val Ala Ala Leu Ser Glu Arg Tyr Asp Lys Leu Lys Gln Asn Leu Glu
            210                 215                 220
Ser Asn Leu Thr Asn Leu Ile Lys Arg Asn Thr Glu Leu Glu Thr Leu
225                 230                 235                 240
Leu Ala Lys Leu Ile Gln Thr Cys Gln His Val Glu Val Asn Ala Ser
                    245                 250                 255
Arg Gln Glu Ala Lys Leu Thr Glu Glu Cys Asp Leu Leu Ile Glu Ile
            260                 265                 270
Ile Gln Gln Arg Arg Gln Ile Ile Gly Thr Lys Ile Lys Glu Gly Lys
            275                 280                 285
Val Met Arg Leu Arg Lys Leu Ala Gln Gln Ile Ala Asn Cys Lys Gln
            290                 295                 300
Cys Ile Glu Arg Ser Ala Ser Leu Ile Ser Gln Ala Glu His Ser Leu
305                 310                 315                 320
Lys Glu Asn Asp His Ala Arg Phe Leu Gln Thr Ala Lys Asn Ile Thr
                    325                 330                 335
Glu Arg Val Ser Met Ala Thr Ala Ser Ser Gln Val Leu Ile Pro Glu
                    340                 345                 350
Ile Asn Leu Asn Asp Thr Phe Asp Thr Phe Ala Leu Asp Phe Ser Arg
                    355                 360                 365
Glu Lys Lys Leu Leu Glu Cys Leu Asp Tyr Leu Thr Ala Pro Asn Pro
            370                 375                 380
Pro Thr Ile Arg Glu Glu Leu Cys Thr Ala Ser Tyr Asp Thr Ile Thr
385                 390                 395                 400
Val His Trp Thr Ser Asp Asp Glu Phe Ser Val Val Ser Tyr Glu Leu
                    405                 410                 415
Gln Tyr Thr Ile Phe Thr Gly Gln Ala Asn Val Val Ser Leu Cys Asn
                    420                 425                 430
Ser Ala Asp Ser Trp Met Ile Val Pro Asn Ile Lys Gln Asn His Tyr
            435                 440                 445
Thr Val His Gly Leu Gln Ser Gly Thr Lys Tyr Ile Phe Met Val Lys
            450                 455                 460
Ala Ile Asn Gln Ala Gly Ser Arg Ser Ser Glu Pro Gly Lys Leu Lys
465                 470                 475                 480
Thr Asn Ser Gln Pro Phe Lys Leu Asp Pro Lys Ser Ala His Arg Lys
                    485                 490                 495
Leu Lys Val Ser His Asp Asn Leu Thr Val Glu Arg Asp Glu Ser Ser
                    500                 505                 510
```

-continued

```
Ser Lys Lys Ser His Thr Pro Glu Arg Phe Thr Ser Gln Gly Ser Tyr
            515                 520                 525

Gly Val Ala Gly Asn Val Phe Ile Asp Ser Gly Arg His Tyr Trp Glu
        530                 535                 540

Val Val Ile Ser Gly Ser Thr Trp Tyr Ala Ile Gly Leu Ala Tyr Lys
545                 550                 555                 560

Ser Ala Pro Lys His Glu Trp Ile Gly Lys Asn Ser Ala Ser Trp Ala
                565                 570                 575

Leu Cys Arg Cys Asn Asn Asn Trp Val Val Arg His Asn Ser Lys Glu
            580                 585                 590

Ile Pro Ile Glu Pro Ala Pro His Leu Arg Arg Val Gly Ile Leu Leu
        595                 600                 605

Asp Tyr Asp Asn Gly Ser Ile Ala Phe Tyr Asp Ala Leu Asn Ser Ile
610                 615                 620

His Leu Tyr Thr Phe Asp Val Ala Phe Ala Gln Pro Val Cys Pro Thr
625                 630                 635                 640

Phe Thr Val Trp Asn Lys Cys Leu Thr Ile Ile Thr Gly Leu Pro Ile
                645                 650                 655

Pro Asp His Leu Asp Cys Thr Glu Gln Leu Pro
                660                 665

<210> SEQ ID NO 87
<211> LENGTH: 19
<212> TYPE: RNA
<213> ORGANISM: Homo Sapiens

<400> SEQUENCE: 87
cagcaaagac gacagauua                                                        19

<210> SEQ ID NO 88
<211> LENGTH: 19
<212> TYPE: RNA
<213> ORGANISM: Homo Sapiens

<400> SEQUENCE: 88
gcugauagcu ggaugauag                                                        19

<210> SEQ ID NO 89
<211> LENGTH: 19
<212> TYPE: RNA
<213> ORGANISM: Homo Sapiens

<400> SEQUENCE: 89
gaacaagugu cugacgauu                                                        19

<210> SEQ ID NO 90
<211> LENGTH: 19
<212> TYPE: RNA
<213> ORGANISM: Homo Sapiens

<400> SEQUENCE: 90
agaagaaacu gcuagaaug                                                        19

<210> SEQ ID NO 91
<211> LENGTH: 435
<212> TYPE: PRT
<213> ORGANISM: Homo Sapiens

<400> SEQUENCE: 91

Met Glu Pro Ala Pro Ala Arg Ser Pro Arg Pro Gln Gln Asp Pro Ala
```

-continued

```
1               5                   10                  15
Arg Pro Gln Glu Pro Thr Met Pro Pro Glu Thr Pro Ser Glu Gly
                20                  25                  30
Arg Gln Pro Ser Pro Ser Pro Ser Pro Thr Glu Arg Ala Pro Ala Ser
                35                  40                  45
Glu Glu Glu Phe Gln Phe Leu Arg Cys Gln Gln Cys Gln Ala Glu Ala
 50                  55                  60
Lys Cys Pro Lys Leu Leu Pro Cys Leu His Thr Leu Cys Ser Gly Cys
 65                  70                  75                  80
Leu Glu Ala Ser Gly Met Gln Cys Pro Ile Cys Gln Ala Pro Trp Pro
                85                  90                  95
Leu Gly Ala Asp Thr Pro Ala Leu Asp Asn Val Phe Phe Glu Ser Leu
                100                 105                 110
Gln Arg Arg Leu Ser Val Tyr Arg Gln Ile Val Asp Ala Gln Ala Val
                115                 120                 125
Cys Thr Arg Cys Lys Glu Ser Ala Asp Phe Trp Cys Phe Glu Cys Glu
                130                 135                 140
Gln Leu Leu Cys Ala Lys Cys Phe Glu Ala His Gln Trp Phe Leu Lys
145                 150                 155                 160
His Glu Ala Arg Pro Leu Ala Glu Leu Arg Asn Gln Ser Val Arg Glu
                165                 170                 175
Phe Leu Asp Gly Thr Arg Lys Thr Asn Asn Ile Phe Cys Ser Asn Pro
                180                 185                 190
Asn His Arg Thr Pro Thr Leu Thr Ser Ile Tyr Cys Arg Gly Cys Ser
                195                 200                 205
Lys Pro Leu Cys Cys Ser Cys Ala Leu Leu Asp Ser Ser His Ser Glu
                210                 215                 220
Leu Lys Cys Asp Ile Ser Ala Glu Ile Gln Arg Gln Glu Glu Leu
225                 230                 235                 240
Asp Ala Met Thr Gln Ala Leu Gln Glu Gln Asp Ser Ala Phe Gly Ala
                245                 250                 255
Val His Ala Gln Met His Ala Ala Val Gly Gln Leu Gly Arg Ala Arg
                260                 265                 270
Ala Glu Thr Glu Glu Leu Ile Arg Glu Arg Val Arg Gln Val Val Ala
                275                 280                 285
His Val Arg Ala Gln Glu Arg Glu Leu Leu Glu Ala Val Asp Ala Arg
                290                 295                 300
Tyr Gln Arg Asp Tyr Glu Glu Met Ala Ser Arg Leu Gly Arg Leu Asp
305                 310                 315                 320
Ala Val Leu Gln Arg Ile Arg Thr Gly Ser Ala Leu Val Gln Arg Met
                325                 330                 335
Lys Cys Tyr Ala Ser Asp Gln Glu Val Leu Asp Met His Gly Phe Leu
                340                 345                 350
Arg Gln Ala Leu Cys Arg Leu Arg Gln Glu Pro Gln Ser Leu Gln
                355                 360                 365
Ala Ala Val Arg Thr Asp Gly Phe Asp Glu Phe Lys Val Arg Leu Gln
                370                 375                 380
Asp Leu Ser Ser Cys Ile Thr Gln Gly Lys Asp Ala Ala Val Ser Lys
385                 390                 395                 400
Lys Ala Ser Pro Glu Ala Ala Ser Thr Pro Arg Asp Pro Ile Asp Val
                405                 410                 415
Asp Leu Leu Pro Pro Ala His Ala Leu Thr Gly Pro Ala Gln Ser
                420                 425                 430
```

Ser Thr His
        435

<210> SEQ ID NO 92
<211> LENGTH: 19
<212> TYPE: RNA
<213> ORGANISM: Homo Sapiens

<400> SEQUENCE: 92
ggggaaagau gcagcugua                                                   19

<210> SEQ ID NO 93
<211> LENGTH: 19
<212> TYPE: RNA
<213> ORGANISM: Homo Sapiens

<400> SEQUENCE: 93
gcaaagaguc ggccgacuu                                                   19

<210> SEQ ID NO 94
<211> LENGTH: 19
<212> TYPE: RNA
<213> ORGANISM: Homo Sapiens

<400> SEQUENCE: 94
gcgcuggugc agaggauga                                                   19

<210> SEQ ID NO 95
<211> LENGTH: 19
<212> TYPE: RNA
<213> ORGANISM: Homo Sapiens

<400> SEQUENCE: 95
ccgauggcuu cgacgaguu                                                   19

<210> SEQ ID NO 96
<211> LENGTH: 781
<212> TYPE: PRT
<213> ORGANISM: Homo Sapiens

<400> SEQUENCE: 96

Met Ala Lys Thr Pro Ser Asp His Leu Leu Ser Thr Leu Glu Glu Leu
1               5                   10                  15

Val Pro Tyr Asp Phe Glu Lys Phe Lys Phe Lys Leu Gln Asn Thr Ser
                20                  25                  30

Val Gln Lys Glu His Ser Arg Ile Pro Arg Ser Gln Ile Gln Arg Ala
            35                  40                  45

Arg Pro Val Lys Met Ala Thr Leu Leu Val Thr Tyr Tyr Gly Glu Glu
        50                  55                  60

Tyr Ala Val Gln Leu Thr Leu Gln Val Leu Arg Ala Ile Asn Gln Arg
65                  70                  75                  80

Leu Leu Ala Glu Glu Leu His Arg Ala Ala Ile Gln Glu Tyr Ser Thr
                85                  90                  95

Gln Glu Asn Gly Thr Asp Asp Ser Ala Ala Ser Ser Ser Leu Gly Glu
            100                 105                 110

Asn Lys Pro Arg Ser Leu Lys Thr Pro Asp His Pro Glu Gly Asn Glu
        115                 120                 125

Gly Asn Gly Pro Arg Pro Tyr Gly Gly Gly Ala Ala Ser Leu Arg Cys
    130                 135                 140

```
Ser Gln Pro Glu Ala Gly Arg Gly Leu Ser Arg Lys Pro Leu Ser Lys
145                 150                 155                 160

Arg Arg Glu Lys Ala Ser Glu Gly Leu Asp Ala Gln Gly Lys Pro Arg
                165                 170                 175

Thr Arg Ser Pro Ala Leu Pro Gly Gly Arg Ser Pro Gly Pro Cys Arg
            180                 185                 190

Ala Leu Glu Gly Gly Gln Ala Glu Val Arg Leu Arg Arg Asn Ala Ser
        195                 200                 205

Ser Ala Gly Arg Leu Gln Gly Leu Ala Gly Gly Ala Pro Gly Gln Lys
    210                 215                 220

Glu Cys Arg Pro Phe Glu Val Tyr Leu Pro Ser Gly Lys Met Arg Pro
225                 230                 235                 240

Arg Ser Leu Glu Val Thr Ile Ser Thr Gly Glu Lys Ala Pro Ala Asn
                245                 250                 255

Pro Glu Ile Leu Leu Thr Leu Glu Glu Lys Thr Ala Ala Asn Leu Asp
            260                 265                 270

Ser Ala Thr Glu Pro Arg Ala Arg Pro Thr Pro Asp Gly Gly Ala Ser
        275                 280                 285

Ala Asp Leu Lys Glu Gly Pro Gly Asn Pro Glu His Ser Val Thr Gly
290                 295                 300

Arg Pro Pro Asp Thr Ala Ala Ser Pro Arg Cys His Ala Gln Glu Gly
305                 310                 315                 320

Asp Pro Val Asp Gly Thr Cys Val Arg Asp Ser Cys Ser Phe Pro Glu
                325                 330                 335

Ala Val Ser Gly His Pro Gln Ala Ser Gly Ser Arg Ser Pro Gly Cys
            340                 345                 350

Pro Arg Cys Gln Asp Ser His Glu Arg Lys Ser Pro Gly Ser Leu Ser
        355                 360                 365

Pro Gln Pro Leu Pro Gln Cys Lys Arg His Leu Lys Gln Val Gln Leu
    370                 375                 380

Leu Phe Cys Glu Asp His Asp Glu Pro Ile Cys Leu Ile Cys Ser Leu
385                 390                 395                 400

Ser Gln Glu His Gln Gly His Arg Val Arg Pro Ile Glu Glu Val Ala
                405                 410                 415

Leu Glu His Lys Lys Lys Ile Gln Lys Gln Leu Glu His Leu Lys Lys
            420                 425                 430

Leu Arg Lys Ser Gly Glu Glu Gln Arg Ser Tyr Gly Glu Glu Lys Ala
        435                 440                 445

Val Ser Phe Leu Lys Gln Thr Glu Ala Leu Lys Gln Arg Val Gln Arg
    450                 455                 460

Lys Leu Glu Gln Val Tyr Tyr Phe Leu Glu Gln Gln Glu His Phe Phe
465                 470                 475                 480

Val Ala Ser Leu Glu Asp Val Gly Gln Met Val Gly Gln Ile Arg Lys
                485                 490                 495

Ala Tyr Asp Thr Arg Val Ser Gln Asp Ile Ala Leu Leu Asp Ala Leu
            500                 505                 510

Ile Gly Glu Leu Glu Ala Lys Glu Cys Gln Ser Glu Trp Glu Leu Leu
        515                 520                 525

Gln Asp Ile Gly Asp Ile Leu His Arg Ala Lys Thr Val Pro Val Pro
    530                 535                 540

Glu Lys Trp Thr Thr Pro Gln Glu Ile Lys Gln Lys Ile Gln Leu Leu
545                 550                 555                 560

His Gln Lys Ser Glu Phe Val Glu Lys Ser Thr Lys Tyr Phe Ser Glu
```

```
                        565                 570                 575
        Thr Leu Arg Ser Glu Met Glu Met Phe Asn Val Pro Glu Leu Ile Gly
                    580                 585                 590

Ala Gln Ala His Ala Val Asn Val Ile Leu Asp Ala Glu Thr Ala Tyr
                    595                 600                 605

Pro Asn Leu Ile Phe Ser Asp Leu Lys Ser Val Arg Leu Gly Asn
                610                 615                 620

Lys Trp Glu Arg Leu Pro Asp Gly Pro Gln Arg Phe Asp Ser Cys Ile
        625                 630                 635                 640

Ile Val Leu Gly Ser Pro Ser Phe Leu Ser Gly Arg Arg Tyr Trp Glu
                        645                 650                 655

Val Glu Val Gly Asp Lys Thr Ala Trp Ile Leu Gly Ala Cys Lys Thr
                    660                 665                 670

Ser Ile Ser Arg Lys Gly Asn Met Thr Leu Ser Pro Glu Asn Gly Tyr
                        675                 680                 685

Trp Val Val Ile Met Met Lys Glu Asn Glu Tyr Gln Ala Ser Ser Val
                    690                 695                 700

Pro Pro Thr Arg Leu Leu Ile Lys Glu Pro Pro Lys Arg Val Gly Ile
        705                 710                 715                 720

Phe Val Asp Tyr Arg Val Gly Ser Ile Ser Phe Tyr Asn Val Thr Ala
                        725                 730                 735

Arg Ser His Ile Tyr Thr Phe Ala Ser Cys Ser Phe Ser Gly Pro Leu
                    740                 745                 750

Gln Pro Ile Phe Ser Pro Gly Thr Arg Asp Gly Gly Lys Asn Thr Ala
                    755                 760                 765

Pro Leu Thr Ile Cys Pro Val Gly Gly Gln Gly Pro Asp
                770                 775                 780

<210> SEQ ID NO 97
<211> LENGTH: 19
<212> TYPE: RNA
<213> ORGANISM: Homo Sapiens

<400> SEQUENCE: 97
gaccacuccu caagagaua                                                    19

<210> SEQ ID NO 98
<211> LENGTH: 19
<212> TYPE: RNA
<213> ORGANISM: Homo Sapiens

<400> SEQUENCE: 98
gagaauggcu acugggugg                                                    19

<210> SEQ ID NO 99
<211> LENGTH: 19
<212> TYPE: RNA
<213> ORGANISM: Homo Sapiens

<400> SEQUENCE: 99
gcccgcaaau ccagaaauu                                                    19

<210> SEQ ID NO 100
<211> LENGTH: 19
<212> TYPE: RNA
<213> ORGANISM: Homo Sapiens

<400> SEQUENCE: 100
```
gcauaugaca cccgcguau                                                            19

<210> SEQ ID NO 101
<211> LENGTH: 475
<212> TYPE: PRT
<213> ORGANISM: Homo Sapiens

<400> SEQUENCE: 101

Met Ala Ser Ala Ala Arg Leu Thr Met Met Trp Glu Val Thr Cys
1               5                   10                  15

Pro Ile Cys Leu Asp Pro Phe Val Glu Pro Val Ser Ile Glu Cys Gly
                20                  25                  30

His Ser Phe Cys Gln Glu Cys Ile Ser Gln Val Gly Lys Gly Gly
                35                  40                  45

Ser Val Cys Pro Val Cys Arg Gln Arg Phe Leu Leu Lys Asn Leu Arg
        50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
                        85                  90                  95

Glu Arg Leu His Leu Phe Cys Glu Lys Asp Gly Lys Ala Leu Cys Trp
                100                 105                 110

Val Cys Ala Gln Ser Arg Lys His Arg Asp His Ala Met Val Pro Leu
            115                 120                 125

Glu Glu Ala Ala Gln Glu Tyr Gln Glu Lys Leu Gln Val Ala Leu Gly
    130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
                180                 185                 190

Glu Gln Arg Gln Leu Gln Glu Leu Glu Lys Asp Glu Arg Glu Gln Leu
            195                 200                 205

Arg Ile Leu Gly Glu Lys Glu Ala Lys Leu Ala Gln Gln Ser Gln Ala
    210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
                245                 250                 255

Trp Asn Leu Lys Asp Leu Asp Ile Thr Ser Pro Glu Leu Arg Ser Val
                260                 265                 270

Cys His Val Pro Gly Leu Lys Lys Met Leu Arg Thr Cys Ala Val His
            275                 280                 285

Ile Thr Leu Asp Pro Asp Thr Ala Asn Pro Trp Leu Ile Leu Ser Glu
    290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
                325                 330                 335

Phe His Ser Gly Lys His Tyr Trp Glu Val Asp Val Thr Gly Lys Glu
                340                 345                 350

Ala Trp Asp Leu Gly Val Cys Arg Asp Ser Val Arg Arg Lys Gly His
            355                 360                 365

-continued

```
Phe Leu Leu Ser Ser Lys Ser Gly Phe Trp Thr Ile Trp Leu Trp Asn
        370                 375                 380
Lys Gln Lys Tyr Glu Ala Gly Thr Tyr Pro Gln Thr Pro Leu His Leu
385                 390                 395                 400
Gln Val Pro Pro Cys Gln Val Gly Ile Phe Leu Asp Tyr Glu Ala Gly
                405                 410                 415
Met Val Ser Phe Tyr Asn Ile Thr Asp His Gly Ser Leu Ile Tyr Ser
            420                 425                 430
Phe Ser Glu Cys Ala Phe Thr Gly Pro Leu Arg Pro Phe Phe Ser Pro
        435                 440                 445
Gly Phe Asn Asp Gly Lys Asn Thr Ala Pro Leu Thr Leu Cys Pro
    450                 455                 460
Leu Asn Ile Gly Ser Gln Gly Ser Thr Asp Tyr
465                 470                 475
```

<210> SEQ ID NO 102
<211> LENGTH: 19
<212> TYPE: RNA
<213> ORGANISM: Homo Sapiens

<400> SEQUENCE: 102
ucucagagcu agaucgaag                                                19

<210> SEQ ID NO 103
<211> LENGTH: 19
<212> TYPE: RNA
<213> ORGANISM: Homo Sapiens

<400> SEQUENCE: 103
gagcauaccu ggaaaugaa                                                19

<210> SEQ ID NO 104
<211> LENGTH: 19
<212> TYPE: RNA
<213> ORGANISM: Homo Sapiens

<400> SEQUENCE: 104
ggugauaauu guccuggaa                                                19

<210> SEQ ID NO 105
<211> LENGTH: 19
<212> TYPE: RNA
<213> ORGANISM: Homo Sapiens

<400> SEQUENCE: 105
aagaguggcu ucuggacaa                                                19

<210> SEQ ID NO 106
<211> LENGTH: 498
<212> TYPE: PRT
<213> ORGANISM: Homo Sapiens

<400> SEQUENCE: 106

```
Met Asp Phe Ser Val Lys Val Asp Ile Glu Lys Glu Val Thr Cys Pro
1               5                   10                  15
Ile Cys Leu Glu Leu Leu Thr Glu Pro Leu Ser Leu Asp Cys Gly His
                20                  25                  30
Ser Phe Cys Gln Ala Cys Ile Thr Ala Lys Ile Lys Glu Ser Val Ile
            35                  40                  45
Ile Ser Arg Gly Glu Ser Ser Cys Pro Val Cys Gln Thr Arg Phe Gln
```

-continued

```
                50                  55                  60
Pro Gly Asn Leu Arg Pro Asn Arg His Leu Ala Asn Ile Val Glu Arg
 65                  70                  75                  80

Val Lys Glu Val Lys Met Ser Pro Gln Glu Gly Gln Lys Arg Asp Val
                 85                  90                  95

Cys Glu His His Gly Lys Lys Leu Gln Ile Phe Cys Lys Glu Asp Gly
                100                 105                 110

Lys Val Ile Cys Trp Val Cys Glu Leu Ser Gln Glu His Gln Gly His
                115                 120                 125

Gln Thr Phe Arg Ile Asn Glu Val Val Lys Glu Cys Gln Glu Lys Leu
                130                 135                 140

Gln Val Ala Leu Gln Arg Leu Ile Lys Glu Asp Gln Glu Ala Glu Lys
145                 150                 155                 160

Leu Glu Asp Asp Ile Arg Gln Glu Arg Thr Ala Trp Lys Asn Tyr Ile
                165                 170                 175

Gln Ile Glu Arg Gln Lys Ile Leu Lys Gly Phe Asn Glu Met Arg Val
                180                 185                 190

Ile Leu Asp Asn Glu Glu Gln Arg Glu Leu Gln Lys Leu Glu Glu Gly
                195                 200                 205

Glu Val Asn Val Leu Asp Asn Leu Ala Ala Ala Thr Asp Gln Leu Val
                210                 215                 220

Gln Gln Arg Gln Asp Ala Ser Thr Leu Ile Ser Asp Leu Gln Arg Arg
225                 230                 235                 240

Leu Arg Gly Ser Ser Val Glu Met Leu Gln Asp Val Ile Asp Val Met
                245                 250                 255

Lys Arg Ser Glu Ser Trp Thr Leu Lys Lys Pro Lys Ser Val Ser Lys
                260                 265                 270

Lys Leu Lys Ser Val Phe Arg Val Pro Asp Leu Ser Gly Met Leu Gln
                275                 280                 285

Val Leu Lys Glu Leu Thr Asp Val Gln Tyr Tyr Trp Val Asp Val Met
                290                 295                 300

Leu Asn Pro Gly Ser Ala Thr Ser Asn Val Ala Ile Ser Val Asp Gln
305                 310                 315                 320

Arg Gln Val Lys Thr Val Arg Thr Cys Thr Phe Lys Asn Ser Asn Pro
                325                 330                 335

Cys Asp Phe Ser Ala Phe Gly Val Phe Gly Cys Gln Tyr Phe Ser Ser
                340                 345                 350

Gly Lys Tyr Tyr Trp Glu Val Asp Val Ser Gly Lys Ile Ala Trp Ile
                355                 360                 365

Leu Gly Val His Ser Lys Ile Ser Ser Leu Asn Lys Arg Lys Ser Ser
                370                 375                 380

Gly Phe Ala Phe Asp Pro Ser Val Asn Tyr Lys Val Tyr Ser Arg
385                 390                 395                 400

Tyr Arg Pro Gln Tyr Gly Tyr Trp Val Ile Gly Leu Gln Asn Thr Cys
                405                 410                 415

Glu Tyr Asn Ala Phe Glu Asp Ser Ser Ser Asp Pro Lys Val Leu
                420                 425                 430

Thr Leu Phe Met Ala Val Pro Pro Cys Arg Ile Gly Val Phe Leu Asp
                435                 440                 445

Tyr Glu Ala Gly Ile Val Ser Phe Phe Asn Val Thr Asn His Gly Ala
                450                 455                 460

Leu Ile Tyr Lys Phe Ser Gly Cys Arg Phe Ser Arg Pro Ala Tyr Pro
465                 470                 475                 480
```

```
Tyr Phe Asn Pro Trp Asn Cys Leu Val Pro Met Thr Val Cys Pro Pro
                485                 490                 495

Ser Ser

<210> SEQ ID NO 107
<211> LENGTH: 19
<212> TYPE: RNA
<213> ORGANISM: Homo Sapiens

<400> SEQUENCE: 107
guacgcaccu gcacauuua                                                19

<210> SEQ ID NO 108
<211> LENGTH: 19
<212> TYPE: RNA
<213> ORGANISM: Homo Sapiens

<400> SEQUENCE: 108
caccaaacau uccgcauaa                                                19

<210> SEQ ID NO 109
<211> LENGTH: 19
<212> TYPE: RNA
<213> ORGANISM: Homo Sapiens

<400> SEQUENCE: 109
ccagauauag accucaaua                                                19

<210> SEQ ID NO 110
<211> LENGTH: 19
<212> TYPE: RNA
<213> ORGANISM: Homo Sapiens

<400> SEQUENCE: 110
agaauuauau ccagaucga                                                19

<210> SEQ ID NO 111
<211> LENGTH: 574
<212> TYPE: PRT
<213> ORGANISM: Homo Sapiens

<400> SEQUENCE: 111

Met Ala Thr Leu Val Val Asn Lys Leu Gly Ala Gly Val Asp Ser Gly
1               5                   10                  15

Arg Gln Gly Ser Arg Gly Thr Ala Val Val Lys Val Leu Glu Cys Gly
                20                  25                  30

Val Cys Glu Asp Val Phe Ser Leu Gln Gly Asp Lys Val Pro Arg Leu
            35                  40                  45

Leu Leu Cys Gly His Thr Val Cys His Asp Cys Leu Thr Arg Leu Pro
        50                  55                  60

Leu His Gly Arg Ala Ile Arg Cys Pro Phe Asp Arg Gln Val Thr Asp
65                  70                  75                  80

Leu Gly Asp Ser Gly Val Trp Gly Leu Lys Lys Asn Phe Ala Leu Leu
                85                  90                  95

Glu Leu Leu Glu Arg Leu Gln Asn Gly Pro Ile Gly Gln Tyr Gly Ala
                100                 105                 110

Ala Glu Glu Ser Ile Gly Ile Ser Gly Glu Ser Ile Ile Arg Cys Asp
            115                 120                 125

Glu Asp Glu Ala His Leu Ala Ser Val Tyr Cys Thr Val Cys Ala Thr
```

```
                130           135           140
His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Cys Val Cys Lys Glu Tyr
                195                 200                 205

Gly Lys His Gln Gly His Lys His Ser Val Leu Glu Pro Glu Ala Asn
        210                 215                 220

Gln Ile Arg Ala Ser Ile Leu Asp Met Ala His Cys Ile Arg Thr Phe
225                 230                 235                 240

Thr Glu Glu Ile Ser Asp Tyr Ser Arg Lys Leu Val Gly Ile Val Gln
                245                 250                 255

His Ile Glu Gly Gly Glu Gln Ile Val Glu Asp Gly Ile Gly Met Ala
            260                 265                 270

His Thr Glu His Val Pro Gly Thr Ala Glu Asn Ala Arg Ser Cys Ile
        275                 280                 285

Arg Ala Tyr Phe Tyr Asp Leu His Glu Thr Leu Cys Arg Gln Glu Glu
        290                 295                 300

Met Ala Leu Ser Val Val Asp Ala His Val Arg Glu Lys Leu Ile Trp
305                 310                 315                 320

Leu Arg Gln Gln Gln Glu Asp Met Thr Ile Leu Leu Ser Glu Val Ser
                325                 330                 335

Ala Ala Cys Leu His Cys Glu Lys Thr Leu Gln Gln Asp Asp Cys Arg
            340                 345                 350

Val Val Leu Ala Lys Gln Glu Ile Thr Arg Leu Leu Glu Thr Leu Gln
        355                 360                 365

Lys Gln Gln Gln Gln Phe Thr Glu Val Ala Asp His Ile Gln Leu Asp
        370                 375                 380

Ala Ser Ile Pro Val Thr Phe Thr Lys Asp Asn Arg Val His Ile Gly
385                 390                 395                 400

Pro Lys Met Glu Ile Arg Val Val Thr Leu Gly Leu Asp Gly Ala Gly
                405                 410                 415

Lys Thr Thr Ile Leu Phe Lys Leu Lys Gln Asp Glu Phe Met Gln Pro
            420                 425                 430

Ile Pro Thr Ile Gly Phe Asn Val Glu Thr Val Glu Tyr Lys Asn Leu
        435                 440                 445

Lys Phe Thr Ile Trp Asp Val Gly Gly Lys His Lys Leu Arg Pro Leu
        450                 455                 460

Trp Lys His Tyr Tyr Leu Asn Thr Gln Ala Val Phe Val Val Asp
465                 470                 475                 480

Ser Ser His Arg Asp Arg Ile Ser Glu Ala His Ser Glu Leu Ala Lys
            485                 490                 495

Leu Leu Thr Glu Lys Glu Leu Arg Asp Ala Leu Leu Leu Ile Phe Ala
                500                 505                 510

Asn Lys Gln Asp Val Ala Gly Ala Leu Ser Val Glu Glu Ile Thr Glu
            515                 520                 525

Leu Leu Ser Leu His Lys Leu Cys Cys Gly Arg Ser Trp Tyr Ile Gln
        530                 535                 540

Gly Cys Asp Ala Arg Ser Gly Met Gly Leu Tyr Glu Gly Leu Asp Trp
545                 550                 555                 560
```

```
Leu Ser Arg Gln Leu Val Ala Ala Gly Val Leu Asp Val Ala
            565                 570

<210> SEQ ID NO 112
<211> LENGTH: 19
<212> TYPE: RNA
<213> ORGANISM: Homo Sapiens

<400> SEQUENCE: 112
gaagaagguu gucaaacua                                                        19

<210> SEQ ID NO 113
<211> LENGTH: 19
<212> TYPE: RNA
<213> ORGANISM: Homo Sapiens

<400> SEQUENCE: 113
ucacaagcau ucaguauug                                                        19

<210> SEQ ID NO 114
<211> LENGTH: 19
<212> TYPE: RNA
<213> ORGANISM: Homo Sapiens

<400> SEQUENCE: 114
gcaaaguugu uaacggaaa                                                        19

<210> SEQ ID NO 115
<211> LENGTH: 19
<212> TYPE: RNA
<213> ORGANISM: Homo Sapiens

<400> SEQUENCE: 115
ggagagagca ucauucguu                                                        19

<210> SEQ ID NO 116
<211> LENGTH: 1016
<212> TYPE: PRT
<213> ORGANISM: Homo Sapiens

<400> SEQUENCE: 116

Met Glu Val Ala Val Glu Lys Ala Val Ala Ala Ala Ala Ala Ser
1               5                   10                  15

Ala Ala Ala Ser Gly Gly Pro Ser Ala Ala Pro Ser Gly Glu Asn Glu
            20                  25                  30

Ala Glu Ser Arg Gln Gly Pro Asp Ser Glu Arg Gly Gly Glu Ala Ala
        35                  40                  45

Arg Leu Asn Leu Leu Asp Thr Cys Ala Val Cys His Gln Asn Ile Gln
    50                  55                  60

Ser Arg Ala Pro Lys Leu Leu Pro Cys Leu His Ser Phe Cys Gln Arg
65                  70                  75                  80

Cys Leu Pro Ala Pro Gln Arg Tyr Leu Met Leu Pro Ala Pro Met Leu
                85                  90                  95

Gly Ser Ala Glu Thr Pro Pro Pro Val Pro Ala Pro Gly Ser Pro Val
            100                 105                 110

Ser Gly Ser Ser Pro Phe Ala Thr Gln Val Gly Val Ile Arg Cys Pro
        115                 120                 125

Val Cys Ser Gln Glu Cys Ala Glu Arg His Ile Ile Asp Asn Phe Phe
    130                 135                 140
```

```
Val Lys Asp Thr Thr Glu Val Pro Ser Ser Thr Val Glu Lys Ser Asn
145                 150                 155                 160

Gln Val Cys Thr Ser Cys Glu Asp Asn Ala Glu Ala Asn Gly Phe Cys
                165                 170                 175

Val Glu Cys Val Glu Trp Leu Cys Lys Thr Cys Ile Arg Ala His Gln
            180                 185                 190

Arg Val Lys Phe Thr Lys Asp His Thr Val Arg Gln Lys Glu Glu Val
        195                 200                 205

Ser Pro Glu Ala Val Gly Val Thr Ser Gln Arg Pro Val Phe Cys Pro
    210                 215                 220

Phe His Lys Lys Glu Gln Leu Lys Leu Tyr Cys Glu Thr Cys Asp Lys
225                 230                 235                 240

Leu Thr Cys Arg Asp Cys Gln Leu Leu Glu His Lys Glu His Arg Tyr
                245                 250                 255

Gln Phe Ile Glu Glu Ala Phe Gln Asn Gln Lys Val Ile Ile Asp Thr
                260                 265                 270

Leu Ile Thr Lys Leu Met Glu Lys Thr Lys Tyr Ile Lys Phe Thr Gly
            275                 280                 285

Asn Gln Ile Gln Asn Arg Ile Ile Glu Val Asn Gln Asn Gln Lys Gln
290                 295                 300

Val Glu Gln Asp Ile Lys Val Ala Ile Phe Thr Leu Met Val Glu Ile
305                 310                 315                 320

Asn Lys Lys Gly Lys Ala Leu Leu His Gln Leu Glu Ser Leu Ala Lys
                325                 330                 335

Asp His Arg Met Lys Leu Met Gln Gln Gln Glu Val Ala Gly Leu
                340                 345                 350

Ser Lys Gln Leu Glu His Val Met His Phe Ser Lys Trp Ala Val Ser
        355                 360                 365

Ser Gly Ser Ser Thr Ala Leu Leu Tyr Ser Lys Arg Leu Ile Thr Tyr
    370                 375                 380

Arg Leu Arg His Leu Leu Arg Ala Arg Cys Asp Ala Ser Pro Val Thr
385                 390                 395                 400

Asn Asn Thr Ile Gln Phe His Cys Asp Pro Ser Phe Trp Ala Gln Asn
                405                 410                 415

Ile Ile Asn Leu Gly Ser Leu Val Ile Glu Asp Lys Glu Ser Gln Pro
            420                 425                 430

Gln Met Pro Lys Gln Asn Pro Val Val Glu Gln Asn Ser Gln Pro Pro
        435                 440                 445

Ser Gly Leu Ser Ser Asn Gln Leu Ser Lys Phe Pro Thr Gln Ile Ser
    450                 455                 460

Leu Ala Gln Leu Arg Leu Gln His Met Gln Gln Gln Pro Pro
465                 470                 475                 480

Arg Leu Ile Asn Phe Gln Asn His Ser Pro Lys Pro Asn Gly Pro Val
                485                 490                 495

Leu Pro Pro His Pro Gln Gln Leu Arg Tyr Pro Pro Asn Gln Asn Ile
            500                 505                 510

Pro Arg Gln Ala Ile Lys Pro Asn Pro Leu Gln Met Ala Phe Leu Ala
        515                 520                 525

Gln Gln Ala Ile Lys Gln Trp Gln Ile Ser Ser Gly Gln Gly Thr Pro
    530                 535                 540

Ser Thr Thr Asn Ser Thr Ser Ser Thr Pro Ser Ser Pro Thr Ile Thr
545                 550                 555                 560

Ser Ala Ala Gly Tyr Asp Gly Lys Ala Phe Gly Ser Pro Met Ile Asp
```

-continued

```
                565                 570                 575
Leu Ser Ser Pro Val Gly Gly Ser Tyr Asn Leu Pro Ser Leu Pro Asp
            580                 585                 590

Ile Asp Cys Ser Ser Thr Ile Met Leu Asp Asn Ile Val Arg Lys Asp
            595                 600                 605

Thr Asn Ile Asp His Gly Gln Pro Arg Pro Ser Asn Arg Thr Val
            610                 615                 620

Gln Ser Pro Asn Ser Ser Val Pro Ser Pro Gly Leu Ala Gly Pro Val
625                 630                 635                 640

Thr Met Thr Ser Val His Pro Pro Ile Arg Ser Pro Ser Ala Ser Ser
                645                 650                 655

Val Gly Ser Arg Gly Ser Ser Gly Ser Ser Ser Lys Pro Ala Gly Ala
                660                 665                 670

Asp Ser Thr His Lys Val Pro Val Val Met Leu Glu Pro Ile Arg Ile
                675                 680                 685

Lys Gln Glu Asn Ser Gly Pro Pro Glu Asn Tyr Asp Phe Pro Val Val
            690                 695                 700

Ile Val Lys Gln Glu Ser Asp Glu Glu Ser Arg Pro Gln Asn Ala Asn
705                 710                 715                 720

Tyr Pro Arg Ser Ile Leu Thr Ser Leu Leu Leu Asn Ser Ser Gln Ser
                725                 730                 735

Ser Thr Ser Glu Glu Thr Val Leu Arg Ser Asp Ala Pro Asp Ser Thr
            740                 745                 750

Gly Asp Gln Pro Gly Leu His Gln Asp Asn Ser Ser Asn Gly Lys Ser
            755                 760                 765

Glu Trp Leu Asp Pro Ser Gln Lys Ser Pro Leu His Val Gly Glu Thr
770                 775                 780

Arg Lys Glu Asp Asp Pro Asn Glu Asp Trp Cys Ala Val Cys Gln Asn
785                 790                 795                 800

Gly Gly Glu Leu Leu Cys Cys Glu Lys Cys Pro Lys Val Phe His Leu
                805                 810                 815

Ser Cys His Val Pro Thr Leu Thr Asn Phe Pro Ser Gly Glu Trp Ile
                820                 825                 830

Cys Thr Phe Cys Arg Asp Leu Ser Lys Pro Glu Val Glu Tyr Asp Cys
            835                 840                 845

Asp Ala Pro Ser His Asn Ser Glu Lys Lys Thr Glu Gly Leu Val
            850                 855                 860

Lys Leu Thr Pro Ile Asp Lys Arg Lys Cys Glu Arg Leu Leu Leu Phe
865                 870                 875                 880

Leu Tyr Cys His Glu Met Ser Leu Ala Phe Gln Asp Pro Val Pro Leu
                885                 890                 895

Thr Val Pro Asp Tyr Tyr Lys Ile Ile Lys Asn Pro Met Asp Leu Ser
            900                 905                 910

Thr Ile Lys Lys Arg Leu Gln Glu Asp Tyr Ser Met Tyr Ser Lys Pro
            915                 920                 925

Glu Asp Phe Val Ala Asp Phe Arg Leu Ile Phe Gln Asn Cys Ala Glu
            930                 935                 940

Phe Asn Glu Pro Asp Ser Glu Val Ala Asn Ala Gly Ile Lys Leu Glu
945                 950                 955                 960

Asn Tyr Phe Glu Glu Leu Leu Lys Asn Leu Tyr Pro Glu Lys Arg Phe
                965                 970                 975

Pro Lys Pro Glu Phe Arg Asn Glu Ser Glu Asp Asn Lys Phe Ser Asp
            980                 985                 990
```

Asp Ser Asp Asp Asp Phe Val Gln Pro Arg Lys Lys Arg Leu Lys Ser
       995                 1000                1005

Ile Glu Glu Arg Gln Leu Leu Lys
    1010                1015

<210> SEQ ID NO 117
<211> LENGTH: 19
<212> TYPE: RNA
<213> ORGANISM: Homo Sapiens

<400> SEQUENCE: 117
gaacauacca cgacaagca                                                    19

<210> SEQ ID NO 118
<211> LENGTH: 19
<212> TYPE: RNA
<213> ORGANISM: Homo Sapiens

<400> SEQUENCE: 118
agacuuaucu aaaccagaa                                                    19

<210> SEQ ID NO 119
<211> LENGTH: 19
<212> TYPE: RNA
<213> ORGANISM: Homo Sapiens

<400> SEQUENCE: 119
cuuuaguaau cgaggauaa                                                    19

<210> SEQ ID NO 120
<211> LENGTH: 19
<212> TYPE: RNA
<213> ORGANISM: Homo Sapiens

<400> SEQUENCE: 120
cuuuauagca aacgacuga                                                    19

<210> SEQ ID NO 121
<211> LENGTH: 630
<212> TYPE: PRT
<213> ORGANISM: Homo Sapiens

<400> SEQUENCE: 121

Met Ala Glu Leu Cys Pro Leu Ala Glu Glu Leu Ser Cys Ser Ile Cys
1               5                   10                  15

Leu Glu Pro Phe Lys Glu Pro Val Thr Thr Pro Cys Gly His Asn Phe
            20                  25                  30

Cys Gly Ser Cys Leu Asn Glu Thr Trp Ala Val Gln Gly Ser Pro Tyr
        35                  40                  45

Leu Cys Pro Gln Cys Arg Ala Val Tyr Gln Ala Arg Pro Gln Leu His
    50                  55                  60

Lys Asn Thr Val Leu Cys Asn Val Val Glu Gln Phe Leu Gln Ala Asp
65                  70                  75                  80

Leu Ala Arg Glu Pro Pro Ala Asp Val Trp Thr Pro Pro Ala Arg Ala
                85                  90                  95

Ser Ala Pro Ser Pro Asn Ala Gln Val Ala Cys Asp His Cys Leu Lys
            100                 105                 110

Glu Ala Ala Val Lys Thr Cys Leu Val Cys Met Ala Ser Phe Cys Gln
        115                 120                 125

```
Glu His Leu Gln Pro His Phe Asp Ser Pro Ala Phe Gln Asp His Pro
130                 135                 140

Leu Gln Pro Pro Val Arg Asp Leu Leu Arg Arg Lys Cys Ser Gln His
145                 150                 155                 160

Asn Arg Leu Arg Glu Phe Phe Cys Pro Glu His Ser Glu Cys Ile Cys
                165                 170                 175

His Ile Cys Leu Val Glu His Lys Thr Cys Ser Pro Ala Ser Leu Ser
            180                 185                 190

Gln Ala Ser Ala Asp Leu Glu Ala Thr Leu Arg His Lys Leu Thr Val
        195                 200                 205

Met Tyr Ser Gln Ile Asn Gly Ala Ser Arg Ala Leu Asp Asp Val Arg
210                 215                 220

Asn Arg Gln Gln Asp Val Arg Met Thr Ala Asn Arg Lys Val Glu Gln
225                 230                 235                 240

Leu Gln Gln Glu Tyr Thr Glu Met Lys Ala Leu Leu Asp Ala Ser Glu
                245                 250                 255

Thr Thr Ser Thr Arg Lys Ile Lys Glu Glu Lys Arg Val Asn Ser
            260                 265                 270

Lys Phe Asp Thr Ile Tyr Gln Ile Leu Leu Lys Lys Ser Glu Ile
            275                 280                 285

Gln Thr Leu Lys Glu Glu Ile Glu Gln Ser Leu Thr Lys Arg Asp Glu
290                 295                 300

Phe Glu Phe Leu Glu Lys Ala Ser Lys Leu Arg Gly Ile Ser Thr Lys
305                 310                 315                 320

Pro Val Tyr Ile Pro Glu Val Glu Leu Asn His Lys Leu Ile Lys Gly
                325                 330                 335

Ile His Gln Ser Thr Ile Asp Leu Lys Asn Glu Leu Lys Gln Cys Ile
            340                 345                 350

Gly Arg Leu Gln Glu Pro Thr Pro Ser Ser Gly Asp Pro Gly Glu His
        355                 360                 365

Asp Pro Ala Ser Thr His Lys Ser Thr Arg Pro Val Lys Lys Val Ser
370                 375                 380

Lys Glu Glu Lys Lys Ser Lys Lys Pro Pro Val Pro Ala Leu Pro
385                 390                 395                 400

Ser Lys Leu Pro Thr Phe Gly Ala Pro Glu Gln Leu Val Asp Leu Lys
                405                 410                 415

Gln Ala Gly Leu Glu Ala Ala Ala Lys Ala Thr Ser Ser His Pro Asn
            420                 425                 430

Ser Thr Ser Leu Lys Ala Lys Val Leu Glu Thr Phe Leu Ala Lys Ser
        435                 440                 445

Arg Pro Glu Leu Leu Glu Tyr Tyr Ile Lys Val Ile Leu Asp Tyr Asn
450                 455                 460

Thr Ala His Asn Lys Val Ala Leu Ser Glu Cys Tyr Thr Val Ala Ser
465                 470                 475                 480

Val Ala Glu Met Pro Gln Asn Tyr Arg Pro His Pro Gln Arg Phe Thr
                485                 490                 495

Tyr Cys Ser Gln Val Leu Gly Leu His Cys Tyr Lys Lys Gly Ile His
            500                 505                 510

Tyr Trp Glu Val Glu Leu Gln Lys Asn Asn Phe Cys Gly Val Gly Ile
        515                 520                 525

Cys Tyr Gly Ser Met Asn Arg Gln Gly Pro Glu Ser Arg Leu Gly Arg
530                 535                 540

Asn Ser Ala Ser Trp Cys Val Glu Trp Phe Asn Thr Lys Ile Ser Ala
```

-continued

```
             545                 550                 555                 560
Trp His Asn Asn Val Glu Lys Thr Leu Pro Ser Thr Lys Ala Thr Arg
                 565                 570                 575

Val Gly Val Leu Leu Asn Cys Asp His Gly Phe Val Ile Phe Phe Ala
                 580                 585                 590

Val Ala Asp Lys Val His Leu Met Tyr Lys Phe Arg Val Asp Phe Thr
                 595                 600                 605

Glu Ala Leu Tyr Pro Ala Phe Trp Val Phe Ser Ala Gly Ala Thr Leu
                 610                 615                 620

Ser Ile Cys Ser Pro Lys
625                 630

<210> SEQ ID NO 122
<211> LENGTH: 19
<212> TYPE: RNA
<213> ORGANISM: Homo Sapiens

<400> SEQUENCE: 122
gaccgcagcu gcacaagaa                                                 19

<210> SEQ ID NO 123
<211> LENGTH: 19
<212> TYPE: RNA
<213> ORGANISM: Homo Sapiens

<400> SEQUENCE: 123
caaacuaacu gucauguac                                                 19

<210> SEQ ID NO 124
<211> LENGTH: 19
<212> TYPE: RNA
<213> ORGANISM: Homo Sapiens

<400> SEQUENCE: 124
caacaagaau acacggaaa                                                 19

<210> SEQ ID NO 125
<211> LENGTH: 19
<212> TYPE: RNA
<213> ORGANISM: Homo Sapiens

<400> SEQUENCE: 125
gcggaugacu gcaaacaga                                                 19

<210> SEQ ID NO 126
<211> LENGTH: 513
<212> TYPE: PRT
<213> ORGANISM: Homo Sapiens

<400> SEQUENCE: 126

Met Ala Ser Gly Ser Val Ala Glu Cys Leu Gln Gln Glu Thr Thr Cys
1               5                   10                  15

Pro Val Cys Leu Gln Tyr Phe Ala Glu Pro Met Met Leu Asp Cys Gly
                20                  25                  30

His Asn Ile Cys Cys Ala Cys Leu Ala Arg Cys Trp Gly Thr Ala Glu
            35                  40                  45

Thr Asn Val Ser Cys Pro Gln Cys Arg Glu Thr Phe Pro Gln Arg His
        50                  55                  60

Met Arg Pro Asn Arg His Leu Ala Asn Val Thr Gln Leu Val Lys Gln
65                  70                  75                  80
```

-continued

```
Leu Arg Thr Glu Arg Pro Ser Gly Pro Gly Gly Glu Met Gly Val Cys
                85                  90                  95
Glu Lys His Arg Glu Pro Leu Lys Leu Tyr Cys Glu Glu Asp Gln Met
            100                 105                 110
Pro Ile Cys Val Val Cys Asp Arg Ser Arg Glu His Arg Gly His Ser
        115                 120                 125
Val Leu Pro Leu Glu Glu Ala Val Glu Gly Phe Lys Glu Gln Ile Gln
130                 135                 140
Asn Gln Leu Asp His Leu Lys Arg Val Lys Asp Leu Lys Lys Arg Arg
145                 150                 155                 160
Arg Ala Gln Gly Glu Gln Ala Arg Ala Glu Leu Leu Ser Leu Thr Gln
                165                 170                 175
Met Glu Arg Glu Lys Ile Val Trp Glu Phe Glu Gln Leu Tyr His Ser
            180                 185                 190
Leu Lys Glu His Glu Tyr Arg Leu Leu Ala Arg Leu Glu Glu Leu Asp
        195                 200                 205
Leu Ala Ile Tyr Asn Ser Ile Asn Gly Ala Ile Thr Gln Phe Ser Cys
210                 215                 220
Asn Ile Ser His Leu Ser Ser Leu Ile Ala Gln Leu Glu Glu Lys Gln
225                 230                 235                 240
Gln Gln Pro Thr Arg Glu Leu Leu Gln Asp Ile Gly Asp Thr Leu Ser
                245                 250                 255
Arg Ala Glu Arg Ile Arg Ile Pro Glu Pro Trp Ile Thr Pro Pro Asp
            260                 265                 270
Leu Gln Glu Lys Ile His Ile Phe Ala Gln Lys Cys Leu Phe Leu Thr
        275                 280                 285
Glu Ser Leu Lys Gln Phe Thr Glu Lys Met Gln Ser Asp Met Glu Lys
290                 295                 300
Ile Gln Glu Leu Arg Glu Ala Gln Leu Tyr Ser Val Asp Val Thr Leu
305                 310                 315                 320
Asp Pro Asp Thr Ala Tyr Pro Ser Leu Ile Leu Ser Asp Asn Leu Arg
                325                 330                 335
Gln Val Arg Tyr Ser Tyr Leu Gln Gln Asp Leu Pro Asn Pro Glu
            340                 345                 350
Arg Phe Asn Leu Phe Pro Cys Val Leu Gly Ser Pro Cys Phe Ile Ala
        355                 360                 365
Gly Arg His Tyr Trp Glu Val Glu Val Gly Asp Lys Ala Lys Trp Thr
370                 375                 380
Ile Gly Val Cys Glu Asp Ser Val Cys Arg Lys Gly Val Thr Ser
385                 390                 395                 400
Ala Pro Gln Asn Gly Phe Trp Ala Val Ser Leu Trp Tyr Gly Lys Glu
                405                 410                 415
Tyr Trp Ala Leu Thr Ser Pro Met Thr Ala Leu Pro Leu Arg Thr Pro
            420                 425                 430
Leu Gln Arg Val Gly Ile Phe Leu Asp Tyr Asp Ala Gly Glu Val Ser
        435                 440                 445
Phe Tyr Asn Val Thr Glu Arg Cys His Thr Phe Thr Phe Ser His Ala
450                 455                 460
Thr Phe Cys Gly Pro Val Arg Pro Tyr Phe Ser Leu Ser Tyr Ser Gly
465                 470                 475                 480
Gly Lys Ser Ala Ala Pro Leu Ile Ile Cys Pro Met Ser Gly Ile Asp
                485                 490                 495
```

```
Gly Phe Ser Gly His Val Gly Asn His Gly His Ser Met Glu Thr Ser
            500                 505                 510

Pro

<210> SEQ ID NO 127
<211> LENGTH: 19
<212> TYPE: RNA
<213> ORGANISM: Homo Sapiens

<400> SEQUENCE: 127
gagcagggcu gaaagaauc                                                    19

<210> SEQ ID NO 128
<211> LENGTH: 19
<212> TYPE: RNA
<213> ORGANISM: Homo Sapiens

<400> SEQUENCE: 128
uaagagaggc ucaguuaua                                                    19

<210> SEQ ID NO 129
<211> LENGTH: 19
<212> TYPE: RNA
<213> ORGANISM: Homo Sapiens

<400> SEQUENCE: 129
gcugaacucu ugagccuaa                                                    19

<210> SEQ ID NO 130
<211> LENGTH: 19
<212> TYPE: RNA
<213> ORGANISM: Homo Sapiens

<400> SEQUENCE: 130
gaagauuguu ugggaguuu                                                    19

<210> SEQ ID NO 131
<211> LENGTH: 835
<212> TYPE: PRT
<213> ORGANISM: Homo Sapiens

<400> SEQUENCE: 131

Met Ala Ala Ser Ala Ala Ala Ala Ser Ala Ala Ala Ser Ala Ala
1               5                   10                  15

Ser Gly Ser Pro Gly Pro Gly Glu Gly Ser Ala Gly Gly Glu Lys Arg
                20                  25                  30

Ser Thr Ala Pro Ser Ala Ala Ala Ser Ala Ser Ala Ser Ala Ala Ala
        35                  40                  45

Ser Ser Pro Ala Gly Gly Gly Ala Glu Ala Leu Glu Leu Leu Glu His
    50                  55                  60

Cys Gly Val Cys Arg Glu Arg Leu Arg Pro Glu Arg Glu Pro Arg Leu
65                  70                  75                  80

Leu Pro Cys Leu His Ser Ala Cys Ser Ala Cys Leu Gly Pro Ala Ala
                85                  90                  95

Pro Ala Ala Ala Asn Ser Ser Gly Asp Gly Gly Ala Ala Gly Asp Gly
                100                 105                 110

Thr Val Val Asp Cys Pro Val Cys Lys Gln Gln Cys Phe Ser Lys Asp
        115                 120                 125

Ile Val Glu Asn Tyr Phe Met Arg Asp Ser Gly Ser Lys Ala Ala Thr
    130                 135                 140
```

```
Asp Ala Gln Asp Ala Asn Gln Cys Cys Thr Ser Cys Glu Asp Asn Ala
145                 150                 155                 160

Pro Ala Thr Ser Tyr Cys Val Glu Cys Ser Glu Pro Leu Cys Glu Thr
                165                 170                 175

Cys Val Glu Ala His Gln Arg Val Lys Tyr Thr Lys Asp His Thr Val
            180                 185                 190

Arg Ser Thr Gly Pro Ala Lys Ser Arg Asp Gly Glu Arg Thr Val Tyr
        195                 200                 205

Cys Asn Val His Lys His Glu Pro Leu Val Leu Phe Cys Glu Ser Cys
    210                 215                 220

Asp Thr Leu Thr Cys Arg Asp Cys Gln Leu Asn Ala His Lys Asp His
225                 230                 235                 240

Gln Tyr Gln Phe Leu Glu Asp Ala Val Arg Asn Gln Arg Lys Leu Leu
                245                 250                 255

Ala Ser Leu Val Lys Arg Leu Gly Asp Lys His Ala Thr Leu Gln Lys
            260                 265                 270

Ser Thr Lys Glu Val Arg Ser Ser Ile Arg Gln Val Ser Asp Val Gln
        275                 280                 285

Lys Arg Val Gln Val Asp Val Lys Met Ala Ile Leu Gln Ile Met Lys
290                 295                 300

Glu Leu Asn Lys Arg Gly Arg Val Leu Val Asn Asp Ala Gln Lys Val
305                 310                 315                 320

Thr Glu Gly Gln Gln Glu Arg Leu Glu Arg Gln His Trp Thr Met Thr
                325                 330                 335

Lys Ile Gln Lys His Gln Glu His Ile Leu Arg Phe Ala Ser Trp Ala
            340                 345                 350

Leu Glu Ser Asp Asn Asn Thr Ala Leu Leu Leu Ser Lys Lys Leu Ile
        355                 360                 365

Tyr Phe Gln Leu His Arg Ala Leu Lys Met Ile Val Asp Pro Val Glu
370                 375                 380

Pro His Gly Glu Met Lys Phe Gln Trp Asp Leu Asn Ala Trp Thr Lys
385                 390                 395                 400

Ser Ala Glu Ala Phe Gly Lys Ile Val Ala Glu Arg Pro Gly Thr Asn
                405                 410                 415

Ser Thr Gly Pro Ala Pro Met Ala Pro Pro Arg Ala Pro Gly Pro Leu
            420                 425                 430

Ser Lys Gln Gly Ser Gly Ser Ser Gln Pro Met Glu Val Gln Glu Gly
        435                 440                 445

Tyr Gly Phe Gly Ser Gly Asp Asp Pro Tyr Ser Ser Ala Glu Pro His
450                 455                 460

Val Ser Gly Val Lys Arg Ser Arg Ser Gly Glu Gly Glu Val Ser Gly
465                 470                 475                 480

Leu Met Arg Lys Val Pro Arg Val Ser Leu Glu Arg Leu Asp Leu Asp
                485                 490                 495

Leu Thr Ala Asp Ser Gln Pro Val Phe Lys Val Phe Pro Gly Ser
            500                 505                 510

Thr Thr Glu Asp Tyr Asn Leu Ile Val Ile Glu Arg Gly Ala Ala Ala
        515                 520                 525

Ala Ala Thr Gly Gln Pro Gly Thr Ala Pro Gly Thr Pro Gly Ala
530                 535                 540

Pro Pro Leu Ala Gly Met Ala Ile Val Lys Glu Glu Thr Glu Ala
545                 550                 555                 560
```

-continued

```
Ala Ile Gly Ala Pro Pro Thr Ala Thr Glu Gly Pro Glu Thr Lys Pro
                565                 570                 575
Val Leu Met Ala Leu Ala Glu Gly Pro Gly Ala Glu Gly Pro Arg Leu
            580                 585                 590
Ala Ser Pro Ser Gly Ser Thr Ser Ser Gly Leu Glu Val Val Ala Pro
        595                 600                 605
Glu Gly Thr Ser Ala Pro Gly Gly Pro Gly Thr Leu Asp Asp Ser
    610                 615                 620
Ala Thr Ile Cys Arg Val Cys Gln Lys Pro Gly Asp Leu Val Met Cys
625                 630                 635                 640
Asn Gln Cys Glu Phe Cys Phe His Leu Asp Cys His Leu Pro Ala Leu
                645                 650                 655
Gln Asp Val Pro Gly Glu Glu Trp Ser Cys Ser Leu Cys His Val Leu
            660                 665                 670
Pro Asp Leu Lys Glu Glu Asp Gly Ser Leu Ser Leu Asp Gly Ala Asp
        675                 680                 685
Ser Thr Gly Val Val Ala Lys Leu Ser Pro Ala Asn Gln Arg Lys Cys
    690                 695                 700
Glu Arg Val Leu Leu Ala Leu Phe Cys His Glu Pro Cys Arg Pro Leu
705                 710                 715                 720
His Gln Leu Ala Thr Asp Ser Thr Phe Ser Leu Asp Gln Pro Gly Gly
                725                 730                 735
Thr Leu Asp Leu Thr Leu Ile Arg Ala Arg Leu Gln Glu Lys Leu Ser
            740                 745                 750
Pro Pro Tyr Ser Ser Pro Gln Glu Phe Ala Gln Asp Val Gly Arg Met
        755                 760                 765
Phe Lys Gln Phe Asn Lys Leu Thr Glu Asp Lys Ala Asp Val Gln Ser
    770                 775                 780
Ile Ile Gly Leu Gln Arg Phe Phe Glu Thr Arg Met Asn Glu Ala Phe
785                 790                 795                 800
Gly Asp Thr Lys Phe Ser Ala Val Leu Val Glu Pro Pro Met Ser
                805                 810                 815
Leu Pro Gly Ala Gly Leu Ser Ser Gln Glu Leu Ser Gly Gly Pro Gly
            820                 825                 830
Asp Gly Pro
    835
```

<210> SEQ ID NO 132
<211> LENGTH: 19
<212> TYPE: RNA
<213> ORGANISM: Homo Sapiens

<400> SEQUENCE: 132
gaccaaaccu gugcuuaug        19

<210> SEQ ID NO 133
<211> LENGTH: 19
<212> TYPE: RNA
<213> ORGANISM: Homo Sapiens

<400> SEQUENCE: 133
gaugaucccu acucaagug        19

<210> SEQ ID NO 134
<211> LENGTH: 19
<212> TYPE: RNA
<213> ORGANISM: Homo Sapiens

<400> SEQUENCE: 134
gcgaucuggu uaugugcaa                                                19

<210> SEQ ID NO 135
<211> LENGTH: 19
<212> TYPE: RNA
<213> ORGANISM: Homo Sapiens

<400> SEQUENCE: 135
agaauuauuu caugcguga                                                19

<210> SEQ ID NO 136
<211> LENGTH: 588
<212> TYPE: PRT
<213> ORGANISM: Homo Sapiens

<400> SEQUENCE: 136

Met Glu Ala Ala Asp Ala Ser Arg Ser Asn Gly Ser Ser Pro Glu Ala
1               5                   10                  15

Arg Asp Ala Arg Ser Pro Ser Gly Pro Ser Gly Ser Leu Glu Asn Gly
            20                  25                  30

Thr Lys Ala Asp Gly Lys Asp Ala Lys Thr Thr Asn His Gly Gly
        35                  40                  45

Glu Ala Ala Glu Gly Lys Ser Leu Gly Ser Ala Leu Lys Pro Gly Glu
    50                  55                  60

Gly Arg Ser Ala Leu Phe Ala Gly Asn Glu Trp Arg Arg Pro Ile Ile
65                  70                  75                  80

Gln Phe Val Glu Ser Gly Asp Asp Lys Asn Ser Asn Tyr Phe Ser Met
                85                  90                  95

Asp Ser Met Glu Gly Lys Arg Ser Pro Tyr Ala Gly Leu Gln Leu Gly
            100                 105                 110

Ala Ala Lys Lys Pro Pro Val Thr Phe Ala Glu Lys Gly Glu Leu Arg
        115                 120                 125

Lys Ser Ile Phe Ser Glu Ser Arg Lys Pro Thr Val Ser Ile Met Glu
    130                 135                 140

Pro Gly Glu Thr Arg Arg Asn Ser Tyr Pro Arg Ala Asp Thr Gly Leu
145                 150                 155                 160

Phe Ser Arg Ser Lys Ser Gly Ser Glu Glu Val Leu Cys Asp Ser Cys
                165                 170                 175

Ile Gly Asn Lys Gln Lys Ala Val Lys Ser Cys Leu Val Cys Gln Ala
            180                 185                 190

Ser Phe Cys Glu Leu His Leu Lys Pro His Leu Glu Gly Ala Ala Phe
        195                 200                 205

Arg Asp His Gln Leu Leu Glu Pro Ile Arg Asp Phe Glu Ala Arg Lys
    210                 215                 220

Cys Pro Val His Gly Lys Thr Met Glu Leu Phe Cys Gln Thr Asp Gln
225                 230                 235                 240

Thr Cys Ile Cys Tyr Leu Cys Met Phe Gln Glu His Lys Asn His Ser
                245                 250                 255

Thr Val Thr Val Glu Glu Ala Lys Ala Glu Lys Glu Thr Glu Leu Ser
            260                 265                 270

Leu Gln Lys Glu Gln Leu Gln Leu Lys Ile Ile Glu Ile Glu Asp Glu
        275                 280                 285

Ala Glu Lys Trp Gln Lys Glu Lys Asp Arg Ile Lys Ser Phe Thr Thr
    290                 295                 300

Asn Glu Lys Ala Ile Leu Glu Gln Asn Phe Arg Asp Leu Val Arg Asp
305                 310                 315                 320

Leu Glu Lys Gln Lys Glu Val Arg Ala Ala Leu Glu Gln Arg Glu
            325                 330                 335

Gln Asp Ala Val Asp Gln Val Lys Val Ile Met Asp Ala Leu Asp Glu
            340                 345                 350

Arg Ala Lys Val Leu His Glu Asp Lys Gln Thr Arg Glu Gln Leu His
                355                 360                 365

Ser Ile Ser Asp Ser Val Leu Phe Leu Gln Glu Phe Gly Ala Leu Met
            370                 375                 380

Ser Asn Tyr Ser Leu Pro Pro Leu Pro Thr Tyr His Val Leu Leu
385                 390                 395                 400

Glu Gly Glu Gly Leu Gly Gln Ser Leu Gly Asn Phe Lys Asp Leu
                405                 410                 415

Leu Asn Val Cys Met Arg His Val Glu Lys Met Cys Lys Ala Asp Leu
            420                 425                 430

Ser Arg Asn Phe Ile Glu Arg Asn His Met Glu Asn Gly Gly Asp His
                435                 440                 445

Arg Tyr Val Asn Asn Tyr Thr Asn Ser Phe Gly Gly Glu Trp Ser Ala
450                 455                 460

Pro Asp Thr Met Lys Arg Tyr Ser Met Tyr Leu Thr Pro Lys Gly Gly
465                 470                 475                 480

Val Arg Thr Ser Tyr Gln Pro Ser Ser Pro Gly Arg Phe Thr Lys Glu
                485                 490                 495

Thr Thr Gln Lys Asn Phe Asn Asn Leu Tyr Gly Thr Lys Gly Asn Tyr
            500                 505                 510

Thr Ser Arg Val Trp Glu Tyr Ser Ser Ile Gln Asn Ser Asp Asn
            515                 520                 525

Asp Leu Pro Val Val Gln Gly Ser Ser Phe Ser Leu Lys Gly Tyr
530                 535                 540

Pro Ser Leu Met Arg Ser Gln Ser Pro Lys Ala Gln Pro Gln Thr Trp
545                 550                 555                 560

Lys Ser Gly Lys Gln Thr Met Leu Ser His Tyr Arg Pro Phe Tyr Val
                565                 570                 575

Asn Lys Gly Asn Gly Ile Gly Ser Asn Glu Ala Pro
                580                 585

<210> SEQ ID NO 137
<211> LENGTH: 19
<212> TYPE: RNA
<213> ORGANISM: Homo Sapiens

<400> SEQUENCE: 137
gcaggaauuu ggugcauug                                                19

<210> SEQ ID NO 138
<211> LENGTH: 19
<212> TYPE: RNA
<213> ORGANISM: Homo Sapiens

<400> SEQUENCE: 138
gaucauggau gcucuggau                                                19

<210> SEQ ID NO 139
<211> LENGTH: 19
<212> TYPE: RNA

<213> ORGANISM: Homo Sapiens

<400> SEQUENCE: 139
gaagagauac uccauguac                                                        19

<210> SEQ ID NO 140
<211> LENGTH: 19
<212> TYPE: RNA
<213> ORGANISM: Homo Sapiens

<400> SEQUENCE: 140
ccagaagaau uucaacaau                                                        19

<210> SEQ ID NO 141
<211> LENGTH: 425
<212> TYPE: PRT
<213> ORGANISM: Homo Sapiens

<400> SEQUENCE: 141

```
Met Ala Ser Gly Gln Phe Val Asn Lys Leu Gln Glu Val Ile Cys
1               5                   10                  15

Pro Ile Cys Leu Asp Ile Leu Gln Lys Pro Val Thr Ile Asp Cys Gly
                20                  25                  30

His Asn Phe Cys Leu Lys Cys Ile Thr Gln Ile Gly Glu Thr Ser Cys
            35                  40                  45

Gly Phe Phe Lys Cys Pro Leu Cys Lys Thr Ser Val Arg Lys Asn Ala
        50                  55                  60

Ile Arg Phe Asn Ser Leu Leu Arg Asn Leu Val Glu Lys Ile Gln Ala
65                  70                  75                  80

Leu Gln Ala Ser Glu Val Gln Ser Lys Arg Lys Glu Ala Thr Cys Pro
                85                  90                  95

Arg His Gln Glu Met Phe His Tyr Phe Cys Glu Asp Asp Gly Lys Phe
            100                 105                 110

Leu Cys Phe Val Cys Arg Glu Ser Lys Asp His Lys Ser His Asn Val
        115                 120                 125

Ser Leu Ile Glu Glu Ala Ala Gln Asn Tyr Gln Gly Gln Ile Gln Glu
    130                 135                 140

Gln Ile Gln Val Leu Gln Gln Lys Glu Lys Glu Thr Val Gln Val Lys
145                 150                 155                 160

Ala Gln Gly Val His Arg Val Asp Val Phe Thr Asp Gln Val Glu His
                165                 170                 175

Glu Lys Gln Arg Ile Leu Thr Glu Phe Glu Leu Leu His Gln Val Leu
            180                 185                 190

Glu Glu Glu Lys Asn Phe Leu Leu Ser Arg Ile Tyr Trp Leu Gly His
        195                 200                 205

Glu Gly Thr Glu Ala Gly Lys His Tyr Val Ala Ser Thr Glu Pro Gln
    210                 215                 220

Leu Asn Asp Leu Lys Lys Leu Val Asp Ser Leu Lys Thr Lys Gln Asn
225                 230                 235                 240

Met Pro Pro Arg Gln Leu Leu Glu Asp Ile Lys Val Val Leu Cys Arg
                245                 250                 255

Ser Glu Glu Phe Gln Phe Leu Asn Pro Thr Pro Val Pro Leu Glu Leu
            260                 265                 270

Glu Lys Lys Leu Ser Glu Ala Lys Ser Arg His Asp Ser Ile Thr Gly
        275                 280                 285

Ser Leu Lys Lys Phe Lys Asp Gln Leu Gln Ala Asp Arg Lys Lys Asp
```

```
                290             295             300
Glu Asn Arg Phe Phe Lys Ser Met Asn Lys Asn Asp Met Lys Ser Trp
305                 310                 315                 320

Gly Leu Leu Gln Lys Asn Asn His Lys Met Asn Lys Thr Ser Glu Pro
            325                 330                 335

Gly Ser Ser Ala Gly Gly Arg Thr Thr Ser Gly Pro Pro Asn His
            340                 345                 350

His Ser Ser Ala Pro Ser His Ser Leu Phe Arg Ala Ser Ser Ala Gly
        355                 360                 365

Lys Val Thr Phe Pro Val Cys Leu Leu Ala Ser Tyr Asp Glu Ile Ser
    370                 375                 380

Gly Gln Gly Ala Ser Ser Gln Asp Thr Lys Thr Phe Asp Val Ala Leu
385                 390                 395                 400

Ser Glu Glu Leu His Ala Ala Leu Ser Glu Trp Leu Thr Ala Ile Arg
                405                 410                 415

Ala Trp Phe Cys Glu Val Pro Ser Ser
            420                 425

<210> SEQ ID NO 142
<211> LENGTH: 19
<212> TYPE: RNA
<213> ORGANISM: Homo Sapiens

<400> SEQUENCE: 142
cgaagaagcu gcccagaau                                              19

<210> SEQ ID NO 143
<211> LENGTH: 19
<212> TYPE: RNA
<213> ORGANISM: Homo Sapiens

<400> SEQUENCE: 143
ggagaagaau uuccugcua                                              19

<210> SEQ ID NO 144
<211> LENGTH: 19
<212> TYPE: RNA
<213> ORGANISM: Homo Sapiens

<400> SEQUENCE: 144
gaugagauuu cuggucaag                                              19

<210> SEQ ID NO 145
<211> LENGTH: 19
<212> TYPE: RNA
<213> ORGANISM: Homo Sapiens

<400> SEQUENCE: 145
gagccacagu ugaacgauc                                              19

<210> SEQ ID NO 146
<211> LENGTH: 653
<212> TYPE: PRT
<213> ORGANISM: Homo Sapiens

<400> SEQUENCE: 146

Met Ala Ala Ala Ala Ser His Leu Asn Leu Asp Ala Leu Arg Glu
1               5                   10                  15

Val Leu Glu Cys Pro Ile Cys Met Glu Ser Phe Thr Glu Glu Gln Leu
                20                  25                  30
```

```
Arg Pro Lys Leu Leu His Cys Gly His Thr Ile Cys Arg Gln Cys Leu
         35                  40                  45

Glu Lys Leu Leu Ala Ser Ser Ile Asn Gly Val Arg Cys Pro Phe Cys
 50                  55                  60

Ser Lys Ile Thr Arg Ile Thr Ser Leu Thr Gln Leu Thr Asp Asn Leu
 65              70                  75                      80

Thr Val Leu Lys Ile Ile Asp Thr Ala Gly Leu Ser Glu Ala Val Gly
                 85                  90                  95

Leu Leu Met Cys Arg Ser Cys Gly Arg Arg Leu Pro Arg Gln Phe Cys
             100                 105                 110

Arg Ser Cys Gly Leu Val Leu Cys Glu Pro Cys Arg Glu Ala Asp His
         115                 120                 125

Gln Pro Pro Gly His Cys Thr Leu Pro Val Lys Glu Ala Ala Glu Glu
     130                 135                 140

Arg Arg Arg Asp Phe Gly Glu Lys Leu Thr Arg Leu Arg Glu Leu Met
145                 150                 155                 160

Gly Glu Leu Gln Arg Arg Lys Ala Ala Leu Glu Gly Val Ser Lys Asp
                 165                 170                 175

Leu Gln Ala Arg Tyr Lys Ala Val Leu Gln Glu Tyr Gly His Glu Glu
             180                 185                 190

Arg Arg Val Gln Asp Glu Leu Ala Arg Ser Lys Phe Phe Thr Gly
         195                 200                 205

Ser Leu Ala Glu Val Glu Lys Ser Asn Ser Gln Val Glu Glu Gln
    210                 215                 220

Ser Tyr Leu Leu Asn Ile Ala Glu Val Gln Ala Val Ser Arg Cys Asp
225                 230                 235                 240

Tyr Phe Leu Ala Lys Ile Lys Gln Ala Asp Val Ala Leu Leu Glu Glu
                245                 250                 255

Thr Ala Asp Glu Glu Pro Glu Leu Thr Ala Ser Leu Pro Arg Glu
             260                 265                 270

Leu Thr Leu Gln Asp Val Glu Leu Leu Lys Val Gly His Val Gly Pro
    275                 280                 285

Leu Gln Ile Gly Gln Ala Val Lys Lys Pro Arg Thr Val Asn Val Glu
    290                 295                 300

Asp Ser Trp Ala Met Glu Ala Thr Ala Ser Ala Ala Ser Thr Ser Val
305                 310                 315                 320

Thr Phe Arg Glu Met Asp Met Ser Pro Glu Glu Val Val Ala Ser Pro
                325                 330                 335

Arg Ala Ser Pro Ala Lys Gln Arg Gly Pro Glu Ala Ala Ser Asn Ile
             340                 345                 350

Gln Gln Cys Leu Phe Leu Lys Lys Met Gly Ala Lys Gly Ser Thr Pro
         355                 360                 365

Gly Met Phe Asn Leu Pro Val Ser Leu Tyr Val Thr Ser Gln Gly Glu
    370                 375                 380

Val Leu Val Ala Asp Arg Gly Asn Tyr Arg Ile Gln Val Phe Thr Arg
385                 390                 395                 400

Lys Gly Phe Leu Lys Glu Ile Arg Arg Ser Pro Ser Gly Ile Asp Ser
                405                 410                 415

Phe Val Leu Ser Phe Leu Gly Ala Asp Leu Pro Asn Leu Thr Pro Leu
             420                 425                 430

Ser Val Ala Met Asn Cys Gln Gly Leu Ile Gly Val Thr Asp Ser Tyr
         435                 440                 445
```

Asp Asn Ser Leu Lys Val Tyr Thr Leu Asp Gly His Cys Val Ala Cys
450                 455                 460

His Arg Ser Gln Leu Ser Lys Pro Trp Gly Ile Thr Ala Leu Pro Ser
465                 470                 475                 480

Gly Gln Phe Val Val Thr Asp Val Glu Gly Gly Lys Leu Trp Cys Phe
                485                 490                 495

Thr Val Asp Arg Gly Ser Gly Val Val Lys Tyr Ser Cys Leu Cys Ser
            500                 505                 510

Ala Val Arg Pro Lys Phe Val Thr Cys Asp Ala Glu Gly Thr Val Tyr
        515                 520                 525

Phe Thr Gln Gly Leu Gly Leu Asn Leu Glu Asn Arg Gln Asn Glu His
530                 535                 540

His Leu Glu Gly Gly Phe Ser Ile Gly Ser Val Gly Pro Asp Gly Gln
545                 550                 555                 560

Leu Gly Arg Gln Ile Ser His Phe Phe Ser Glu Asn Glu Asp Phe Arg
                565                 570                 575

Cys Ile Ala Gly Met Cys Val Asp Ala Arg Gly Asp Leu Ile Val Ala
            580                 585                 590

Asp Ser Ser Arg Lys Glu Ile Leu His Phe Pro Lys Gly Gly Gly Tyr
        595                 600                 605

Ser Val Leu Ile Arg Glu Gly Leu Thr Cys Pro Val Gly Ile Ala Leu
610                 615                 620

Thr Pro Lys Gly Gln Leu Val Leu Asp Cys Trp Asp His Cys Ile
625                 630                 635                 640

Lys Ile Tyr Ser Tyr His Leu Arg Arg Tyr Ser Thr Pro
                645                 650

<210> SEQ ID NO 147
<211> LENGTH: 19
<212> TYPE: RNA
<213> ORGANISM: Homo Sapiens

<400> SEQUENCE: 147
gaucaggggu ggucaaaua                                                   19

<210> SEQ ID NO 148
<211> LENGTH: 19
<212> TYPE: RNA
<213> ORGANISM: Homo Sapiens

<400> SEQUENCE: 148
gcauagcccu aacuccuaa                                                   19

<210> SEQ ID NO 149
<211> LENGTH: 19
<212> TYPE: RNA
<213> ORGANISM: Homo Sapiens

<400> SEQUENCE: 149
gagcuguggu uugguguua                                                   19

<210> SEQ ID NO 150
<211> LENGTH: 19
<212> TYPE: RNA
<213> ORGANISM: Homo Sapiens

<400> SEQUENCE: 150
gugaaguacu agucgcuga                                                   19

<210> SEQ ID NO 151
<211> LENGTH: 1110
<212> TYPE: PRT
<213> ORGANISM: Homo Sapiens

<400> SEQUENCE: 151

```
Met Ala Glu Asn Lys Gly Gly Gly Glu Ala Glu Ser Gly Gly Gly Gly
1               5                   10                  15

Ser Gly Ser Ala Pro Val Thr Ala Gly Ala Gly Pro Ala Ala Gln
            20                  25                  30

Glu Ala Glu Pro Pro Leu Thr Ala Val Leu Val Glu Glu Glu Glu
        35                  40                  45

Glu Gly Gly Arg Ala Gly Ala Glu Gly Gly Ala Ala Gly Pro Asp Asp
    50                  55                  60

Gly Gly Val Ala Ala Ser Ser Gly Ser Ala Gln Ala Ala Ser Ser
65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Pro Gly Pro Ser Ala Gly
            100                 105                 110

Pro Pro Pro Gly Pro Pro Ala Ser Leu Leu Asp Thr Cys Ala Val Cys
        115                 120                 125

Gln Gln Ser Leu Gln Ser Arg Arg Glu Ala Glu Pro Lys Leu Leu Pro
    130                 135                 140

Cys Leu His Ser Phe Cys Leu Arg Cys Leu Pro Glu Pro Glu Arg Gln
145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
            180                 185                 190

Leu Val Asp Asn Tyr Phe Val Lys Asp Thr Ser Glu Ala Pro Ser Ser
        195                 200                 205

Ser Asp Glu Lys Ser Glu Gln Val Cys Thr Ser Cys Glu Asp Asn Ala
    210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
            260                 265                 270

Pro Val Phe Cys Pro Val His Lys Gln Glu Gln Leu Lys Leu Phe Cys
        275                 280                 285

Glu Thr Cys Asp Arg Leu Thr Cys Arg Asp Cys Gln Leu Leu Glu His
    290                 295                 300

Lys Glu His Arg Tyr Gln Phe Leu Glu Glu Ala Phe Gln Asn Gln Lys
305                 310                 315                 320

Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
            340                 345                 350

Glu Thr Asn Lys Arg Val Glu Gln Glu Ile Lys Val Ala Ile Phe Thr
        355                 360                 365

Leu Ile Asn Glu Ile Asn Lys Lys Gly Lys Ser Leu Leu Gln Gln Leu
    370                 375                 380
```

Glu Asn Val Thr Lys Glu Arg Gln Met Lys Leu Leu Gln Gln Asn
385                 390                 395                 400

Asp Ile Thr Gly Leu Ser Arg Gln Val Lys His Val Met Asn Phe Thr
            405                 410                 415

Asn Trp Ala Ile Ala Ser Gly Ser Thr Ala Leu Leu Tyr Ser Lys
            420                 425                 430

Arg Leu Ile Thr Phe Gln Leu Arg His Ile Leu Lys Ala Arg Cys Asp
            435                 440                 445

Pro Val Pro Ala Ala Asn Gly Ala Ile Arg Phe His Cys Asp Pro Thr
450                 455                 460

Phe Trp Ala Lys Asn Val Val Asn Leu Gly Asn Leu Val Ile Glu Ser
465                 470                 475                 480

Lys Pro Ala Pro Gly Tyr Thr Pro Asn Val Val Gly Gln Val Pro
                485                 490                 495

Pro Gly Thr Asn His Ile Ser Lys Thr Pro Gly Gln Ile Asn Leu Ala
            500                 505                 510

Gln Leu Arg Leu Gln His Met Gln Gln Val Tyr Ala Gln Lys His
            515                 520                 525

Gln Gln Leu Gln Gln Met Arg Met Gln Gln Pro Ala Pro Val Pro
530                 535                 540

Thr Thr Thr Thr Thr Thr Gln Gln His Pro Arg Gln Ala Ala Pro Gln
545                 550                 555                 560

Met Leu Gln Gln Gln Pro Arg Leu Ile Ser Val Gln Thr Met Gln
                565                 570                 575

Arg Gly Asn Met Asn Cys Gly Ala Phe Gln Ala His Gln Met Arg Leu
            580                 585                 590

Ala Gln Asn Ala Ala Arg Ile Pro Gly Ile Pro Arg His Ser Gly Pro
            595                 600                 605

Gln Tyr Ser Met Met Gln Pro His Leu Gln Arg Gln His Ser Asn Pro
    610                 615                 620

Gly His Ala Gly Pro Phe Pro Val Val Ser Val His Asn Thr Thr Ile
625                 630                 635                 640

Asn Pro Thr Ser Pro Thr Thr Ala Thr Met Ala Asn Ala Asn Arg Gly
            645                 650                 655

Pro Thr Ser Pro Ser Val Thr Ala Ile Glu Leu Ile Pro Ser Val Thr
            660                 665                 670

Asn Pro Glu Asn Leu Pro Ser Leu Pro Asp Ile Pro Pro Ile Gln Leu
            675                 680                 685

Glu Asp Ala Gly Ser Ser Leu Asp Asn Leu Leu Ser Arg Tyr Ile
690                 695                 700

Ser Gly Ser His Leu Pro Pro Gln Pro Thr Ser Thr Met Asn Pro Ser
705                 710                 715                 720

Pro Gly Pro Ser Ala Leu Ser Pro Gly Ser Ser Gly Leu Ser Asn Ser
            725                 730                 735

His Thr Pro Val Arg Pro Pro Ser Thr Ser Ser Thr Gly Ser Arg Gly
            740                 745                 750

Ser Cys Gly Ser Ser Gly Arg Thr Ala Glu Lys Thr Ser Leu Ser Phe
            755                 760                 765

Lys Ser Asp Gln Val Lys Val Lys Gln Glu Pro Gly Thr Glu Asp Glu
            770                 775                 780

Ile Cys Ser Phe Ser Gly Gly Val Lys Gln Glu Lys Thr Glu Asp Gly
785                 790                 795                 800

```
Arg Arg Ser Ala Cys Met Leu Ser Ser Pro Glu Ser Ser Leu Thr Pro
                805                 810                 815

Pro Leu Ser Thr Asn Leu His Leu Glu Ser Glu Leu Asp Ala Leu Ala
            820                 825                 830

Ser Leu Glu Asn His Val Lys Ile Glu Pro Ala Asp Met Asn Glu Ser
        835                 840                 845

Cys Lys Gln Ser Gly Leu Ser Ser Leu Val Asn Gly Lys Ser Pro Ile
    850                 855                 860

Arg Ser Leu Met His Arg Ser Ala Arg Ile Gly Gly Asp Gly Asn Asn
865                 870                 875                 880

Lys Asp Asp Asp Pro Asn Glu Asp Trp Cys Ala Val Cys Gln Asn Gly
                885                 890                 895

Gly Asp Leu Leu Cys Cys Glu Lys Cys Pro Lys Val Phe His Leu Thr
            900                 905                 910

Cys His Val Pro Thr Leu Leu Ser Phe Pro Ser Gly Asp Trp Ile Cys
        915                 920                 925

Thr Phe Cys Arg Asp Ile Gly Lys Pro Glu Val Glu Tyr Asp Cys Asp
    930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Glu Pro Val Pro Ala Ser Ile Pro Asn
            980                 985                 990

Tyr Tyr Lys Ile Ile Lys Lys Pro Met Asp Leu Ser Thr Val Lys Lys
        995                 1000                1005

Lys Leu Gln Lys Lys His Ser Gln His Tyr Gln Ile Pro Asp Asp
    1010                1015                1020

Phe Val Ala Asp Val Arg Leu Ile Phe Lys Asn Cys Glu Arg Phe
    1025                1030                1035

Asn Glu Ala Asp Ser Glu Val Ala Gln Ala Gly Lys Ala Val Ala
    1040                1045                1050

Leu Tyr Phe Glu Asp Lys Leu Thr Glu Ile Tyr Ser Asp Arg Thr
    1055                1060                1065

Phe Ala Pro Leu Pro Glu Phe Glu Gln Glu Glu Asp Asp Gly Glu
    1070                1075                1080

Val Thr Glu Asp Ser Asp Glu Asp Phe Ile Gln Pro Arg Arg Lys
    1085                1090                1095

Arg Leu Lys Ser Asp Glu Arg Pro Val His Ile Lys
    1100                1105                1110

<210> SEQ ID NO 152
<211> LENGTH: 19
<212> TYPE: RNA
<213> ORGANISM: Homo Sapiens

<400> SEQUENCE: 152
ggacaaacca cauuaguaa                                            19

<210> SEQ ID NO 153
<211> LENGTH: 19
<212> TYPE: RNA
<213> ORGANISM: Homo Sapiens

<400> SEQUENCE: 153
gcaagcgacu gauuacuuu                                            19
```

<210> SEQ ID NO 154
<211> LENGTH: 19
<212> TYPE: RNA
<213> ORGANISM: Homo Sapiens

<400> SEQUENCE: 154
ugaaacaugu gauagauug                                                    19

<210> SEQ ID NO 155
<211> LENGTH: 19
<212> TYPE: RNA
<213> ORGANISM: Homo Sapiens

<400> SEQUENCE: 155
gugauaauuu gcaacauag                                                    19

<210> SEQ ID NO 156
<211> LENGTH: 270
<212> TYPE: PRT
<213> ORGANISM: Homo Sapiens

<400> SEQUENCE: 156

Met Ala Ser Lys Ile Leu Leu Asn Val Gln Glu Val Thr Cys Pro
1               5                   10                  15

Ile Cys Leu Glu Leu Leu Thr Glu Pro Leu Ser Leu Asp Cys Gly His
                20                  25                  30

Ser Leu Cys Arg Ala Cys Ile Thr Val Ser Asn Lys Glu Ala Val Thr
        35                  40                  45

Ser Met Gly Gly Lys Ser Ser Cys Pro Val Cys Gly Ile Ser Tyr Ser
    50                  55                  60

Phe Glu His Leu Gln Ala Asn Gln His Leu Ala Asn Ile Val Glu Arg
65                  70                  75                  80

Leu Lys Glu Val Lys Leu Ser Pro Asp Asn Gly Lys Lys Arg Asp Leu
                85                  90                  95

Cys Asp His His Gly Glu Lys Leu Leu Leu Phe Cys Lys Glu Asp Arg
            100                 105                 110

Lys Val Ile Cys Trp Leu Cys Glu Arg Ser Gln Glu His Arg Gly His
        115                 120                 125

His Thr Val Leu Thr Glu Glu Val Phe Lys Glu Cys Gln Glu Lys Leu
    130                 135                 140

Gln Ala Val Leu Lys Arg Leu Lys Lys Glu Glu Glu Ala Glu Lys
145                 150                 155                 160

Leu Glu Ala Asp Ile Arg Glu Glu Lys Thr Ser Trp Lys Tyr Gln Val
                165                 170                 175

Gln Thr Glu Arg Gln Arg Ile Gln Thr Glu Phe Asp Gln Leu Arg Ser
            180                 185                 190

Ile Leu Asn Asn Glu Glu Gln Arg Glu Leu Gln Arg Leu Glu Glu Glu
        195                 200                 205

Glu Lys Lys Thr Leu Asp Lys Phe Ala Glu Ala Glu Asp Glu Leu Val
    210                 215                 220

Gln Gln Lys Gln Leu Val Arg Glu Leu Ile Ser Asp Val Glu Cys Arg
225                 230                 235                 240

Ser Gln Trp Ser Thr Met Glu Leu Leu Gln Asp Met Ser Gly Ile Met
                245                 250                 255

Lys Trp Cys Val Trp Val Ala Arg Ser Gly Ala Cys Glu Leu
            260                 265                 270

<210> SEQ ID NO 157
<211> LENGTH: 19
<212> TYPE: RNA
<213> ORGANISM: Homo Sapiens

<400> SEQUENCE: 157
gaaaagaaga cgcuggaua                                                19

<210> SEQ ID NO 158
<211> LENGTH: 19
<212> TYPE: RNA
<213> ORGANISM: Homo Sapiens

<400> SEQUENCE: 158
ggaggaagua uucaaggaa                                                19

<210> SEQ ID NO 159
<211> LENGTH: 19
<212> TYPE: RNA
<213> ORGANISM: Homo Sapiens

<400> SEQUENCE: 159
ugucggaguc aguggucaa                                                19

<210> SEQ ID NO 160
<211> LENGTH: 19
<212> TYPE: RNA
<213> ORGANISM: Homo Sapiens

<400> SEQUENCE: 160
aaaucuugcu uaacguaca                                                19

<210> SEQ ID NO 161
<211> LENGTH: 493
<212> TYPE: PRT
<213> ORGANISM: Homo Sapiens

<400> SEQUENCE: 161

Met Glu Arg Ser Pro Asp Val Ser Pro Gly Pro Ser Arg Ser Phe Lys
1               5                   10                  15

Glu Glu Leu Leu Cys Ala Val Cys Tyr Asp Pro Phe Arg Asp Ala Val
            20                  25                  30

Thr Leu Arg Cys Gly His Asn Phe Cys Arg Gly Cys Val Ser Arg Cys
        35                  40                  45

Trp Glu Val Gln Val Ser Pro Thr Cys Pro Val Cys Lys Asp Arg Ala
    50                  55                  60

Ser Pro Ala Asp Leu Arg Thr Asn His Thr Leu Asn Asn Leu Val Glu
65                  70                  75                  80

Lys Leu Leu Arg Glu Glu Ala Glu Gly Ala Arg Trp Thr Ser Tyr Arg
                85                  90                  95

Phe Ser Arg Val Cys Arg Leu His Arg Gly Gln Leu Ser Leu Phe Cys
            100                 105                 110

Leu Glu Asp Lys Glu Leu Leu Cys Cys Ser Cys Gln Ala Asp Pro Arg
        115                 120                 125

His Gln Gly His Arg Val Gln Pro Val Lys Asp Thr Ala His Asp Phe
    130                 135                 140

Arg Ala Lys Cys Arg Asn Met Glu His Ala Leu Arg Glu Lys Ala Lys
145                 150                 155                 160

Ala Phe Trp Ala Met Arg Arg Ser Tyr Glu Ala Ile Ala Lys His Asn
            165                 170                 175

Gln Val Glu Ala Ala Trp Leu Glu Gly Arg Ile Arg Gln Glu Phe Asp
        180                 185                 190

Lys Leu Arg Glu Phe Leu Arg Val Glu Glu Gln Ala Ile Leu Asp Ala
    195                 200                 205

Met Ala Glu Glu Thr Arg Gln Lys Gln Leu Leu Ala Asp Glu Lys Met
210                 215                 220

Lys Gln Leu Thr Glu Thr Glu Val Leu His Glu Ile Glu Arg
225                 230                 235                 240

Leu Gln Met Glu Met Lys Glu Asp Asp Val Ser Phe Leu Met Lys His
                245                 250                 255

Lys Ser Arg Lys Arg Arg Leu Phe Cys Thr Met Glu Pro Glu Pro Val
            260                 265                 270

Gln Pro Gly Met Leu Ile Asp Val Cys Lys Tyr Leu Gly Ser Leu Gln
        275                 280                 285

Tyr Arg Val Trp Lys Lys Met Leu Ala Ser Val Glu Ser Val Pro Phe
    290                 295                 300

Ser Phe Asp Pro Asn Thr Ala Ala Gly Trp Leu Ser Val Ser Asp Asp
305                 310                 315                 320

Leu Thr Ser Val Thr Asn His Gly Tyr Arg Val Gln Val Glu Asn Pro
                325                 330                 335

Glu Arg Phe Ser Ser Ala Pro Cys Leu Leu Gly Ser Arg Val Phe Ser
            340                 345                 350

Gln Gly Ser His Ala Trp Glu Val Ala Leu Gly Leu Gln Ser Trp
        355                 360                 365

Arg Val Gly Val Val Arg Val Arg Gln Asp Ser Gly Ala Glu Gly His
    370                 375                 380

Ser His Ser Cys Tyr His Asp Thr Arg Ser Gly Phe Trp Tyr Val Cys
385                 390                 395                 400

Arg Thr Gln Gly Val Glu Gly Asp His Cys Val Thr Ser Asp Pro Ala
                405                 410                 415

Thr Ser Pro Leu Val Leu Ala Ile Pro Arg Arg Leu Arg Val Glu Leu
            420                 425                 430

Glu Cys Glu Glu Gly Glu Leu Ser Phe Tyr Asp Ala Glu Arg His Cys
        435                 440                 445

His Leu Tyr Thr Phe His Ala Arg Phe Gly Glu Val Arg Pro Tyr Phe
    450                 455                 460

Tyr Leu Gly Gly Ala Arg Gly Ala Gly Pro Pro Glu Pro Leu Arg Ile
465                 470                 475                 480

Cys Pro Leu His Ile Ser Val Lys Glu Glu Leu Asp Gly
                485                 490

<210> SEQ ID NO 162
<211> LENGTH: 19
<212> TYPE: RNA
<213> ORGANISM: Homo Sapiens

<400> SEQUENCE: 162
gaccugcgca ccaaccaca                                                    19

<210> SEQ ID NO 163
<211> LENGTH: 19
<212> TYPE: RNA
<213> ORGANISM: Homo Sapiens

```
<400> SEQUENCE: 163
acaaggagcu gcugugcug                                                19

<210> SEQ ID NO 164
<211> LENGTH: 19
<212> TYPE: RNA
<213> ORGANISM: Homo Sapiens

<400> SEQUENCE: 164
ccaccugccc agugugcaa                                                19

<210> SEQ ID NO 165
<211> LENGTH: 19
<212> TYPE: RNA
<213> ORGANISM: Homo Sapiens

<400> SEQUENCE: 165
gugcagccgg ugaaggaca                                                19

<210> SEQ ID NO 166
<211> LENGTH: 728
<212> TYPE: PRT
<213> ORGANISM: Homo Sapiens

<400> SEQUENCE: 166
```

Met Ser Glu Ser Gly Glu Met Ser Glu Phe Gly Tyr Ile Met Glu Leu
1               5                   10                  15

Ile Ala Lys Gly Lys Val Thr Ile Lys Asn Ile Glu Arg Glu Leu Ile
            20                  25                  30

Cys Pro Ala Cys Lys Glu Leu Phe Thr His Pro Leu Ile Leu Pro Cys
        35                  40                  45

Gln His Ser Ile Cys His Lys Cys Val Lys Glu Leu Leu Leu Thr Leu
    50                  55                  60

Asp Asp Ser Phe Asn Asp Val Gly Ser Asp Asn Ser Asn Gln Ser Ser
65                  70                  75                  80

Pro Arg Leu Arg Leu Pro Ser Pro Ser Met Asp Lys Ile Asp Arg Ile
                85                  90                  95

Asn Arg Pro Gly Trp Lys Arg Asn Ser Leu Thr Pro Arg Thr Thr Val
            100                 105                 110

Phe Pro Cys Pro Gly Cys Glu His Asp Val Asp Leu Gly Glu Arg Gly
        115                 120                 125

Ile Asn Gly Leu Phe Arg Asn Phe Thr Leu Glu Thr Ile Val Glu Arg
    130                 135                 140

Tyr Arg Gln Ala Ala Arg Ala Ala Thr Ala Ile Met Cys Asp Leu Cys
145                 150                 155                 160

Lys Pro Pro Pro Gln Glu Ser Thr Lys Ser Cys Met Asp Cys Ser Ala
                165                 170                 175

Ser Tyr Cys Asn Glu Cys Phe Lys Ile His His Pro Trp Gly Thr Ile
            180                 185                 190

Lys Ala Gln His Glu Tyr Val Gly Pro Thr Thr Asn Phe Arg Pro Lys
        195                 200                 205

Ile Leu Met Cys Pro Glu His Glu Thr Glu Arg Ile Asn Met Tyr Cys
    210                 215                 220

Glu Leu Cys Arg Arg Pro Val Cys His Leu Cys Lys Leu Gly Gly Asn
225                 230                 235                 240

His Ala Asn His Arg Val Thr Thr Met Ser Ser Ala Tyr Lys Thr Leu
                245                 250                 255

-continued

Lys Glu Lys Leu Ser Lys Asp Ile Asp Tyr Leu Ile Gly Lys Glu Ser
            260                 265                 270

Gln Val Lys Ser Gln Ile Ser Glu Leu Asn Leu Leu Met Lys Glu Thr
        275                 280                 285

Glu Cys Asn Gly Glu Arg Ala Lys Glu Ala Ile Thr His Phe Glu
    290                 295                 300

Lys Leu Phe Glu Val Leu Glu Glu Arg Lys Ser Ser Val Leu Lys Ala
305                 310                 315                 320

Ile Asp Ser Ser Lys Lys Leu Arg Leu Asp Lys Phe Gln Thr Gln Met
                325                 330                 335

Glu Glu Tyr Gln Gly Leu Leu Glu Asn Asn Gly Leu Val Gly Tyr Ala
            340                 345                 350

Gln Glu Val Leu Lys Glu Thr Asp Gln Ser Cys Phe Val Gln Thr Ala
        355                 360                 365

Lys Gln Leu His Leu Arg Ile Gln Lys Ala Thr Glu Ser Leu Lys Ser
    370                 375                 380

Phe Arg Pro Ala Ala Gln Thr Ser Phe Glu Asp Tyr Val Val Asn Thr
385                 390                 395                 400

Ser Lys Gln Thr Glu Leu Leu Gly Glu Leu Ser Phe Phe Ser Ser Gly
                405                 410                 415

Ile Asp Val Pro Glu Ile Asn Glu Glu Gln Ser Lys Val Tyr Asn Asn
            420                 425                 430

Ala Leu Ile Asn Trp His His Pro Glu Lys Asp Lys Ala Asp Ser Tyr
        435                 440                 445

Val Leu Glu Tyr Arg Lys Ile Asn Arg Asp Asp Glu Met Ser Trp Asn
    450                 455                 460

Glu Ile Glu Val Cys Gly Thr Ser Lys Ile Ile Gln Asp Leu Glu Asn
465                 470                 475                 480

Ser Ser Thr Tyr Ala Phe Arg Val Arg Ala Tyr Lys Gly Ser Ile Cys
                485                 490                 495

Ser Pro Cys Ser Arg Glu Leu Ile Leu His Thr Pro Ala Pro Val
            500                 505                 510

Phe Ser Phe Leu Phe Asp Glu Lys Cys Gly Tyr Asn Asn Glu His Leu
        515                 520                 525

Leu Leu Asn Leu Lys Arg Asp Arg Val Glu Ser Arg Ala Gly Phe Asn
    530                 535                 540

Leu Leu Leu Ala Ala Glu Arg Ile Gln Val Gly Tyr Tyr Thr Ser Leu
545                 550                 555                 560

Asp Tyr Ile Ile Gly Asp Thr Gly Ile Thr Lys Gly Lys His Phe Trp
                565                 570                 575

Ala Phe Arg Val Glu Pro Tyr Ser Tyr Leu Val Lys Val Gly Val Ala
            580                 585                 590

Ser Ser Asp Lys Leu Gln Glu Trp Leu Arg Ser Pro Arg Asp Ala Val
        595                 600                 605

Ser Pro Arg Tyr Glu Gln Asp Ser Gly His Asp Ser Gly Ser Glu Asp
    610                 615                 620

Ala Cys Phe Asp Ser Ser Gln Pro Phe Thr Leu Val Thr Ile Gly Met
625                 630                 635                 640

Gln Lys Phe Phe Ile Pro Lys Ser Pro Thr Ser Ser Asn Glu Pro Glu
                645                 650                 655

Asn Arg Val Leu Pro Met Pro Thr Ser Ile Gly Ile Phe Leu Asp Cys
            660                 665                 670

```
Asp Lys Gly Lys Val Asp Phe Tyr Asp Met Asp Gln Met Lys Cys Leu
            675                 680                 685

Tyr Glu Arg Gln Val Asp Cys Ser His Thr Leu Tyr Pro Ala Phe Ala
            690                 695                 700

Leu Met Gly Ser Gly Gly Ile Gln Leu Glu Glu Pro Ile Thr Ala Lys
705                 710                 715                 720

Tyr Leu Glu Tyr Gln Glu Asp Met
                725

<210> SEQ ID NO 167
<211> LENGTH: 964
<212> TYPE: PRT
<213> ORGANISM: Homo Sapiens

<400> SEQUENCE: 167

Met Asp Glu Gln Ser Val Glu Ser Ile Ala Glu Val Phe Arg Cys Phe
1               5                   10                  15

Ile Cys Met Glu Lys Leu Arg Asp Ala Arg Leu Cys Pro His Cys Ser
                20                  25                  30

Lys Leu Cys Cys Phe Ser Cys Ile Arg Arg Trp Leu Thr Glu Gln Arg
            35                  40                  45

Ala Gln Cys Pro His Cys Arg Ala Pro Leu Gln Leu Arg Glu Leu Val
        50                  55                  60

Asn Cys Arg Trp Ala Glu Glu Val Thr Gln Gln Leu Asp Thr Leu Gln
65                  70                  75                  80

Leu Cys Ser Leu Thr Lys His Glu Glu Asn Glu Lys Asp Lys Cys Glu
                85                  90                  95

Asn His His Glu Lys Leu Ser Val Phe Cys Trp Thr Cys Lys Lys Cys
                100                 105                 110

Ile Cys His Gln Cys Ala Leu Trp Gly Gly Met His Gly Gly His Thr
            115                 120                 125

Phe Lys Pro Leu Ala Glu Ile Tyr Glu Gln His Val Thr Lys Val Asn
        130                 135                 140

Glu Glu Val Ala Lys Leu Arg Arg Arg Leu Met Glu Leu Ile Ser Leu
145                 150                 155                 160

Val Gln Glu Val Glu Arg Asn Val Glu Ala Val Arg Asn Ala Lys Asp
                165                 170                 175

Glu Arg Val Arg Glu Ile Arg Asn Ala Val Glu Met Met Ile Ala Arg
            180                 185                 190

Leu Asp Thr Gln Leu Lys Asn Lys Leu Ile Thr Leu Met Gly Gln Lys
        195                 200                 205

Thr Ser Leu Thr Gln Glu Thr Glu Leu Leu Glu Ser Leu Leu Gln Glu
210                 215                 220

Val Glu His Gln Leu Arg Ser Cys Ser Lys Ser Glu Leu Ile Ser Lys
225                 230                 235                 240

Ser Ser Glu Ile Leu Met Met Phe Gln Gln Val His Arg Lys Pro Met
                245                 250                 255

Ala Ser Phe Val Thr Thr Pro Val Pro Pro Asp Phe Thr Ser Glu Leu
            260                 265                 270

Val Pro Ser Tyr Asp Ser Ala Thr Phe Val Leu Glu Asn Phe Ser Thr
        275                 280                 285

Leu Arg Gln Arg Ala Asp Pro Val Tyr Ser Pro Leu Gln Val Ser
    290                 295                 300

Gly Leu Cys Trp Arg Leu Lys Val Tyr Pro Asp Gly Asn Gly Val Val
305                 310                 315                 320
```

```
Arg Gly Tyr Tyr Leu Ser Val Phe Leu Glu Leu Ser Ala Gly Leu Pro
            325                 330                 335
Glu Thr Ser Lys Tyr Glu Tyr Arg Val Glu Met Val His Gln Ser Cys
            340                 345                 350
Asn Asp Pro Thr Lys Asn Ile Ile Arg Glu Phe Ala Ser Asp Phe Glu
            355                 360                 365
Val Gly Glu Cys Trp Gly Tyr Asn Arg Phe Phe Arg Leu Asp Leu Leu
    370                 375                 380
Ala Asn Glu Gly Tyr Leu Asn Pro Gln Asn Asp Thr Val Ile Leu Arg
385                 390                 395                 400
Phe Gln Val Arg Ser Pro Thr Phe Phe Gln Lys Ser Arg Asp Gln His
                405                 410                 415
Trp Tyr Ile Thr Gln Leu Glu Ala Ala Gln Thr Ser Tyr Ile Gln Gln
                420                 425                 430
Ile Asn Asn Leu Lys Glu Arg Leu Thr Ile Glu Leu Ser Arg Thr Gln
                435                 440                 445
Lys Ser Arg Asp Leu Ser Pro Pro Asp Asn His Leu Ser Pro Gln Asn
    450                 455                 460
Asp Asp Ala Leu Glu Thr Arg Ala Lys Lys Ser Ala Cys Ser Asp Met
465                 470                 475                 480
Leu Leu Glu Gly Gly Pro Thr Thr Ala Ser Val Arg Glu Ala Lys Glu
                485                 490                 495
Asp Glu Glu Asp Glu Glu Lys Ile Gln Asn Glu Asp Tyr His His Glu
                500                 505                 510
Leu Ser Asp Gly Asp Leu Asp Leu Val Tyr Glu Asp Glu Val
    515                 520                 525
Asn Gln Leu Asp Gly Ser Ser Ser Ala Ser Ser Thr Ala Thr Ser
    530                 535                 540
Asn Thr Glu Glu Asn Asp Ile Asp Glu Glu Thr Met Ser Gly Glu Asn
545                 550                 555                 560
Asp Val Glu Tyr Asn Asn Met Glu Leu Glu Glu Gly Glu Leu Met Glu
                565                 570                 575
Asp Ala Ala Ala Gly Pro Ala Gly Ser Ser His Gly Tyr Val Gly
                580                 585                 590
Ser Ser Ser Arg Ile Ser Arg Arg Thr His Leu Cys Ser Ala Ala Thr
    595                 600                 605
Ser Ser Leu Leu Asp Ile Asp Pro Leu Ile Leu Ile His Leu Leu Asp
    610                 615                 620
Leu Lys Asp Arg Ser Ser Ile Glu Asn Leu Trp Gly Leu Gln Pro Arg
625                 630                 635                 640
Pro Pro Ala Ser Leu Leu Gln Pro Thr Ala Ser Tyr Ser Arg Lys Asp
                645                 650                 655
Lys Asp Gln Arg Lys Gln Gln Ala Met Trp Arg Val Pro Ser Asp Leu
                660                 665                 670
Lys Met Leu Lys Arg Leu Lys Thr Gln Met Ala Glu Val Arg Cys Met
                675                 680                 685
Lys Thr Asp Val Lys Asn Thr Leu Ser Glu Ile Lys Ser Ser Ser Ala
                690                 695                 700
Ala Ser Gly Asp Met Gln Thr Ser Leu Phe Ser Ala Asp Gln Ala Ala
705                 710                 715                 720
Leu Ala Ala Cys Gly Thr Glu Asn Ser Gly Arg Leu Gln Asp Leu Gly
                725                 730                 735
```

```
Met Glu Leu Leu Ala Lys Ser Ser Val Ala Asn Cys Tyr Ile Arg Asn
                740                 745                 750

Ser Thr Asn Lys Lys Ser Asn Ser Pro Lys Pro Ala Arg Ser Ser Val
        755                 760                 765

Ala Gly Ser Leu Ser Leu Arg Arg Ala Val Asp Pro Gly Glu Asn Ser
    770                 775                 780

Arg Ser Lys Gly Asp Cys Gln Thr Leu Ser Glu Gly Ser Pro Gly Ser
785                 790                 795                 800

Ser Gln Ser Gly Ser Arg His Ser Ser Pro Arg Ala Leu Ile His Gly
                805                 810                 815

Ser Ile Gly Asp Ile Leu Pro Lys Thr Glu Asp Arg Gln Cys Lys Ala
            820                 825                 830

Leu Asp Ser Asp Ala Val Val Val Ala Val Phe Ser Gly Leu Pro Ala
        835                 840                 845

Val Glu Lys Arg Arg Lys Met Val Thr Leu Gly Ala Asn Ala Lys Gly
    850                 855                 860

Gly His Leu Glu Gly Leu Gln Met Thr Asp Leu Glu Asn Asn Ser Glu
865                 870                 875                 880

Thr Gly Glu Leu Gln Pro Val Leu Pro Glu Gly Ala Ser Ala Ala Pro
                885                 890                 895

Glu Glu Gly Met Ser Ser Asp Ser Asp Ile Glu Cys Asp Thr Glu Asn
            900                 905                 910

Glu Glu Gln Glu Glu His Thr Ser Val Gly Gly Phe His Asp Ser Phe
        915                 920                 925

Met Val Met Thr Gln Pro Pro Asp Glu Asp Thr His Ser Ser Phe Pro
    930                 935                 940

Asp Gly Glu Gln Ile Gly Pro Glu Asp Leu Ser Phe Asn Thr Asp Glu
945                 950                 955                 960

Asn Ser Gly Arg

<210> SEQ ID NO 168
<211> LENGTH: 19
<212> TYPE: RNA
<213> ORGANISM: Homo Sapiens

<400> SEQUENCE: 168
ggacauaccu uuaaaccuu                                               19

<210> SEQ ID NO 169
<211> LENGTH: 19
<212> TYPE: RNA
<213> ORGANISM: Homo Sapiens

<400> SEQUENCE: 169
acacacagcu gaagaauaa                                               19

<210> SEQ ID NO 170
<211> LENGTH: 19
<212> TYPE: RNA
<213> ORGANISM: Homo Sapiens

<400> SEQUENCE: 170
gcagaugacu gauuuggaa                                               19

<210> SEQ ID NO 171
<211> LENGTH: 19
<212> TYPE: RNA
<213> ORGANISM: Homo Sapiens
```

<400> SEQUENCE: 171
uacgagaacu aguaaauug                                                        19

<210> SEQ ID NO 172
<211> LENGTH: 465
<212> TYPE: PRT
<213> ORGANISM: Homo Sapiens

<400> SEQUENCE: 172

Met Ala Ser Thr Thr Ser Thr Lys Lys Met Met Glu Glu Ala Thr Cys
1               5                   10                  15

Ser Ile Cys Leu Ser Leu Met Thr Asn Pro Val Ser Ile Asn Cys Gly
            20                  25                  30

His Ser Tyr Cys His Leu Cys Ile Thr Asp Phe Phe Lys Asn Pro Ser
        35                  40                  45

Gln Lys Gln Leu Arg Gln Glu Thr Phe Cys Cys Pro Gln Cys Arg Ala
    50                  55                  60

Pro Phe His Met Asp Ser Leu Arg Pro Asn Lys Gln Leu Gly Ser Leu
65                  70                  75                  80

Ile Glu Ala Leu Lys Glu Thr Asp Gln Glu Met Ser Cys Glu Glu His
                85                  90                  95

Gly Glu Gln Phe His Leu Phe Cys Glu Asp Glu Gly Gln Leu Ile Cys
            100                 105                 110

Trp Arg Cys Glu Arg Ala Pro Gln His Lys Gly His Thr Thr Ala Leu
        115                 120                 125

Val Glu Asp Val Cys Gln Gly Tyr Lys Glu Lys Leu Gln Lys Ala Val
    130                 135                 140

Thr Lys Leu Lys Gln Leu Glu Asp Arg Cys Thr Glu Gln Lys Leu Ser
145                 150                 155                 160

Thr Ala Met Arg Ile Thr Lys Trp Lys Glu Lys Val Gln Ile Gln Arg
                165                 170                 175

Gln Lys Ile Arg Ser Asp Phe Lys Asn Leu Gln Cys Phe Leu His Glu
            180                 185                 190

Glu Glu Lys Ser Tyr Leu Trp Arg Leu Glu Lys Glu Gln Gln Thr
        195                 200                 205

Leu Ser Arg Leu Arg Asp Tyr Glu Ala Gly Leu Gly Leu Lys Ser Asn
    210                 215                 220

Glu Leu Lys Ser His Ile Leu Glu Leu Glu Glu Lys Cys Gln Gly Ser
225                 230                 235                 240

Ala Gln Lys Leu Leu Gln Asn Val Asn Asp Thr Leu Ser Arg Ser Trp
                245                 250                 255

Ala Val Lys Leu Glu Thr Ser Glu Ala Val Ser Leu Glu Leu His Thr
            260                 265                 270

Met Cys Asn Val Ser Lys Leu Tyr Phe Asp Val Lys Lys Met Leu Arg
        275                 280                 285

Ser His Gln Val Ser Val Thr Leu Asp Pro Asp Thr Ala His His Glu
    290                 295                 300

Leu Ile Leu Ser Glu Asp Arg Arg Gln Val Thr Arg Gly Tyr Thr Gln
305                 310                 315                 320

Glu Asn Gln Asp Thr Ser Ser Arg Arg Phe Thr Ala Phe Pro Cys Val
                325                 330                 335

Leu Gly Cys Glu Gly Phe Thr Ser Gly Arg Arg Tyr Phe Glu Val Asp
            340                 345                 350

| | | | | | | | | | | | |
|---|---|---|---|---|---|---|---|---|---|---|---|
|Val|Gly|Glu|Gly|Thr|Gly|Trp|Asp|Leu|Gly|Val|Cys|Met|Glu|Asn|Val|
| | |355| | | |360| | | |365| |

Gln Arg Gly Thr Gly Met Lys Gln Glu Pro Gln Ser Gly Phe Trp Thr
       370                 375                 380

Leu Arg Leu Cys Lys Lys Lys Gly Tyr Val Ala Leu Thr Ser Pro Pro
385                 390                 395                 400

Thr Ser Leu His Leu His Glu Gln Pro Leu Leu Val Gly Ile Phe Leu
               405                 410                 415

Asp Tyr Glu Ala Gly Val Val Ser Phe Tyr Asn Gly Asn Thr Gly Cys
               420                 425                 430

His Ile Phe Thr Phe Pro Lys Ala Ser Phe Ser Asp Thr Leu Arg Pro
               435                 440                 445

Tyr Phe Gln Val Tyr Gln Tyr Ser Pro Leu Phe Leu Pro Pro Pro Gly
   450                 455                 460

Asp
465

<210> SEQ ID NO 173
<211> LENGTH: 19
<212> TYPE: RNA
<213> ORGANISM: Homo Sapiens

<400> SEQUENCE: 173
gcgaauaacu aaauggaaa                                              19

<210> SEQ ID NO 174
<211> LENGTH: 19
<212> TYPE: RNA
<213> ORGANISM: Homo Sapiens

<400> SEQUENCE: 174
agaaauugcu gcagaaugu                                              19

<210> SEQ ID NO 175
<211> LENGTH: 19
<212> TYPE: RNA
<213> ORGANISM: Homo Sapiens

<400> SEQUENCE: 175
caacuugaag acagaugua                                              19

<210> SEQ ID NO 176
<211> LENGTH: 19
<212> TYPE: RNA
<213> ORGANISM: Homo Sapiens

<400> SEQUENCE: 176
agauacagcu caucacgaa                                              19

<210> SEQ ID NO 177
<211> LENGTH: 488
<212> TYPE: PRT
<213> ORGANISM: Homo Sapiens

<400> SEQUENCE: 177

Met Ala Glu Thr Ser Leu Leu Glu Ala Gly Ala Ser Ala Ala Ser Thr
1               5                   10                  15

Ala Ala Ala Leu Glu Asn Leu Gln Val Glu Ala Ser Cys Ser Val Cys
            20                  25                  30

Leu Glu Tyr Leu Lys Glu Pro Val Ile Ile Glu Cys Gly His Asn Phe

```
                35                  40                  45
Cys Lys Ala Cys Ile Thr Arg Trp Trp Glu Asp Leu Glu Arg Asp Phe
             50                  55                  60

Pro Cys Pro Val Cys Arg Lys Thr Ser Arg Tyr Arg Ser Leu Arg Pro
 65                  70                  75                  80

Asn Arg Gln Leu Gly Ser Met Val Glu Ile Ala Lys Gln Leu Gln Ala
                     85                  90                  95

Val Lys Arg Lys Ile Arg Asp Glu Ser Leu Cys Pro Gln His His Glu
                100                 105                 110

Ala Leu Ser Leu Phe Cys Tyr Glu Asp Gln Glu Ala Val Cys Leu Ile
                115                 120                 125

Cys Ala Ile Ser His Thr His Arg Ala His Thr Val Val Pro Leu Asp
            130                 135                 140

Asp Ala Thr Gln Glu Tyr Lys Glu Lys Leu Gln Lys Cys Leu Glu Pro
145                 150                 155                 160

Leu Glu Gln Lys Leu Gln Glu Ile Thr Arg Cys Lys Ser Ser Glu Glu
                165                 170                 175

Lys Lys Pro Gly Glu Leu Lys Arg Leu Val Glu Ser Arg Arg Gln Gln
            180                 185                 190

Ile Leu Arg Glu Phe Glu Leu His Arg Arg Leu Asp Glu Glu Gln
            195                 200                 205

Gln Val Leu Leu Ser Arg Leu Glu Glu Glu Gln Asp Ile Leu Gln
210                 215                 220

Arg Leu Arg Glu Asn Ala Ala His Leu Gly Asp Lys Arg Arg Asp Leu
225                 230                 235                 240

Ala His Leu Ala Ala Glu Val Glu Gly Lys Cys Leu Gln Ser Gly Phe
                245                 250                 255

Glu Met Leu Lys Asp Val Lys Ser Thr Leu Glu Lys Cys Glu Lys Val
                260                 265                 270

Lys Thr Met Glu Val Thr Ser Val Ser Ile Glu Leu Glu Lys Asn Phe
            275                 280                 285

Ser Asn Phe Pro Arg Gln Tyr Phe Ala Leu Arg Lys Ile Leu Lys Gln
290                 295                 300

Leu Ile Ala Asp Val Thr Leu Asp Pro Glu Thr Ala His Pro Asn Leu
305                 310                 315                 320

Val Leu Ser Glu Asp Arg Lys Ser Val Lys Phe Val Glu Thr Arg Leu
                325                 330                 335

Arg Asp Leu Pro Asp Thr Pro Arg Arg Phe Thr Phe Tyr Pro Cys Val
            340                 345                 350

Leu Ala Thr Glu Gly Phe Thr Ser Gly Arg His Tyr Trp Glu Val Glu
            355                 360                 365

Val Gly Asp Lys Thr His Trp Ala Val Gly Val Cys Arg Asp Ser Val
            370                 375                 380

Ser Arg Lys Gly Glu Leu Thr Pro Leu Pro Glu Thr Gly Tyr Trp Arg
385                 390                 395                 400

Val Arg Leu Trp Asn Gly Asp Lys Tyr Ala Ala Thr Thr Thr Pro Phe
                405                 410                 415

Thr Pro Leu His Ile Lys Val Lys Pro Lys Arg Val Gly Ile Phe Leu
            420                 425                 430

Asp Tyr Glu Ala Gly Thr Leu Ser Phe Tyr Asn Val Thr Asp Arg Ser
            435                 440                 445

His Ile Tyr Thr Phe Thr Asp Thr Phe Thr Glu Lys Leu Trp Pro Leu
450                 455                 460
```

Phe Tyr Pro Gly Ile Arg Ala Gly Arg Lys Asn Ala Ala Pro Leu Thr
465                 470                 475                 480

Ile Arg Pro Pro Thr Asp Trp Glu
                485

<210> SEQ ID NO 178
<211> LENGTH: 19
<212> TYPE: RNA
<213> ORGANISM: Homo Sapiens

<400> SEQUENCE: 178
gaaggaaccu gucaucauu                                                      19

<210> SEQ ID NO 179
<211> LENGTH: 19
<212> TYPE: RNA
<213> ORGANISM: Homo Sapiens

<400> SEQUENCE: 179
ugacuucagu auccauaga                                                      19

<210> SEQ ID NO 180
<211> LENGTH: 19
<212> TYPE: RNA
<213> ORGANISM: Homo Sapiens

<400> SEQUENCE: 180
gcuucgagau gcuuaagga                                                      19

<210> SEQ ID NO 181
<211> LENGTH: 19
<212> TYPE: RNA
<213> ORGANISM: Homo Sapiens

<400> SEQUENCE: 181
aggguaaggu ugcgauuau                                                      19

<210> SEQ ID NO 182
<211> LENGTH: 229
<212> TYPE: PRT
<213> ORGANISM: Homo Sapiens

<400> SEQUENCE: 182

Met Ile Pro Leu Gln Lys Asp Asn Gln Glu Glu Gly Val Cys Pro Ile
1               5                   10                  15

Cys Gln Glu Ser Leu Lys Glu Ala Val Ser Thr Asn Cys Gly His Leu
                20                  25                  30

Phe Cys Arg Val Cys Leu Thr Gln His Val Glu Lys Ala Ser Ala Ser
            35                  40                  45

Gly Val Phe Cys Cys Pro Leu Cys Arg Lys Pro Cys Ser Glu Glu Val
        50                  55                  60

Leu Gly Thr Gly Tyr Ile Cys Pro Asn His Gln Lys Arg Val Cys Arg
65                  70                  75                  80

Phe Cys Glu Glu Ser Arg Leu Leu Leu Cys Val Glu Cys Leu Val Ser
                85                  90                  95

Pro Glu His Met Ser His His Glu Leu Thr Ile Glu Asn Ala Leu Ser
                100                 105                 110

His Tyr Lys Glu Arg Leu Asn Arg Arg Ser Arg Lys Leu Arg Lys Asp
            115                 120                 125

Ile Ala Glu Leu Gln Arg Leu Lys Ala Gln Gln Glu Lys Lys Leu Gln
130                 135                 140

Ala Leu Gln Gln Trp Leu Gly Gln Leu Glu His Met Pro Ala Glu Ala
145                 150                 155                 160

Ala Arg Ile Leu Asp Ile Ser Arg Ala Val Thr Gln Leu Arg Ser Leu
            165                 170                 175

Val Ile Asp Leu Glu Arg Thr Ala Lys Glu Leu Asp Thr Asn Thr Leu
            180                 185                 190

Lys Asn Ala Gly Asp Leu Leu Asn Arg Ser Ala Pro Gln Lys Leu Glu
            195                 200                 205

Val Ile Tyr Pro Gln Leu Glu Lys Gly Val Ser Glu Leu Leu Leu Gln
210                 215                 220

Pro Pro Gln Lys Leu
225

<210> SEQ ID NO 183
<211> LENGTH: 19
<212> TYPE: RNA
<213> ORGANISM: Homo Sapiens

<400> SEQUENCE: 183
ccacagaaau uagagguua                                            19

<210> SEQ ID NO 184
<211> LENGTH: 19
<212> TYPE: RNA
<213> ORGANISM: Homo Sapiens

<400> SEQUENCE: 184
gagcagacuu cuucuaugu                                            19

<210> SEQ ID NO 185
<211> LENGTH: 19
<212> TYPE: RNA
<213> ORGANISM: Homo Sapiens

<400> SEQUENCE: 185
ucagaagccu ggucauuga                                            19

<210> SEQ ID NO 186
<211> LENGTH: 19
<212> TYPE: RNA
<213> ORGANISM: Homo Sapiens

<400> SEQUENCE: 186
ggacggccaa ggaauuaga                                            19

<210> SEQ ID NO 187
<211> LENGTH: 518
<212> TYPE: PRT
<213> ORGANISM: Homo Sapiens

<400> SEQUENCE: 187

Met Ala Ala Val Ala Met Thr Pro Asn Pro Val Gln Thr Leu Gln Glu
1               5                   10                  15

Glu Ala Val Cys Ala Ile Cys Leu Asp Tyr Phe Thr Asp Pro Val Ser
                20                  25                  30

Ile Gly Cys Gly His Asn Phe Cys Arg Val Cys Val Thr Gln Leu Trp
            35                  40                  45

Gly Gly Glu Asp Glu Glu Asp Arg Asp Glu Leu Asp Arg Glu Glu Glu

```
                50                  55                  60
Glu Glu Asp Gly Glu Glu Glu Val Glu Ala Val Gly Ala Gly Ala
 65                  70                  75                  80

Gly Trp Asp Thr Pro Met Arg Asp Glu Asp Tyr Glu Gly Asp Met Glu
                     85                  90                  95

Glu Glu Val Glu Glu Glu Glu Gly Val Phe Trp Thr Ser Gly Met
            100                 105                 110

Ser Arg Ser Ser Trp Asp Asn Met Asp Tyr Val Trp Glu Glu Asp
            115                 120                 125

Glu Glu Glu Asp Leu Asp Tyr Tyr Leu Gly Asp Met Glu Glu Asp
            130                 135                 140

Leu Arg Gly Glu Asp Glu Asp Glu Glu Val Leu Glu Glu Val
145                 150                 155                 160

Glu Glu Glu Asp Leu Asp Pro Val Thr Pro Leu Pro Pro Pro Ala
            165                 170                 175

Pro Arg Arg Cys Phe Thr Cys Pro Gln Cys Arg Lys Ser Phe Pro Arg
            180                 185                 190

Arg Ser Phe Arg Pro Asn Leu Gln Leu Ala Asn Met Val Gln Val Ile
            195                 200                 205

Arg Gln Met His Pro Thr Pro Gly Arg Gly Ser Arg Val Thr Asp Gln
            210                 215                 220

Gly Ile Cys Pro Lys His Gln Glu Ala Leu Lys Leu Phe Cys Glu Val
225                 230                 235                 240

Asp Glu Glu Ala Ile Cys Val Val Cys Arg Glu Ser Arg Ser His Lys
                245                 250                 255

Gln His Ser Val Val Pro Leu Glu Glu Val Val Gln Glu Tyr Lys Ala
                260                 265                 270

Lys Leu Gln Gly His Val Glu Pro Leu Arg Lys His Leu Glu Ala Val
                275                 280                 285

Gln Lys Met Lys Ala Lys Glu Glu Arg Arg Val Thr Glu Leu Lys Ser
290                 295                 300

Gln Met Lys Ser Glu Leu Ala Ala Val Ala Ser Glu Phe Gly Arg Leu
305                 310                 315                 320

Thr Arg Phe Leu Ala Glu Glu Gln Ala Gly Leu Glu Arg Arg Leu Arg
                325                 330                 335

Glu Met His Glu Ala Gln Leu Gly Arg Ala Gly Ala Ala Ser Arg
                340                 345                 350

Leu Ala Glu Gln Ala Ala Gln Leu Ser Arg Leu Leu Ala Glu Ala Gln
                355                 360                 365

Glu Arg Ser Gln Gln Gly Gly Leu Arg Leu Leu Gln Asp Ile Lys Glu
                370                 375                 380

Thr Phe Asn Arg Cys Glu Glu Val Gln Leu Pro Pro Glu Val Trp
385                 390                 395                 400

Ser Pro Asp Pro Cys Gln Pro His Ser His Asp Phe Leu Thr Asp Ala
                405                 410                 415

Ile Val Arg Lys Met Ser Arg Met Phe Cys Gln Ala Ala Arg Val Asp
                420                 425                 430

Leu Thr Leu Asp Pro Asp Thr Ala His Pro Ala Leu Met Leu Ser Pro
                435                 440                 445

Asp Arg Arg Gly Val Arg Leu Ala Glu Arg Arg Gln Glu Val Ala Asp
                450                 455                 460

His Pro Lys Arg Phe Ser Ala Asp Cys Cys Val Leu Gly Ala Gln Gly
465                 470                 475                 480
```

-continued

```
Phe Arg Ser Gly Arg His Tyr Trp Glu Glu Pro Lys Glu Pro Ser Trp
                485                 490                 495

Pro Pro Ala Gln Pro Ser Leu Thr Tyr Tyr Val Cys Pro Thr Asp Arg
            500                 505                 510

Pro Glu Phe Ser Phe Thr
            515

<210> SEQ ID NO 188
<211> LENGTH: 19
<212> TYPE: RNA
<213> ORGANISM: Homo Sapiens

<400> SEQUENCE: 188
caaggagacu uucaauagg                                                     19

<210> SEQ ID NO 189
<211> LENGTH: 19
<212> TYPE: RNA
<213> ORGANISM: Homo Sapiens

<400> SEQUENCE: 189
ccaauauggu ccaggugau                                                     19

<210> SEQ ID NO 190
<211> LENGTH: 19
<212> TYPE: RNA
<213> ORGANISM: Homo Sapiens

<400> SEQUENCE: 190
gagaugaguu agaucggga                                                     19

<210> SEQ ID NO 191
<211> LENGTH: 19
<212> TYPE: RNA
<213> ORGANISM: Homo Sapiens

<400> SEQUENCE: 191
ggaugaagac uacgagggu                                                     19

<210> SEQ ID NO 192
<211> LENGTH: 723
<212> TYPE: PRT
<213> ORGANISM: Homo Sapiens

<400> SEQUENCE: 192

Met Glu Thr Ala Met Cys Val Cys Cys Pro Cys Cys Thr Trp Gln Arg
1               5                   10                  15

Cys Cys Pro Gln Leu Cys Ser Cys Leu Cys Cys Lys Phe Ile Phe Thr
            20                  25                  30

Ser Glu Arg Asn Cys Thr Cys Phe Pro Cys Pro Tyr Lys Asp Glu Arg
        35                  40                  45

Asn Cys Gln Phe Cys His Cys Thr Cys Ser Glu Ser Pro Asn Cys His
    50                  55                  60

Trp Cys Cys Cys Ser Trp Ala Asn Asp Pro Asn Cys Lys Cys Cys Cys
65                  70                  75                  80

Thr Ala Ser Ser Asn Leu Asn Cys Tyr Tyr Tyr Glu Ser Arg Cys Cys
                85                  90                  95

Arg Asn Thr Ile Ile Thr Phe His Lys Gly Arg Leu Arg Ser Ile His
            100                 105                 110
```

```
Thr Ser Ser Lys Thr Ala Leu Arg Thr Gly Ser Ser Asp Thr Gln Val
            115                 120                 125

Asp Glu Val Lys Ser Ile Pro Ala Asn Ser His Leu Val Asn His Leu
130                 135                 140

Asn Cys Pro Met Cys Ser Arg Leu Arg Leu His Ser Phe Met Leu Pro
145                 150                 155                 160

Cys Asn His Ser Leu Cys Glu Lys Cys Leu Arg Gln Leu Gln Lys His
                165                 170                 175

Ala Glu Val Thr Glu Asn Phe Phe Ile Leu Ile Cys Pro Val Cys Asp
            180                 185                 190

Arg Ser His Cys Met Pro Tyr Ser Asn Lys Met Gln Leu Pro Glu Asn
            195                 200                 205

Tyr Leu His Gly Arg Leu Thr Lys Arg Tyr Met Gln Glu His Gly Tyr
210                 215                 220

Leu Lys Trp Arg Phe Asp Arg Ser Ser Gly Pro Ile Leu Cys Gln Val
225                 230                 235                 240

Cys Arg Asn Lys Arg Ile Ala Tyr Lys Arg Cys Ile Thr Cys Arg Leu
                245                 250                 255

Asn Leu Cys Asn Asp Cys Leu Lys Ala Phe His Ser Asp Val Ala Met
            260                 265                 270

Gln Asp His Val Phe Val Asp Thr Ser Ala Glu Glu Gln Asp Glu Lys
            275                 280                 285

Ile Cys Ile His His Pro Ser Arg Ile Ile Glu Tyr Cys Arg Asn
            290                 295                 300

Asp Asn Lys Leu Leu Cys Thr Phe Cys Lys Phe Ser Phe His Asn Gly
305                 310                 315                 320

His Asp Thr Ile Ser Leu Ile Asp Ala Cys Ser Glu Arg Ala Ala Ser
            325                 330                 335

Leu Phe Ser Ala Ile Ala Lys Phe Lys Ala Val Arg Tyr Glu Ile Asp
            340                 345                 350

Asn Asp Leu Met Glu Phe Asn Ile Leu Lys Asn Ser Phe Lys Ala Asp
            355                 360                 365

Lys Glu Ala Lys Arg Lys Glu Ile Arg Asn Gly Phe Leu Lys Leu Arg
370                 375                 380

Ser Ile Leu Gln Glu Lys Glu Lys Ile Ile Met Glu Gln Ile Glu Asn
385                 390                 395                 400

Leu Glu Val Ser Arg Gln Lys Glu Ile Glu Lys Tyr Val Tyr Val Thr
                405                 410                 415

Thr Met Lys Val Asn Glu Met Asp Gly Leu Ile Ala Tyr Ser Lys Glu
            420                 425                 430

Ala Leu Lys Glu Thr Gly Gln Val Ala Phe Leu Gln Ser Ala Lys Ile
            435                 440                 445

Leu Val Asp Gln Ile Glu Asp Gly Ile Gln Thr Thr Tyr Arg Pro Asp
450                 455                 460

Pro Gln Leu Arg Leu His Ser Ile Asn Tyr Val Pro Leu Asp Phe Val
465                 470                 475                 480

Glu Leu Ser Ser Ala Ile His Glu Leu Phe Pro Thr Gly Pro Lys Lys
                485                 490                 495

Val Arg Ser Ser Gly Asp Ser Leu Pro Ser Pro Tyr Pro Val His Ser
            500                 505                 510

Glu Thr Met Ile Ala Arg Lys Val Thr Phe Ser Thr His Ser Leu Gly
            515                 520                 525

Asn Gln His Ile Tyr Gln Arg Ser Ser Ser Met Leu Ser Phe Ser Asn
```

```
                530            535             540
Thr Asp Lys Lys Ala Lys Val Gly Leu Glu Ala Cys Gly Arg Ala Gln
545                 550                 555                 560

Ser Ala Thr Pro Ala Lys Pro Thr Asp Gly Leu Tyr Thr Tyr Trp Ser
                565                 570                 575

Ala Gly Ala Asp Ser Gln Ser Val Gln Asn Ser Ser Phe His Asn
            580                 585                 590

Trp Tyr Ser Phe Asn Asp Gly Ser Val Lys Thr Pro Gly Pro Ile Val
        595                 600                 605

Ile Tyr Gln Thr Leu Val Tyr Pro Arg Ala Ala Lys Val Tyr Trp Thr
        610                 615                 620

Cys Pro Ala Glu Asp Val Asp Ser Phe Glu Met Glu Phe Tyr Glu Val
625                 630                 635                 640

Ile Thr Ser Pro Pro Asn Asn Val Gln Met Glu Leu Cys Gly Gln Ile
                645                 650                 655

Arg Asp Ile Met Gln Gln Asn Leu Glu Leu His Asn Leu Thr Pro Asn
                660                 665                 670

Thr Glu Tyr Val Phe Lys Val Arg Ala Ile Asn Asp Asn Gly Pro Gly
                675                 680                 685

Gln Trp Ser Asp Ile Cys Lys Val Val Thr Pro Asp Gly His Gly Lys
690                 695                 700

Asn Arg Ala Lys Trp Gly Leu Leu Lys Asn Ile Gln Ser Ala Leu Gln
705                 710                 715                 720

Lys His Phe
```

<210> SEQ ID NO 193
<211> LENGTH: 19
<212> TYPE: RNA
<213> ORGANISM: Homo Sapiens

<400> SEQUENCE: 193
gcaauaccau caucacuuu                                                  19

<210> SEQ ID NO 194
<211> LENGTH: 19
<212> TYPE: RNA
<213> ORGANISM: Homo Sapiens

<400> SEQUENCE: 194
ccaaugaucc caacuguaa                                                  19

<210> SEQ ID NO 195
<211> LENGTH: 19
<212> TYPE: RNA
<213> ORGANISM: Homo Sapiens

<400> SEQUENCE: 195
caaguucucu uuccacaau                                                  19

<210> SEQ ID NO 196
<211> LENGTH: 19
<212> TYPE: RNA
<213> ORGANISM: Homo Sapiens

<400> SEQUENCE: 196
cagaauacgu guuuaaagu                                                  19

<210> SEQ ID NO 197

<211> LENGTH: 446
<212> TYPE: PRT
<213> ORGANISM: Homo Sapiens

<400> SEQUENCE: 197

```
Met Asp Ser Asp Phe Ser His Ala Phe Gln Lys Glu Leu Thr Cys Val
1               5                   10                  15

Ile Cys Leu Asn Tyr Leu Val Asp Pro Val Thr Ile Cys Cys Gly His
            20                  25                  30

Ser Phe Cys Arg Pro Cys Leu Cys Leu Ser Trp Glu Ala Gln Ser
        35                  40                  45

Pro Ala Asn Cys Pro Ala Cys Arg Glu Pro Ser Pro Lys Met Asp Phe
    50                  55                  60

Lys Thr Asn Ile Leu Leu Lys Asn Leu Val Thr Ile Ala Arg Lys Ala
65                  70                  75                  80

Ser Leu Trp Gln Phe Leu Ser Ser Glu Lys Gln Ile Cys Gly Thr His
            85                  90                  95

Arg Gln Thr Lys Lys Met Phe Cys Asp Met Asp Lys Ser Leu Leu Cys
            100                 105                 110

Leu Leu Cys Ser Asn Ser Gln Glu His Gly Ala His Lys His His Pro
        115                 120                 125

Ile Glu Glu Ala Ala Glu His Arg Glu Lys Leu Leu Lys Gln Met
    130                 135                 140

Arg Ile Leu Trp Lys Lys Ile Gln Glu Asn Gln Arg Asn Leu Tyr Glu
145                 150                 155                 160

Glu Gly Arg Thr Ala Phe Leu Trp Arg Gly Asn Val Val Leu Arg Ala
            165                 170                 175

Gln Met Ile Arg Asn Glu Tyr Arg Lys Leu His Pro Val Leu His Lys
        180                 185                 190

Glu Glu Lys Gln His Leu Glu Arg Leu Asn Lys Glu Tyr Gln Glu Ile
    195                 200                 205

Phe Gln Gln Leu Gln Arg Ser Trp Val Lys Met Asp Gln Lys Ser Lys
    210                 215                 220

His Leu Lys Glu Met Tyr Gln Glu Leu Met Glu Met Cys His Lys Pro
225                 230                 235                 240

Asp Val Glu Leu Leu Gln Asp Leu Gly Asp Ile Val Ala Arg Ser Glu
            245                 250                 255

Ser Val Leu Leu His Met Pro Gln Pro Val Asn Pro Glu Leu Thr Ala
        260                 265                 270

Gly Pro Ile Thr Gly Leu Val Tyr Arg Leu Asn Arg Phe Arg Val Glu
    275                 280                 285

Ile Ser Phe His Phe Glu Val Thr Asn His Asn Ile Arg Leu Phe Glu
    290                 295                 300

Asp Val Arg Ser Trp Met Phe Arg Arg Gly Pro Leu Asn Ser Asp Arg
305                 310                 315                 320

Ser Asp Tyr Phe Ala Ala Trp Gly Ala Arg Val Phe Ser Phe Gly Lys
            325                 330                 335

His Tyr Trp Glu Leu Asp Val Asp Asn Ser Cys Asp Trp Ala Leu Gly
        340                 345                 350

Val Cys Asn Asn Ser Trp Ile Arg Lys Asn Ser Thr Met Val Asn Ser
    355                 360                 365

Glu Asp Ile Phe Leu Leu Leu Cys Leu Lys Val Asp Asn His Phe Asn
    370                 375                 380

Leu Leu Thr Thr Ser Pro Val Phe Pro His Tyr Ile Glu Lys Pro Leu
```

```
            385                 390                 395                 400
Gly Arg Val Gly Val Phe Leu Asp Phe Glu Ser Gly Ser Val Ser Phe
                    405                 410                 415

Leu Asn Val Thr Lys Ser Ser Leu Ile Trp Ser Tyr Pro Ala Gly Ser
                420                 425                 430

Leu Thr Phe Pro Val Arg Pro Phe Phe Tyr Thr Gly His Arg
            435                 440                 445

<210> SEQ ID NO 198
<211> LENGTH: 19
<212> TYPE: RNA
<213> ORGANISM: Homo Sapiens

<400> SEQUENCE: 198
ccagagaagu ugggucaaa                                                    19

<210> SEQ ID NO 199
<211> LENGTH: 19
<212> TYPE: RNA
<213> ORGANISM: Homo Sapiens

<400> SEQUENCE: 199
ggacccauag gcaaacaaa                                                    19

<210> SEQ ID NO 200
<211> LENGTH: 19
<212> TYPE: RNA
<213> ORGANISM: Homo Sapiens

<400> SEQUENCE: 200
uguacaggcu caaccgcuu                                                    19

<210> SEQ ID NO 201
<211> LENGTH: 19
<212> TYPE: RNA
<213> ORGANISM: Homo Sapiens

<400> SEQUENCE: 201
cgguucucca uaaggaaga                                                    19

<210> SEQ ID NO 202
<211> LENGTH: 344
<212> TYPE: PRT
<213> ORGANISM: Homo Sapiens

<400> SEQUENCE: 202

Met Ala Ser Gly Val Gly Ala Ala Phe Glu Glu Leu Pro His Asp Gly
1               5                   10                  15

Thr Cys Asp Glu Cys Glu Pro Asp Glu Ala Pro Gly Ala Glu Glu Val
                20                  25                  30

Cys Arg Glu Cys Gly Phe Cys Tyr Cys Arg Arg His Ala Glu Ala His
            35                  40                  45

Arg Gln Lys Phe Leu Ser His His Leu Ala Glu Tyr Val His Gly Ser
        50                  55                  60

Gln Ala Trp Thr Pro Pro Ala Asp Gly Glu Gly Ala Gly Lys Glu Glu
65                  70                  75                  80

Ala Glu Val Lys Val Glu Gln Glu Arg Glu Ile Glu Ser Glu Ala Gly
                85                  90                  95

Glu Glu Ser Glu Ser Glu Glu Ser Glu Ser Glu Glu Glu Ser Glu
                100                 105                 110
```

Thr Glu Glu Glu Ser Glu Asp Glu Ser Asp Glu Gly Glu Asp
    115                 120                 125

Ser Glu Glu Met Glu Asp Glu Gln Glu Ser Glu Ala Glu Asp
    130                 135                 140

Asn Gln Glu Glu Gly Glu Ser Glu Ala Glu Thr Glu Ala Glu
145                 150                 155                 160

Ser Glu Phe Asp Pro Glu Ile Glu Met Glu Ala Glu Arg Val Ala Lys
            165                 170                 175

Arg Lys Cys Pro Asp His Gly Leu Asp Leu Ser Thr Tyr Cys Gln Glu
            180                 185                 190

Asp Arg Gln Leu Ile Cys Val Leu Cys Pro Val Ile Gly Ala His Gln
            195                 200                 205

Gly His Gln Leu Ser Thr Leu Asp Glu Ala Phe Glu Glu Leu Arg Ser
    210                 215                 220

Lys Asp Ser Gly Gly Leu Lys Ala Ala Met Ile Glu Leu Val Glu Arg
225                 230                 235                 240

Leu Lys Phe Lys Ser Ser Asp Pro Lys Val Thr Arg Asp Gln Met Lys
                245                 250                 255

Met Phe Ile Gln Gln Glu Phe Lys Lys Val Gln Lys Val Ile Ala Asp
                260                 265                 270

Glu Glu Gln Lys Ala Leu His Leu Val Asp Ile Gln Glu Ala Met Ala
            275                 280                 285

Thr Ala His Val Thr Glu Ile Leu Ala Asp Ile Gln Ser His Met Asp
            290                 295                 300

Arg Leu Met Thr Gln Met Ala Gln Ala Lys Glu Gln Leu Asp Thr Ser
305                 310                 315                 320

Asn Glu Ser Ala Glu Pro Lys Ala Glu Gly Asp Glu Gly Pro Ser
                325                 330                 335

Gly Ala Ser Glu Glu Glu Asp Thr
            340

<210> SEQ ID NO 203
<211> LENGTH: 19
<212> TYPE: RNA
<213> ORGANISM: Homo Sapiens

<400> SEQUENCE: 203
gaggaagugu gccgagaau                                          19

<210> SEQ ID NO 204
<211> LENGTH: 19
<212> TYPE: RNA
<213> ORGANISM: Homo Sapiens

<400> SEQUENCE: 204
gucaccaucu ggccgaaua                                          19

<210> SEQ ID NO 205
<211> LENGTH: 19
<212> TYPE: RNA
<213> ORGANISM: Homo Sapiens

<400> SEQUENCE: 205
acgaagccuu ugaagaauu                                          19

<210> SEQ ID NO 206
<211> LENGTH: 19

```
<212> TYPE: RNA
<213> ORGANISM: Homo Sapiens

<400> SEQUENCE: 206
gcuuugugcu cccgaguaa                                                    19

<210> SEQ ID NO 207
<211> LENGTH: 580
<212> TYPE: PRT
<213> ORGANISM: Homo Sapiens

<400> SEQUENCE: 207
```

Met Ser Glu Asn Arg Lys Pro Leu Leu Gly Phe Val Ser Lys Leu Thr
1               5                   10                  15

Ser Gly Thr Ala Leu Gly Asn Ser Gly Lys Thr His Cys Pro Leu Cys
            20                  25                  30

Leu Gly Leu Phe Lys Ala Pro Arg Leu Leu Pro Cys Leu His Thr Val
        35                  40                  45

Cys Thr Thr Cys Leu Glu Gln Leu Glu Pro Phe Ser Val Val Asp Ile
    50                  55                  60

Arg Gly Gly Asp Ser Asp Thr Ser Ser Glu Gly Ser Ile Phe Gln Glu
65                  70                  75                  80

Leu Lys Pro Arg Ser Leu Gln Ser Gln Ile Gly Ile Leu Cys Pro Val
                85                  90                  95

Cys Asp Ala Gln Val Asp Leu Pro Met Gly Gly Val Lys Ala Leu Thr
            100                 105                 110

Ile Asp His Leu Ala Val Asn Asp Val Met Leu Glu Ser Leu Arg Gly
        115                 120                 125

Glu Gly Gln Gly Leu Val Cys Asp Leu Cys Asn Asp Arg Glu Val Glu
    130                 135                 140

Lys Arg Cys Gln Thr Cys Lys Ala Asn Leu Cys His Phe Cys Cys Gln
145                 150                 155                 160

Ala His Arg Arg Gln Lys Lys Thr Thr Tyr His Thr Met Val Asp Leu
                165                 170                 175

Lys Asp Leu Lys Gly Tyr Ser Arg Ile Gly Lys Pro Ile Leu Cys Pro
            180                 185                 190

Val His Pro Ala Glu Glu Leu Arg Leu Phe Cys Glu Phe Cys Asp Arg
        195                 200                 205

Pro Val Cys Gln Asp Cys Val Val Gly Glu His Arg Glu His Pro Cys
    210                 215                 220

Asp Phe Thr Ser Asn Val Ile His Lys His Gly Asp Ser Val Trp Glu
225                 230                 235                 240

Leu Leu Lys Gly Thr Gln Pro His Val Glu Ala Leu Glu Glu Ala Leu
                245                 250                 255

Ala Gln Ile His Ile Ile Asn Ser Ala Leu Gln Lys Arg Val Glu Ala
            260                 265                 270

Val Ala Ala Asp Val Arg Thr Phe Ser Glu Gly Tyr Ile Lys Ala Ile
        275                 280                 285

Glu Glu His Arg Asp Lys Leu Leu Lys Gln Leu Glu Asp Ile Arg Ala
    290                 295                 300

Gln Lys Glu Asn Ser Leu Gln Leu Gln Lys Ala Gln Leu Glu Gln Leu
305                 310                 315                 320

Leu Ala Asp Met Arg Thr Gly Val Glu Phe Thr Glu His Leu Leu Thr
                325                 330                 335

Ser Gly Ser Asp Leu Glu Ile Leu Ile Thr Lys Arg Val Val Val Glu

```
                    340                 345                 350
    Arg Leu Arg Lys Leu Asn Lys Val Gln Tyr Ser Thr Arg Pro Gly Val
                355                 360                 365

Asn Asp Lys Ile Arg Phe Cys Pro Gln Glu Lys Ala Gly Gln Cys Arg
            370                 375                 380

Gly Tyr Glu Ile Tyr Gly Thr Ile Asn Thr Lys Glu Val Asp Pro Ala
    385                 390                 395                 400

Lys Cys Val Leu Gln Gly Glu Asp Leu His Arg Ala Arg Glu Lys Gln
                    405                 410                 415

Thr Ala Ser Phe Thr Leu Leu Cys Lys Asp Ala Ala Gly Glu Ile Met
                420                 425                 430

Gly Arg Gly Gly Asp Asn Val Gln Val Ala Val Val Pro Lys Asp Lys
            435                 440                 445

Lys Asp Ser Pro Val Arg Thr Met Val Gln Asp Asn Lys Asp Gly Thr
        450                 455                 460

Tyr Tyr Ile Ser Tyr Thr Pro Lys Glu Pro Gly Val Tyr Thr Val Trp
    465                 470                 475                 480

Val Cys Ile Lys Glu Gln His Val Gln Gly Ser Pro Phe Thr Val Met
                    485                 490                 495

Val Arg Arg Lys His Arg Pro His Ser Gly Val Phe His Cys Cys Thr
                500                 505                 510

Phe Cys Ser Ser Gly Gly Gln Lys Thr Ala Arg Cys Ala Cys Gly Gly
            515                 520                 525

Thr Met Pro Gly Gly Tyr Leu Gly Cys Gly His Gly His Lys Gly His
    530                 535                 540

Pro Gly His Pro His Trp Ser Cys Cys Gly Lys Phe Asn Glu Lys Ser
    545                 550                 555                 560

Glu Cys Thr Trp Thr Gly Gly Gln Ser Ala Pro Arg Ser Leu Leu Arg
                    565                 570                 575

Thr Val Ala Leu
                580

<210> SEQ ID NO 208
<211> LENGTH: 19
<212> TYPE: RNA
<213> ORGANISM: Homo Sapiens

<400> SEQUENCE: 208
gcaccgagga gucuacuua                                                       19

<210> SEQ ID NO 209
<211> LENGTH: 19
<212> TYPE: RNA
<213> ORGANISM: Homo Sapiens

<400> SEQUENCE: 209
ggacauacua cauuuccua                                                       19

<210> SEQ ID NO 210
<211> LENGTH: 19
<212> TYPE: RNA
<213> ORGANISM: Homo Sapiens

<400> SEQUENCE: 210
gugcagggcu cgccauuca                                                       19

<210> SEQ ID NO 211
```

```
<211> LENGTH: 19
<212> TYPE: RNA
<213> ORGANISM: Homo Sapiens

<400> SEQUENCE: 211
gggaggagac aacguucaa                                                    19

<210> SEQ ID NO 212
<211> LENGTH: 759
<212> TYPE: PRT
<213> ORGANISM: Homo Sapiens

<400> SEQUENCE: 212
```

| | | | | | | | | | | | | | | | |
|---|---|---|---|---|---|---|---|---|---|---|---|---|---|---|---|
| Met | Ala | Glu | Gly | Glu | Asp | Met | Gln | Thr | Phe | Thr | Ser | Ile | Met | Asp | Ala |
| 1 | | | | 5 | | | | | 10 | | | | | 15 | |
| Leu | Val | Arg | Ile | Ser | Thr | Ser | Met | Lys | Asn | Met | Glu | Lys | Glu | Leu | Leu |
| | | | 20 | | | | | 25 | | | | | 30 | | |
| Cys | Pro | Val | Cys | Gln | Glu | Met | Tyr | Lys | Gln | Pro | Leu | Val | Leu | Pro | Cys |
| | | 35 | | | | | 40 | | | | | 45 | | | |
| Thr | His | Asn | Val | Cys | Gln | Ala | Cys | Ala | Arg | Glu | Val | Leu | Gly | Gln | Gln |
| | 50 | | | | | 55 | | | | | 60 | | | | |
| Gly | Tyr | Ile | Gly | His | Gly | Gly | Asp | Pro | Ser | Ser | Glu | Pro | Thr | Ser | Pro |
| 65 | | | | | 70 | | | | | 75 | | | | | 80 |
| Ala | Ser | Thr | Pro | Ser | Thr | Arg | Ser | Pro | Arg | Leu | Ser | Arg | Arg | Thr | Leu |
| | | | | 85 | | | | | 90 | | | | | 95 | |
| Pro | Lys | Pro | Asp | Arg | Leu | Asp | Arg | Leu | Leu | Lys | Ser | Gly | Phe | Gly | Thr |
| | | | 100 | | | | | 105 | | | | | 110 | | |
| Tyr | Pro | Gly | Arg | Lys | Arg | Gly | Ala | Leu | His | Pro | Gln | Val | Ile | Met | Phe |
| | | 115 | | | | | 120 | | | | | 125 | | | |
| Pro | Cys | Pro | Ala | Cys | Gln | Gly | Asp | Val | Glu | Leu | Gly | Glu | Arg | Gly | Leu |
| | 130 | | | | | 135 | | | | | 140 | | | | |
| Ala | Gly | Leu | Phe | Arg | Asn | Leu | Thr | Leu | Glu | Arg | Val | Val | Glu | Arg | Tyr |
| 145 | | | | | 150 | | | | | 155 | | | | | 160 |
| Arg | Gln | Ser | Val | Ser | Val | Gly | Gly | Ala | Ile | Leu | Cys | Gln | Leu | Cys | Lys |
| | | | | 165 | | | | | 170 | | | | | 175 | |
| Pro | Pro | Pro | Leu | Glu | Ala | Thr | Lys | Gly | Cys | Thr | Glu | Cys | Arg | Ala | Thr |
| | | | 180 | | | | | 185 | | | | | 190 | | |
| Phe | Cys | Asn | Glu | Cys | Phe | Lys | Leu | Phe | His | Pro | Trp | Gly | Thr | Gln | Lys |
| | | 195 | | | | | 200 | | | | | 205 | | | |
| Ala | Gln | His | Glu | Pro | Thr | Leu | Pro | Thr | Leu | Ser | Phe | Arg | Pro | Lys | Gly |
| | 210 | | | | | 215 | | | | | 220 | | | | |
| Leu | Met | Cys | Pro | Asp | His | Lys | Glu | Glu | Val | Thr | His | Tyr | Cys | Lys | Thr |
| 225 | | | | | 230 | | | | | 235 | | | | | 240 |
| Cys | Gln | Arg | Leu | Val | Cys | Gln | Leu | Cys | Arg | Val | Arg | Arg | Thr | His | Ser |
| | | | | 245 | | | | | 250 | | | | | 255 | |
| Gly | His | Lys | Ile | Thr | Pro | Val | Leu | Ser | Ala | Tyr | Gln | Ala | Leu | Lys | Asp |
| | | | 260 | | | | | 265 | | | | | 270 | | |
| Lys | Leu | Thr | Lys | Ser | Leu | Thr | Tyr | Ile | Leu | Gly | Asn | Gln | Asp | Thr | Val |
| | | 275 | | | | | 280 | | | | | 285 | | | |
| Gln | Thr | Gln | Ile | Cys | Glu | Leu | Glu | Glu | Ala | Val | Arg | His | Thr | Glu | Val |
| | 290 | | | | | 295 | | | | | 300 | | | | |
| Ser | Gly | Gln | Gln | Ala | Lys | Glu | Glu | Val | Ser | Gln | Leu | Val | Arg | Gly | Leu |
| 305 | | | | | 310 | | | | | 315 | | | | | 320 |
| Gly | Ala | Val | Leu | Glu | Glu | Lys | Arg | Ala | Ser | Leu | Leu | Gln | Ala | Ile | Glu |
| | | | | 325 | | | | | 330 | | | | | 335 | |

```
Glu Cys Gln Gln Glu Arg Leu Ala Arg Leu Ser Ala Gln Ile Gln Glu
            340                 345                 350

His Arg Ser Leu Leu Asp Gly Ser Gly Leu Val Gly Tyr Ala Gln Glu
            355                 360                 365

Val Leu Lys Glu Thr Asp Gln Pro Cys Phe Val Gln Ala Ala Lys Gln
            370                 375                 380

Leu His Asn Arg Ile Ala Arg Ala Thr Glu Ala Leu Gln Thr Phe Arg
385                 390                 395                 400

Pro Ala Ala Ser Ser Phe Arg His Cys Gln Leu Asp Val Gly Arg
                405                 410                 415

Glu Met Lys Leu Leu Thr Glu Leu Asn Phe Leu Arg Val Pro Glu Ala
            420                 425                 430

Pro Val Ile Asp Thr Gln Arg Thr Phe Ala Tyr Asp Gln Ile Phe Leu
            435                 440                 445

Cys Trp Arg Leu Pro Pro His Ser Pro Pro Ala Trp His Tyr Thr Val
            450                 455                 460

Glu Phe Arg Arg Thr Asp Val Pro Ala Gln Pro Gly Pro Thr Arg Trp
465                 470                 475                 480

Gln Arg Arg Glu Glu Val Arg Gly Thr Ser Ala Leu Leu Glu Asn Pro
            485                 490                 495

Asp Thr Gly Ser Val Tyr Val Leu Arg Val Arg Gly Cys Asn Lys Ala
            500                 505                 510

Gly Tyr Gly Glu Tyr Ser Glu Asp Val His Leu His Thr Pro Pro Ala
            515                 520                 525

Pro Val Leu His Phe Phe Leu Asp Ser Arg Trp Gly Ala Ser Arg Glu
            530                 535                 540

Arg Leu Ala Ile Ser Lys Asp Gln Arg Ala Val Arg Ser Val Pro Gly
545                 550                 555                 560

Leu Pro Leu Leu Leu Ala Ala Asp Arg Leu Leu Thr Gly Cys His Leu
            565                 570                 575

Ser Val Asp Val Val Leu Gly Asp Val Ala Val Thr Gln Gly Arg Ser
            580                 585                 590

Tyr Trp Ala Cys Ala Val Asp Pro Ala Ser Tyr Leu Val Lys Val Gly
            595                 600                 605

Val Gly Leu Glu Ser Lys Leu Gln Glu Ser Phe Gln Gly Ala Pro Asp
            610                 615                 620

Val Ile Ser Pro Arg Tyr Asp Pro Asp Ser Gly His Asp Ser Gly Ala
625                 630                 635                 640

Glu Asp Ala Thr Val Glu Ala Ser Pro Pro Phe Ala Phe Leu Thr Ile
            645                 650                 655

Gly Met Gly Lys Ile Leu Leu Gly Ser Gly Ala Ser Ser Asn Ala Gly
            660                 665                 670

Leu Thr Gly Arg Asp Gly Pro Thr Ala Gly Cys Thr Val Pro Leu Pro
            675                 680                 685

Pro Arg Leu Gly Ile Cys Leu Asp Tyr Glu Arg Gly Arg Val Ser Phe
            690                 695                 700

Leu Asp Ala Val Ser Phe Arg Gly Leu Leu Glu Cys Pro Leu Asp Cys
705                 710                 715                 720

Ser Gly Pro Val Cys Pro Ala Phe Cys Phe Ile Gly Gly Ala Val
            725                 730                 735

Gln Leu Gln Glu Pro Val Gly Thr Lys Pro Glu Arg Lys Val Thr Ile
            740                 745                 750

Gly Gly Phe Ala Lys Leu Asp
```

<210> SEQ ID NO 213
<211> LENGTH: 19
<212> TYPE: RNA
<213> ORGANISM: Homo Sapiens

<400> SEQUENCE: 213
ugacauacau ccugggaaa                                                      19

<210> SEQ ID NO 214
<211> LENGTH: 19
<212> TYPE: RNA
<213> ORGANISM: Homo Sapiens

<400> SEQUENCE: 214
ggacauaccc ugggaggaa                                                      19

<210> SEQ ID NO 215
<211> LENGTH: 19
<212> TYPE: RNA
<213> ORGANISM: Homo Sapiens

<400> SEQUENCE: 215
gcgaauacag ugaagaugu                                                      19

<210> SEQ ID NO 216
<211> LENGTH: 19
<212> TYPE: RNA
<213> ORGANISM: Homo Sapiens

<400> SEQUENCE: 216
gucaagagau guacaagca                                                      19

<210> SEQ ID NO 217
<211> LENGTH: 638
<212> TYPE: PRT
<213> ORGANISM: Homo Sapiens

<400> SEQUENCE: 217

Met Asp Gly Ser Gly Pro Phe Ser Cys Pro Ile Cys Leu Glu Pro Leu
1               5                   10                  15

Arg Glu Pro Val Thr Leu Pro Cys Gly His Asn Phe Cys Leu Ala Cys
                20                  25                  30

Leu Gly Ala Leu Trp Pro His Arg Gly Ala Ser Gly Ala Gly Gly Pro
            35                  40                  45

Gly Gly Ala Ala Arg Cys Pro Leu Cys Gln Glu Pro Phe Pro Asp Gly
        50                  55                  60

Leu Gln Leu Arg Lys Asn His Thr Leu Ser Glu Leu Leu Gln Leu Arg
65                  70                  75                  80

Gln Gly Ser Gly Pro Gly Ser Gly Pro Gly Pro Ala Pro Ala Leu Ala
                85                  90                  95

Pro Glu Pro Ser Ala Pro Ser Ala Leu Pro Ser Val Pro Glu Pro Ser
                100                 105                 110

Ala Pro Cys Ala Pro Glu Pro Trp Pro Ala Gly Glu Glu Pro Val Arg
            115                 120                 125

Cys Asp Ala Cys Pro Glu Gly Ala Ala Leu Pro Ala Ala Leu Ser Cys
        130                 135                 140

Leu Ser Cys Leu Ala Ser Phe Cys Pro Ala His Leu Gly Pro His Glu
145                 150                 155                 160

```
Arg Ser Pro Ala Leu Arg Gly His Arg Leu Val Pro Pro Leu Arg Arg
                165                 170                 175

Leu Glu Glu Ser Leu Cys Pro Arg His Leu Arg Pro Leu Glu Arg Tyr
                180                 185                 190

Cys Arg Ala Glu Arg Val Cys Leu Cys Glu Ala Cys Ala Ala Gln Glu
                195                 200                 205

His Arg Gly His Glu Leu Val Pro Leu Glu Gln Glu Arg Ala Leu Gln
            210                 215                 220

Glu Ala Glu Gln Ser Lys Val Leu Ser Ala Val Glu Asp Arg Met Asp
225                 230                 235                 240

Glu Leu Gly Ala Gly Ile Ala Gln Ser Arg Arg Thr Val Ala Leu Ile
                245                 250                 255

Lys Ser Ala Ala Val Ala Glu Arg Glu Arg Val Ser Arg Leu Phe Ala
                260                 265                 270

Asp Ala Ala Ala Leu Gln Gly Phe Gln Thr Gln Val Leu Gly Phe
                275                 280                 285

Ile Glu Glu Gly Glu Ala Ala Met Leu Gly Arg Ser Gln Gly Asp Leu
290                 295                 300

Arg Arg Gln Glu Glu Gln Arg Ser Arg Leu Ser Arg Ala Arg Gln Asn
305                 310                 315                 320

Leu Ser Gln Val Pro Glu Ala Asp Ser Val Ser Phe Leu Gln Glu Leu
                325                 330                 335

Leu Ala Leu Arg Leu Ala Leu Glu Asp Gly Cys Gly Pro Gly Pro Gly
                340                 345                 350

Pro Pro Arg Glu Leu Ser Phe Thr Lys Ser Ser Gln Ala Val Arg Ala
                355                 360                 365

Val Arg Asp Met Leu Ala Val Ala Cys Val Asn Gln Trp Glu Gln Leu
                370                 375                 380

Arg Gly Pro Gly Gly Asn Glu Asp Gly Pro Gln Lys Leu Asp Ser Glu
385                 390                 395                 400

Ala Asp Ala Glu Pro Gln Asp Leu Glu Ser Thr Asn Leu Leu Glu Ser
                405                 410                 415

Glu Ala Pro Arg Asp Tyr Phe Leu Lys Phe Ala Tyr Ile Val Asp Leu
                420                 425                 430

Asp Ser Asp Thr Ala Asp Lys Phe Leu Gln Leu Phe Gly Thr Lys Gly
                435                 440                 445

Val Lys Arg Val Leu Cys Pro Ile Asn Tyr Pro Leu Ser Pro Thr Arg
                450                 455                 460

Phe Thr His Cys Glu Gln Val Leu Gly Glu Gly Ala Leu Asp Arg Gly
465                 470                 475                 480

Thr Tyr Tyr Trp Glu Val Glu Ile Ile Glu Gly Trp Val Ser Met Gly
                485                 490                 495

Val Met Ala Glu Asp Phe Ser Pro Gln Glu Pro Tyr Asp Arg Gly Arg
                500                 505                 510

Leu Gly Arg Asn Ala His Ser Cys Cys Leu Gln Trp Asn Gly Arg Ser
                515                 520                 525

Phe Ser Val Trp Phe His Gly Leu Glu Ala Pro Leu Pro His Pro Phe
                530                 535                 540

Ser Pro Thr Val Gly Val Cys Leu Glu Tyr Ala Asp Arg Ala Leu Ala
545                 550                 555                 560

Phe Tyr Ala Val Arg Asp Gly Lys Met Ser Leu Leu Arg Arg Leu Lys
                565                 570                 575
```

```
Ala Ser Arg Pro Arg Arg Gly Gly Ile Pro Ala Ser Pro Ile Asp Pro
            580                 585                 590

Phe Gln Ser Arg Leu Asp Ser His Phe Ala Gly Leu Phe Thr His Arg
        595                 600                 605

Leu Lys Pro Ala Phe Phe Leu Glu Ser Val Asp Ala His Leu Gln Ile
            610                 615                 620

Gly Pro Leu Lys Lys Ser Cys Ile Ser Val Leu Lys Arg Arg
625                 630                 635

<210> SEQ ID NO 218
<211> LENGTH: 19
<212> TYPE: RNA
<213> ORGANISM: Homo Sapiens

<400> SEQUENCE: 218
guacgggacg gcaagauga                                                    19

<210> SEQ ID NO 219
<211> LENGTH: 19
<212> TYPE: RNA
<213> ORGANISM: Homo Sapiens

<400> SEQUENCE: 219
gaaccaaagg ugucaagag                                                    19

<210> SEQ ID NO 220
<211> LENGTH: 19
<212> TYPE: RNA
<213> ORGANISM: Homo Sapiens

<400> SEQUENCE: 220
gcauauccgu gcugaagag                                                    19

<210> SEQ ID NO 221
<211> LENGTH: 19
<212> TYPE: RNA
<213> ORGANISM: Homo Sapiens

<400> SEQUENCE: 221
caucaagagu gcagccgua                                                    19

<210> SEQ ID NO 222
<211> LENGTH: 224
<212> TYPE: PRT
<213> ORGANISM: Homo Sapiens

<400> SEQUENCE: 222

Met Ser Arg Arg Ile Ile Val Gly Thr Leu Gln Arg Thr Gln Arg Asn
1               5                   10                  15

Met Asn Ser Gly Ile Ser Gln Val Phe Gln Arg Glu Leu Thr Cys Pro
            20                  25                  30

Ile Cys Met Asn Tyr Phe Ile Asp Pro Val Thr Ile Asp Cys Gly His
        35                  40                  45

Ser Phe Cys Arg Pro Cys Phe Tyr Leu Asn Trp Gln Asp Ile Pro Ile
    50                  55                  60

Leu Thr Gln Cys Phe Glu Cys Ile Lys Thr Ile Gln Gln Arg Asn Leu
65                  70                  75                  80

Lys Thr Asn Ile Arg Leu Lys Lys Met Ala Ser Leu Ala Arg Lys Ala
                85                  90                  95

Ser Leu Trp Leu Phe Leu Ser Ser Glu Glu Gln Met Cys Gly Ile His
```

```
            100                 105                 110
Arg Glu Thr Lys Lys Met Phe Cys Glu Val Asp Arg Ser Leu Leu Cys
            115                 120                 125

Leu Leu Cys Ser Ser Ser Gln Glu His Arg Tyr His Arg His Cys Pro
            130                 135                 140

Ala Glu Trp Ala Ala Glu His Trp Glu Lys Leu Leu Lys Lys Met
145                 150                 155                 160

Gln Ser Leu Trp Glu Lys Ala Cys Glu Asn Gln Arg Asn Leu Asn Val
            165                 170                 175

Glu Thr Thr Arg Ile Ser His Trp Lys Ala Phe Gly Asp Ile Leu Tyr
            180                 185                 190

Arg Ser Glu Ser Val Leu Leu His Met Pro Gln Pro Leu Asn Leu Ala
            195                 200                 205

Leu Arg Ala Gly Pro Ile Thr Gly Leu Arg Asp Arg Leu Asn Gln Phe
            210                 215                 220
```

<210> SEQ ID NO 223
<211> LENGTH: 19
<212> TYPE: RNA
<213> ORGANISM: Homo Sapiens

<400> SEQUENCE: 223
gcauaaagac aauacagca                                             19

<210> SEQ ID NO 224
<211> LENGTH: 19
<212> TYPE: RNA
<213> ORGANISM: Homo Sapiens

<400> SEQUENCE: 224
cagagaaacc ugaaugugg                                             19

<210> SEQ ID NO 225
<211> LENGTH: 19
<212> TYPE: RNA
<213> ORGANISM: Homo Sapiens

<400> SEQUENCE: 225
ugcuuugaau gcauaaaga                                             19

<210> SEQ ID NO 226
<211> LENGTH: 19
<212> TYPE: RNA
<213> ORGANISM: Homo Sapiens

<400> SEQUENCE: 226
gaaggcuuuu ggagacaua                                             19

<210> SEQ ID NO 227
<211> LENGTH: 452
<212> TYPE: PRT
<213> ORGANISM: Homo Sapiens

<400> SEQUENCE: 227

```
Met Asn Ser Gly Ile Leu Gln Val Phe Gln Gly Glu Leu Ile Cys Pro
1               5                   10                  15

Leu Cys Met Asn Tyr Phe Ile Asp Pro Val Thr Ile Asp Cys Gly His
                20                  25                  30

Ser Phe Cys Arg Pro Cys Phe Tyr Leu Asn Trp Gln Asp Ile Pro Phe
            35                  40                  45
```

```
Leu Val Gln Cys Ser Glu Cys Thr Lys Ser Thr Glu Gln Ile Asn Leu
    50                  55                  60

Lys Thr Asn Ile His Leu Lys Lys Met Ala Ser Leu Ala Arg Lys Val
 65              70                  75                      80

Ser Leu Trp Leu Phe Leu Ser Ser Glu Gln Met Cys Gly Thr His
                85                  90                  95

Arg Glu Thr Lys Lys Ile Phe Cys Glu Val Asp Arg Ser Leu Leu Cys
            100                 105                 110

Leu Leu Cys Ser Ser Ser Gln Glu His Arg Tyr His Arg His Arg Pro
        115                 120                 125

Ile Glu Trp Ala Ala Glu His Arg Glu Lys Leu Leu Gln Lys Met
    130                 135                 140

Gln Ser Leu Trp Glu Lys Ala Cys Glu Asn His Arg Asn Leu Asn Val
145                 150                 155                 160

Glu Thr Thr Arg Thr Arg Cys Trp Lys Asp Tyr Val Asn Leu Arg Leu
                165                 170                 175

Glu Ala Ile Arg Ala Glu Tyr Gln Lys Met Pro Ala Phe His His Glu
                180                 185                 190

Glu Glu Lys His Asn Leu Glu Met Leu Lys Lys Gly Lys Glu Ile
        195                 200                 205

Phe His Arg Leu His Leu Ser Lys Ala Lys Met Ala His Arg Met Glu
    210                 215                 220

Ile Leu Arg Gly Met Tyr Glu Glu Leu Asn Glu Met Cys His Lys Pro
225                 230                 235                 240

Asp Val Glu Leu Leu Gln Ala Phe Gly Asp Ile Leu His Arg Ser Glu
                245                 250                 255

Ser Val Leu Leu His Met Pro Gln Pro Leu Asn Pro Glu Leu Ser Ala
                260                 265                 270

Gly Pro Ile Thr Gly Leu Arg Asp Arg Leu Asn Gln Phe Arg Val His
            275                 280                 285

Ile Thr Leu His His Glu Glu Ala Asn Asn Asp Ile Phe Leu Tyr Glu
    290                 295                 300

Ile Leu Arg Ser Met Cys Ile Gly Cys Asp His Gln Asp Val Pro Tyr
305                 310                 315                 320

Phe Thr Ala Thr Pro Arg Ser Phe Leu Ala Trp Gly Val Gln Thr Phe
                325                 330                 335

Thr Ser Gly Lys Tyr Tyr Trp Glu Val His Val Gly Asp Ser Trp Asn
                340                 345                 350

Trp Ala Phe Gly Val Cys Asn Met Tyr Arg Lys Glu Lys Asn Gln Asn
            355                 360                 365

Glu Lys Ile Asp Gly Lys Ala Gly Leu Phe Leu Leu Gly Cys Val Lys
    370                 375                 380

Asn Asp Ile Gln Cys Ser Leu Phe Thr Thr Ser Pro Leu Met Leu Gln
385                 390                 395                 400

Tyr Ile Pro Lys Pro Thr Ser Arg Val Gly Leu Phe Leu Asp Cys Glu
                405                 410                 415

Ala Lys Thr Val Ser Phe Val Asp Val Asn Gln Ser Ser Leu Ile Tyr
                420                 425                 430

Thr Ile Pro Asn Cys Ser Phe Ser Pro Pro Leu Arg Pro Ile Phe Cys
            435                 440                 445

Cys Ile His Phe
        450
```

<210> SEQ ID NO 228
<211> LENGTH: 19
<212> TYPE: RNA
<213> ORGANISM: Homo Sapiens

<400> SEQUENCE: 228
gaagaagcca acaaugaua                                                    19

<210> SEQ ID NO 229
<211> LENGTH: 19
<212> TYPE: RNA
<213> ORGANISM: Homo Sapiens

<400> SEQUENCE: 229
ggaaggauua ugugaauuu                                                    19

<210> SEQ ID NO 230
<211> LENGTH: 19
<212> TYPE: RNA
<213> ORGANISM: Homo Sapiens

<400> SEQUENCE: 230
gaacgaaaug ugccauaaa                                                    19

<210> SEQ ID NO 231
<211> LENGTH: 19
<212> TYPE: RNA
<213> ORGANISM: Homo Sapiens

<400> SEQUENCE: 231
gaaucagaau gagaagaua                                                    19

<210> SEQ ID NO 232
<211> LENGTH: 487
<212> TYPE: PRT
<213> ORGANISM: Homo Sapiens

<400> SEQUENCE: 232

Met Ala Trp Gln Val Ser Leu Pro Glu Leu Glu Asp Arg Leu Gln Cys
1               5                   10                  15

Pro Ile Cys Leu Glu Val Phe Lys Glu Pro Leu Met Leu Gln Cys Gly
            20                  25                  30

His Ser Tyr Cys Lys Gly Cys Leu Val Ser Leu Ser Cys His Leu Asp
        35                  40                  45

Ala Glu Leu Arg Cys Pro Val Cys Arg Gln Ala Val Asp Gly Ser Ser
    50                  55                  60

Ser Leu Pro Asn Val Ser Leu Ala Arg Val Ile Glu Ala Leu Arg Leu
65                  70                  75                  80

Pro Gly Asp Pro Glu Pro Lys Val Cys Val His His Arg Asn Pro Leu
                85                  90                  95

Ser Leu Phe Cys Glu Lys Asp Gln Glu Leu Ile Cys Gly Leu Cys Gly
            100                 105                 110

Leu Leu Gly Ser His Gln His Pro Val Thr Pro Val Ser Thr Val
        115                 120                 125

Tyr Ser Arg Met Lys Glu Glu Leu Ala Ala Leu Ile Ser Glu Leu Lys
    130                 135                 140

Gln Glu Gln Lys Lys Val Asp Glu Leu Ile Ala Lys Leu Val Asn Asn
145                 150                 155                 160

Arg Thr Arg Ile Val Asn Glu Ser Asp Val Phe Ser Trp Val Ile Arg

```
                    165                 170                 175
Arg Glu Phe Gln Glu Leu His His Leu Val Asp Glu Lys Ala Arg
                180                 185                 190

Cys Leu Glu Gly Ile Gly Gly His Thr Arg Gly Leu Val Ala Ser Leu
            195                 200                 205

Asp Met Gln Leu Glu Gln Ala Gln Gly Thr Arg Glu Arg Leu Ala Gln
        210                 215                 220

Ala Glu Cys Val Leu Glu Gln Phe Gly Asn Glu Asp His His Lys Phe
225                 230                 235                 240

Ile Arg Lys Phe His Ser Met Ala Ser Arg Ala Glu Met Pro Gln Ala
                245                 250                 255

Arg Pro Leu Glu Gly Ala Phe Ser Pro Ile Ser Phe Lys Pro Gly Leu
            260                 265                 270

His Gln Ala Asp Ile Lys Leu Thr Val Trp Lys Arg Leu Phe Arg Lys
        275                 280                 285

Val Leu Pro Ala Pro Glu Pro Leu Lys Leu Asp Pro Ala Thr Ala His
290                 295                 300

Pro Leu Leu Glu Leu Ser Lys Gly Asn Thr Val Val Gln Cys Gly Leu
305                 310                 315                 320

Leu Ala Gln Arg Arg Ala Ser Gln Pro Glu Arg Phe Asp Tyr Ser Thr
                325                 330                 335

Cys Val Leu Ala Ser Arg Gly Phe Ser Cys Gly Arg His Tyr Trp Glu
            340                 345                 350

Val Val Val Gly Ser Lys Ser Asp Trp Arg Leu Gly Val Ile Lys Gly
        355                 360                 365

Thr Ala Ser Arg Lys Gly Lys Leu Asn Arg Ser Pro Glu His Gly Val
370                 375                 380

Trp Leu Ile Gly Leu Lys Glu Gly Arg Val Tyr Glu Ala Phe Ala Cys
385                 390                 395                 400

Pro Arg Val Pro Leu Pro Val Ala Gly His Pro His Arg Ile Gly Leu
                405                 410                 415

Tyr Leu His Tyr Glu Gln Gly Glu Leu Thr Phe Phe Asp Ala Asp Arg
            420                 425                 430

Pro Asp Asp Leu Arg Pro Leu Tyr Thr Phe Gln Ala Asp Phe Gln Gly
        435                 440                 445

Lys Leu Tyr Pro Ile Leu Asp Thr Cys Trp His Glu Arg Gly Ser Asn
450                 455                 460

Ser Leu Pro Met Val Leu Pro Pro Ser Gly Pro Gly Pro Leu Ser
465                 470                 475                 480

Pro Glu Gln Pro Thr Lys Leu
                485

<210> SEQ ID NO 233
<211> LENGTH: 19
<212> TYPE: RNA
<213> ORGANISM: Homo Sapiens

<400> SEQUENCE: 233
ggacccgaau cgucaauga                                          19

<210> SEQ ID NO 234
<211> LENGTH: 19
<212> TYPE: RNA
<213> ORGANISM: Homo Sapiens

<400> SEQUENCE: 234
```

-continued

```
ggcucuaccu gcacuauga                                                    19

<210> SEQ ID NO 235
<211> LENGTH: 19
<212> TYPE: RNA
<213> ORGANISM: Homo Sapiens

<400> SEQUENCE: 235
gcaacucgcu gcccauggu                                                    19

<210> SEQ ID NO 236
<211> LENGTH: 19
<212> TYPE: RNA
<213> ORGANISM: Homo Sapiens

<400> SEQUENCE: 236
ucgcagcccu caucucuga                                                    19

<210> SEQ ID NO 237
<211> LENGTH: 452
<212> TYPE: PRT
<213> ORGANISM: Homo Sapiens

<400> SEQUENCE: 237
```

Met Asn Ser Gly Ile Leu Gln Val Phe Gln Arg Ala Leu Thr Cys Pro
1               5                   10                  15

Ile Cys Met Asn Tyr Phe Leu Asp Pro Val Thr Ile Asp Cys Gly His
            20                  25                  30

Ser Phe Cys Arg Pro Cys Leu Tyr Leu Asn Trp Gln Asp Thr Ala Val
        35                  40                  45

Leu Ala Gln Cys Ser Glu Cys Lys Lys Thr Thr Arg Gln Arg Asn Leu
    50                  55                  60

Asn Thr Asp Ile Cys Leu Lys Asn Met Ala Phe Ile Ala Arg Lys Ala
65                  70                  75                  80

Ser Leu Arg Gln Phe Leu Ser Ser Glu Glu Gln Ile Cys Gly Met His
                85                  90                  95

Arg Glu Thr Lys Lys Met Phe Cys Glu Val Asp Lys Ser Leu Leu Cys
            100                 105                 110

Leu Pro Cys Ser Asn Ser Gln Glu His Arg Asn His Ile His Cys Pro
        115                 120                 125

Ile Glu Trp Ala Ala Glu Glu Arg Glu Glu Leu Leu Lys Lys Met
    130                 135                 140

Gln Ser Leu Trp Glu Lys Ala Cys Glu Asn Leu Arg Asn Leu Asn Met
145                 150                 155                 160

Glu Thr Thr Arg Thr Arg Cys Trp Lys Asp Tyr Val Ser Leu Arg Ile
                165                 170                 175

Glu Ala Ile Arg Ala Glu Tyr Gln Lys Met Pro Ala Phe Leu His Glu
            180                 185                 190

Glu Glu Gln His His Leu Glu Arg Leu Arg Lys Glu Gly Glu Asp Ile
        195                 200                 205

Phe Gln Gln Leu Asn Glu Ser Lys Ala Arg Met Glu His Ser Arg Glu
    210                 215                 220

Leu Leu Arg Gly Met Tyr Glu Asp Leu Lys Gln Met Cys His Lys Ala
225                 230                 235                 240

Asp Val Glu Leu Leu Gln Ala Phe Gly Asp Ile Leu His Arg Tyr Glu
                245                 250                 255

```
Ser Leu Leu Leu Gln Val Ser Glu Pro Val Asn Pro Glu Leu Ser Ala
            260                 265                 270

Gly Pro Ile Thr Gly Leu Leu Asp Ser Leu Ser Gly Phe Arg Val Asp
        275                 280                 285

Phe Thr Leu Gln Pro Glu Arg Ala Asn Ser His Ile Phe Leu Cys Gly
    290                 295                 300

Asp Leu Arg Ser Met Asn Val Gly Cys Asp Pro Gln Asp Asp Pro Asp
305                 310                 315                 320

Ile Thr Gly Lys Ser Glu Cys Phe Leu Val Trp Gly Ala Gln Ala Phe
                325                 330                 335

Thr Ser Gly Lys Tyr Tyr Trp Glu Val His Met Gly Asp Ser Trp Asn
            340                 345                 350

Trp Ala Phe Gly Val Cys Asn Asn Tyr Trp Lys Glu Lys Arg Gln Asn
        355                 360                 365

Asp Lys Ile Asp Gly Glu Glu Gly Leu Phe Leu Leu Gly Cys Val Lys
    370                 375                 380

Glu Asp Thr His Cys Ser Leu Phe Thr Thr Ser Pro Leu Val Val Gln
385                 390                 395                 400

Tyr Val Pro Arg Pro Thr Ser Thr Val Gly Leu Phe Leu Asp Cys Glu
                405                 410                 415

Gly Arg Thr Val Ser Phe Val Asp Val Asp Gln Ser Ser Leu Ile Tyr
            420                 425                 430

Thr Ile Pro Asn Cys Ser Phe Ser Pro Pro Leu Arg Pro Ile Phe Cys
        435                 440                 445

Cys Ser His Phe
    450

<210> SEQ ID NO 238
<211> LENGTH: 19
<212> TYPE: RNA
<213> ORGANISM: Homo Sapiens

<400> SEQUENCE: 238
ggaaggauua ugugaguuu                                                    19

<210> SEQ ID NO 239
<211> LENGTH: 19
<212> TYPE: RNA
<213> ORGANISM: Homo Sapiens

<400> SEQUENCE: 239
acuuggaaag gcugcgaaa                                                    19

<210> SEQ ID NO 240
<211> LENGTH: 19
<212> TYPE: RNA
<213> ORGANISM: Homo Sapiens

<400> SEQUENCE: 240
aagcagaugu ggagcuacu                                                    19

<210> SEQ ID NO 241
<211> LENGTH: 19
<212> TYPE: RNA
<213> ORGANISM: Homo Sapiens

<400> SEQUENCE: 241
ggacagccuc aguggauuc                                                    19
```

```
<210> SEQ ID NO 242
<211> LENGTH: 297
<212> TYPE: PRT
<213> ORGANISM: Homo Sapiens

<400> SEQUENCE: 242

Met Ala Gly Tyr Ala Thr Thr Pro Ser Pro Met Gln Thr Leu Gln Glu
  1               5                  10                  15

Glu Ala Val Cys Ala Ile Cys Leu Asp Tyr Phe Lys Asp Pro Val Ser
             20                  25                  30

Ile Ser Cys Gly His Asn Phe Cys Arg Gly Cys Val Thr Gln Leu Trp
         35                  40                  45

Ser Lys Glu Asp Glu Asp Gln Asn Glu Glu Asp Glu Trp Glu
 50                  55                  60

Glu Glu Glu Asp Glu Glu Ala Val Gly Ala Met Asp Gly Trp Asp Gly
 65                  70                  75                  80

Ser Ile Arg Glu Val Leu Tyr Arg Gly Asn Ala Asp Glu Glu Leu Phe
                 85                  90                  95

Gln Asp Gln Asp Asp Asp Glu Leu Trp Leu Gly Asp Ser Gly Ile Thr
            100                 105                 110

Asn Trp Asp Asn Val Asp Tyr Met Trp Asp Glu Glu Glu Glu Glu
            115                 120                 125

Glu Glu Asp Gln Asp Tyr Tyr Leu Gly Gly Leu Arg Pro Asp Leu Arg
        130                 135                 140

Ile Asp Val Tyr Arg Glu Glu Ile Leu Glu Ala Tyr Asp Glu Asp
145                 150                 155                 160

Glu Asp Glu Glu Leu Tyr Pro Asp Ile His Pro Pro Ser Leu Pro
                165                 170                 175

Leu Pro Gly Gln Phe Thr Cys Pro Gln Cys Arg Lys Ser Phe Thr Arg
            180                 185                 190

Arg Ser Phe Arg Pro Asn Leu Gln Leu Ala Asn Met Val Gln Ile Ile
        195                 200                 205

Arg Gln Met Cys Pro Thr Pro Tyr Arg Gly Asn Arg Ser Asn Asp Gln
    210                 215                 220

Gly Met Cys Phe Lys His Gln Glu Ala Leu Lys Leu Phe Cys Glu Val
225                 230                 235                 240

Asp Lys Glu Ala Ile Cys Val Val Cys Arg Glu Ser Arg Ser His Lys
                245                 250                 255

Gln His Ser Val Leu Pro Leu Glu Val Val Gln Glu Tyr Gln Glu
            260                 265                 270

Ile Lys Leu Glu Thr Thr Leu Val Gly Ile Leu Gln Ile Glu Gln Glu
        275                 280                 285

Ser Ile His Ser Lys Ala Tyr Asn Gln
    290                 295

<210> SEQ ID NO 243
<211> LENGTH: 19
<212> TYPE: RNA
<213> ORGANISM: Homo Sapiens

<400> SEQUENCE: 243
gaccugaccu gagaauuga                                              19

<210> SEQ ID NO 244
<211> LENGTH: 19
<212> TYPE: RNA
```

<213> ORGANISM: Homo Sapiens

<400> SEQUENCE: 244
ugacccagcu guggaguaa                                                19

<210> SEQ ID NO 245
<211> LENGTH: 19
<212> TYPE: RNA
<213> ORGANISM: Homo Sapiens

<400> SEQUENCE: 245
gggacaacgu agacuauau                                                19

<210> SEQ ID NO 246
<211> LENGTH: 19
<212> TYPE: RNA
<213> ORGANISM: Homo Sapiens

<400> SEQUENCE: 246
acgaagaguu guuccaaga                                                19

<210> SEQ ID NO 247
<211> LENGTH: 358
<212> TYPE: PRT
<213> ORGANISM: Homo Sapiens

<400> SEQUENCE: 247

Met Asn Phe Thr Val Gly Phe Lys Pro Leu Leu Gly Asp Ala His Ser
1               5                   10                  15

Met Asp Asn Leu Glu Lys Gln Leu Ile Cys Pro Ile Cys Leu Glu Met
            20                  25                  30

Phe Ser Lys Pro Val Val Ile Leu Pro Cys Gln His Asn Leu Cys Arg
        35                  40                  45

Lys Cys Ala Asn Asp Val Phe Gln Ala Ser Asn Pro Leu Trp Gln Ser
    50                  55                  60

Arg Gly Ser Thr Thr Val Ser Ser Gly Gly Arg Phe Arg Cys Pro Ser
65                  70                  75                  80

Cys Arg His Glu Val Val Leu Asp Arg His Gly Val Tyr Gly Leu Gln
                85                  90                  95

Arg Asn Leu Leu Val Glu Asn Ile Ile Asp Ile Tyr Lys Gln Glu Ser
            100                 105                 110

Ser Arg Pro Leu His Ser Lys Ala Glu Gln His Leu Met Cys Glu Glu
        115                 120                 125

His Glu Glu Glu Lys Ile Asn Ile Tyr Cys Leu Ser Cys Glu Val Pro
    130                 135                 140

Thr Cys Ser Leu Cys Lys Val Phe Gly Ala His Lys Asp Cys Glu Val
145                 150                 155                 160

Ala Pro Leu Pro Thr Ile Tyr Lys Arg Gln Lys Ser Glu Leu Ser Asp
                165                 170                 175

Gly Ile Ala Met Leu Val Ala Gly Asn Asp Arg Val Gln Ala Val Ile
            180                 185                 190

Thr Gln Met Glu Glu Val Cys Gln Thr Ile Glu Asp Asn Ser Arg Arg
        195                 200                 205

Gln Lys Gln Leu Leu Asn Gln Arg Phe Glu Ser Leu Cys Ala Val Leu
    210                 215                 220

Glu Glu Arg Lys Gly Glu Leu Leu Gln Ala Leu Ala Arg Glu Gln Glu
225                 230                 235                 240

```
Glu Lys Leu Gln Arg Val Arg Gly Leu Ile Arg Gln Tyr Gly Asp His
                245                 250                 255

Leu Glu Ala Ser Ser Lys Leu Val Glu Ser Ala Ile Gln Ser Met Glu
            260                 265                 270

Glu Pro Gln Met Ala Leu Tyr Leu Gln Ala Lys Glu Leu Ile Asn
        275                 280                 285

Lys Val Gly Ala Met Ser Lys Val Glu Leu Ala Gly Arg Pro Glu Pro
    290                 295                 300

Gly Tyr Glu Ser Met Glu Gln Phe Thr Val Arg Val Glu His Val Ala
305                 310                 315                 320

Glu Met Leu Arg Thr Ile Asp Phe Gln Pro Gly Ala Ser Gly Glu Glu
                325                 330                 335

Glu Glu Val Ala Pro Asp Gly Glu Gly Ser Ala Gly Pro Glu Glu
            340                 345                 350

Glu Arg Pro Asp Gly Pro
        355
```

<210> SEQ ID NO 248
<211> LENGTH: 19
<212> TYPE: RNA
<213> ORGANISM: Homo Sapiens

<400> SEQUENCE: 248
gaggaggugu gccagacua                                                    19

<210> SEQ ID NO 249
<211> LENGTH: 19
<212> TYPE: RNA
<213> ORGANISM: Homo Sapiens

<400> SEQUENCE: 249
gaacauuauc gacauuuac                                                    19

<210> SEQ ID NO 250
<211> LENGTH: 19
<212> TYPE: RNA
<213> ORGANISM: Homo Sapiens

<400> SEQUENCE: 250
ucuacggccu gcagcgaaa                                                    19

<210> SEQ ID NO 251
<211> LENGTH: 19
<212> TYPE: RNA
<213> ORGANISM: Homo Sapiens

<400> SEQUENCE: 251
caauaaagaa cucgagcgu                                                    19

<210> SEQ ID NO 252
<211> LENGTH: 241
<212> TYPE: PRT
<213> ORGANISM: Homo Sapiens

<400> SEQUENCE: 252

```
Met Ser Ala Ser Leu Asn Tyr Lys Ser Phe Ser Lys Glu Gln Gln Thr
1               5                   10                  15

Met Asp Asn Leu Glu Lys Gln Leu Ile Cys Pro Ile Cys Leu Glu Met
            20                  25                  30

Phe Thr Lys Pro Val Val Ile Leu Pro Cys Gln His Asn Leu Cys Arg
```

```
                35                  40                  45
Lys Cys Ala Ser Asp Ile Phe Gln Ala Ser Asn Pro Tyr Leu Pro Thr
 50                  55                  60

Arg Gly Gly Thr Thr Met Ala Ser Gly Gly Arg Phe Arg Cys Pro Ser
 65                  70                  75                  80

Cys Arg His Glu Val Leu Asp Arg His Gly Val Tyr Gly Leu Gln
                 85                  90                  95

Arg Asn Leu Leu Val Glu Asn Ile Ile Asp Ile Tyr Lys Gln Glu Ser
                100                 105                 110

Thr Arg Pro Glu Lys Lys Ser Asp Gln Pro Met Cys Glu His Glu
            115                 120                 125

Glu Glu Arg Ile Asn Ile Tyr Cys Leu Asn Cys Glu Val Pro Thr Cys
130                 135                 140

Ser Leu Cys Lys Val Phe Gly Ala His Lys Asp Cys Gln Val Ala Pro
145                 150                 155                 160

Leu Thr His Val Phe Gln Arg Gln Lys Ser Glu Leu Ser Asp Gly Ile
                165                 170                 175

Ala Ile Leu Val Gly Ser Asn Asp Arg Val Gln Gly Val Ile Ser Gln
            180                 185                 190

Leu Glu Asp Thr Cys Lys Thr Ile Glu Ile Gly Phe Glu Ala Pro Pro
        195                 200                 205

Leu Gln Gly Gln Ala Ala Pro Ala Ser Gly Ser Gly Ala Asp Ser
210                 215                 220

Glu Pro Ala Arg His Ile Phe Ser Phe Ser Trp Leu Asn Ser Leu Asn
225                 230                 235                 240

Glu
```

<210> SEQ ID NO 253
<211> LENGTH: 19
<212> TYPE: RNA
<213> ORGANISM: Homo Sapiens

<400> SEQUENCE: 253
gcgcaucucu gaauuacaa                                              19

<210> SEQ ID NO 254
<211> LENGTH: 19
<212> TYPE: RNA
<213> ORGANISM: Homo Sapiens

<400> SEQUENCE: 254
gaaaugugcc agugauauu                                              19

<210> SEQ ID NO 255
<211> LENGTH: 19
<212> TYPE: RNA
<213> ORGANISM: Homo Sapiens

<400> SEQUENCE: 255
gguugaacuc ccuaaauga                                              19

<210> SEQ ID NO 256
<211> LENGTH: 19
<212> TYPE: RNA
<213> ORGANISM: Homo Sapiens

<400> SEQUENCE: 256
caugaagagg agcgcauca                                              19

<210> SEQ ID NO 257
<211> LENGTH: 755
<212> TYPE: PRT
<213> ORGANISM: Homo Sapiens

<400> SEQUENCE: 257

Met Val Ser His Gly Ser Ser Pro Ser Leu Glu Ala Leu Ser Ser
1               5                   10                  15

Asp Phe Leu Ala Cys Lys Ile Cys Leu Glu Gln Leu Arg Ala Pro Lys
            20                  25                  30

Thr Leu Pro Cys Leu His Thr Tyr Cys Gln Asp Cys Leu Ala Gln Leu
        35                  40                  45

Ala Asp Gly Gly Arg Val Arg Cys Pro Glu Cys Arg Glu Thr Val Pro
    50                  55                  60

Val Pro Pro Glu Gly Val Ala Ser Phe Lys Thr Asn Phe Phe Val Asn
65                  70                  75                  80

Gly Leu Leu Asp Leu Val Lys Ala Arg Ala Cys Gly Asp Leu Arg Ala
                85                  90                  95

Gly Lys Pro Ala Cys Ala Leu Cys Pro Leu Val Gly Gly Thr Ser Thr
            100                 105                 110

Gly Gly Pro Ala Thr Ala Arg Cys Leu Asp Cys Ala Asp Asp Leu Cys
        115                 120                 125

Gln Ala Cys Ala Asp Gly His Arg Cys Thr Arg Gln Thr His Thr His
    130                 135                 140

Arg Val Val Asp Leu Val Gly Tyr Arg Ala Gly Trp Tyr Asp Glu Glu
145                 150                 155                 160

Ala Arg Glu Arg Gln Ala Ala Gln Cys Pro Gln His Pro Gly Glu Ala
                165                 170                 175

Leu Arg Phe Leu Cys Gln Pro Cys Ser Gln Leu Leu Cys Arg Glu Cys
            180                 185                 190

Arg Leu Asp Pro His Leu Asp His Pro Cys Leu Pro Leu Ala Glu Ala
        195                 200                 205

Val Arg Ala Arg Arg Pro Gly Leu Glu Gly Leu Leu Ala Gly Val Asp
    210                 215                 220

Asn Asn Leu Val Glu Leu Glu Ala Ala Arg Arg Val Glu Lys Glu Ala
225                 230                 235                 240

Leu Ala Arg Leu Arg Glu Gln Ala Ala Arg Val Gly Thr Gln Val Glu
                245                 250                 255

Glu Ala Ala Glu Gly Val Leu Arg Ala Leu Ala Gln Lys Gln Glu
            260                 265                 270

Val Leu Gly Gln Leu Arg Ala His Val Glu Ala Ala Glu Ala Ala
    275                 280                 285

Arg Glu Arg Leu Ala Glu Leu Glu Gly Arg Glu Gln Val Ala Arg Ala
    290                 295                 300

Ala Ala Ala Phe Ala Arg Arg Val Leu Ser Leu Gly Arg Glu Ala Glu
305                 310                 315                 320

Ile Leu Ser Leu Glu Gly Ala Ile Ala Gln Arg Leu Arg Gln Leu Gln
                325                 330                 335

Gly Cys Pro Trp Ala Pro Gly Pro Ala Pro Cys Leu Leu Pro Gln Leu
            340                 345                 350

Glu Leu His Pro Gly Leu Leu Asp Lys Asn Cys His Leu Leu Arg Leu
        355                 360                 365

Ser Phe Glu Glu Gln Gln Pro Gln Lys Asp Gly Gly Lys Asp Gly Ala

```
              370                 375                 380
Gly Thr Gln Gly Gly Glu Ser Gln Ser Arg Arg Glu Asp Glu Pro
385                 390                 395                 400

Lys Thr Glu Arg Gln Gly Val Gln Pro Ala Gly Asp Gly Ala
                405                 410                 415

Gln Thr Pro Lys Glu Lys Ala Gln Thr Thr Arg Glu Glu Gly Ala
                420                 425                 430

Gln Thr Leu Glu Glu Asp Arg Ala Gln Thr Pro His Glu Asp Gly Gly
            435                 440                 445

Pro Gln Pro His Arg Gly Gly Arg Pro Asn Lys Lys Lys Phe Lys
        450                 455                 460

Gly Arg Leu Lys Ser Ile Ser Arg Glu Pro Ser Ala Leu Gly Pro
465                 470                 475                 480

Asn Leu Asp Gly Ser Gly Leu Leu Pro Arg Pro Ile Phe Tyr Cys Ser
                485                 490                 495

Phe Pro Thr Arg Met Pro Gly Asp Lys Arg Ser Pro Arg Ile Thr Gly
                500                 505                 510

Leu Cys Pro Phe Gly Pro Arg Glu Ile Leu Val Ala Asp Glu Gln Asn
            515                 520                 525

Arg Ala Leu Lys Arg Phe Ser Leu Asn Gly Asp Tyr Lys Gly Thr Val
                530                 535                 540

Pro Val Pro Glu Gly Cys Ser Pro Cys Ser Val Ala Ala Leu Gln Ser
545                 550                 555                 560

Ala Val Ala Phe Ser Ala Ser Ala Arg Leu Tyr Leu Ile Asn Pro Asn
                565                 570                 575

Gly Glu Val Gln Trp Arg Arg Ala Leu Ser Leu Ser Gln Ala Ser His
                580                 585                 590

Ala Val Ala Ala Leu Pro Ser Gly Asp Arg Val Ala Val Ser Val Ala
                595                 600                 605

Gly His Val Glu Val Tyr Asn Met Glu Gly Ser Leu Ala Thr Arg Phe
            610                 615                 620

Ile Pro Gly Gly Lys Ala Ser Arg Gly Leu Arg Ala Leu Val Phe Leu
625                 630                 635                 640

Thr Thr Ser Pro Gln Gly His Phe Val Gly Ser Asp Trp Gln Gln Asn
                645                 650                 655

Ser Val Val Ile Cys Asp Gly Leu Gly Gln Val Val Gly Glu Tyr Lys
                660                 665                 670

Gly Pro Gly Leu His Gly Cys Gln Pro Gly Ser Val Ser Val Asp Lys
            675                 680                 685

Lys Gly Tyr Ile Phe Leu Thr Leu Arg Glu Val Asn Lys Val Val Ile
        690                 695                 700

Leu Asp Pro Lys Gly Ser Leu Leu Gly Asp Phe Leu Thr Ala Tyr His
705                 710                 715                 720

Gly Leu Glu Lys Pro Arg Val Thr Thr Met Val Asp Gly Arg Tyr Leu
                725                 730                 735

Val Val Ser Leu Ser Asn Gly Thr Ile His Ile Phe Arg Val Arg Ser
                740                 745                 750

Pro Asp Ser
        755

<210> SEQ ID NO 258
<211> LENGTH: 19
<212> TYPE: RNA
<213> ORGANISM: Homo Sapiens
```

```
<400> SEQUENCE: 258
ggacugugcc gaugacuug                                               19

<210> SEQ ID NO 259
<211> LENGTH: 19
<212> TYPE: RNA
<213> ORGANISM: Homo Sapiens

<400> SEQUENCE: 259
gguguggccu ccuucaaga                                               19

<210> SEQ ID NO 260
<211> LENGTH: 19
<212> TYPE: RNA
<213> ORGANISM: Homo Sapiens

<400> SEQUENCE: 260
gcggaugccu ggagacaag                                               19

<210> SEQ ID NO 261
<211> LENGTH: 19
<212> TYPE: RNA
<213> ORGANISM: Homo Sapiens

<400> SEQUENCE: 261
gauaagaagg gcuacaucu                                               19

<210> SEQ ID NO 262
<211> LENGTH: 486
<212> TYPE: PRT
<213> ORGANISM: Homo Sapiens

<400> SEQUENCE: 262
```

Met Ala Trp Ala Pro Gly Glu Arg Leu Arg Glu Asp Ala Arg Cys
1               5                   10                  15

Pro Val Cys Leu Asp Phe Leu Gln Glu Pro Val Ser Val Asp Cys Gly
                20                  25                  30

His Ser Phe Cys Leu Arg Cys Ile Ser Glu Phe Cys Glu Lys Ser Asp
            35                  40                  45

Gly Ala Gln Gly Gly Val Tyr Ala Cys Pro Gln Cys Arg Gly Pro Phe
        50                  55                  60

Arg Pro Ser Gly Phe Arg Pro Asn Arg Gln Leu Ala Gly Leu Val Glu
65                  70                  75                  80

Ser Val Arg Arg Leu Gly Leu Gly Ala Gly Pro Gly Ala Arg Arg Cys
                85                  90                  95

Ala Arg His Gly Glu Asp Leu Ser Arg Phe Cys Glu Glu Asp Glu Ala
            100                 105                 110

Ala Leu Cys Trp Val Cys Asp Ala Gly Pro Glu His Arg Thr His Arg
        115                 120                 125

Thr Ala Pro Leu Gln Glu Ala Ala Gly Ser Tyr Gln Val Lys Leu Gln
    130                 135                 140

Met Ala Leu Glu Leu Met Arg Lys Glu Leu Glu Asp Ala Leu Thr Gln
145                 150                 155                 160

Glu Ala Asn Val Gly Lys Lys Thr Val Ile Trp Lys Glu Lys Val Glu
                165                 170                 175

Met Gln Arg Gln Arg Phe Arg Leu Glu Phe Glu Lys His Arg Gly Phe
            180                 185                 190

```
Leu Ala Gln Glu Glu Gln Arg Gln Leu Arg Arg Leu Glu Ala Glu
            195                 200                 205

Arg Ala Thr Leu Gln Arg Leu Arg Glu Ser Lys Ser Arg Leu Val Gln
210                 215                 220

Gln Ser Lys Ala Leu Lys Glu Leu Ala Asp Glu Leu Gln Glu Arg Cys
225                 230                 235                 240

Gln Arg Pro Ala Leu Gly Leu Leu Glu Gly Val Arg Gly Val Leu Ser
                245                 250                 255

Arg Ser Lys Ala Val Thr Arg Leu Glu Ala Glu Asn Ile Pro Met Glu
            260                 265                 270

Leu Lys Thr Ala Cys Cys Ile Pro Gly Arg Arg Glu Leu Leu Arg Lys
275                 280                 285

Phe Gln Val Asp Val Lys Leu Asp Pro Ala Thr Ala His Pro Ser Leu
            290                 295                 300

Leu Leu Thr Ala Asp Leu Arg Ser Val Gln Asp Gly Glu Pro Trp Arg
305                 310                 315                 320

Asp Val Pro Asn Asn Pro Glu Arg Phe Asp Thr Trp Pro Cys Ile Leu
                325                 330                 335

Gly Leu Gln Ser Phe Ser Ser Gly Arg His Tyr Trp Glu Val Leu Val
            340                 345                 350

Gly Glu Gly Ala Glu Trp Gly Leu Gly Val Cys Gln Asp Thr Leu Pro
        355                 360                 365

Arg Lys Gly Glu Thr Thr Pro Ser Pro Glu Asn Gly Val Trp Ala Leu
370                 375                 380

Trp Leu Leu Lys Gly Asn Glu Tyr Met Val Leu Ala Ser Pro Ser Val
385                 390                 395                 400

Pro Leu Leu Gln Leu Glu Ser Pro Arg Cys Ile Gly Ile Phe Leu Asp
                405                 410                 415

Tyr Glu Ala Gly Glu Ile Ser Phe Tyr Asn Val Thr Asp Gly Ser Tyr
            420                 425                 430

Ile Tyr Thr Phe Asn Gln Leu Phe Ser Gly Leu Leu Arg Pro Tyr Phe
        435                 440                 445

Phe Ile Cys Asp Ala Thr Pro Leu Ile Leu Pro Pro Thr Thr Ile Ala
450                 455                 460

Gly Ser Gly Asn Trp Ala Ser Arg Asp His Leu Asp Pro Ala Ser Asp
465                 470                 475                 480

Val Arg Asp Asp His Leu
                485

<210> SEQ ID NO 263
<211> LENGTH: 19
<212> TYPE: RNA
<213> ORGANISM: Homo Sapiens

<400> SEQUENCE: 263
gaaaguccuc gcugcauug                                              19

<210> SEQ ID NO 264
<211> LENGTH: 19
<212> TYPE: RNA
<213> ORGANISM: Homo Sapiens

<400> SEQUENCE: 264
cuaugaagcc ggugaaauu                                              19

<210> SEQ ID NO 265
```

```
<211> LENGTH: 19
<212> TYPE: RNA
<213> ORGANISM: Homo Sapiens

<400> SEQUENCE: 265
gauuggaguu ugagaagca                                                19

<210> SEQ ID NO 266
<211> LENGTH: 19
<212> TYPE: RNA
<213> ORGANISM: Homo Sapiens

<400> SEQUENCE: 266
ggaaagaguu ggaggacgc                                                19

<210> SEQ ID NO 267
<211> LENGTH: 403
<212> TYPE: PRT
<213> ORGANISM: Homo Sapiens

<400> SEQUENCE: 267
```

| | | | | | | | | | | | | | | |
|---|---|---|---|---|---|---|---|---|---|---|---|---|---|---|
|Met|His|Asn|Phe|Glu|Glu|Leu|Thr|Cys|Pro|Ile|Cys|Tyr|Ser|Ile|
|1| | |  |5|   |   |   |   |10 |   |   |   |   |15 |

Phe Glu Asp Pro Arg Val Leu Pro Cys Ser His Thr Phe Cys Arg Asn
                20                  25                  30

Cys Leu Glu Asn Ile Leu Gln Ala Ser Gly Asn Phe Tyr Ile Trp Arg
        35                  40                  45

Pro Leu Arg Ile Pro Leu Lys Cys Pro Asn Cys Arg Ser Ile Thr Glu
50                  55                  60

Ile Ala Pro Thr Gly Ile Glu Ser Leu Pro Val Asn Phe Ala Leu Arg
65                  70                  75                  80

Ala Ile Ile Glu Lys Tyr Gln Gln Glu Asp His Pro Asp Ile Val Thr
                85                  90                  95

Cys Pro Glu His Tyr Arg Gln Pro Leu Asn Val Tyr Cys Leu Leu Asp
            100                 105                 110

Lys Lys Leu Val Cys Gly His Cys Leu Thr Ile Gly Gln His His Gly
        115                 120                 125

His Pro Ile Asp Asp Leu Gln Ser Ala Tyr Leu Lys Glu Lys Asp Thr
    130                 135                 140

Pro Gln Lys Leu Leu Glu Gln Leu Thr Asp Thr His Trp Thr Asp Leu
145                 150                 155                 160

Thr His Leu Ile Glu Lys Leu Lys Glu Gln Lys Ser His Ser Glu Lys
                165                 170                 175

Met Ile Gln Gly Asp Lys Glu Ala Val Leu Gln Tyr Phe Lys Glu Leu
            180                 185                 190

Asn Asp Thr Leu Glu Gln Lys Lys Lys Ser Phe Leu Thr Ala Leu Cys
        195                 200                 205

Asp Val Gly Asn Leu Ile Asn Gln Glu Tyr Thr Pro Gln Ile Glu Arg
    210                 215                 220

Met Lys Glu Ile Arg Glu Gln Leu Glu Leu Met Ala Leu Thr Ile
225                 230                 235                 240

Ser Leu Gln Glu Glu Ser Pro Leu Lys Phe Leu Glu Lys Val Asp Asp
                245                 250                 255

Val Arg Gln His Val Gln Ile Leu Lys Gln Arg Pro Leu Pro Glu Val
            260                 265                 270

Gln Pro Val Glu Ile Tyr Pro Arg Val Ser Lys Ile Leu Lys Glu Glu
        275                 280                 285

-continued

```
Trp Ser Arg Thr Glu Ile Gly Gln Ile Lys Asn Val Leu Ile Pro Lys
    290                 295                 300

Met Lys Ile Ser Pro Lys Arg Met Ser Cys Ser Trp Pro Gly Lys Asp
305                 310                 315                 320

Glu Lys Glu Val Glu Phe Leu Lys Ile Leu Asn Ile Val Val Val Thr
                325                 330                 335

Leu Ile Ser Val Ile Leu Met Ser Ile Leu Phe Phe Asn Gln His Ile
            340                 345                 350

Ile Thr Phe Leu Ser Glu Ile Thr Leu Ile Trp Phe Ser Glu Ala Ser
        355                 360                 365

Leu Ser Val Tyr Gln Ser Leu Ser Asn Ser Leu His Lys Val Lys Asn
    370                 375                 380

Ile Leu Cys His Ile Phe Tyr Leu Leu Lys Glu Phe Val Trp Lys Ile
385                 390                 395                 400

Val Ser His

<210> SEQ ID NO 268
<211> LENGTH: 19
<212> TYPE: RNA
<213> ORGANISM: Homo Sapiens

<400> SEQUENCE: 268
guacagaucu ugaaacaaa                                                  19

<210> SEQ ID NO 269
<211> LENGTH: 19
<212> TYPE: RNA
<213> ORGANISM: Homo Sapiens

<400> SEQUENCE: 269
caacuggcau ugaaucuuu                                                  19

<210> SEQ ID NO 270
<211> LENGTH: 19
<212> TYPE: RNA
<213> ORGANISM: Homo Sapiens

<400> SEQUENCE: 270
gcacuaaggg cuauuauug                                                  19

<210> SEQ ID NO 271
<211> LENGTH: 19
<212> TYPE: RNA
<213> ORGANISM: Homo Sapiens

<400> SEQUENCE: 271
gauguuggca aucuaauua                                                  19

<210> SEQ ID NO 272
<211> LENGTH: 471
<212> TYPE: PRT
<213> ORGANISM: Homo Sapiens

<400> SEQUENCE: 272

Met Glu Phe Val Thr Ala Leu Val Asn Leu Gln Glu Glu Ser Ser Cys
1               5                   10                  15

Pro Ile Cys Leu Glu Tyr Leu Lys Asp Pro Val Thr Ile Asn Cys Gly
            20                  25                  30

His Asn Phe Cys Arg Ser Cys Leu Ser Val Ser Trp Lys Asp Leu Asp
```

```
                35                  40                  45
Asp Thr Phe Pro Cys Pro Val Cys Arg Phe Cys Phe Pro Tyr Lys Ser
 50                  55                  60

Phe Arg Arg Asn Pro Gln Leu Arg Asn Leu Thr Glu Ile Ala Lys Gln
65                  70                  75                  80

Leu Gln Ile Arg Arg Ser Lys Arg Lys Arg Gln Lys Glu Asn Ala Met
                85                  90                  95

Cys Glu Lys His Asn Gln Phe Leu Thr Leu Phe Cys Val Lys Asp Leu
            100                 105                 110

Glu Ile Leu Cys Thr Gln Cys Ser Phe Ser Thr Lys His Gln Lys His
        115                 120                 125

Tyr Ile Cys Pro Ile Lys Lys Ala Ala Ser Tyr His Arg Glu Ile Leu
    130                 135                 140

Glu Gly Ser Leu Glu Pro Leu Arg Asn Asn Ile Glu Arg Val Glu Lys
145                 150                 155                 160

Val Ile Ile Leu Gln Gly Ser Lys Ser Val Glu Leu Lys Lys Lys Val
                165                 170                 175

Glu Tyr Lys Arg Glu Glu Ile Asn Ser Glu Phe Glu Gln Ile Arg Leu
            180                 185                 190

Phe Leu Gln Asn Glu Gln Glu Met Ile Leu Arg Gln Ile Gln Asp Glu
        195                 200                 205

Glu Met Asn Ile Leu Ala Lys Leu Asn Glu Asn Leu Val Glu Leu Ser
    210                 215                 220

Asp Tyr Val Ser Thr Leu Lys His Leu Leu Arg Glu Val Glu Gly Lys
225                 230                 235                 240

Ser Val Gln Ser Asn Leu Glu Leu Leu Thr Gln Ala Lys Ser Met His
                245                 250                 255

His Lys Tyr Gln Asn Leu Lys Cys Pro Glu Leu Phe Ser Phe Arg Leu
            260                 265                 270

Thr Lys Tyr Gly Phe Ser Leu Pro Pro Gln Tyr Ser Gly Leu Asp Arg
        275                 280                 285

Ile Ile Lys Pro Phe Gln Val Asp Val Ile Leu Asp Leu Asn Thr Ala
    290                 295                 300

His Pro Gln Leu Leu Val Ser Glu Asp Arg Lys Ala Val Arg Tyr Glu
305                 310                 315                 320

Arg Lys Lys Arg Asn Ile Cys Tyr Asp Pro Arg Arg Phe Tyr Val Cys
                325                 330                 335

Pro Ala Val Leu Gly Ser Gln Arg Phe Ser Ser Gly Arg His Tyr Trp
            340                 345                 350

Glu Val Glu Val Gly Asn Lys Pro Lys Trp Ile Leu Gly Val Cys Gln
        355                 360                 365

Asp Cys Leu Leu Arg Asn Trp Gln Asp Gln Pro Ser Val Leu Gly Gly
    370                 375                 380

Phe Trp Ala Ile Gly Arg Tyr Met Lys Ser Gly Tyr Val Ala Ser Gly
385                 390                 395                 400

Pro Lys Thr Thr Gln Leu Leu Pro Val Val Lys Pro Ser Lys Ile Gly
                405                 410                 415

Ile Phe Leu Asp Tyr Glu Leu Gly Asp Leu Ser Phe Tyr Asn Met Asn
            420                 425                 430

Asp Arg Ser Ile Leu Tyr Thr Phe Asn Asp Cys Phe Thr Glu Ala Val
        435                 440                 445

Trp Pro Tyr Phe Tyr Thr Gly Thr Asp Ser Glu Pro Leu Lys Ile Cys
    450                 455                 460
```

-continued

Ser Val Ser Asp Ser Glu Arg
465                 470

<210> SEQ ID NO 273
<211> LENGTH: 19
<212> TYPE: RNA
<213> ORGANISM: Homo Sapiens

<400> SEQUENCE: 273
gaaagagaau gccaugugu                                                    19

<210> SEQ ID NO 274
<211> LENGTH: 19
<212> TYPE: RNA
<213> ORGANISM: Homo Sapiens

<400> SEQUENCE: 274
ggaucuagau gauaccuuu                                                    19

<210> SEQ ID NO 275
<211> LENGTH: 19
<212> TYPE: RNA
<213> ORGANISM: Homo Sapiens

<400> SEQUENCE: 275
ggucuauucu cuauacuuu                                                    19

<210> SEQ ID NO 276
<211> LENGTH: 19
<212> TYPE: RNA
<213> ORGANISM: Homo Sapiens

<400> SEQUENCE: 276
gcaauugggc gauacauga                                                    19

<210> SEQ ID NO 277
<211> LENGTH: 209
<212> TYPE: PRT
<213> ORGANISM: Homo Sapiens

<400> SEQUENCE: 277

Met Glu Phe Val Thr Ala Leu Ala Asp Leu Arg Ala Glu Ala Ser Cys
1               5                   10                  15

Pro Ile Cys Leu Asp Tyr Leu Lys Asp Pro Val Thr Ile Ser Cys Gly
                20                  25                  30

His Asn Phe Cys Leu Ser Cys Ile Ile Met Ser Trp Lys Asp Leu His
            35                  40                  45

Asp Ser Phe Pro Cys Pro Phe Cys His Phe Cys Cys Pro Glu Arg Lys
        50                  55                  60

Phe Ile Ser Asn Pro Gln Leu Gly Ser Leu Thr Glu Ile Ala Lys Gln
65                  70                  75                  80

Leu Gln Ile Arg Ser Lys Lys Arg Lys Arg Gln Glu Glu Lys His Val
                85                  90                  95

Cys Lys Lys His Asn Gln Val Leu Thr Phe Phe Cys Gly Lys Asp Leu
            100                 105                 110

Glu Leu Leu Cys Pro Arg Cys Ser Leu Ser Thr Asp His Gln His His
        115                 120                 125

Cys Val Trp Pro Ile Lys Lys Ala Ala Ser Tyr His Arg Lys Lys Leu
    130                 135                 140

Glu Glu Tyr Asn Ala Pro Trp Lys Glu Arg Val Glu Leu Ile Glu Lys
145                 150                 155                 160

Val Ile Thr Met Gln Thr Arg Lys Ser Leu Glu Leu Lys Lys Lys Met
                165                 170                 175

Glu Ser Pro Ser Val Thr Arg Leu Glu Cys Ser Cys Thr Ile Ser Ala
            180                 185                 190

His Phe Asn Leu Arg Leu Pro Gly Ser Ser Asp Ser Ser Ala Ser Gly
        195                 200                 205

Ser

<210> SEQ ID NO 278
<211> LENGTH: 19
<212> TYPE: RNA
<213> ORGANISM: Homo Sapiens

<400> SEQUENCE: 278
ucagaaagac cuagagcuu                                               19

<210> SEQ ID NO 279
<211> LENGTH: 19
<212> TYPE: RNA
<213> ORGANISM: Homo Sapiens

<400> SEQUENCE: 279 cugguaguu ugacugaaa                                                19

<210> SEQ ID NO 280
<211> LENGTH: 19
<212> TYPE: RNA
<213> ORGANISM: Homo Sapiens

<400> SEQUENCE: 280
uaagaagcau aaucagguu                                               19

<210> SEQ ID NO 281
<211> LENGTH: 19
<212> TYPE: RNA
<213> ORGANISM: Homo Sapiens

<400> SEQUENCE: 281
gagagagugg aacuaauug                                               19

<210> SEQ ID NO 282
<211> LENGTH: 475
<212> TYPE: PRT
<213> ORGANISM: Homo Sapiens

<400> SEQUENCE: 282

Met Ala Cys Ser Leu Lys Asp Glu Leu Leu Cys Ser Ile Cys Leu Ser
1               5                   10                  15

Ile Tyr Gln Asp Pro Val Ser Leu Gly Cys Glu His Tyr Phe Cys Arg
                20                  25                  30

Arg Cys Ile Thr Glu His Trp Val Arg Gln Glu Ala Gln Gly Ala Arg
            35                  40                  45

Asp Cys Pro Glu Cys Arg Arg Thr Phe Ala Glu Pro Ala Leu Ala Pro
        50                  55                  60

Ser Leu Lys Leu Ala Asn Ile Val Glu Arg Tyr Ser Ser Phe Pro Leu
65                  70                  75                  80

Asp Ala Ile Leu Asn Ala Arg Arg Ala Arg Pro Cys Gln Ala His
                85                  90                  95

```
Asp Lys Val Lys Leu Phe Cys Leu Thr Asp Arg Ala Leu Leu Cys Phe
            100                 105                 110

Phe Cys Asp Glu Pro Ala Leu His Glu Gln His Val Thr Gly Ile
        115                 120                 125

Asp Asp Ala Phe Asp Glu Leu Gln Arg Glu Leu Lys Asp Gln Leu Gln
130                 135                 140

Ala Leu Gln Asp Ser Glu Arg Glu His Thr Glu Ala Leu Gln Leu Leu
145                 150                 155                 160

Lys Arg Gln Leu Ala Glu Thr Lys Ser Ser Thr Lys Ser Leu Arg Thr
                165                 170                 175

Thr Ile Gly Glu Ala Phe Glu Arg Leu His Arg Leu Leu Arg Glu Arg
            180                 185                 190

Gln Lys Ala Met Leu Glu Glu Leu Glu Ala Asp Thr Ala Arg Thr Leu
        195                 200                 205

Thr Asp Ile Glu Gln Lys Val Gln Arg Tyr Ser Gln Gln Leu Arg Lys
210                 215                 220

Val Gln Glu Gly Ala Gln Ile Leu Gln Glu Arg Leu Ala Glu Thr Asp
225                 230                 235                 240

Arg His Thr Phe Leu Ala Gly Val Ala Ser Leu Ser Glu Arg Leu Lys
                245                 250                 255

Gly Lys Ile His Glu Thr Asn Leu Thr Tyr Glu Asp Phe Pro Thr Ser
            260                 265                 270

Lys Tyr Thr Gly Pro Leu Gln Tyr Thr Ile Trp Lys Ser Leu Phe Gln
        275                 280                 285

Asp Ile His Pro Val Pro Ala Leu Thr Leu Asp Pro Gly Thr Ala
290                 295                 300

His Gln Arg Leu Ile Leu Ser Asp Asp Cys Thr Ile Val Ala Tyr Gly
305                 310                 315                 320

Asn Leu His Pro Gln Pro Leu Gln Asp Ser Pro Lys Arg Phe Asp Val
                325                 330                 335

Glu Val Ser Val Leu Gly Ser Glu Ala Phe Ser Ser Gly Val His Tyr
            340                 345                 350

Trp Glu Val Val Ala Glu Lys Thr Gln Trp Val Ile Gly Leu Ala
        355                 360                 365

His Glu Ala Ala Ser Arg Lys Gly Ser Ile Gln Ile Gln Pro Ser Arg
370                 375                 380

Gly Phe Tyr Cys Ile Val Met His Asp Gly Asn Gln Tyr Ser Ala Cys
385                 390                 395                 400

Thr Glu Pro Trp Thr Arg Leu Asn Val Arg Asp Lys Leu Asp Lys Val
                405                 410                 415

Gly Val Phe Leu Asp Tyr Asp Gln Gly Leu Leu Ile Phe Tyr Asn Ala
            420                 425                 430

Asp Asp Met Ser Trp Leu Tyr Thr Phe Arg Glu Lys Phe Pro Gly Lys
        435                 440                 445

Leu Cys Ser Tyr Phe Ser Pro Gly Gln Ser His Ala Asn Gly Lys Asn
450                 455                 460

Val Gln Pro Leu Arg Ile Asn Thr Val Arg Ile
465                 470                 475

<210> SEQ ID NO 283
<211> LENGTH: 19
<212> TYPE: RNA
<213> ORGANISM: Homo Sapiens
```

<400> SEQUENCE: 283
cuacaaugcu gaugacaug                                                    19

<210> SEQ ID NO 284
<211> LENGTH: 19
<212> TYPE: RNA
<213> ORGANISM: Homo Sapiens

<400> SEQUENCE: 284
ucggacgacu gcaccauug                                                    19

<210> SEQ ID NO 285
<211> LENGTH: 19
<212> TYPE: RNA
<213> ORGANISM: Homo Sapiens

<400> SEQUENCE: 285
cgccaaagcg cuucgaugu                                                    19

<210> SEQ ID NO 286
<211> LENGTH: 19
<212> TYPE: RNA
<213> ORGANISM: Homo Sapiens

<400> SEQUENCE: 286
ggaucaacac cguccgcau                                                    19

<210> SEQ ID NO 287
<211> LENGTH: 353
<212> TYPE: PRT
<213> ORGANISM: Homo Sapiens

<400> SEQUENCE: 287

```
Met Asp Tyr Lys Ser Ser Leu Ile Gln Asp Gly Asn Pro Met Glu Asn
1               5                   10                  15

Leu Glu Lys Gln Leu Ile Cys Pro Ile Cys Leu Glu Met Phe Thr Lys
            20                  25                  30

Pro Val Val Ile Leu Pro Cys Gln His Asn Leu Cys Arg Lys Cys Ala
        35                  40                  45

Asn Asp Ile Phe Gln Ala Ala Asn Pro Tyr Trp Thr Ser Arg Gly Ser
    50                  55                  60

Ser Val Ser Met Ser Gly Gly Arg Phe Arg Cys Pro Thr Cys Arg His
65                  70                  75                  80

Glu Val Ile Met Asp Arg His Gly Val Tyr Gly Leu Gln Arg Asn Leu
                85                  90                  95

Leu Val Glu Asn Ile Ile Asp Ile Tyr Lys Gln Glu Cys Ser Ser Arg
            100                 105                 110

Pro Leu Gln Lys Gly Ser His Pro Met Cys Lys Glu His Glu Asp Glu
        115                 120                 125

Lys Ile Asn Ile Tyr Cys Leu Thr Cys Glu Val Pro Thr Cys Ser Met
    130                 135                 140

Cys Lys Val Phe Gly Ile His Lys Ala Cys Glu Val Ala Pro Leu Gln
145                 150                 155                 160

Ser Val Phe Gln Gly Gln Lys Thr Glu Leu Asn Asn Cys Ile Ser Met
                165                 170                 175

Leu Val Ala Gly Asn Asp Arg Val Gln Thr Ile Ile Thr Gln Leu Glu
            180                 185                 190

Asp Ser Arg Arg Val Thr Lys Glu Asn Ser His Gln Val Lys Glu Glu
```

-continued

```
                195                 200                 205
Leu Ser Gln Lys Phe Asp Thr Leu Tyr Ala Ile Leu Asp Glu Lys Lys
210                 215                 220

Ser Glu Leu Leu Gln Arg Ile Thr Gln Glu Gln Lys Lys Leu Ser
225                 230                 235                 240

Phe Ile Glu Ala Leu Ile Gln Gln Tyr Gln Glu Gln Leu Asp Lys Ser
                245                 250                 255

Thr Lys Leu Val Glu Thr Ala Ile Gln Ser Leu Asp Glu Pro Gly Gly
260                 265                 270

Ala Thr Phe Leu Leu Thr Ala Lys Gln Leu Ile Lys Ser Ile Val Glu
                275                 280                 285

Ala Ser Lys Gly Cys Gln Leu Gly Lys Thr Glu Gln Gly Phe Glu Asn
290                 295                 300

Met Asp Phe Phe Thr Leu Asp Leu Glu His Ile Ala Asp Ala Leu Arg
305                 310                 315                 320

Ala Ile Asp Phe Gly Thr Asp Glu Glu Glu Glu Phe Ile Glu Glu
                325                 330                 335

Glu Asp Gln Glu Glu Glu Glu Ser Thr Glu Gly Lys Glu Glu Gly His
                340                 345                 350

Gln
```

```
<210> SEQ ID NO 288
<211> LENGTH: 19
<212> TYPE: RNA
<213> ORGANISM: Homo Sapiens

<400> SEQUENCE: 288
ggaagaagga caccaguaa                                          19

<210> SEQ ID NO 289
<211> LENGTH: 19
<212> TYPE: RNA
<213> ORGANISM: Homo Sapiens

<400> SEQUENCE: 289
ucacucagcu ggaggauuc                                          19

<210> SEQ ID NO 290
<211> LENGTH: 19
<212> TYPE: RNA
<213> ORGANISM: Homo Sapiens

<400> SEQUENCE: 290
gaacauggac uucuuuacu                                          19

<210> SEQ ID NO 291
<211> LENGTH: 19
<212> TYPE: RNA
<213> ORGANISM: Homo Sapiens

<400> SEQUENCE: 291
ggaaucccau ggagaacuu                                          19

<210> SEQ ID NO 292
<211> LENGTH: 449
<212> TYPE: PRT
<213> ORGANISM: Homo Sapiens

<400> SEQUENCE: 292
```

-continued

```
Met Asp Ser Asp Asp Leu Gln Val Phe Gln Asn Glu Leu Ile Cys Cys
1               5                   10                  15

Ile Cys Val Asn Tyr Phe Ile Asp Pro Val Thr Ile Asp Cys Gly His
                20                  25                  30

Ser Phe Cys Arg Pro Cys Leu Cys Leu Cys Ser Glu Glu Gly Arg Ala
            35                  40                  45

Pro Met Arg Cys Pro Ser Cys Arg Lys Ile Ser Glu Lys Pro Asn Phe
    50                  55                  60

Asn Thr Asn Val Val Leu Lys Lys Leu Ser Leu Ala Arg Gln Thr
65                  70                  75                  80

Arg Pro Gln Asn Ile Asn Ser Ser Asp Asn Ile Cys Val Leu His Glu
                85                  90                  95

Glu Thr Lys Glu Leu Phe Cys Glu Ala Asp Lys Arg Leu Leu Cys Gly
            100                 105                 110

Pro Cys Ser Glu Ser Pro Glu His Met Ala His Ser His Ser Pro Ile
        115                 120                 125

Gly Trp Ala Ala Glu Glu Cys Arg Glu Lys Leu Ile Lys Glu Met Asp
130                 135                 140

Tyr Leu Trp Glu Ile Asn Gln Glu Thr Arg Asn Asn Leu Asn Gln Glu
145                 150                 155                 160

Thr Arg Thr Phe His Ser Leu Lys Asp Tyr Val Ser Val Arg Lys Arg
                165                 170                 175

Ile Ile Thr Ile Gln Tyr Gln Lys Met Pro Ile Phe Leu Asp Glu Glu
            180                 185                 190

Glu Gln Arg His Leu Gln Ala Leu Glu Arg Glu Ala Glu Glu Leu Phe
        195                 200                 205

Gln Gln Leu Gln Asp Ser Gln Val Arg Met Thr Gln His Leu Glu Arg
    210                 215                 220

Met Lys Asp Met Tyr Arg Glu Leu Trp Glu Thr Cys His Val Pro Asp
225                 230                 235                 240

Val Glu Leu Leu Gln Asp Val Arg Asn Val Ser Ala Arg Thr Asp Leu
                245                 250                 255

Ala Gln Met Gln Lys Pro Gln Pro Val Asn Pro Glu Leu Thr Ser Trp
            260                 265                 270

Cys Ile Thr Gly Val Leu Asp Met Leu Asn Asn Phe Arg Val Asp Ser
        275                 280                 285

Ala Leu Ser Thr Glu Met Ile Pro Cys Tyr Ile Ser Leu Ser Glu Asp
    290                 295                 300

Val Arg Tyr Val Ile Phe Gly Asp Asp His Leu Ser Ala Pro Thr Asp
305                 310                 315                 320

Pro Gln Gly Val Asp Ser Phe Ala Val Trp Gly Ala Gln Ala Phe Thr
                325                 330                 335

Ser Gly Lys His Tyr Trp Glu Val Asp Val Thr Leu Ser Ser Asn Trp
            340                 345                 350

Ile Leu Gly Val Cys Gln Asp Ser Arg Thr Ala Asp Ala Asn Phe Val
        355                 360                 365

Ile Asp Ser Asp Glu Arg Phe Phe Leu Ile Ser Ser Lys Arg Ser Asn
    370                 375                 380

His Tyr Ser Leu Ser Thr Asn Ser Pro Leu Ile Gln Tyr Val Gln
385                 390                 395                 400

Arg Pro Leu Gly Gln Val Gly Val Phe Leu Asp Tyr Asp Asn Gly Ser
                405                 410                 415

Val Ser Phe Phe Asp Val Ser Lys Gly Ser Leu Ile Tyr Gly Phe Pro
```

```
              420                 425                 430
Pro Ser Ser Phe Ser Ser Pro Leu Arg Pro Phe Phe Cys Phe Gly Cys
                435                 440                 445
Thr

<210> SEQ ID NO 293
<211> LENGTH: 19
<212> TYPE: RNA
<213> ORGANISM: Homo Sapiens

<400> SEQUENCE: 293
ucaguaagga agaggauaa                                                19

<210> SEQ ID NO 294
<211> LENGTH: 19
<212> TYPE: RNA
<213> ORGANISM: Homo Sapiens

<400> SEQUENCE: 294
ugugguuaug aaugggaua                                                19

<210> SEQ ID NO 295
<211> LENGTH: 19
<212> TYPE: RNA
<213> ORGANISM: Homo Sapiens

<400> SEQUENCE: 295
aaaguugguu ucacgauga                                                19

<210> SEQ ID NO 296
<211> LENGTH: 19
<212> TYPE: RNA
<213> ORGANISM: Homo Sapiens

<400> SEQUENCE: 296
aagcauucac cuccggcaa                                                19

<210> SEQ ID NO 297
<211> LENGTH: 517
<212> TYPE: PRT
<213> ORGANISM: Homo Sapiens

<400> SEQUENCE: 297

Met Ala Ala Gln Leu Leu Glu Glu Lys Leu Thr Cys Ala Ile Cys Leu
1               5                   10                  15

Gly Leu Tyr Gln Asp Pro Val Thr Leu Pro Cys Gly His Asn Phe Cys
                20                  25                  30

Gly Ala Cys Ile Arg Asp Trp Trp Asp Arg Cys Gly Lys Ala Cys Pro
            35                  40                  45

Glu Cys Arg Glu Pro Phe Pro Asp Gly Ala Glu Leu Arg Arg Asn Val
        50                  55                  60

Ala Leu Ser Gly Val Leu Glu Val Val Arg Ala Gly Pro Ala Arg Asp
65                  70                  75                  80

Pro Gly Pro Asp Pro Gly Pro Gly Pro Asp Pro Ala Ala Arg Cys Pro
                85                  90                  95

Arg His Gly Arg Pro Leu Glu Leu Phe Cys Arg Thr Glu Gly Arg Cys
                100                 105                 110

Val Cys Ser Val Cys Thr Val Arg Glu Cys Arg Leu His Glu Arg Ala
            115                 120                 125
```

Leu Leu Asp Ala Glu Arg Leu Lys Arg Glu Ala Gln Leu Arg Ala Ser
130                 135                 140

Leu Glu Val Thr Gln Gln Ala Thr Gln Ala Glu Gly Gln Leu Leu
145                 150                 155                 160

Glu Leu Arg Lys Gln Ser Ser Gln Ile Gln Asn Ser Ala Cys Ile Leu
                165                 170                 175

Ala Ser Trp Val Ser Gly Lys Phe Ser Ser Leu Leu Gln Ala Leu Glu
            180                 185                 190

Ile Gln His Thr Thr Ala Leu Arg Ser Ile Glu Val Ala Lys Thr Gln
        195                 200                 205

Ala Leu Ala Gln Ala Arg Asp Glu Glu Gln Arg Leu Arg Val His Leu
210                 215                 220

Glu Ala Val Ala Arg His Gly Cys Arg Ile Arg Glu Leu Leu Glu Gln
225                 230                 235                 240

Val Asp Glu Gln Thr Phe Leu Gln Glu Ser Gln Leu Leu Gln Pro Pro
                245                 250                 255

Gly Pro Leu Gly Pro Leu Thr Pro Leu Gln Trp Asp Glu Asp Gln Gln
            260                 265                 270

Leu Gly Asp Leu Lys Gln Leu Leu Ser Arg Leu Cys Gly Leu Leu Leu
        275                 280                 285

Glu Glu Gly Ser His Pro Gly Ala Pro Ala Lys Pro Val Asp Leu Ala
290                 295                 300

Pro Val Glu Ala Pro Gly Pro Leu Ala Pro Val Pro Ser Thr Val Cys
305                 310                 315                 320

Pro Leu Arg Arg Lys Leu Trp Gln Asn Tyr Arg Asn Leu Thr Phe Asp
                325                 330                 335

Pro Val Ser Ala Asn Arg His Phe Tyr Leu Ser Arg Gln Asp Gln Gln
            340                 345                 350

Val Lys His Cys Arg Gln Ser Arg Gly Pro Gly Pro Gly Ser Phe
        355                 360                 365

Glu Leu Trp Gln Val Gln Cys Ala Gln Ser Phe Gln Ala Gly His His
        370                 375                 380

Tyr Trp Glu Val Arg Ala Ser Asp His Ser Val Thr Leu Gly Val Ser
385                 390                 395                 400

Tyr Pro Gln Leu Pro Arg Cys Arg Leu Gly Pro His Thr Asp Asn Ile
                405                 410                 415

Gly Arg Gly Pro Cys Ser Trp Gly Leu Cys Val Gln Glu Asp Ser Leu
            420                 425                 430

Gln Ala Trp His Asn Gly Glu Ala Gln Arg Leu Pro Gly Val Ser Gly
        435                 440                 445

Arg Leu Leu Gly Met Asp Leu Asp Leu Ala Ser Gly Cys Leu Thr Phe
450                 455                 460

Tyr Ser Leu Glu Pro Gln Thr Gln Pro Leu Tyr Thr Phe His Ala Leu
465                 470                 475                 480

Phe Asn Gln Pro Leu Thr Pro Val Phe Trp Leu Leu Glu Gly Arg Thr
                485                 490                 495

Leu Thr Leu Cys His Gln Pro Gly Ala Val Phe Pro Leu Gly Pro Gln
            500                 505                 510

Glu Glu Val Leu Ser
        515

<210> SEQ ID NO 298
<211> LENGTH: 19
<212> TYPE: RNA

-continued

```
<213> ORGANISM: Homo Sapiens

<400> SEQUENCE: 298
gcagccagau ccagaacuc                                                19

<210> SEQ ID NO 299
<211> LENGTH: 19
<212> TYPE: RNA
<213> ORGANISM: Homo Sapiens

<400> SEQUENCE: 299
agccaagccu guggacuua                                                19

<210> SEQ ID NO 300
<211> LENGTH: 19
<212> TYPE: RNA
<213> ORGANISM: Homo Sapiens

<400> SEQUENCE: 300
guaggacccu gacccugug                                                19

<210> SEQ ID NO 301
<211> LENGTH: 19
<212> TYPE: RNA
<213> ORGANISM: Homo Sapiens

<400> SEQUENCE: 301
uggcagaauu aucgcaauc                                                19

<210> SEQ ID NO 302
<211> LENGTH: 1216
<212> TYPE: PRT
<213> ORGANISM: Homo Sapiens

<400> SEQUENCE: 302
```

Met Ala Arg Asn Cys Ser Glu Cys Lys Glu Lys Arg Ala Ala His Ile
1               5                   10                  15

Leu Cys Thr Tyr Cys Asn Arg Trp Leu Cys Ser Ser Cys Thr Glu Glu
            20                  25                  30

His Arg His Ser Pro Val Pro Gly Gly Pro Phe Phe Pro Arg Ala Gln
        35                  40                  45

Lys Gly Ser Pro Gly Val Asn Gly Gly Pro Gly Asp Phe Thr Leu Tyr
    50                  55                  60

Cys Pro Leu His Thr Gln Glu Val Leu Lys Leu Phe Cys Glu Thr Cys
65                  70                  75                  80

Asp Met Leu Thr Cys His Ser Cys Leu Val Val Glu His Lys Glu His
                85                  90                  95

Arg Cys Arg His Val Glu Glu Val Leu Gln Asn Gln Arg Met Leu Leu
            100                 105                 110

Glu Gly Val Thr Thr Gln Val Ala His Lys Lys Ser Ser Leu Gln Thr
        115                 120                 125

Ser Ala Lys Gln Ile Glu Asp Arg Ile Phe Glu Val Lys His Gln His
    130                 135                 140

Arg Lys Val Glu Asn Gln Ile Lys Met Ala Lys Met Val Leu Met Asn
145                 150                 155                 160

Glu Leu Asn Lys Gln Ala Asn Gly Leu Ile Glu Glu Leu Glu Gly Ile
                165                 170                 175

Thr Asn Glu Arg Lys Arg Lys Leu Glu Gln Gln Leu Gln Ser Ile Met
            180                 185                 190

```
Val Leu Asn Arg Gln Phe Glu His Val Gln Asn Phe Ile Asn Trp Ala
        195                 200                 205

Val Cys Ser Lys Thr Ser Val Pro Phe Leu Phe Ser Lys Glu Leu Ile
        210                 215                 220

Val Phe Gln Met Gln Arg Leu Leu Glu Thr Ser Cys Asn Thr Asp Pro
225                 230                 235                 240

Gly Ser Pro Trp Ser Ile Arg Phe Thr Trp Glu Pro Asn Phe Trp Thr
                245                 250                 255

Lys Gln Leu Ala Ser Leu Gly Cys Ile Thr Thr Glu Gly Gly Gln Met
                260                 265                 270

Ser Arg Ala Asp Ala Pro Ala Tyr Gly Leu Gln Gly Ser Ser Pro
                275                 280                 285

Phe Tyr Gln Ser His Gln Ser Pro Val Ala Gln Glu Ala Leu Ser
        290                 295                 300

His Pro Ser His Lys Phe Gln Ser Pro Ala Val Cys Ser Ser Ser Val
305                 310                 315                 320

Cys Cys Ser His Cys Ser Pro Val Ser Pro Ser Leu Lys Gly Gln Val
                325                 330                 335

Pro Pro Pro Ser Ile His Pro Ala His Ser Phe Arg Gln Pro Pro Glu
                340                 345                 350

Met Val Pro Gln Gln Leu Gly Ser Leu Gln Cys Ser Ala Leu Leu Pro
        355                 360                 365

Arg Glu Lys Glu Leu Ala Cys Ser Pro His Pro Lys Leu Leu Gln
        370                 375                 380

Pro Trp Leu Glu Thr Gln Pro Pro Val Glu Gln Ser Thr Ser Gln
385                 390                 395                 400

Arg Leu Gly Gln Gln Leu Thr Ser Gln Pro Val Cys Ile Val Pro Pro
                405                 410                 415

Gln Asp Val Gln Gln Gly Ala His Ala Gln Pro Thr Leu Gln Thr Pro
                420                 425                 430

Ser Ile Gln Val Gln Phe Gly His His Gln Lys Leu Lys Leu Ser His
        435                 440                 445

Phe Gln Gln Gln Pro Gln Gln Leu Pro Pro Pro Pro Pro Leu
        450                 455                 460

Pro His Pro Pro Pro Leu Pro Pro Pro Gln Gln Pro His Pro
465                 470                 475                 480

Pro Leu Pro Pro Ser Gln His Leu Ala Ser Ser Gln His Glu Ser Pro
                485                 490                 495

Pro Gly Pro Ala Cys Ser Gln Asn Met Asp Ile Met His His Lys Phe
                500                 505                 510

Glu Leu Glu Glu Met Lys Asp Leu Glu Leu Leu Leu Gln Ala Gln
        515                 520                 525

Gln Pro Ser Leu Gln Leu Ser Gln Thr Lys Ser Pro Gln His Leu Gln
        530                 535                 540

Gln Thr Ile Val Gly Gln Ile Asn Tyr Ile Val Arg Gln Pro Ala Pro
545                 550                 555                 560

Val Gln Ser Gln Ser Gln Glu Glu Thr Leu Gln Ala Thr Asp Glu Pro
                565                 570                 575

Pro Ala Ser Gln Gly Ser Lys Pro Ala Leu Pro Leu Asp Lys Asn Thr
                580                 585                 590

Ala Ala Ala Leu Pro Gln Ala Ser Gly Glu Glu Thr Pro Leu Ser Val
        595                 600                 605
```

```
Pro Pro Val Asp Ser Thr Ile Gln His Ser Ser Pro Asn Val Val Arg
    610                 615                 620

Lys His Ser Thr Ser Leu Ser Ile Met Gly Phe Ser Asn Thr Leu Glu
625                 630                 635                 640

Met Glu Leu Ser Ser Thr Arg Leu Glu Arg Pro Leu Glu Pro Gln Ile
            645                 650                 655

Gln Ser Val Ser Asn Leu Thr Ala Gly Ala Pro Gln Ala Val Pro Ser
                660                 665                 670

Leu Leu Ser Ala Pro Pro Lys Met Val Ser Ser Leu Thr Ser Val Gln
            675                 680                 685

Asn Gln Ala Met Pro Ser Leu Thr Thr Ser His Leu Gln Thr Val Pro
690                 695                 700

Ser Leu Val His Ser Thr Phe Gln Ser Met Pro Asn Leu Ile Ser Asp
705                 710                 715                 720

Ser Pro Gln Ala Met Ala Ser Leu Ala Ser Asp His Pro Gln Ala Gly
                725                 730                 735

Pro Ser Leu Met Ser Gly His Thr Gln Ala Val Pro Ser Leu Ala Thr
            740                 745                 750

Cys Pro Leu Gln Ser Ile Pro Pro Val Ser Asp Met Gln Pro Glu Thr
            755                 760                 765

Gly Ser Ser Ser Ser Gly Arg Thr Ser Gly Ser Leu Cys Pro Arg
770                 775                 780

Asp Gly Ala Asp Pro Ser Leu Glu Asn Ala Leu Cys Lys Val Lys Leu
785                 790                 795                 800

Glu Glu Pro Ile Asn Leu Ser Val Lys Lys Pro Pro Leu Ala Pro Val
                805                 810                 815

Val Ser Thr Ser Thr Ala Leu Gln Gln Tyr Gln Asn Pro Lys Glu Cys
            820                 825                 830

Glu Asn Phe Glu Gln Gly Ala Leu Glu Leu Asp Ala Lys Glu Asn Gln
            835                 840                 845

Ser Ile Arg Ala Phe Asn Ser Glu His Lys Ile Pro Tyr Val Arg Leu
850                 855                 860

Glu Arg Leu Lys Ile Cys Ala Ala Ser Ser Gly Glu Met Pro Val Phe
865                 870                 875                 880

Lys Leu Lys Pro Gln Lys Asn Asp Gln Asp Gly Ser Phe Leu Leu Ile
                885                 890                 895

Ile Glu Cys Gly Thr Glu Ser Ser Ser Met Ser Ile Lys Val Ser Gln
            900                 905                 910

Asp Arg Leu Ser Glu Ala Thr Gln Ala Pro Gly Leu Glu Gly Arg Lys
            915                 920                 925

Val Thr Val Thr Ser Leu Ala Gly Gln Arg Pro Pro Glu Val Glu Gly
930                 935                 940

Thr Ser Pro Glu Glu His Arg Leu Ile Pro Arg Thr Pro Gly Ala Lys
945                 950                 955                 960

Lys Gly Pro Pro Ala Pro Ile Glu Asn Glu Asp Phe Cys Ala Val Cys
                965                 970                 975

Leu Asn Gly Gly Glu Leu Leu Cys Cys Asp Arg Cys Pro Lys Val Phe
            980                 985                 990

His Leu Ser Cys His Val Pro Ala  Leu Leu Ser Phe Pro  Gly Gly Glu
            995                 1000                1005

Trp Val Cys Thr Leu Cys Arg  Ser Leu Thr Gln Pro  Glu Met Glu
    1010                1015                1020

Tyr Asp Cys Glu Asn Ala Cys  Tyr Asn Gln Pro Gly  Met Arg Ala
```

```
              1025                1030                1035
Ser Pro Gly Leu Ser Met Tyr Asp Gln Lys Lys Cys Glu Lys Leu
        1040                1045                1050

Val Leu Ser Leu Cys Cys Asn Asn Leu Ser Leu Pro Phe His Glu
        1055                1060                1065

Pro Val Ser Pro Leu Ala Arg His Tyr Tyr Gln Ile Ile Lys Arg
        1070                1075                1080

Pro Met Asp Leu Ser Ile Ile Arg Arg Lys Leu Gln Lys Lys Asp
        1085                1090                1095

Pro Ala His Tyr Thr Thr Pro Glu Glu Val Val Ser Asp Val Arg
        1100                1105                1110

Leu Met Phe Trp Asn Cys Ala Lys Phe Asn Tyr Pro Asp Ser Glu
        1115                1120                1125

Val Ala Glu Ala Gly Arg Cys Leu Glu Val Phe Phe Glu Gly Trp
        1130                1135                1140

Leu Lys Glu Ile Tyr Pro Glu Lys Arg Phe Ala Gln Pro Arg Gln
        1145                1150                1155

Glu Asp Ser Asp Ser Glu Glu Val Ser Ser Ser Gly Cys Ser
        1160                1165                1170

Thr Pro Gln Gly Phe Pro Trp Pro Pro Tyr Met Gln Glu Gly Ile
        1175                1180                1185

Gln Pro Lys Arg Arg Arg His Met Glu Asn Glu Arg Ala Lys
        1190                1195                1200

Arg Met Ser Phe Arg Leu Ala Asn Ser Ile Ser Gln Val
        1205                1210                1215

<210> SEQ ID NO 303
<211> LENGTH: 19
<212> TYPE: RNA
<213> ORGANISM: Homo Sapiens

<400> SEQUENCE: 303
cggcauuauu accagauua                                           19

<210> SEQ ID NO 304
<211> LENGTH: 19
<212> TYPE: RNA
<213> ORGANISM: Homo Sapiens

<400> SEQUENCE: 304
gcacagagga acaccgaca                                           19

<210> SEQ ID NO 305
<211> LENGTH: 19
<212> TYPE: RNA
<213> ORGANISM: Homo Sapiens

<400> SEQUENCE: 305
ccuucaauag ugagcauaa                                           19

<210> SEQ ID NO 306
<211> LENGTH: 19
<212> TYPE: RNA
<213> ORGANISM: Homo Sapiens

<400> SEQUENCE: 306
uguuucagau gcagcgauu                                           19
```

```
<210> SEQ ID NO 307
<211> LENGTH: 783
<212> TYPE: PRT
<213> ORGANISM: Homo Sapiens

<400> SEQUENCE: 307

Met Glu Glu Leu Lys Cys Pro Val Cys Gly Ser Leu Phe Arg Glu
1               5                   10                  15

Pro Ile Ile Leu Pro Cys Ser His Asn Val Cys Leu Pro Cys Ala Arg
                20                  25                  30

Thr Ile Ala Val Gln Thr Pro Asp Gly Glu Gln His Leu Pro Gln Pro
            35                  40                  45

Leu Leu Leu Ser Arg Gly Ser Gly Leu Gln Ala Gly Ala Ala Ala
    50                  55                  60

Ala Ser Leu Glu His Asp Ala Ala Ala Gly Pro Ala Cys Gly Gly Ala
65                  70                  75                  80

Gly Gly Ser Ala Ala Gly Gly Leu Gly Gly Ala Gly Gly Gly
                85                  90                  95

Asp His Ala Asp Lys Leu Ser Leu Tyr Ser Glu Thr Asp Ser Gly Tyr
                100                 105                 110

Gly Ser Tyr Thr Pro Ser Leu Lys Ser Pro Asn Gly Val Arg Val Leu
            115                 120                 125

Pro Met Val Pro Ala Pro Pro Gly Ser Ser Ala Ala Ala Arg Gly
130                 135                 140

Ala Ala Cys Ser Ser Leu Ser Ser Ser Ser Ser Ile Thr Cys Pro
145                 150                 155                 160

Gln Cys His Arg Ser Ala Ser Leu Asp His Arg Gly Leu Arg Gly Phe
                165                 170                 175

Gln Arg Asn Arg Leu Leu Glu Ala Ile Val Gln Arg Tyr Gln Gln Gly
            180                 185                 190

Arg Gly Ala Val Pro Gly Thr Ser Ala Ala Ala Val Ala Ile Cys
195                 200                 205

Gln Leu Cys Asp Arg Thr Pro Pro Glu Pro Ala Ala Thr Leu Cys Glu
210                 215                 220

Gln Cys Asp Val Leu Tyr Cys Ser Ala Cys Gln Leu Lys Cys His Pro
225                 230                 235                 240

Ser Arg Gly Pro Phe Ala Lys His Arg Leu Val Gln Pro Pro Pro
                245                 250                 255

Pro Pro Pro Pro Ala Glu Ala Ala Ser Gly Pro Thr Gly Thr Ala Gln
            260                 265                 270

Gly Ala Pro Ser Gly Gly Gly Cys Lys Ser Pro Gly Gly Ala Gly
    275                 280                 285

Ala Gly Ala Thr Gly Gly Ser Thr Ala Arg Lys Phe Pro Thr Cys Pro
290                 295                 300

Glu His Glu Met Glu Asn Tyr Ser Met Tyr Cys Val Ser Cys Arg Thr
305                 310                 315                 320

Pro Val Cys Tyr Leu Cys Leu Glu Glu Gly Arg His Ala Lys His Glu
                325                 330                 335

Val Lys Pro Leu Gly Ala Met Trp Lys Gln His Lys Ala Gln Leu Ser
            340                 345                 350

Gln Ala Leu Asn Gly Val Ser Asp Lys Ala Lys Glu Ala Lys Glu Phe
    355                 360                 365

Leu Val Gln Leu Lys Asn Ile Leu Gln Gln Ile Gln Glu Asn Gly Leu
        370                 375                 380
```

Asp Tyr Glu Ala Cys Leu Val Ala Gln Cys Asp Ala Leu Val Asp Ala
385                 390                 395                 400

Leu Thr Arg Gln Lys Ala Lys Leu Leu Thr Lys Val Thr Lys Glu Arg
            405                 410                 415

Glu His Lys Leu Lys Met Val Trp Asp Gln Ile Asn His Cys Thr Leu
        420                 425                 430

Lys Leu Arg Gln Ser Thr Gly Leu Met Glu Tyr Cys Leu Glu Val Ile
    435                 440                 445

Lys Glu Asn Asp Pro Ser Gly Phe Leu Gln Ile Ser Asp Ala Leu Ile
450                 455                 460

Lys Arg Val Gln Val Ser Gln Glu Gln Trp Val Lys Gly Ala Leu Glu
465                 470                 475                 480

Pro Lys Val Ser Ala Glu Phe Asp Leu Thr Leu Asp Ser Glu Pro Leu
            485                 490                 495

Leu Gln Ala Ile His Gln Leu Asp Phe Ile Gln Met Lys Cys Arg Val
        500                 505                 510

Pro Pro Val Pro Leu Leu Gln Leu Glu Lys Cys Cys Thr Arg Asn Asn
    515                 520                 525

Ser Val Thr Leu Ala Trp Arg Met Pro Pro Phe Thr His Ser Pro Val
530                 535                 540

Asp Gly Tyr Ile Leu Glu Leu Asp Asp Gly Ala Gly Gly Gln Phe Arg
545                 550                 555                 560

Glu Val Tyr Val Gly Lys Glu Thr Leu Cys Thr Ile Asp Gly Leu His
            565                 570                 575

Phe Asn Ser Thr Tyr Asn Ala Arg Val Lys Ala Phe Asn Ser Ser Gly
        580                 585                 590

Val Gly Pro Tyr Ser Lys Thr Val Val Leu Gln Thr Ser Asp Val Ala
    595                 600                 605

Trp Phe Thr Phe Asp Pro Asn Ser Gly His Arg Asp Ile Ile Leu Ser
610                 615                 620

Asn Asp Asn Gln Thr Ala Thr Cys Ser Ser Tyr Asp Asp Arg Val Val
625                 630                 635                 640

Leu Gly Thr Ala Ala Phe Ser Lys Gly Val His Tyr Trp Glu Leu His
            645                 650                 655

Val Asp Arg Tyr Asp Asn His Pro Asp Pro Ala Phe Gly Val Ala Arg
        660                 665                 670

Ala Ser Val Val Lys Asp Met Met Leu Gly Lys Asp Asp Lys Ala Trp
    675                 680                 685

Ala Met Tyr Val Asp Asn Asn Arg Ser Trp Phe Met His Cys Asn Ser
690                 695                 700

His Thr Asn Arg Thr Glu Gly Gly Val Cys Lys Gly Ala Thr Val Gly
705                 710                 715                 720

Val Leu Leu Asp Leu Asn Lys His Thr Leu Thr Phe Phe Ile Asn Gly
            725                 730                 735

Gln Gln Gln Gly Pro Thr Ala Phe Ser His Val Asp Gly Val Phe Met
        740                 745                 750

Pro Ala Leu Ser Leu Asn Arg Asn Val Gln Val Thr Leu His Thr Gly
    755                 760                 765

Leu Glu Val Pro Thr Asn Leu Gly Arg Pro Lys Leu Ser Gly Asn
770                 775                 780

<210> SEQ ID NO 308
<211> LENGTH: 19
<212> TYPE: RNA

```
<213> ORGANISM: Homo Sapiens

<400> SEQUENCE: 308
gguaaggaga cuuugugua                                                              19

<210> SEQ ID NO 309
<211> LENGTH: 19
<212> TYPE: RNA
<213> ORGANISM: Homo Sapiens

<400> SEQUENCE: 309
gcacauugaa gcugcguca                                                              19

<210> SEQ ID NO 310
<211> LENGTH: 19
<212> TYPE: RNA
<213> ORGANISM: Homo Sapiens

<400> SEQUENCE: 310
gaaagugucu gcggaguuu                                                              19

<210> SEQ ID NO 311
<211> LENGTH: 19
<212> TYPE: RNA
<213> ORGANISM: Homo Sapiens

<400> SEQUENCE: 311
gagaaaugcu gcacccgua                                                              19

<210> SEQ ID NO 312
<211> LENGTH: 485
<212> TYPE: PRT
<213> ORGANISM: Homo Sapiens

<400> SEQUENCE: 312
```

Met Asp Pro Thr Ala Leu Val Glu Ala Ile Val Glu Glu Val Ala Cys
1               5                   10                  15

Pro Ile Cys Met Thr Phe Leu Arg Glu Pro Met Ser Ile Asp Cys Gly
            20                  25                  30

His Ser Phe Cys His Ser Cys Leu Ser Gly Leu Trp Glu Ile Pro Gly
        35                  40                  45

Glu Ser Gln Asn Trp Gly Tyr Thr Cys Pro Leu Cys Arg Ala Pro Val
    50                  55                  60

Gln Pro Arg Asn Leu Arg Pro Asn Trp Gln Leu Ala Asn Val Val Glu
65                  70                  75                  80

Lys Val Arg Leu Leu Arg Leu His Pro Gly Met Gly Leu Lys Gly Asp
                85                  90                  95

Leu Cys Glu Arg His Gly Glu Lys Leu Lys Met Phe Cys Lys Glu Asp
            100                 105                 110

Val Leu Ile Met Cys Glu Ala Cys Ser Gln Ser Pro Glu His Glu Ala
        115                 120                 125

His Ser Val Val Pro Met Glu Asp Val Ala Trp Glu Tyr Lys Trp Glu
    130                 135                 140

Leu His Glu Ala Leu Glu His Leu Lys Lys Gln Glu Glu Ala Trp
145                 150                 155                 160

Lys Leu Glu Val Gly Glu Arg Lys Arg Thr Ala Thr Trp Lys Ile Gln
                165                 170                 175

Val Glu Thr Arg Lys Gln Ser Ile Val Trp Glu Phe Glu Lys Tyr Gln
            180                 185                 190

```
Arg Leu Leu Glu Lys Lys Gln Pro Pro His Arg Gln Leu Gly Ala Glu
            195                 200                 205

Val Ala Ala Leu Ala Ser Leu Gln Arg Glu Ala Ala Glu Thr Met
210                 215                 220

Gln Lys Leu Glu Leu Asn His Ser Glu Leu Ile Gln Gln Ser Gln Val
225                 230                 235                 240

Leu Trp Arg Met Ile Ala Glu Leu Lys Glu Arg Ser Gln Arg Pro Val
                245                 250                 255

Arg Trp Met Leu Gln Asp Ile Gln Glu Val Leu Asn Arg Ser Lys Ser
            260                 265                 270

Trp Ser Leu Gln Gln Pro Glu Pro Ile Ser Leu Glu Leu Lys Thr Asp
        275                 280                 285

Cys Arg Val Leu Gly Leu Arg Glu Ile Leu Lys Thr Tyr Ala Ala Asp
        290                 295                 300

Val Arg Leu Asp Pro Asp Thr Ala Tyr Ser Arg Leu Ile Val Ser Glu
305                 310                 315                 320

Asp Arg Lys Arg Val His Tyr Gly Asp Thr Asn Gln Lys Leu Pro Asp
                325                 330                 335

Asn Pro Glu Arg Phe Tyr Arg Tyr Asn Ile Val Leu Gly Ser Gln Cys
            340                 345                 350

Ile Ser Ser Gly Arg His Tyr Trp Glu Val Glu Val Gly Asp Arg Ser
        355                 360                 365

Glu Trp Gly Leu Gly Val Cys Lys Gln Asn Val Asp Arg Lys Glu Val
370                 375                 380

Val Tyr Leu Ser Pro His Tyr Gly Phe Trp Val Ile Arg Leu Arg Lys
385                 390                 395                 400

Gly Asn Glu Tyr Arg Ala Gly Thr Asp Glu Tyr Pro Ile Leu Ser Leu
                405                 410                 415

Pro Val Pro Pro Arg Arg Val Gly Ile Phe Val Asp Tyr Glu Ala His
            420                 425                 430

Asp Ile Ser Phe Tyr Asn Val Thr Asp Cys Gly Ser His Ile Phe Thr
        435                 440                 445

Phe Pro Arg Tyr Pro Phe Pro Gly Arg Leu Leu Pro Tyr Phe Ser Pro
        450                 455                 460

Cys Tyr Ser Ile Gly Thr Asn Asn Thr Ala Pro Leu Ala Ile Cys Ser
465                 470                 475                 480

Leu Asp Gly Glu Asp
                485

<210> SEQ ID NO 313
<211> LENGTH: 19
<212> TYPE: RNA
<213> ORGANISM: Homo Sapiens

<400> SEQUENCE: 313
gagagauccu gaagacuua                                              19

<210> SEQ ID NO 314
<211> LENGTH: 19
<212> TYPE: RNA
<213> ORGANISM: Homo Sapiens

<400> SEQUENCE: 314
caaggaaccu gcggccuaa                                              19
```

<210> SEQ ID NO 315
<211> LENGTH: 19
<212> TYPE: RNA
<213> ORGANISM: Homo Sapiens

<400> SEQUENCE: 315
gggaaaagcu gaagauguu                                                   19

<210> SEQ ID NO 316
<211> LENGTH: 19
<212> TYPE: RNA
<213> ORGANISM: Homo Sapiens

<400> SEQUENCE: 316
ggaggaugau ugcagaguu                                                   19

<210> SEQ ID NO 317
<211> LENGTH: 500
<212> TYPE: PRT
<213> ORGANISM: Homo Sapiens

<400> SEQUENCE: 317

Met Glu Val Ser Thr Asn Pro Ser Ser Asn Ile Asp Pro Gly Asp Tyr
1               5                   10                  15

Val Glu Met Asn Asp Ser Ile Thr His Leu Pro Ser Lys Val Val Ile
            20                  25                  30

Gln Asp Ile Thr Met Glu Leu His Cys Pro Leu Cys Asn Asp Trp Phe
        35                  40                  45

Arg Asp Pro Leu Met Leu Ser Cys Gly His Asn Phe Cys Glu Ala Cys
50                  55                  60

Ile Gln Asp Phe Trp Arg Leu Gln Ala Lys Glu Thr Phe Cys Pro Glu
65                  70                  75                  80

Cys Lys Met Leu Cys Gln Tyr Asn Asn Cys Thr Phe Asn Pro Val Leu
                85                  90                  95

Asp Lys Leu Val Glu Lys Ile Lys Lys Leu Pro Leu Leu Lys Gly His
            100                 105                 110

Pro Gln Cys Pro Glu His Gly Glu Asn Leu Lys Leu Phe Ser Lys Pro
        115                 120                 125

Asp Gly Lys Leu Ile Cys Phe Gln Cys Lys Asp Ala Arg Leu Ser Val
130                 135                 140

Gly Gln Ser Lys Glu Phe Leu Gln Ile Ser Asp Ala Val His Phe Phe
145                 150                 155                 160

Thr Glu Glu Leu Ala Ile Gln Gln Gly Gln Leu Glu Thr Thr Leu Lys
                165                 170                 175

Glu Leu Gln Thr Leu Arg Asn Met Gln Lys Glu Ala Ile Ala Ala His
            180                 185                 190

Lys Glu Asn Lys Leu His Leu Gln Gln His Val Ser Met Glu Phe Leu
        195                 200                 205

Lys Leu His Gln Phe Leu His Ser Lys Glu Lys Asp Ile Leu Thr Glu
210                 215                 220

Leu Arg Glu Glu Gly Lys Ala Leu Asn Glu Glu Met Glu Leu Asn Leu
225                 230                 235                 240

Ser Gln Leu Gln Glu Gln Cys Leu Leu Ala Lys Asp Met Leu Val Ser
                245                 250                 255

Ile Gln Ala Lys Thr Glu Gln Gln Asn Ser Phe Asp Phe Leu Lys Asp
            260                 265                 270

Ile Thr Thr Leu Leu His Ser Leu Glu Gln Gly Met Lys Val Leu Ala

```
                275                 280                 285
Thr Arg Glu Leu Ile Ser Arg Lys Leu Asn Leu Gly Gln Tyr Lys Gly
        290                 295                 300
Pro Ile Gln Tyr Met Val Trp Arg Glu Met Gln Asp Thr Leu Cys Pro
305                 310                 315                 320
Gly Leu Ser Pro Leu Thr Leu Asp Pro Lys Thr Ala His Pro Asn Leu
                325                 330                 335
Val Leu Ser Lys Ser Gln Thr Ser Val Trp His Gly Asp Ile Lys Lys
            340                 345                 350
Ile Met Pro Asp Asp Pro Glu Arg Phe Asp Ser Ser Val Ala Val Leu
        355                 360                 365
Gly Ser Arg Gly Phe Thr Ser Gly Lys Trp Tyr Trp Glu Val Glu Val
    370                 375                 380
Ala Lys Lys Thr Lys Trp Thr Val Gly Val Val Arg Glu Ser Ile Ile
385                 390                 395                 400
Arg Lys Gly Ser Cys Pro Leu Thr Pro Glu Gln Gly Phe Trp Leu Leu
                405                 410                 415
Arg Leu Arg Asn Gln Thr Asp Leu Lys Ala Leu Asp Leu Pro Ser Phe
            420                 425                 430
Ser Leu Thr Leu Thr Asn Asn Leu Asp Lys Val Gly Ile Tyr Leu Asp
        435                 440                 445
Tyr Glu Gly Gly Gln Leu Ser Phe Tyr Asn Ala Lys Thr Met Thr His
    450                 455                 460
Ile Tyr Thr Phe Ser Asn Thr Phe Met Glu Lys Leu Tyr Pro Tyr Phe
465                 470                 475                 480
Cys Pro Cys Leu Asn Asp Gly Glu Asn Lys Glu Pro Leu His Ile
                485                 490                 495
Leu His Pro Gln
        500

<210> SEQ ID NO 318
<211> LENGTH: 868
<212> TYPE: PRT
<213> ORGANISM: Homo Sapiens

<400> SEQUENCE: 318

Met Ala Ser Phe Pro Glu Thr Asp Phe Gln Ile Cys Leu Leu Cys Lys
1               5                   10                  15
Glu Met Cys Gly Ser Pro Ala Pro Leu Ser Ser Asn Ser Ser Ala Ser
            20                  25                  30
Ser Ser Ser Ser Gln Thr Ser Thr Ser Ser Gly Gly Gly Gly Gly Gly
        35                  40                  45
Pro Gly Ala Ala Ala Arg Arg Leu His Val Leu Pro Cys Leu His Ala
    50                  55                  60
Phe Cys Arg Pro Cys Leu Glu Ala His Arg Leu Pro Ala Ala Gly Gly
65                  70                  75                  80
Gly Ala Ala Gly Glu Pro Leu Lys Leu Arg Cys Pro Val Cys Asp Gln
                85                  90                  95
Lys Val Val Leu Ala Glu Ala Gly Met Asp Ala Leu Pro Ser Ser
            100                 105                 110
Ala Phe Leu Leu Ser Asn Leu Leu Asp Ala Val Val Ala Thr Ala Asp
        115                 120                 125
Glu Pro Pro Pro Lys Asn Gly Arg Ala Gly Ala Pro Ala Gly Ala Gly
    130                 135                 140
```

```
Gly His Ser Asn His Arg His His Ala His His Ala His Pro Arg Ala
145                 150                 155                 160

Ser Ala Ser Ala Pro Pro Leu Pro Gln Ala Pro Gln Pro Pro Ala Pro
            165                 170                 175

Ser Arg Ser Ala Pro Gly Gly Pro Ala Ala Ser Pro Ser Ala Leu Leu
        180                 185                 190

Leu Arg Arg Pro His Gly Cys Ser Cys Asp Glu Gly Asn Ala Ala
    195                 200                 205

Ser Ser Arg Cys Leu Asp Cys Gln Glu His Leu Cys Asp Asn Cys Val
    210                 215                 220

Arg Ala His Gln Arg Val Arg Leu Thr Lys Asp His Tyr Ile Glu Arg
225                 230                 235                 240

Gly Pro Pro Gly Pro Gly Ala Ala Ala Ala Gln Gln Leu Gly Leu
                245                 250                 255

Gly Pro Pro Phe Pro Gly Pro Pro Phe Ser Ile Leu Ser Val Phe Pro
            260                 265                 270

Glu Arg Leu Gly Phe Cys Gln His His Asp Asp Glu Val Leu His Leu
        275                 280                 285

Tyr Cys Asp Thr Cys Ser Val Pro Ile Cys Arg Glu Cys Thr Met Gly
    290                 295                 300

Arg His Gly Gly His Ser Phe Ile Tyr Leu Gln Glu Ala Leu Gln Asp
305                 310                 315                 320

Ser Arg Ala Leu Thr Ile Gln Leu Leu Ala Asp Ala Gln Gly Arg
                325                 330                 335

Gln Ala Ile Gln Leu Ser Ile Glu Gln Ala Gln Thr Val Ala Glu Gln
            340                 345                 350

Val Glu Met Lys Ala Lys Val Val Gln Ser Glu Val Lys Ala Val Thr
        355                 360                 365

Ala Arg His Lys Lys Ala Leu Glu Glu Arg Glu Cys Glu Leu Leu Trp
370                 375                 380

Lys Val Glu Lys Ile Arg Gln Val Lys Ala Lys Ser Leu Tyr Leu Gln
385                 390                 395                 400

Val Glu Lys Leu Arg Gln Asn Leu Asn Lys Leu Glu Ser Thr Ile Ser
                405                 410                 415

Ala Val Gln Gln Val Leu Glu Glu Gly Arg Ala Leu Asp Ile Leu Leu
            420                 425                 430

Ala Arg Asp Arg Met Leu Ala Gln Val Gln Glu Leu Lys Thr Val Arg
        435                 440                 445

Ser Leu Leu Gln Pro Gln Glu Asp Asp Arg Val Met Phe Thr Pro Pro
450                 455                 460

Asp Gln Ala Leu Tyr Leu Ala Ile Lys Ser Phe Gly Phe Val Ser Ser
465                 470                 475                 480

Gly Ala Phe Ala Pro Leu Thr Lys Ala Thr Gly Asp Gly Leu Lys Arg
                485                 490                 495

Ala Leu Gln Gly Lys Val Ala Ser Phe Thr Val Ile Gly Tyr Asp His
            500                 505                 510

Asp Gly Glu Pro Arg Leu Ser Gly Gly Asp Leu Met Ser Ala Val Val
        515                 520                 525

Leu Gly Pro Asp Gly Asn Leu Phe Gly Ala Glu Val Ser Asp Gln Gln
    530                 535                 540

Asn Gly Thr Tyr Val Val Ser Tyr Arg Pro Gln Leu Glu Gly Glu His
545                 550                 555                 560

Leu Val Ser Val Thr Leu Cys Asn Gln His Ile Glu Asn Ser Pro Phe
```

```
                     565                 570                 575
        Lys Val Val Lys Ser Gly Arg Ser Tyr Val Gly Ile Gly Leu Pro
                 580                 585                 590

Gly Leu Ser Phe Gly Ser Glu Gly Asp Ser Asp Gly Lys Leu Cys Arg
                     595                 600                 605

Pro Trp Gly Val Ser Val Asp Lys Glu Gly Tyr Ile Ile Val Ala Asp
            610                 615                 620

Arg Ser Asn Asn Arg Ile Gln Val Phe Lys Pro Cys Gly Ala Phe His
        625                 630                 635                 640

His Lys Phe Gly Thr Leu Gly Ser Arg Pro Gly Gln Phe Asp Arg Pro
                        645                 650                 655

Ala Gly Val Ala Cys Asp Ala Ser Arg Arg Ile Val Val Ala Asp Lys
                        660                 665                 670

Asp Asn His Arg Ile Gln Ile Phe Thr Phe Glu Gly Gln Phe Leu Leu
                        675                 680                 685

Lys Phe Gly Glu Lys Gly Thr Lys Asn Gly Gln Phe Asn Tyr Pro Trp
                    690                 695                 700

Asp Val Ala Val Asn Ser Glu Gly Lys Ile Leu Val Ser Asp Thr Arg
        705                 710                 715                 720

Asn His Arg Ile Gln Leu Phe Gly Pro Asp Gly Val Phe Leu Asn Lys
                            725                 730                 735

Tyr Gly Phe Glu Gly Ala Leu Trp Lys His Phe Asp Ser Pro Arg Gly
                        740                 745                 750

Val Ala Phe Asn His Glu Gly His Leu Val Val Thr Asp Phe Asn Asn
                            755                 760                 765

His Arg Leu Leu Val Ile His Pro Asp Cys Gln Ser Ala Arg Phe Leu
            770                 775                 780

Gly Ser Glu Gly Thr Gly Asn Gly Gln Phe Leu Arg Pro Gln Gly Val
        785                 790                 795                 800

Ala Val Asp Gln Glu Gly Arg Ile Ile Val Ala Asp Ser Arg Asn His
                        805                 810                 815

Arg Val Gln Met Phe Glu Ser Asn Gly Ser Phe Leu Cys Lys Phe Gly
                        820                 825                 830

Ala Gln Gly Ser Gly Phe Gly Gln Met Asp Arg Pro Ser Gly Ile Ala
                        835                 840                 845

Ile Thr Pro Asp Gly Met Ile Val Val Asp Phe Gly Asn Asn Arg
                    850                 855                 860

Ile Leu Val Phe
        865

<210> SEQ ID NO 319
<211> LENGTH: 19
<212> TYPE: RNA
<213> ORGANISM: Homo Sapiens

<400> SEQUENCE: 319
ggaggagggu agagcgcua                                                 19

<210> SEQ ID NO 320
<211> LENGTH: 19
<212> TYPE: RNA
<213> ORGANISM: Homo Sapiens

<400> SEQUENCE: 320
agaaaguagu gcuagccga                                                 19
```

```
<210> SEQ ID NO 321
<211> LENGTH: 19
<212> TYPE: RNA
<213> ORGANISM: Homo Sapiens

<400> SEQUENCE: 321
cuugggaugu ggcggugaa                                                    19

<210> SEQ ID NO 322
<211> LENGTH: 19
<212> TYPE: RNA
<213> ORGANISM: Homo Sapiens

<400> SEQUENCE: 322
caccaaggcc acaggcgau                                                    19

<210> SEQ ID NO 323
<211> LENGTH: 477
<212> TYPE: PRT
<213> ORGANISM: Homo Sapiens

<400> SEQUENCE: 323
```

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

```
Lys Phe Gln Val Trp Arg Lys Met Phe Arg Ala Leu Met Pro Ala Leu
            275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
465                 470                 475

<210> SEQ ID NO 324
<211> LENGTH: 19
<212> TYPE: RNA
<213> ORGANISM: Homo Sapiens

<400> SEQUENCE: 324
ccacgcgcau uggccuuua                                                   19

<210> SEQ ID NO 325
<211> LENGTH: 19
<212> TYPE: RNA
<213> ORGANISM: Homo Sapiens

<400> SEQUENCE: 325
ucuccgaggg cgagcacua                                                   19

<210> SEQ ID NO 326
<211> LENGTH: 19
<212> TYPE: RNA
<213> ORGANISM: Homo Sapiens

<400> SEQUENCE: 326
gacauccagc ugccaauua                                                   19

<210> SEQ ID NO 327
<211> LENGTH: 19
<212> TYPE: RNA
<213> ORGANISM: Homo Sapiens

<400> SEQUENCE: 327
cggacaagcc gcagacuga                                                   19
```

<210> SEQ ID NO 328
<211> LENGTH: 250
<212> TYPE: PRT
<213> ORGANISM: Homo Sapiens

<400> SEQUENCE: 328

Met Ala Trp Gln Val Ser Leu Leu Glu Leu Glu Asp Arg Leu Gln Cys
1               5                   10                  15

Pro Ile Cys Leu Glu Val Phe Lys Glu Ser Leu Met Leu Gln Cys Gly
            20                  25                  30

His Ser Tyr Cys Lys Gly Cys Leu Val Ser Ser Tyr His Leu Asp
        35                  40                  45

Thr Lys Val Arg Cys Pro Met Cys Trp Gln Val Val Asp Gly Ser Ser
    50                  55                  60

Ser Leu Pro Asn Val Ser Leu Ala Trp Val Ile Glu Ala Leu Arg Leu
65                  70                  75                  80

Pro Gly Asp Pro Glu Pro Lys Val Cys Val His His Arg Asn Pro Leu
                85                  90                  95

Ser Leu Phe Cys Glu Lys Asp Gln Glu Leu Ile Cys Gly Leu Cys Gly
            100                 105                 110

Leu Leu Gly Ser His Gln His Pro Val Thr Pro Val Ser Thr Val
        115                 120                 125

Cys Ser Arg Met Lys Glu Glu Leu Ala Ala Leu Phe Ser Glu Leu Lys
130                 135                 140

Gln Glu Gln Lys Lys Val Asp Glu Leu Ile Ala Lys Leu Val Lys Asn
145                 150                 155                 160

Arg Thr Arg Ile Val Asn Glu Ser Asp Val Phe Ser Trp Val Ile Arg
                165                 170                 175

Arg Glu Phe Gln Glu Leu Arg His Pro Val Asp Glu Lys Ala Arg
            180                 185                 190

Cys Leu Glu Gly Ile Gly Gly His Thr Arg Gly Leu Val Ala Ser Leu
        195                 200                 205

Asp Met Gln Leu Glu Gln Ala Gln Gly Thr Arg Glu Arg Leu Ala Gln
    210                 215                 220

Ala Glu Cys Val Leu Glu Gln Phe Gly Asn Glu Asp His His Glu Phe
225                 230                 235                 240

Ile Trp Lys Phe His Ser Met Ala Ser Arg
                245                 250

<210> SEQ ID NO 329
<211> LENGTH: 19
<212> TYPE: RNA
<213> ORGANISM: Homo Sapiens

<400> SEQUENCE: 329
ggacccgaau cgucaauga                                          19

<210> SEQ ID NO 330
<211> LENGTH: 19
<212> TYPE: RNA
<213> ORGANISM: Homo Sapiens

<400> SEQUENCE: 330
caaggagucc cuaaugcua                                          19

<210> SEQ ID NO 331
<211> LENGTH: 19

```
<212> TYPE: RNA
<213> ORGANISM: Homo Sapiens

<400> SEQUENCE: 331
ucgcagcccu cuucucuga                                                19

<210> SEQ ID NO 332
<211> LENGTH: 19
<212> TYPE: RNA
<213> ORGANISM: Homo Sapiens

<400> SEQUENCE: 332
agugugugcu ggaacaguu                                                19

<210> SEQ ID NO 333
<211> LENGTH: 250
<212> TYPE: PRT
<213> ORGANISM: Homo Sapiens

<400> SEQUENCE: 333
```

Met Ala Trp Gln Val Ser Leu Leu Glu Leu Glu Asp Trp Leu Gln Cys
1               5                   10                  15

Pro Ile Cys Leu Glu Val Phe Lys Glu Ser Leu Met Leu Gln Cys Gly
            20                  25                  30

His Ser Tyr Cys Lys Gly Cys Leu Val Ser Leu Ser Tyr His Leu Asp
        35                  40                  45

Thr Lys Val Arg Cys Pro Met Cys Trp Gln Val Val Asp Gly Ser Ser
    50                  55                  60

Ser Leu Pro Asn Val Ser Leu Ala Trp Val Ile Glu Ala Leu Arg Leu
65                  70                  75                  80

Pro Gly Asp Pro Glu Pro Lys Val Cys Val His His Arg Asn Pro Leu
                85                  90                  95

Ser Leu Phe Cys Glu Lys Asp Gln Glu Leu Ile Cys Gly Leu Cys Gly
            100                 105                 110

Leu Leu Gly Ser His Gln His His Pro Val Thr Pro Val Ser Thr Val
        115                 120                 125

Cys Ser Arg Met Lys Glu Leu Ala Ala Leu Phe Ser Glu Leu Lys
    130                 135                 140

Gln Glu Gln Lys Lys Val Asp Glu Leu Ile Ala Lys Leu Val Lys Asn
145                 150                 155                 160

Arg Thr Arg Ile Val Asn Glu Ser Asp Val Phe Ser Trp Val Ile Arg
                165                 170                 175

Arg Glu Phe Gln Glu Leu Arg His Pro Val Asp Glu Lys Ala Arg
            180                 185                 190

Cys Leu Glu Gly Ile Gly Gly His Thr Arg Gly Leu Val Ala Ser Leu
        195                 200                 205

Asp Met Gln Leu Glu Gln Ala Gln Gly Thr Arg Glu Arg Leu Ala Gln
    210                 215                 220

Ala Glu Cys Val Leu Glu Gln Phe Gly Asn Glu Asp His His Glu Phe
225                 230                 235                 240

Ile Trp Lys Phe His Ser Met Ala Ser Arg
                245                 250

```
<210> SEQ ID NO 334
<211> LENGTH: 19
<212> TYPE: RNA
<213> ORGANISM: Homo Sapiens
```

```
<400> SEQUENCE: 334
gaaaugagga ccaccauga                                                  19

<210> SEQ ID NO 335
<211> LENGTH: 19
<212> TYPE: RNA
<213> ORGANISM: Homo Sapiens

<400> SEQUENCE: 335
ggacccgaau cgucaauga                                                  19

<210> SEQ ID NO 336
<211> LENGTH: 19
<212> TYPE: RNA
<213> ORGANISM: Homo Sapiens

<400> SEQUENCE: 336
caaggagucc cuaaugcua                                                  19

<210> SEQ ID NO 337
<211> LENGTH: 19
<212> TYPE: RNA
<213> ORGANISM: Homo Sapiens

<400> SEQUENCE: 337
ucgcagcccu cuucucuga                                                  19

<210> SEQ ID NO 338
<211> LENGTH: 468
<212> TYPE: PRT
<213> ORGANISM: Homo Sapiens

<400> SEQUENCE: 338
```

Met Ala Val Ala Ala Ala Leu Thr Gly Leu Gln Ala Glu Ala Lys Cys
1               5                   10                  15

Ser Ile Cys Leu Asp Tyr Leu Ser Asp Pro Val Thr Ile Glu Cys Gly
                20                  25                  30

His Asn Phe Cys Arg Ser Cys Ile Gln Gln Ser Trp Leu Asp Leu Gln
            35                  40                  45

Glu Leu Phe Pro Cys Pro Val Cys Arg His Gln Cys Gln Glu Gly His
        50                  55                  60

Phe Arg Ser Asn Thr Gln Leu Gly Arg Met Ile Glu Ile Ala Lys Leu
65                  70                  75                  80

Leu Gln Ser Thr Lys Ser Asn Lys Arg Lys Gln Glu Glu Thr Thr Leu
                85                  90                  95

Cys Glu Lys His Asn Gln Pro Leu Ser Val Phe Cys Lys Glu Asp Leu
            100                 105                 110

Met Val Leu Cys Pro Leu Cys Thr Gln Pro Pro Asp His Gln Gly His
        115                 120                 125

His Val Arg Pro Ile Glu Lys Ala Ala Ile His Tyr Arg Lys Arg Phe
    130                 135                 140

Cys Ser Tyr Ile Gln Pro Leu Lys Lys Gln Leu Ala Asp Leu Gln Lys
145                 150                 155                 160

Leu Ile Ser Thr Gln Ser Lys Lys Pro Leu Glu Leu Arg Glu Met Val
                165                 170                 175

Glu Asn Gln Arg Gln Glu Leu Ser Ser Glu Phe Glu His Leu Asn Gln
            180                 185                 190

Phe Leu Asp Arg Glu Gln Gln Ala Val Leu Ser Arg Leu Ala Glu Glu

```
                195                 200                 205
Glu Lys Asp Asn Gln Gln Lys Leu Ser Ala Asn Ile Thr Ala Phe Ser
210                 215                 220

Asn Tyr Ser Ala Thr Leu Lys Ser Gln Leu Ser Lys Val Val Glu Leu
225                 230                 235                 240

Ser Glu Leu Ser Glu Leu Leu Ser Gln Ile Lys Ile Phe Tyr
                245                 250                 255

Glu Ser Glu Asn Glu Ser Ser Pro Ser Ile Phe Ser Ile His Leu Lys
            260                 265                 270

Arg Asp Gly Cys Ser Phe Pro Pro Gln Tyr Ser Ala Leu Gln Arg Ile
                275                 280                 285

Ile Lys Lys Phe Lys Val Glu Ile Ile Leu Asp Pro Glu Thr Ala His
            290                 295                 300

Pro Asn Leu Ile Val Ser Glu Asp Lys Lys Arg Val Arg Phe Thr Lys
305                 310                 315                 320

Arg Lys Gln Lys Val Pro Gly Phe Pro Lys Arg Phe Thr Val Lys Pro
                325                 330                 335

Val Val Leu Gly Phe Pro Tyr Phe His Ser Gly Arg His Phe Trp Glu
                340                 345                 350

Ile Glu Val Gly Asp Lys Ser Glu Trp Ala Ile Gly Ile Cys Lys Asp
                355                 360                 365

Ser Leu Pro Thr Lys Ala Arg Arg Pro Ser Ser Ala Gln Gln Glu Cys
370                 375                 380

Trp Arg Ile Glu Leu Gln Asp Asp Gly Tyr His Ala Pro Gly Ala Phe
385                 390                 395                 400

Pro Thr Pro Leu Leu Leu Glu Val Lys Ala Arg Ala Ile Gly Ile Phe
                405                 410                 415

Leu Asp Tyr Glu Met Gly Glu Ile Ser Phe Tyr Asn Met Ala Glu Lys
                420                 425                 430

Ser His Ile Cys Thr Phe Thr Asp Thr Phe Thr Gly Pro Leu Arg Pro
                435                 440                 445

Tyr Phe Tyr Val Gly Pro Asp Ser Gln Pro Leu Arg Ile Cys Thr Gly
    450                 455                 460

Thr Val Cys Glu
465

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342
```

-continued

```
<210> SEQ ID NO 343
<211> LENGTH: 4069
<212> TYPE: PRT
<213> ORGANISM: Homo Sapiens

<400> SEQUENCE: 343
```

| | | | | | | | | | | | | | | | |
|---|---|---|---|---|---|---|---|---|---|---|---|---|---|---|---|
| Met | Ala | Ser | Arg | Asp | Ser | Asn | His | Ala | Gly | Glu | Ser | Phe | Leu | Gly | Ser |
| 1 | | | | 5 | | | | | 10 | | | | | 15 | |
| Asp | Gly | Asp | Glu | Glu | Ala | Thr | Arg | Glu | Leu | Glu | Thr | Glu | Glu | Glu | Ser |
| | | | 20 | | | | | 25 | | | | | 30 | | |
| Glu | Gly | Glu | Glu | Asp | Glu | Thr | Ala | Ala | Glu | Ser | Glu | Glu | Pro | Asp | |
| | | 35 | | | | | 40 | | | | | 45 | | | |
| Ser | Arg | Leu | Ser | Asp | Gln | Asp | Glu | Glu | Gly | Lys | Ile | Lys | Gln | Glu | Tyr |
| | 50 | | | | | 55 | | | | | 60 | | | | |
| Ile | Ile | Ser | Asp | Pro | Ser | Phe | Ser | Met | Val | Thr | Val | Gln | Arg | Glu | Asp |
| 65 | | | | | 70 | | | | | 75 | | | | | 80 |
| Ser | Gly | Ile | Thr | Trp | Glu | Thr | Asn | Ser | Ser | Arg | Ser | Ser | Thr | Pro | Trp |
| | | | | 85 | | | | | 90 | | | | | 95 | |
| Ala | Ser | Glu | Glu | Ser | Gln | Thr | Ser | Gly | Val | Cys | Ser | Arg | Glu | Gly | Ser |
| | | | 100 | | | | | 105 | | | | | 110 | | |
| Thr | Val | Asn | Ser | Pro | Pro | Gly | Asn | Val | Ser | Phe | Ile | Val | Asp | Glu | Val |
| | | | 115 | | | | | 120 | | | | | 125 | | |
| Lys | Lys | Val | Arg | Lys | Arg | Thr | His | Lys | Ser | Lys | His | Gly | Ser | Pro | Ser |
| 130 | | | | | 135 | | | | | 140 | | | | | |
| Leu | Arg | Arg | Lys | Gly | Asn | Arg | Lys | Arg | Asn | Ser | Phe | Glu | Ser | Gln | Asp |
| 145 | | | | | 150 | | | | | 155 | | | | | 160 |
| Val | Pro | Thr | Asn | Lys | Lys | Gly | Ser | Pro | Leu | Thr | Ser | Ala | Ser | Gln | Val |
| | | | | 165 | | | | | 170 | | | | | 175 | |
| Leu | Thr | Thr | Glu | Lys | Glu | Lys | Ser | Tyr | Thr | Gly | Ile | Tyr | Asp | Lys | Ala |
| | | | 180 | | | | | 185 | | | | | 190 | | |
| Arg | Lys | Lys | Lys | Thr | Thr | Ser | Asn | Thr | Pro | Pro | Ile | Thr | Gly | Ala | Ile |
| | | 195 | | | | | 200 | | | | | 205 | | | |
| Tyr | Lys | Glu | His | Lys | Pro | Leu | Val | Leu | Arg | Pro | Val | Tyr | Ile | Gly | Thr |
| | 210 | | | | | 215 | | | | | 220 | | | | |
| Val | Gln | Tyr | Lys | Ile | Lys | Met | Phe | Asn | Ser | Val | Lys | Glu | Glu | Leu | Ile |
| 225 | | | | | 230 | | | | | 235 | | | | | 240 |
| Pro | Leu | Gln | Phe | Tyr | Gly | Thr | Leu | Pro | Lys | Gly | Tyr | Val | Ile | Lys | Glu |
| | | | | 245 | | | | | 250 | | | | | 255 | |
| Ile | His | Tyr | Arg | Lys | Gly | Lys | Asp | Ala | Ser | Ile | Ser | Leu | Glu | Pro | Asp |
| | | | 260 | | | | | 265 | | | | | 270 | | |
| Leu | Asp | Asn | Ser | Gly | Ser | Asn | Thr | Val | Ser | Lys | Thr | Arg | Lys | Leu | Val |
| | | 275 | | | | | 280 | | | | | 285 | | | |
| Ala | Gln | Ser | Ile | Glu | Asp | Lys | Val | Lys | Glu | Val | Phe | Pro | Pro | Trp | Arg |
| | 290 | | | | | 295 | | | | | 300 | | | | |
| Gly | Ala | Leu | Ser | Lys | Gly | Ser | Glu | Ser | Leu | Thr | Leu | Met | Phe | Ser | His |
| 305 | | | | | 310 | | | | | 315 | | | | | 320 |
| Glu | Asp | Gln | Lys | Lys | Ile | Tyr | Ala | Asp | Ser | Pro | Leu | Asn | Ala | Thr | Ser |
| | | | | 325 | | | | | 330 | | | | | 335 | |
| Ala | Leu | Glu | His | Thr | Val | Pro | Ser | Tyr | Ser | Ser | Gly | Arg | Ala | Glu | |
| | | | 340 | | | | | 345 | | | | | 350 | | |
| Gln | Gly | Ile | Gln | Leu | Arg | His | Ser | Gln | Ser | Val | Pro | Gln | Gln | Pro | Glu |
| | | 355 | | | | | 360 | | | | | 365 | | | |

-continued

```
Asp Glu Ala Lys Pro His Glu Val Glu Pro Ser Val Thr Pro Asp
    370                 375                 380

Thr Pro Ala Thr Met Phe Leu Arg Thr Thr Lys Glu Glu Cys Glu Leu
385                 390                 395                 400

Ala Ser Pro Gly Thr Ala Ala Ser Glu Asn Asp Ser Ser Val Ser Pro
                405                 410                 415

Ser Phe Ala Asn Glu Val Lys Lys Glu Asp Val Tyr Ser Ala His His
            420                 425                 430

Ser Ile Ser Leu Glu Ala Ala Ser Pro Gly Leu Ala Ala Ser Thr Gln
            435                 440                 445

Asp Gly Leu Asp Pro Asp Gln Glu Gln Pro Asp Leu Thr Ser Ile Glu
450                 455                 460

Arg Ala Glu Pro Val Ser Ala Lys Leu Thr Pro Thr His Pro Ser Val
465                 470                 475                 480

Lys Gly Glu Lys Glu Glu Asn Met Leu Glu Pro Ser Ile Ser Leu Ser
                485                 490                 495

Glu Pro Leu Met Leu Glu Glu Pro Glu Lys Glu Ile Glu Thr Ser
                500                 505                 510

Leu Pro Ile Ala Ile Thr Pro Glu Pro Glu Asp Ser Asn Leu Val Glu
                515                 520                 525

Glu Glu Ile Val Glu Leu Asp Tyr Pro Glu Ser Pro Leu Val Ser Glu
530                 535                 540

Lys Pro Phe Pro Pro His Met Ser Pro Glu Val His Lys Glu Glu
545                 550                 555                 560

Glu Leu Ile Leu Pro Leu Leu Ala Ala Ser Ser Pro Glu His Val Ala
                565                 570                 575

Leu Ser Glu Glu Glu Arg Glu Glu Ile Ala Ser Val Ser Thr Gly Ser
                580                 585                 590

Ala Phe Val Ser Glu Tyr Ser Val Pro Gln Asp Leu Asn His Glu Leu
            595                 600                 605

Gln Glu Gln Glu Gly Glu Pro Val Pro Pro Ser Asn Val Glu Ala Ile
610                 615                 620

Ala Glu His Ala Val Leu Ser Glu Glu Glu Asn Glu Glu Phe Glu Ala
625                 630                 635                 640

Tyr Ser Pro Ala Ala Pro Thr Ser Glu Ser Ser Leu Ser Pro Ser
                645                 650                 655

Thr Thr Glu Lys Thr Ser Glu Asn Gln Ser Pro Leu Phe Ser Thr Val
                660                 665                 670

Thr Pro Glu Tyr Met Val Leu Ser Gly Asp Glu Ala Ser Glu Ser Gly
            675                 680                 685

Cys Tyr Thr Pro Asp Ser Thr Ser Ala Ser Glu Tyr Ser Val Pro Ser
690                 695                 700

Leu Ala Thr Lys Glu Ser Leu Lys Lys Thr Ile Asp Arg Lys Ser Pro
705                 710                 715                 720

Leu Ile Leu Lys Gly Val Ser Glu Tyr Met Ile Pro Ser Glu Glu Lys
                725                 730                 735

Glu Asp Thr Gly Ser Phe Thr Pro Ala Val Ala Pro Ala Ser Glu Pro
            740                 745                 750

Ser Leu Ser Pro Ser Thr Thr Glu Lys Thr Ser Glu Cys Gln Ser Pro
            755                 760                 765

Leu Pro Ser Thr Ala Thr Ser Glu His Val Val Pro Ser Glu Gly Glu
            770                 775                 780

Asp Leu Gly Ser Glu Arg Phe Thr Pro Asp Ser Lys Leu Ile Ser Lys
```

-continued

```
           785                 790                 795                 800
Tyr Ala Ala Pro Leu Asn Ala Thr Gln Glu Ser Gln Lys Lys Ile Ile
                805                 810                 815

Asn Glu Ala Ser Gln Phe Lys Pro Lys Gly Ile Ser Glu His Thr Val
                820                 825                 830

Leu Ser Val Asp Gly Lys Glu Val Ile Gly Pro Ser Ser Pro Asp Leu
                835                 840                 845

Val Val Ala Ser Glu His Ser Phe Pro Pro His Thr Thr Glu Met Thr
    850                 855                 860

Ser Glu Cys Gln Ala Pro Pro Leu Ser Ala Thr Pro Ser Glu Tyr Val
865                 870                 875                 880

Val Leu Ser Asp Glu Glu Ala Val Glu Leu Glu Arg Tyr Thr Pro Ser
                885                 890                 895

Ser Thr Ser Ala Ser Glu Phe Ser Val Pro Pro Tyr Ala Thr Pro Glu
                900                 905                 910

Ala Gln Glu Glu Glu Ile Val His Arg Ser Leu Asn Leu Lys Gly Ala
                915                 920                 925

Ser Ser Pro Met Asn Leu Ser Glu Glu Asp Gln Glu Asp Ile Gly Pro
    930                 935                 940

Phe Ser Pro Asp Ser Ala Phe Val Ser Glu Phe Ser Phe Pro Pro Tyr
945                 950                 955                 960

Ala Thr Gln Glu Ala Glu Lys Arg Glu Phe Glu Cys Asp Ser Pro Ile
                965                 970                 975

Cys Leu Thr Ser Pro Ser Glu His Thr Ile Leu Ser Asp Glu Asp Thr
                980                 985                 990

Glu Glu Ala Glu Leu Phe Ser Pro  Asp Ser Ala Ser Gln  Val Ser Ile
                995                1000                1005

Pro Pro  Phe Arg Ile Ser Glu   Thr Glu Lys Asn Glu  Leu Glu Pro
        1010                1015                1020

Asp Ser  Leu Leu Thr Ala Val  Ser Ala Ser Gly Tyr  Ser Cys Phe
        1025                1030                1035

Ser Glu  Ala Asp Glu Glu Asp  Ile Gly Ser Thr Ala  Ala Thr Pro
        1040                1045                1050

Val Ser  Glu Gln Phe Ser Ser  Ser Gln Lys Gln Lys  Ala Glu Thr
        1055                1060                1065

Phe Pro  Leu Met Ser Pro Leu  Glu Asp Leu Ser Leu  Pro Pro Ser
        1070                1075                1080

Thr Asp  Lys Ser Glu Lys Ala  Glu Ile Lys Pro Glu  Ile Pro Thr
        1085                1090                1095

Thr Ser  Thr Ser Val Ser Glu  Tyr Leu Ile Leu Ala  Gln Lys Gln
        1100                1105                1110

Lys Thr  Gln Ala Tyr Leu Glu  Pro Glu Ser Glu Asp  Leu Ile Pro
        1115                1120                1125

Ser His  Leu Thr Ser Glu Val  Glu Lys Gly Glu Arg  Glu Ala Ser
        1130                1135                1140

Ser Ser  Val Ala Ala Ile Pro  Ala Ala Leu Pro Ala  Gln Ser Ser
        1145                1150                1155

Ile Val  Lys Glu Glu Thr Lys  Pro Ala Ser Pro His  Ser Val Leu
        1160                1165                1170

Pro Asp  Ser Val Pro Ala Ile  Lys Lys Glu Gln Glu  Pro Thr Ala
        1175                1180                1185

Ala Leu  Thr Leu Lys Ala Ala  Asp Glu Gln Met Ala  Leu Ser Lys
        1190                1195                1200
```

-continued

```
Val Arg Lys Glu Glu Ile Val Pro Asp Ser Gln Glu Ala Thr Ala
1205                1210                1215

His Val Ser Gln Asp Gln Lys Met Glu Pro Gln Pro Pro Asn Val
1220                1225                1230

Pro Glu Ser Glu Met Lys Tyr Ser Val Leu Pro Asp Met Val Asp
1235                1240                1245

Glu Pro Lys Lys Gly Val Lys Pro Lys Leu Val Leu Asn Val Thr
1250                1255                1260

Ser Glu Leu Glu Gln Arg Lys Leu Ser Lys Asn Glu Pro Glu Val
1265                1270                1275

Ile Lys Pro Tyr Ser Pro Leu Lys Glu Thr Ser Leu Ser Gly Pro
1280                1285                1290

Glu Ala Leu Ser Ala Val Lys Met Glu Met Lys His Asp Ser Lys
1295                1300                1305

Ile Thr Thr Thr Pro Ile Val Leu His Ser Ala Ser Ser Gly Val
1310                1315                1320

Glu Lys Gln Val Glu His Gly Pro Pro Ala Leu Ala Phe Ser Ala
1325                1330                1335

Leu Ser Glu Glu Ile Lys Lys Glu Ile Glu Pro Ser Ser Ser Thr
1340                1345                1350

Thr Thr Ala Ser Val Thr Lys Leu Asp Ser Asn Leu Thr Arg Ala
1355                1360                1365

Val Lys Glu Glu Ile Pro Thr Asp Ser Ser Leu Ile Thr Pro Val
1370                1375                1380

Asp Arg Pro Val Leu Thr Lys Val Gly Lys Gly Glu Leu Gly Ser
1385                1390                1395

Gly Leu Pro Pro Leu Val Thr Ser Ala Asp Glu His Ser Val Leu
1400                1405                1410

Ala Glu Glu Asp Lys Val Ala Ile Lys Gly Ala Ser Pro Ile Glu
1415                1420                1425

Thr Ser Ser Lys His Leu Ala Trp Ser Glu Ala Glu Lys Glu Ile
1430                1435                1440

Lys Phe Asp Ser Leu Pro Ser Val Ser Ser Ile Ala Glu His Ser
1445                1450                1455

Val Leu Ser Glu Val Glu Ala Lys Glu Val Lys Ala Gly Leu Pro
1460                1465                1470

Val Ile Lys Thr Ser Ser Ser Gln His Ser Asp Lys Ser Glu Glu
1475                1480                1485

Ala Arg Val Glu Asp Lys Gln Asp Leu Leu Phe Ser Thr Val Cys
1490                1495                1500

Asp Ser Glu Arg Leu Val Ser Ser Gln Lys Lys Ser Leu Met Ser
1505                1510                1515

Thr Ser Glu Val Leu Glu Pro Glu His Glu Leu Pro Leu Ser Leu
1520                1525                1530

Trp Gly Glu Ile Lys Lys Lys Glu Thr Glu Leu Pro Ser Ser Gln
1535                1540                1545

Asn Val Ser Pro Ala Ser Lys His Ile Ile Pro Lys Gly Lys Asp
1550                1555                1560

Glu Glu Thr Ala Ser Ser Ser Pro Glu Leu Glu Asn Leu Ala Ser
1565                1570                1575

Gly Leu Ala Pro Thr Leu Leu Leu Leu Ser Asp Asp Lys Asn Lys
1580                1585                1590
```

```
Pro Ala Val Glu Val Ser Ser Thr Ala Gln Gly Asp Phe Pro Ser
1595                1600                1605

Glu Lys Gln Asp Val Ala Leu Ala Glu Leu Ser Leu Glu Pro Glu
1610                1615                1620

Lys Lys Asp Lys Pro His Gln Pro Leu Glu Leu Pro Asn Ala Gly
1625                1630                1635

Ser Glu Phe Ser Ser Asp Leu Gly Arg Gln Ser Gly Ser Ile Gly
1640                1645                1650

Thr Lys Gln Ala Lys Ser Pro Ile Thr Glu Thr Glu Asp Ser Val
1655                1660                1665

Leu Glu Lys Gly Pro Ala Glu Leu Arg Ser Arg Glu Gly Lys Glu
1670                1675                1680

Glu Asn Arg Glu Leu Cys Ala Ser Ser Thr Met Pro Ala Ile Ser
1685                1690                1695

Glu Leu Ser Ser Leu Leu Arg Glu Glu Ser Gln Asn Glu Glu Ile
1700                1705                1710

Lys Pro Phe Ser Pro Lys Ile Ile Ser Leu Glu Ser Lys Glu Pro
1715                1720                1725

Pro Ala Ser Val Ala Glu Gly Gly Asn Pro Glu Glu Phe Gln Pro
1730                1735                1740

Phe Thr Phe Ser Leu Lys Gly Leu Ser Glu Glu Val Ser His Pro
1745                1750                1755

Ala Asp Phe Lys Lys Gly Gly Asn Gln Glu Ile Gly Pro Leu Pro
1760                1765                1770

Pro Thr Gly Asn Leu Lys Ala Gln Val Met Gly Asp Ile Leu Asp
1775                1780                1785

Lys Leu Ser Glu Glu Thr Gly His Pro Asn Ser Ser Gln Val Leu
1790                1795                1800

Gln Ser Ile Thr Glu Pro Ser Lys Ile Ala Pro Ser Asp Leu Leu
1805                1810                1815

Val Glu Gln Lys Lys Thr Glu Lys Ala Leu His Ser Asp Gln Thr
1820                1825                1830

Val Lys Leu Pro Asp Val Ser Thr Ser Ser Glu Asp Lys Gln Asp
1835                1840                1845

Leu Gly Ile Lys Gln Phe Ser Leu Met Arg Glu Asn Leu Pro Leu
1850                1855                1860

Glu Gln Ser Lys Ser Phe Met Thr Thr Lys Pro Ala Asp Val Lys
1865                1870                1875

Glu Thr Lys Met Glu Glu Phe Phe Ile Ser Pro Lys Asp Glu Asn
1880                1885                1890

Trp Met Leu Gly Lys Pro Glu Asn Val Ala Ser Gln His Glu Gln
1895                1900                1905

Arg Ile Ala Gly Ser Val Gln Leu Asp Ser Ser Ser Asn Glu
1910                1915                1920

Leu Arg Pro Gly Gln Leu Lys Ala Ala Val Ser Ser Lys Asp His
1925                1930                1935

Thr Cys Glu Val Arg Lys Gln Val Leu Pro His Ser Ala Glu Glu
1940                1945                1950

Ser His Leu Ser Ser Gln Glu Ala Val Ser Ala Leu Asp Thr Ser
1955                1960                1965

Ser Gly Asn Thr Glu Thr Leu Ser Ser Lys Ser Tyr Ser Ser Glu
1970                1975                1980

Glu Val Lys Leu Ala Glu Glu Pro Lys Ser Leu Val Leu Ala Gly
```

-continued

```
              1985                1990                1995

Asn Val Glu Arg Asn Ile Ala Glu Gly Lys Glu Ile His Ser Leu
        2000                2005                2010

Met Glu Ser Glu Ser Leu Leu Leu Glu Lys Ala Asn Thr Glu Leu
        2015                2020                2025

Ser Trp Pro Ser Lys Glu Asp Ser Gln Glu Lys Ile Lys Leu Pro
        2030                2035                2040

Pro Glu Arg Phe Phe Gln Lys Pro Val Ser Gly Leu Ser Val Glu
        2045                2050                2055

Gln Val Lys Ser Glu Thr Ile Ser Ser Ser Val Lys Thr Ala His
        2060                2065                2070

Phe Pro Ala Glu Gly Val Glu Pro Ala Leu Gly Asn Glu Lys Glu
        2075                2080                2085

Ala His Arg Ser Thr Pro Pro Phe Pro Glu Glu Lys Pro Leu Glu
        2090                2095                2100

Glu Ser Lys Met Val Gln Ser Lys Val Ile Asp Asp Ala Asp Glu
        2105                2110                2115

Gly Lys Lys Pro Ser Pro Glu Val Lys Ile Pro Thr Gln Arg Lys
        2120                2125                2130

Pro Ile Ser Ser Ile His Ala Arg Glu Pro Gln Ser Pro Glu Ser
        2135                2140                2145

Pro Glu Val Thr Gln Asn Pro Pro Thr Gln Pro Lys Val Ala Lys
        2150                2155                2160

Pro Asp Leu Pro Glu Glu Lys Gly Lys Lys Gly Ile Ser Ser Phe
        2165                2170                2175

Lys Ser Trp Met Ser Ser Leu Phe Phe Gly Ser Ser Thr Pro Asp
        2180                2185                2190

Asn Lys Val Ala Glu Gln Glu Asp Leu Glu Thr Gln Pro Ser Pro
        2195                2200                2205

Ser Val Glu Lys Ala Val Thr Val Ile Asp Pro Glu Gly Thr Ile
        2210                2215                2220

Pro Thr Asn Phe Asn Val Ala Glu Lys Pro Ala Asp His Ser Leu
        2225                2230                2235

Ser Glu Val Lys Leu Lys Thr Ala Asp Glu Pro Arg Gly Thr Leu
        2240                2245                2250

Val Lys Ser Gly Asp Gly Gln Asn Val Lys Glu Lys Ser Met Ile
        2255                2260                2265

Leu Ser Asn Val Glu Asp Leu Gln Gln Pro Lys Phe Ile Ser Glu
        2270                2275                2280

Val Ser Arg Glu Asp Tyr Gly Lys Lys Glu Ile Ser Gly Asp Ser
        2285                2290                2295

Glu Glu Met Asn Ile Asn Ser Val Val Thr Ser Ala Asp Gly Glu
        2300                2305                2310

Asn Leu Glu Ile Gln Ser Tyr Ser Leu Ile Gly Glu Lys Leu Val
        2315                2320                2325

Met Glu Glu Ala Lys Thr Ile Val Pro Pro His Val Thr Asp Ser
        2330                2335                2340

Lys Arg Val Gln Lys Pro Ala Ile Ala Pro Pro Ser Lys Trp Asn
        2345                2350                2355

Ile Ser Ile Phe Lys Glu Glu Pro Arg Ser Asp Gln Lys Gln Lys
        2360                2365                2370

Ser Leu Leu Ser Phe Asp Val Val Asp Lys Val Pro Gln Gln Pro
        2375                2380                2385
```

```
Lys Ser Ala Ser Ser Asn Phe Ala Ser Lys Asn Ile Thr Lys Glu
    2390            2395            2400

Ser Glu Lys Pro Glu Ser Ile Ile Leu Pro Val Glu Glu Ser Lys
    2405            2410            2415

Gly Ser Leu Ile Asp Phe Ser Glu Asp Arg Leu Lys Lys Glu Met
    2420            2425            2430

Gln Asn Pro Thr Ser Leu Lys Ile Ser Glu Glu Thr Lys Leu
    2435            2440            2445

Arg Ser Val Ser Pro Thr Glu Lys Lys Asp Asn Leu Glu Asn Arg
    2450            2455            2460

Ser Tyr Thr Leu Ala Glu Lys Lys Val Leu Ala Glu Lys Gln Asn
    2465            2470            2475

Ser Val Ala Pro Leu Glu Leu Arg Asp Ser Asn Glu Ile Gly Lys
    2480            2485            2490

Thr Gln Ile Thr Leu Gly Ser Arg Ser Thr Glu Leu Lys Glu Ser
    2495            2500            2505

Lys Ala Asp Ala Met Pro Gln His Phe Tyr Gln Asn Glu Asp Tyr
    2510            2515            2520

Asn Glu Arg Pro Lys Ile Ile Val Gly Ser Glu Lys Glu Lys Gly
    2525            2530            2535

Glu Glu Lys Glu Asn Gln Val Tyr Val Leu Ser Glu Gly Lys Lys
    2540            2545            2550

Gln Gln Glu His Gln Pro Tyr Ser Val Asn Val Ala Glu Ser Met
    2555            2560            2565

Ser Arg Glu Ser Asp Ile Ser Leu Gly His Ser Leu Gly Glu Thr
    2570            2575            2580

Gln Ser Phe Ser Leu Val Lys Ala Thr Ser Val Thr Glu Lys Ser
    2585            2590            2595

Glu Ala Met Leu Ala Glu Ala His Pro Glu Ile Arg Glu Ala Lys
    2600            2605            2610

Ala Val Gly Thr Gln Pro His Pro Leu Glu Glu Ser Lys Val Leu
    2615            2620            2625

Val Glu Lys Thr Lys Thr Phe Leu Pro Val Ala Leu Ser Cys Arg
    2630            2635            2640

Asp Glu Ile Glu Asn His Ser Leu Ser Gln Glu Gly Asn Leu Val
    2645            2650            2655

Leu Glu Lys Ser Ser Arg Asp Met Pro Asp His Ser Glu Glu Lys
    2660            2665            2670

Glu Gln Phe Arg Glu Ser Glu Leu Ser Lys Gly Gly Ser Val Asp
    2675            2680            2685

Ile Thr Lys Glu Thr Val Lys Gln Gly Phe Gln Glu Lys Ala Val
    2690            2695            2700

Gly Thr Gln Pro Arg Pro Leu Glu Glu Ser Lys Val Leu Val Glu
    2705            2710            2715

Lys Thr Lys Thr Phe Leu Pro Val Val Leu Ser Cys His Asp Glu
    2720            2725            2730

Ile Glu Asn His Ser Leu Ser Gln Glu Gly Asn Leu Val Leu Glu
    2735            2740            2745

Lys Ser Ser Arg Asp Met Pro Asp His Ser Glu Glu Lys Glu Gln
    2750            2755            2760

Phe Lys Glu Ser Glu Leu Trp Lys Gly Gly Ser Val Asp Ile Thr
    2765            2770            2775
```

-continued

| | | | | | | | | | | | |
|---|---|---|---|---|---|---|---|---|---|---|---|
|Lys|Glu|Ser|Met|Lys|Glu|Gly|Phe|Pro|Ser|Lys|Glu|Ser|Glu|Arg|
| |2780| | | |2785| | | |2790| | |

Lys Glu Ser Met Lys Glu Gly Phe Pro Ser Lys Glu Ser Glu Arg
    2780              2785              2790

Thr Leu Ala Arg Pro Phe Asp Glu Thr Lys Ser Ser Glu Thr Pro
    2795              2800              2805

Pro Tyr Leu Leu Ser Pro Val Lys Pro Gln Thr Leu Ala Ser Gly
    2810              2815              2820

Ala Ser Pro Glu Ile Asn Ala Val Lys Lys Glu Met Pro Arg
    2825              2830              2835

Ser Glu Leu Thr Pro Glu Arg His Thr Val His Thr Ile Gln Thr
    2840              2845              2850

Ser Lys Asp Asp Thr Ser Asp Val Pro Lys Gln Ser Val Leu Val
    2855              2860              2865

Ser Lys His His Leu Glu Ala Ala Glu Asp Thr Arg Val Lys Glu
    2870              2875              2880

Pro Leu Ser Ser Ala Lys Ser Asn Tyr Ala Gln Phe Ile Ser Asn
    2885              2890              2895

Thr Ser Ala Ser Asn Ala Asp Lys Met Val Ser Asn Lys Glu Met
    2900              2905              2910

Pro Lys Glu Pro Glu Asp Thr Tyr Ala Lys Gly Glu Asp Phe Thr
    2915              2920              2925

Val Thr Ser Lys Pro Ala Gly Leu Ser Glu Asp Gln Lys Thr Ala
    2930              2935              2940

Phe Ser Ile Ile Ser Glu Gly Cys Glu Ile Leu Asn Ile His Ala
    2945              2950              2955

Pro Ala Phe Ile Ser Ser Ile Asp Gln Glu Glu Ser Glu Gln Met
    2960              2965              2970

Gln Asp Lys Leu Glu Tyr Leu Glu Glu Lys Ala Ser Phe Lys Thr
    2975              2980              2985

Ile Pro Leu Pro Asp Asp Ser Glu Thr Val Ala Cys His Lys Thr
    2990              2995              3000

Leu Lys Ser Arg Leu Glu Asp Glu Lys Val Thr Pro Leu Lys Glu
    3005              3010              3015

Asn Lys Gln Lys Glu Thr His Lys Thr Lys Glu Glu Ile Ser Thr
    3020              3025              3030

Asp Ser Glu Thr Asp Leu Ser Phe Ile Gln Pro Thr Ile Pro Ser
    3035              3040              3045

Glu Glu Asp Tyr Phe Glu Lys Tyr Thr Leu Ile Asp Tyr Asn Ile
    3050              3055              3060

Ser Pro Asp Pro Glu Lys Gln Lys Ala Pro Gln Lys Leu Asn Val
    3065              3070              3075

Glu Glu Lys Leu Ser Lys Glu Val Thr Glu Glu Thr Ile Ser Phe
    3080              3085              3090

Pro Val Ser Ser Val Glu Ser Ala Leu Glu His Glu Tyr Asp Leu
    3095              3100              3105

Val Lys Leu Asp Glu Ser Phe Tyr Gly Pro Glu Lys Gly His Asn
    3110              3115              3120

Ile Leu Ser His Pro Glu Thr Gln Ser Gln Asn Ser Ala Asp Arg
    3125              3130              3135

Asn Val Ser Lys Asp Thr Lys Arg Asp Val Asp Ser Lys Ser Pro
    3140              3145              3150

Gly Met Pro Leu Phe Glu Ala Glu Glu Gly Val Leu Ser Arg Thr
    3155              3160              3165

Gln Ile Phe Pro Thr Thr Ile Lys Val Ile Asp Pro Glu Phe Leu

```
              3170              3175              3180
Glu Glu Pro Pro Ala Leu Ala Phe Leu Tyr Lys Asp Leu Tyr Glu
    3185              3190              3195
Glu Ala Val Gly Glu Lys Lys Lys Glu Glu Thr Ala Ser Glu
    3200              3205              3210
Gly Asp Ser Val Asn Ser Glu Ala Ser Phe Pro Ser Arg Asn Ser
    3215              3220              3225
Asp Thr Asp Asp Gly Thr Gly Ile Tyr Phe Glu Lys Tyr Ile Leu
    3230              3235              3240
Lys Asp Asp Ile Leu His Asp Thr Ser Leu Thr Gln Lys Asp Gln
    3245              3250              3255
Gly Gln Gly Leu Glu Glu Lys Arg Val Gly Lys Asp Asp Ser Tyr
    3260              3265              3270
Gln Pro Ile Ala Ala Glu Gly Glu Ile Trp Gly Lys Phe Gly Thr
    3275              3280              3285
Ile Cys Arg Glu Lys Ser Leu Glu Glu Gln Lys Gly Val Tyr Gly
    3290              3295              3300
Glu Gly Glu Ser Val Asp His Val Glu Thr Val Gly Asn Val Ala
    3305              3310              3315
Met Gln Lys Lys Ala Pro Ile Thr Glu Asp Val Arg Val Ala Thr
    3320              3325              3330
Gln Lys Ile Ser Tyr Ala Val Pro Phe Glu Asp Thr His His Val
    3335              3340              3345
Leu Glu Arg Ala Asp Glu Ala Gly Ser His Gly Asn Glu Val Gly
    3350              3355              3360
Asn Ala Ser Pro Glu Val Asn Leu Asn Val Pro Val Gln Val Ser
    3365              3370              3375
Phe Pro Glu Glu Glu Phe Ala Ser Gly Ala Thr His Val Gln Glu
    3380              3385              3390
Thr Ser Leu Glu Glu Pro Lys Ile Leu Val Pro Pro Glu Pro Ser
    3395              3400              3405
Glu Glu Arg Leu Arg Asn Ser Pro Val Gln Asp Glu Tyr Glu Phe
    3410              3415              3420
Thr Glu Ser Leu His Asn Glu Val Val Pro Gln Asp Ile Leu Ser
    3425              3430              3435
Glu Glu Leu Ser Ser Glu Ser Thr Pro Glu Asp Val Leu Ser Gln
    3440              3445              3450
Gly Lys Glu Ser Phe Glu His Ile Ser Glu Asn Glu Phe Ala Ser
    3455              3460              3465
Glu Ala Glu Gln Ser Thr Pro Ala Glu Gln Lys Glu Leu Gly Ser
    3470              3475              3480
Glu Arg Lys Glu Glu Asp Gln Leu Ser Ser Glu Val Val Thr Glu
    3485              3490              3495
Lys Ala Gln Lys Glu Leu Lys Ser Gln Ile Asp Thr Tyr Cys
    3500              3505              3510
Tyr Thr Cys Lys Cys Pro Ile Ser Ala Thr Asp Lys Val Phe Gly
    3515              3520              3525
Thr His Lys Asp His Glu Val Ser Thr Leu Asp Thr Ala Ile Ser
    3530              3535              3540
Ala Val Lys Val Gln Leu Ala Glu Phe Leu Glu Asn Leu Gln Glu
    3545              3550              3555
Lys Ser Leu Arg Ile Glu Ala Phe Val Ser Glu Ile Glu Ser Phe
    3560              3565              3570
```

Phe Asn Thr Ile Glu Glu Asn Cys Ser Lys Asn Glu Lys Arg Leu
3575                3580                3585

Glu Glu Gln Asn Glu Glu Met Met Lys Lys Val Leu Ala Gln Tyr
3590                3595                3600

Asp Glu Lys Ala Gln Ser Phe Glu Glu Val Lys Lys Lys Lys Met
3605                3610                3615

Glu Phe Leu His Glu Gln Met Val His Phe Leu Gln Ser Met Asp
3620                3625                3630

Thr Ala Lys Asp Thr Leu Glu Thr Ile Val Arg Glu Ala Glu Glu
3635                3640                3645

Leu Asp Glu Ala Val Phe Leu Thr Ser Phe Glu Glu Ile Asn Glu
3650                3655                3660

Arg Leu Leu Ser Ala Met Glu Ser Thr Ala Ser Leu Glu Lys Met
3665                3670                3675

Pro Ala Ala Phe Ser Leu Phe Glu His Tyr Asp Asp Ser Ser Ala
3680                3685                3690

Arg Ser Asp Gln Met Leu Lys Gln Val Ala Val Pro Gln Pro Pro
3695                3700                3705

Arg Leu Glu Pro Gln Glu Pro Asn Ser Ala Thr Ser Thr Thr Ile
3710                3715                3720

Ala Val Tyr Trp Ser Met Asn Lys Glu Asp Val Ile Asp Ser Phe
3725                3730                3735

Gln Val Tyr Cys Met Glu Glu Pro Gln Asp Asp Gln Glu Val Asn
3740                3745                3750

Glu Leu Val Glu Glu Tyr Arg Leu Thr Val Lys Glu Ser Tyr Cys
3755                3760                3765

Ile Phe Glu Asp Leu Glu Pro Asp Arg Cys Tyr Gln Val Trp Val
3770                3775                3780

Met Ala Val Asn Phe Thr Gly Cys Ser Leu Pro Ser Glu Arg Ala
3785                3790                3795

Ile Phe Arg Thr Ala Pro Ser Thr Pro Val Ile Arg Ala Glu Asp
3800                3805                3810

Cys Thr Val Cys Trp Asn Thr Ala Thr Ile Arg Trp Arg Pro Thr
3815                3820                3825

Thr Pro Glu Ala Thr Glu Thr Tyr Thr Leu Glu Tyr Cys Arg Gln
3830                3835                3840

His Ser Pro Glu Gly Glu Gly Leu Arg Ser Phe Ser Gly Ile Lys
3845                3850                3855

Gly Leu Gln Leu Lys Val Asn Leu Gln Pro Asn Asp Asn Tyr Phe
3860                3865                3870

Phe Tyr Val Arg Ala Ile Asn Ala Phe Gly Thr Ser Glu Gln Ser
3875                3880                3885

Glu Ala Ala Leu Ile Ser Thr Arg Gly Thr Arg Phe Leu Leu Leu
3890                3895                3900

Arg Glu Thr Ala His Pro Ala Leu His Ile Ser Ser Ser Gly Thr
3905                3910                3915

Val Ile Ser Phe Gly Glu Arg Arg Arg Leu Thr Glu Ile Pro Ser
3920                3925                3930

Val Leu Gly Glu Glu Leu Pro Ser Cys Gly Gln His Tyr Trp Glu
3935                3940                3945

Thr Thr Val Thr Asp Cys Pro Ala Tyr Arg Leu Gly Ile Cys Ser
3950                3955                3960

```
Ser  Ser  Ala  Val  Gln  Ala  Gly  Ala  Leu  Gly  Gln  Gly  Glu  Thr  Ser
     3965                3970                3975

Trp  Tyr  Met  His  Cys  Ser  Glu  Pro  Gln  Arg  Tyr  Thr  Phe  Phe  Tyr
     3980                3985                3990

Ser  Gly  Ile  Val  Ser  Asp  Val  His  Val  Thr  Glu  Arg  Pro  Ala  Arg
     3995                4000                4005

Val  Gly  Ile  Leu  Leu  Asp  Tyr  Asn  Asn  Gln  Arg  Leu  Ile  Phe  Ile
     4010                4015                4020

Asn  Ala  Glu  Ser  Glu  Gln  Leu  Leu  Phe  Ile  Ile  Arg  His  Arg  Phe
     4025                4030                4035

Asn  Glu  Gly  Val  His  Pro  Ala  Phe  Ala  Leu  Glu  Lys  Pro  Gly  Lys
     4040                4045                4050

Cys  Thr  Leu  His  Leu  Gly  Ile  Glu  Pro  Pro  Asp  Ser  Val  Arg  His
     4055                4060                4065

Lys

<210> SEQ ID NO 344
<211> LENGTH: 19
<212> TYPE: RNA
<213> ORGANISM: Homo Sapiens

<400> SEQUENCE: 344
gcacaacaau ugcaguuua                                               19

<210> SEQ ID NO 345
<211> LENGTH: 19
<212> TYPE: RNA
<213> ORGANISM: Homo Sapiens

<400> SEQUENCE: 345
ggaaaucaau gaaagguug                                               19

<210> SEQ ID NO 346
<211> LENGTH: 19
<212> TYPE: RNA
<213> ORGANISM: Homo Sapiens

<400> SEQUENCE: 346
ggaaggaguu cuaucacga                                               19

<210> SEQ ID NO 347
<211> LENGTH: 19
<212> TYPE: RNA
<213> ORGANISM: Homo Sapiens

<400> SEQUENCE: 347
gaacuucacu ggauguagc                                               19

<210> SEQ ID NO 348
<211> LENGTH: 539
<212> TYPE: PRT
<213> ORGANISM: Homo Sapiens

<400> SEQUENCE: 348

Met  Ala  Thr  Ser  Ala  Pro  Leu  Arg  Ser  Leu  Glu  Glu  Glu  Val  Thr  Cys
1                   5                   10                  15

Ser  Ile  Cys  Leu  Asp  Tyr  Leu  Arg  Asp  Pro  Val  Thr  Ile  Asp  Cys  Gly
                20                  25                  30

His  Val  Phe  Cys  Arg  Ser  Cys  Thr  Thr  Asp  Val  Arg  Pro  Ile  Ser  Gly
            35                  40                  45
```

```
Ser Arg Pro Val Cys Pro Leu Cys Lys Lys Pro Phe Lys Lys Glu Asn
    50              55              60
Ile Arg Pro Val Trp Gln Leu Ala Ser Leu Val Glu Asn Ile Glu Arg
65              70              75              80
Leu Lys Val Asp Lys Gly Arg Gln Pro Gly Glu Val Thr Arg Glu Gln
                85              90              95
Gln Asp Ala Lys Leu Cys Glu Arg His Arg Glu Lys Leu His Tyr Tyr
            100             105             110
Cys Glu Asp Asp Gly Lys Leu Leu Cys Val Met Cys Arg Glu Ser Arg
        115             120             125
Glu His Arg Pro His Thr Ala Val Leu Met Glu Lys Ala Ala Gln Pro
    130             135             140
His Arg Glu Lys Ile Leu Asn His Leu Ser Thr Leu Arg Arg Asp Arg
145             150             155             160
Asp Lys Ile Gln Gly Phe Gln Ala Lys Gly Glu Ala Asp Ile Leu Ala
                165             170             175
Ala Leu Lys Lys Leu Gln Asp Gln Arg Gln Tyr Ile Val Ala Glu Phe
            180             185             190
Glu Gln Gly His Gln Phe Leu Arg Glu Arg Glu His Leu Leu Glu
        195             200             205
Gln Leu Ala Lys Leu Glu Gln Glu Leu Thr Glu Gly Arg Glu Lys Phe
    210             215             220
Lys Ser Arg Gly Val Gly Glu Leu Ala Arg Leu Ala Leu Val Ile Ser
225             230             235             240
Glu Leu Glu Gly Lys Ala Gln Gln Pro Ala Ala Glu Leu Met Gln Asp
                245             250             255
Thr Arg Asp Phe Leu Asn Arg Tyr Pro Arg Lys Lys Phe Trp Val Gly
            260             265             270
Lys Pro Ile Ala Arg Val Val Lys Lys Thr Gly Glu Phe Ser Asp
    275             280             285
Lys Leu Leu Ser Leu Gln Arg Gly Leu Arg Glu Phe Gln Gly Lys Leu
290             295             300
Leu Arg Asp Leu Glu Tyr Lys Thr Val Ser Val Thr Leu Asp Pro Gln
305             310             315             320
Ser Ala Ser Gly Tyr Leu Gln Leu Ser Glu Asp Trp Lys Cys Val Thr
            325             330             335
Tyr Thr Ser Leu Tyr Lys Ser Ala Tyr Leu His Pro Gln Gln Phe Asp
            340             345             350
Cys Glu Pro Gly Val Leu Gly Ser Lys Gly Phe Thr Trp Gly Lys Val
        355             360             365
Tyr Trp Glu Val Glu Val Glu Arg Glu Gly Trp Ser Glu Asp Glu Glu
    370             375             380
Glu Gly Asp Glu Glu Glu Gly Glu Glu Glu Glu Glu Glu Glu
385             390             395             400
Ala Gly Tyr Gly Asp Gly Tyr Asp Asp Trp Glu Thr Asp Glu Asp
                405             410             415
Glu Ser Leu Gly Asp Glu Glu Glu Glu Glu Glu Glu Glu Glu
            420             425             430
Val Leu Glu Ser Cys Met Val Gly Val Ala Arg Asp Ser Val Lys Arg
            435             440             445
Lys Gly Asp Leu Ser Leu Arg Pro Glu Asp Gly Val Trp Ala Leu Arg
450             455             460
```

-continued

```
Leu Ser Ser Ser Gly Ile Trp Ala Asn Thr Ser Pro Glu Ala Glu Leu
465                 470                 475                 480

Phe Pro Ala Leu Arg Pro Arg Arg Val Gly Ile Ala Leu Asp Tyr Glu
            485                 490                 495

Gly Gly Thr Val Thr Phe Thr Asn Ala Glu Ser Gln Glu Leu Ile Tyr
                500                 505                 510

Thr Phe Thr Ala Thr Phe Thr Arg Arg Leu Val Pro Phe Leu Trp Leu
        515                 520                 525

Lys Trp Pro Gly Thr Arg Leu Leu Leu Arg Pro
    530                 535
```

IRGM AND PRECISION AUTOPHAGY CONTROLS FOR ANTIMICROBIAL AND INFLAMMATORY DISEASE STATES AND METHODS OF DETECTION OF AUTOPHAGY

This application is a United States national phase patent application based upon international patent application no. PCT/US2016/019599 filed Feb. 25, 2016, entitled "IRGM and Precision Autophagy Controls for Antimicrobial and Inflammatory Disease States and Methods of Detection of Autophagy", which claims the benefit of priority of provisional applications U.S. 62/121,232, filed 26 Feb. 2015, entitled "IRGM Controls the Core Autophagy Machinery to Conduct Antimicrobial Defense and Modulate Inflammatory Disease States" and U.S. 62/165,357, filed May 22, 2015, entitled "Methods for Regulating Inflammation By Precision Autophagy", the entire contents of each of these applications is incorporated by reference in its entirety herein.

RELATED APPLICATIONS AND GRANT SUPPORT

This invention was made with government support under grant nos. AI04229 and AI111935, awarded by National Institutes of Health and grant no. ULTR000041, awarded by the National Center for Advancing Translation Sciences. The government has certain rights in the invention.

FIELD OF THE INVENTION

The present invention relates to the discovery that IRGM, encoded by a uniquely human gene which confers risk for inflammatory diseases, affects autoophagy through a hitherto unknown mechanism. The present invention shows that IRGM controls autophagy and that IRGM modulators, in particular, double-stranded RNA, including poly I:C, poly-UG (polyUGUGU) and polyICLC and muramyldipeptide and related analogs of same, including N-acetyl muramyl-L-alanyl-D-isoglutamine (Muramyl dipeptide or MDP) and numerous other compounds as identified herein, which may be used alone, in combination, or in combination with alternative autophagy modulators and/or additional bioactive agents to provide effective therapies for a number of diseases, including cancer, bacterial infections and inflammatory diseases, especially including tuberculosis infections and Crohn's disease, among others.

The present invention is also directed to compositions and methods for treating inflammatory or autophagy-related diseases including diseases which cause excessive inflammation in patients. The approach taken to the treatment of these disease states and conditions which cause excessive inflammation is referred to as precision autophagy. This method utilizes interferon, especially interferon-gamma (IFN-gamma), pegylated interferon (PEG-IFN) and related compounds and/or certain TRIM proteins or variants thereof having at least 90% sequence identity as described herein, in particular, TRIM1 (SEQ ID NO:1), TRIM3 (SEQ ID NO:11), TRIM8 (SEQ ID NO:36), TRIM10 (SEQ ID NO:46), TRIM13 (SEQ ID NO:56), TRIM17 (SEQ ID NO:81), TRIM19 (SEQ ID NO:91), TRIM20 (SEQ ID NO:96), TRIM21 (SEQ ID NO:101), TRIM22 (SEQ ID NO:106), TRIM38 (SEQ ID NO:172), TRIM 41 (SEQ ID NO:187), TRIM43 (SEQ ID NO:197), TRIM44 (SEQ ID NO:202), TRIM45 (SEQ ID NO:207), TRIM46 (SEQ ID NO:212), TRIM54 (SEQ ID NO:247), TRIM55 (SEQ ID NO:252), TRIM56 (SEQ ID NO:257), TRIM58 (SEQ ID NO:262), TRIM59 (SEQ ID NO:267), TRIM60 (SEQ ID NO:272), TRIM65 (SEQ ID NO:297), TRIM66 (SEQ ID NO:302), TRIM75 (SEQ ID NO:338) and mixtures thereof, preferably TRIM 1 (SEQ ID NO:1), TRIM 8 (SEQ ID NO:36), TRIM 20 (SEQ ID NO:96), TRIM 21 (SEQ ID NO:101), TRIM 22 (SEQ ID NO:106), TRIM 56 (SEQ ID NO:257), TRIM 65 (SEQ ID NO:297), and mixtures thereof to treat extreme inflammation associated with disease states that cause excessive inflammation. Methods and pharmaceutical compositions are disclosed herein.

BACKGROUND OF THE INVENTION

Autophagy is a cellular homeostatic mechanism with broad roles in human health and disease (Mizushima et al., 2008). Autophagy is at the intersection of metabolic (Rabinowitz and White, 2010; Settembre and Ballabio, 2014) and antimicrobial processes (Deretic et al., 2013; Ma et al., 2013). Thus, the system responds to a range of inputs such as starvation (Chauhan et al., 2013; Efeyan et al., 2013; Mihaylova and Shaw, 2011), lysosomal disruption (Settembre and Ballabio, 2014), endogenous danger associated molecular patterns and microbial products commonly referred to as pathogen-associated molecular patterns (PAMPS) (Deretic et al., 2013; Ma et al., 2013). Autophagic responses to PAMPS lead to direct antimicrobial action through a process termed xenophagy (Gomes and Dikic, 2014; Levine, 2005) and control of inflammation and other immune processes (Deretic et al., 2013).

Among the better-established links between autophagy and human diseases are the genetic polymorphisms in ATG16L1 and IRGM conferring risk for Crohn's disease (CD), an intestinal inflammatory disorder (Consortium, 2007; Craddock et al., 2010; Murthy et al., 2014). The human population polymorphisms in IRGM have been linked to autophagy (Consortium, 2007; Craddock et al., 2010) and to its effector outputs including antimicrobial defense (Brest et al., 2011; McCarroll et al., 2008). In keeping with its autophagy-mediated antimicrobial role, IRGM is additionally a genetic risk factor for tuberculosis in different human populations (Bahari et al., 2012; Che et al., 2010; Intemann et al., 2009; King et al., 2011; Song et al., 2014) and may afford protection in leprosy (Yang et al., 2014). However, the molecular mechanism of IRGM's function in autophagy has remained a mystery.

IRGM has no homologs among the Atg genes in yeast, which makes it difficult to assign to it an autophagy-specific function; instead, IRGM has been considered to affect autophagy indirectly (Singh et al., 2006). A complicating factor in understanding the exact function of IRGM is that it is distinctly a human gene (Bekpen et al., 2010). Its orthologs are present only in African great apes and *Homo sapiens* but active alleles are absent in ancestral evolutionary lineages leading up to them (Bekpen et al., 2009). The mouse genome encodes a large family of immunity related GTPase (21 IRG genes) compared to a single gene (IRGM) in humans; furthermore, all murine IRGs encode ca. 40-kDa proteins that are much larger then the human IRGM (21 kDa). The prevailing view of the murine IRGs is that they have predominantly non-autophagy functions (Choi et al., 2014; Zhao et al., 2008). Thus the significant information gathered in the murine systems may have limited import on how the human IRGM works.

Given the significance of IRGM in human populations and the notoriously high prevalence of diseases such as CD and tuberculosis, it is surprising that IRGM's mechanism of action in autophagy remains unknown. Here we report that unexpectedly, IRGM physically interacts with key autophagy regulators, ULK1, Beclin 1, ATG14L and ATG16L1. We also show that, remarkably, IRGM links inputs from PAMP sensors by making molecular complexes with NOD2, another genetic risk factor in CD (Eckmann and Karin, 2005; Hugot et al., 2001; Ogura et al., 2001). The formation of NOD2-IRGM complex is stimulated in response to PAMPs, whereas increased association of NOD2 with IRGM promotes IRGMdirected assembly of autophagy regulators. IRGM undergoes post-translational modifications that stabilize components of the core autophagic machinery, and mutant IRGM protein that cannot direct these modifications is disabled for its role in autophagic defense against invasive bacteria.

Therapies to modulate autophagy are entering clinical trials but methods of monitoring whether drugs modulate autophagy in patients during such treatment are currently unavailable, but badly needed. In one aspect, the present invention addresses that need.

BRIEF DESCRIPTION OF THE INVENTION

IRGM, encoded by a uniquely human gene conferring risk for inflammatory diseases, affects autophagy through a hitherto unknown mechanism. The present invention is directed to showing that IRGM controls autophagy. IRGM interacts with ULK1 and Beclin 1 and promotes their coassembly into molecular complexes. IRGM stabilizes ULK1 and affects the stability of Beclin 1-interactors thus governing the composition of autophagy initiation complexes. We further show that IRGM interacts with pattern recognition receptors including NOD2. IRGM, NOD2 and ATG16L1, all of which are Crohn's disease risk factors and form a molecular complex to modulate autophagic responses to microbial products. NOD2 enhances K63-linked polyubiquitination of IRGM, which is required for interactions of IRGM with the core autophagy factors and for bacterial clearance. Thus, IRGM plays a direct role in organizing the core autophagy machinery to endow it with antimicrobial functions.

In one embodiment, the present invention relates to the use of IRGM modulators for the treatment of disease, in particular, bacterial infections and inflammatory diseases, most notably tuberculosis and Crohn's disease amongst a number of others. The compounds which are useful as modulators of IRGM include the double stranded RNA compounds, including poly I:C, poly-UG (poly UGUGU) and poly ICLC, among others, and muramyl dipeptide and its analogs and derivates as otherwise disclosed herein.

In one embodiment, the present invention provides a method of modulating autophagy in a biological system, in particular a patient or subject. In this aspect of the invention, a compound identified herein as an IRGM modulator (which can be an inhibitor or agonist of IRGM and/or its pathway (s), is presented to the biological system, including administration to a patient or subject in need, in order to modulate autophagy and effect a favorable result in the biological system, often a patient or subject. The resulting modulation may be monitored or applied in the biological system to effect a favorable result, including the inhibition, treatment and/or prevention of cancer, including metastasis of cancer, or the inhibition, treatment (including the amerlioration of symptoms) and/or prevention of one or more disease states or conditions in which the modulation, especially including upregulation or inhibition of autophagy provides a favorable result in numerous disease states and/or conditions including neurodegeneration (including, for example, Alzheimer's disease, Parkinson's disease; other ataxias), chronic inflammatory diseases (including, for example, inflammatory bowel disease, including Crohn's disease, rheumatoid arthritis, lupus, multiple sclerosis, chronic obstructive pulmony disease/COPD, pulmonary fibrosis, cystic fibrosis, Sjogren's disease), diabetes and metabolic syndrome, muscle degeneration and atrophy, frailty in aging, stroke and spinal cord injury, arteriosclerosis, infectious diseases, especially bacterial infections such as tuberculosis, viral infections (HIV I and II, HBV, HCV, including secondary disease states or conditions associated with infectious diseases, including AIDS) and tuberculosis, among others. The common principle of this embodiment of the invention is that compounds which modulate IRGM, are outstanding autophagy modulators (i.e., inhibitors or activators of autophagy), depending upon the disease state, condition or symptom to be treated, may cure, prevent (including reducing the likelihood of), improve prognosis, ameliorate symptoms and/or improve the quality of the patient's or subject's life. In addition, in the therapeutic aspects of the invention, the administration of an autophagy modulator (i.e., one or more IRGM modulators alone or in combination with an additional autophagy modulator and/or an additional bioactive agent) may prolong the life of the patient, as well as improve the quality of life in the aging patient or subject.

In one embodiment the method of treating an autophagy-mediated disease state or condition comprising administering at least one dsRNA or a muramyl dipeptide analog or derivative (collective referred to as "IRGM modulators"), optionally in combination with at least one additional autophagy modulator and/or bioactive agent to a patient in need. In this method at least one IRGM modulator as described above, alone or in combination with an additional autophagy modulator, such as an autophagy modulator selected from the group consisting of flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile and phenylmercuric acetate, pharmaceutically acceptable salts thereof and mixtures thereof, alone, optionally in further combination with at least one additional bioactive agent, optionally in combination with a pharmaceutically acceptable carrier, additive or excipient, may be administered to a patient or subject in need to treat an autophagy-mediated disease state and/or condition. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline and their pharmaceutically acceptable salts show activity as agonists or inducers of autophagy in the treatment of an autophagy-mediated disease, tetrachlorisophthalonitrile, phenylmercuric acetate and their pharmaceutically acceptable salts, find use as antagonists or inhibitors of autophagy. All of these compounds will find use as modulators of autophagy in the various autophagy-mediated disease states and conditions described herein, with the agonists being preferred in most disease states other than cancer and in the case of the treatment of cancer, the inhibitors described above are preferred, alone or in combination with an autophagy agonist as described above and/or an additional anticancer agent as otherwise described herein.

Pharmaceutical compositions according to the present invention comprise an effective amount of at least one IRGM modulator as described herein in combination with an autophagy modulator selected from the group consisting of flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, tetrachlorisophthalonitrile, phenylmercuric acetate and their pharmaceutically acceptable salts, optionally in combination with a pharmaceutically acceptable carrier, additive and/or excipient and further optionally, in combination with at least one additional bioactive agent (e.g., an anticancer agent, antibiotic, anti-tuberculosis agent, antiviral agent such as an anti-HIV agent, anti-HBV agent or anti-HCV agent, etc.), preferably at least one anticancer agent as otherwise disclosed herein or at least one additional autophagy modulator as otherwise described herein. In the present invention, an additional autophagy modulator (autostatin) may be selected from the group consisting of may be combined with an additional autophagy modulator selected from the group consisting of benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, betaescin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene and mixtures thereof.

In still another embodiment, the invention provides a method of treating a subject who has been infected with tuberculosis (e.g. *M. tuberculosis*) or who is at risk of such infection, the method comprising administering to the subject a pharmaceutically effective amount of a IRGM modulator as described hereinafter. In another embodiment, the invention provides a method of treating Crohn's disease comprising administering to a patient in need a pharmaceutically effective amount of a IRGM modulator as described hereinafter.

The present invention provides methods of treating inflammatory or autophagy-related diseases. Autophagy is a eukaryotic intracellular pathway that carries out key aspects of cytoplasmic homeostasis. Autophagy has many biological effects that include immunological processes and inflammation, and one aspect is regulation of activation inflammasome activity. We disclose the methods to regulate disease-causing excessive inflammation by one form of selective autophagy named precision autophagy. This method provide therapeutic options for inflammatory or autophagy-related diseases by modulating precision autophagy. Several forms of precision autophagy could be induced by compounds, such as IFN-gamma, or related compounds. The present invention could be used to upregulate autophagy, for example in the case of disease states such as tuberculosis and other disease states where an upregulation of autophagy would be beneficial for disease treatment. This therapy could be effected by administering an effective amount of one or more TRIM proteins as otherwise described herein to a patient in need, the result being the upregulation of autophagy and the treatment of a disease state and/or condition which is mediated through authophagy (an autophagy-mediated disease). In other instances, the present invention could be used to regulate (i.e. down-regulate) some forms of precision autophagy, and precision autophagy in turn modulate several forms of inflammation, such as inflammasome or type I interferon response in order to bring the autophagy response back in to balance. The targeting disorders for precision autophagy down-regulation include autophagy-related diseases or inflammatory diseases, including autoimmune diseases, infectious diseases, cardiovascular diseases, and metabolic diseases including diabetes mellitus. For example, the inflammatory response is essential to human beings, however, excessive inflammatory response is a lethal condition seen in several diseases in different stages, including autoimmune diseases and acute viral/bacterial infection. The inventors have found that the excessive inflammation associated with these disease states and/or conditions could be regulated by precision autophagy, including the administration of siRNAs as described herein which specifically inhibit one or more TRIM proteins as otherwise described herein. In addition, the inventors find that certain disease states could benefit from an initial upregulation of autophagy which could benefit the disease treatment, followed by down-regulation of autophagy during the course of therapy for the disease state and/or condition in order to reduce an excessive autophagy response.

Thus, the present invention utilizes certain preferred precision autophagy modulators to treat disease states and conditions which cause excessive inflammation and particularly seen in a number of disease states, especially including inflammatory diseases as otherwise described herein, autoimmune diseases, infectious diseases (generally, after an initial period of beneficial upregulation of autophagy), cardiovascular diseases and metabolic diseases, including diabetes mellitus. These precision autophagy modulators may include interferons such as interferon gamma (IFN-gamma) and pegylated interferon (PEG-IFN), as well as the preferred TRIM (tripartite motif containing) proteins or variants exhibiting 90% sequence identity to the TRIM proteins, preferably TRIM proteins selected from at least one TRIM protein selected from the group consisting of TRIM1, TRIM3, TRIM8, TRIM10, TRIM13, TRIM17, TRIM19, TRIM20, TRIM21, TRIM22, TRIM38, TRIM 41, TRIM43, TRIM44, TRIM45, TRIM46, TRIM54, TRIM55, TRIM56, TRIM58, TRIM59, TRIM60, TRIM65, TRIM66 and TRIM75 with TRIM 1, TRIM 8, TRIM 20, TRIM 21, TRIM 22, TRIM 56 and TRIM 65 and mixtures thereof being preferred as autophagy upregulators.

The present invention relates to a method of treating excessive inflammation in inflammatory diseases, autoimmune diseases, infectious diseases, cardiovascular diseases and metabolic diseases in a patient in need thereof comprising administering to said patient an effective amount of a precision autophagy modulator selected from the group consisting of an interferon, including interferon gamma (IFN-gamma) and pegylated interferon (PEG-IFN) and at least one TRIM protein (including a TRIM protein variant), preferably a TRIM protein selected from the group consisting of TRIM1 (SEQ ID NO:1), TRIM3 (SEQ ID NO:11), TRIM8 (SEQ ID NO:36), TRIM10 (SEQ ID NO:46), TRIM13 (SEQ ID NO:56), TRIM17 (SEQ ID NO:81), TRIM19 (SEQ ID NO:91), TRIM20 (SEQ ID NO:96), TRIM21 (SEQ ID NO:101), TRIM22 (SEQ ID NO:106), TRIM38 (SEQ ID NO:172), TRIM 41 (SEQ ID NO:187), TRIM43 (SEQ ID NO:197), TRIM44 (SEQ ID NO:202), TRIM45 (SEQ ID NO:207), TRIM46 (SEQ ID NO:212), TRIM54 (SEQ ID NO:247), TRIM55 (SEQ ID NO:252), TRIM56 (SEQ ID NO:257), TRIM58 (SEQ ID NO:262), TRIM59 (SEQ ID NO:267), TRIM60 (SEQ ID NO:272), TRIM65 (SEQ ID NO:297), TRIM66 (SEQ ID NO:302), TRIM75 (SEQ ID NO:338) and mixtures thereof, preferably TRIM 1 (SEQ ID NO:1), TRIM 8 (SEQ ID NO:36), TRIM 20 (SEQ ID NO:96), TRIM 21 (SEQ ID NO:101), TRIM 22 (SEQ ID NO:106), TRIM 56 (SEQ ID NO:257), TRIM 65 (SEQ ID NO:297), and mixtures thereof, optionally in combination with an additional autophagy modulator (including an alternative TRIM protein) and/or an additional bioactive agent. In certain instances, it may be beneficial to down-regulate autophagy and inhibit TRIM protein response in order to reduce an excessive autophagy response through the use of one or more siRNA as described herein which specifically inhibits one or more TRIM protein. Additional autophagy modulators for use in the present invention include, for example, flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, tetrachlorisophthalonitrile and phenylmercuric acetate, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof, alternative TRIM proteins or variants exhibiting 90% sequence identity to the TRIM proteins, including, but are not limited to, TRIM2 (SEQ ID NO:6), TRIM 4 (SEQ ID NO:16), TRIM5 (TRIM5α) (SEQ ID NO:21), TRIM6 (SEQ ID NO:26), TRIM7 (SEQ ID NO:31), TRIM9 (SEQ ID NO:41), TRIM11 (SEQ ID NO:51), TRIM14 (SEQ ID NO:61), TRIM15 (SEQ ID NO:66), TRIM16 (SEQ ID NO:71), TRIM18 (SEQ ID NO:86), TRIM23 (SEQ ID NO:111), TRIM24 (SEQ ID NO:116), TRIM25 (SEQ ID NO:121), TRIM27 (SEQ ID NO:126), TRIM28 (SEQ ID NO:131), TRIM29 (SEQ ID NO:136), TRIM30, TRIM 31 (SEQ ID NO:141), TRIM32 (SEQ ID NO:146), TRIM33 (SEQ ID NO:151), TRIM34 (SEQ ID NO:156), TRIM35 (SEQ ID NO:161), TRIM36 (SEQ ID NO:166), TRIM37 (SEQ ID NO:167), TRIM39 (SEQ ID NO:177), TRIM40 (SEQ ID NO:182), TRIM42 (SEQ ID NO:192), TRIM47 (SEQ ID NO:217), TRIM48 (SEQ ID NO:222), TRIM49 (SEQ ID NO:227), TRIM50 (SEQ ID NO:232), TRIM51 (SEQ ID NO:237), TRIM55 (SEQ ID NO:252), TRIM68 (SEQ ID NO:312), TRIM72 (SEQ ID NO:323), TRIM73 (SEQ ID NO:328), TRIM74 (SEQ ID NO:333), TRIM76 (SEQ ID NO:343), and mixtures thereof, with TRIM2 (SEQ ID NO:6), TRIM5 (SEQ ID NO:21), TRIM6 (SEQ ID NO:26), TRIM11 (SEQ ID NO:51), TRIM23 (SEQ ID NO: 111), TRIM27 (SEQ ID NO:126), TRIM28 (SEQ ID NO:131), TRIM31 (SEQ ID NO:141), TRIM 32 (SEQ ID NO:146), TRIM33 (SEQ ID NO:151), TRIM42 (SEQ ID NO:192), TRIM49 (SEQ ID NO:227), TRIM50 (SEQ ID NO:232), TRIM51 (SEQ ID NO:237), TRIM68 (SEQ ID NO:312), TRIM72 (SEQ ID NO:323), TRIM73 (SEQ ID NO:328), TRIM74 (SEQ ID NO:333) and TRIM (SEQ ID NO:343) being preferred. Neutral lipids such as lipids selected from the group consisting of triglycerides, diglycerides, monoglycerides, glycolated mono- or diacylglycerdies, dolichol, polyprenol, polyprenal or very long chain fatty acids may also be administered in combination with the precision autophagy modulators according to the present invention to increase lipid storage and enhance the therapeutic effect of autophagy modulators used to treat excessive inflammation as otherwise disclosed herein. Additional bioactive agents as otherwise described herein may be administered in combination with the one or more of the above precision autophagy modulators and optionally, additional modulators and bioactive agents as otherwise described herein.

Pharmaceutical compositions according to the present invention comprise an effective amount of interferon, including interferon gamma (IFN-gamma) and pegylated interferon (PEG-IFN) in combination with at least one TRIM protein or a variant thereof, preferably a TRIM protein selected from the group consisting of TRIM1 (SEQ ID NO:1), TRIM3 (SEQ ID NO:11), TRIM8 (SEQ ID NO:36), TRIM10 (SEQ ID NO:46), TRIM13 (SEQ ID NO:56), TRIM17 (SEQ ID NO:81), TRIM19 (SEQ ID NO:91), TRIM20 (SEQ ID NO:96), TRIM21 (SEQ ID NO:101), TRIM22 (SEQ ID NO:106), TRIM38 (SEQ ID NO:172), TRIM 41 (SEQ ID NO:187), TRIM43 (SEQ ID NO:197), TRIM44 (SEQ ID NO:202), TRIM45 (SEQ ID NO:207), TRIM46 (SEQ ID NO:212), TRIM54 (SEQ ID NO:247), TRIM55 (SEQ ID NO:252), TRIM56 (SEQ ID NO:257), TRIM58 (SEQ ID NO:262), TRIM59 (SEQ ID NO:267), TRIM60 (SEQ ID NO:272), TRIM65 (SEQ ID NO:297), TRIM66 (SEQ ID NO:302), TRIM75 (SEQ ID NO:338) and mixtures thereof, preferably TRIM 1 (SEQ ID NO:1), TRIM 8 (SEQ ID NO:36), TRIM 20 (SEQ ID NO:96), TRIM 21 (SEQ ID NO:101), TRIM 22 (SEQ ID NO:106), TRIM 56 (SEQ ID NO:257), TRIM 65 (SEQ ID NO:297) and mixtures thereof, optionally in combination with an additional autophagy modulator (including an alternative TRIM protein as otherwise described herein) and/or an additional bioactive agent as otherwise described herein in combination with a pharmaceutically acceptable carrier, additive or excipient. Compositions comprising an effective amount of at least one TRIM protein or a variant thereof, preferably a TRIM protein selected from the group consisting of TRIM1 (SEQ ID NO: 1), TRIM3 (SEQ ID NO:11), TRIM8 (SEQ ID NO:36), TRIM10 (SEQ ID NO:46), TRIM13 (SEQ ID NO:56), TRIM17 (SEQ ID NO:81), TRIM19 (SEQ ID NO:91), TRIM20 (SEQ ID NO:96), TRIM21 (SEQ ID NO:101), TRIM22 (SEQ ID NO:106), TRIM38 (SEQ ID NO:172), TRIM 41 (SEQ ID NO:187), TRIM43 (SEQ ID NO:197), TRIM44 (SEQ ID NO:202), TRIM45 (SEQ ID NO:207), TRIM46 (SEQ ID NO:212), TRIM54 (SEQ ID NO:247), TRIM55 (SEQ ID NO:252), TRIM56 (SEQ ID NO:257), TRIM58 (SEQ ID NO:262), TRIM59 (SEQ ID NO:267), TRIM60 (SEQ ID NO:272), TRIM65 (SEQ ID NO:297), TRIM66 (SEQ ID NO:302), TRIM75 (SEQ ID NO:338) and mixtures thereof, with TRIM 1 (SEQ ID NO:1), TRIM 8 (SEQ ID NO:36), TRIM 20 (SEQ ID NO:96), TRIM 21 (SEQ ID NO:101), TRIM 22 (SEQ ID NO:106), TRIM 56 (SEQ ID NO:257), TRIM 65 (SEQ ID NO:297), and mixtures thereof being preferred in combination with at least one additional bioactive agent, including an autophagy modulator as otherwise described herein including an alternative TRIM protein. In addition, neutral lipids such as lipids selected from the group consisting of triglycerides, diglycerides, monoglycerides, glycolated mono- or diacylglycerdies, dolichol, polyprenol, polyprenal or very long chain fatty acids may also be included in the pharmaceutical compositions according to the present invention in combination with the precision autophagy modulators according to the present invention to increase lipid storage and enhance the therapeutic effect of autophagy modulators used to treat excessive inflammation as otherwise disclosed herein Methods of treating a disease state and/or condition with precision autophagy in a patient or subject in need (where upregulation of autophagy is desirable) comprise administering to said patient an effective amount of at least one compound selected from the group consisting of interferon gamma (IFN-gamma), pegylated interferon (PEG-IFN) and at least one TRIM protein or a variant thereof, preferably a TRIM protein selected from the group consisting of TRIM1 (SEQ ID NO:1), TRIM3 (SEQ ID NO: 11), TRIM8 (SEQ ID NO:36), TRIM10 (SEQ ID NO:46), TRIM13 (SEQ ID NO:56), TRIM17 (SEQ ID NO:81), TRIM19 (SEQ ID NO:91), TRIM20 (SEQ ID NO:96), TRIM21 (SEQ ID NO:101), TRIM22 (SEQ ID NO:106), TRIM38 (SEQ ID NO:172), TRIM 41 (SEQ ID NO:187), TRIM43 (SEQ ID NO:197), TRIM44 (SEQ ID NO:202), TRIM45 (SEQ ID NO:207), TRIM46 (SEQ ID NO:212), TRIM54 (SEQ ID NO:247), TRIM55 (SEQ ID NO:252), TRIM56 (SEQ ID NO:257), TRIM58 (SEQ ID NO:262), TRIM59 (SEQ ID NO:267), TRIM60 (SEQ ID NO:272), TRIM65 (SEQ ID NO:297), TRIM66 (SEQ ID NO:302), TRIM75 (SEQ ID NO:338) and mixtures thereof, preferably TRIM 1 (SEQ ID NO:1), TRIM 8 (SEQ ID NO:36), TRIM 20 (SEQ ID NO:96), TRIM 21 (SEQ ID NO:101), TRIM 22 (SEQ ID NO:106), TRIM 56 (SEQ ID NO:257), TRIM 65 (SEQ ID NO:297) and mixtures thereof, optionally in combination with an additional autophagy modulator (including an alternative TRIM protein) and/or an additional bioactive agent. In these methods, neutral lipids such as lipids selected from the group consisting of triglycerides, diglycerides, monoglycerides, glycolated mono- or diacylglycerdies, dolichol, polyprenol, polyprenal or very long chain fatty acids may also be administered in combination with the precision autophagy modulators according to the present invention to increase lipid storage and enhance the therapeutic effect of autophagy modulators used to treat excessive inflammation as otherwise disclosed herein. The present methods apply to a number of disease states and/or conditions which are mediated through autophagy and which often can result in an excessive autophagy response. In certain preferred aspects, the administration of TRIM20, alone or in combination with an additional autophagy modulator and/or bioactive agent as otherwise described herein is useful for upregulating autophagy and treating disease through modulation (up-regulation) of autophagy. This approach is especially useful in the case of certain disease states and/or conditions, especially microbial infections such as bacterial and viral infections where upregulation of TRIM proteins, especially TRIM20 is useful in inhibiting early stages of disease, especially viral and bacterial infections, including early stage tuberculosis (note that in later stage tuberculosis it may be preferable to down-regulate the autophagy response and inhibit the TRIM proteins by administering a TRIM protein inhibitor, especially including a siRNA). In this embodiment, a TRIM protein, especially including TRIM20 may be administered alone or in combination with interferon-gamma (IFN-gamma), pegylated interferon (PEG-IFN) and/or an additional autophagy modulator and/or an additional bioactive agent in order to treat a disease state and/or condition which is mediated through autophagy (an autophagy-mediated disease state and/or condition).

Methods according to the present invention also include down-regulating autophagy where an inflammatory response is elevated (in autoimmune disease, inflammatory diseases and in later stage disease states such as viral and/or bacterial infections, especially including tuberculosis, among others, the method comprising administering an inhibitor of a TRIM protein (including TRIM21) as otherwise set forth herein, especially siRNA which is an inhibitor of a TRIM protein. In preferred aspects, a siRNA inhibitor of TRIM21 is particularly useful in treating these disease states, especially including tuberculosis at any time during a tuberculosis infection. In other embodiments, a siRNA inhibitor of TRIM20 is administered at a later stage of tuberculosis in order to enhance the therapy of the disease state by reducing and/or the impact of autophagy.

BRIEF DESCRIPTION OF THE FIGURES

FIG. 12, related to FIG. 5 shows that NOD2 enhances ubiquitination of IRGM. (A) HEK293T cell lysates expressing the indicated set of proteins were subjected to immunoprecipitation with Flag antibody and Western blotted with antibodies as indicated. (B) HEK293T cell lysates co-expressing GFP-IRGM alone or along with NOD2 were subjected to immunoprecipitation with GFP antibody and Western blotted with antibody to GFP. (C) HEK293T cell lysates co-expressing IRGM-V5 and HA-K63 were subjected to immunoprecipitation with V5 antibody and Western blotted with antibody to HA. (D) Analysis of effect of NOD2 on IRGM/IRGMkmut-Beclin 1 interaction by Co-IP experiment.

DETAILED DESCRIPTION OF THE INVENTION

Figure 1:
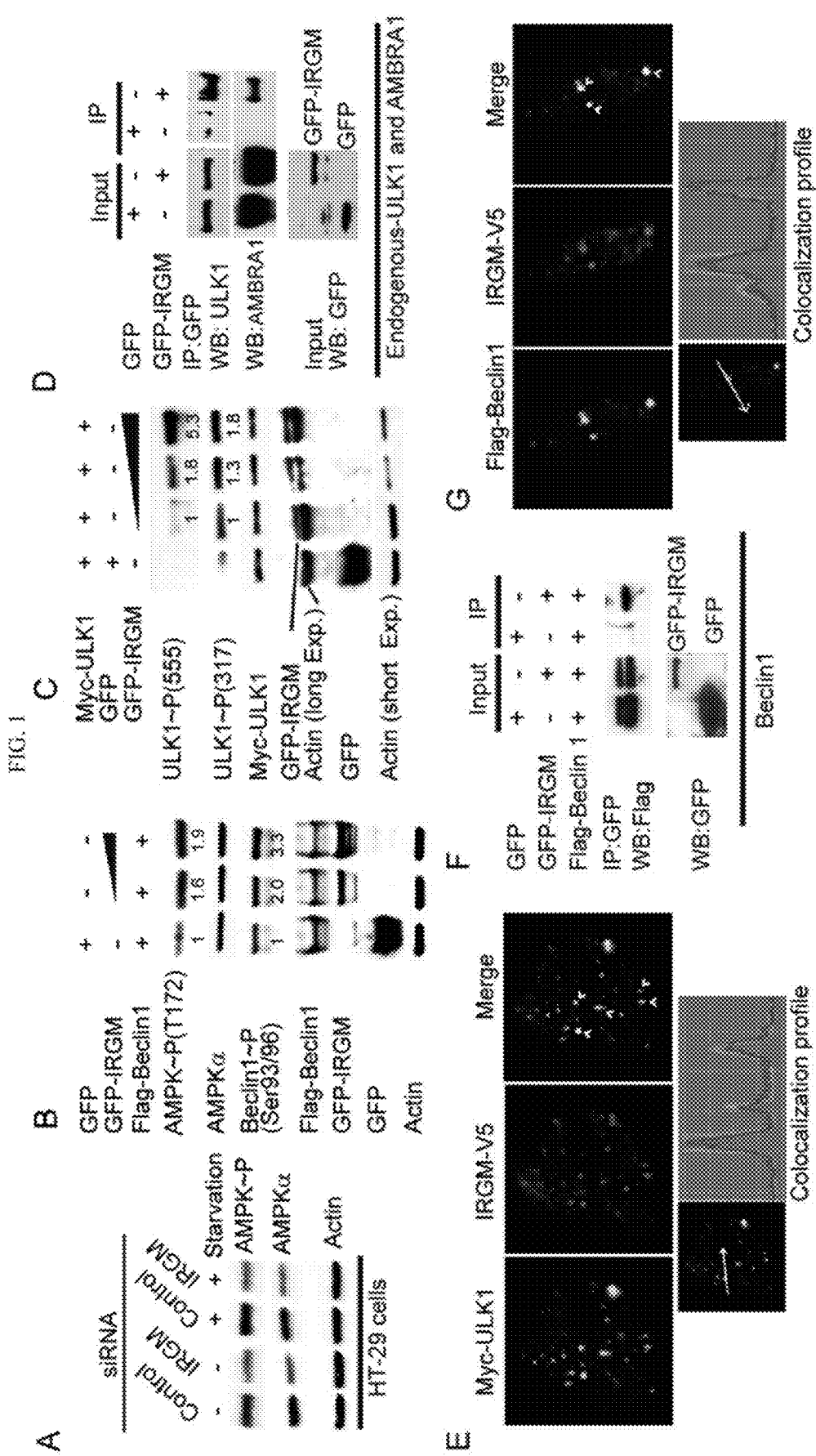
FIG. 1 shows that IRGM activates AMPK signaling and interacts with core autophagy machinery. (A) Lysates from HT-29 colon epithelial cells transfected with control and IRGM siRNA were subjected to Western blotting with antibodies to phospho-AMPK (Thr-172), AMPK, IRGM and actin. (B) Levels of phospho-AMPK (Thr-172) and phospho-Beclin 1 (Ser-93/96) in lysates from HEK293T cells co-expressing Flag-Beclin 1 and GFP or GFP-IRGM. (C) Levels of active phospho-ULK1 (Ser-555 and Ser-317) in lysates of HEK293T cells co-expressing Myc-ULK1 and either GFP or GFP-IRGM. Numbers beneath bands in B, C, quantification of phosphorylated proteins relative to the total abundance of the same protein. (D) Co-immunoprecipitation (Co-IP) analysis of interaction between IRGM and endogenous ULK1 and AMBRA1 in HEK293T lysates of cells expressing GFP or GFP-IRGM. (E) Top, confocal microscopy images of HEK293T cells expressing IRGM-V5 and Myc-ULK1 subjected to starvation for 2 h. Arrowheads, co-localization. Bottom, fluorescence intensity line tracing. (F) Co-IP analysis in lysates of HEK293T cells expressing indicated proteins. (G) Confocal microscopy images of HEK293T cells transiently expressing V5-IRGM and Flag-Beclin1 subjected to starvation for 2 h. Details as for panel E. (H) Lysates of HEK293T cells expressing GFP or GFP-IRGM with Myc-ULK1 subjected to immunoprecipitation with anti-GFP and blots probed with phospho-ULK1 Ser-317 or Ser-757 antibodies. (I) Lysates of cells expressing Myc-ULK1, Flag-Beclin-1 and increasing concentrations of GFP-IRGM subjected to immunoprecipitation with anti-Flag; blots probed as indicated. (J) HEK293T cell lysates co-expressing GFP-IRGM and Flag-Beclin 1 subjected to Western blotting with antibody to phospho-Beclin 1 (Ser-15) and antibodies as indicated. (K) Co-IP analysis of Flag-IRGM and endogenous ATG14. (L, M) Mapping of Beclin 1 regions interacting with IRGM. (L) Lysates of HEK293T cells co-expressing GFP-IRGM and Flag-Beclin 1 variants in panel M were subjected to immunoprecipitation with anti-Flag and blots probed as indicated. (M) Beclin 1 domain organization indicating its interacting proteins along with deletion constructs used in Co-IP analysis in panel L. (N) Co-IP analysis of the effects of IRGM overexpression on the interaction of Beclin 1 with its regulatory proteins. Lysates of HEK293T cells co-expressing GFP-IRGM and Flag- Beclin 1 were subjected to immunoprecipitation with anti-Flag and blots probed as indicated. (O) Model of IRGM-dependent autophagy induction based on the results obtained in FIG. 1 and FIG. 8 See also FIG. 8.
Figure 1:
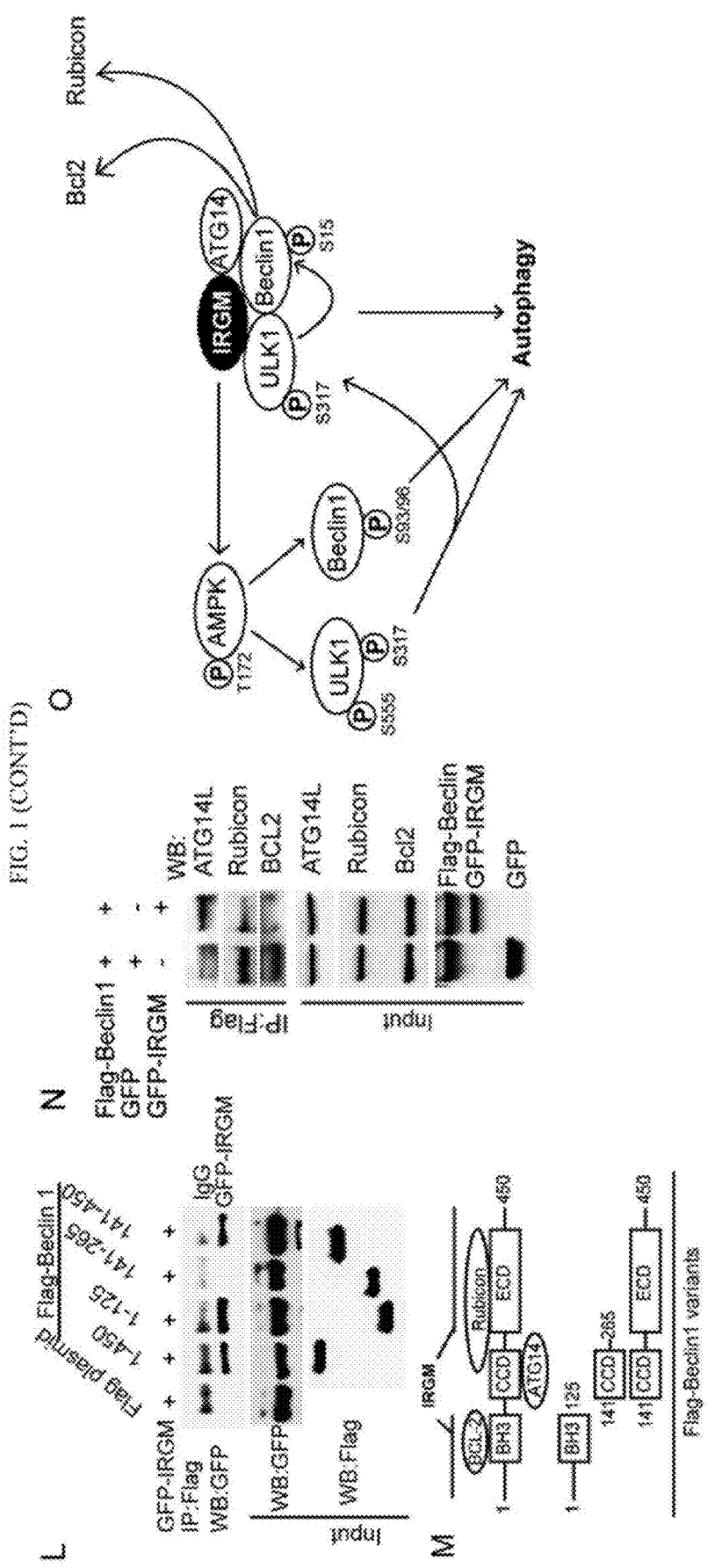

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, for example the modulation of autophagy within the context of a particular treatment or alternatively, the effect of a bioactive agent which is coadministered with the autophagy modulator (autotoxin) in the treatment of disease.

The terms "treat", "treating", and "treatment", etc., as used herein, refer to any action providing a benefit to a patient at risk for or afflicted by an autophagy mediated disease state or condition as otherwise described herein. The benefit may be in curing the disease state or condition, inhibition its progression, or ameliorating, lessening or suppressing one or more symptom of an autophagy mediated disease state or condition, as well as inhibiting or reducing excessive autophagy. Treatment, as used herein, encompasses both prophylactic and therapeutic treatment.

As used herein, the term "autophagy mediated disease state or condition" (which term may include the term "IRGM modulated disease" as a subset) refers to a disease state or condition that results from disruption in autophagy or cellular self-digestion and wherein IRGM or its pathway and/or the TRIM proteins and their pathways are involved in the disease state or condition. Autophagy is a cellular pathway involved in protein and organelle degradation, and has a large number of connections to human disease. Autophagic dysfunction is associated with cancer, neurodegeneration, microbial infection and ageing, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, cancer, including metastasis of cancer, lysosomal storage diseases (discussed hereinbelow), neurodegeneration (including, for example, Alzheimer's disease, Parkinson's disease, Huntington's disease; other ataxias), immune response (T cell maturation, B cell and T cell homeostasis, counters damaging inflammation) and chronic inflammatory diseases (may promote excessive cytokines when autophagy is defective), including, for example, inflammatory bowel disease, including Crohn's disease, rheumatoid arthritis, lupus, multiple sclerosis, chronic obstructive pulmony disease/COPD, pulmonary fibrosis, cystic fibrosis, Sjogren's disease; hyperglycemic disorders, diabetes (I and II), affecting lipid metabolism islet function and/or structure, excessive autophagy may lead to pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides) and metabolic syndrome, liver disease (excessive autophagic removal of cellular entities-endoplasmic reticulum), renal disease (apoptosis in plaques, glomerular disease), cardiovascular disease (especially including ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, atherosclerosis and associated conditions such as cardiac and neurological both central and peripheral manifestations including stroke, age-associated dementia and sporadic form of Alzheimer's disease, pre-cancerous states, and psychiatric conditions including depression), stroke and spinal cord injury, arteriosclerosis, infectious diseases (microbial infections, removes microbes, provides a protective inflammatory response to microbial products, limits adaptation of authophagy of host by microbe for enhancement of microbial growth, regulation of innate immunity) including bacterial, especially including *M. tuberculosis*, fungal, cellular and viral (including secondary disease states or conditions associated with infectious diseases), including HIV I and II, hepatitis B and C, AIDS and tuberculosis, among others, development (including erythrocyte differentiation), embryogenesis/fertility/infertility (embryo implantation and neonate survival after termination of transplacental supply of nutrients, removal of dead cells during programmed cell death) and ageing (increased autophagy leads to the removal of damaged organelles or aggregated macromolecules to increase health and prolong life, but increased levels of autophagy in children/young adults may lead to muscle and organ wasting resulting in ageing/progeria).

The term "lysosomal storage disorder" refers to a disease state or condition that results from a defect in lysosomomal storage. These disease states or conditions generally occur when the lysosome malfunctions. Lysosomal storage disorders are caused by lysosomal dysfunction usually as a consequence of deficiency of a single enzyme required for the metabolism of lipids, glycoproteins or mucopolysaccharides. The incidence of lysosomal storage disorder (collectively) occurs at an incidence of about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators (autostatins) as described herein. All of these diseases share a common biochemical characteristic, i.e., that all lysosomal disorders originate from an abnormal accumulation of substances inside the lysosome. Lysosomal storage diseases mostly affect children who often die as a consequence at an early stage of life, many within a few months or years of birth. Many other children die of this disease following years of suffering from various symptoms of their particular disorder.

Examples of lysosomal storage diseases include, for example, activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM! Ganliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs and Wolman disease, among others.

The term "modulator of autophagy", "regulator of autophagy" or "autophagy modulator" is used to refer to a compound or composition which modulates IRGM "ARGM modulator") or its pathway or TRIM proteins and their pathways ("precision authophagy modulators" or "TRIM protein modulators") and has an influence on treating diseases which are modulated through those mechanisms. IRGM modulators pursuant to the present invention include double stranded RNA (dsRNA), in particular poly I:C, poly U-G (UGUGU) and modified dsRNA such as poly ICLC (poly I; C modified with lysine and carboxymethyl cellulose) and muramyl peptides or muramyl dipeptides as disclosed herein. TRIM protein modulators include interferon gamma, pegylated interferon or preferably, any one or more of the TRIM proteins otherwise disclosed herein or an inhibitor of a TRIM protein such as a siRNA which specifically inhibits one or more TRIM proteins.

The term "muramyl peptide" or "muramyl dipeptide" include compounds according to the chemical structure:

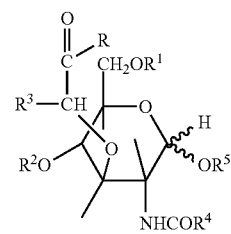

wherein:
$R^1$ represents a hydrogen atom or a $C_1$-$C_{22}$ acyl group;
$R^2$ represents a hydrogen atom or a $C_1$-$C_{22}$ acyl group;
$R^3$ represents a hydrogen atom or a $C_1$-$C_6$ alkyl group;
$R^4$ represents a $C_1$-$C_{21}$ alkyl group or a $C_5$ or $C_{10}$ aryl group;
$R^5$ represents a hydrogen atom; and
R represents the residue of an amino acid or a linear peptide built up of from 2 to 6 amino acid residues, at least one of the residues being optionally substituted with a lipophilic group including muramyl dipeptide and desmethylmuramyl dipeptide.

Preferred acyl groups for $R^1$ and $R^2$ are $C_1$-$C_5$ acyl groups such as acetyl; it will be appreciated that the carbon count in the acyl group does not include the carbonyl moiety. Preferred alkyl groups for $R^3$ are $C_1$-$C_4$ alkyl groups such as methyl and ethyl. Preferred alkyl groups for R4 and C1-C6 alkyl groups, particularly C1-C4 alkyl groups, such as methyl or ethyl; phenyl is a preferred aryl group. R preferably represents a mono-, di- or tri-peptide, more often a dipeptide. The proximal peptide residue (or the only peptide residue, if there is only one) is preferably that of an L-amino acid.

Examples Include:
L-alanyl
L-valyl
L-leucyl
L-isoleucyl
L-a-aminobutyryl
L-seryl
L-threonyl
L-tryptophanyl
L-lysyl
L-ornithyl
L-arginyl
L-histidyl
L-glutamyl
L-glutaminyl
L-methionyl
L-cysteinyl
L-phenylalanyl
L-tyrosyl L-aspartyl
L-asparaginyl
L-prolyl
L-hydroxyprolyl
L-alanyl is preferred, as is L-threonyl.

The next amino acid from the proximal end of the peptide is preferably of the D-configuration. It is preferably acidic and may be D-glutamic or D-aspartic acid or a mono-, di- or mixed $C_1$-$C_{22}$ (preferably $C_1$-$C_5$) alkyl ester, amide or $C_1$-$C_4$ alkyl amide thereof. (The expression "mixed" is illustrated when one carboxyl group is amidated and the other esterified. D-isoglutamine and D-glutamate are preferred. A third amino acid residue from the proximal end of the chain, if there is one, is preferably of the L-configuration, as indicated above in relation to the proximal amino acid residue. L-alanyl and L-lysyl are preferred.

The amino acid residue or linear peptide is optionally substituted with at least one lipophilic group. The lipophilic group may be a $C_{10}$-$C_{22}$ acyl group such as stearoyl or a di-($C_{10}$-$C_{22}$ acyl)-sn-glycero-3'-hydroxyphospheryloxy group wherein for example each of the $C_{10}$-$C_{22}$ acyl groups can be a palmitoyl group. The lipophilic group may alternatively (or in addition, as more than one substitution may be present) be a $C_1$-$C_{10}$ ester group, such as a $C_2$-$C_6$ ester group: an acetyl group or a butyl ester are examples.

Examples of muramyl dipeptides within the scope of general formula I include: muroctasin, otherwise known as MDP-Lys (L18) ($N^2$-(Nacetylmuramyl-L-alanyl-D-isoglutaminyl)-$N^6$-stearoyl-L-lysine); MTP-PE (N-acetyl-muramyl-L-alanyl-D-isoglutaminyl-Lalanyl-2-(1',2'-dipalmitoyl-sn-glycero-3'-hydroxyphosphoryloxy)ethylamide, monosodium); murabutide (N-acetylmuramyl-L-alanyl-D-glutamine-aN-butyl ester); and t-MDP (N-acetylmuramyl-L-threonyl-D-isoglutamine).

The preparation of these and other compounds pursuant to the present invention is disclosed in EPA-15 0021367, USA-4317771, EPA-0025495, Lefrancier, et al, *J. Med. Chem.*, 25 87 (1982), as well as methods generally known in the art. Patent publications which give details of the preparations of muramyl peptide compounds generally include BEA-0834753, BEA-0834754, BEA-0847103, BEA-0849214, DEA-2710455, DEA-2922533, DEA-2747379, DE-A-2912865, FR-A-2355505, FRA-2358159, FRA-2375249, EP-A-0004512, EP-A-0002677, JP-A-54063016, JP-25 A-54073729, JPA-55019236, U.S. Pat. Nos. 4,082, 735 and 4,082,736, among others. The preparation of prototype muramyl dipeptide is disclosed in DE-A-2450355 and USA-4235771.) All the documents referred to in this specification are incorporated herein by reference.

Other useful compounds are disclosed in WO96/01645 (the structures of these compounds may be found in the published PCT application and include the following compounds, among others:
GMDP;
GMDP-LL;
GMDP-Obu;
GMDO-Lys;
GMDB-Lys(St);
GMDBA-Lys(St);
GMDPA(OBzl)$_2$;
MeGMDP;
(GMDP)$_2$;
(GMDPA)$_2$;
(GMDPLys)$_2$;
[GMDP-Lys(St)]$_2$;
GMDP-Ad;
GMDP-tuftsin E;
GMDP-tuftsin A;
GMDP-tuftsin lipophilic;
GMDP-bursin;
GMDP-thymogen I;
GMDP-thymogen II;
GMDP-thymogen III;
Thr-MDP The term "TRIM protein" or "tripartite motif containing protein" is used to describe a TRIM protein or variant thereof as otherwise disclosed herein which is integral to an autophagy response and may be integral as part of an upregulation of autphagy (TRIM20, etc.) or down-regulation of autophagy (TRIM21, etc.). Many TRIM proteins are induced by interferons, which are important components of resistance to pathogens and a number of TRIM proteins are known to be required for the restriction of infection by lentiviruses. In instances where a patient or subject is interferon deficient, the administration of TRIM proteins alone or in combination with interferon gamma and/or pegylated interferon may assist in treating disease, especially infections such as viral infections or bacterial infections, especially *Mycobacterium* infections such as *M. tuberculosis* infections. TRIM proteins are involved in pathogen-recognition and by regulation of transcriptional pathways in host defence. Numerous TRIM proteins may be used in the present invention as otherwise described herein. Sequences of these proteins are included as are the accession numbers for identifying these proteins. TRIM proteins are known in the art. TRIM proteins which are useful and preferred in the present invention include the human full length TRIM proteins (TRIM1-75) as otherwise described herein. The sequences of TRIM proteins 1-75 as shown as well as polypeptide variants which have at least about a 90% sequence identity, and preferably at least about 95% sequence identify (about 96%, about 97%, about 98% and about 99% sequence identify) to the wild type polypeptide sequences of homo sapien TRIM proteins 1-75 are useful in the present invention. These sequences are set forth in the attached table on pages 92-116 just before the presentation of the claims. Note that TRIM proteins or polypeptide variants thereof or a pharmaceutically acceptable salt thereof may be used in the present invention. All 75 TRIM proteins as identified herein may be used in the present invention, although the preferred TRIM proteins have been identified and are more often used to modulate autophagy (either up-regulation or down-regulation) in order to favorably effect an intended outcome. SEQ ID NOs for TRIM proteins 1-75 and siRNA TRIM protein inhibitors are set forth in the table on pages 92-116 of the present application just before the claims.

In addition to TRIM proteins which find use in the present invention (pharmaceutical compositions comprising these proteins may be administered to patients in order to regulate (up- or down-regulate autophagy), inhibitors of these proteins, especially including small inhibitory RNAs or small interfering RNAs (siRNAs) may also be used to impact autophagy and treat disease states and/or conditions which are mediated through autophagy. A number of siRNAs can be used to inhibit any one or more of the TRIM proteins pursuant to the present invention. Exemplary siRNAs are presented herein in the table just before the claims. Thus, siRNAs which can be used in the present invention include the siRNAs according to the specific sequences indicated in the attached table, as well as oligos which are plus/minus up to five nucleotide units upstream or downstream of the identified siRNAs. Additional variants of these variants include those with 90% sequence identity to the siRNAs set forth in the table on pages 92-116 or variants that exhibit polymorphism to the disclosed siRNAs. These siRNAs range in size from about 9-10 nucleotide units up to about 29-30 nucleotide units, with 19-23 nucleotide units being preferred. Preferably, these siRNAs are the specific siRNAs which are disclosed in the table on pages 92-116 hereof or siRNAs which contain up to five nucleotide units more upstream and/or downstream to the disclosed siRNAs.

The term "modulator of autophagy", "regulator of autophagy" or "autostatin" is used to refer to a compound which functions as an agonist (inducer or up-regulator) or antagonist (inhibitor or down-regulator) of autophagy and are unrelated to the IRGM modulators, inteferons, TRIM proteins or TRIM protein inhibitors (e.g. siRNAs as disclosed herein). These modulators may be used in combination with an IRGM modulator and/or a TRIM protein, interferon or siRNA inhibitor in methods and compositions pursuant to the present invention. Depending upon the disease state or condition, autophagy may be upregulated (and require inhibition of autophagy for therapeutic intervention) or down-regulated (and require upregulation of autophagy for therapeutic intervention). In most instances, in the case of cancer treatment with a modulator of autophagy as otherwise described herein, the autophagy modulator is often an antagonist of autophagy. In the case of cancer, the antagonist (inhibitor) of autophagy may be used alone or combined with an agonist of autophagy The following compounds have been identified as autophagy modulators according to the present invention and can be used in combination with an IRGM modulator or Trim protein as disclosed herein in the treatment of an autophagy mediated disease state or condition as otherwise described herein. It is noted that an inhibitor of autophagy is utilized where the disease state or condition is mediated through upregulation or an increase in autophagy which causes the disease state or condition and an agonist of autophagy is utilized where the disease state or condition is mediated through downregulation or a decrease in autophagy. The following compounds have been identified as autophagy modulators (autotaxins) in autophagy assays according to the present invention: flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile, phenylmercuric acetate and pharmaceutically acceptable salts thereof. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline and their pharmaceutically acceptable salts show activity as agonists or inducers of autophagy in the treatment of an autophagy-mediated disease, whereas tetrachlorisophthalonitrile, phenylmercuric acetate and their pharmaceutically acceptable salts, find use as antagonists or inhibitors of autophagy. All of these compounds will find use as modulators of autophagy in the various autophagy-mediated disease states and conditions described herein, with the agonists being preferred in most disease states other than cancer (although inhibitors may also be used alone, or preferably in combination with the agonists) and in the case of the treatment of cancer, the inhibitors described above are preferred, alone or in combination with an autophagy agonist as described above and/or an additional anticancer agent as otherwise described herein.

Other compounds which may be used in combination with the IRGM modulators and/or TRIM proteins and/or siRNAs as otherwise described herein either alone or in combination with the autophagy modulators which are described above, include for example, other "additional autophagy modulators" or "additional autostatins" which are known in the art. These can be combined with one or more of the autophagy modulators which are disclosed above to provide novel pharmaceutical compositions and/or methods of treating autophagy mediated disease states and conditions which are otherwise described herein. These additional autophagy modulators including benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene and mixtures thereof.

The following compounds have been identified as autophagy modulators according to the present invention and can be used in the treatment of an autophagy mediated disease state or condition as otherwise described herein. These include interferon, especially interferon-gamma (IFN-gamma), pegylated interferon (PEG-IFN) and related compounds and certain TRIM proteins and variants thereof, including TRIM1, TRIM3, TRIM8, TRIM10, TRIM13, TRIM17, TRIM19, TRIM20, TRIM21, TRIM22, TRIM38, TRIM 41, TRIM43, TRIM44, TRIM45, TRIM46, TRIM54, TRIM55, TRIM56, TRIM58, TRIM59, TRIM60, TRIM65, TRIM66 and TRIM75 with TRIM 1, TRIM 8, TRIM 20, TRIM 21, TRIM 22, TRIM 56 and TRIM 65 and mixtures thereof and preferably, TRIM 1, TRIM 8, TRIM 20, TRIM 21, TRIM 22, TRIM 56, TRIM 65 and mixtures thereof. The following compounds have been identified as autophagy modulators which may be used in combination with the above-identified autophagy agents. These agents include, for example flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile, phenylmercuric acetate and pharmaceutically acceptable salts thereof. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene, and mixtures thereof. Additional autophagy agents include alternative TRIM proteins or variants thereof, such as, but not limited to, TRIM5α, TRIM6, TRIM10, TRIM17, TRIM41, TRIM55, TRIM72, TRIM76, TRIM2, TRIM23, TRIM26, TRIM28, TRIM31, TRIM 32, TRIM33, TRIM38, TRIM42, TRIM44, TRIM45, TRIM49, TRIM50, TRIM51, TRIM58, TRIM59, TRIM68, TRIM73, TRIM74 and TRIM76 and mixtures thereof. Neutral lipids such as lipids selected from the group consisting of triglycerides, diglycerides, monoglycerides, glycolated mono- or diacylglycerdies, dolichol, polyprenol, polyprenal or very long chain fatty acids and mixtures thereof and their pharmaceutically acceptable salts may also be included for use in the present invention either alone or preferably in combination with one or more TRIM protein. All of these compounds will find use as modulators of autophagy in the various autophagy-mediated disease states and conditions described herein.

The term "co-administration" or "combination therapy" is used to describe a therapy in which at least two active compounds in effective amounts are used to treat an autophagy mediated disease state or condition as otherwise described herein, either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an autophagy modulator) is administered at approximately the same time (contemporaneously), or from about one to several minutes to about 24 hours or more than the other bioactive agent coadministered with the autophagy modulator. The additional bioactive agent may be any bioactive agent, but is generally selected from an additional autophagy mediated compound as described herein, an additional anticancer agent, or another agent, such as a mTOR inhibitor such as pp242, rapamycin, envirolimus, everolimus or cidaforollimus, among others including epigallocatechin gallate (EGCG), caffeine, curcumin or reseveratrol (which mTOR inhibitors find particular use as enhancers of autophagy using the compounds disclosed herein and in addition, in the treatment of cancer with an autophagy modulator (inhibitor) as described herein, including in combination with tetrachlorisophthalonitrile, phenylmercuric acetate and their pharmaceutically acceptable salts, which are inhibitors of autophagy. It is noted that in the case of the treatment of cancer, the use of an autophagy inhibitor is preferred, alone or in combination with an autophagy inducer (agonist) as otherwise described herein and/or a mTOR inhibitor as described above. In certain embodiments, an mTOR inhibitor selected from the group consisting of pp242, rapamycin, envirolimus, everolimus, cidaforollimus, epigallocatechin gallate (EGCG), caffeine, curcumin, reseveratrol and mixtures thereof may be combined with at least one agent selected from the group consisting of digoxin, xylazine, hexetidine and sertindole, the combination of such agents being effective as autophagy modulators in combination.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer (especially basal cell carcinoma or squamous cell carcinoma), acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. In certain aspects, the cancer which is treated is lung cancer, breast cancer, ovarian cancer and/or prostate cancer.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, *vinca* alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

Co-administration of one of the formulations of the invention with another anticancer agent will often result in a synergistic enhancement of the anticancer activity of the other anticancer agent, an unexpected result. One or more of the present formulations comprising an IRGM modulator optionally in combination with an autophagy modulator (autostatin) as described herein may also be co-administered with another bioactive agent (e.g., antiviral agent, antihyperproliferative disease agent, agents which treat chronic inflammatory disease, among others as otherwise described herein).

The term "antiviral agent" refers to an agent which may be used in combination with authophagy modulators (autostatins) as otherwise described herein to treat viral infections, especially including HIV infections, HBV infections and/or HCV infections. Exemplary anti-HIV agents include, for example, nucleoside reverse transcriptase inhibitors (NRTI), non-nucloeoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddl (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated intergeron, ribavirin, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

An "inflammation-associated metabolic disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia or a lipid-related metabolic disorder (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

An "inflammation-associated metabolic disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, "inflammation-associated metabolic disorder" includes: central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *Mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

In many countries the only measure for TB control has been vaccination with *M. bovis* bacille Calmette-Guerin (BCG). The overall vaccine efficacy of BCG against TB, however, is about 50% with extreme variations ranging from 0% to 80% between different field trials. The widespread emergence of multiple drug-resistant *M. tuberculosis* strains is also a concern.

*M. tuberculosis* belongs to the group of intracellular bacteria that replicate within the phagosomal vacuoles of resting macrophages, thus protection against TB depends on T cell-mediated immunity. Several studies in mice and humans, however, have shown that Mycobacteria stimulate antigen-specific, major histocompatibility complex (MHC) class II- or class I-restricted CD4 and CD8 T cells, respectively. The important role of MHC class I-restricted CD8 T cells was convincingly demonstrated by the failure of β2-microglobulin) deficient mice to control experimental *M. tuberculosis* infection.

As used herein, the term "tuberculosis" comprises disease states usually associated with infections caused by mycobacteria species comprising *M. tuberculosis* complex. The term "tuberculosis" is also often associated with mycobacterial infections caused by mycobacteria other than *M. tuberculosis*. Other mycobacterial species include *M. avium-intracellulare, M. kansarii, M. fortuitum, M. chelonae, M. leprae, M. africanum,* and *M. microti, M. avium paratuberculosis, M. intracellulare, M. scrofulaceum, M. xenopi, M. marinum, M. ulcerans*.

An "infectious disease" includes but is limited to those caused by bacterial, mycological, parasitic, and viral agents. Examples of such infectious agents include the following: staphylococcus, streptococcaceae, neisseriaaceae, cocci, enterobacteriaceae, pseudomonadaceae, vibrionaceae, *campylobacter*, pasteurellaceae, *bordetella, francisella, brucella*, legionellaceae, bacteroidaceae, gram-negative bacilli, *clostridium, corynebacterium, propionibacterium*, gram-positive bacilli, anthrax, *actinomyces, nocardia, mycobacterium, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses (B and C, among others), orthomyxoviruses, paramyxoviruses, coronaviruses, picornaviruses, reoviruses, togaviruses, flaviviruses, bunyaviridae, rhabdoviruses, human immunodeficiency virus (I and II) and retroviruses.

In certain embodiments, an "infectious disease" is selected from the group consisting of tuberculosis, leprosy, Crohn's Disease, acquired immunodeficiency syndrome, Lyme disease, cat-scratch disease, Rocky Mountain spotted fever and influenza or a viral infection selected from HIV (I and/or II), hepatitis B virus (HBV) or hepatitis C virus (HCV).

While not being limited by way of theory, it is believed that autophagy-mediated disease states which evidence upregulated autophagy and upregulated TRIM proteins include inflammatory disease states and autoimmune disease states as otherwise described herein. These disease states and/or conditions may benefit from the inhibition of TRIM proteins where there is evidence that autophagy is up-regulated and needs to be brought back into balance in order to facilitate healing of the disease state and/or condition. In these disease states, the inhibition of TRIM proteins, including inhibiting TRIM proteins by administration of small interfering RNAs (siRNAs) which inhibit the synthesis of the TRIM protein to be reduced in order to down regulate autophagy may be useful. This approach may provide beneficial treatment in a large number of disease states and conditions where upregulation of autophagy is responsible for the disease state and/or exacerbating the disease state. In other disease states, in particular, bacterial and viral infections, especially tuberculosis and in some instances of cancer, autophagy is often down-regulated and may benefit from the upregulation of autophagy through the administration of one or more TRIM proteins (especially TRIM20) alone or in combination with interferon-gamma, pegylated interferon and/or one more additional autophagy agents including alternative TRIM proteins as otherwise disclosed herein.

According to various embodiments, the compounds according to the present invention may be used for treatment or prevention purposes in the form of a pharmaceutical composition. This pharmaceutical composition may comprise one or more of an active ingredient as described herein.

As indicated, the pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, sublingual, nasal, intramuscular, transcutaneous, transdermal, intranasal, intratracheal, intrathecal, pulmonary, intraperitoneal, and topical, among others. The pharmaceutical compositions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 100 μg or even less to at least about 500 mg up to a gram or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient which is administered to a human patient preferably ranges from about 0.05 mg/kg to about 10 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered at the first signs of the onset of an autophagy mediated disease state, condition or symptom. For example, the dose may be administered for the purpose of lung or heart function and/or treating or reducing the likelihood of any one or more of the disease states or conditions which become manifest during an inflammation-associated metabolic disorder or tuberculosis or associated disease states or conditions, including pain, high blood pressure, renal failure, or lung failure. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

Synthesis of TRIM proteins according to the present invention may be performed by the routineer skilled in the art and may be provided by engineering polynucleotide sequences corresponding to the amino acid sequences of the TRIM proteins into plasmids for expression, transfecting the plasmids into both eukaryotic and/or prokaryotic cells and accumulating protein from the growth of the cells containing the plasmids. Alternatively, the proteins may be readily synthesized by standard, well-known peptide synthesis methods, including solid phase synthesis.

The following examples are provided to further describe the present invention. The examples, while descriptive of the present invention, are not to be construed as limiting the present invention.

EXAMPLES

First Set—IRGM Examples

Antibodies, Plasmids, and siRNA

Antibodies were from Cell Signaling (AMPK, AMPK Thr-172, ULK, ULK1 p-Ser 317, p-Ser 757, p-Ser555, NOD2, Beclin 1 p-Ser-93/96 and ATG5), MBL international corp. (ATG16L1, ATG14L, Rubicon and UVRAG), Abcam (GFP, IRGM, LPS, TRAF6 and BCL2), Sigma (LC3B, Flag), Millipore (V5 tag and HA tag), Abbiotec (Beclin 1 p-Ser15) and Novus biological (AMBRA1). GFP-tagged IRGM expression plasmid (GFP-IRGMd) was described previously (Singh et al., 2010). GFP-IRGM-K$^{mut}$ was generated from GFP-IRGMd plasmid by replacing wild type IRGMd gene with synthetic mutated IRGMd gene (GeneScript) with all lysine residues mutated to arginine. Flag-IRGM and IRGM-V5 were generated by Gateway cloning (Life technologies). HA-UbiquitinC, HA-UbiquitinC-K63 (all lysine mutated except K63, Plasmid 17606), HA-UbiquitinC-K48 (all lysine mutated except K48, Plasmid 17605), Flag-TLR3 (Plasmid 13084) and YFP-TLR4 (Plasmid 13018) were from Addgene. Flag-NOD2 and variants were from Dr. Thomas Kufer (University of Cologne, Germany). Flag-ATG16L1 and variants were from Dr. Ramnik Xavier (Massachusetts General Hospital, Boston). Flag-TRAF6 was from Dr. Edward Harhaj (Johns Hopkins School of Medicine, US). IRGM siRNA, TRAF6 siRNA, AMPKα2 siRNA were from Dharmacon (siGENOME SMART pool).

Autophagy Induction

U937 cells were treated with LPS (500 ng/ml) for 4 h or by transfecting MDP (5 g/ml) with calcium phosphate for 8 h. For induction of autophagy by starvation, cells were cultured in EBSS.

Protein Interactions Analyses

For co-immunoprecipitation assays, the cells were lysed using NP-40 buffer containing protease inhibitor cocktail and PMSF. Lysates were incubated with antibody for 2 h followed by incubation with proteinG Dynabeads (Life technologies) for 2 h. Beads were washed for four times with 1×PBS and then boiled with SDS-PAGE buffer for analysis of interacting protein by Immunoblotting. Immunoblots were quantified using Image J software.

Microscopy Analyses and Quantification

Immunofluorescence was performed as described earlier (Kyei et al., 2009). For quantification of puncta, images from different fields were captured and analyzed. For quantification of total cell fluorescence, image J was used as described previously (Chauhan et al., 2013).

Gene Expression Analysis

Total RNA was isolated from cell culture using Trizol as per the manufacturer's instruction (Invitrogen). For quantitative real-time PCR: TURBO DNA-free kit (Ambion) was used to remove contaminating residual DNA; cDNA was prepared using the high capacity cDNA reverse transcription kit as per the manufacturer's instruction (Applied Biosytem). Taqman probes (Applied Biosystem) and realtime PCR master mixes (Applied Biosystem) were used for real-time PCR as per the manufacturer's instruction. Data were normalized using GAPDH.

Bacterial Survival Analyses

AIEC LF82 survival assay was performed as described previously (Lapaquette et al., 2009). HEK293T cells were infected with AIEC LF82 of MOI of 1:20 for 3 h. Cells were treated with gentamycin (100 µg/ml) for 1 h followed by incubation in fresh media for 2 h. Cells were lysed and surviving bacteria quantified by plating and determining colony forming units.

Cytokine and NF-kB Responses

For NFkB-p65 nuclear localization assay, HeLa cells were platted on cover slips a day before infection. Cells were infected with AIEC LF82 strain at MOI of 1:20 for 2 h followed by washings with PBS and fixing the cells with 4% paraformaldehyde. Immunofluorescence imaging was performed as described earlier (Kyei et al., 2009). Cells were visualized using a laser confocal microscope and images were captured using LSM510 software. For IL-1β measurement, IL-1β transcription was determined using qRT-PCR in THP-1 cells.

Results (IRGM Examples)

IRGM Activates the Core Regulators of Autophagy

Prior work has indicated that IRGM affects autophagy through processes influencing mitochondrial function, including mitochondrial fission and membrane potential collapse (Singh et al., 2010). Similar changes in mitochondrial function often lead to AMPK activation (Romanello et al., 2010; Turkieh et al., 2014). Thus, we tested the activation status of AMPK. A knockdown of IRGM reduced the total amounts of AMPK in both control or starved cells (FIG. 1A) and decreased the levels of the activated form of AMPK phosphorylated at Thr-172 (FIG. 1A). Overexpression of IRGM increased levels of Thr-172 phosphorylated AMPK (FIG. 1B).

AMPK has been previously shown to induce autophagy by directly phosphorylating ULK1 (Egan et al., 2011; Kim et al., 2011) and Beclin 1 (Kim et al., 2013). When we tested the phosphorylation status of ULK1 and Beclin 1, we observed that the expression of IRGM, which caused induction of autophagy (FIG. 8A), enhanced phosphorylation at activating sites of Beclin 1 at Ser93/96 (Kim et al., 2013), and ULK1 at Ser-555 (Egan et al., 2011) and at Ser-317 (Kim et al., 2011) (FIG. 1B,C).

IRGM Assembles the Core Regulatory Machinery for Autophagy

Figure 8:
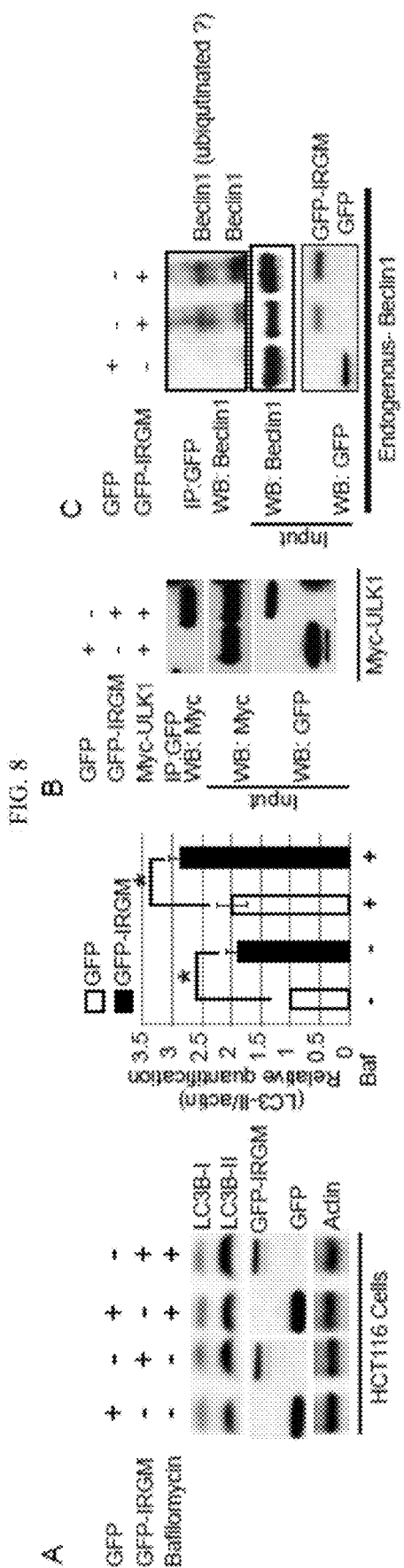
FIG. 8, related to FIG. 1 shows that IRGM interacts with core autophagy machinery. (A) Left panel, Western blotting with lysates of bafilomycin (100 nM, 2 hr) treated or untreated HCT116 cells expressing GFP or GFP-IRGM. Right panel, densitometric analysis of Western blots. (B) Co-IP analysis with HEK293T cell co-expressing either GFP or GFP-IRGM and Myc-ULK1. (C-F) Co-IP experiment with HEK293T cell expressing GFP or GFP-IRGM (C, D, F) and Myc-AMBRA1 (E) were subjected to Western blotting with indicated antibodies.
Figure 8:
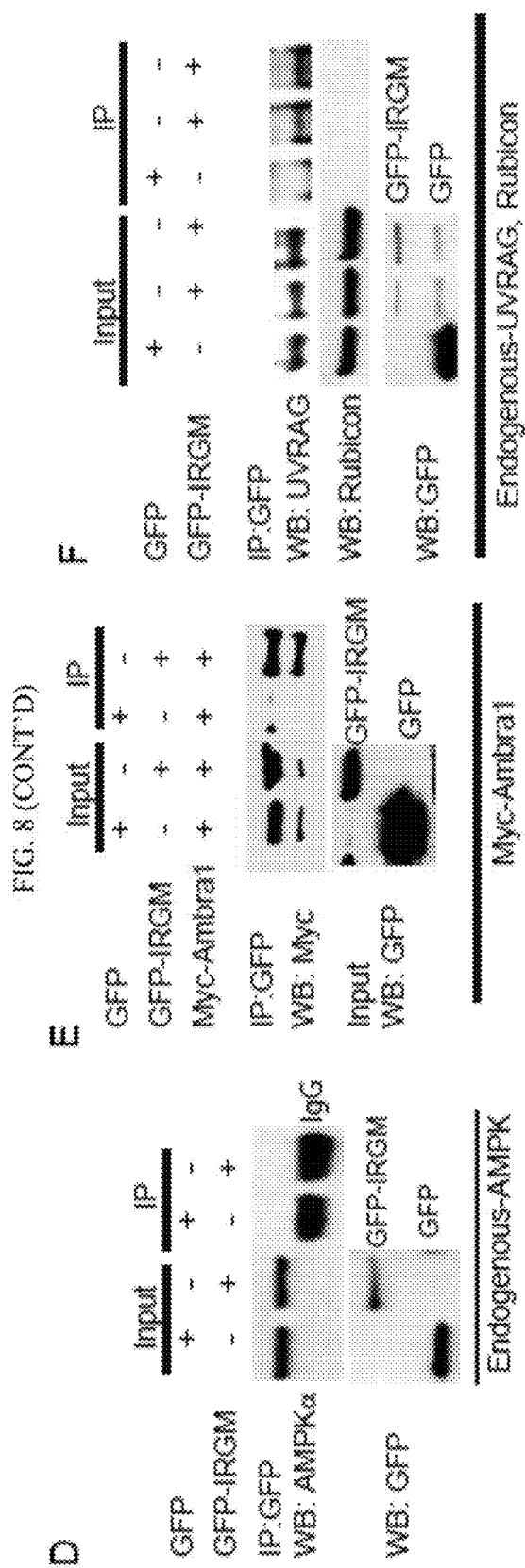

The entire signaling cascade described above could explain how IRGM induces autophagy, e.g. by its effects on AMPK and activation of downstream autophagy regulators. However, IRGM showed a further, more direct role by interacting with the key regulators of autophagy. We found that IRGM co-immunoprecipitated and co-localized with both endogenous and overexpressed ULK1 and Beclin 1 (FIGS. 1D-G and 8B-C) but not with AMPK (FIG. 8D). IRGM complexes with ULK1 were enriched for the activated, AMPK-dependent Ser-317, form of ULK1 relative to the inhibitory, mTOR-dependent, Ser-757 form (FIG. 1H). Furthermore, expression of IRGM enriched ULK1 in the immunoprecipitated Beclin 1 complexes (FIGS. 1I and 8G). In keeping with this, cells overexpressing IRGM also showed increased Beclin 1 Ser-15 phosphorylation, the phosphorylated form of Beclin 1 dependent on ULK1 activity (Kim et al., 2013) (FIG. 1J).

IRGM Determines the Composition of the Beclin 1 Complex

We found that IRGM complexes also included autophagy-enhancing Beclin1 interactors, AMBRA1 (FIGS. 1D and 8E), ATG14L (FIG. 1K) and UVRAG (FIG. 8F) but not the autophagy inhibitory factor Rubicon (FIG. 8F) (Fimia et al., 2007; Itakura et al., 2008; Matsunaga et al., 2009). Next, we mapped Beclin 1 regions required for interaction with IRGM (FIG. 1M). IRGM interacted with two Beclin 1 regions: (i) BH3-containing 1-125 N-terminal portion, and (ii) a segment encompassing CCD and ECD, whereas it did not bind to the intervening CCD domain alone (FIG. 1L,M).

Incidentally, two Beclin1 negative regulators Bcl-2 and Rubicon bind respectively to the regions spanning Beclin 1's BH3 domain and Beclin 1's CCD and ECD domains, whereas ATG14L, a factor enabling Beclin 1 to activate the initiation complex (Kim et al., 2013), binds to the CCD domain of Beclin 1 (Sun et al., 2008). This domain occupancy on Beclin1 is compatible with simultaneous binding of IRGM and ATG14L and exclusion of autophagy negative regulators. When IRGM was overexpressed, it dis-enriched Rubicon and Bcl-2 from Beclin 1 and enriched ATG14L in Beclin 1 complexes (FIG. 1N).

The above data indicate that IRGM forms protein complexes with the central regulators of autophagy and activates Beclin 1 by displacing its negative regulators (FIG. 1O, Right). This, taken together with IRGM's ability to sponsor the phosphorylation cascade that activates ULK1 and Beclin 1, shows how IRGM promotes autophagy (FIG. 1O, Left).

IRGM Affects Levels of Autophagy Regulators

Figure 2:
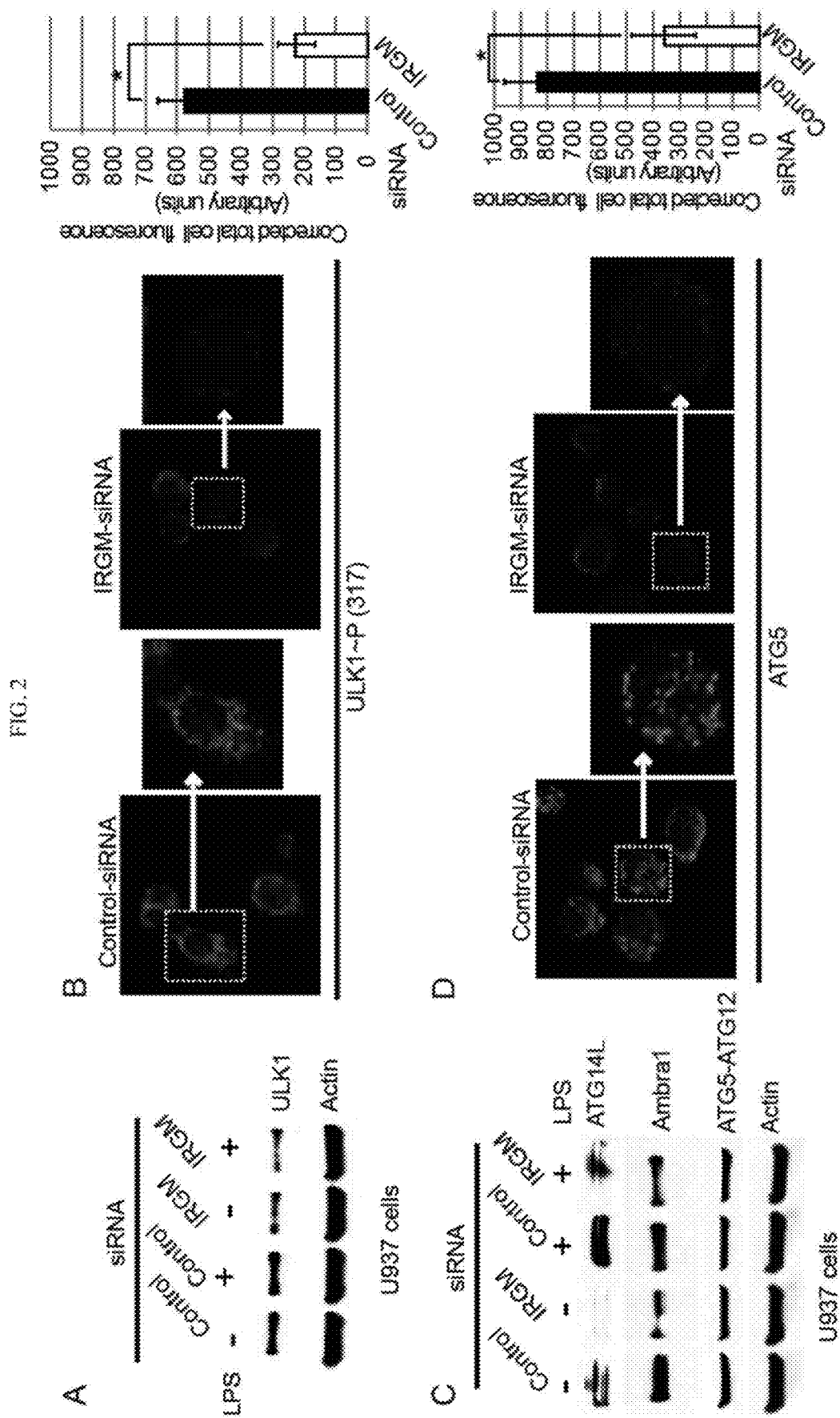
FIG. 2 shows that IRGM is required for stable levels of the autophagy initiation proteins. (A,C,E) U937 cells transfected with control or IRGM siRNAs, untreated or treated with LPS (500 ng/ml for 4 h) were lysed and subjected to Western blotting with antibody to (A) ULK1, (C) ATG14L, AMBRA1 and ATG5, and (E) ATG16L1. IRGM knock down efficiency and quantifications are shown in Supplementary FIG. 9 A,B. (B,D,F) Left, confocal images of U937 cells transfected with control or IRGM siRNA treated with LPS (500 ng/ml for 4 h), Immunofluorescence analysis was performed with (B) phopho-ULK1 (Ser-317), (D) ATG5, and (F) ATG16L1. Graphs, means±SD (corrected total cell fluorescence of cells; >30 cells from 5 fields measured using Image J). *, p<0.05 (Student's unpaired t test). (G) Lysates from HEK293T cells expressing GFP or GFP-IRGM were subjected to immunoprecipitation with anti-GFP and blot probed with indicated antibodies. (H) Schematic of ATG16L1 domain structure indicating IRGM interacting regions mapped in panels I. (I) Lysates of HEK293T cells co-expressing GFP-IRGM and the indicated Flag-ATG16L1 variants in panel H were subjected to immunoprecipitation with anti-Flag and blots probed as indicated. Results, representative of three independent experiments. See also FIG. 9.
Figure 9:
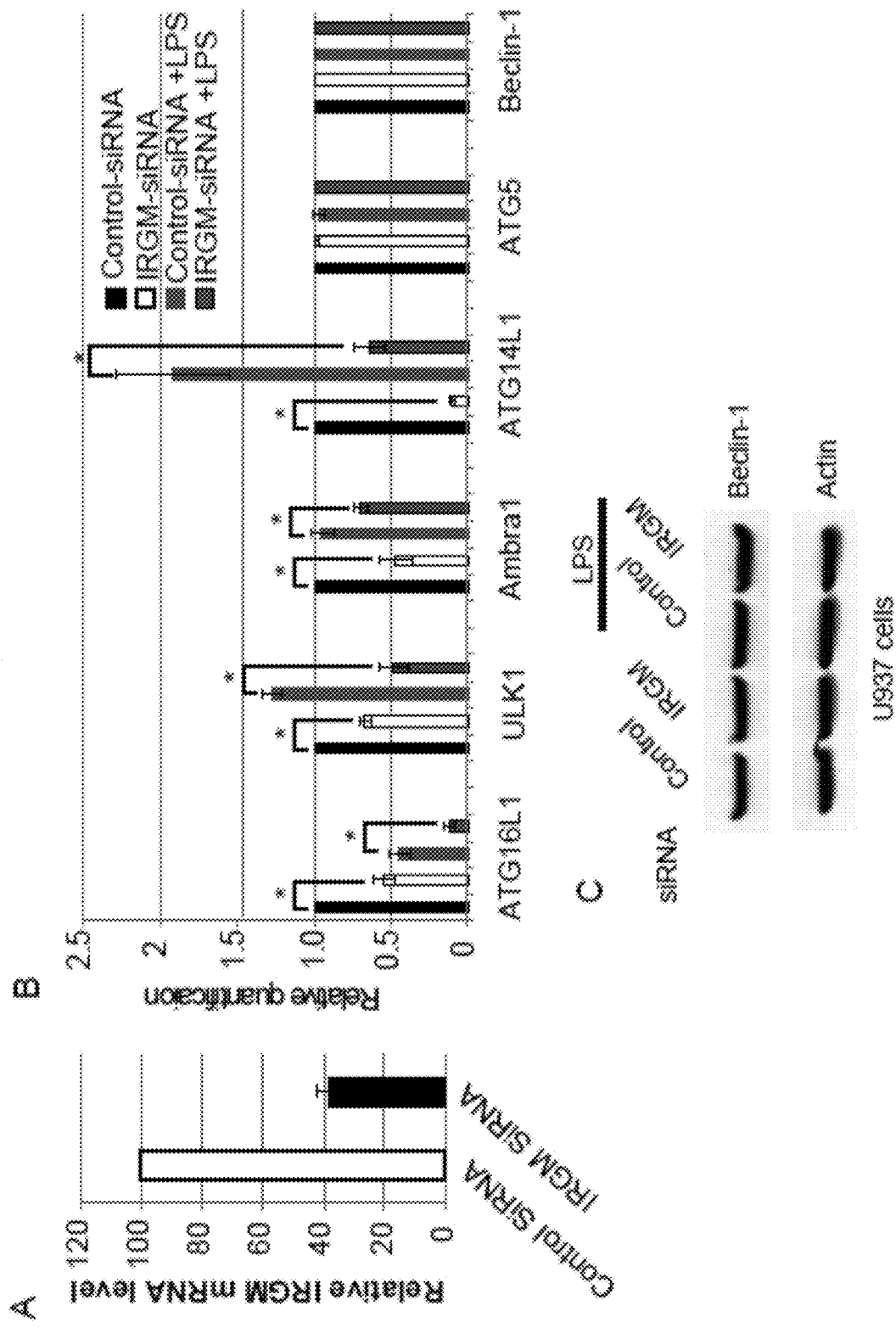
FIG. 9, related to FIG. 2 shows that IRGM stabilizes core autophagy machinery. (A) Graph showing the knockdown efficiency of IRGM in U937 monocytic cells. (B) Graph showing the densitometric analysis of Western blots in FIG. 2 2 A, C, E. Result shown are mean±S.D of three independent experiments. *, p>0.05. (C) U937 monocyte cells transfected with control or IRGM siRNA, untreated or treated with LPS (500 ng/ml for 4 h) were lysed and subjected to Western blotting with indicated antibodies.

As observed with AMPK (FIG. 1A), IRGM affected the levels of a number of other autophagy regulators. IRGM knockdown in U937 monocytic cells (FIG. 9A) reduced total amount of ULK1 (FIG. 2A,B, FIG. 9B), ATG14L (FIG. 2C, FIG. 9B), and AMBRA1 (FIG. 2C, FIG. 9B). In contrast to the above suite of autophagy regulators, Beclin 1 was not affected (FIG. 9C). In addition to Beclin 1, IRGM did not alter cytoplasmic levels of ATG5-ATG12 conjugates (FIG. 2C). However, the physical organization of ATG5-ATG12 was affected, since the numbers of its puncta, revealed by ATG5 immunofluorescence, were reduced upon IRGM knockdown (FIG. 2D). ATG5 puncta formation is governed by ATG16L1 (Mizushima, 2003). We thus looked at the effects of IRGM on ATG16L1 levels and observed that they were reduced in IRGM knockdown cells (FIG. 2E,F). This prompted us to test whether IRGM might interact with ATG16L1. IRGM was in complexes with endogenous Atg16L1 (FIG. 2G). Further domain mapping showed that IRGM primarily interacted with the WD repeats region of ATG16L1 (FIG. 2H,I). The residual weak interaction between IRGM and ATG16L1 outside of the WD repeats (construct ATG16L1 (1-341)) was not due to FIP200, previously shown to bridge ATG16L1 with ULK1 (Gammoh et al., 2013) since interaction was not reduced upon FIP200 knockdown, and if anything was slightly increased (FIG. 9D). In summary, in addition to directing the assembly of key autophagy-specific regulators, IRGM also stabilizes them. Furthermore IRGM interacts with and stabilizes ATG16L1, a component of the ATG5-Atg12/ATG16L1 E3 complex, which governs LC3 conjugation and autophagosome formation (Mizushima, 2003).

Figure 3:
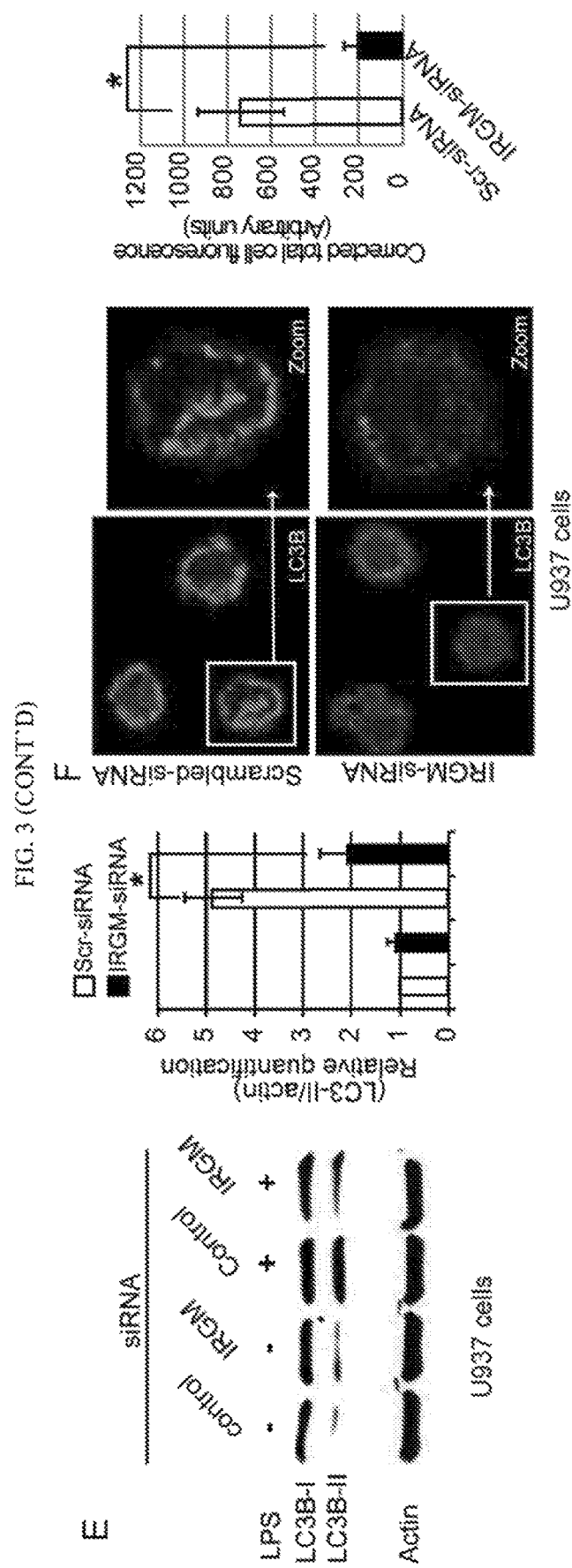
FIG. 3 shows that IRGM is required for PAMPs induced autophagy. (A) Abundance of IRGM mRNA (relative to GAPDH) in THP-1 cells (control or infected with invasive E. coli LF82) determined by quantitative real-time PCR (qRT-PCR). (B) Effect of LPS (30 min) or (C) MDP exposure (16 h) on IRGM mRNA levels in U937 cells. Gene expression (qRT-PCR) was normalized relative to GAPDH. Data, means±SD (n>3); *, p<0.05 (Student's unpaired t test). (D) Schematic summary of the physiological signals activating IRGM expression based on data in panels A-C and in FIGS. 10A-H. (E, F) Left, Western blot analysis of LC3-II abundance in U937 cells transfected with control or IRGM siRNA: (E) treated or not with LPS (500 ng/ml; 4 h); (F) treated or not with MDP (5 µg/ml for 8 h). Right, densitometric analysis of Western blots using ImageJ software. (G, H) Left, confocal images of LC3 puncta in LPS treated (500 ng/ml; 4 h) (G) or MDP-treated (5 µg/ml; 8 h), (H) U937 cells transfected with control or IRGM siRNA. Graphs (right of panels G and H), represent mean corrected total cell fluorescence+SE (25-35 cells from 10-15 fields measured using ImageJ. *, p<0.05 (ANOVA). See also FIG. 10.
Figure 3:
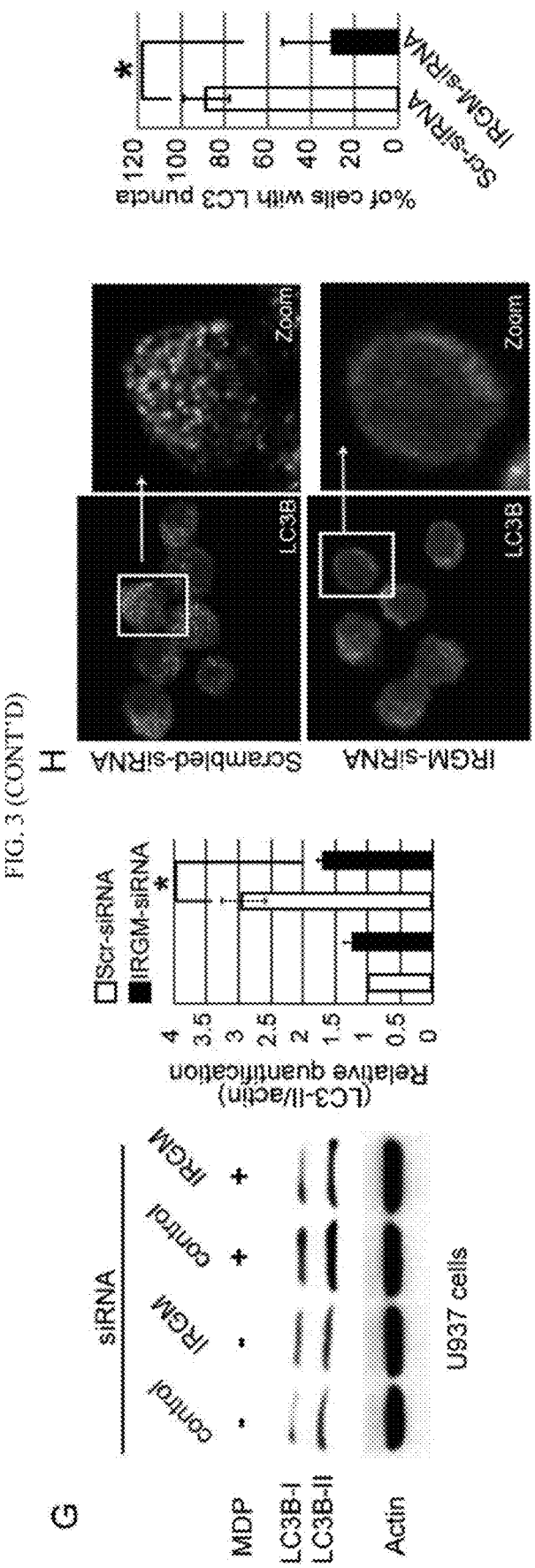

Expression of IRGM and its Assembly with Autophagy Factors Responds to Microbial Signals Infection with CD-associated adhesive invasive *Escherichia coli* (AIEC) LF82 (Lapaquette et al., 2010) or treatment with LPS or muramyl dipeptide (MDP) induced IRGM expression in U937 cells (FIGS. 3A-C). The induction of IRGM was similar to other physiological inducers of autophagy: starvation and IFN-γ (Gutierrez et al., 2004) which acted in a cell type-dependent manner, and, in the case of starvation, showed AMPK dependence (FIG. 3D, FIGS. 10A-I). When autophagy was induced by LPS (FIG. 10J) or MDP (FIG. 10K) (Cooney et al., 2010), a knockdown of IRGM (FIG. 10L) precluded LC3B-II conversion and LC3B puncta formation in response to these stimuli (FIGS. 3E-H). Thus, IRGM is required for autophagy elicited by microbial products.

In experiments with endogenous proteins, we could not detect interactions of IRGM with ULK1 and ATG16L1 under basal conditions. However, when a monocytic cell line (THP-1) was infected with *E. coli* LF82, immunoprecipitates of endogenous IRGM contained ULK1 and ATG16L1. Similar effects were observed with MDP and LPS. Of note, MDP (a NOD2-cogante ligand) was a stronger promoter of these effects than LPS. In contrast to ULK1 and ATG16L1, which showed interactions with endogenous IRGM only in samples from cells infected or treated with MDP or LPS, AMBRA1 showed association with endogenous IRGM even under basal conditions. Thus, exposure of cells to microbes or their products affects IRGM expression and also influences interactions with the autophagic apparatus.

Three Crohn's Disease Risk Factors, NOD2, IRGM, and ATG16L1 Interact

Figure 4:
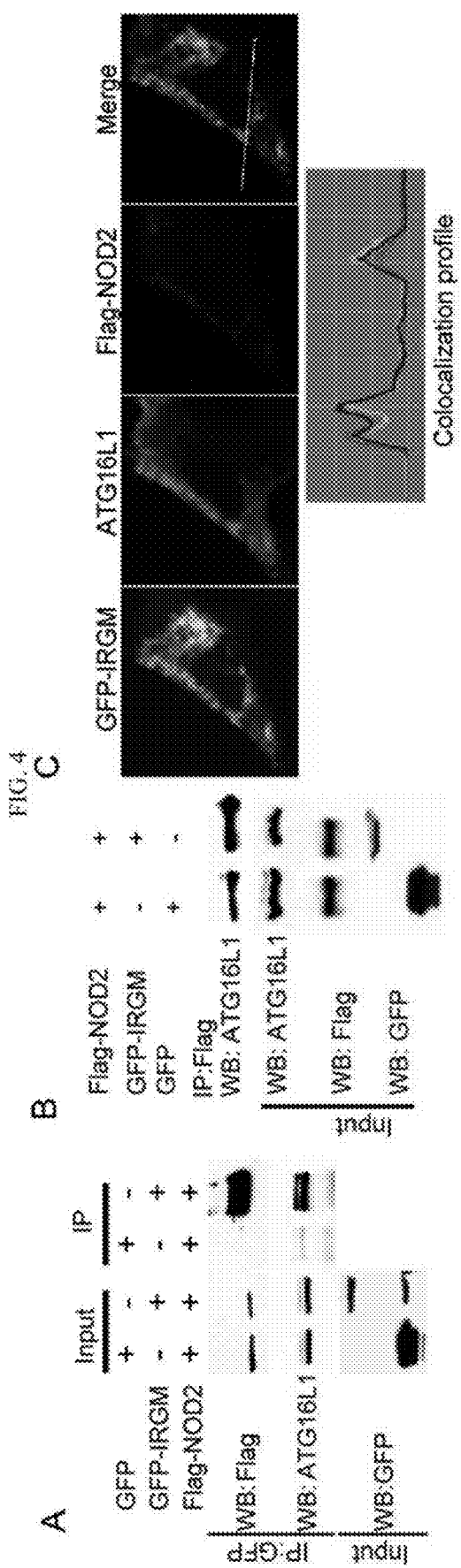
FIG. 4 shows that IRGM interacts and co-localizes with ATG16L1 and NOD2. (A, B) Co-IP analysis of endogenous (A) or overexpressed (B) IRGM, with NOD2 and ATG16L1 in (A) starved HT29 cells and (B) HEK293T cells. (C) Top, confocal microscopy images of HEK293T cells transiently expressing GFP-IRGM and Flag-NOD2. Bottom, fluorescence intensity line tracing corresponding to dashed line. (D) Schematic of NOD2 domain organization along with deletion constructs used in Co-IP analysis in panel E. (E) Left panel, lysates of HEK293T cells co-expressing GFP-IRGM and the Flag-NOD2 variants shown in panel D subjected to immunoprecipitation with anti-Flag and blot probed with antibodies as indicated. Right panel, densitometric analysis of Western blots (IP blot/Input blot). (F) Flag tag pull-down assays performed with affinity purified NOD2 variants from 293T cell lysates and purified recombinant GST-IRGM shown in the schematic (left panel). (G) Top, confocal microscopy images showing co-localization of GFP-IRGM and Flag-NOD2 and Rhodamine-MDP in HEK293T cells. Bottom, fluorescence intensity line tracing corresponding to red line. (H) Effect of MDP (10 µg/ml, 8 h) on GFP-IRGM and Flag-NOD2 interactions in HCT116 cells. (I) Model of IRGM-NOD2 interactions. See also FIG. 11.
Figure 4:
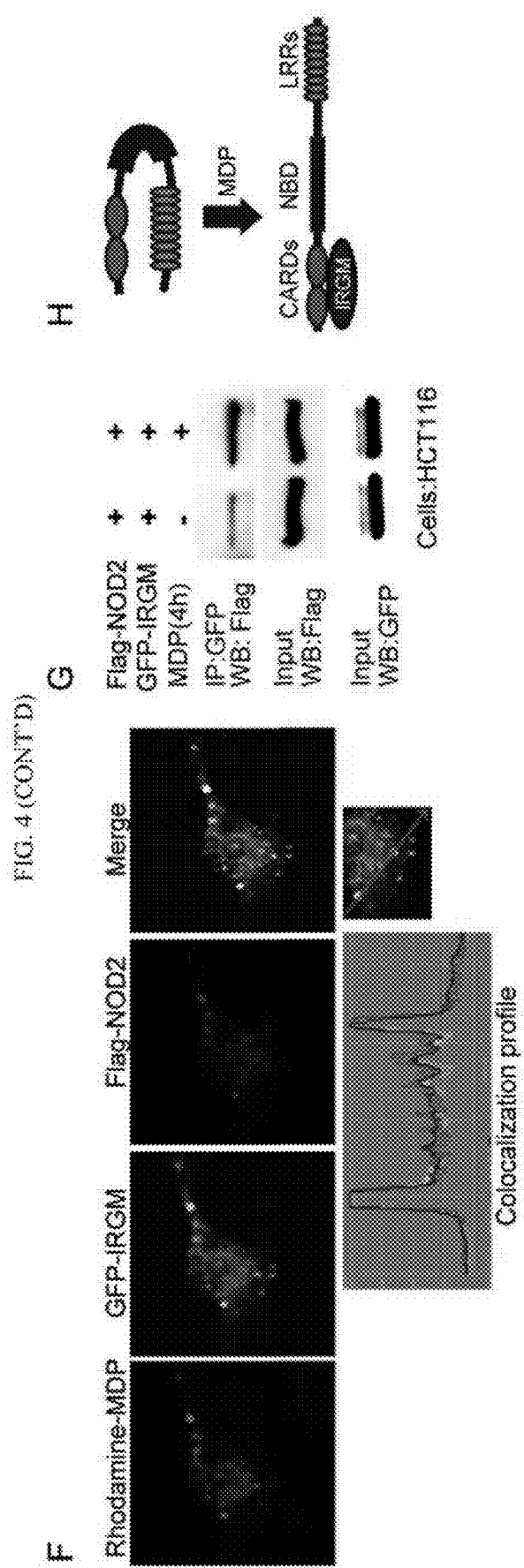
Figure 11:
FIG. 11, related to FIG. 4 shows that IRGM interacts and co-localizes with ATG16L1 and NOD2. (A) Endogenous IRGM interact with NOD2 and ATG16L1 in starved HT-29 cells. Co-IP analysis using IRGM antibody and Western blotting with indicated antibodies. (B) Lysates from cells expressing GFP-IRGM and Flag-NOD2 were subjected to immunoprecipitation with anti-GFP and blots were probed with antibodies as indicated. (C) Representative confocal images of HEK293T cells expressing GFP-IRGM alone or with NOD2 (D, E) HEK293T cells expressing GFP-IRGM (D) or GFP-IRGM and Flag-NOD2 (E) were subjected to immunofluorescence with Tom 20 (mitochondrial marker) antibody. Bottom, co-localization profile measurement along straight line using LSM 510 software.

A known receptor for MDP is NOD2, a risk factor for familial CD (Ogura et al., 2001). Furthermore, ATG16L1, harboring an important CD-associated polymorphism (Consortium, 2007), interacts with NOD2 (Cooney et al., 2010; Travassos et al., 2010). Hence, we wondered whether IRGM, a third genetic CD risk factor (incidentally co-discovered with ATG16L1) (Consortium, 2007), is a part of this complex. Endogenous and overexpressed IRGM immunoprecipitates contained both NOD2 and ATG16L1 (FIG. 4A, B). IRGM increased interactions between NOD2 and ATG16L1 (FIG. 11A). In contrast, co-expression of NOD2 did not affect IRGM-ATG16L1 interactions (FIG. 11B), suggesting that IRGM is important for promoting the assembly of the tri-partite complex. Morphologically, NOD2 co-expression changed IRGM intracellular distribution from diffuse cytosolic to punctate (FIG. 11C). A subset of these profiles colocalized with mitochondrial markers (Tom20; FIGS. 11D, E), in keeping with a partial NOD2 colocalization with mitochondrial antiviral signaling protein MAVS (Sabbah et al., 2009), and the previously reported partial IRGM localization to mitochondria (Singh et al., 2010).

All three factors, IRGM, ATG16L1, and NOD2 co-localized in co-transfected cells (FIG. 4C). Mapping of interaction domains revealed that association of IRGM with NOD2 is likely a regulated event. A region containing the two CARD domains of NOD2 was required for IRGM interaction (FIGS. 4D,E). A deletion of the LRR domains in NOD2 enhanced interactions between IRGM and NOD2 (FIGS. 4D,E). The LRR domain region is known to be inhibitory to the previously established NOD2 activities (Tanabe et al., 2004) by keeping NOD2 in a closed conformation until it is activated through stimuli such as MDP (Tanabe et al., 2004). IRGM and NOD2 interaction was confirmed by proximity ligation assay (PLA; FIG. 11F), which reports direct protein-protein interactions in situ. Positive PLA readouts of direct in situ interactions between proteins appear as fluorescent dots, the products of in situ PCR that generates a fluorescent product physically attached to antibodies against the two proteins that are <16 nm (FRET distance) apart. A deletion of the CARD domains in NOD2 reduced the NOD2-IRGM PLA signal (FIG. 11F), in keeping with the importance of CARDs for the interactions between IRGM and NOD2. We carried out additional interaction experiments with purified GST-IRGM protein (Singh et al., 2010), prepared from insect cells (FIG. 11G, isoform d, used in all experiments in this work), and Flag-NOD2 (full length and its variants ΔCARD and ΔLRR) prepared from 293T overexpressing cells. The results show that IRGM interacts with full length NOD2 and ΔLRR NOD2, but not with ΔCARD NOD2 (FIG. 4F). These findings demonstrate that the NOD2 CARD domain is key for interactions with IRGM.

Fluorescently labeled MDP co-localized with NOD2 and IRGM in the cells (FIG. 4G). In the presence of MDP, interactions between IRGM and NOD2 were enhanced (FIG. 4H). These findings are consistent with the inhibitory action of LRRs in the resting state of NOD2, and with the observation that following activation with MDP, NOD2 becomes available for interactions with IRGM (FIG. 4I). In summary, IRGM, NOD2, and ATG16L1 form a complex, with IRGM-NOD2 assembly being controlled by MDP, thus rendering the IRGM autophagy-promoting system responsive to microbial products.

NOD2 Enhances IRGM Interactions with ULK1 and Beclin 1

Figure 5:
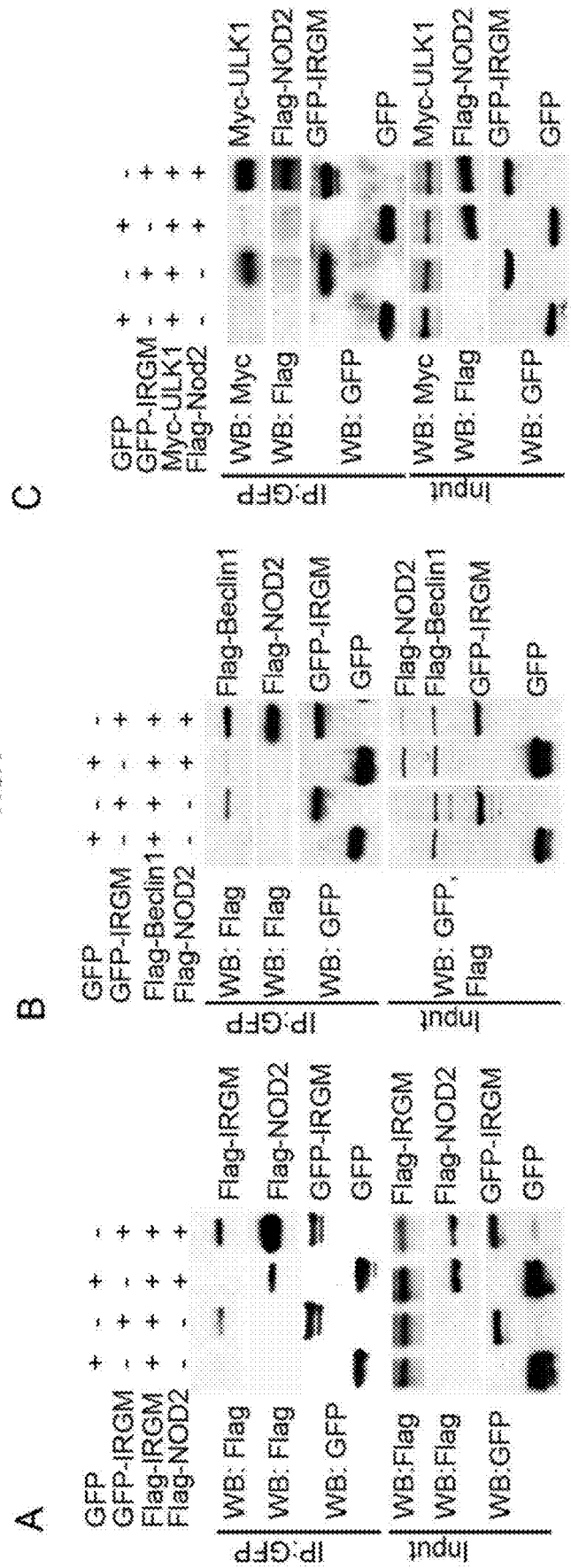
FIG. 5 shows that NOD2 promotes K63-linked polyubiquitination of IRGM, enhancing its interactions with autophagy initiation factors. (A-C) Effects of NOD2 expression on IRGM self-association (A), and IRGM's interaction with Beclin 1 (B) or with ULK1 (C) in HEK293T cells. (D, E) Analysis of IRGM ubiquitination in HEK293T cells. Cells co-expressing GFP or GFP-IRGM and (D) HA-tagged Ubiquitin C or (E) HA-tagged Ubiquitin C mutated for all lysines except lysine 48 (HA-K48) or Lysine 63 (HA-K63) and Flag-NOD2 were subjected to immunoprecipitation with GFP antibody and blots probed with indicated antibodies. Blot in (E) was processed to remove irrelevant lanes (dashed vertical line). (F) Cells co-expressing GFP-IRGM, HA-K63 and Flag-NOD2 deletion variants as in FIG. 4D were subjected to immunoprecipitation analysis with anti-GFP and blot probed with indicated antibodies. (G) Cells co-expressing GFP or GFP-IRGM or GFP-IRGM-K$^{mut}$ (IRGM variant with all lysine residues mutated to alanine) and HA-K63 were subjected to immunoprecipitation analysis with anti-GFP and blot was probed with indicated antibodies. Blot was processed (dashed vertical line) to remove irrelevant lanes. (H) Lysates of cells co-expressing GFP or GFP-IRGM or GFP-IRGM-K$^{mut}$ and Flag-IRGM were subjected to immunoprecipitation with anti-GFP and blot probed with indicated antibodies. (I) Lysates of cells expressing GFP or GFP-IRGM or GFP-IRGM-K$^{mut}$ were subjected to immunoprecipitation with anti-GFP and blots probed with indicated antibodies. Results representative of three independent experiments. See also FIG. 12.
Figure 5:
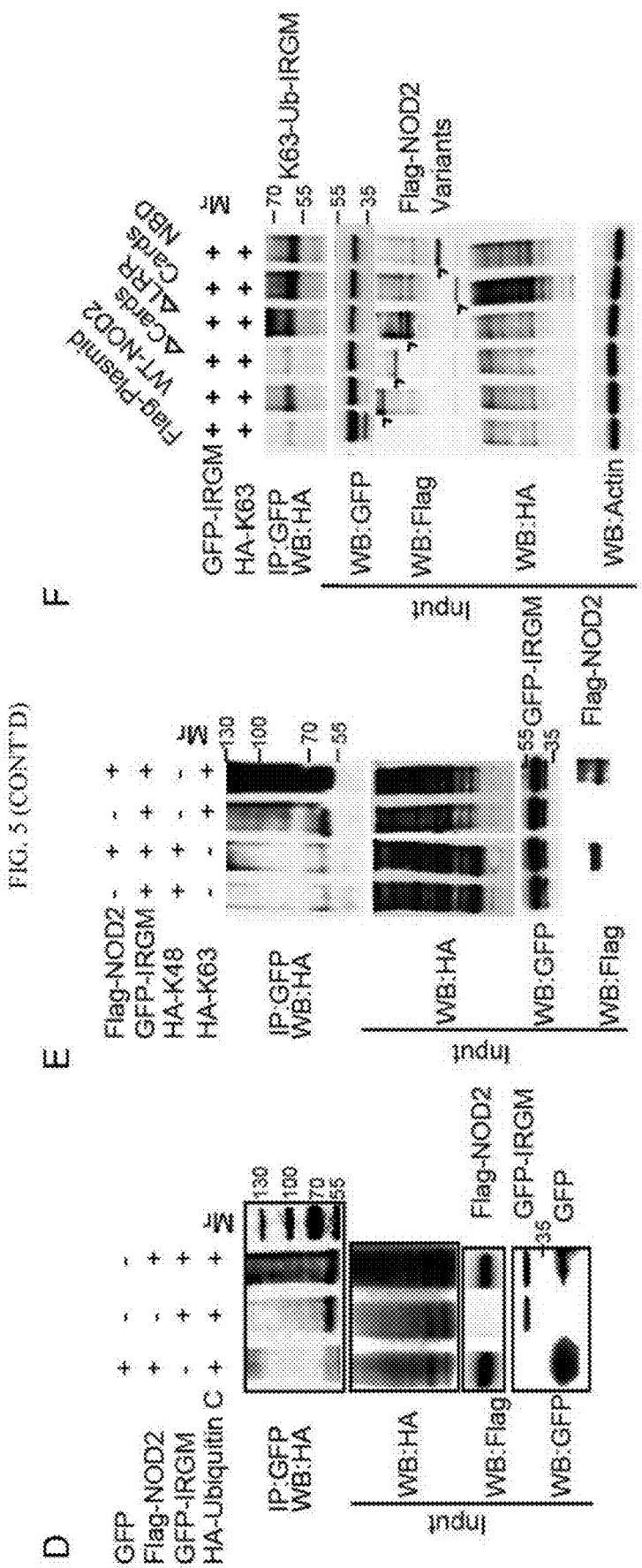
Figure 5:
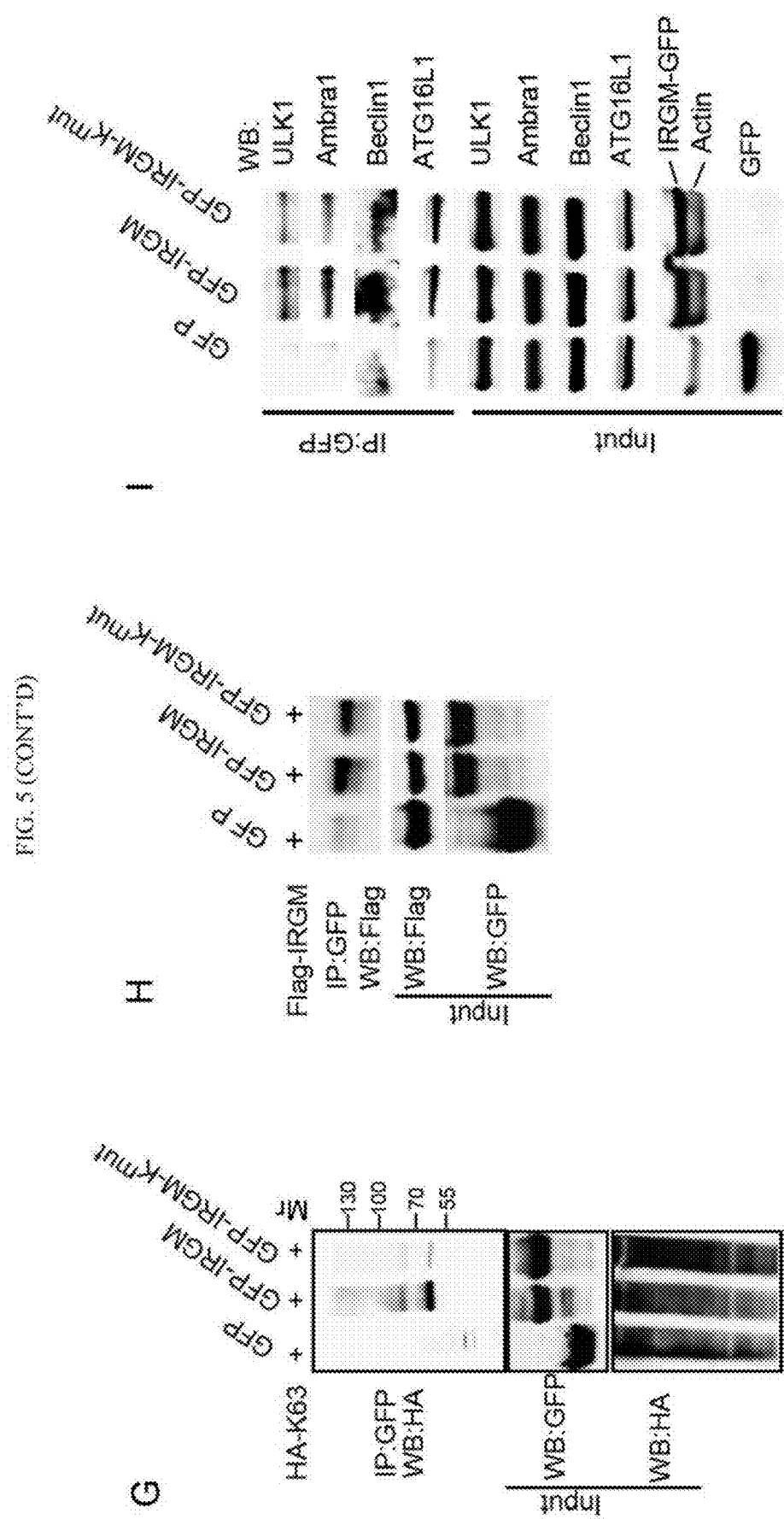
Figure 12:
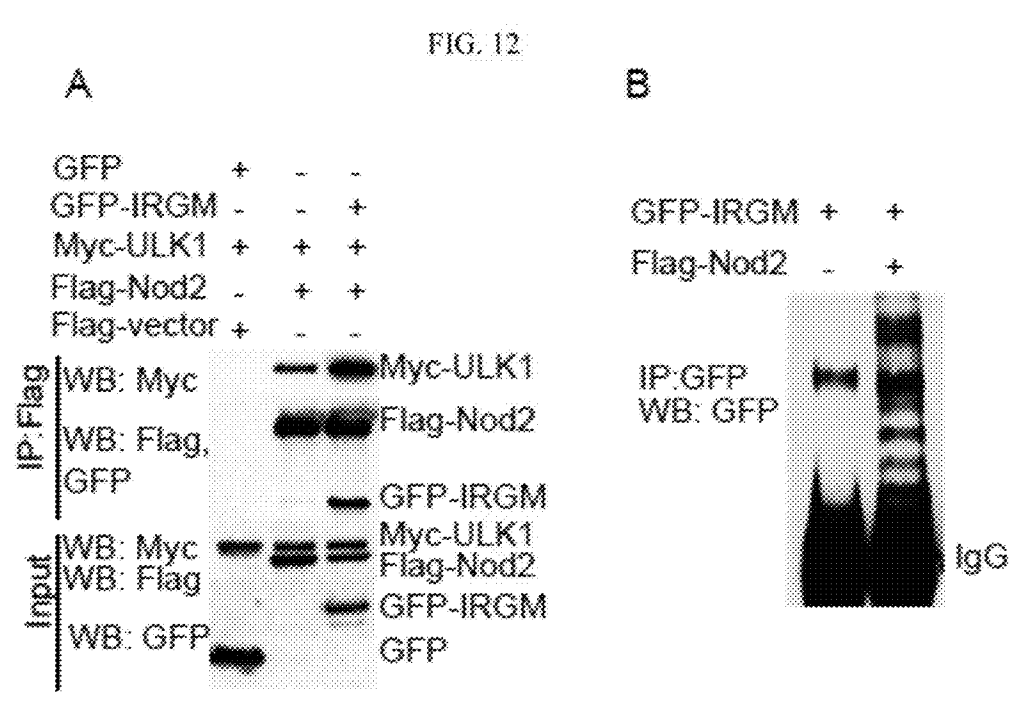

NOD2 affected IRGM quaternary structure. Co-expression of NOD2 and IRGM induced IRGM oligomerization within protein complexes (FIG. 5A). NOD2 furthermore promoted interactions between IRGM and ULK1 as well as between IRGM and Beclin 1 (FIGS. 5B,C). Incidentally, NOD2 was also found in complexes with ULK1 (FIG. 12A). IRGM co-expression increased ULK1-NOD2 complexes (FIG. 12A). Thus, NOD2 modulates IRGM interactions with ULK1 and Beclin 1, in contrast to the above-described (FIG. 11B) absence of NOD2 effects on IRGM-ATG16L1 complex formation. Based on these and above observations, IRGM is a pivotal organizer of the core parts of the autophagy initiation machinery (ULK1/Beclin1 and ATG16L1) along with NOD2.

Polyubiquitination of IRGM Promotes its Assembly with ULK1 and Beclin 1

In the co-immunoprecipitation experiments of NOD2 with IRGM, we observed the presence of multiple GFP-IRGM bands (FIG. 12B). NOD2 is known to promote ubiquitination of several target proteins (Abbott et al., 2007; Hasegawa et al., 2008). We tested whether IRGM was ubiquitinated and observed that it can be polyubiquitinated whereas NOD2 enhanced IRGM ubiquitination (FIG. 5D). To determine which ubiquitination linkage was involved, we co-expressed GFP-IRGM with two HA-tagged ubiquitin variants, one that can be ubiquitinated only at K63 and another one that can be ubiquitinated only at K48. The IRGM ubiquitination showed a much stronger signal with the HA-Ub-K63 (FIG. 5E). Endogenous IRGM as well as a construct with a tag smaller than GFP (V5 tag; IRGM-V5) were K63 polyubiquitinated (FIGS. 12C, 12D). The K63 ubiquitination of IRGM was strongly enhanced in the presence of NOD2 (FIG. 5E). Overexpression or downregulation of TRAF6, an E3 ligase known to work in concert within the NOD2 pathway (Abbott et al., 2007; Yang et al., 2007) increased or decreased IRGM ubiquitination (FIGS. 12E and 12F) suggesting a role for TRAF6 in IRGM ubiquitination. However, TRAF6 knockdown destabilized NOD2, so it was not possible to conclude that TRAF6 was the only E3 ligase responsible for IRGM ubiquitination. Next, we mapped which of the NOD2 domains are necessary for effective ubiquitination of IRGM, and found that deletion of the CARD domain in NOD2 prevented IRGM ubiquitination, consistent with IRGM's ability to bind to that region of NOD2 (FIG. 5F). Moreover, when the CARD domain of NOD2 was expressed alone, it enhanced IRGM K63 ubiquitination (FIG. 5F).

Mutation of either individual or small clusters of K (Lys) residues in IRGM did not prevent K-63 linkage ubiquitination of IRGM in the presence of NOD2 (FIG. 12G). In the absence of NOD2, the low level ubiquitination (see FIG. 5E) of the same series of K mutants of IRGM also persisted (FIG. 12H). A similar phenomenon, i.e. an absence of a dominant ubiquitination residue, has been described for several proteins including p53 (Chan et al., 2006) and cyclins (Fung et al., 2005). Paradoxically, mutation of the K-23/K-27 cluster in IRGM, enhanced K-63 linkage ubiquitination (FIG. 12H); it nevertheless reduced K-48 linked ubiquitination (FIG. 12I) suggesting that K-23/K-27 cluster may be a dominant K-48 ubiquitination site, and that its elimination enhances K-63 ubiquitination of IRGM. Thus, multiple K residues in IRGM are K63-ubiquitinated. When we mutated all twelve lysine residues in IRGM (IRGM-$K^{mut}$; K residues converted to R), the GFP-IRGM fusion lost ubiquitination capacity (FIG. 5G). Nevertheless, GFP-IRGM-$K^{mut}$ still bound ATG16L1 equally well as the wild type IRGM (FIG. 5I). In contrast to its unaltered association with ATG16L1, GFP-IRGM-$K^{mut}$ showed a reduced ability to oligomerize within protein complexes (revealed by using IRGM with two different tags; FIG. 5H) and displayed diminished capacity for interactions with ULK1, Beclin 1 and AMBRA1 (FIG. 5I). In addition, NOD2 could not increase Beclin 1-IRGM-$K^{mut}$ interactions, although NOD2 increased Beclin 1 interactions with wild type IRGM (FIG. 12J). Thus, polyubiquitination of IRGM is important for the assembly of the core regulatory machinery centered on ULK1 and Beclin 1, and this modification of IRGM is under the control by NOD2.

Polyubiquitinated IRGM Inversely Controls NOD2 and ULK1 Protein Levels

Figure 6:
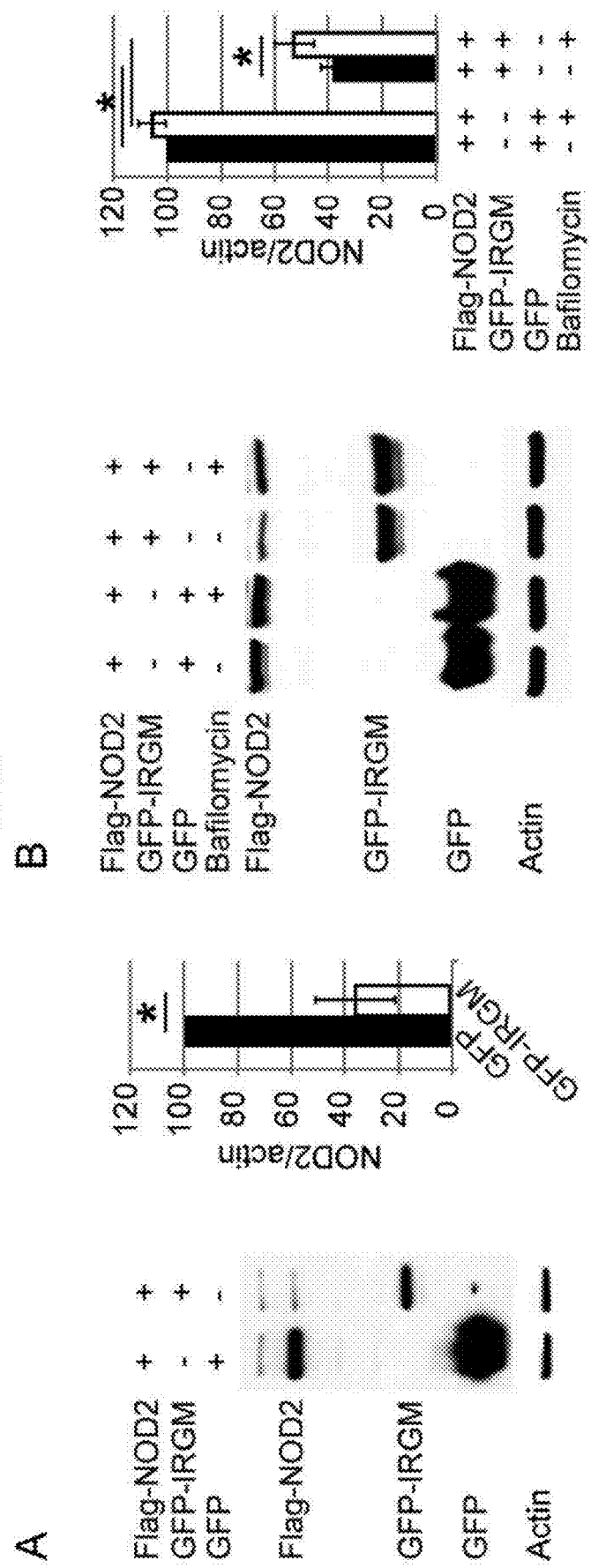
FIG. 6 shows that ubiquitination of IRGM is required for NOD2 degradation and ULK1 stability. (A) Effects of IRGM expression on NOD2 levels in transfected HEK293T cells. Data, means±SE; *, p<0.05 (Student's unpaired t test). (B) Lysates of HEK293T cell co-expressing GFP or GFP-IRGM and Flag-NOD2, untreated/treated with Bafilomycin A1 (100 nM for 8 h) were subjected to Western blotting. (C) Lysates of cells co-expressing Flag-NOD2 and GFP, GFP-IRGM, or GFP-IRGM-K$^{mut}$ were subjected to Western blotting. (D, E) Lysates from HEK293T cells co-expressing Myc-ULK1 and either GFP or increasing amounts of GFP-IRGM were subjected to Western blotting as in (D) with the relative abundance of Myc-ULK1 shown in (E). Blot was processed (dashed vertical line) to remove irrelevant lanes. (F) HEK293T cells transfected with plasmids encoding GFP, GFP-IRGM, or GFP-IRGM-K$^{mut}$ and either Myc-ULK1 or Flag-Beclin 1 were lysed and subjected to Western blotting. Data from densitometric analyses of Western blots (B, C, E), means±SE, n=3*, p<0.05 (ANOVA). (G) Depiction of the role of IRGM ubiquitination in NOD2 degradation and ULK1 stabilization. See also FIG. 13.
Figure 6:
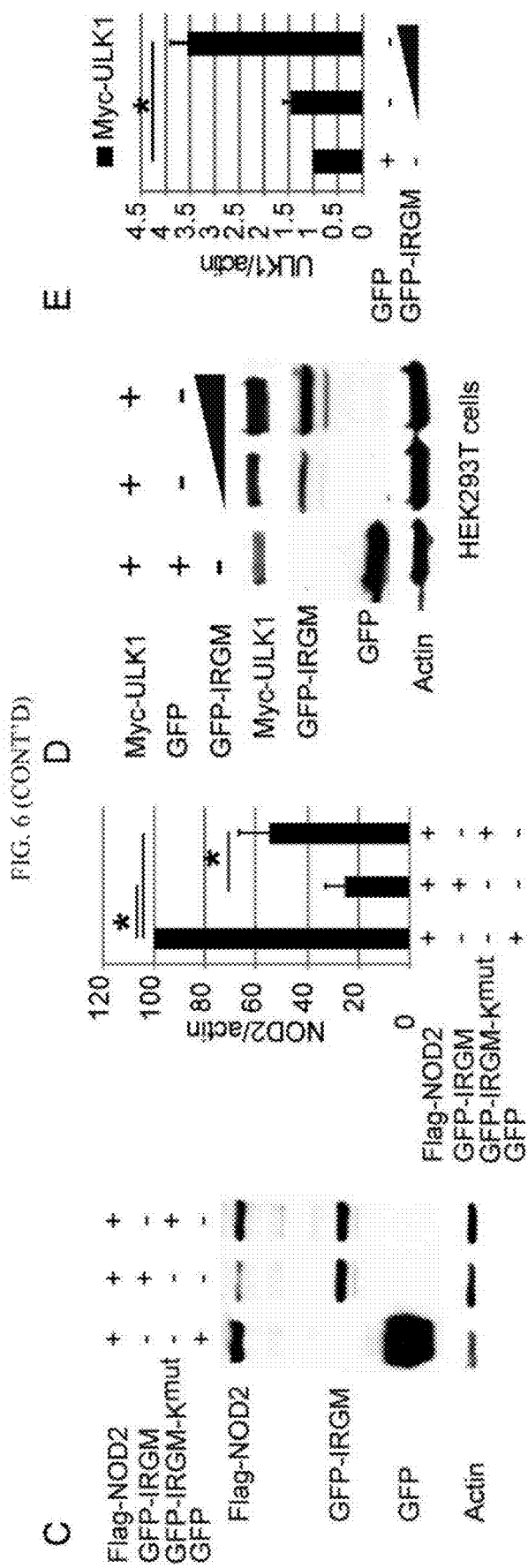
Figure 6:
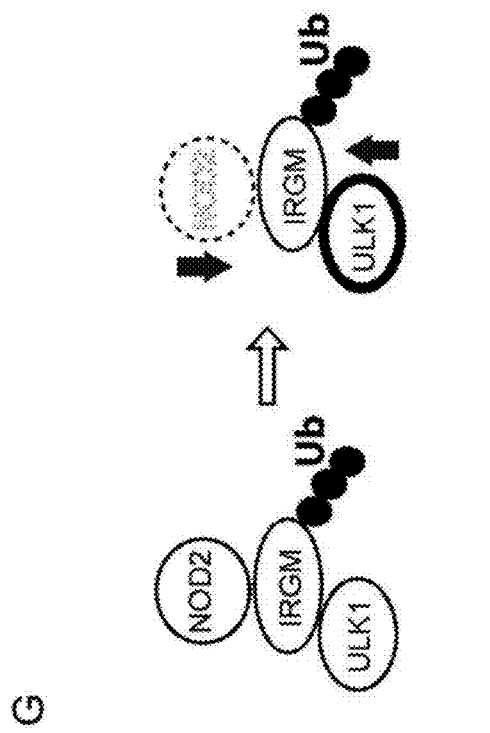
Figure 6:
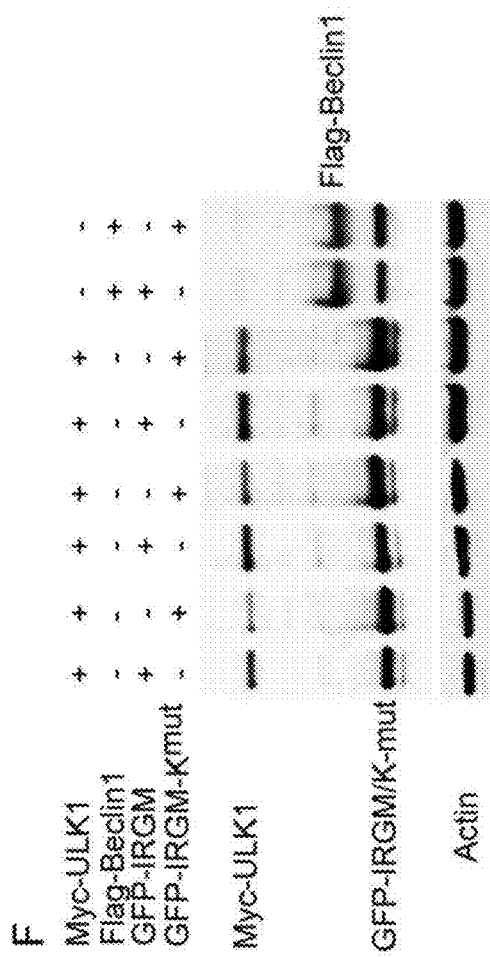
Figure 10:
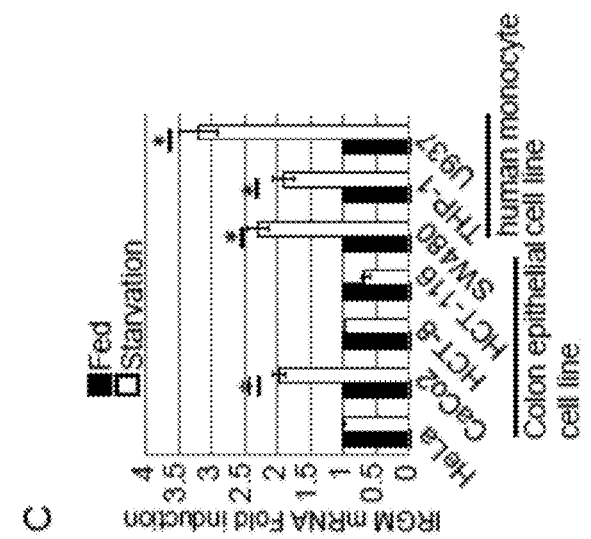
FIG. 10, related to FIG. 3 shows that starvation induces IRGM expression through AMPK. (A, B) Analysis of IRGM expression in several cell lines by quantitative real-time PCR (qRT-PCR). PBMC-Peripheral blood mononuclear cell (C, D) Starvation induces IRGM expression in several cell lines and notably in (D) HT-29 cells (~20 fold). RNA isolated from fed and starved cells were subjected to qRT-PCR. (E) Western blot from fed and starved HT-29 cells lysates showing induction of IRGM and LC3B. (F, G) AMPK is required for starvation induced IRGM expression in HT-29 cells. (F) qRT-PCR from RNA isolated from fed or starved HT-29 cells, treated with increasing concentration of compound C (20, 40, 80, 160 μM). Compound C is potent inhibitor of AMPK. (G) Knocking down AMPKα2 blunted starvation induced IRGM expression. Inset, Western blotting showing AMPKα2 knock down efficiency. (H) RNA isolated from U937 cells treated with IFNγ were subjected to qRT-PCR. (I) Graph showing knockdown efficiency of IRGM in U937 monocytic cells.
Figure 10:
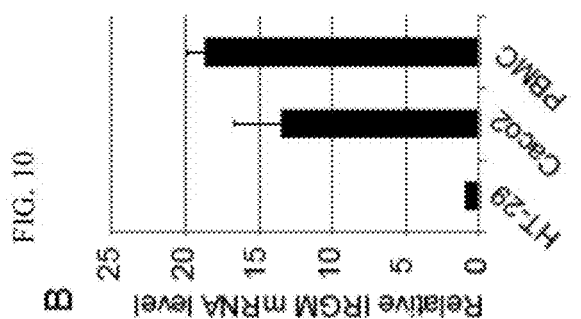
Figure 10:
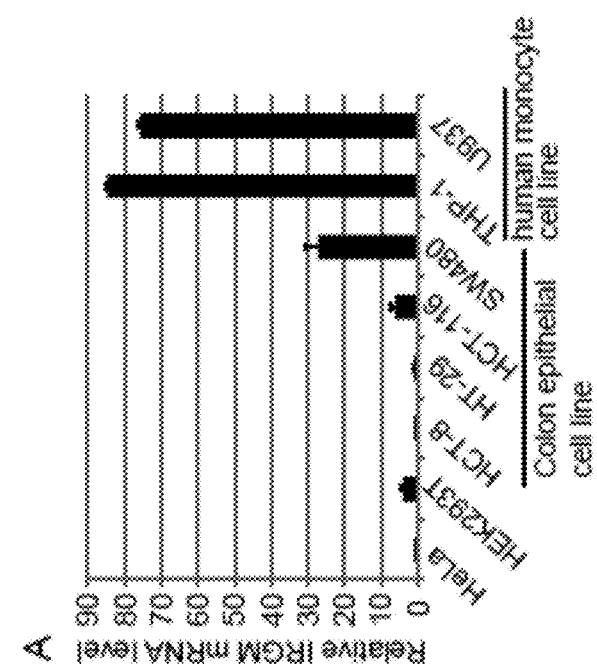
Figure 10:
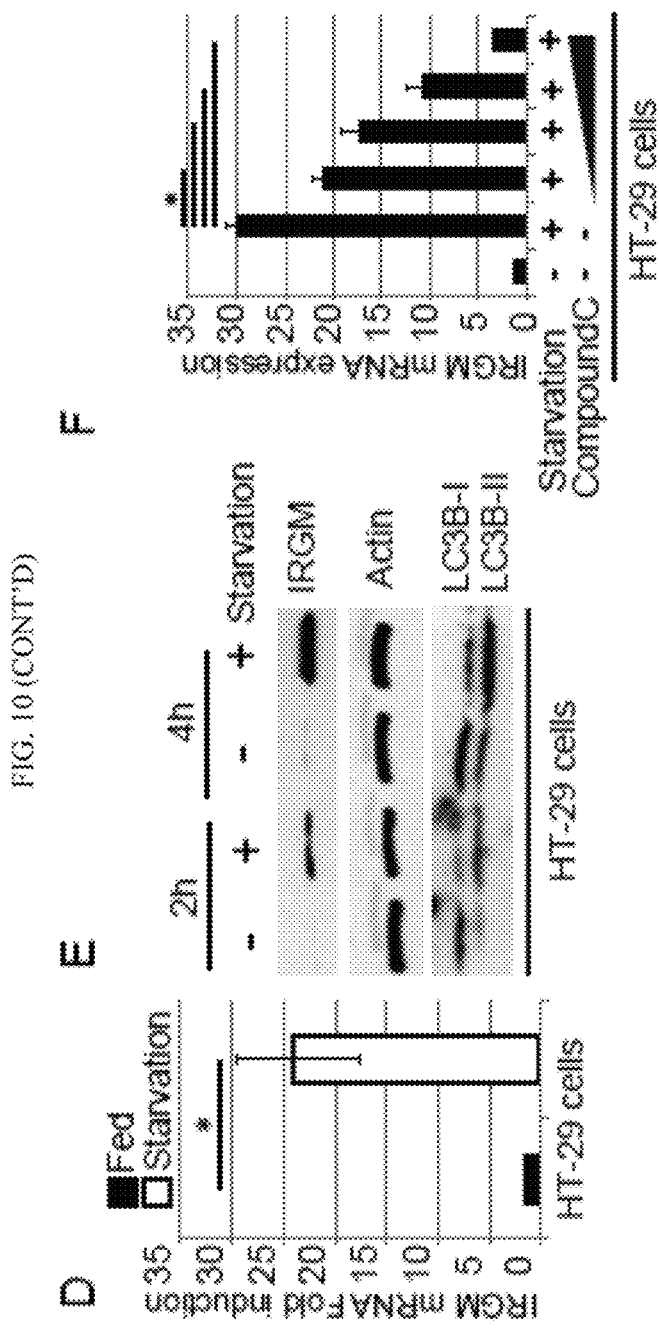
Figure 10:
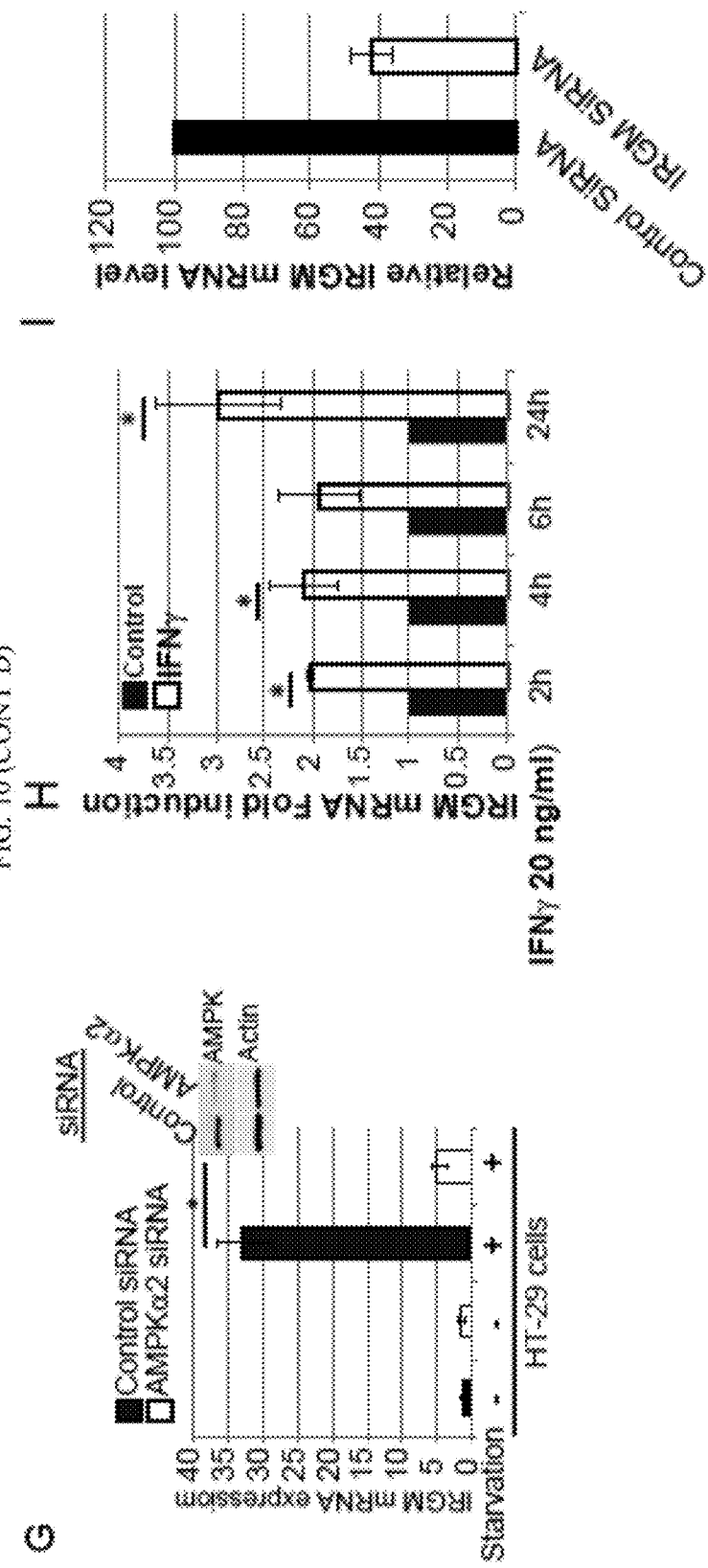

We observed that co-expression of GFP-IRGM had an effect on NOD2 protein amount, by diminishing its levels relative to control (FIG. 6A). IRGM promoted NOD2 degradation, which was partially blocked by bafilomycin A1, commonly used to inhibit autolysosomal degradation (FIG. 6B). The IRGM-$K^{mut}$ variant of IRGM displayed a decreased ability to commit NOD2 for degradation (FIG. 6C). In contrast to the destabilizing effects of IRGM on NOD2, expression of IRGM increased co-expressed myc-ULK1 in a dose-dependent manner (FIG. 6D). The total amount of ULK1 was not increased when the IRGM-Kmut variant was co-expressed (FIG. 6E). This effect was ULK1-specific, since Beclin 1 levels were not affected when IRGM vs IRGM-$K^{mut}$ were compared, corroborating with a related finding that IRGM did not affect Beclin 1 stability (FIG. 10B). Thus, polyubiquitinated IRGM protects ULK1 and promotes degradation of NOD2 (FIG. 6F). This represents a negative feedback regulatory loop, which induces autophagy but at the same time limits NOD2's ability to continue unabated stimulation of this process (FIG. 6G).

Figure 7:
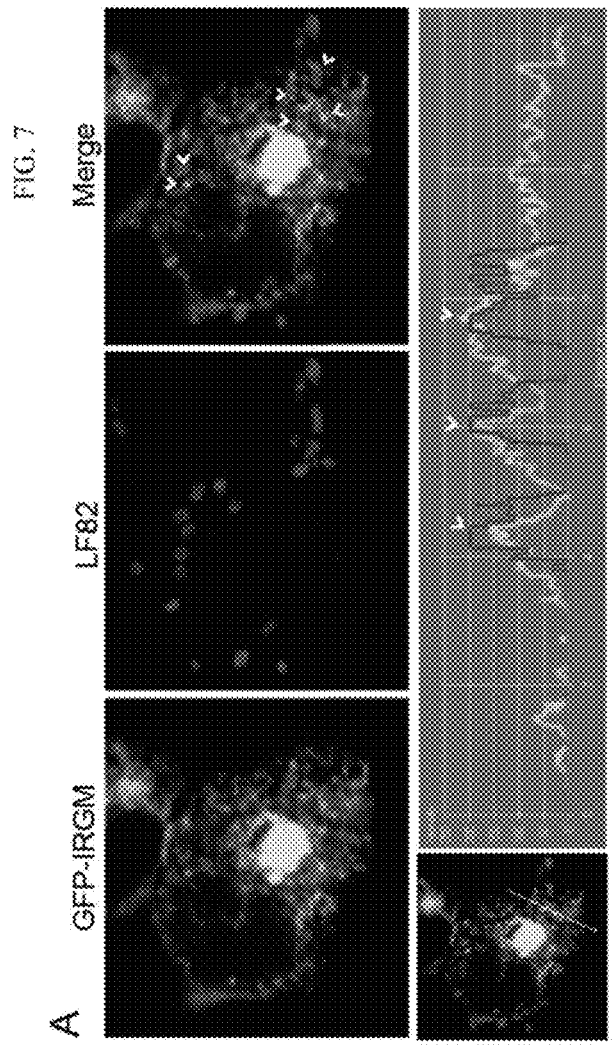
FIG. 7 shows that ubiquitination of IRGM is important for preventing inflammation. (A) Effect of IRGM (WT and K$^{mut}$) expression with and without NOD2 on the nuclear localization of NF-kB-p65 in HeLa cells upon E. coli LF82 infection. (B) Graph, mean % cells with NFkB-p65 nuclear localization (from 10 microscopic fields)±SD; *, p<0.05 (ANOVA). (C) Effect of E. coli infection on IL-1β mRNA expression in THP-1 cells subjected to IRGM knockdown (qRT-PCR normalized to GAPDH). Data, means±SD (n>3); *, p<0.05 (ANOVA). (D, E, F) Lysates of cells co-expressing either GFP or GFP-IRGM and (D) Flag-NOD1, (E) Flag-Rig-1, or (F) Flag-TLR3, subjected to immunoprecipitation with anti-GFP (D, E) or anti-Flag (F); blots were probed with indicated antibodies. (G) Effect of FLAG-tagged NOD1, RIG-I, or TLR3 expression on IRGM ubiquitination (K63-linked) in HEK293T cells. (H) Model of IRGM-mediated xenophagy. IRGM expression is induced by physiological cues including starvation, microbes, or microbial products (PAMPs). IRGM protein increases the abundance of active AMPK, which subsequently promotes autophagy by activating ULK1 and Beclin 1. Not only does IRGM amplify this fundamental autophagy signaling but it also assembles the core autophagy machinery. Association of IRGM with NOD2, which is enhanced in the presence of MDP, promotes IRGM ubiquitination and the assembly of autophagy initiation factors. Together, these molecular events promote antimicrobial autophagy and suppress excessive inflammatory responses. See also FIG. 13.
Figure 7:
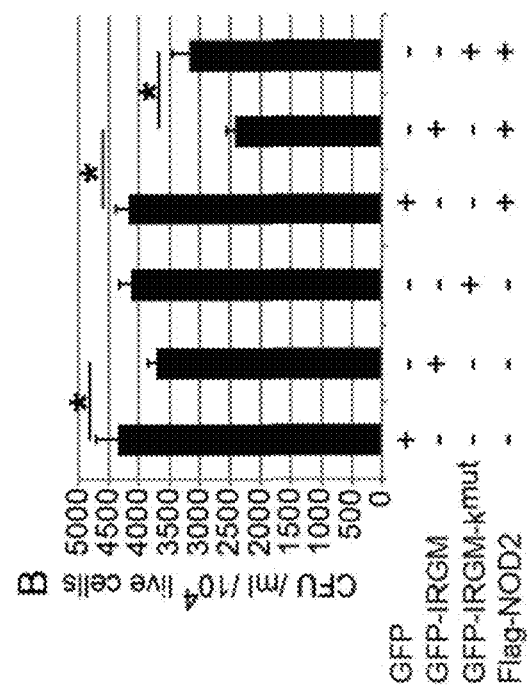
Figure 7:
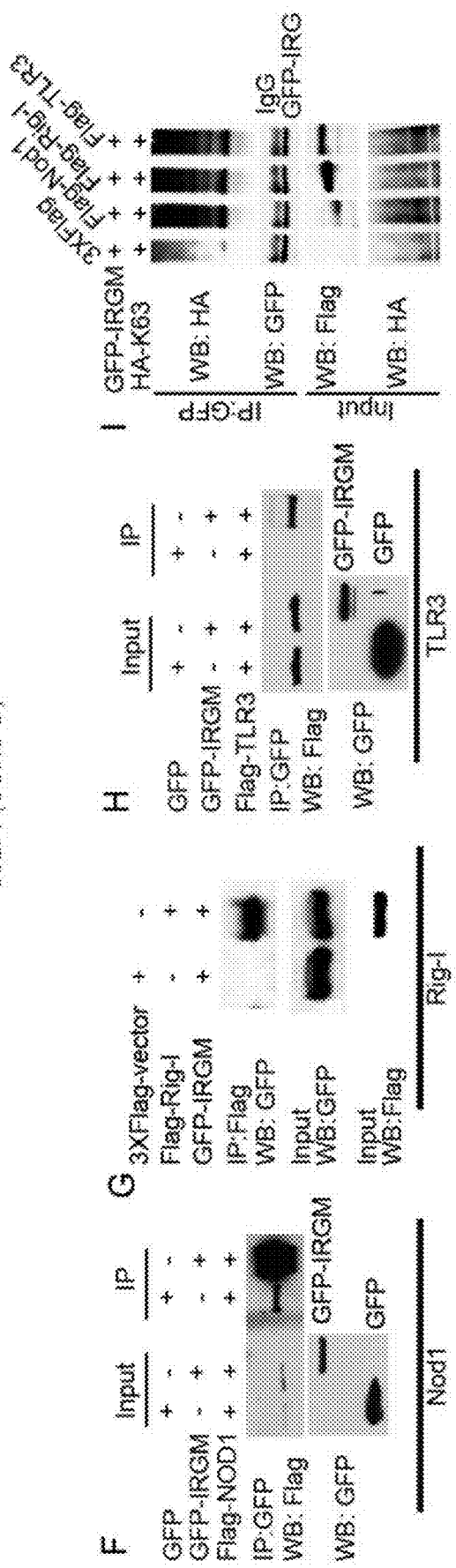
Figure 7:
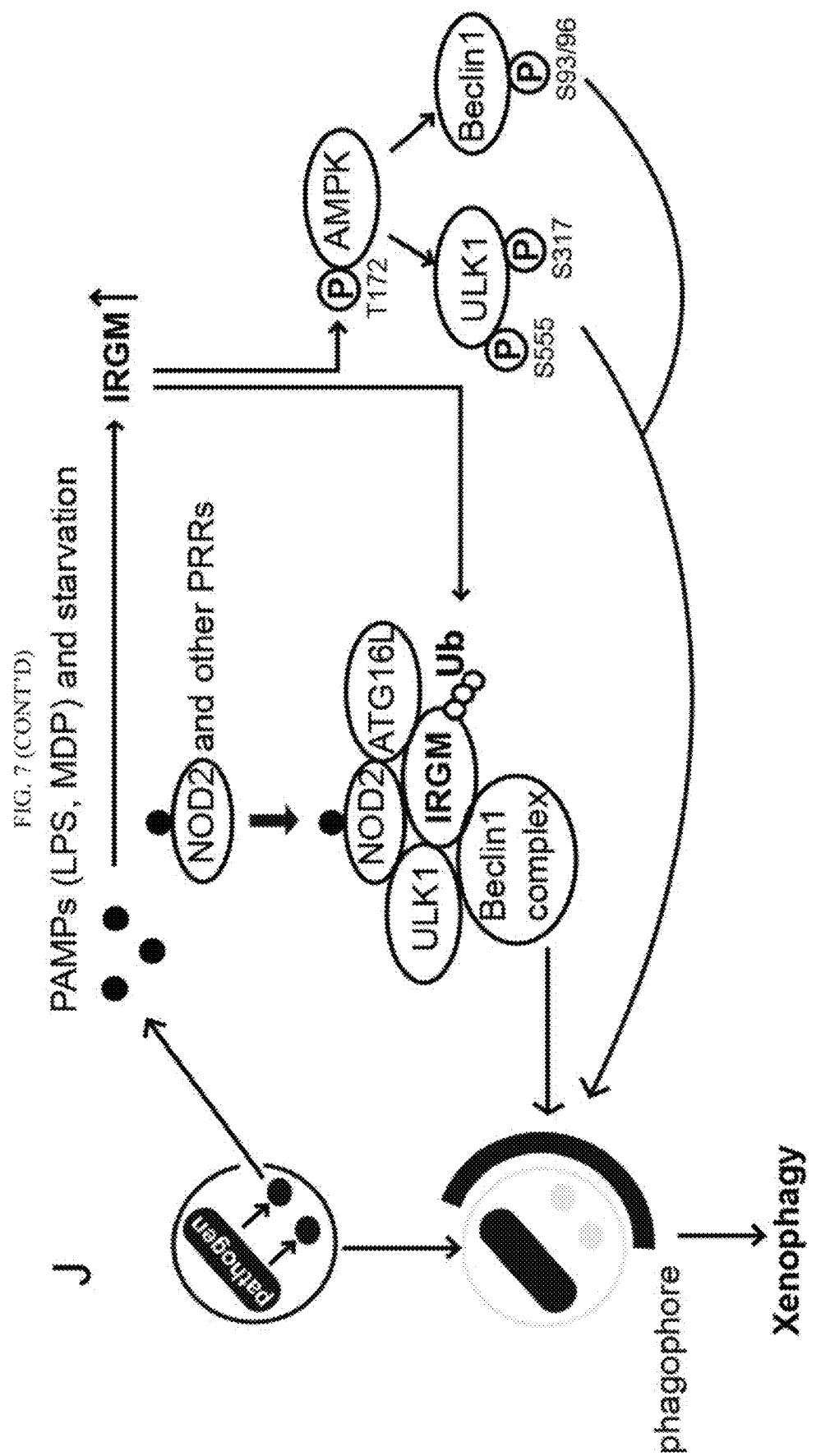
Figure 13:
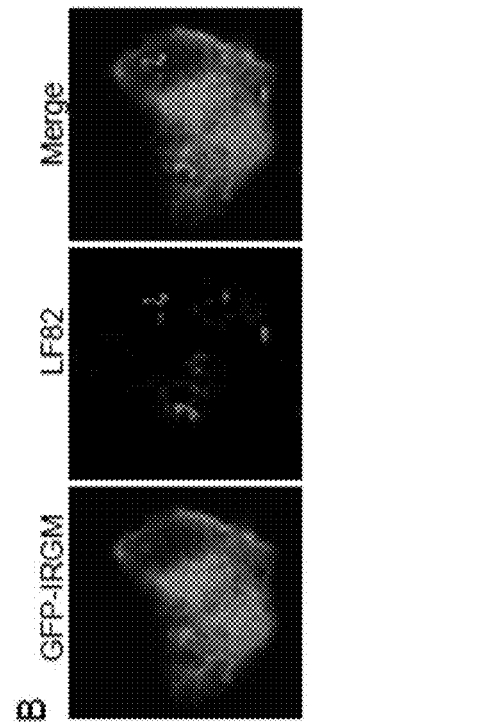
FIG. 13, related to FIG. 7 shows that ubiquitination of IRGM is important for its anti-inflammatory function. (A) Starvation reduces intracellular replication of invasive *E. coli* LF82 in HEK 293T cells. Results are expressed as mean±standard error of colony-forming units (cfu) per ml per 104 live cells. *, p<0.05. (B) Representative confocal images of GFP-IRGM transfected HEK293T cells infected with invasive *E. coli* LF82 (red, LPS antibody). (C) Analysis of NFκB-p65 nuclear translocation following LF82 infection in HeLa cells expressing GFP or GFP-IRGM or GFP-IRGM-Kmut and/or Flag-NOD2. (D) Graph showing the knock down efficiency of IRGM in LF82 infected THP-1 cells (E) Lysates of cells co-expressing control vector or Flag-IRGM and GFP-TLR4 were subjected to immunoprecipitation with anti-Flag and blots were probed with indicated antibodies.
Figure 13:
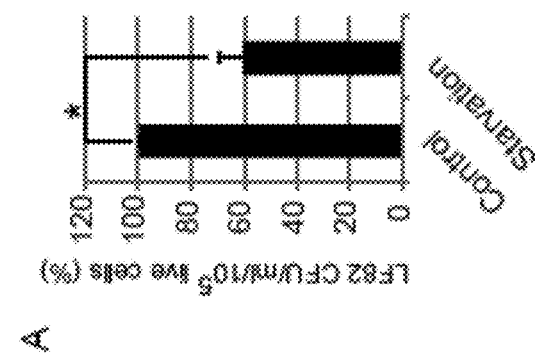
Figure 13:
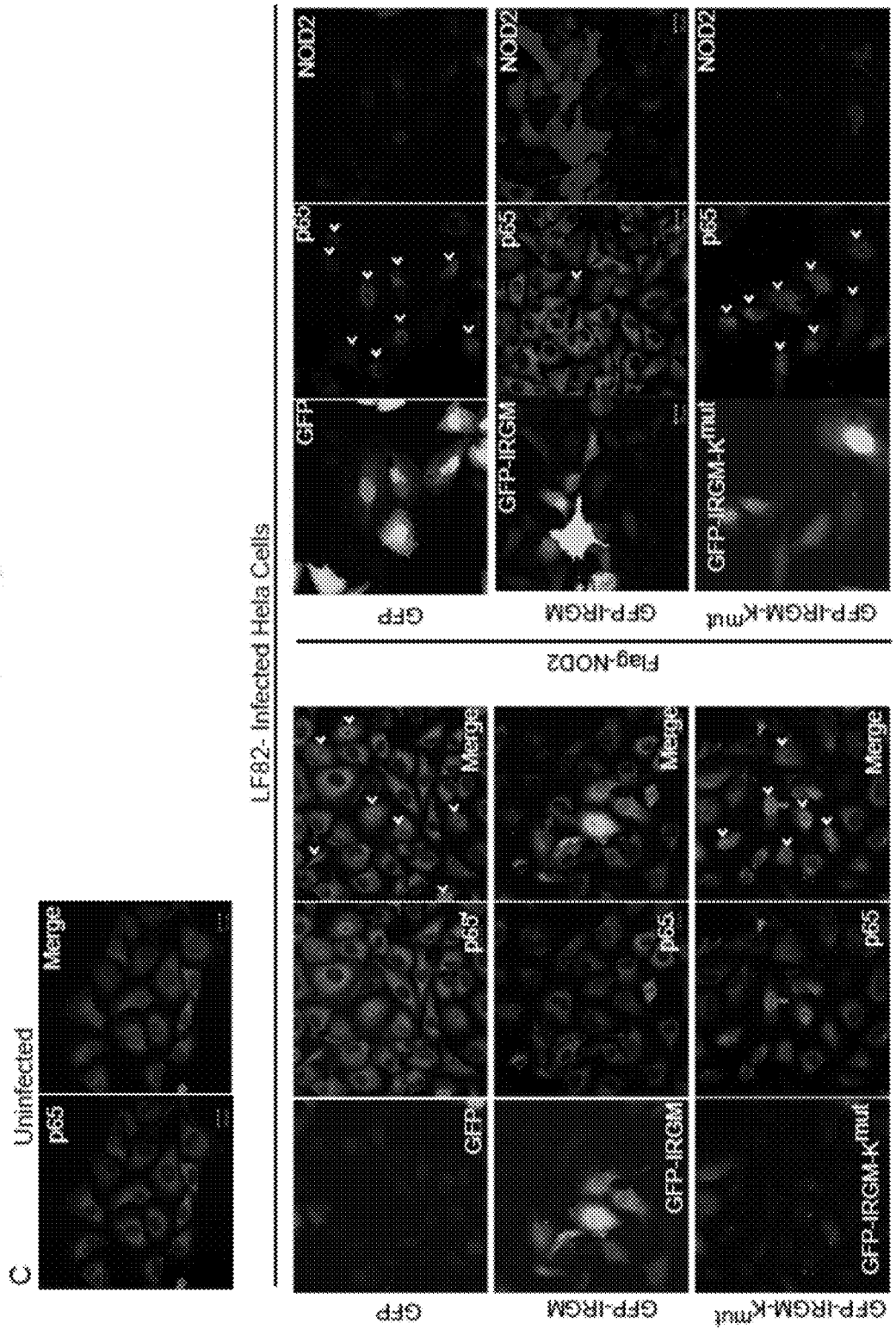

IRGM Affects Antimicrobial and Inflammatory Outputs and Interfaces with Several Innate Immunity Systems IRGM has been shown to control intracellular bacteria (Brest et al., 2011; McCarroll et al., 2008] (Singh et al., 2006). Using a model system of transfected epithelial cells previously developed by others (Brest et al., 2011; Lapaquette et al., 2010) for monitoring autophagic handling of invasive bacteria, we tested how IRGM-$K^{mut}$, the mutant form of IRGM disabled for ubiquitination and examined for its effects in molecular relationships above, affected a subset of IRGM's immune outputs. Co-expression of NOD2 with IRGM-$K^{mut}$ resulted in increased NF-kB p65 nuclear translocation in response to E. coli LF82 (a CD isolate of adherent invasive E. coli) (Lapaquette et al., 2010) relative to NOD2 co-expression with IRGM wild type (FIGS. 7A,B, FIG. 13A). Consistent with this observation, a monocytic cell line THP-1 infected with E. coli LF82 showed elevated pro-inflammatory response (increased IL-1β transcription) when IRGM was knocked down (FIG. 7C, FIG. 13B). The increased NF-kB response with IRGM-$K^{mut}$ (FIGS. 7A,B) was mirrored in the effects of expressing IRGM or IRGM-$K^{mut}$ on bacterial survival, reflected in the diminished ability of IRGM-$K^{mut}$ to control E. coli LF82 (FIG. 13C). Although IRGM expression on its own enhanced bacterial elimination, this was increased by co-expression with NOD2, an effect that was diminished when IRGM-$K^{mut}$ was employed (FIG. 13C). Although the overall magnitude of the effects on bacterial killing was subtle, it was in keeping with the known limitations of the system (Brest et al., 2011; Lapaquette et al., 2010) as reflected in its maximum output (upon starvation induction) of bacterial control by autophagy (FIG. 13D). Based on the above experiments with IRGM-$K^{mut}$, the properties of IRGM that are essential for the assembly of the core autophagy machinery affect its antimicrobial and inflammatory outputs.

The inventors also tested localization of IRGM relative to the CD isolate E. coli LF82 (Lapaquette et al., 2010). We observed that without the co-expression of NOD2, IRGM had a diffuse cytosolic localization even when the cells were infected with bacteria (FIG. 7A). However, when NOD2 was co-expressed with GFP-IRGM, IRGM was recruited to the invading bacteria (FIG. 7B), in keeping the previously observed recruitment of ATG16L1 and NOD2 to bacterial entry sites (Travassos et al., 2010). While studying IRGM interacting partners, we observed a further ability of IRGM to engage other pattern recognition receptors (PRRs), such as NOD1, RIG-I, and TLR3 (FIGS. 7D-F). In contrast, IRGM did not interact with TLR4 (FIG. 7C). Similarly to NOD2, NOD1, RIG-I, and TLR3 induced IRGM ubiquitination (FIG. 7G). In conclusion, not only does IRGM assemble the core autophagy machinery to control innate immune responses to NOD2 agonists, but IRGM potentially has a broader repertoire of interactors among the PRR systems.

Discussion (IRGM Examples)

In these examples, the inventors have shown that human IRGM, hitherto believed to have indirect effects on autophagy, directly governs the assembly of the principal autophagy regulators. Furthermore, it physically links the microbial sensors, including NOD2, to the core autophagic apparatus. This solves the long-standing puzzle regarding how IRGM works, and places it mechanistically at the center of action in autophagic responses to microbes. IRGM assembles ULK1 and Beclin 1 in their activated forms to promote autophagy. Of relevance for how these proteins become activated is that IRGM also stimulates AMPK by stabilizing it in its Thr-172 phosphorylated form, which is required for AMPK activation (Mihaylova and Shaw, 2011). This is likely due to effects of IRGM on mitochondria (Singh et al., 2010), which activates AMPK (Romanello et al., 2010; Turkieh et al., 2014), and may involve specific kinases upstream of AMPK including TAK1 (Criollo et al., 2011) and CAMKKβ (Hoyer-Hansen et al., 2007) that have been shown to phosphorylate AMPK at Thr-172 (Mihaylova and Shaw, 2011) and activate autophagy (Criollo et al., 2011; Hoyer-Hansen et al., 2007). The stabilization of phospho-Thr-172 AMPK likely contributes to AMPK-dependent phosphorylation and activation of ULK1 (Egan et al., 2011; Kim et al., 2011) and Beclin 1 (Kim et al., 2013). Consistent with this, IRGM increases total activated ULK1 phosphorylated at Ser-317 and Ser-555 by AMPK (Egan et al., 2011; Kim et al., 2011), and the activated form of Beclin 1 that is phosphorylated at Ser-15 by ULK1 (Kim et al., 2013) and at Ser-93 and Ser-96 by AMPK (Kim et al., 2013). IRGM has a second effect on autophagic regulators by assembling the activated ULK1 with Beclin 1. Thus, IRGM promotes phosphorylation cascade of key autophagy regulators and assembles them into autophagy initiation complexes (FIG. 7J).

Of interest is that IRGM increases levels of a number of autophagy regulators (ULK1, ATG14L, AMBRA1, and ATGL1) but does not affect the stability of others (Beclin 1 and the ATG5-ATG12 complex). The apparent absence of effects on Beclin 1 stability may be explained by the bulk of Beclin 1 being predominantly in non-autophagy related hVPS34 complexes whereas ATG14L-associated Beclin 1 represents a minority of Beclin 1 species in the cell (Kim et al., 2013). IRGM also has an effect on NOD2 levels. However, IRGM reduces NOD2 levels, in contrast to IRGM-dependent stabilization of autophagy regulators. We interpret this dichotomy as a part of the well tuned circuitry in response to microbial challenge: whereas autophagy is activated as an antimicrobial effector mechanism, the stimulatory inputs into the system mediated by NOD2 are downregulated lest the system overcommits, which in turn may result in detrimental consequences for the host. PAMP (e.g. MDP) tolerance is an important mechanism to avoid septic shock, which is in part achieved by NOD2 degradation (Zurek et al., 2012).

It has been previously shown that ATG16L1 and NOD2 interact (Cooney et al., 2010; Travassos et al., 2010). This has placed two of the Crohn's disease-genetic risk factors together, but has left the role of IRGM unexplained. The data presented here show that IRGM is in complexes with ATG16L1 and NOD2 and that IRGM enhances assembly of Atg16L1 with NOD2. Moreover, IRGM affects the stability of each of the components of this complex. Although bringing ATG16L1 to the bacterial entry site marked by NOD2 is a previously known important step (Travassos et al., 2010), how this links up with the core autophagy regulators including ULK1 and Beclin 1 has not been addressed in prior studies. In this work we show that IRGM plays that bridging role by stimulating phosphorylation and activation of key autophagy regulators and placing them together with ATG16L1 (FIG. 7J). This point is not trivial, as for example it has not been easy to connect the two seemingly separate systems of autophagy initiation: ULK1-Beclin1 complexes vs. LC3-II conjugation and localized autophagosomal membrane build up. Only recently a part of this key issue has been solved for conventional (non-immunological) autophagy by showing that ATG16L1 and WIPI2 directly interact (Dooley et al., 2014), with WIPI2 recognizing the lipid modification products of the Beclin 1-directed hVPS34 activity. We propose here that IRGM acts with a similar purpose by bridging ULK1-Beclin 1 complexes with the autophagy conjugation machinery, as shown here for ATG16L1. This can additionally explain why ATG5 is found in IRGM complexes (Gregoire et al., 2011).

Ubiquitination has been implicated in autophagy in several ways primarily in targeting of substrates for autophagic elimination (Stolz et al., 2014). However, the role of K63-linked polyubiquitination has also begun to be appreciated as a mechanism for stabilization of large autophagy-initiating complexes (Nazio et al., 2013; Shi and Kehrl, 2010). Polyubiquitination of IRGM and its role in autophagy (FIG. 7J) does not play a role in targeting substrates for autophagy; instead, it stabilizes multi-protein autophagy initiation complexes. The ubiquitination of IRGM is under the control by NOD2. NOD2 enhances association of ubiquitination-competent IRGM with ULK1 and Beclin 1, whereas NOD2 has no similar effect on the ubiquitination-null mutant of IRGM (IRGM-$K^{mut}$). Importantly, IRGM-$K^{mut}$ retains certain activities: it maintains the ability to bind ATG16L1 equally well as the ubiquitination-competent IRGM.

IRGM gene expression is cell-type dependent and responds to both starvation and microbial products. IRGM is particularly inducible in cells (intestinal epithelial cells and macrophages) derived from tissues affected in diseases where IRGM has been implicated as a genetic risk factor: CD and tuberculosis (Consortium, 2007; Craddock et al., 2010; Intemann et al., 2009). PAMPs induce autophagy in macrophages through IRGM linking the PAMP detection by NOD2 with the autophagic machinery activation (FIG. 7J). IRGM controls not just initiation of autophagy but may also affect its maturation. IRGM complexes include UVRAG, a regulator of autophagic maturation (Itakura et al., 2008). IRGM displaces Rubicon, known to inhibit maturation complexes (Matsunaga et al., 2009). Thus, IRGM controls several points along the autophagy pathway and contributes to efficient xenophagy. In conclusion, IRGM orchestrates antimicrobial autophagic responses. We have shown here how IRGM does that and what are the exact molecular processes that IRGM controls. This explains the hitherto mysterious role of IRGM in autophagy, places it at the center of molecular complexes controlling and executing autophagy, and molecularly connects biological inputs with autophagic outputs. Finally, our findings indicate that IRGM links up not only with NOD2 but also with several other PRRs, such as NOD1, RIG-I and TLR3. Thus, IRGM and possibly its distant IRG homologs in other vertebrates may act as transmission modules between a selective sub-repertoire of innate immune responses and the autophagy machinery.

FURTHER EXAMPLES

Second Set—Precision Autophagy Examples

Material and Methods
Cells, Plasmids, siRNA, and Transfection

THP-1, HeLa and HEK293T cells were from ATCC. Human peripheral blood monocytes were from StemCell Technologies or from healthy individual donors, and cultured as described previously (Gutierrez et al., 2004). THP-1 cells were differentiated with PMA (50 nM) for overnight before use. Full-length human TRIM20 was synthesized and TRIM21 was purchased from DNASU, and both were cloned by PCR into pDONR221. The TRIMs mutants were generated by site-directed mutagenesis and confirmed by sequencing. pENTR or pDONR221 vectors were generated by BP cloning and expression vectors were made by the LR reaction (Gateway; Invitrogen). Other plasmids used were Beclin 1 and its deletion mutants (from B. Levine), ULK1 (from S. Tooze), ATG16L1 and its deletion mutants (from R. Xavier), pCI-Caspase 1 (from K. Fitzgerald), IRF3 (DNASU), pUNO1-hNLRP3a and pUNO1-hNLRP1 (Invivogen). siRNAs were from Dharmacon, and were delivered to cells by either RNAiMax (Lifetechnologies) or nucleoporation (Amaxa). Plasmid transfections were performed by either calcium phosphate or nucleoporation (Amaxa). Herring testis (HT)-DNA (Sigma) was transfected as described previously (Gao et al., 2013).

Bacterial and Viral Infection

For infection studies, *Escherichia coli* strain LF82 (Lapaquette et al., 2010) was infected at MOI of 1:20. Single-cycle infection HIV-1 viruses were generated as previously described (Mandell et al., 2014), were infected to undifferentiated THP-1 cells (Gao et al., 2013).

Antibodies and Reagents

Antibodies used were: Flag (Sigma), HA (Roche), LC3 (Sigma), AMPK, ULK1 p-Ser 317 and p-Ser 555 (Cell signalling), NLRP1 (Cell signaling), NLRP3 (Adipogen), Caspase-1 and ULK1 (Santa Cruz), and GFP, IRF3, Myc and Actin (Abcam). To determine autophagic activity by immunoblotting, cells were cultured in the presence of bafilomycin A1, and lysates were subjected to immunoblotting as described previously (Mizushima et al., 2010). The reagents used were Ultrapure LPS (Invivogen), IFN-γ (PeproTech), Cytotoxic LDH assay (Promega), TO-PRO-3 Iodide (lifetechnologies). Immunoblotting, immunostaining were conducted as described (Kyei et al., 2009). FAM-YVAD-FMK stainings (FLICA, ImmunoChemistry Technologies) were performed according to the manufacture's instruction.

IL-1β Measurement

For IL-1β secretion, THP-1 cells that had been subjected to the differentiation with PMA (50 nM) for overnight, were treated with 2.5 µg/mL LPS for 2 h, and then treated with nigericin (20 µM) for 30 min. IL-1β measurements were performed using HEK-Blue IL-1β Cells (Invivogen).

TRIM Family Screen

THP-1 cells were cultured in 96-well plates containing SMARTpool siRNA (Dharmacon), RNAiMax (Lifetechnologies), and PMA. Culture media were changed after overnight incubation, and forty-eight hours after plating, cells were treated with IFN-γ or vehicle for 4 hr, and then fixed and stained to detect endogenous LC3 (Alexa Fluor 488 as a flurochrome) and nuclei (Hoechst 33342). Plates with cells were subjected to high content analysis for image acquisition and data processing. Two separate siRNA screen for induced autophagy were carried out with the cutoff (>3 SDs change relative to the mean of stimulated control) for hits.

High Content Image Analysis

High content imaging and analysis was performed using a Cellomics $V^{TI}$ HCS scanner and iDEV software (Thermo-Scientific). Automated epifluorescence image collection was carried out until a minimum of 500 cells per well per siRNA knockdown per plate was acquired. Epifluorescnece images were machine analyzed using present scanning parameters and object mask definitions. Hoechst 33342 staining were used to automatically detect cellular outlines based on background staining of the cytoplasm, and the mean count of LC3 puncta per cell was determined. Autophagy induction with IFN-γ resulted in a Z' value of 0.87.

High Content Analysis of Puncta in Subpopulations of Transfected Cells

HeLa and THP-1 cells were transfected with plasmids or siRNA, and cultured in full media for overnight (plasmids) or 48 h (siRNA). Cells were then fixed and stained to detect, LC3 (Alexa Fluor 488 or 568 as fluorochromes), GFP, and nuclei. High content imaging and analysis was performed using a Cellomics $V^{TI}$ HCS scanner and iDEV software (ThermoScientific). >200 cells were analyzed in more than quadruplicate manner using a 20× objective at room temperature. Hoechst 33342 staining were used to automatically detect cellular outlines based on background Hoechst staining, and the mean total count or area of punctate of LC3, or TRIM20 per cell was determined. For sub-population analyses, cells that have above the threshold of the background fluorescence were gated as successfully transfected ones.

Fluorescence Confocal Microscope Image Acquisition

Fluorescence confocal microscopy was carried out as described previously (Kyei et al., 2009). In brief, Images were acquired using a Zeiss META microscope equipped with a 63×/1.4 NA oil objective, LSM META camera and AIM software (Zeiss) at room temperature. Fluorochromes associated with secondary antibodies were Alexa Fluor 488, 568, or 647. The images were adjusted for brightness and contrast using ImageJ.

IRF3 Dimerization Assay and Quantitative RT-PCR.

Detection of IRF3 dimerization was performed by native polyacrylamide gel electrophoresis (PAGE) as previously described (Takahasi et al., 2003). Quantitative RT-PCR was performed as previously described (Kimura et al., 2013) using the following primer sets: ULK1, (AGATGTTCCA-GCACCGTGAG, AATGCACAGCTTGCACTTGG); BECN1, (GGAGAACCTCAGCCGAAGAC, ACGTT-GAGCTGAGTGTCCAG); ACTIN, (GGGCATGGGTCA-GAAGGATT, TCGATGGGGTACTTCAGGGT); TRIM1, (AAGAATGTGACGAGTTGGTAGAG, ATGAGGACT-GTTGACCGTTC); TRIM5, (CATGCCTCACTGCAAAC-CAC, GGTAACTGATCCGGCACACA); TRIM8, (ATC-CTGATGGACAGGACCCA, CTCCTTCTTGGCCACTTCGT); TRIM16, (GTAAGC-CCACGAACACAAATG, TCCAGCCCTGAAACTTCT-ATTC); TRIM20, (CTGAGTCAGGAGCACCAAGG, GCTGCTCCTCCCCTGATTTT); TRIM21, (CAGTCTCG-GAAACACCGTGA, AATGCCACCTGGAGCTTCTC); TRIM22, (CTCGACCTGCTTATCCGTATTT, CTCAGCA-CAAGGGCTACTATG); TRIM28, (CCATACTGT-GCGCTCTACTG, GGTTCATGCTTGTGTACGTTG); TRIM56, (TTCTTCGTCAATGGGCTGCT, AAGT-CATCGGCACAGTCCAG); and TRIM65, (GATCTACCT-GAACTTGCCTCTG, GAGGAGGGAGGAATCTGTCT). For IFN-β and GAPDH, Taqman probes and real-time PCR master mixes were used.

Co-Immunoprecipitation and GST Pull-Down

Co-immunoprecipitations were performed as previously described (Kyei et al., 2009) with slight modification. In brief, cells were lysed with NP-40 buffer (lifetechnologies) containing 1 mM PMSF and protease inhibitor cocktail (Roche) for 45 min, followed by centrifugation. Supernatants were incubated for 2 h with antibodies at 4° C. The immune complexes were captured with Dynabeads (lifetechnologies). Immunoprecipitates were washed three times with PBS, eluted with Laemmli SDS-PAGE sample buffer, and subjected to immunoblots analysis.

GST and GST-tagged proteins were expressed in *Escherichia coli* BL21 (DE3) or SoluBL21 (Amsbio). GST and GST-fusion proteins were purified and immobilized on glutathione-coupled sepharose beads (Amersham Bioscience, Glutathione-sepharose 4 Fast Flow) and pull-down assays with in vitro translated [$^{35}$S]-labeled proteins were done as described previously (Pankiv et al., 2007). The [$^{35}$S] labeled proteins were produced using the TNT T7 Quick Coupled Transcription/Translation System (Promega) in the presence of [35 S] L-methionine. The proteins were eluted from washed beads by boiling for 5 min in SDS-PAGE gel loading buffer, separated by SDS-PAGE, and radiolabeled proteins detected in a Fujifilm bioimaging analyzer BAS-5000 (Fuji).

Peptide Array Overlay Assay

Peptide arrays were synthesized on cellulose membrane using a MultiPep automated peptide synthesizer (INTAVIS Bioanalytical Instruments AG, Germany) as described previously (Kramer et al., 1996). Interaction analyses between peptide and recombinant protein were probed by overlaying the membranes with recombinant protein, and bound proteins were detected with HRP-conjugated anti-GST antibody (clone RPN1236; GE Healthcare).

Statistical Analyses

Either a two-tailed Student's t test or ANOVA were used. Statistical significance was defined as P<0.05.

Cell Culture

Cell lines were maintained and primary human peripheral blood-monocyte-derived macrophages were isolated and maintained as described (Gutierrez et al., 2004).

Transfections

Plasmid transfections in HEK293T were performed using ProFection Mammalian Transfection System from Promega; siRNAs were delivered to cells by nucleoporation (Amaxa).

Microscopy Analyses and Quantification

Immunofluorescence was performed as described earlier (Kyei et al., 2009). For quantification of puncta, images from different fields were captured and analyzed. For quantification of total cell fluorescence, image J was used as described previously (Chauhan et al., 2013).

Gene Expression Analysis

Total RNA was isolated from cell culture using Trizol as per the manufacturer's instruction (Invitrogen). For quantitative real-time PCR: TURBO DNA-free kit (Ambion) was used to remove contaminating residual DNA; cDNA was prepared using the high capacity cDNA reverse transcription kit as per the manufacturer's instruction (Applied Biosytem). Taqman probes (Applied Biosystem) and real-time PCR master mixes (Applied Biosystem) were used for real-time PCR as per the manufacturer's instruction. Data were normalized using GAPDH.

Cytokine and NF-kB Responses

For NFkB-p65 nuclear localization assay, HeLa cells were platted on cover slips a day before infection. Cells were infected with AIEC LF82 strain at MOI of 1:20 for 2 h followed by washings with PBS and fixing the cells with 4% paraformaldehyde. Cells were visualized using a laser confocal microscope and images were captured using LSM510 software. For IL-1β measurement, IL-1β transcription was determined using qRT-PCR in THP-1 cells.

Bacterial Survival Analyses

AIEC LF82 survival assay was performed as described previously (Lapaquette et al., 2010). HEK293T cells were infected with AIEC LF82 of MOI of 1:20 for 3 h. Cells were treated with gentamycin (100 µg/ml) for 1 h followed by incubation in fresh media for 2 h. Cells were lysed and surviving bacteria quantified by plating and determining colony forming units.

Proximity Ligation Assay (PLA)

HEK293T cells transiently expressing the plasmid constructs were fixed and PLA (Soderberg et al., 2006) performed according to the manufacturer's protocol (Olink Bioscience). Samples were then imaged and analyzed by high content microscopy using a CellomicsArrayScan (Thermo Scientific) with images analyzed using pre-set parameters for cell and PLA puncta identification within iDev software (Thermo Scientific). The average total area of red PLA puncta was determined per cell for a minimum of 500 GFP-IRGM positive cells.

Flag Pull-Down Assay

Figure 14:
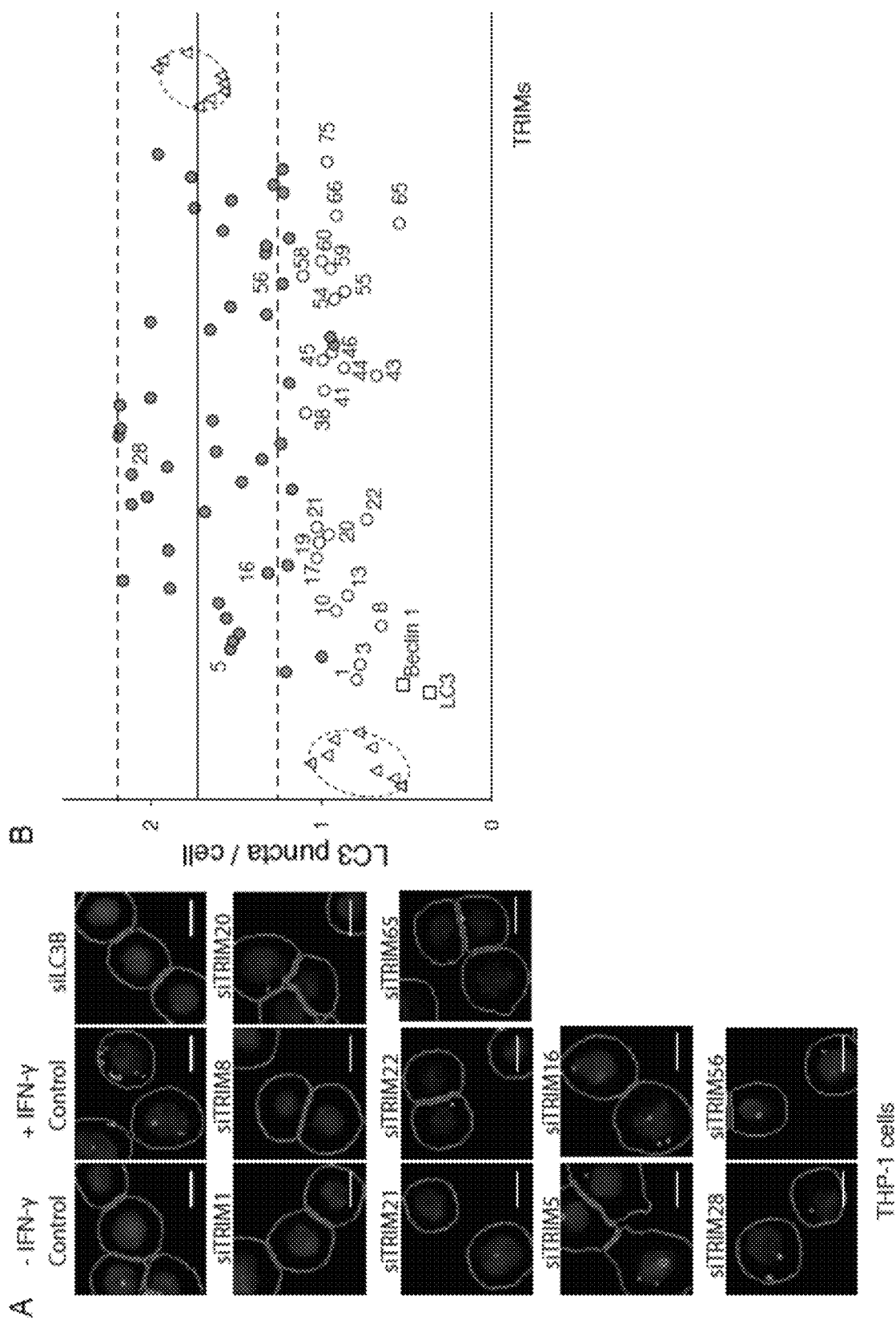
FIG. 14 shows that TRIM proteins regulate IFN-γ-induced autophagy. (A) THP-1 cells were subjected to TRIM knockdown, treated with 1,000 U/mL IFN-γ for 4 h, and high content (HC) analysis was performed using a Cellomics HCS scanner (epifluorescence) and iDEV software. HC (magenta, endogenous LC3B immunofluorescence [IF]; blue, nuclei stained with Hoechst). Mask overlay, software-defined objects (primary objects, cell outlines; internal secondary objects, LC3 puncta). (B) Average count of LC3 puncta per cell from cells treated as in (A) (Data from two 96-well plates with identical siRNA arrangements; the corresponding data are shown in Supplementary FIG. 1C). Encircled are INF-γ-treated wells (right) and wells with vehicle controls (bottom left). TRIM knockdowns that reduced LC3 puncta readout in both two experiments by 3 SDs (horizontal dot lines) from the average of IFN-γ-treated controls (horizontal solid line) are indicated by corresponding TRIM numbers (open circle). TRIMs that were chosen in follow-up experiments in FIG. 1C are also indicated with number. (C) Similar to (B), except that THP-1 cells were subjected to specific TRIM or scrambled (Scr; control) knockdown, and were analyzed in more than quadruplicate manner. (D) Model of TRIMs-mediated IFN-γ-induced autophagy based on the results obtained in FIG. 1 and FIG. S1 thus far. (E) THP-1 cells were treated with TRIM20 or Scr siRNAs, treated with or without IFN-γ for 4 h in the presence of bafilomycin A1, and LC3-II conversion was determined by immunoblots. (F) HeLa cells were transfected with GFP or GFP-TRIM20, and HC analysis performed. Data, means±SE, n≥3, *P<0.05; †P≥0.05 (ANOVA). Scale bars, 5 μm.
Figure 14:
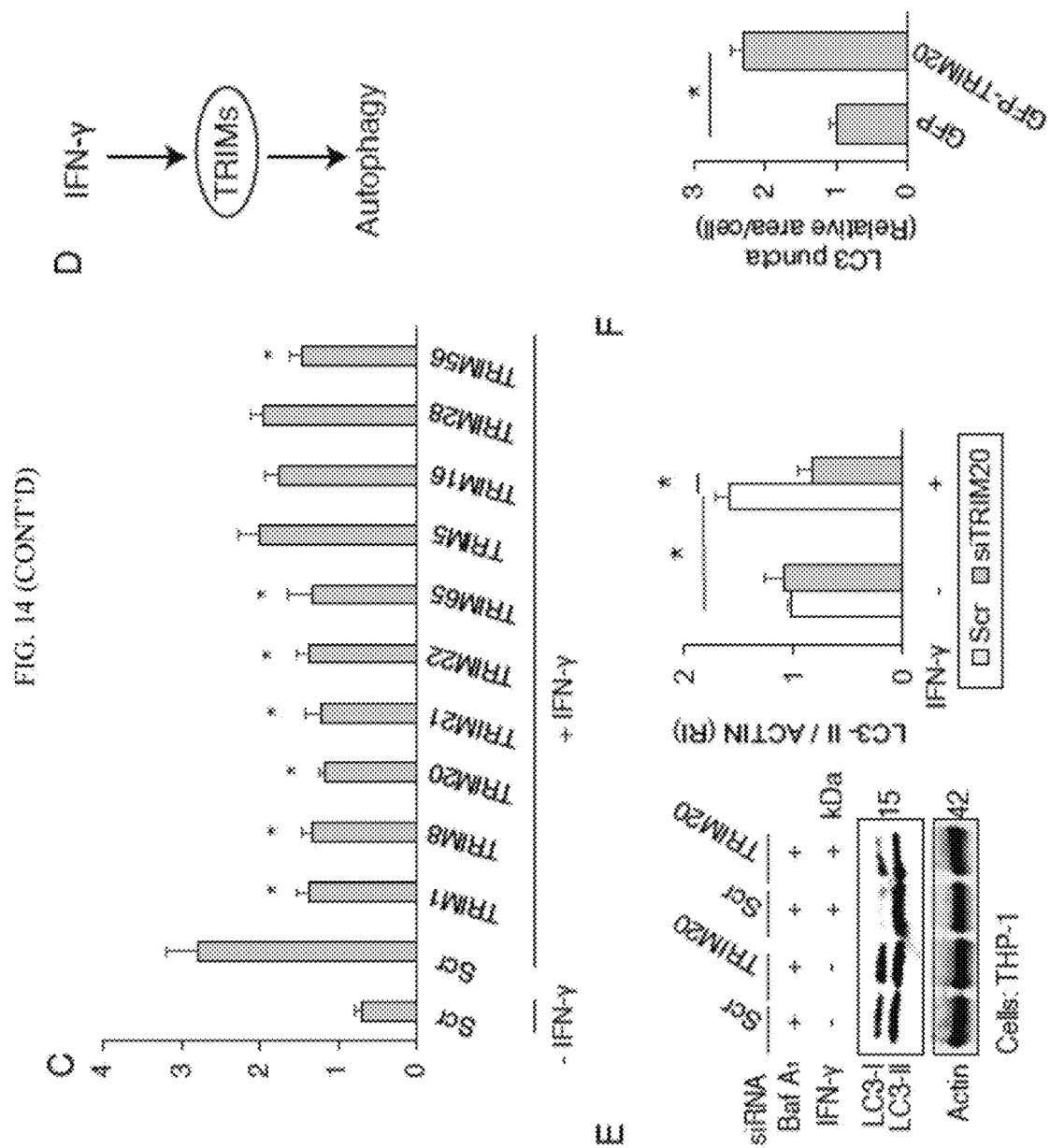
Figure 22:
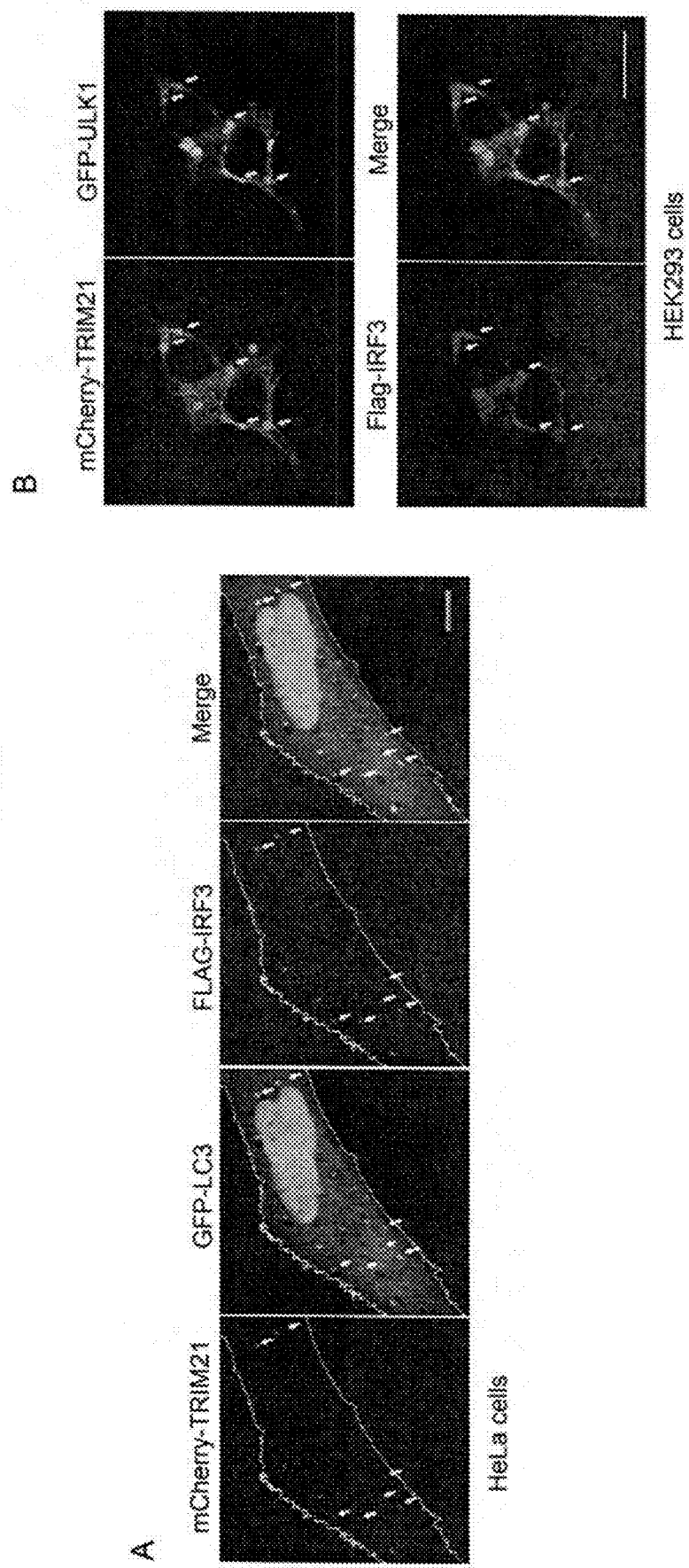
FIG. 22 shows that TRIM proteins regulate IFN-γ-induced autophagy. (A and B) High content image analysis of LC3 puncta in (A) THP-1 cells or (B) human MDM cells treated with IFN-γ for 4 h. HC and mask overlays are as in FIG. 1. (C) Screen data from FIG. 1B showing average±range. (D) Knockdown efficacy of TRIMs were determined by RT-PCR. (E and F) THP-1 cells were treated with (E) escalating doses of IFN-γ for 4 h or (F) 1,000 U/ml of IFN-γ for indicated times, and TRIM20 mRNA levels were determined by quantitative RT-PCR. Values are standardized to (E) no IFN-γ control or (F) 0 h time point. (G) THP-1 cells were subjected to TRIM20 or scrambled siRNA, treated with IFN-γ for 4 h, and HC analysis performed. (H) Knockdown of TRIM20 mRNA levels was examined by quantitative RT-PCR. Values are standardized to control (Scr, scrambled; no IFN-γ). (I) LC3-II conversion in HEK293 cells transfected with GFP-TRIM20 (T20) or GFP. Data, means±SE, n≥3 experiments, except panel (C). Scale bars, 5 μm. *P<0.05, †P≥0.05 (t test in (B) or ANOVA (other panels)).
Figure 22:
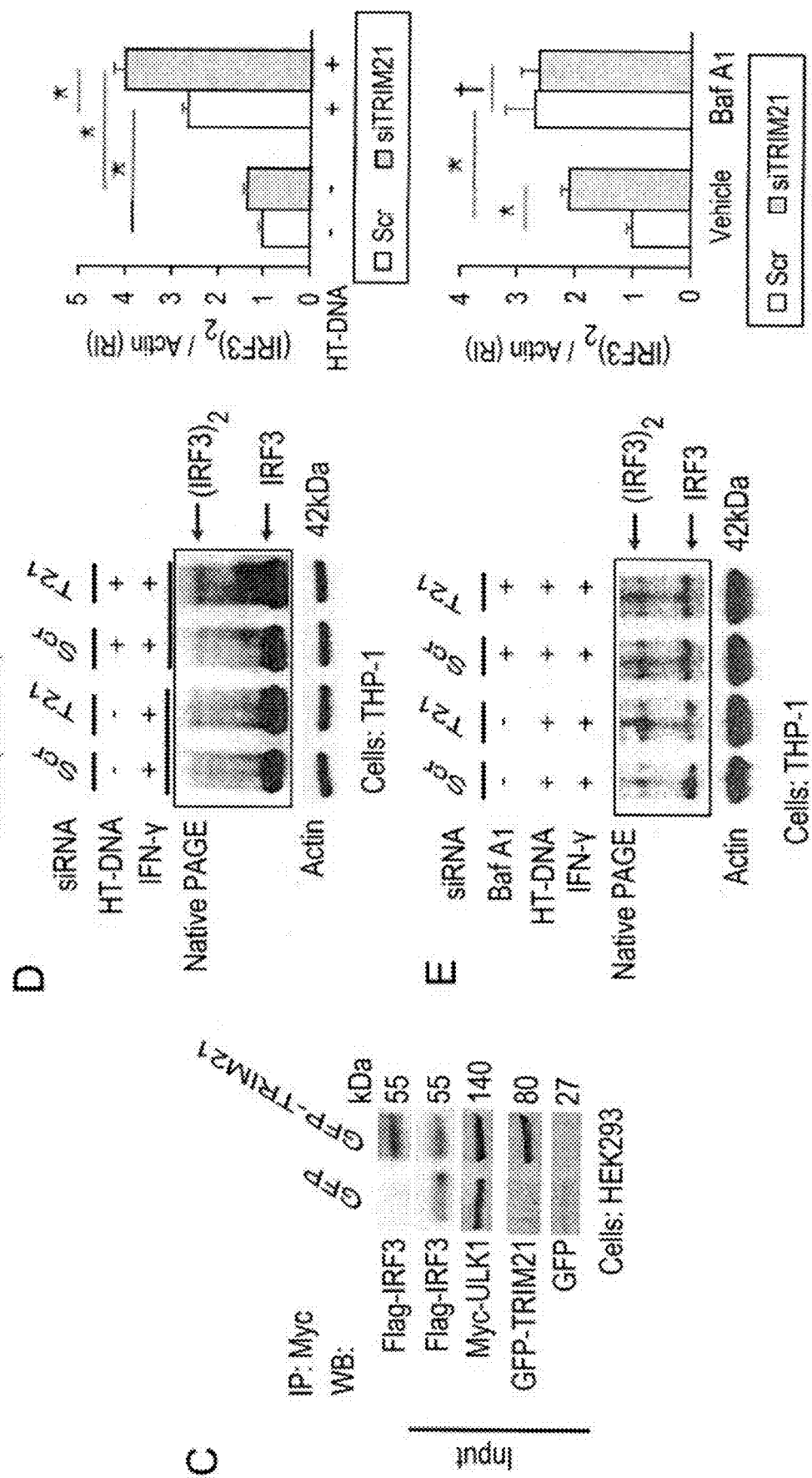
Figure 22:
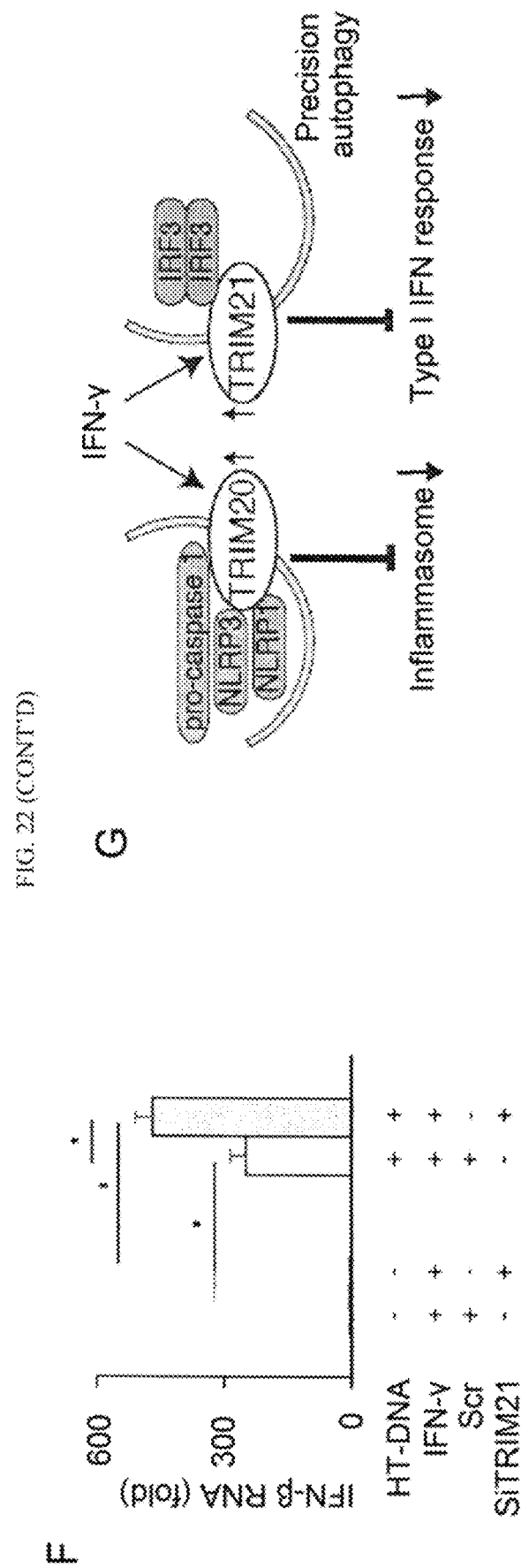

Lysates of HEK293T cells transiently expressing the Flag-NOD2 constructs were incubated with anti-Flag magnetic beads (Sigma) for 2 h. Beads were washed thoroughly (5×) to remove unbound contaminants. The collected beads were incubated with purified recombinant proteins (GST or GST-IRGMd (Singh et al., 2010)) for 2 h and then washed again (5×). The beads were boiled in SDS-PAGE buffer and subjected to Western blotting IFN-γ induces autophagy (Fabri et al., 2011; Gutierrez et al., 2004; Inbal et al., 2002) and influences cytokine networks and polarization of immune systems (Ghezzi and Dinarello, 1988; Mishra et al., 2013; Schroder and Tschopp, 2010), whereas TRIMs are involved in immune responses (Kawai and Akira, 2011) and, through an assortment of proposed mechanisms affect autophagy (Barde et al., 2013; Khan et al., 2014; Mandell et al., 2014; Niida et al., 2010; Pineda et al., 2015; Pizon et al., 2013; Tomar et al., 2012; Yang et al., 2013). IFN-γ can induce expression of a subset of TRIMs (Carthagena et al., 2009). We wondered whether TRIMs might be contributing mediators to autophagy induction by IFN-γ. We employed an image-based high content (HC) analysis of LC3 puncta (FIG. 14A) to screen for effects of TRIM knockdowns on IFN-γ-induced autophagy in human myelomonocytic cells. IFN-γ induced autophagy in THP-1 (FIG. 14A), also showing dose dependence (FIG. 22A PRECISION), and in primary human macrophages (FIG. 22B). For standardization, we used THP-1 cells for the screen (FIG. 1B and FIG. 22C). Out of the 70 human TRIMs tested, knockdowns of 24 different TRIMs reduced endogenous LC3 puncta per cell under IFN-γ treatment (FIG. 14B, open circles; FIG. 22C shows average±range values from two independent screens). We followed this up by individual knockdowns of a subset of 6 positive and 4 neutral TRIMs from the screen (FIG. 14C). All 6 TRIMs that were positive hits from the screen, TRIM1, TRIM8, TRIM20, TRIM21, TRIM22, and TRIM65 (knockdowns were evaluated in FIG. 22D), were required for optimal induction of autophagy by IFNγ (FIG. 14C). Of the neutral TRIMs, TRIM56 that was marginally positive in the screen, showed a borderline but statistically significant effect (FIG. 14C). Thus, TRIMs contribute to autophagy induction in response to INF-γ (FIG. 14D).

TRIM20 Induces Autophagy

The inventors focused on TRIM20 as a TRIM strongly induced by IFN-γ (Carthagena et al., 2009; Chae et al., 2011). We confirmed that TRIM20 expression was responsive to IFN-γ in our system and tested its kinetics and dose-response (FIGS. 22E, F). The inventors next used HC analysis to establish in a dose response setting that TRIM20 was required for IFN-γ-induced autophagy (FIGS. 22G, H). This was confirmed in immunoblot assays of LC3 lipidation in the presence of bafilomycin A1, an inhibitor of autophagic flux (LC3-II conversion; FIG. 14E). Mirroring these findings, overexpression of GFP-TRIM20 increased LC3 puncta (FIG. 14F), and enhanced LC3-II conversion in immunoblots (FIG. 22I); as expected, the LC3-II band was revealed only in bafilomycin A1-treated cells, which protects it from degradation through autophagic flux. These results indicate that activation of autophagy by IFN-γ depends on TRIM20 and that elevated expression of TRIM20, a TRIM whose transcription is known to be strongly activated by IFN-γ (Carthagena et al., 2009; Chae et al., 2011), induces autophagy.

TRIM20 Interacts with ULK1, Beclin 1 and ATL16L1

Figure 15:
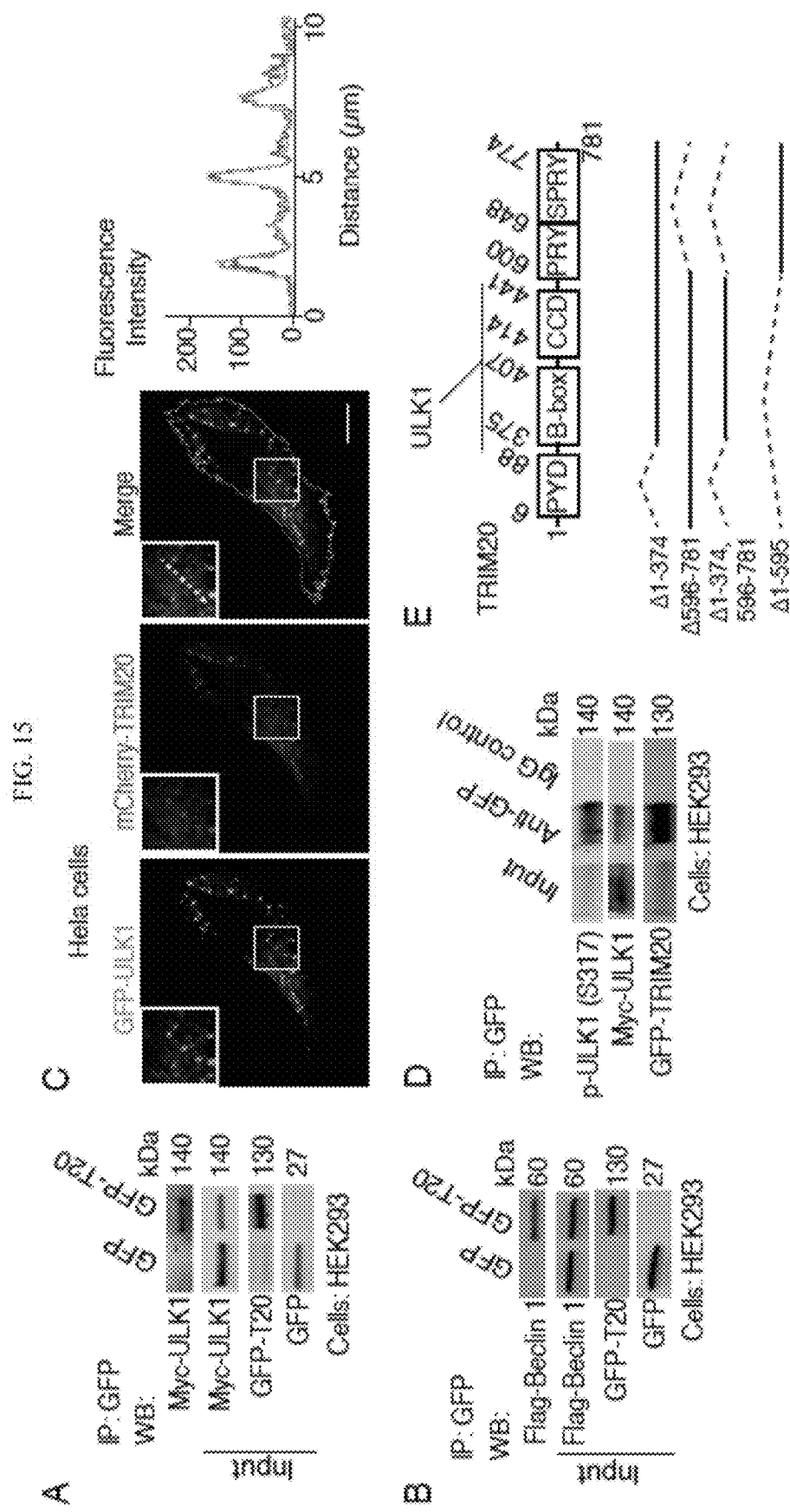
FIG. 15 shows that TRIM20 interacts with ULK1 and Beclin 1. (A,B) Co-immunoprecipitation analysis of GFP-TRIM20 (T20) with (A) Myc-ULK1 or (B) Flag-Beclin 1 in HEK293 cells extracts. IP, immunoprecipitation; WB, western blot. (C) Confocal microscopy of HeLa cells co-expressing mCherry-TRIM20 with GFP-ULK1. Line tracing corresponds to arrow. White outline, cell boundary defined by background fluorescence. Scale bars, 10 µm. (D) Co-immunoprecipitation analysis of TRIM20 complexes with p-ULK1 (Ser-317) in HEK293 cells. (E) TRIM20 domains and deletion constructs used. Dotted lines, deleted regions. (F) Co-immunoprecipitation analysis of interactions between deletion variants of TRIM20 (as GFP fusions) with Myc-ULK1 in HEK293 cells. (G) GST pull-down analysis of radiolabeled Myc-ULK1 with GST-tagged deletion variants of TRIM20. Top, autoradiogram of pull-down products. Bottom, Coomassie Brilliant Blue (CBB)-stained SDS-polyacrylamide gel with GST-deletion variants of TRIM20. Data representative of three or more experiments.
Figure 15:
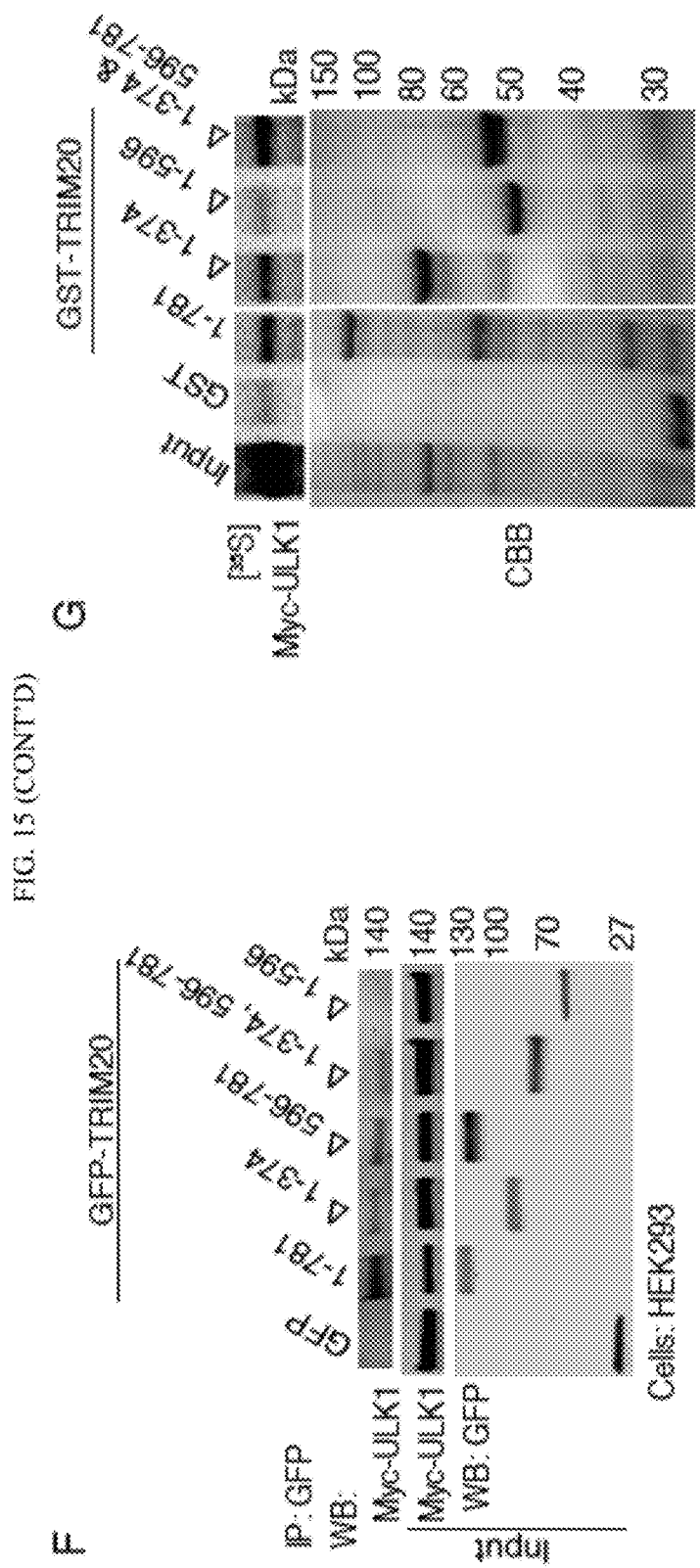

The inventors next examined how TRIM20 induced autophagy. Autophagy requires ULK1 and Beclin 1, both of which play pivotal roles in autophagy initiation in mammalian cells (He and Levine, 2010; Mizushima et al., 2011). We detected GFP-TRIM20 in immunoprecipitates with co-expressed Myc-ULK1 and Flag-Beclin 1 (FIGS. 15A and B) and with endogenous ULK1 and Beclin 1 (FIGS. 9A and B). TRIM20 puncta colocalized with ULK1 in the cytoplasm (FIG. 15C). Induction of autophagy depends on a phosphorylation cascade, which includes activation of ULK1 by phosphorylation at Ser-317 (Kim et al., 2011). Active p-ULK1 (Ser-317) co-immunoprecipitated with TRIM20 (FIG. 15D). We next mapped ULK1-binding regions within TRIM20 (FIG. 15E). Like the majority of TRIMs (Kawai and Akira, 2011; Reymond et al., 2001), TRIM20 has B box, CCD and PRY/SPRY domains, but lacks an E3 ligase RING domain, and is uniquely endowed with a pyrin (PYD) domain. TRIM20 constructs lacking PYD and PRY/SPRY domains still bound ULK1 in immunoprecipitation assays (FIG. 15F). Direct biding between TRIM20 and ULK1 was established in GST pull-down experiments (FIG. 15G). Both in vivo and in vitro experiments pointed to the middle portion (including B-box and CCD) of TRIM20 as being critical for association with ULK1, whereas the N-terminal PYD and the C-terminal SPRY domains were dispensable (FIG. 15E).

Figure 23:
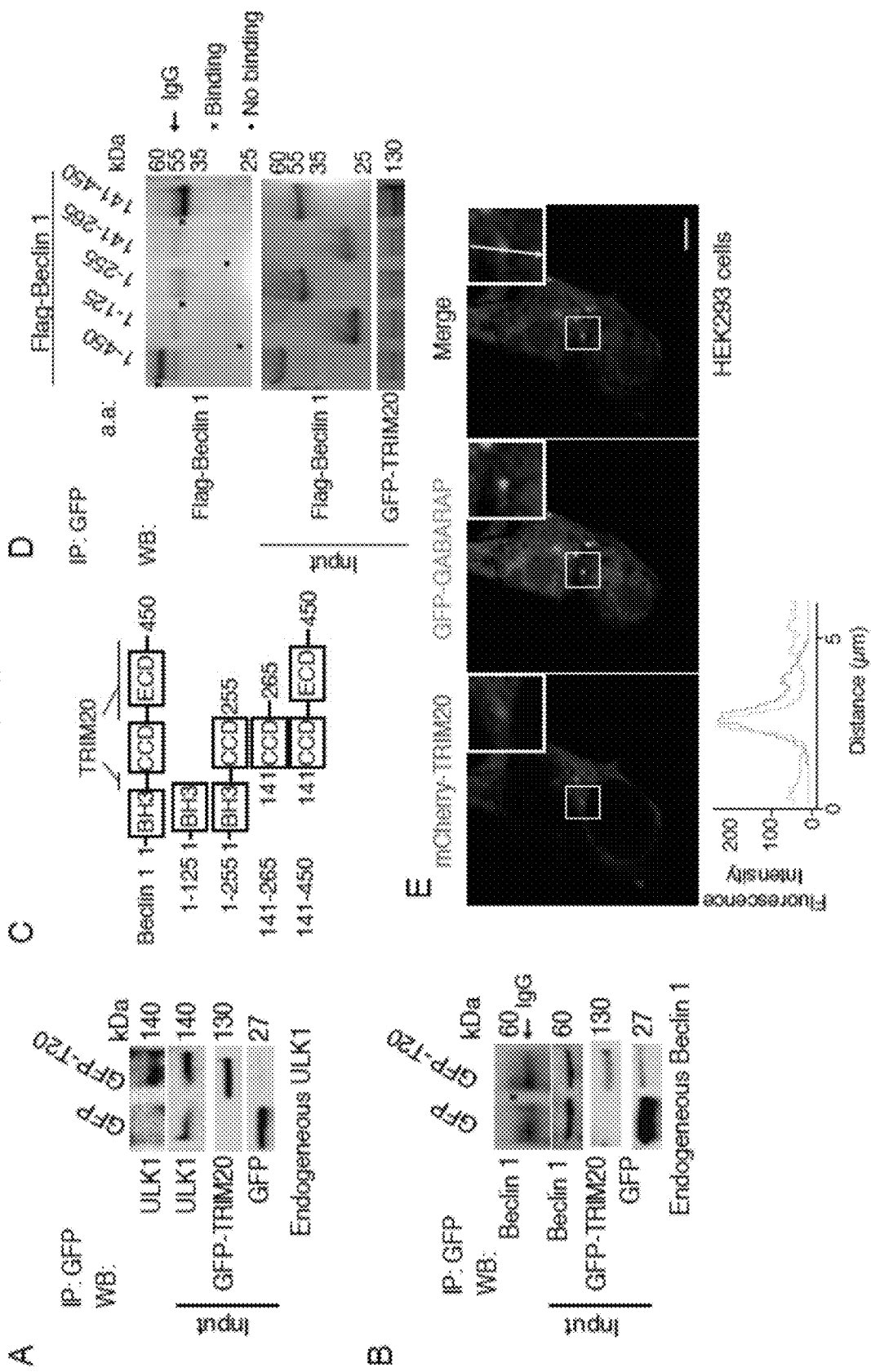
FIG. 23 shows that TRIM20 interacts with ULK1, Beclin 1, and mAtg8s. (A,B) Co-immunoprecipitation analysis of GFP-TRIM20 with endogenous (A) ULK1 or (B) Beclin 1 in HEK293 cells extracts. (C) Beclin 1 domains and deletion constructs used. (D) Co-immunoprecipitation analysis of interactions between deletion variants of Flag-Beclin 1 (asterisks and squares in the top blot denote presence or absence of Flag-Beclin 1, respectively) and GFP-TRIM20 in HEK293 cells. (E) Confocal microscopy of HEK293 cells co-expressing mCherry-TRIM20 with GFP-GABARAP. Line tracings correspond to arrows. (F) Confocal microscopy of HeLa cells co-expressing mCherry-TRIM20 with GFP-LC3B in the presence of bafilomycin A1. Line tracing corresponds to arrows. (G) GST pull-down analysis of interaction between radiolabeled Myc-TRIM20 harboring single or double mutants (corresponding to FIG. 17D) and GST-GABARAP. Data representative of three independent experiments. Scale bars, (E) 5 μm (2 μm for inset) and (F) 10 μm.
Figure 23:
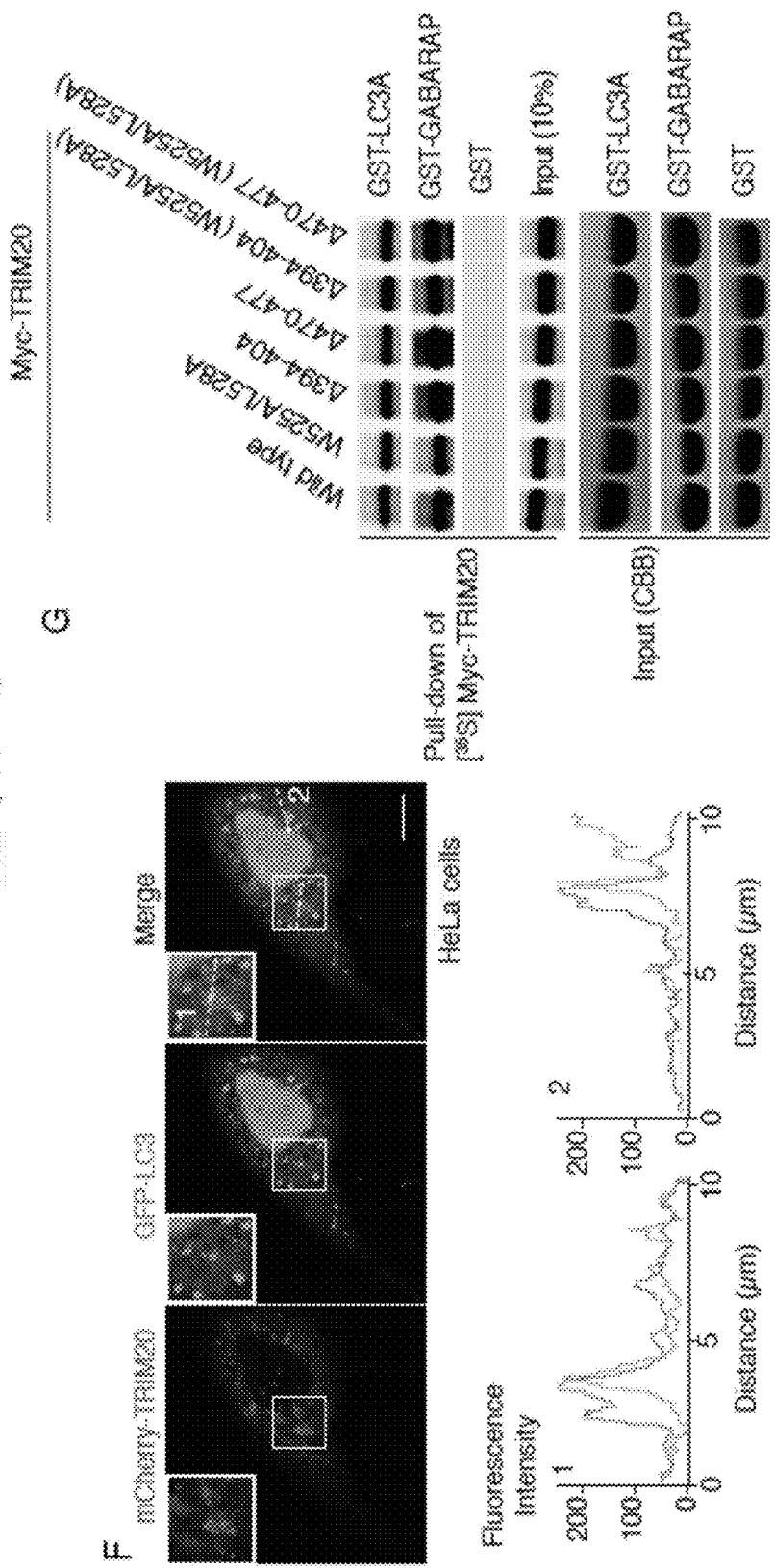

Beclin 1 showed a more complex domain-requirement for inclusion in TRIM20 complexes, with either the middle portion (including B-box and CCD) or the C-terminal region (PRY/SPRY) displaying an independent capacity to bring down Beclin 1 in immunoprecipitates (FIGS. 16A and B). We also examined Beclin 1 for regions required for the ability to co-immunoprecipitate with TRIM20 (FIGS. 23C and D). Two Beclin 1 regions appeared to be required: the first one between BH3 and CCD and the second one overlapping with the ECD domain of Beclin 1 (FIGS. 23C and D). Furthermore, in the presence of TRIM20, the immunoprecipitated Beclin 1 complexes were enriched for ULK1 (FIG. 16C). Thus, TRIM20 can interact simultaneously with multiple autophagy factors and serves as a platform for co-assembly of ULK1 and Beclin1.

Figure 16:
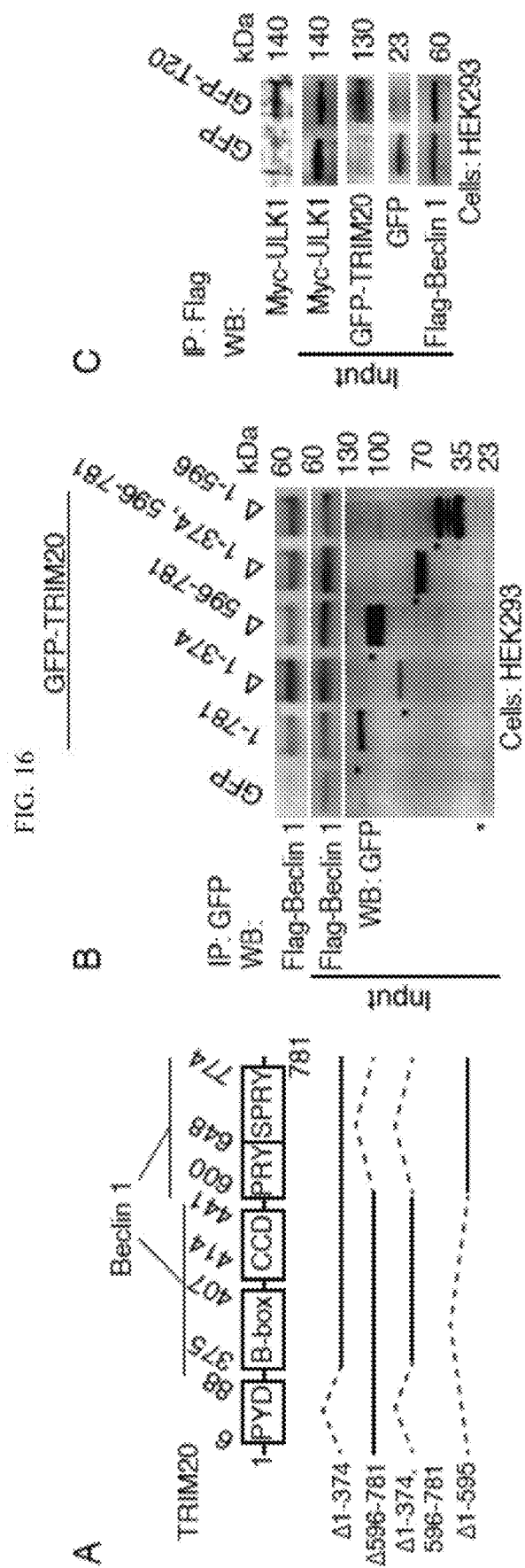
FIG. 16 shows that TRIM20 assembles ULK1 and Beclin 1 in a complex and interacts with ATG16L1. (A) TRIM20 domains and deletion constructs used. (B) Co-immunoprecipitation analysis of interaction between deletion variants of TRIM20 (as GFP fusions; asterisks denote fusion products on the bottom blot) with Flag-Beclin 1 in HEK293 cells. (C) Co-immunoprecipitation analysis of ULK1 in Beclin 1 complexes in the presence and absence of TRIM20 from HEK293T cell lysates. (D) Co-immunoprecipitation analysis of GFP-TRIM20 with endogenous ATG16L1. (E) TRIM20 domains and deletion constructs used. (F) Co-immunoprecipitation analysis of interaction between deletion variants of TRIM20 with Flag-ATG16L1 in HEK293 cells. (G) ATG16L1 domains and deletion constructs used. (H) Co-immunoprecipitation analysis of interactions between deletion variants of Flag-ATG16L1 and GFP-TRIM20 in HEK293 cells. (I) Model of TRIM20-dependent autophagy induction based on FIG. 15, FIG. 16, and FIG. 23. Data representative of three or more experiments.

The inventors also found that TRIM20 co-immunoprecipitated with ATG16L1 (FIG. 3D). TRIM20 displayed a complex domain requirement for inclusion in ATG16L1 complexes, with either the middle portion (including B-box and CCD) or the C-terminal region (PRY/SPRY) showing an independent capacity to bring down ATG16L1 in immunoprecipitates (FIGS. 16E and F). TRIM20 primarily interacted with the WD repeat of ATG16L1 (FIGS. 16, G and H). Thus, the TRIM20 platform (FIG. 16I) contains other autophagy regulators, such as ATG16L1, a component of the autophagy E3-like complex that regulates LC3 conjugation and autophagosome formation (Mizushima et al., 2003).

TRIM20 Interacts with a Subset of Mammalian Atg8 Paralogs

Figure 17:
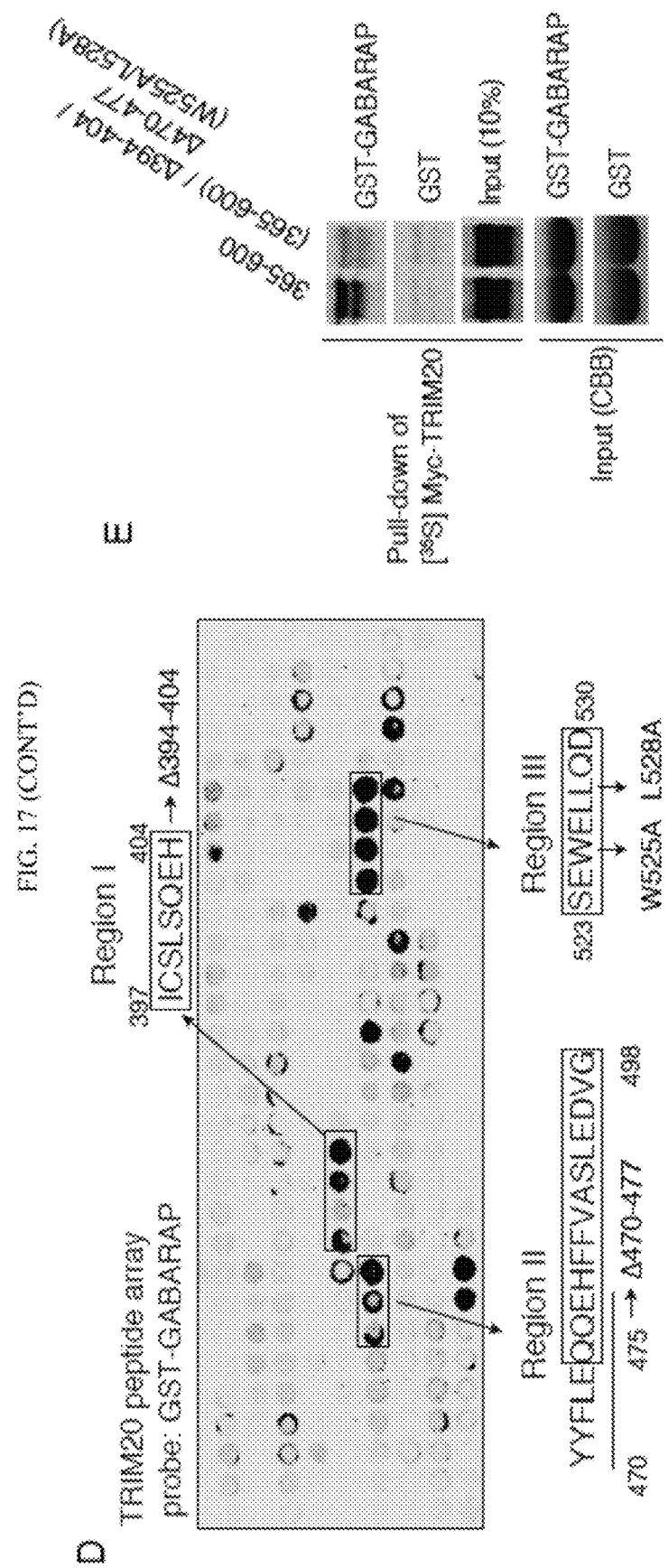
FIG. 17 shows that TRIM20 interacts with mammalian Atg8 paralogs (mAtg8s). (A) GST pull-down analysis of interactions between radiolabeled Myc-TRIM20 and GST-tagged mAtg8s. Top, autoradiogram of pull-down products. Bottom, CBB-stained SDS-polyacrylamide gel with GST-mAtg8s. (B) TRIM20 domains and deletion constructs used. (C) GST pull-down analysis of binding between radiolabeled Myc-TRIM20 deletion variants and GST-GABARAP and GST-LC3A. (D) Identification of GABARAP interacting regions on TRIM20 by peptide array. Three series of TRIM20 peptides (regions of primary sequence staggered by 3 amino acid residues), with either three or four positive consecutive binding signals, were identified. The peptide sequences corresponding to the positive binding signals (encompassed spots; defined as Region I, II, III) were mutated as described, and were subjected to the GST pull-down experiments in (E) and FIG. 23F. (E) GST pull-down analysis of interaction between radiolabeled Myc-TRIM20 triple mutants and GST-GABARAP. Data representative of three or more experiments.

The inventors examined whether TRIM20 possessed the ability to interact with mammalian Atg8 paralogs (mAtg8s), factors required for autophagosomal membrane formation (Mizushima et al., 2011). Although no binding was detected with LC3B, the commonly used marker for autophagic membrane (Kabeya et al., 2000), GST pull-down experiments revealed interactions of TRIM20 with GABARAP and GABARAPL1, and to a lesser extent with LC3A, LC3C, and GABARAPL2 (FIG. 17A). GABARAP colocalized with TRIM20 (FIG. 23E). Albeit TRIM20 did not directly interact with LC3B, mCherry-TRIM20 profiles were closely juxtaposed to conventional LC3-positive puncta (FIG. 23F). The region of TRIM20 (FIG. 17B) responsible for the interaction with mAtg8s, GABARAP and LC3A, was mapped. A TRIM20 deletion construct spanning residues 375-595 retained capacity to bind GABARAP or LC3A (FIGS. 17B and C). To delimit further the TRIM20 sequence required for mAtg8s binding we used GST-GABARAP as bait in a binding assay with an array of TRIM20 peptides (FIG. 17D). Three series of TRIM20 peptides (regions of primary sequence staggered by 3 amino acid residues), with either three or four positive consecutive binding signals, were identified (FIG. 17D). The most upstream region (397-ICSLSHQEH-404; Region I) did not contain a recognizable LIR motif, whereas Region II (470-YYFLEQQE-HFFVSLEDVG-498) and Region III (523-SEWELLQD-530) contained potential LIR motifs (Birgisdottir et al., 2013). In follow-up mutational analyses, no single or double alterations of the Regions I-III abrogated GABARAP binding (FIG. 23G). Only when all three regions (I, II and III) were mutated, did this cause loss of GABARAP binding (FIG. 17E and FIG. 23G). Thus, all three regions contribute to the binding of TRIM20 to mAtg8s. Collectively the above findings and experiments described in previous sections demonstrate that TRIM20 assembles both the key regulators of autophagy (ULK1, Beclin 1, ATG16L1) and a subset of effector factors (mAtg8s).

TRIM20 is a Receptor for Selective Autophagy of Inflammasome Components

Figure 24:
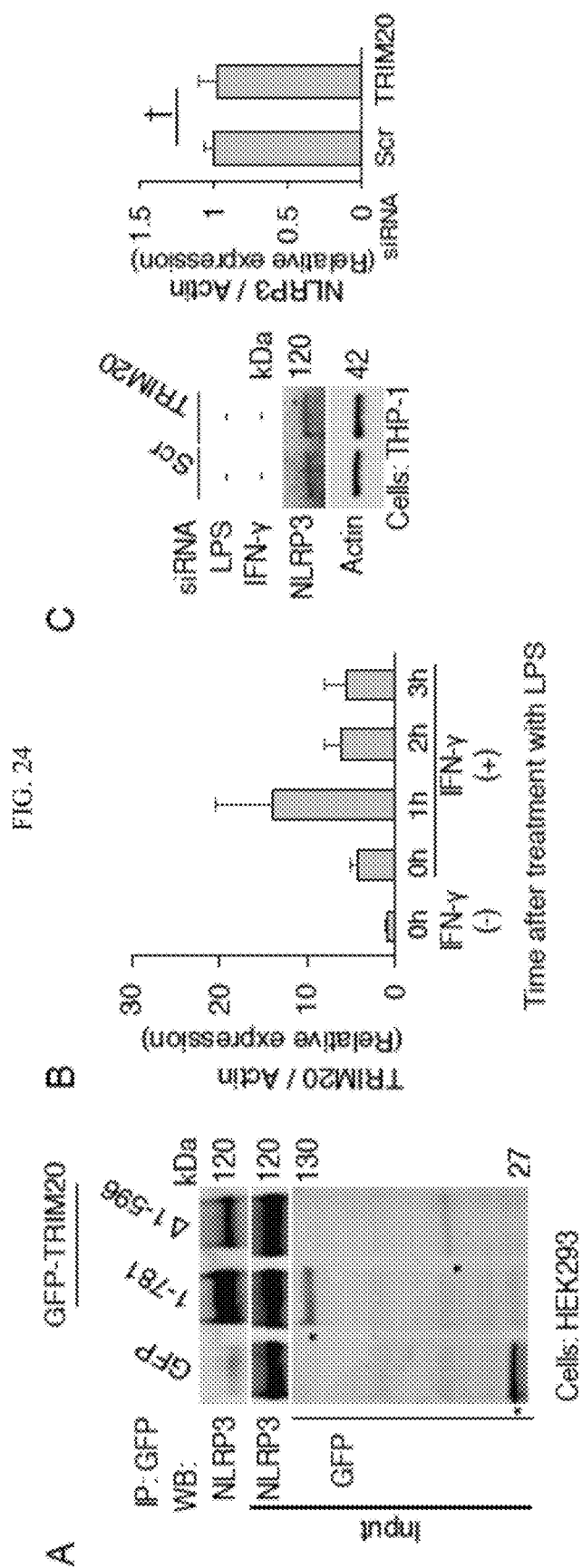
FIG. 24 shows that TRIM20 degrades NLRP3 through autophagy. (A) Co-immunoprecipitation analysis of deletion variants of TRIM20 (as GFP fusions; asterisks denote fusion products on the bottom blot) with NLRP3 in HEK293 cells. (B) THP-1 cells were treated with IFN-γ for 3 h, additionally treated with 2.5 μg/ml of LPS for indicated periods, and TRIM20 mRNA levels were determined by quantitative PCR. Values are standardized to IFN-γ-untreated control. (C and D) Levels of NLRP3 were determined in lysates from THP-1 cells subjected to TRIM20 or Scr siRNA were (C) untreated either IFN-γ or LPS, or (D) LPS alone for 2 h. (E) THP-1 cells were treated with 1.0 μg/ml of LPS for 3 h, and levels of NLRP3 in lysate were determined by immunoblots. (F) Knockdown efficacies of ULK1 and Beclin 1 by siRNA were examined by quantitative RT-PCR. (G and H) Levels of GFP-TRIM20 were determined in cells co-expressing (G) with or (H) without NLRP3 following autophagy induction (EBSS, 3 h) in the presence or absence of bafilomycin A1. (I) Co-immunoprecipitation analysis of ULK1 in NLRP3 protein complexes in the presence and absence of TRIM20 knockdown. Lysates from THP-1 cell subjected to each knockdown and treatment of 200 U/mL IFN-γ for 3 h and additional LPS (1.0 μg/ml) treatment 2 h, were immunoprecipitated with anti-NLRP3, and immunoblots were probed as indicated. (J) Co-immunoprecipitation analysis of AMPK in GFP-TRIM20 complexes in HEK293T cells expressing Myc-ULK1 and Flag-NLRP3 (or not). Data, means±SE, n≥3 experiments, *P<0.05, †P≥0.05 (C, t-test; D, ANOVA).
Figure 24:
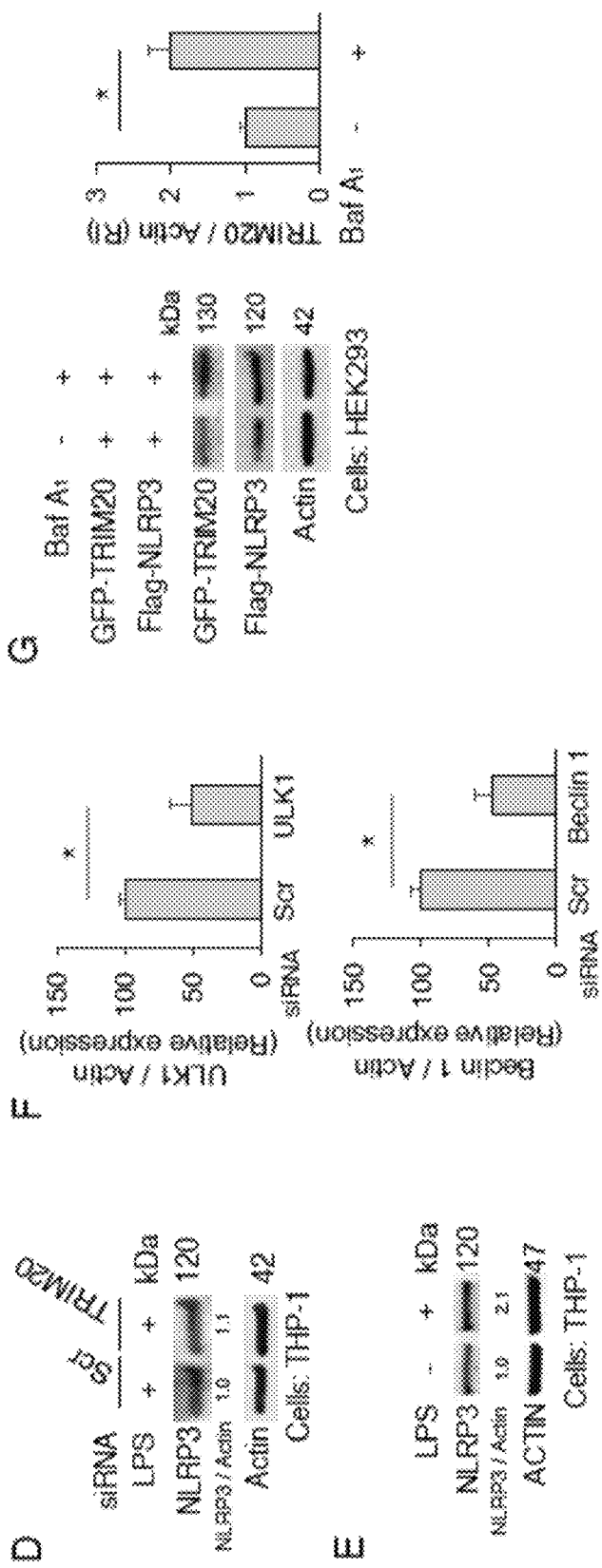
Figure 24:
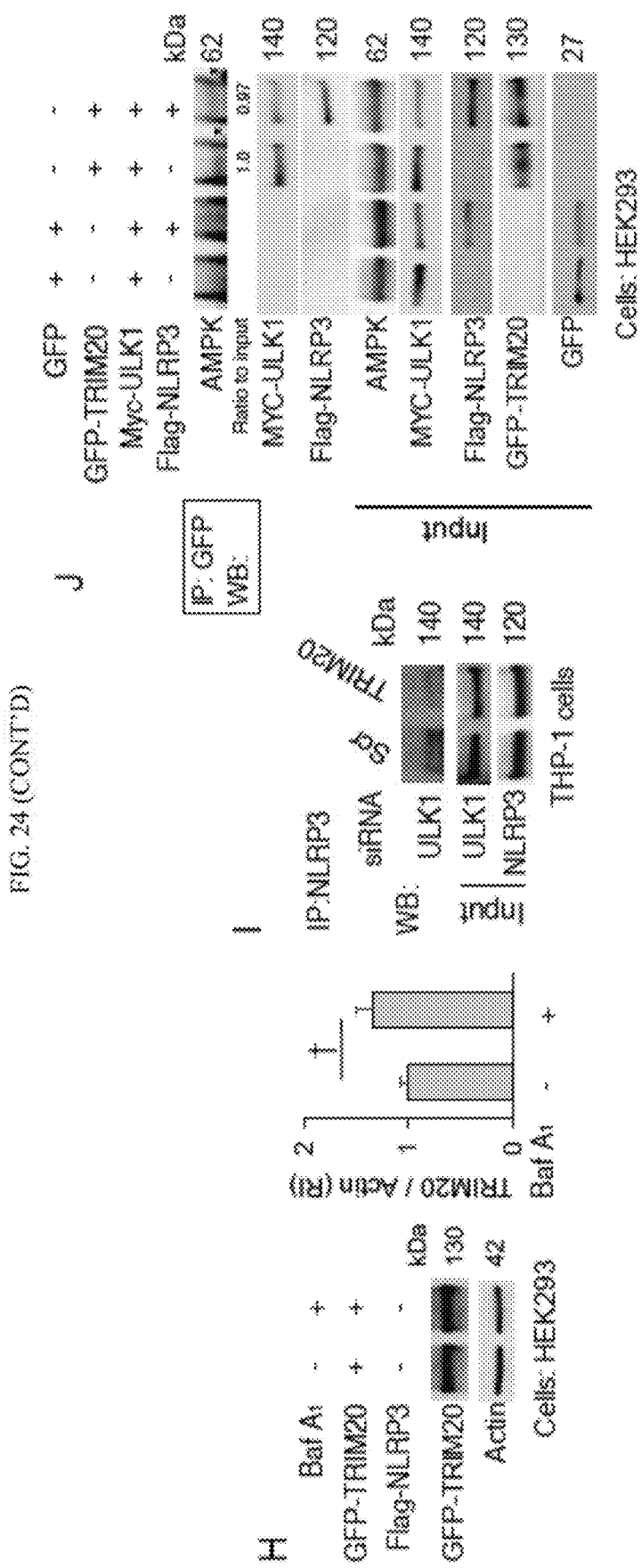

TRIM20, encoded by the MEFV gene, is a risk locus for familial Mediterranean fever (FMF) French FMF Consortium, 1997, The International FMF Consortium, 1997. TRIM20 has 305 FMF-associated variants website fmf.igh-.cnrs.fr/ISSAID/infevers/, with frequent mutations in its PRY/SPRY domain (Masters et al., 2009). The PYD domain of TRIM20 has been the primary focus of interest in inflammasome regulation due to its potential to bind the cognate PYD domain of ASC (Schroder and Tschopp, 2010). However, it has been reported that the PRY/SPRY domain, located at the other end of TRIM20, recognizes and binds to NLRP3 (Papin et al., 2007). The latter relationship has remained obscure despite the frequency of mutations in the PRY/SPRY domain (Masters et al., 2009). We explored the significance of the interactions between the TRIM20 PRY/SPRY domain and NLRP3 in the context of the above recognized function of TRIM20 in autophagy. The full length TRIM20 and a TRIM20 construct containing only the PRY/SPRY domain both interacted with NLRP3 (FIG. 24A). A knockdown of TRIM20 spared NLRP3 from degradation in cells treated with IFN-γ and LPS (FIG. 18A; FIGS. 24B and C). When cells were treated with LPS alone, a knockdown of TRIM20 had no effect on NLRP3 levels (FIG. 24D), albeit LPS alone increased NLRP3 levels (FIG. 24E) as expected (Bauemfeind et al., 2009), in keeping with TRIM20 acting to transduce the effects of IFN-γ. Bafilomycin A1 (an inhibitor of autophagic degradation) protected NLRP3, whereas TRIM20 knockdown increased amounts of NLRP3 and eliminated the protective effects of bafilomycin A1 (FIG. 18B). Similar effects were observed with THP-1 cells exposed to pathogens (adherent-invasive *Escherichia coli* LF82 (Lapaquette et al., 2010)) and with primary human peripheral blood monocyte-derived macrophages (MDMs) treated as above (FIGS. 18C and D).

Degradation of NLRP3 depended on ULK1 and Beclin 1, establishing that disposal of NLRP3 was through autophagy (FIG. 18E; and FIG. 24F). Conversely, expression of TRIM20 decreased levels of co-expressed NLRP3 (FIG. 18F). The destabilizing effect of TRIM20 overexpression on NLRP3 levels was suppressed by bafilomycin A1 (FIG. 18F). Additionally, TRIM20 was protected by bafilomycin A1 from degradation in the presence of NLRP3 (FIG. 24G and H), indicating that TRIM20 is degraded along with the delivery of its substrate to autolysosomal compartments.

Figure 18:
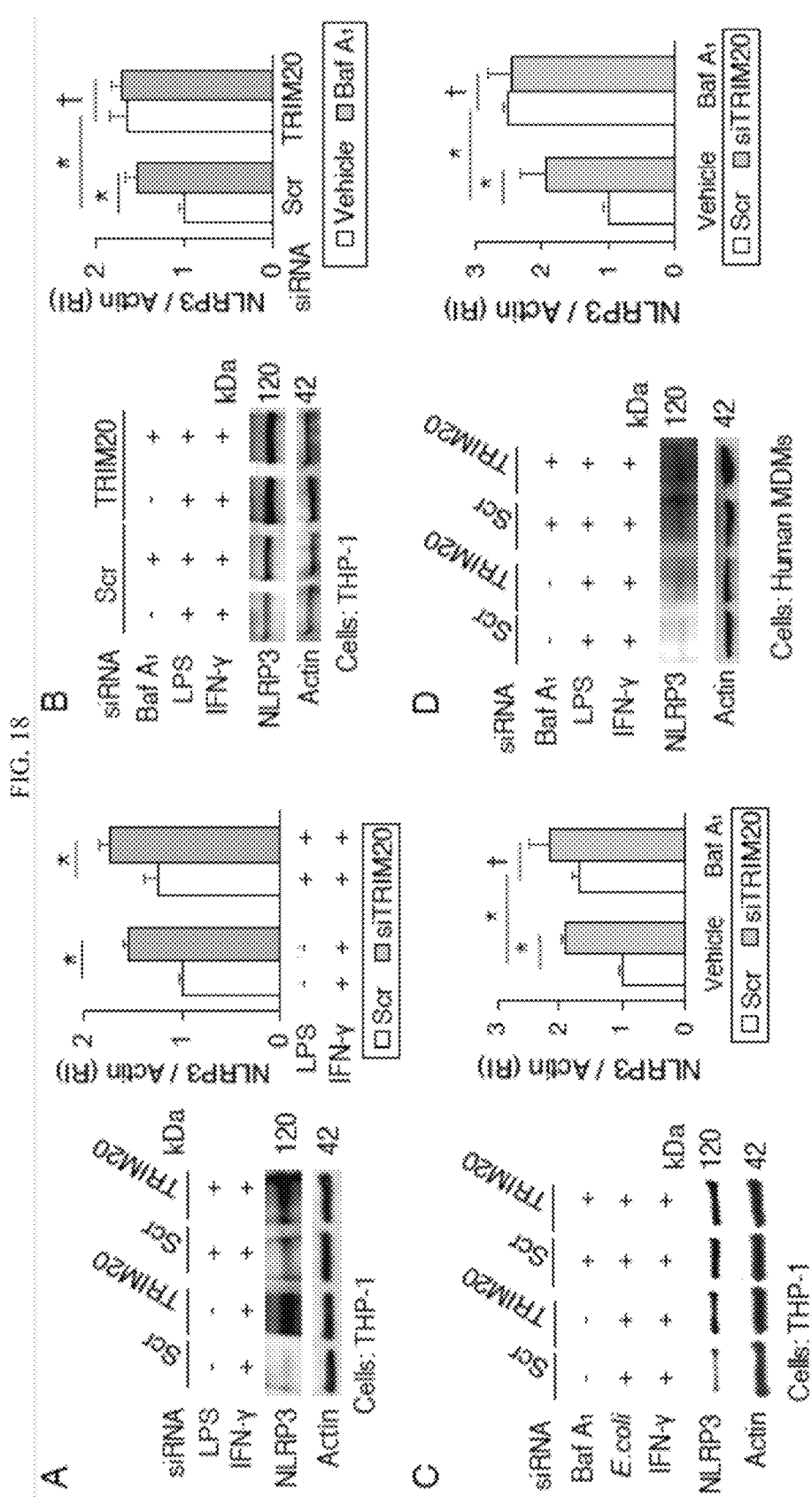
FIG. 18 shows that TRIM20 degrades inflammasome components through autophagy. (A) Levels of NLRP3 were determine in lysates from THP-1 cells subjected to TRIM20 or Scr siRNA were activated with 1,000 U/mL IFN-γ for 3 h, and 2.5 µg/mL LPS for 2 h (for optimal TRIM20 expression; Supplementary FIG. 24B). RI, relative intensity. (B) Levels of NLRP3 were determined from THP-1 subjected to TRIM20 or control knockdown and treated or not with bafilomycin A1 (Baf A$_1$). (C) The abundance of NLRP3 protein was determined from THP-1 cells subjected to TRIM20 or control knockdown and exposed to *Escherichia coli* strain LF82 and IFN-γ in the presence or absence of bafilomycin. (D) The abundance of NLRP3 protein was determined from primary human MDMs subjected to TRIM20 or control knockdown and exposed to LPS and IFN-γ in the presence or absence of bafilomycin. (E) Levels of NLRP3 were determined from THP-1 cells subjected to ULK1, Beclin 1, or Scr siRNA were treated with IFN-γ and LPS. (F-H) Levels of NLRP3 (F), NLRP1 (G), or pro-capsase 1 (H) were determined in cells expressing GFP or GFP-TRIM20 following autophagy induction (EBSS, 3 h) in the presence or absence of bafilomycin A1. Data, means±SE, n≥3, *P<0.05, †P≥0.05 (ANOVA).
Figure 18:
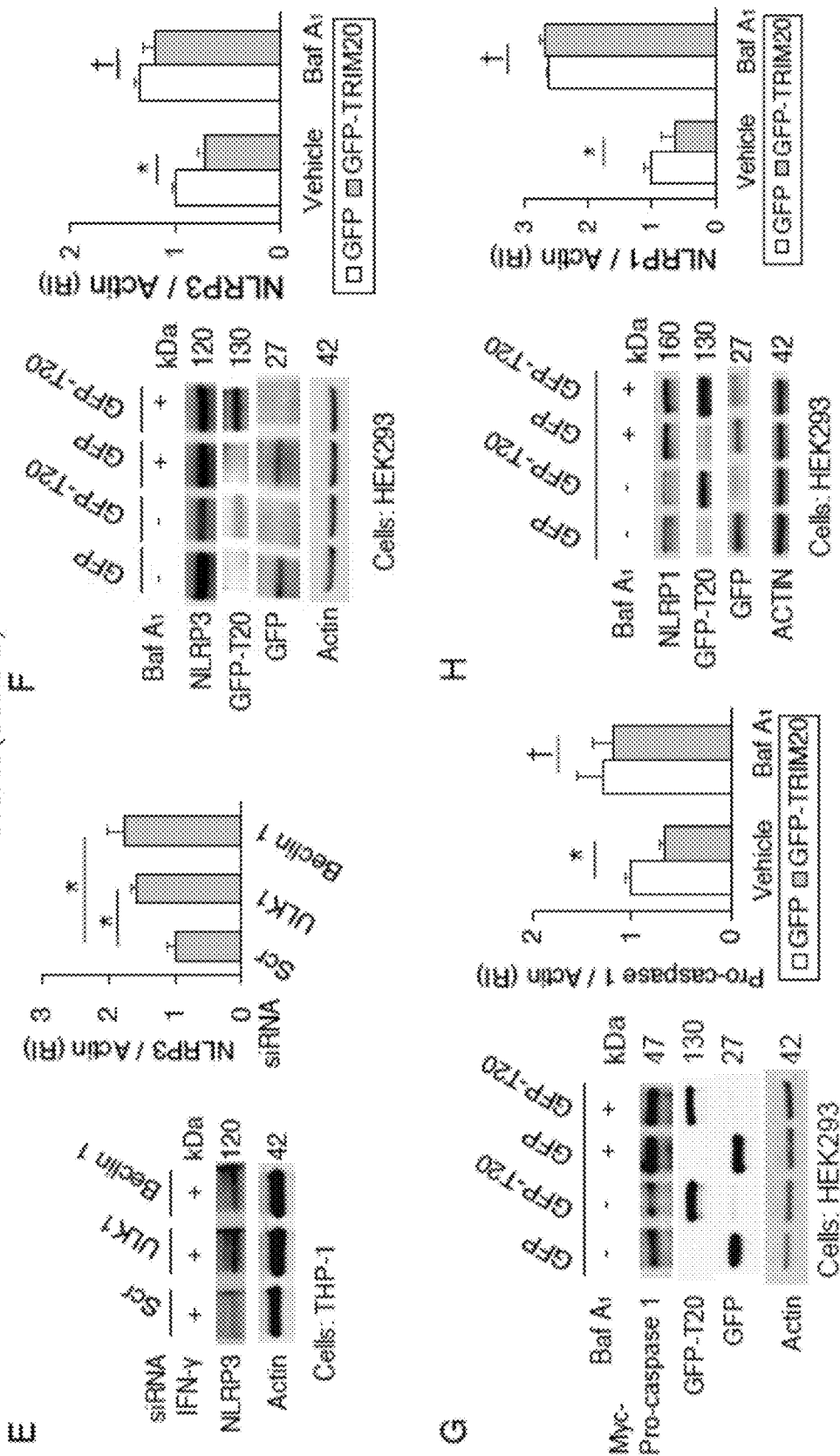

In addition to NLRP3, other inflammasome components, pro-caspase 1 (Chae et al., 2006; Papin et al., 2007) and NLRP1 (Papin et al., 2007), have been previously shown to interact with the PRY/SPRY domain of TRIM20. When pro-caspase 1 and NLRP1 were co-expressed with TRIM20, they too were subject to degradation inhabitable by bafilomycin A1 (FIGS. 18, G and H). These data show that TRIM20 acts as an autophagy receptor for degradation of inflammasome components and that TRIM20 is responsible for delivery of NLRP3 and other tested inflammasome components for autophagic degradation.

Figure 19:
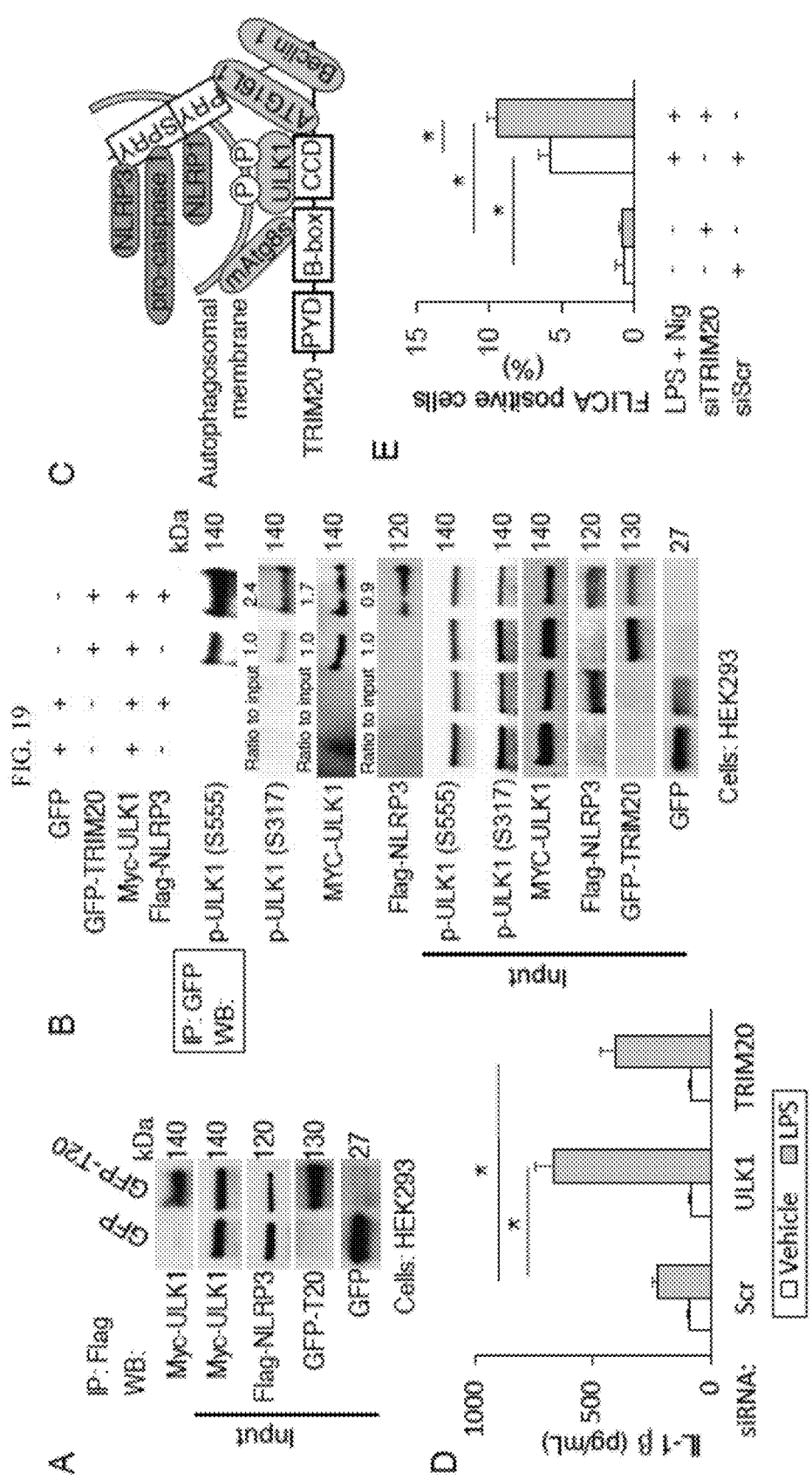
FIG. 19 shows that ULK1 is recruited to NLRP3 complexes by wild type TRIM20 but not by FMF disease-associate TRIM20 mutants. (A) Co-immunoprecipitation analysis of ULK1 in NLRP3 complexes in HEK293T cells expressing GFP-TRIM20 or GFP alone. (B) The effect of NLRP3 expression on the presence of phospho-ULK1 in TRIM20 complexes. Lysates from HEK293 cells transiently expressing Myc-ULK1, GFP-TRIM20 (or GFP alone), and Flag-NLRP3 (or not) were immunoprecipitated with anti-GFP and immunoblots were probed as indicated. (C) Model of TRIM20's function in autophagy as a regulator-receptor: TRIM20 assembles autophagy machinery (ULK1, Beclin 1, ATG16L1, mAtg8s) and recognizes substrates (NLRP3, pro-caspase 1 and NLRP1) delivering them for autophagic degradation. The recognition of substrate enriches active p-ULK1 on the TRIM20 platform. (D) FLICA-positive cells were quantified using THP-1 cells that had been subjected to knockdown of TRIM20, treated with IFN-γ, and then treated with or without LPS (2 h) and nigericin (10 min), and stained for active caspase-1 (with FLICA); >150 cells per experiment were analyzed for quantification. (E) The levels of IL-1β were determined from supernatants of THP-1 cells that had been subjected to knockdown of ULK1 or TRIM20, treated with IFN-γ and LPS, and stimulated with nigericin for 30 min. (F) Predominant FMF-associated point mutations of TRIM20 reside in the PRY/SPRY domain. (G) Levels of NLRP3 were determined from lysates of HEK293 cell expressing GFP-TRIM20 (wild type or FMF-associated variants) or GFP and induced for autophagy by starvation in EBSS for 3 h. (H) Effects of FMF-associated variants on ULK1 presence in TRIM20 complexes. HEK293 cells were transiently transfected with Myc-ULK1, and either GFP-TRIM20 (wild type or FMF-associated variants) or GFP alone. Lysates were immunoprecipitated with anti-GFP, and immunoblots were probed as indicated. Numbers indicate relative intensity of the indicated band. (I) Model of FMF-associated mutation in NLRP3 degradation. The presence of NLRP3 promote phosphorylation of ULK1 in TRIM20 complex, leading to autophagic degradation of NLRP3. TRIM20 mutants harbored less ULK1 and phospho-ULK1, which results in less autophagic activity and less degradation of inflammasome components. Asterisks denote common FMF-associated point mutations in TRIM20. Data, means±SE, n≥3, *P<0.05, (ANOVA).
Figure 19:
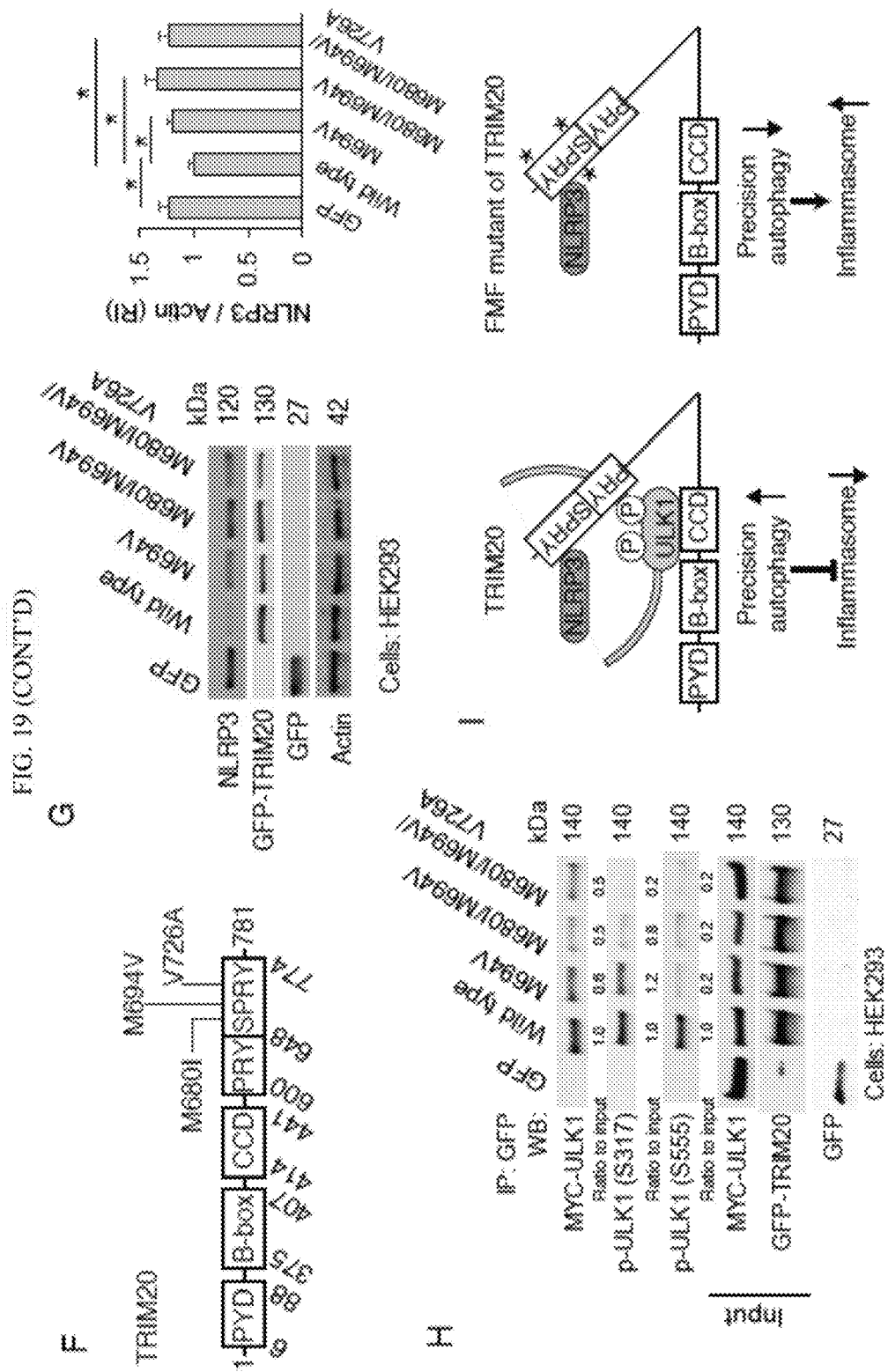

Presence of Target Substrate Potentiates Assembly of Activated Autophagic Components on the TRIM20 Platform The inventors tested whether the availability of substrate, NLRP3, influenced TRIM20 assembly with ULK. Although ULK1 was enriched in NLRP3 immunoprecipitates when cells expressed TRIM20 (FIG. 19A) this was reduced when cells were subjected to TRIM20 knockdown (FIG. 24I), the presence of NLRP3 did not affect levels of total ULK1 in TRIM20 immunoprecipitates (FIG. 19B). However, the presence of NLRP3 increased the amount of active p-ULK1 (Ser-317 and Ser-555) (Egan et al., 2011; Kim et al., 2013) associated with TRIM20 (FIG. 19B). Because these two sites of ULK1 are phosphorylated by AMPK (Egan et al., 2011; Kim et al., 2011), we tested whether AMPK is recruited to the TRIM20 complex. AMPK was found in TRIM20 complexes with or without NLRP3 (FIG. 24J). These data indicate that modulation of TRIM20 action, in the presence of its cognate autophagic target, is reflected in ULK1 phosphorylation state and not in ULK1 or AMPK levels. These and above data suggest a model in which not only does TRIM20 organize autophagic machinery by serving as a platform for the assembly of ULK1, Beclin 1, ATG16L1, and mAtg8s, but it also recognizes autophagic substrates via its PRY/SPRY domain, and that this substrate recognition enriches ULK1 in its activated state on the TRIM20 platform (FIG. 19C).

Disease-Associated Mutations in TRIM20 Diminish its Autophagic Potency

Figure 25:
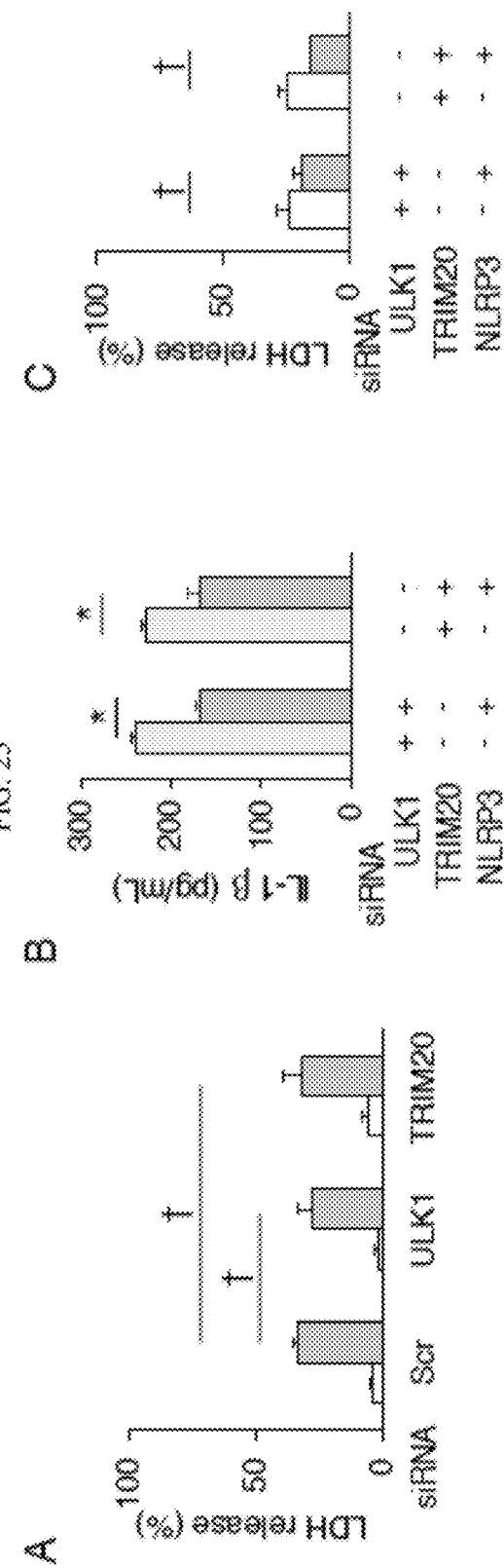
FIG. 25 shows the effects of TRIM20 on inflammasome activity and FMF-associated variants of TRIM20 decrease number of TRIM20 and LC3 puncta. (A) LDH release of supernatants in FIG. 6D. (B and C) Supernatants were harvested from THP-1 cells that had been subjected to double knockdown as indicated, treated with IFN-γ and LPS, additionally stimulated with nigericin (20 vM) for 30 min, and levels of IL-1β and LDH release were measured. (D) Knockdown efficacy of NLRP3 by siRNA was examined by immunoblotting. (E) Confocal microscopy of THP-1 cells that had been subjected to knockdown of TRIM20, treated with IFN-γ, and then treated with or without LPS (2 h) and nigericin (10 min), and stained for active caspase-1 (with FLICA) and nucleus (TO-PRO-3). Arrowheads, FLICA-positive puncta; asterisk, cell; white outline, cell boundary. (F) Confocal microscopy of GFP-TRIM20 (wild type or FMF-associated variants) or GFP in HEK293 cells. (G) HC image (epifluorescence) analysis of TRIM20 puncta in HeLa cells expressing GFP-TRIM20 (wild type or FMF-associated variants) or GFP. (H) HC image analysis of LC3 puncta in HeLa cells expressing GFP-TRIM20 (wild type or triple mutant TRIM20). Data, means±SE, n≥3 experiments, *P<0.05, †P≥0.05 (t test or ANOVA). Scale bar, 5 μm.
Figure 25:
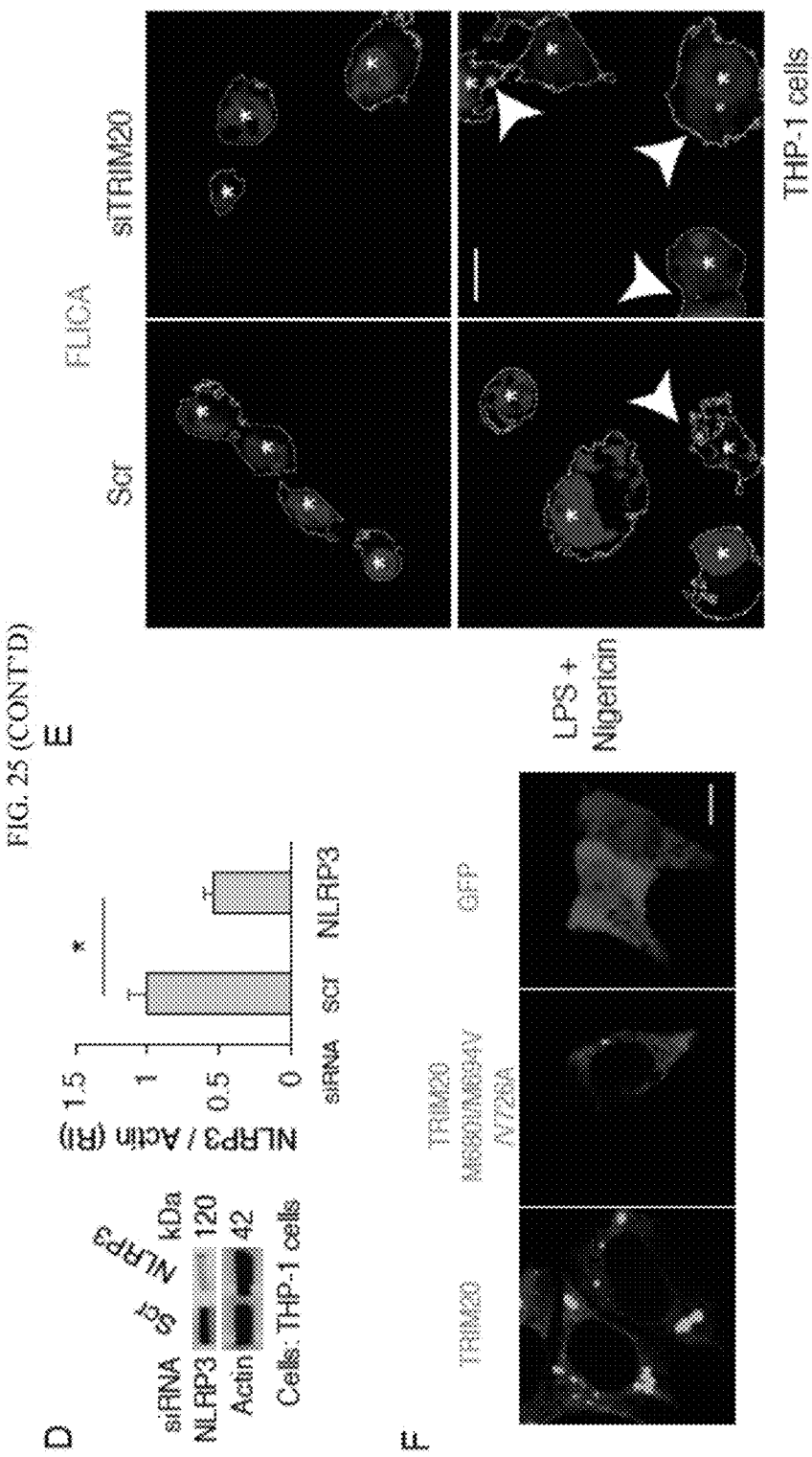
Figure 25:
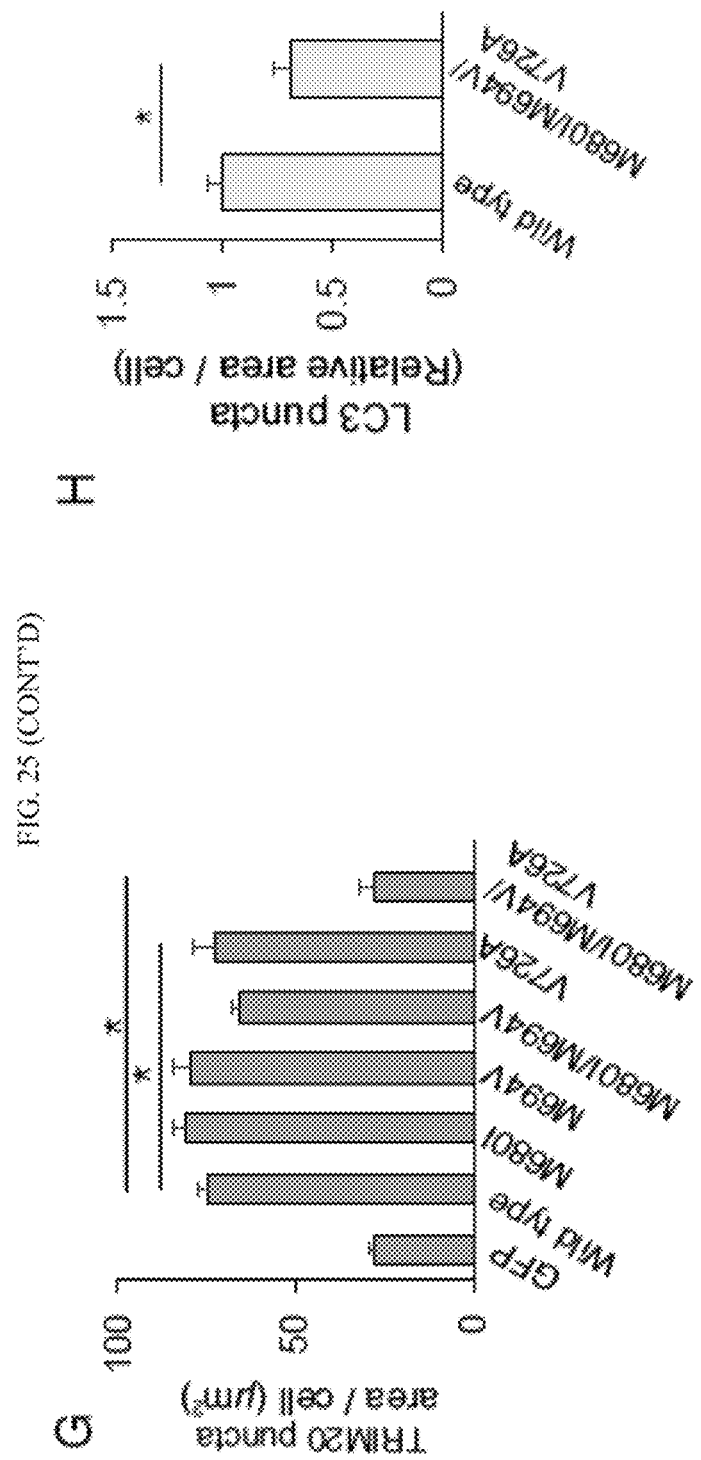

A physiologically relevant consequence of TRIM20 mutations in FMF is excessive IL-1β production (Chae et al., 2011; Meinzer et al., 2011; Omenetti et al., 2014). In patients (Omenetti et al., 2014), albeit not in murine systems (Chae et al., 2011), this is dependent on NLRP3 in the context of TRIM20 mutations. A knockdown of ULK1 or TRIM20 elevated IL-1β responses (FIG. 19E; specifically for IL-1β since LDH release was unaffected, 25B). When the cells knocked down for either ULK1 or TRIM20 were also subjected to knockdowns of NLRP3, the latter normalized IL-1β expression (FIG. 25C-E). When cells were subjected to inflammasome activation with LPS and nigericin, FLICA staining (based on a fluorogenic probe FAM-YVAD-FMK for detection of in situ caspase 1 activity) revealed active caspase-1 puncta, as reported previously (Broz et al., 2010). The number of FLICA-positive cells increased when cells were subjected to a TRIM20 knockdown (FIGS. 19D and 25A). Thus, TRIM20 suppresses caspase-1 activation and IL-1β production. We then tested whether the disease-causing variants of TRIM20 affected autophagy and clearance of inflammasome components. We chose the three most frequent variants found in FMF patients (Masters et al., 2009), M680I, M694V and V726A (FIG. 19F). Compound (double or triple) mutant variants of TRIM20 formed fewer TRIM20 puncta (FIGS. 25F and G). Whereas expression of wild type TRIM20 resulted in degradation of NLRP3, overexpression of TRIM20 single (M694V), double (M680I and M694V) and triple (M680I, M694V and V726A) mutants showed diminished degradation of NLRP3 (FIG. 19G). Furthermore, protein complexes with the M694V, double (M680I+M694V), and triple (M680I+M694V+V726A) TRIM20 mutants harbored less ULK1, a trend that was paralleled by phospho-ULK1 levels (FIG. 19H). Consistent with this, there were fewer LC3 puncta per cell induced through expression of the triple mutant TRIM20 (M680I+M694V+V726A) than by the wild type TRIM20 (FIG. 25H). Thus, the disease-associated mutations in the PRY/SPRY domain of TRIM20 perturb ULK1 recruitment and autophagic degradation of NLRP3 and hence may contribute to the inflammatory phenotype associated with FMF mutations (FIG. 19I).

TRIM21 Interacts with Autophagy Factors

Figure 20:
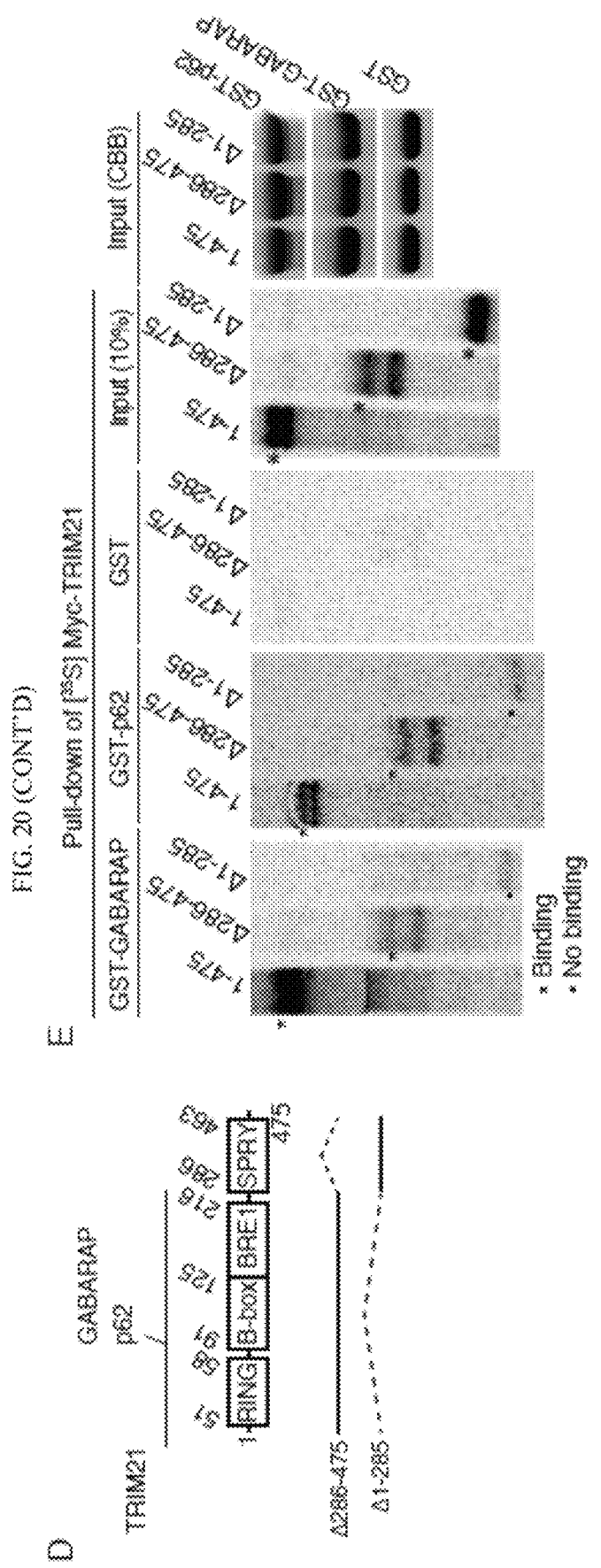
FIG. 20 shows that TRIM21 interacts with autophagy regulators and effectors. (A and B) Co-immunoprecipitation analyses of GFP-TRIM21 (T21) with (A) Myc-ULK1 and (B) Flag-Beclin 1 in HEK293 cells extracts. (C) GST pull-down analysis of binding between radiolabeled Myc-TRIM21 and GST-mAtg8s. Top, autoradiogram of pull-down products. Bottom, CBB-stained SDS-polyacrylamide gel with GST-mAtg8s. (D) TRIM21 domains and deletion constructs used. (E) GST pull-down analysis of binding between radiolabeled Myc-TRIM21 deletion mutants and GST-GABARAP and GST-p62. Asterisks and squares denote presence or absence of Myc-TRIM21, respectively. (F) p62 domains and deletion constructs used. (G) GST pull-down analysis of interaction between radiolabeled Myc-TRIM21 and GST-tagged p62. Data representative of three or more experiments.
Figure 20:
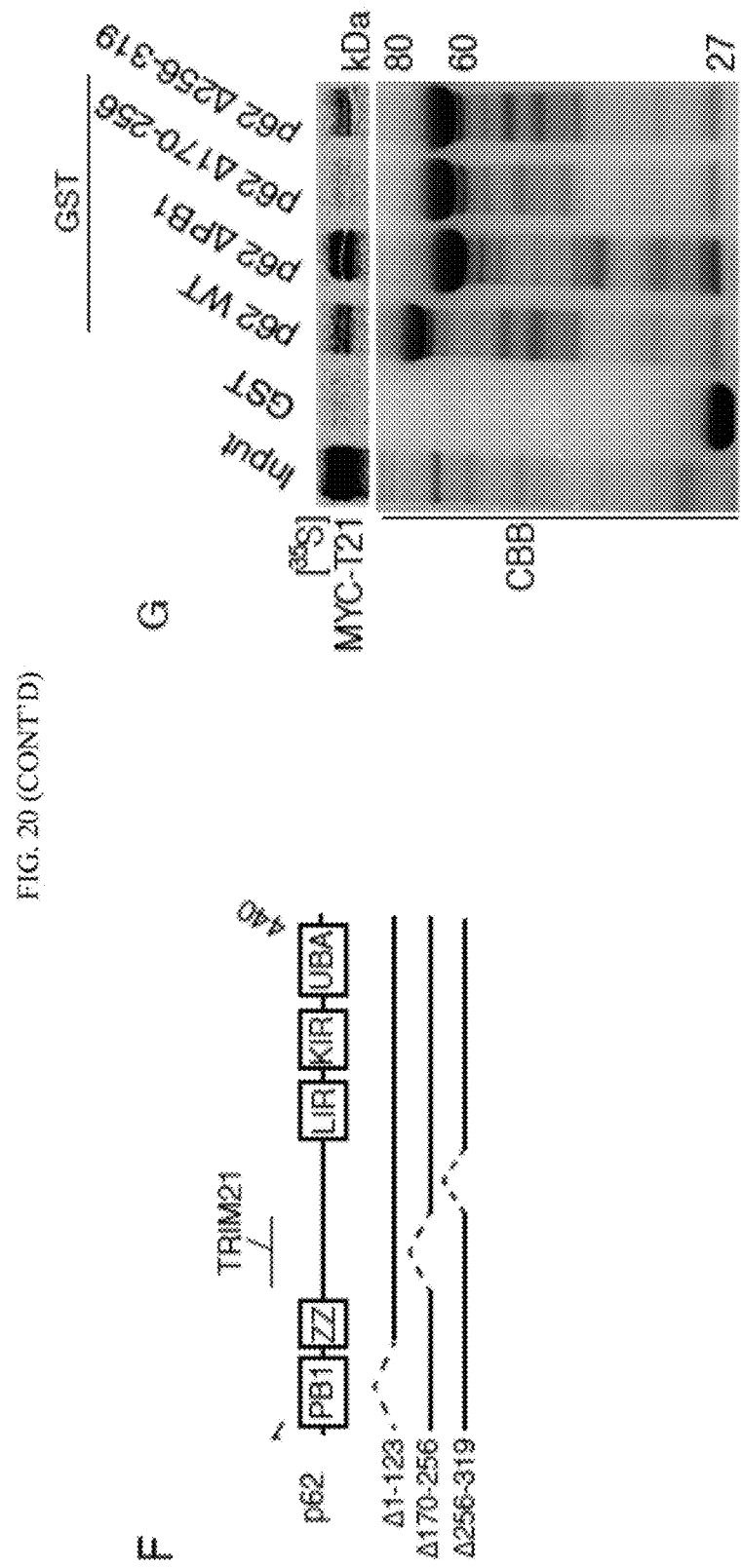
Figure 26:
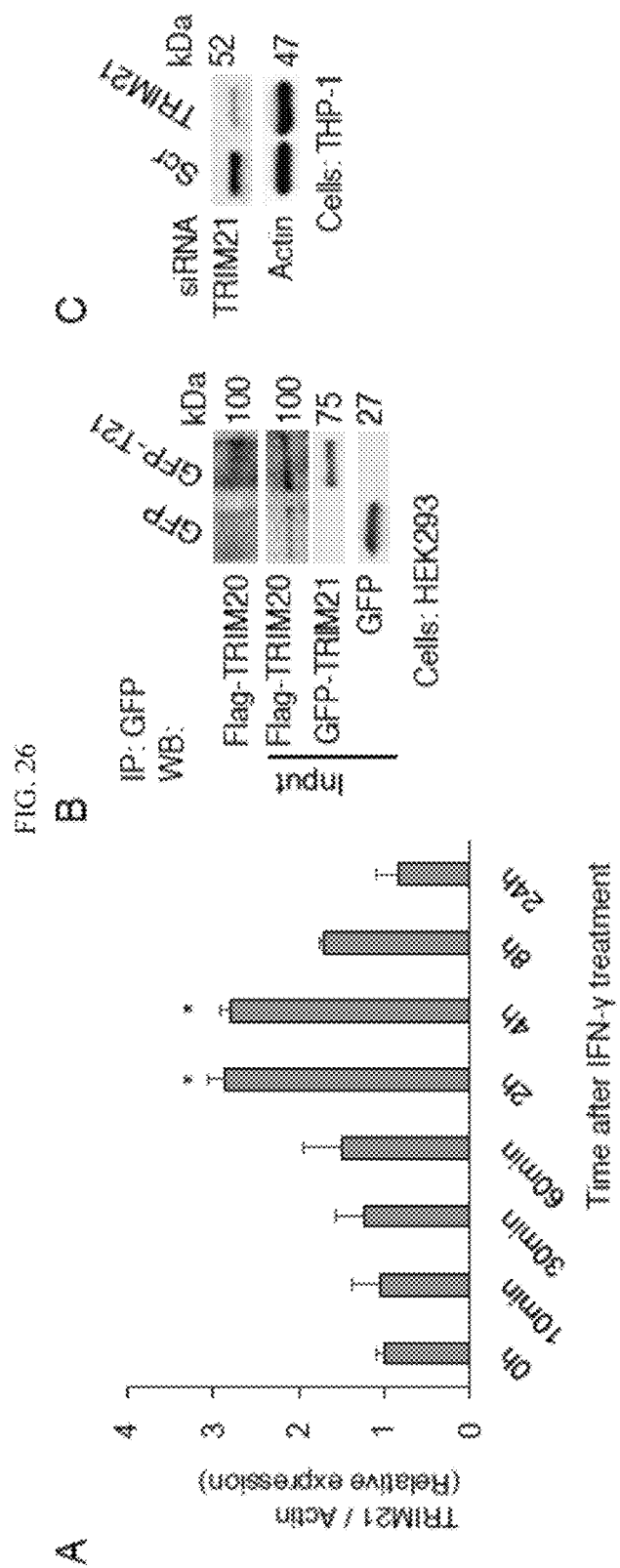
FIG. 26 shows that TRIM21 affects the level of dimerized IRF3 in HIV1 infection. (A) THP-1 cells were treated with 1,000 U/ml of IFN-γ for indicated times, and TRIM21 mRNA levels were determined by quantitative RT-PCR. (B) Co-immunoprecipitation analysis of GFP-TRIM20 with Flag-TRIM21 in HEK293 cells extracts. (C) Knockdown efficacy of TRIM21 level was examined by immunoblotting. (D) Levels of dimerized IRF3 were assessed by native PAGE from THP-1 cells subjected to TRIM21 or control knockdown, untreated with IFN-γ, and transfected with herring testis DNA (HT-DNA). (E and F) THP-1 cells subjected to TRIM21 or control knockdown were infected with a single-round infection HIV1 virus in the presence of 200 U/mL IFN-γ for 20 h, and (E) the levels of dimerized IRF3 or (F) mRNA levels of IFN-β were determined. (G) Model of TRIM21's dual function in autophagy as a regulator-receptor: TRIM21 assembles autophagy machinery (ULK1, Beclin 1, and mAtg8s) and recognizes substrates (dimerized IRF3) delivering them for autophagic degradation to suppress type I IFN response and inflammation. Dashed outlines (ULK1 and Beclin 1), domain binding location not mapped; solid outline for mAtg8 (GABARAP) reflects mapping data. (H) The effect of TRIM21 knockdown on IFN-β mRNA levels following stimulation of THP-1 cells with 1,000 U/ml IFN-γ for 3 h and then with 2.5 μg/mL LPS for 2 h. Data, means±SE, n≥3 experiments, *$P<0.05$ (ANOVA).
Figure 26:
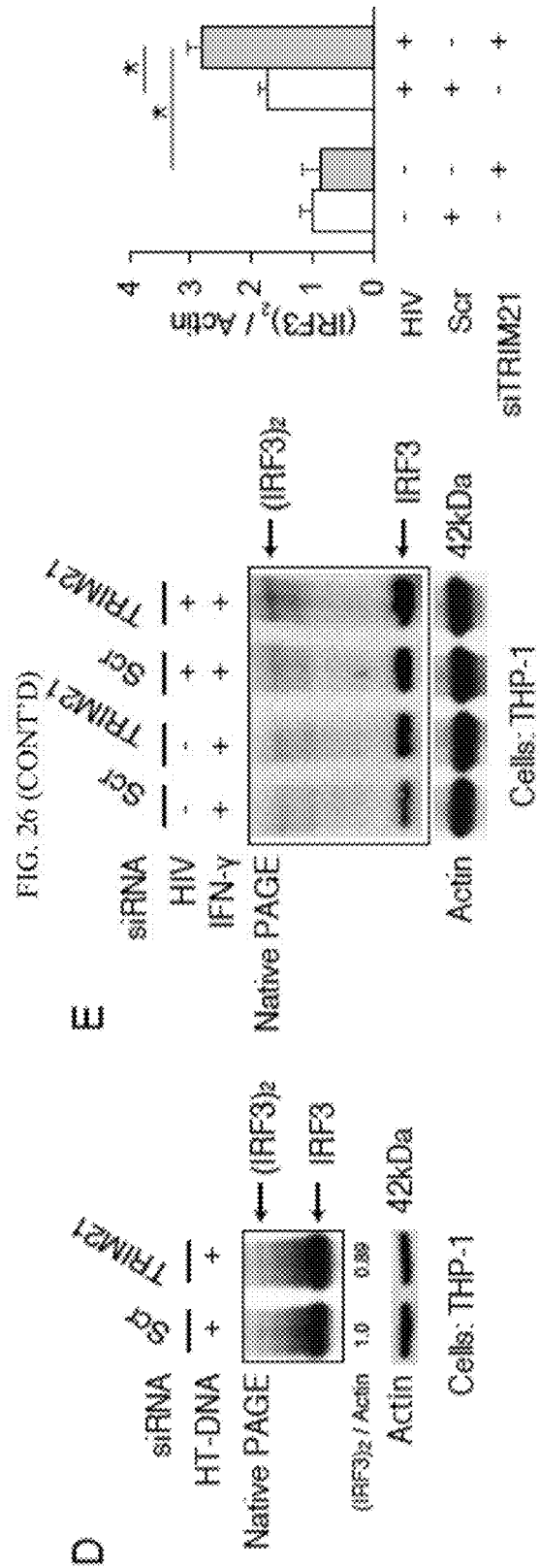

The IFN-γ screen with TRIM family of proteins yielded additional hits beside TRIM20 (FIG. 14B), several of which were validated in follow-up analyses (FIG. 14C). Among these was TRIM21 (also known as Ro52/SSA associated with Sjögren syndrome), which is transiently induced by IFN-γ (FIG. 26A). Incidentally, TRIM20 and 21 could be co-immunoprecipitated (FIG. 26B). The IFN-γ induction of TRIM21 expression was in agreement with previous reports (Carthagena et al., 2009; Espinosa et al., 2009). TRIM21 has an acknowledged role in regulating type I interferon responses (Espinosa et al., 2009; Higgs et al., 2008; McEwan et al., 2013; Yoshimi et al., 2009; Zhang et al., 2013). In one mechanism, TRIM21 has been reported to cause IKKβ degradation most likely through autophagy, based on its 3-methyladenine protection and LC3 localization (Niida et al., 2010). Based on our detailed studies with TRIM20 described above, we wondered whether TRIM21 might also act as a platform for assembly of autophagic regulatory factors. Indeed, TRIM21 bound both regulators, ULK1 and Beclin 1 (FIGS. 20A and B), and a subset of mAtg8s, most prominently GABARAP (FIG. 20C). GABARAP binding to TRIM21 did not require the SPRY domain of TRIM21 (FIGS. 20D and E). Unlike TRIM20, which does not bind Sequestosome1/p62 (p62) (Mandell et al., 2014), a well-known autophagic receptor (Birgisdottir et al., 2013), TRIM21 did bind p62 (FIGS. 20F and G). The TRIM21-binding region within p62 was delimited to the residues 170-256 of p62 (FIGS. 20F and G). The regions of TRIM21 binding p62 excluded its SPRY domain (FIGS. 20D and E). Thus, TRIM21 interacts with multiple regulators and effectors of autophagy.

TRIM21 is a Regulator-Receptor for Autophagic Degradation of Activated IRF3

Figure 21:
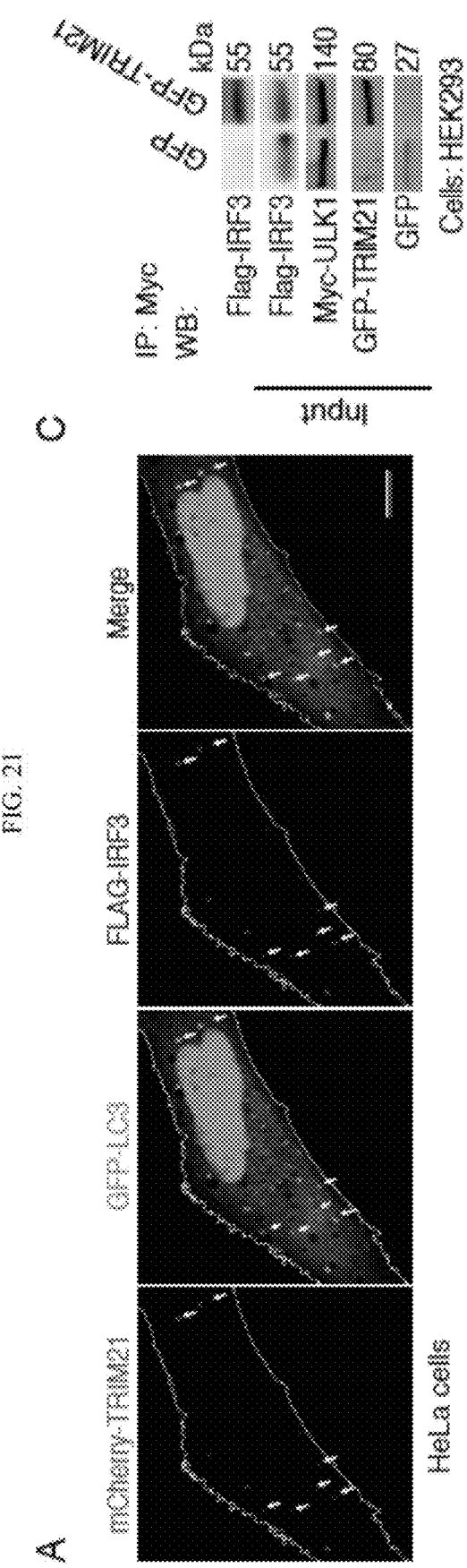
FIG. 21 shows that TRIM21 promotes autophagic degradation of IRF3 dimers and attenuates type I interferon production. (A) Confocal microscopy of HeLa cells co-expressing mCherry-TRIM21, Flag-IRF3, and GFP-LC3B in the presence of bafilomycin A1. White outline, cell boundary. Arrows indicate the colocalization. (B) Confocal microscopy of HEK293 cells co-expressing mCherry-TRIM21, Flag-IRF3, and GFP-ULK1. (C) Co-immunoprecipitation analysis of IRF3-ULK1 complexes in the presence and absence of TRIM21. Lysates from HEK293 cells transiently expressing Myc-ULK1, Flag-IRF3, and either GFP-TRIM20 or GFP were immunoprecipitated with anti-Myc, and immunoblots were probed as indicated. (D) Levels of dimerized IRF3 were assessed by native PAGE from THP-1 cells subjected to TRIM21 or control knockdown, and stimulated for 12 h by herring testis DNA (HT-DNA) transfected into the cells in the presence of 200 U/mL IFN-γ. (E) The effect of autophagy inhibition with bafilomycin on TRIM21-dependent IRF3 dimer degradation in THP-1 cells. (F) The effect of TRIM21 knockdown on IFN-β mRNA levels following stimulation of THP-1 cells with IFN-γ and HT-DNA. (G) Model of TRIMs' roles in regulation of inflammation by precision autophagy. TRIM20 targets the inflammasome components for autophagic degradation, whereas TRIM21 targets IRF3, to suppress inflammasome activity and type I IFN response, respectively. TRIM20 and TRIM21, both of whose expression response to IFN-γ, directly bind their respective cargo, cooperate in IFN-γ induction of autophagy (dashed line), and recruit autophagic machinery to execute degradation. Scale bars, 10 μm. Data, means±SE, n≥3, *P<0.05, †P≥0.05 (ANOVA).
Figure 21:
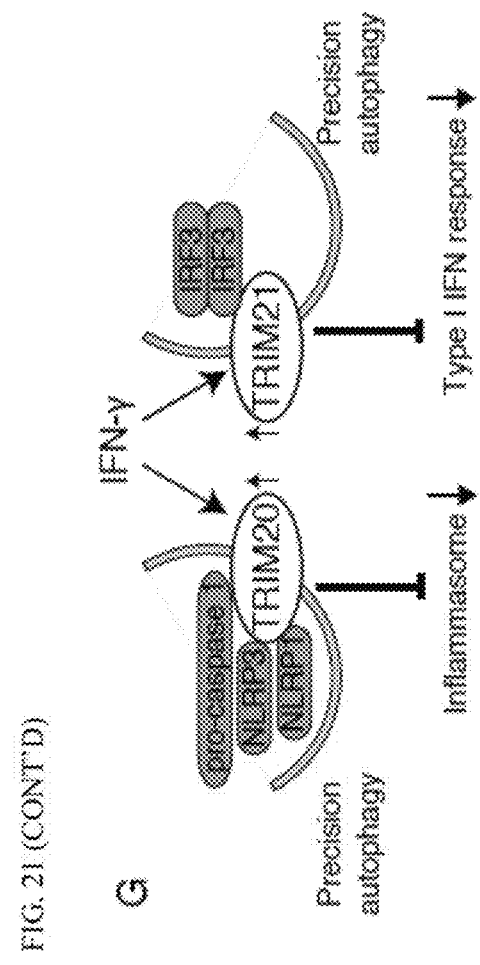
Figure 21:
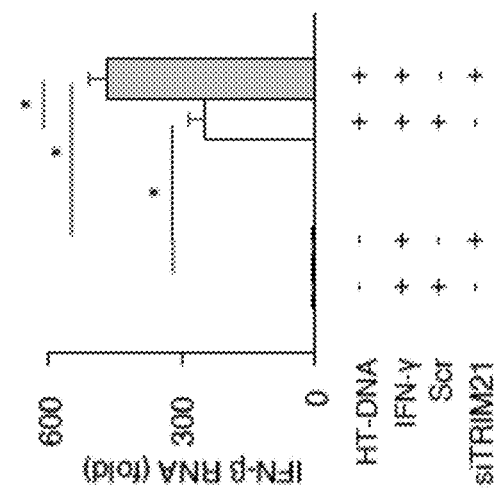

TRIM21 is known to interact with the transcription factor IRF3 through its SPRY domain (Higgs et al., 2008). It has been proposed that TRIM21 can suppress type I IFN response (Espinosa et al., 2009; Higgs et al., 2008; Yoshimi et al., 2009; Zhang et al., 2013), albeit an activation effect (McEwan et al., 2013) has also been reported. The proposed mechanism for negative regulation of IRF3 is mainly focused on proteasomal degradation of IRF3 (Higgs et al., 2008; Saitoh et al., 2006). However, autophagy is also known to play a suppressive role on type I IFN (Deretic et al., 2015; Jounai et al., 2007; Mathew et al., 2014; Saitoh et al., 2009). We thus wondered if TRIM21 could cause autophagic degradation of IRF3, analogous to what we observed with TRIM20 and NLRP3. IRF3 colocalized with TRIM21 in LC3-positive dots (FIG. 21A). Furthermore, IRF3$^+$ TRIM21$^+$ profiles were also ULK1 positive (FIG. 21B). Moreover, IRF3 was found in protein complexes with ULK1 when TRIM21 was present (FIG. 21C).

Cytosolic DNA (during viral infection, e.g. with HIV) induces type I interferon response through endogenous second messenger (cyclic GMP-AMP) by utilizing its adaptor protein STING that results in IRF3 dimerization/activation (Gao et al., 2013). It is the dimerized form of IRF3 that activates type I IFN responses (Takahasi et al., 2003). A knockdown of TRIM21 increased levels of IRF3 dimers in IFN-γ-treated cells stimulated with double stranded DNA (HT-DNA) transfected into the cells (FIG. 21D) but not in cells treated with HT-DNA alone, i.e. in the absence of IFN-γ (FIG. 26D), in keeping with the role of TRIM21 in acting as an effector of IFN-γ. A knockdown of TRIM21 also increased IRF3 dimers in cells infected with a single-cycle infection HIV-1 virus under conditions when cells were treated with INF-γ (FIG. 26E). Bafilomycin A1 protected dimerized IRF3 from degradation; this protection was no longer apparent in cells knocked down for TRIM21 (FIG. 21E), indicating that dimerized IRF3 was routed for autophagic degradation by TRIM21. As a physiologically relevant consequence, knockdown of TRIM21 resulted in increased levels of IFN-β expression after DNA transfection or infection with HIV-1 (FIG. 21F; and FIG. 26G). These data show that TRIM21 acts as a platform for IRF3 degradation, connecting it with the autophagic regulators (ULK1) and effectors (mAtg8s)(FIG. 26I). A knockdown of TRIM21 resulted in increased levels of IFN-β response to LPS (FIG. 26H), in keeping with the proposed autophagic targeting of IKKβ (Niida et al., 2010)) within a parallel pathway to IRF3-dependent activation of type I interferon responses.

Collectively, the present findings show that multiple TRIMs participate in autophagic response to IFN-γ. Specifically, TRIM20 and TRIM21 organize autophagic apparatus to degrade their cognate targets and downregulate responses via inflammasome/IL-1β and IRF3/type I IFN (FIG. 21G). Tapering of such responses may be essential to prevent excessive inflammation.

Discussion Precision Autophagy

The inventors' findings show that a subset of TRIMs act as receptors and regulators for selective autophagy targeting components of the inflammasome and type I interferon response systems. TRIM20 recognizes the inflammasome components, NLRP1, NLRP3, and pro-caspase 1, and leads to their autophagic degradation. A similar principle is at work with TRIM21, which targets activated (dimerized) IRF3 for autophagy. Not only do TRIM20 and TRIM21 directly bind their respective cargo, but they also recruit autophagic machinery thus coordinating target recognition with assembly of the autophagic apparatus and initiation of autophagy. These studies increase the repertoire of currently known autophagic receptors (Birgisdottir et al., 2013; Johansen and Lamark, 2011), and expand the target-receptor role of TRIMs in autophagy, previously indicted only for TRIM5α (Mandell et al., 2014). Thus, direct target recognition and assembly of autophagic machinery to conduct a process referred to as precision autophagy (Deretic et al., 2015) is a more general feature of the TRIM family of proteins.

The recognition of cognate targets by TRIM20 and TRIM21 is reminiscent of direct retroviral capsid recognition by TRIM5α (Stremlau et al., 2006) (Stremlau et al, 2006), which, as recently shown (Mandell et al., 2014) leads to autophagic degradation of HIV. The principles of precision autophagy (Deretic et al., 2015) may differ fundamentally from targeting of a variety of ubiquitinated cargo earmarked for autophagy by ubiquitin-binding receptors (Stolz et al., 2014). Incidentally, TRIM20 does not possess the RING E3 ubiquitin ligase domain, and does not bind p62 (Mandell et al., 2014). The absence of a RING domain and absence of binding to p62 underscores the ubiquitin-independent nature of target recognition by TRIM20. However, engagement of other Sequestosome 1-like receptors, a class (Deretic et al., 2013) of ubiquitin and galectin recognizing receptors (Gomes and Dikic, 2014; Randow and Youle, 2014) may not be ruled out, as well as a non-targeting role for ubiquitination in stabilizing autophagy initiation complexes (Chauhan et al., 2015; Nazio et al., 2013; Shi and Kehrl, 2010). Furthermore, inclusion of additional cytoplasmic material along with specific targets during TRIM-directed autophagy may not be ruled out.

Importantly, these findings indicate that substrate recognition by TRIM20 also directs precision autophagy machinery assembled by TRIM20. Thus, in their role in autophagy, TRIM20 and TRIM21 act not only as receptors for autophagy but also as platforms for assembly of regulators (ULK1, Beclin 1) and effectors (mAtg8s; p62 in the case of TRIM21), into initiation complexes. The presence in TRIM20 complexes of ATG16L1 may reflect direct association or reinforcement of indirect links between ULK1 and ATG16L1 (Gammoh et al., 2013; Nishimura et al., 2013). Other TRIMs may function similarly, as observed with TRIM5α and preliminarily with TRIM6, TRIM17, TRIM22, TRIM49, and TRIM55 (Mandell et al., 2014). The concept of platforms for assembly of autophagic machinery in mammalian cells also extends to generic, starvation induced autophagy, which utilizes exocyst components specifically endowed with Exo84 (Bodemann et al., 2011). However, TRIM engagement with autophagy may entail other mechanisms, as for example TRIM28 has multiple (both positive and negative) proposed mechanisms of action (Barde et al., 2013; Pineda et al., 2015; Yang et al., 2013), whereas the mechanism of autophagy induction for TRIM13 in response to the ER stress has not been fully delineated (Tomar et al., 2012) although it shows a relationship with p62 and DFCP, an ER-derived autophagy precursor compartment termed omegasome (Axe et al., 2008).

A further major biological finding reported here is that TRIMs are mediators of IFN-γ induced autophagy. The engagement of multiple TRIMs reveled in our screen should not be surprising, as multiple systems can trigger INF-γ-induced autophagy, such as the previously described DAPK phosphorylation of Beclin 1 (Inbal et al., 2002; Zalckvar et al., 2009) and immunity related GTPases (IRG)-dependent induction of autophagy (Gutierrez et al., 2004), which has recently been shown to act through a co-assembly of ULK1 and Beclin 1 (Chauhan et al., 2015). Additional upstream mechanisms may be controlled by TRIMs detected in our screen, as in the case of TRIM8, which is known to be inducible by IFN-γ (Toniato et al., 2002). TRIM8 activates TAK1 (Li et al., 2011), which is proposed to occur through K63 polyubiquitination. TAK1, in turn, activates AMPK-dependent autophagy (Criollo et al., 2011; Herrero-Martin et al., 2009; Kanayama et al., 2004) by phosphorylating AMPK (Xie et al., 2006). Hence, TRIM8 affects upstream pathways known to activate autophagy. This may explain why TRIM8 was identified as a hit in our IFN-γ-dependent autophagy induction screen. Furthermore, it is likely that TRIMs, known to hetero-oligomerize (Bell et al., 2012) as supported by our observations with TRIM20 and TRIM21, cooperate in IFN-γ induction of autophagy.

The finding that TRIM20 is a mediator of IFN-γ suppression of inflammasome activation provides a mechanism for this important IFN-γ effect in prevention of excessive inflammasome activation and associated pathology in infectious and autoimmune diseases (Minguela et al., 2007; Nandi and Behar, 2011), for which a satisfactory definition has been lacking albeit indirect mechanisms have been proposed (Mishra et al., 2013). The TRIM20-dependent direct recognition and autophagic degradation of the inflamamsome components NLRP3, pro-caspase 1, and NLRP1, differs form the previous reports of indirect effect on inflammasome activation via mitophagy (Nakahira et al., 2011; Zhou et al., 2011), and is more akin to the proposed autophagic degradation of AIM2, a sensory component of the DNA-reactive specialized inflamamsome, albeit AIM2 has been proposed to be eliminated by ubiquitin-tag recognizing receptor (Shi et al., 2012). We furthermore demonstrated that FMF disease-associated mutations in the PRY/SPRY domain of TRIM20 (Masters et al., 2009), alter the capacity of TRIM20 to direct autophagic degradation of inflammasome components. These mutations reduced the binding of ULK1, thus explaining in part how the common mutations associated with FMF work. We propose that IFN-γ-TRIM20-autophagy axis normally suppress excessive inflammasome and IL-1β activation, and that this ability is blunted by common disease-associated TRIM20 polymorphisms occurring in FMF.

The reported TRIM21-dependent suppression of type I IFN activation by autophagic degradation of IRF3 dimers mirrors the action of TRIM20 in suppressing inflamamsome activation. TRIM21, an autoantigen associated with Sjögren syndrome and systemic lupus erythematosus, suppresses type I IFN response (Espinosa et al., 2009; Higgs et al., 2008; Yoshimi et al., 2009; Zhang et al., 2013), albeit this has been ascribed to proteasomal degradation of IRF3 (Higgs et al., 2008) and IRF7 (Higgs et al., 2010). Nevertheless, type I IFN can also be activated by NF-kB, and autophagy has been implicated in degradation of the upstream NF-kB activating kinase, IKKβ (Niida et al., 2010). The TRIM21-directed autophagic degradation of activated IRF3 shown here complements the action of TRIM21 on NF-kB (Niida et al., 2010). Although the mechanism is not fully known, activation of type I IFN system is one major feature of Sjögren syndrome and systemic lupus erythematosus (Banchereau and Pascual, 2006). We thus raise the possibility that perturbations of IFN-γ-TRIM21-autophagy axis may cause activation of type I IFN in autoimmune diseases. The inventors' findings reported here broaden the concept of TRIMs acting as autophagic receptors and as platforms for assembly of autophagy initiation complexes. Our findings also link cargo recognition by a TRIM, acting as an autophagic receptor, with the function of the same TRIM in the assembly of autophagic machinery triggering the execution of autophagy of a very specific cytoplasmic targets. This brand of autophagy, termed precision autophagy, is guided by TRIMs and has important biological functions. For example, the TRIM20- and TRIM21-precision autophagy uncovered here balances key innate immunity responses, potentially serving as a guardian against excessive inflammation, which in turn may cause pathology during autoimmune processes or in infections causing cytokine storms. We propose that the large family of TRIMs with 70 members in humans endows cells with a precision in deploying autophagy.

REFERENCES (IRGM)

Abbott, D. W., Yang, Y., Hutti, J. E., Madhavarapu, S., Kelliher, M. A., and Cantley, L. C. (2007). Coordinated regulation of Toll-like receptor and NOD2 signaling by K63-linked polyubiquitin chains. Mol Cell Biol 27, 6012-6025.

Bekpen, C., Marques-Bonet, T., Alkan, C., Antonacci, F., Leogrande, M. B., Ventura, M., Kidd, J. M., Siswara, P., Howard, J. C., and Eichler, E. E. (2009). Death and resurrection of the human IRGM gene. PLoS Genet 5, e1000403.

Brest, P., Lapaquette, P., Souidi, M., Lebrigand, K., Cesaro, A., Vouret-Craviari, V., Mari, B., Barbry, P., Mosnier, J. F., Hebuterne, X., et al. (2011). A synonymous variant in IRGM alters a binding site for miR-196 and causes deregulation of IRGM-dependent xenophagy in Crohn's disease. Nat Genet 43, 242-245.

Chan, W. M., Mak, M. C., Fung, T. K., Lau, A., Siu, W. Y., and Poon, R. Y. (2006). Ubiquitination of p53 at multiple sites in the DNA-binding domain. Mol Cancer Res 4, 15-25.

Choi, J., Park, S., Biering, S. B., Selleck, E., Liu, C. Y., Zhang, X., Fujita, N., Saitoh, T., Akira, S., Yoshimori, T., et al. (2014). The parasitophorous vacuole membrane of Toxoplasma gondii is targeted for disruption by ubiquitin-like conjugation systems of autophagy. Immunity 40, 924-935.

Consortium (2007). Genome-wide association study of 14,000 cases of seven common diseases and 3,000 shared controls. Nature 447, 661-678.

Cooney, R., Baker, J., Brain, O., Danis, B., Pichulik, T., Allan, P., Ferguson, D. J., Campbell, B. J., Jewell, D., and Simmons, A. (2010). NOD2 stimulation induces autophagy in dendritic cells influencing bacterial handling and antigen presentation. Nat Med 16, 90-97.

Craddock, N., Hurles, M. E., Cardin, N., Pearson, R. D., Plagnol, V., Robson, S., Vukcevic, D., Barnes, C., Conrad, D. F., Giannoulatou, E., et al. (2010). Genome-wide association study of CNVs in 16,000 cases of eight common diseases and 3,000 shared controls. Nature 464, 713-720.

Criollo, A., Niso-Santano, M., Malik, S. A., Michaud, M., Morselli, E., Marino, G., Lachkar, S., Arkhipenko, A. V., Harper, F., Pierron, G., et al. (2011). Inhibition of autophagy by TAB2 and TAB3. The EMBO journal 30, 4908-4920.

Deretic, V., Kimura, T., Timmins, G., Moseley, P., Chauhan, S., and Mandell, M. (2015). Immunologic manifestations of autophagy. The Journal of Clinical Investigation 125, 75-84.

Dooley, H. C., Razi, M., Polson, H. E., Girardin, S. E., Wilson, M. I., and Tooze, S. A. (2014). WIPI2 Links LC3 Conjugation with PI3P, Autophagosome Formation, and Pathogen Clearance by Recruiting Atg12-5-16L1. Molecular cell 55, 238-252.

Egan, D. F., Shackelford, D. B., Mihaylova, M. M., Gelino, S., Kohnz, R. A., Mair, W., Vasquez, D. S., Joshi, A., Gwinn, D. M., Taylor, R., et al. (2011). Phosphorylation of ULK1 (hATG1) by AMP-activated protein kinase connects energy sensing to mitophagy. Science 331, 456-461.

Fimia, G. M., Stoykova, A., Romagnoli, A., Giunta, L., Di Bartolomeo, S., Nardacci, R., Corazzari, M., Fuoco, C., Ucar, A., Schwartz, P., et al. (2007). Ambra1 regulates autophagy and development of the nervous system. Nature 447, 1121-1125.

Fung, T. K., Yam, C. H., and Poon, R. Y. (2005). The N-terminal regulatory domain of cyclin A contains redundant ubiquitination targeting sequences and acceptor sites. Cell Cycle 4, 1411-1420.

Gammoh, N., Florey, O., Overholtzer, M., and Jiang, X. (2013). Interaction between FIP200 and ATG16L1 distinguishes ULK1 complex-dependent and -independent autophagy. Nat Struct Mol Biol 20, 144-149.

Gregoire, I. P., Richetta, C., Meyniel-Schicklin, L., Borel, S., Pradezynski, F., Diaz, O., Deloire, A., Azocar, O., Baguet, J., Le Breton, M., et al. (2011). IRGM is a common target of RNA viruses that subvert the autophagy network. PLoS pathogens 7, e1002422.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Hasegawa, M., Fujimoto, Y., Lucas, P. C., Nakano, H., Fukase, K., Nunez, G., and Inohara, N. (2008). A critical role of RICK/RIP2 polyubiquitination in Nod-induced NF-kappaB activation. EMBO J 27, 373-383.

Hoyer-Hansen, M., Bastholm, L., Szyniarowski, P., Campanella, M., Szabadkai, G., Farkas, T., Bianchi, K., Fehrenbacher, N., Elling, F., Rizzuto, R., et al. (2007). Control of macroautophagy by calcium, calmodulin-dependent kinase kinase-beta, and Bcl-2. Molecular cell 25, 193-205.

Hugot, J. P., Chamaillard, M., Zouali, H., Lesage, S., Cezard, J. P., Belaiche, J., Almer, S., Tysk, C., O'Morain, C. A., Gassull, M., et al. (2001). Association of NOD2 leucine-rich repeat variants with susceptibility to Crohn's disease. Nature 411, 599-603.

Intemann, C. D., Thye, T., Niemann, S., Browne, E. N., Amanua Chinbuah, M., Enimil, A., Gyapong, J., Osei, I., Owusu-Dabo, E., Helm, S., et al. (2009). Autophagy gene variant IRGM-261T contributes to protection from tuberculosis caused by *Mycobacterium tuberculosis* but not by *M. africanum* strains. PLoS Pathog 5, e1000577.

Itakura, E., Kishi, C., Inoue, K., and Mizushima, N. (2008). Beclin 1 forms two distinct phosphatidylinositol 3-kinase complexes with mammalian Atg14 and UVRAG. Mol Biol Cell 19, 5360-5372.

Kim, J., Kim, Y. C., Fang, C., Russell, R. C., Kim, J. H., Fan, W., Liu, R., Zhong, Q., and Guan, K. L. (2013). Differential regulation of distinct Vps34 complexes by AMPK in nutrient stress and autophagy. Cell 152, 290-303.

Kim, J., Kundu, M., Viollet, B., and Guan, K. L. (2011). AMPK and mTOR regulate autophagy through direct phosphorylation of Ulk1. Nature cell biology 13, 132-141.

Lapaquette, P., Glasser, A. L., Huett, A., Xavier, R. J., and Darfeuille-Michaud, A. (2010). Crohn's disease-associated adherent-invasive *E. coli* are selectively favoured by impaired autophagy to replicate intracellularly. Cell Microbiol 12, 99-113.

Levine, B., Mizushima, N., and Virgin, H. W. (2011). Autophagy in immunity and inflammation. Nature 469, 323-335.

Matsunaga, K., Saitoh, T., Tabata, K., Omori, H., Satoh, T., Kurotori, N., Maejima, I., Shirahama-Noda, K., Ichimura, T., Isobe, T., et al. (2009). Two Beclin 1-binding proteins, Atg14L and Rubicon, reciprocally regulate autophagy at different stages. Nat Cell Biol 11, 385-396.

McCarroll, S. A., Huett, A., Kuballa, P., Chilewski, S. D., Landry, A., Goyette, P., Zody, M. C., Hall, J. L., Brant, S. R., Cho, J. H., et al. (2008). Deletion polymorphism upstream of IRGM associated with altered IRGM expression and Crohn's disease. Nat Genet 40, 1107-1112.

Mihaylova, M. M., and Shaw, R. J. (2011). The AMPK signalling pathway coordinates cell growth, autophagy and metabolism. Nature cell biology 13, 1016-1023.

Mizushima, N. (2003). Mouse Apg16L, a novel WD-repeat protein, targets to the autophagic isolation membrane with the Apg12-Apg5 conjugate. Journal of cell science 116, 1679-1688.

Mizushima, N., Levine, B., Cuervo, A. M., and Klionsky, D. J. (2008). Autophagy fights disease through cellular self-digestion. Nature 451, 1069-1075.

Nazio, F., Strappazzon, F., Antonioli, M., Bielli, P., Cianfanelli, V., Bordi, M., Gretzmeier, C., Dengjel, J., Piacentini, M., Fimia, G. M., et al. (2013). mTOR inhibits autophagy by controlling ULK1 ubiquitylation, self-association and function through AMBRA1 and TRAF6. Nature cell biology 15, 406-416.

Ogura, Y., Bonen, D. K., Inohara, N., Nicolae, D. L., Chen, F. F., Ramos, R., Britton, H., Moran, T., Karaliuskas, R., Duerr, R. H., et al. (2001). A frameshift mutation in NOD2 associated with susceptibility to Crohn's disease. Nature 411, 603-606.

Romanello, V., Guadagnin, E., Gomes, L., Roder, I., Sandri, C., Petersen, Y., Milan, G., Masiero, E., Del Piccolo, P., Foretz, M., et al. (2010). Mitochondrial fission and remodelling contributes to muscle atrophy. EMBO J 29, 1774-1785.

Sabbah, A., Chang, T. H., Harnack, R., Frohlich, V., Tominaga, K., Dube, P. H., Xiang, Y., and Bose, S. (2009). Activation of innate immune antiviral responses by Nod2. Nat Immunol 10, 1073-1080.

Shi, C. S., and Kehrl, J. H. (2010). TRAF6 and A20 regulate lysine 63-linked ubiquitination of Beclin-1 to control TLR4-induced autophagy. Sci Signal 3, ra42.

Singh, S. B., Davis, A. S., Taylor, G. A., and Deretic, V. (2006). Human IRGM induces autophagy to eliminate intracellular mycobacteria. Science 313, 1438-1441.

Singh, S. B., Omatowski, W., Vergne, I., Naylor, J., Delgado, M., Roberts, E., Ponpuak, M., Master, S., Pilli, M., White, E., et al. (2010). Human IRGM regulates autophagy and cell-autonomous immunity functions through mitochondria. Nat Cell Biol 12, 1154-1165.

Song, J. H., Kim, S. Y., Chung, K. S., Moon, C. M., Kim, S. W., Kim, E. Y., Jung, J. Y., Park, M. S., Kim, Y. S., Kim, S. K., et al. (2014). Association between genetic variants in the IRGM gene and tuberculosis in a Korean population. Infection 42, 655-660.

Stolz, A., Ernst, A., and Dikic, I. (2014). Cargo recognition and trafficking in selective autophagy. Nat Cell Biol 16, 495-501.

Sun, Q., Fan, W., Chen, K., Ding, X., Chen, S., and Zhong, Q. (2008). Identification of Barkor as a mammalian autophagy-specific factor for Beclin 1 and class III phosphatidylinositol 3-kinase. Proceedings of the National Academy of Sciences of the United States of America 105, 19211-19216.

Tanabe, T., Chamaillard, M., Ogura, Y., Zhu, L., Qiu, S., Masumoto, J., Ghosh, P., Moran, A., Predergast, M. M., Tromp, G., et al. (2004). Regulatory regions and critical residues of NOD2 involved in muramyl dipeptide recognition. EMBO J 23, 1587-1597.

Travassos, L. H., Carneiro, L. A., Ramjeet, M., Hussey, S., Kim, Y. G., Magalhaes, J. G., Yuan, L., Soares, F., Chea, E., Le Bourhis, L., et al. (2010). Nod1 and Nod2 direct autophagy by recruiting ATG16L1 to the plasma membrane at the site of bacterial entry. Nature immunology 11, 55-62.

Turkieh, A., Caubere, C., Barutaut, M., Desmoulin, F., Harmancey, R., Galinier, M., Berry, M., Dambrin, C., Polidori, C., Casteilla, L., et al. (2014). Apolipoprotein O is mitochondrial and promotes lipotoxicity in heart. J Clin Invest 124, 2277-2286.

Yang, D., Chen, J., Zhang, L., Cha, Z., Han, S., Shi, W., Ding, R., Ma, L., Xiao, H., Shi, C., et al. (2014). *Mycobacterium leprae* Upregulates IRGM Expression in Monocytes and Monocyte-Derived Macrophages. Inflammation 37, 1028-1034.

Yang, Y., Yin, C., Pandey, A., Abbott, D., Sassetti, C., and Kelliher, M. A. (2007). NOD2 pathway activation by MDP or *Mycobacterium tuberculosis* infection involves the stable polyubiquitination of Rip2. The Journal of biological chemistry 282, 36223-36229.

Zurek, B., Schoultz, I., Neerincx, A., Napolitano, L. M., Birkner, K., Bennek, E., Sellge, G., Lerm, M., Meroni, G., Soderholm, J. D., et al. (2012). TRIM27 negatively regulates NOD2 by ubiquitination and proteasomal degradation. PloS one 7, e41255.

SUPPLEMENTAL REFERENCES (IRGM)

Chauhan, S., Goodwin, J. G., Manyam, G., Wang, J., Kamat, A. M., and Boyd, D. D. (2013). ZKSCAN3 is a master transcriptional repressor of autophagy. Molecular cell 50, 16-28.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Kyei, G. B., Dinkins, C., Davis, A. S., Roberts, E., Singh, S. B., Dong, C., Wu, L., Kominami, E., Ueno, T., Yamamoto, A., et al. (2009). Autophagy pathway intersects with HIV-1 biosynthesis and regulates viral yields in macrophages. The Journal of cell biology 186, 255-268.

Lapaquette, P., Glasser, A. L., Huett, A., Xavier, R. J., and Darfeuille-Michaud, A. (2010). Crohn's disease-associated adherent-invasive *E. coli* are selectively favoured by impaired autophagy to replicate intracellularly. Cell Microbiol 12, 99-113.

Singh, S. B., Omatowski, W., Vergne, I., Naylor, J., Delgado, M., Roberts, E., Ponpuak, M., Master, S., Pilli, M., White, E., et al. (2010). Human IRGM regulates autophagy and cell-autonomous immunity functions through mitochondria. Nat Cell Biol 12, 1154-1165.

Soderberg, O., Gullberg, M., Jarvius, M., Ridderstrale, K., Leuchowius, K. J., Jarvius, J., Wester, K., Hydbring, P., Bahram, F., Larsson, L. G., et al. (2006). Direct observation of individual endogenous protein complexes in situ by proximity ligation. Nature methods 3, 995-1000.

REFERENCES (PRECISION AUTOPHAGY)

Axe, E. L., S. A. Walker, M. Manifava, P. Chandra, H. L. Roderick, A. Habermann, G. Griffiths, and N. T. Ktistakis. 2008. Autophagosome formation from membrane compartments enriched in phosphatidylinositol 3-phosphate and dynamically connected to the endoplasmic reticulum. *J Cell Biol.* 182:685-701.

Banchereau, J., and V. Pascual. 2006. Type I interferon in systemic lupus erythematosus and other autoimmune diseases. *Immunity.* 25:383-392.

Barde, I., B. Rauwel, R. M. Marin-Florez, A. Corsinotti, E. Laurenti, S. Verp, S. Offner, J. Marquis, A. Kapopoulou, J. Vanicek, and D. Trono. 2013. A KRAB/KAP1-miRNA cascade regulates erythropoiesis through stage-specific control of mitophagy. *Science.* 340:350-353.

Bauernfeind, F. G., G. Horvath, A. Stutz, E. S. Alnemri, K. MacDonald, D. Speert, T. Fernandes-Alnemri, J. Wu, B. G. Monks, K. A. Fitzgerald, V. Hornung, and E. Latz. 2009. Cutting edge: NF-kappaB activating pattern recognition and cytokine receptors license NLRP3 inflammasome activation by regulating NLRP3 expression. *J Immunol.* 183:787-791.

Bell, J. L., A. Malyukova, J. K. Holien, J. Koach, M. W. Parker, M. Kavallaris, G. M. Marshall, and B. B. Cheung. 2012. TRIM16 acts as an E3 ubiquitin ligase and can heterodimerize with other TRIM family members. *PLoS One.* 7:e37470.

Birgisdottir, A. B., T. Lamark, and T. Johansen. 2013. The LIR motif—crucial for selective autophagy. *Journal of cell science.* 126:3237-3247.

Bodemann, B. O., A. Orvedahl, T. Cheng, R. R. Ram, Y. H. Ou, E. Formstecher, M. Maiti, C. C. Hazelett, E. M. Wauson, M. Balakireva, J. H. Camonis, C. Yeaman, B. Levine, and M. A. White. 2011. RalB and the Exocyst Mediate the Cellular Starvation Response by Direct Activation of Autophagosome Assembly. *Cell.* 144:253-267.

Broz, P., J. von Moltke, J. W. Jones, R. E. Vance, and D. M. Monack. 2010. Differential requirement for Caspase-1 autoproteolysis in pathogen-induced cell death and cytokine processing. *Cell Host Microbe.* 8:471-483.

Carthagena, L., A. Bergamaschi, J. M. Luna, A. David, P. D. Uchil, F. Margottin-Goguet, W. Mothes, U. Hazan, C. Transy, G. Pancino, and S. Nisole. 2009. Human TRIM gene expression in response to interferons. *PLoS One.* 4:e4894.

Chae, J. J., Y. H. Cho, G. S. Lee, J. Cheng, P. P. Liu, L. Feigenbaum, S. I. Katz, and D. L. Kastner. 2011. Gain-of-function Pyrin mutations induce NLRP3 protein-independent interleukin-1beta activation and severe autoinflammation in mice. *Immunity.* 34:755-768.

Chae, J. J., G. Wood, S. L. Masters, K. Richard, G. Park, B. J. Smith, and D. L. Kastner. 2006. The B30.2 domain of pyrin, the familial Mediterranean fever protein, interacts directly with caspase-1 to modulate IL-1beta production. *Proc Natl Acad Sci USA.* 103:9982-9987.

Chan, E. Y., and S. A. Tooze. 2009. Evolution of Atg1 function and regulation. *Autophagy.* 5:758-765.

Chauhan, S., M. A. Mandell, and V. Deretic. 2015. IRGM Governs the Core Autophagy Machinery to Conduct Antimicrobial Defense. *Molecular cell.* 58:507-521.

Criollo, A., M. Niso-Santano, S. A. Malik, M. Michaud, E. Morselli, G. Marino, S. Lachkar, A. V. Arkhipenko, F. Harper, G. Pierron, J. C. Rain, J. Ninomiya-Tsuji, J. M. Fuentes, S. Lavandero, L. Galluzzi, M. C. Maiuri, and G. Kroemer. 2011. Inhibition of autophagy by TAB2 and TAB3. *The EMBO journal.* 30:4908-4920.

Deretic, V., T. Kimura, G. Timmins, P. Moseley, S. Chauhan, and M. Mandell. 2015. Immunologic manifestations of autophagy. *J Clin Invest.* 125:75-84.

Deretic, V., T. Saitoh, and S. Akira. 2013. Autophagy in infection, inflammation and immunity. *Nat Rev Immunol.* 13:722-737.

Egan, D. F., D. B. Shackelford, M. M. Mihaylova, S. Gelino, R. A. Kohnz, W. Mair, D. S. Vasquez, A. Joshi, D. M. Gwinn, R. Taylor, J. M. Asara, J. Fitzpatrick, A. Dillin, B. Viollet, M. Kundu, M. Hansen, and R. J. Shaw. 2011. Phosphorylation of ULK1 (hATG1) by AMP-activated protein kinase connects energy sensing to mitophagy. *Science.* 331:456-461.

Espinosa, A., V. Dardalhon, S. Brauner, A. Ambrosi, R. Higgs, F. J. Quintana, M. Sjostrand, M. L. Eloranta, J. Ni Gabhann, O. Winqvist, B. Sundelin, C. A. Jefferies, B. Rozell, V. K. Kuchroo, and M. Wahren-Herlenius. 2009. Loss of the lupus autoantigen Ro52/Trim21 induces tissue inflammation and systemic autoimmunity by disregulating the IL-23-Th17 pathway. *J Exp Med.* 206:1661-1671.

Fabri, M., S. Stenger, D. M. Shin, J. M. Yuk, P. T. Liu, S. Realegeno, H. M. Lee, S. R. Krutzik, M. Schenk, P. A. Sieling, R. Teles, D. Montoya, S. S. Iyer, H. Bruns, D. M.

Lewinsohn, B. W. Hollis, M. Hewison, J. S. Adams, A. Steinmeyer, U. Zugel, G. Cheng, E. K. Jo, B. R. Bloom, and R. L. Modlin. 2011. Vitamin D is required for IFN-gamma-mediated antimicrobial activity of human macrophages. Science translational medicine. 3:104ra102.

Frake, R. A., T. Ricketts, F. M. Menzies, and D. C. Rubinsztein. 2015. Autophagy and neurodegeneration. The Journal of Clinical Investigation. 125:65-74.

French_FMF_Consortium. 1997. A candidate gene for familial Mediterranean fever. Nature genetics. 17:25-31.

Gammoh, N., O. Florey, M. Overholtzer, and X. Jiang. 2013. Interaction between FIP200 and ATG16L1 distinguishes ULK1 complex-dependent and -independent autophagy. Nature structural & molecular biology. 20:144-149.

Gao, D., J. Wu, Y. T. Wu, F. Du, C. Aroh, N. Yan, L. Sun, and Z. J. Chen. 2013. Cyclic GMP-AMP synthase is an innate immune sensor of HIV and other retroviruses. Science. 341:903-906.

Ghezzi, P., and C. A. Dinarello. 1988. IL-1 induces IL-1. III. Specific inhibition of IL-1 production by IFN-gamma. J Immunol. 140:4238-4244.

Gomes, L. C., and I. Dikic. 2014. Autophagy in antimicrobial immunity. Molecular cell. 54:224-233.

Gutierrez, M. G., S. S. Master, S. B. Singh, G. A. Taylor, M. I. Colombo, and V. Deretic. 2004. Autophagy is a defense mechanism inhibiting BCG and Mycobacterium tuberculosis survival in infected macrophages. Cell. 119:753-766.

He, C., and B. Levine. 2010. The Beclin 1 interactome. Current opinion in cell biology. 22:140-149.

Herrero-Martin, G., M. Hoyer-Hansen, C. Garcia-Garcia, C. Fumarola, T. Farkas, A. Lopez-Rivas, and M. Jaattela. 2009. TAK1 activates AMPK-dependent cytoprotective autophagy in TRAIL-treated epithelial cells. The EMBO journal. 28:677-685.

Higgs, R., E. Lazzari, C. Wynne, J. Ni Gabhann, A. Espinosa, M. Wahren-Herlenius, and C. A. Jefferies. 2010. Self protection from anti-viral responses—Ro52 promotes degradation of the transcription factor IRF7 downstream of the viral Toll-Like receptors. PLoS One. 5:e11776.

Higgs, R., J. Ni Gabhann, N. Ben Larbi, E. P. Breen, K. A. Fitzgerald, and C. A. Jefferies. 2008. The E3 ubiquitin ligase Ro52 negatively regulates IFN-beta production post-pathogen recognition by polyubiquitin-mediated degradation of IRF3. J Immunol. 181:1780-1786.

Inbal, B., S. Bialik, I. Sabanay, G. Shani, and A. Kimchi. 2002. DAP kinase and DRP-1 mediate membrane blebbing and the formation of autophagic vesicles during programmed cell death. J Cell Biol. 157:455-468.

Johansen, T., and T. Lamark. 2011. Selective autophagy mediated by autophagic adapter proteins. Autophagy. 7:279-296.

Jounai, N., F. Takeshita, K. Kobiyama, A. Sawano, A. Miyawaki, K. Q. Xin, K. J. Ishii, T. Kawai, S. Akira, K. Suzuki, and K. Okuda. 2007. The Atg5 Atg12 conjugate associates with innate antiviral immune responses. Proc Natl Acad Sci USA. 104:14050-14055.

Kabeya, Y., N. Mizushima, T. Ueno, A. Yamamoto, T. Kirisako, T. Noda, E. Kominami, Y. Ohsumi, and T. Yoshimori. 2000. LC3, a mammalian homologue of yeast Apg8p, is localized in autophagosome membranes after processing. The EMBO journal. 19:5720-5728.

Kanayama, A., R. B. Seth, L. Sun, C. K. Ea, M. Hong, A. Shaito, Y. H. Chiu, L. Deng, and Z. J. Chen. 2004. TAB2 and TAB3 activate the NF-kappaB pathway through binding to polyubiquitin chains. Molecular cell. 15:535-548.

Kawai, T., and S. Akira. 2011. Regulation of innate immune signalling pathways by the tripartite motif (TRIM) family proteins. EMBO molecular medicine. 3:513-527.

Kenific, C. M., and J. Debnath. 2015. Cellular and metabolic functions for autophagy in cancer cells. Trends Cell Biol. 25:37-45.

Khan, M. M., S. Strack, F. Wild, A. Hanashima, A. Gasch, K. Brohm, M. Reischl, S. Carnio, D. Labeit, M. Sandri, S. Labeit, and R. Rudolf. 2014. Role of autophagy, SQSTM1, SH3GLB1, and TRIM63 in the turnover of nicotinic acetylcholine receptors. Autophagy. 10:123-136.

Kim, J., Y. C. Kim, C. Fang, R. C. Russell, J. H. Kim, W. Fan, R. Liu, Q. Zhong, and K. L. Guan. 2013. Differential regulation of distinct Vps34 complexes by AMPK in nutrient stress and autophagy. Cell. 152:290-303.

Kim, J., M. Kundu, B. Viollet, and K. L. Guan. 2011. AMPK and mTOR regulate autophagy through direct phosphorylation of Ulk1. Nat Cell Biol. 13:132-141.

Kimura, T., A. Takahashi, Y. Takabatake, T. Namba, T. Yamamoto, J. Y. Kaimori, I. Matsui, H. Kitamura, F. Niimura, T. Matsusaka, T. Soga, H. Rakugi, and Y. Isaka. 2013. Autophagy protects kidney proximal tubule epithelial cells from mitochondrial metabolic stress. Autophagy. 9:1876-1886.

Konno, H., K. Konno, and G. N. Barber. 2013. Cyclic Dinucleotides Trigger ULK1 (ATG1) Phosphorylation of STING to Prevent Sustained Innate Immune Signaling. Cell.

Kramer, R. M., E. F. Roberts, S. L. Um, A. G. Borsch-Haubold, S. P. Watson, M. J. Fisher, and J. A. Jakubowski. 1996. $p^{38}$ mitogen-activated protein kinase phosphorylates cytosolic phospholipase A2 (cPLA2) in thrombin-stimulated platelets. Evidence that proline-directed phosphorylation is not required for mobilization of arachidonic acid by cPLA2. J Biol Chem. 271:27723-27729.

Kroemer, G. 2015. Autophagy: a druggable process that is deregulated in aging and human disease. The Journal of Clinical Investigation. 125:1-4.

Kyei, G. B., C. Dinkins, A. S. Davis, E. Roberts, S. B. Singh, C. Dong, L. Wu, E. Kominami, T. Ueno, A. Yamamoto, M. Federico, A. Panganiban, I. Vergne, and V. Deretic. 2009. Autophagy pathway intersects with HIV-1 biosynthesis and regulates viral yields in macrophages. J Cell Biol. 186:255-268.

Lapaquette, P., A. L. Glasser, A. Huett, R. J. Xavier, and A. Darfeuille-Michaud. 2010. Crohn's disease-associated adherent-invasive E. coli are selectively favoured by impaired autophagy to replicate intracellularly. Cellular microbiology. 12:99-113.

Li, Q., J. Yan, A. P. Mao, C. Li, Y. Ran, H. B. Shu, and Y. Y. Wang. 2011. Tripartite motif 8 (TRIM8) modulates TNFalpha- and IL-1beta-triggered NF-kappaB activation by targeting TAK1 for K63-linked polyubiquitination. Proc Natl Acad Sci USA. 108:19341-19346.

Liang, Q., G. J. Seo, Y. J. Choi, M. J. Kwak, J. Ge, M. A. Rodgers, M. Shi, B. J. Leslie, K. P. Hopfner, T. Ha, B. H. Oh, and J. U. Jung. 2014. Crosstalk between the cGAS DNA sensor and Beclin-1 autophagy protein shapes innate antimicrobial immune responses. Cell Host Microbe. 15:228-238.

Liang, X. H., S. Jackson, M. Seaman, K. Brown, B. Kempkes, H. Hibshoosh, and B. Levine. 1999. Induction of autophagy and inhibition of tumorigenesis by beclin 1. Nature. 402:672-676.

Ma, Y., L. Galluzzi, L. Zitvogel, and G. Kroemer. 2013. Autophagy and cellular immune responses. *Immunity.* 39:211-227.

Maejima, I., A. Takahashi, H. Omori, T. Kimura, Y. Takabatake, T. Saitoh, A. Yamamoto, M. Hamasaki, T. Noda, Y. Isaka, and T. Yoshimori. 2013. Autophagy sequesters damaged lysosomes to control lysosomal biogenesis and kidney injury. *The EMBO journal.* 32:2336-2347.

Mandell, M. A., A. Jain, J. Arko-Mensah, S. Chauhan, T. Kimura, C. Dinkins, G. Silvestri, J. Munch, F. Kirchhoff, A. Simonsen, Y. Wei, B. Levine, T. Johansen, and V. Deretic. 2014. TRIM proteins regulate autophagy and can target autophagic substrates by direct recognition. *Dev Cell.* 30:394-409.

Masters, S. L., A. Simon, I. Aksentijevich, and D. L. Kastner. 2009. Horror autoinflarnmaticus: the molecular pathophysiology of autoinflammatory disease. *Annual review of immunology.* 27:621-668.

Mathew, R., S. Khor, S. R. Hackett, J. D. Rabinowitz, D. H. Perlman, and E. White. 2014. Functional Role of Autophagy-Mediated Proteome Remodeling in Cell Survival Signaling and Innate Immunity. *Molecular cell.*

McEwan, W. A., J. C. Tam, R. E. Watkinson, S. R. Bidgood, D. L. Mallery, and L. C. James. 2013. Intracellular antibody-bound pathogens stimulate immune signaling via the Fc receptor TRIM21. *Nature immunology.* 14:327-336.

Meinzer, U., P. Quartier, J. F. Alexandra, V. Hentgen, F. Retornaz, and I. Kone-Paut. 2011. Interleukin-1 targeting drugs in familial Mediterranean fever: a case series and a review of the literature. *Seminars in arthritis and rheumatism.* 41:265-271.

Minguela, A., S. Pastor, W. Mi, J. A. Richardson, and E. S. Ward. 2007. Feedback regulation of murine autoimmunity via dominant anti-inflammatory effects of interferon gamma. *J Immunol.* 178:134-144.

Mishra, B. B., V. A. Rathinam, G. W. Martens, A. J. Martinot, H. Kornfeld, K. A. Fitzgerald, and C. M. Sassetti. 2013. Nitric oxide controls the immunopathology of tuberculosis by inhibiting NLRP3 inflammasome-dependent processing of IL-1beta. *Nature immunology.* 14:52-60.

Mizushima, N., A. Kuma, Y. Kobayashi, A. Yamamoto, M. Matsubae, T. Takao, T. Natsume, Y. Ohsumi, and T. Yoshimori. 2003. Mouse Apg16L, a novel WD-repeat protein, targets to the autophagic isolation membrane with the Apg12-Apg5 conjugate. *Journal of cell science.* 116:1679-1688.

Mizushima, N., T. Yoshimori, and B. Levine. 2010. Methods in mammalian autophagy research. *Cell.* 140:313-326.

Mizushima, N., T. Yoshimori, and Y. Ohsumi. 2011. The role of atg proteins in autophagosome formation. *Annual review of cell and developmental biology.* 27:107-132.

Nakahira, K., J. A. Haspel, V. A. Rathinam, S. J. Lee, T. Dolinay, H. C. Lam, J. A. Englert, M. Rabinovitch, M. Cernadas, H. P. Kim, K. A. Fitzgerald, S. W. Ryter, and A. M. Choi. 2011. Autophagy proteins regulate innate immune responses by inhibiting the release of mitochondrial DNA mediated by the NALP3 inflammasome. *Nature immunology.* 12:222-230.

Nandi, B., and S. M. Behar. 2011. Regulation of neutrophils by interferon-gamma limits lung inflammation during tuberculosis infection. *J Exp Med.* 208:2251-2262.

Nazio, F., F. Strappazzon, M. Antonioli, P. Bielli, V. Cianfanelli, M. Bordi, C. Gretzmeier, J. Dengjel, M. Piacentini, G. M. Fimia, and F. Cecconi. 2013. mTOR inhibits autophagy by controlling ULK1 ubiquitylation, self-association and function through AMBRA1 and TRAF6. *Nat Cell Biol.* 15:406-416.

Niida, M., M. Tanaka, and T. Kamitani. 2010. Downregulation of active IKK beta by Ro52-mediated autophagy. *Mol Immunol.* 47:2378-2387.

Nishimura, T., T. Kaizuka, K. Cadwell, M. H. Sahani, T. Saitoh, S. Akira, H. W. Virgin, and N. Mizushima. 2013. FIP200 regulates targeting of Atg16L1 to the isolation membrane. *EMBO Rep.* 14:284-291.

Omenetti, A., S. Carta, L. Delfino, A. Martini, M. Gattorno, and A. Rubartelli. 2014. Increased NLRP3-dependent interleukin 1 beta secretion in patients with familial Mediterranean fever: correlation with MEFV genotype. *Annals of the rheumatic diseases.* 73:462-469.

Pankiv, S., T. H. Clausen, T. Lamark, A. Brech, J. A. Bruun, H. Outzen, A. Overvatn, G. Bjorkoy, and T. Johansen. 2007. p62/SQSTM1 binds directly to Atg8/LC3 to facilitate degradation of ubiquitinated protein aggregates by autophagy. *J Biol Chem.* 282:24131-24145.

Papin, S., S. Cuenin, L. Agostini, F. Martinon, S. Werner, H. D. Beer, C. Grutter, M. Grutter, and J. Tschopp. 2007. The SPRY domain of Pyrin, mutated in familial Mediterranean fever patients, interacts with inflammasome components and inhibits proIL-1beta processing. *Cell Death Differ.* 14:1457-1466.

Pineda, C. T., S. Ramanathan, K. Fon Tacer, J. L. Weon, M. B. Potts, Y. H. Ou, M. A. White, and P. R. Potts. 2015. Degradation of AMPK by a Cancer-Specific Ubiquitin Ligase. *Cell.* 160:715-728.

Pizon, V., S. Rybina, F. Gerbal, F. Delort, P. Vicart, G. Baldacci, and E. Karsenti. 2013. MURF2B, a novel LC3-binding protein, participates with MURF2A in the switch between autophagy and ubiquitin proteasome system during differentiation of C2C12 muscle cells. *PLoS One.* 8:e76140.

Rabinowitz, J. D., and E. White. 2010. Autophagy and metabolism. *Science.* 330:1344-1348.

Randow, F., and R. J. Youle. 2014. Self and Nonself: How Autophagy Targets Mitochondria and Bacteria. *Cell Host Microbe.* 15:403-411.

Reymond, A., G. Meroni, A. Fantozzi, G. Merla, S. Cairo, L. Luzi, D. Riganelli, E. Zanaria, S. Messali, S. Cainarca, A. Guffanti, S. Minucci, P. G. Pelicci, and A. Ballabio. 2001. The tripartite motif family identifies cell compartments. *The EMBO journal.* 20:2140-2151.

Rogov, V., V. Dotsch, T. Johansen, and V. Kirkin. 2014. Interactions between autophagy receptors and ubiquitin-like proteins form the molecular basis for selective autophagy. *Molecular cell.* 53:167-178.

Rubinsztein, D. C., P. Codogno, and B. Levine. 2012. Autophagy modulation as a potential therapeutic target for diverse diseases. *Nature reviews. Drug discovery.* 11:709-730.

Russell, R. C., Y. Tian, H. Yuan, H. W. Park, Y. Y. Chang, J. Kim, H. Kim, T. P. Neufeld, A. Dillin, and K. L. Guan. 2013. ULK1 induces autophagy by phosphorylating Beclin-1 and activating VPS34 lipid kinase. *Nat Cell Biol.* 15:741-750.

Saitoh, T., N. Fujita, T. Hayashi, K. Takahara, T. Satoh, H. Lee, K. Matsunaga, S. Kageyama, H. Omori, T. Noda, N. Yamamoto, T. Kawai, K. Ishii, O. Takeuchi, T. Yoshimori, and S. Akira. 2009. Atg9a controls dsDNA-driven dynamic translocation of STING and the innate immune response. *Proc Natl Acad Sci USA*. 106:20842-20846.

Saitoh, T., N. Fujita, M. H. Jang, S. Uematsu, B. G. Yang, T. Satoh, H. Omori, T. Noda, N. Yamamoto, M. Komatsu, K. Tanaka, T. Kawai, T. Tsujimura, O. Takeuchi, T. Yoshimori, and S. Akira. 2008. Loss of the autophagy protein Atg16L1 enhances endotoxin-induced IL-1beta production. *Nature*. 456:264-268.

Saitoh, T., A. Tun-Kyi, A. Ryo, M. Yamamoto, G. Finn, T. Fujita, S. Akira, N. Yamamoto, K. P. Lu, and S. Yamaoka. 2006. Negative regulation of interferon-regulatory factor 3-dependent innate antiviral response by the prolyl isomerase Pin1. *Nature immunology*. 7:598-605.

Schroder, K., and J. Tschopp. 2010. The inflammasomes. *Cell*. 140:821-832.

Shi, C. S., and J. H. Kehrl. 2010. TRAF6 and A20 regulate lysine 63-linked ubiquitination of Beclin-1 to control TLR4-induced autophagy. *Sci Signal*. 3:ra42.

Shi, C. S., K. Shenderov, N. N. Huang, J. Kabat, M. Abu-Asab, K. A. Fitzgerald, A. Sher, and J. H. Kehrl. 2012. Activation of autophagy by inflammatory signals limits IL-1beta production by targeting ubiquitinated inflammasomes for destruction. *Nature immunology*. 13:255-263.

Simonsen, A., and S. A. Tooze. 2009. Coordination of membrane events during autophagy by multiple class III PI3-kinase complexes. *J Cell Biol*. 186:773-782.

Stolz, A., A. Ernst, and I. Dikic. 2014. Cargo recognition and trafficking in selective autophagy. *Nat Cell Biol*. 16:495-501.

Stremlau, M., M. Perron, M. Lee, Y. Li, B. Song, H. Javanbakht, F. Diaz-Griffero, D. J. Anderson, W. I. Sundquist, and J. Sodroski. 2006. Specific recognition and accelerated uncoating of retroviral capsids by the TRIM5alpha restriction factor. *Proc Natl Acad Sci USA*. 103:5514-5519.

Takahasi, K., N. N. Suzuki, M. Horiuchi, M. Mori, W. Suhara, Y. Okabe, Y. Fukuhara, H. Terasawa, S. Akira, T. Fujita, and F. Inagaki. 2003. X-ray crystal structure of IRF-3 and its functional implications. *Nature structural biology*. 10:922-927.

Tal, M. C., M. Sasai, H. K. Lee, B. Yordy, G. S. Shadel, and A. Iwasaki. 2009. Absence of autophagy results in reactive oxygen species-dependent amplification of RLR signaling. *Proc Natl Acad Sci USA*. 106:2770-2775.

The_International_FMF_Consortium. 1997. Ancient missense mutations in a new member of the RoRet gene family are likely to cause familial Mediterranean fever. *Cell*. 90:797-807.

Tomar, D., R. Singh, A. K. Singh, C. D. Pandya, and R. Singh. 2012. TRIM13 regulates ER stress induced autophagy and clonogenic ability of the cells. *Biochimica et biophysica acta*. 1823:316-326.

Toniato, E., X. P. Chen, J. Losman, V. Flati, L. Donahue, and P. Rothman. 2002. TRIM8/GERP RING finger protein interacts with SOCS-1. *J Biol Chem*. 277:37315-37322.

Weidberg, H., T. Shpilka, E. Shvets, A. Abada, F. Shimron, and Z. Elazar. 2011. LC3 and GATE-16 N termini mediate membrane fusion processes required for autophagosome biogenesis. *Developmental cell*. 20:444-454.

Xie, M., D. Zhang, J. R. Dyck, Y. Li, H. Zhang, M. Morishima, D. L. Mann, G. E. Taffet, A. Baldini, D. S. Khoury, and M. D. Schneider. 2006. A pivotal role for endogenous TGF-beta-activated kinase-1 in the LKB1/AMP-activated protein kinase energy-sensor pathway. *Proc Natl Acad Sci USA*. 103:17378-17383.

Yang, Y., W. Fiskus, B. Yong, P. Atadja, Y. Takahashi, T. K. Pandita, H. G. Wang, and K. N. Bhalla. 2013. Acetylated hsp70 and KAP1-mediated Vps34 SUMOylation is required for autophagosome creation in autophagy. *Proc Natl Acad Sci USA*. 110:6841-6846.

Yoshimi, R., T. H. Chang, H. Wang, T. Atsumi, H. C. Morse, 3rd, and K. Ozato. 2009. Gene disruption study reveals a nonredundant role for TRIM21/Ro52 in NF-kappaB-dependent cytokine expression in fibroblasts. *J Immunol*. 182:7527-7538.

Youle, R. J., and D. P. Narendra. 2011. Mechanisms of mitophagy. *Nature reviews. Molecular cell biology*. 12:9-14.

Zalckvar, E., H. Berissi, L. Mizrachy, Y. Idelchuk, I. Koren, M. Eisenstein, H. Sabanay, R. Pinkas-Kramarski, and A. Kimchi. 2009. DAP-kinase-mediated phosphorylation on the BH3 domain of beclin 1 promotes dissociation of beclin 1 from Bcl-X(L) and induction of autophagy. *EMBO Rep*.

Zhang, Z., M. Bao, N. Lu, L. Weng, B. Yuan, and Y. J. Liu. 2013. The E3 ubiquitin ligase TRIM21 negatively regulates the innate immune response to intracellular double-stranded DNA. *Nature immunology*. 14:172-178.

Zhou, R., A. S. Yazdi, P. Menu, and J. Tschopp. 2011. A role for mitochondria in NLRP3 inflammasome activation. *Nature*. 469:221-225.

SUPPLEMENTAL REFERENCES (PRECISION AUTOPHAGY)

Chauhan, S., Goodwin, J. G., Manyam, G., Wang, J., Kamat, A. M., and Boyd, D. D. (2013). ZKSCAN3 is a master transcriptional repressor of autophagy. Molecular cell 50, 16-28.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Kyei, G. B., Dinkins, C., Davis, A. S., Roberts, E., Singh, S. B., Dong, C., Wu, L., Kominami, E., Ueno, T., Yamamoto, A., et al. (2009). Autophagy pathway intersects with HIV-1 biosynthesis and regulates viral yields in macrophages. The Journal of cell biology 186, 255-268.

Lapaquette, P., Glasser, A. L., Huett, A., Xavier, R. J., and Darfeuille-Michaud, A. (2010). Crohn's disease-associated adherent-invasive *E. coli* are selectively favoured by impaired autophagy to replicate intracellularly. Cell Microbiol 12, 99-113.

Singh, S. B., Omatowski, W., Vergne, I., Naylor, J., Delgado, M., Roberts, E., Ponpuak, M., Master, S., Pilli, M., White, E., et al. (2010). Human IRGM regulates autophagy and cell-autonomous immunity functions through mitochondria. Nat Cell Biol 12, 1154-1165.

Soderberg, O., Gullberg, M., Jarvius, M., Ridderstrale, K., Leuchowius, K. J., Jarvius, J., Wester, K., Hydbring, P., Bahram, F., Larsson, L. G., et al. (2006). Direct observation of individual endogenous protein complexes in situ by proximity ligation. Nature methods 3, 995-1000.

| TRIM # | Accession # | Sequence | SiRNA |
|---|---|---|---|
| TRIM1 | NM_012216 | MGESPASVVLNASGGLFSLKMETLESELTCPICLELFEDPLLLP CAHSLCFSCARRILVSSCSSGESIEPITAFQCPTCRYVISLNHR GLDGLKRNVTLQNIDRFQKASVSGPNSPSESRRERTYRPTTAMS SERIACQFCEQDPPRDAVKTCITCEVSYCDRCLRATHPNKKPFT SHRLVEPVPDTHLRGITCLDHENEKVNMYCVSDDQLICALCKLV GRHRDHQVASLNDRFEKLKQTLEMNLTNLVKRNSELENQMAKLI QICQQVEVNTAMHEAKLMEECDELVEIIQQRKQMIAVKIKETKV MKLRKLAQQVANCRQCLERSTVLINQAEHILKENDQARFLQSAK NIAERVAMATASSQVLIPDINFNDAFENFALDFSREKKLLEGLD YLTAPNPPSIREELCTASHDTITVHWISDDEFSISSYELQYTIF TGQANFISKSWCSWGLWPEIRKCKEAVSCSRLAGAPRGLYNSVD SWMIVPNIKQNHYTVHGLQSGTRYIFIVKAINQAGSRNSEPTRL KTNSQPFKLDPKMTHKKLKISNDGLQMEKDESSLKKSHTPERFS GTGCYGAAGNIFIDSGCHYWEVVMGSSTWYAIGIAYKSAPKNEW IGKNASSWVESRCNSNEVVRHNNKEMLVDVPPHLKRLGVLLDYD NNMLSFYDPANSLHLHTFDVTFILPVCPTFTIWNKSLMILSGLP APDFIDYPERQECNCRPQESPYVSGMKTCH SEQ ID NO: 1 | GAUGAAAGCUCUCUAAAGA SEQ ID NO: 2 GAACAAAUCCCUAAUGAUC SEQ ID NO: 3 GUAGACAGCUGGAUGAUUG SEQ ID NO: 4 CAAAUCAGCUCCAAAGAAU SEQ ID NO: 5 |
| TRIM2 | NM_015271 | MHRSGRYGTQQQRAGSKTAGPPCQWSRMASEGTNIPSPVVRQID KQFLICSICLERYKNPKVLPCLHTFCERCLQNYIPAHSLTLSCP VCRQTSILPEKGVAALQNNFFITNLMDVLQRTPGSNAEESSILE TVTAVAAGKPLSCPNHDGNVMEFYCQSCETAMCRECTEGEHAEH PTVPLKDVVEQHKASLQVQLDAVNKRLPEIDSALQFISEIIHQL TNQKASIVDDIHSTFDELQKTLNVRKSVLLMELEVNYGLKHKVL QSQLDTLLQGQESIKSCSNETAQALNHGTETEVLLKKQMSEKL NELADQDFPLHPRENDQLDFIVETEGLKKSIHNLGTILTTNAVA SETVATGEGLRQTIIGQPMSVTITTKDKDGELCKTGNAYLTAEL STPDGSVADGEILDNKNGTYEFLYTVQKEGDFTLSLRLYDQHIR GSPFKLKVIRSADVSPTTEGVKRRVKSPGSGHVKQKAVKRPASM YSTGKRKENPIEDDLIFRVGTKGRNKGEFTNLQGVAASTNGKIL IADSNNQCVQIFSNDGQFKSREGIRGRSPGQLQRPTGVAVHPSG DIIIADYDNKWVSIFSSDGKFKTKIGSGKLMGPKGVSVDRNGHI IVVDNKACCVFIFQPNGKIVTREGSRGNGDRQFAGPHFAAVNSN NEIIITDEHNHSVKVFNQEGEFMLKFGSNGEGNGQFNAPTGVAV DSNGNIIVADWGNSRIQVFDGSGSFLSYINTSADPLYGPQGLAL TSDGHVVADSGNHCFKVYRYLQ SEQ ID NO: 6 | GAACGGCACCUAUGAGUUU SEQ ID NO: 7 GGAAGGAGAAUUCAUGUUG SEQ ID NO: 8 GGAAUGUGAUGGAAUUUUA SEQ ID NO: 9 CAACCAAUGUGUGCAGAUA SEQ ID NO: 10 |
| TRIM3 | NM_006458 | MAKREDSPGPEVQPMDKQFLVCSICLDRYQCPKVLPCLHTFCER CLQNYIPAQSLTLSCPVCRQTSILPEQGVSALQNNFFISSLMEA MQQAPDGAHDPEDPHPLSVVAGRPLSCPNHEGKTMEFYCEACET AMCGECRAGEHREHGTVLLRDVVEQHKAALQRQLEAVRGRLPQL SAAIALVGGISQQLQERKAEALAQISAAFEDLEQALQQRKQALV SDLETICGAKQKVLQSQLDTLRQGQEHIGSSCSFAEQALRLGSA PEVLLVRKHMRERLAALAAQAFPERPHENAQLELVLEVDGLRRS VLNLGALLTTSATAHETVATGEGLRQALVGQPASLTVTTKDKDG RLVRTGSAELRAEITGPDGTRLPVPVVDHKNGTYELVYTARTEG ELLLSVLLYGQPVRGSPFRVRALRPGDLPPSPDDVKRRVKSPGG PGSHVRQKAVRRPSSMYSIGGKRKDNPIEDELVFRVGSRGREKG EFTNLQGVSAASSGRIVVADSNNQCIQVFSNEGQFKFREGVRGR SPGGLQRPTGVAVDINGDIIVADYDNRWVSIFSPEGKFKTKIGA GRLMGPKGVAVDRNGHIIVVDNKSCCVFIFQPNGKLVGRFGGRG ATDRHFAGPHFVAVNNKNEIVVIDFHNHSVKVYSADGEFLFKFG SHGEGNGQFNAPTGVADSNGNIIVADWGNSRIQVFDSSGSFLS YINTSAEPLYGPQGLALTSDGHVVADAGNHCFKAYRYLQ SEQ ID NO: 11 | GCAAGACGAUGGAGUUUUA SEQ ID NO: 12 GAAAGGACAACCCAAUUGA SEQ ID NO: 13 CCACAAGAAUGGCACAUAU SEQ ID NO: 14 GAGAGCGGCUGGCUGCAUU SEQ ID NO: 15 |
| TRIM4 | NM_033017 | MEAEDIQEELTCPICLDYFQDPVSIECGHNFCRGCLHRNWAPGG GPFPCPECRHPSAPAALRPNWALARLTEKTQRRRLGPVPPGLCG RHWEPLRLFCEDDQRPVCLVCRESQEHQTHAMAPIDEAFESYRI GNFDIHVDEWKRRLIRLLLYHFKQEEKLLKSQRNLVAKMKKVMH LQDVEVKNATQWKDKIKSQRMRISTEFSKLHNFLVEEEDLFLQR LNKEEEETKKKLNENTLKLNQTIASLKKILEVGEKSQAPTLEL LQNPKEVLIRSEIQDVNYSLEAVKVKIVCQIPLMKEMLKRFQVA VNLAEDTAHFKLVFSQEGRYVKNTASASSWPVFSSAWNYFAGWR NPQKTAFVERFQHLPCVLGKNVFTSGKHYWEVESRDSLEVAVGV CREDVMGITDRSKMSPDVGIWAIYWSAAGYWPLIGFPGIPTQQE PALHRVGVYLDRGIGNVSFYSAVDGVHLHIFSCSSVSRLRPFFW LSPLASLVIPPVTDRK SEQ ID NO: 16 | CCAAGUGGCUGUAAACCUA SEQ ID NO: 17 GAAGACAGUGUGCCAGAUA SEQ ID NO: 18 GAAGUUGAGAGUAGAGAUA SEQ ID NO: 19 CAAACUAUCGCUUCAUUGA SEQ ID NO: 20 |
| TRIM5 | NM_033034 | MASGILVNVKEEVICPICLELLTQPLSLDCGHSFCQACLTANHK KSMLDKGESSCPVCRISYQPENIRPNRHVANIVEKLREVKLSPE GQKVDHCARHGEKLLLFCQEDGKVICWLCERSQEHRGHHTFLTE EVAREYQVKLQAALEMLRQKQQEAEELEADIREEKASWKTQIQY DKTNVLADFEQLRDILDWEESNELQNLEKEEEDILKSLINSETE MVQQTQSLRELISDLEHRLQGSVMELLQGVDGVIKRTENVTLKK PETFPKNQRRVFRAPDLKGMLEVFRELTDVRRYWVDVTAPNNI | GCAGAAAGUUGAUCAUUGU SEQ ID NO: 22 GAGAGUAGCUGCCCUGUGU SEQ ID NO: 23 GGAAUCCUGGUUAAUGUAA SEQ ID NO: 24 UUACCAGCCUGAGAACAUA |

-continued

| TRIM # | Accession # | Sequence | SiRNA |
|---|---|---|---|
| | | SCAVISEDKRQVSSPKPQIIYGARGTRYQTFVNFNYCTGILGSQ SITSGKHYWEVDVSKKTAWILGVCAGFQFDAMCNIEKNENYQPK YGYWVIGLEEGVKCSAFQDSSFHTPSVPFIVPLSVIICPDRVGV FLDYEACTVSFFNITNHGFLIYKFSHCSFSQPVFPYLNPRKCGV PMTLCSPSS SEQ ID NO: 21 | SEQ ID NO: 25 |
| TRIM6 | NM_058166 | MISPVLVDIREEVICPICLELLTEPLSIDCGHSFCQACITPNGR ESVIGQEGERSCPVCQTSYQPGNLRPNRHLANIVRRLREVVLGF GKQLKAVLCADHGEKLQLFCQEDGKVICWLCERSQEHRGHHTFL VEEVAQEYQEKFQESLKKLKNEEQEAEKLTAFIREKKTSWKNQM EPERCRIQTEFNQLRNILDRVEQRELKKLEQEEKKGLRIIEEAE NDLVHQTQSLRELISDLERRCQGSTMELLQDVSDVTERSEFWTL RKPEALPTKLRSMFRAPDLKRMLRVCRELTDVQSYWVDVTLNPH TANLNLVLAKNRRQVRFVGAKVSGPSCLEKHYDCSVLGSQHFSS GKHYWEVDVAKKTAWILGVCSNSLGPTFSFNEFAQNHSAYSRYQ PQSGYWVIGLQHNHEYRAYEDSSPSLLLSMTVPPRRVGVFLDYE AGIVSFYNVTNHGFPIYTFSKYYFPTTLCPYFNPCNCVIPMTLR RPSS SEQ ID NO: 26 | UAAAGAAGCUGAAGAACGA SEQ ID NO: 27 CUACAAAGCUGAGAAGUAU SEQ ID NO: 28 GGACCUACAUUCUCUUUCA SEQ ID NO: 29 CCACUACUCUUUGUCCAUA SEQ ID NO: 30 |
| TRIM7 | NM_203294 | MAAEQEKVGAEFQALRAFLVEQEGRLLGRLEELSREVAQKQNEN LAQLGVEITQLSKLSSQIQETAQKPDLDFLQEFKSTLSRCSNVP GPKPTTVSSEMKNKVWNVSLKTFVLKGMLKKFKEDLRGELEKEE KVELTLDPDTANPRLILSLDLKGVRLGERAQDLPNHPCRFDTNT RVLASCGFSSGRHHWEVEVGSKDGWAFGVARESVRRKGLTPFTP EEGVWALQLNGGQYWAVTSPERSPLSCGHLSRVRVALDLEVGAV SFYAVEDMRHLYTFRVNFQERVFPLFSVCSTGTYLRIWP SEQ ID NO: 31 | GAAGGGUGGCAGUGGGCUA SEQ ID NO: 32 GCUCUAAACAACACACAGA SEQ ID NO: 33 CAAAUAUGCUCCUGACGGA SEQ ID NO: 34 CAUCCUGACCAAUGCGACA SEQ ID NO: 35 |
| TRIM8 | NM_030912 | MAENWKNCFEEELICPICLHVFVEPVQLPCKHNFCRGCIGEAWA KDSGLVRCPECNQAYNQKPGLEKNLKLTNIVEKFNALHVEKPPA ALHCVFCRRGPPLPAQKVCLRCEAPCCQSHVQTHLQQPSTARGH LLVEADDVRAWSCPQHNAYRLYHCEAEQVAVCQYCCYYSGAHQG HSVCDVEIRRNEIRKMLMKQQDRLEEREQDIEDQLYKLESDKRL VEEKVNQLKEEVRLQYEKLHQLLDEDLRQTVEVLDKAQAKFCSE NAAQALHLGERMQEAKKLLGSLQLLFDKTEDVSFMKNTKSVKIL MDRTQTCTSSSLSPTKIGHLNSKLFLNEVAKKEKQLRKMLEGPF STPVPFLQSVPLYPCGVSSSGAEKRKHSTAFPEASFLETSSGPV GGQYGAAGTASGEGQSGQPLGPCSSTQHLVALPGGAQPVHSSPV FPPSQYPNGSAAQQPMLPQYGGRKILVCSVDNCYCSSVANHGGH QPYPRSGHFPWTVPSQEYSHPLPPTPSVPQSLPSLAVRDWLDAS QQPGHQDFYRVYGQPSTKHYVTS SEQ ID NO: 36 | GCAAGAUUCUCGUCUGUUC SEQ ID NO: 37 GGAAUGAAAUCCGGAAGAU SEQ ID NO: 38 GGACAACUGUUACUGUUCU SEQ ID NO: 39 GAACACCAAGUCUGUGAAA SEQ ID NO: 40 |
| TRIM9 | NM_015163 | MEEMEEELKCPVCGSFYREPIILPCSHNLCQACARNILVQTPES ESPQSHRAAGSGVSDYDYLDLDKMSLYSEADSGYGSYGGFASAP TTPCQKSPNGVRVFPPAMPPPATHLSPALAPVPRNSCITCPQCH RSLILDDRGLRGFPKNRVLEGVIDRYQQSKAAALKCQLCEKAPK EATVMCEQCDVFYCDPCRLRCHPPRGPLAKHRLVPPAQGRVSRR LSPRKVSTCTDHELENHSMYCVQCKMPVCYQCLEEGKHSSHEVK ALGAMWKLHKSQLSQALNGLSDRAKEAKEFLVQLRNMVQQIQEN SVEFEACLVAQCDALIDALNRRKAQLLARVNKEHEHKLKVVRDQ ISHCTVKLRQTTGLMEYCLEVIKENDPSGFLQISDALIRRVHLT EDQWGKGTLTPRMTTDFDLSLDNSPLLQSIHQLDFVQVKASSPV PATPILQLEECCTHNNSATLSWKQPPLSTVPADGYILELDDGNG GQFREVYVGKETMCTVDGLHFNSTYNARVKAFNKTGVSPYSKTL VLQTSEVAWFAFDPGSAHSDIILSNDNLTVTCSSYDDRVVLGKT GFSKGIHYWELTVDRYDNHPDPAFGVARMDVMKDVMLGKDDKAW AMYVDNNRSWFMHNNSHTNRTEGGITKGATIGVLLDLNRKNLTF FINDEQQGPIAFDNVEGLFETAVSLNRNVQVTLHTGLPVPDFYS SRASIA SEQ ID NO: 41 | CCACAGGUCUCAUGGAGUA SEQ ID NO: 42 GCUGGAGGUGAUUAAGGA SEQ ID NO: 43 CAACGGCGUCCGCUGUUU SEQ ID NO: 44 AAACAGGAGUCAGCCCGUA SEQ ID NO: 45 |
| TRIM10 | NM_052828 | MASAASVTSLADEVNCPICQGTLREPVTIDCGHNFCRACLTRYC EIPGPDLEESPTCPLCKEPFRPGSFRPNWQLANVVENIERLQLV STLGLGEEDVCQEHGEKIYFFCEDDEMQLCVVCREAGEHATHTM RFLEDAAPYREQIHKCLKCLRKEREEIQEIQSRENKRMQVLLT QVSTKRQQVISEFAHLRKFLEEQQSILLAQLESQDGDILRQRDE FDLLVAGEICRFSALIEELEEKNERPARELLTDIRSTLIRCETR KCRKPVAVSPELGQRIRDEPQQALPLQREMKMFLEKLCFELDYE PAHISLDPQTSHPKLLLSEDHQRAQFSYKWQNSPDNPQRFDRAT CVLAHTGITGGRHTWVWMARVPGDSGCCQFCSPPSVLGTEVAA SEQ ID NO: 46 | GAGAGGAGAUUCAAGAAAU SEQ ID NO: 47 CAGAAGCACUCUAAUAAGA SEQ ID NO: 48 GGGAACAAAUCCAUAAGUG SEQ ID NO: 49 GCUUUGAGUUGGACUAUGA SEQ ID NO: 50 |

| TRIM # | Accession # | Sequence | SiRNA |
|---|---|---|---|
| TRIM11 | NM_145214 | MAAPDLSTNLQEEATCAICLDYFTDPVMTDCGHNFCRECIRRCW GQPEGPYACPECRELSPQRNLRPNRPLAKMAEMARRLHPPSPVP QGVCPAHREPLAAFCGDELRLLCAACERSGEHWAHRVRPLQDAA EDLKAKLEKSLEHLRKQMQDALLFQAQADETCVLWQKMVESQRQ NVLGEFERLRRLLAEEEQQLLQRLEEEELEVLPRLREGAAHLGQ QSAHLAELIAELEGRCQLPALGLLQDIKDALRRVQDVKLQPPEV VPMELRTVCRVPGLVETLRRERGDVILDPDTANPELILSEDRRS VQRGDLRQALPDSPERFDPGPCVLGQERFTSGRHYWEVEVGDRT SWALGVCRENVNRKEKGELSAGNGFWILVFLGSYYNSSERALAP LRDPPRRVGIFLDYEAGHLSFYSATDGSLLFIFPEIPFSGTLRP LFSPLSSSPTPMTICRPKGGSGDTLAPQ SEQ ID NO: 51 | GGACAUCUCUCUUUCUACA SEQ ID NO: 52<br>GGGAGAACGUGAACAGGAA SEQ ID NO: 53<br>GAGCUGAUCCUGUCUGAAG SEQ ID NO: 54<br>UCACUGCUAUUCAUCUUUC SEQ ID NO: 55 |
| TRIM13 | NM_005798 | MELLEEDLTCPICCSLFDDPRVLPCSHNFCKKCLEGILEGSVRN SLWRPAPFKCPTCRKETSATGINSLQVNYSLKGIVEKYNKIKIS PKMPVCKGHLGQPLNIFCLTDMQLICGICATRGEHTKHVFCSIE DAYAQERDAFESLFQSFETWRRGDALSRLDTLETSKRKSLQLLT KDSDKVKEFFEKLQHTLDQKKNEILSDFETMKLAVMQAYDPEIN KLNTILQEQRMAFNIAEAFKDVSEPIVFLQQMQEFREKIKVIKE TPLPPSNLPASPLMKNFDTSQWEDIKLVDVDKLSLPQDTGTFIS KIPWSFYKLFLLILLLGLVIVFGPTMFLEWSLFDDLATWKGCLS NESSYLIKTADFIEQSVEYWEQVIDGFFIFNERFKNFTLVVLNN VAEFVCKYKLL SEQ ID NO: 56 | GAGGAAAUCCCUACAGUUA SEQ ID NO: 57<br>UGAACAAUGUGGCAGAAUU SEQ ID NO: 58<br>GACACUGGCACAUUCAUUA SEQ ID NO: 59<br>UAACAUUGCUGAGGCUUUC SEQ ID NO: 60 |
| TRIM14 | NM_014788 | MAGAATGSRTPGRSELVEGCGWRCPEHGDRVAELFCRRCRRCVC ALCPVLGAHRGHPVGLALEAAVHVQKLSQECLKQLAIKKQQHID NITQIEDATEKLKANAESSKTWLKGKFTELRLLLDEEEALAKKF IDKNTQLTLQVYREQADSCREQLDIMNDLSNRVWSISQEPDPVQ RLQAYTATEQEMQQQMSLGELCHPVPLSFEPVKSFFKGLVEAVE STLQTPLDIRLKESINCQLSDPSSTKPGTLLKTSPSPERSLLLK YARTPTLDPDTMHARLRLSADRLTVRCGLLGSLGPVPVLRFDAL WQVLARDCFATGRHYWEVDVQEAGAGWWVGAAYASLRRRGASAA ARLGCNRQSWCLKRYDLEYWAFHDGQRSRLRPRDDLDRLGVELD YEAGVLAFYDVIGGMSHLHTFRATFQEPLYPALRLWEGAISIPR LP SEQ ID NO: 61 | CAACAUAACCCAGAUAGAA SEQ ID NO: 62<br>UCCAGAGGCUUCAGGCAUA SEQ ID NO: 63<br>GCUAAUGCAGAGUCAAGUA SEQ ID NO: 64<br>CAGAUUACUACUUGACGAA SEQ ID NO: 65 |
| TRIM15 | NM_033229 | MPATPSLKVVHELPACTLCAGPLEDAVTIPCGHTFCRLCLPALS QMGAQSSGKILLCPLCQEEEQAETPMAPVPLGPLGETYCEEHGE KIYFFCENDAEFLCVFCREGPTHQAHTVGFLDEAIQPYRDRLRS RLEALSTERDEIEDVKCQEDQKLQVLLTQIESKKHQVETAFERL QQELEQQRCLLLARLRELEQQIWKERDEYITKVSEEVTRLGAQV KELEEKCQQPASELLQDVRVNQSRCEMKTFVSPEATSPDLVKKI RDFHRKILTLPEMMRMFSENLAHHLEIDSGVITLDPQTASRSLV LSEDRKSVRYTRQKKSLPDSPLRFDGLPAVLGFPGFSSGRHRWQ VDLQLGDGGGCTVGVAGEGVRRKGEMGLSAEDGVWAVIISHQQC WASTSPGTDLPLSEIPRGVRVALDYEAGQVTLHNAQTQEPIFTE TASFSGKVFPPFFAVWKKGSCLTLKG SEQ ID NO: 66 | CAGCAGAUUUGGAAGGAGA SEQ ID NO: 67<br>CGGAGAGAUGAGAGAUUGA SEQ ID NO: 68<br>GGGAUGAAUAUAUCACAAA SEQ ID NO: 69<br>GGUGUGAGAUGAAGACUUU SEQ ID NO: 70 |
| TRIM16 | NM_006470 | MAELDLMAPGPLPRATAQPPAPLSPDSGSPSPDSGSASPVEEED VGSSEKLGRETEEQDSDSAEQGDPAGEGKEVLCDFCLDDTRRVK AVKSCLTCMVNYCEEHLQPHQVNIKLQSHLLTEPVKDHNWRYCP AHHSPLSAFCCPDQQCICQDCCQEHSGHTIVSLDAARRDKEAEL QCTQLDLERKLKLNENAISRLQANQKSVLVSVSEVKAVAEMQFG ELLAAVRKAQANVMLFLEEKEQAALSQANGIKAHLEYRSAEMEK SKQELERMAAISNTVQFLEEYCKFKNTEDITFPSVYVGLKDKLS GIRKVITESTVHLIQLLENYKKKLQEFSKEEEYDIRTQVSAVVQ RKYWTSKPEPSTREQFLQYAYDITFDPDTAHKYLRLQEENRKVT NTTPWEHPYPDLPSRFLHWRQVLSQQSLYLHRYYFEVEIFGAGT YVGLTCKGIDRKGEERNSCISGNNFSWSLQWNGKEFTAWYSDME TPLKAGPFRRLGVYIDFPGGILSFYGVEYDTMTLVHKFACKFSE PVYAAFWLSKKENAIRIVDLGEEPEKPAPSLVGTAP SEQ ID NO: 71 | GACCACAACUGGCGAUACU SEQ ID NO: 72<br>GCAGUGAAGUCCUGUCUAA SEQ ID NO: 73<br>GGAACAGGACAGCGACUCU SEQ ID NO: 74<br>CCGCAUCAGGUGAACAUCA SEQ ID NO: 75 |
| TRIM16L | NM_001037330 | MQFGELLAAVRKAQANVMLFLEEKEQAALSQANGIKAHLEYRSA EMEKSKQELETMAAISNTVQFLEEYCKFKNTEDITFPSVYIGLK DKLSGIRKVITESTVHLIQLLENYKKKLQEFSKEEEYDIRTQVS AIVQRKYWTSKPEPSTREQFLQYVHDITFDPDTAHKYLRLQEEN RKVTNTTPWEHPYPDLPSRFLHWRQVLSQQSLYLHRYYFEVEIF GAGTYVGLTCKGIDQKGEERSSCISGNNFSWSLQWNGKEFTAWY SDMETPLKAGPFWRLGVYIDPGGILSFYGVEYDSMTLVHKFAC KFSEPVYAAFWLSKKENAIRIVDLGEEPEKPAPSLVGTAP SEQ ID NO: 76 | GAGGAGUACUGCAAGUUUA SEQ ID NO: 77<br>GCAAAGGCAUCGACCAGAA SEQ ID NO: 78<br>GCAAAGUUAUCACGGAAUC SEQ ID NO: 79<br>AGGAUAAACUCUCGGGCAU SEQ ID NO: 80 |

| TRIM # | Accession # | Sequence | SiRNA |
|---|---|---|---|
| TRIM17 | NM_001024940* *NM_001024941 removed from PubMed | MEAVELARKLQEEATCSICLDYFTDPVMTTCGHNFCRACIQLSW EKARGKKGRRRKRKGSFPCPECREMSPQRNLLPNRLLTKVAEMAQ QHPGLQKQDLCQEHHEPLKLFCQKDQSPICVVCRESREHRLHRV LPAEEAVQGYKLKLEEDMEYLREQITRTGNLQAREEQSLAEWQG KVKERRERIVLEFEKMNLYLVEEEQRLLQALETEEEETASRLRE SVACLDRQGHSLELLLLQLEERSTQGPLQMLQDMKEPLSRKNNV SVQCPEVAPPTRPRTVCRVPGQIEVLRGFLEDVVPDATSAYPYL LLYESRQRRYLGSSPEGSGFCSKDRFVAYPCAVGQTAFSSGRHY WEVGMNITGDALWALGVCRDNVSRKDRVPKCPENGFWVVQLSKG TKYLSTFSALTPVMLMEPPSHMGIFLDFEAGEVSFYSVSDGSHL HTYSQATFPGPLQPFFCLGAPKSGQMVISTVTMWVKG SEQ ID NO: 81 | GCUAAGAGGCUUUCUAGAG SEQ ID NO: 82 GGAAGAACAACGUGAGUGU SEQ ID NO: 83 GGUCCCACCUGCACACCUA SEQ ID NO: 84 GAGCGGAGAGAACGCAUUG SEQ ID NO: 85 |
| TRIM18 | NM_033290 | METLESELTCPICLELFEDPLLLPCAHSLCFNCAHRILVSHCAT NESVESITAFQCPTCRHVITLSQRGLDGLKRNVTLQNIIDRFQK ASVSGPNSPSETRRERAFDANTMTSAEKVLCQFCDQDPAQDAVK TCVTCEVSYCDECLKATHPNKKPFTGHRLIEPIPDSHIRGLMCL EHEDEKVNMYCVTDDQLICALCKLVGRHRDHQVAALSERYDKLK QNLESNLTNLIKRNTELETLLAKLIQTCQHVEVNASRQEAKLTE ECDLLIEIIQQRRQIIGTKIKEGKVMRLRKLAQQIANCKQCIER SASLISQAEHSLKENDHARFLQTAKNITERVSMATASSQVLIPE INLNDTFDTFALDFSREKKLLECLDYLTAPNPPTIREELCTASY DTITVHWTSDDEFSVVSYELQYTIPTGQANVSLCNSADSWMIV PNIKQNHYTVHGLQSGTKYIFMVKAINQAGSRSSEPGKLKTNSQ PFKLDPKSAHRKLKVSHDNLTVERDESSSKKSHTPERFTSQGSY GVAGNVFIDSGRHYWEVVISGSTWYAIGLAYKSAPKHEWIGKNS ASWALCRCNNNWVVRHNSKEIPIEPAPHLRRVGILLDYDNGSIA FYDALNSIHLYTFDVAFAQPVCPTFTVWNKCLTIITGLPIPDHL DCTEQLP SEQ ID NO: 86 | CAGCAAAGACGACAGAUUA SEQ ID NO: 87 GCUGAUAGCUGGAUGAUAG SEQ ID NO: 88 GAACAAGUGUCUGACGAUU SEQ ID NO: 89 AGAAGAAACUGCUAGAAUG SEQ ID NO: 90 |
| TRIM19 | NM_033247 | MEPAPARSPRPQQDPARPQEPTMPPPETPSEGRQPSPSPSPTER APASEEEFQFLRCQQCQAEAKCPKLLPCLHTLCSGCLEASGMQC PICQAPWPLGADTPALDNVFFESLQRRLSVYRQIVDAQAVCTRC KESADFWCFECEQLLCAKCFEAHQWFLKHEARPLAELRNQSVRE FLDGTRKTNNIFCSNPNHRTPTLTSIYCRGCSKPLCCSCALLDS SHSELKCDISAEIQQRQEELDAMTQALQEQDSAFGAVHAQMHAA VGQLGRARAETEELIRERVRQVVAHVRAQERELLEAVDARYQRD YEEMASRLGRLDAVLQRIRTGSALVQRMKCYASDQEVLDMHGEL RQALCRLRQEEPQSLQAAVRTDGEDEFKVRLQDLSSCITQGKDA AVSKKASPEAASTPRDPIDVDLLPPPAHALTGPAQSSTH SEQ ID NO: 91 | GGGGAAAGAUGCAGCUGUA SEQ ID NO: 92 GCAAAGAGUCGGCCGACUU SEQ ID NO: 93 GCGCUGGUGCAGAGGAUGA SEQ ID NO: 94 CCGAUGGCUUCGACGAGUU SEQ ID NO: 95 |
| TRIM20 | NM_000243 | MAKTPSDHLLSTLEELVPYDFEKFKFKLQNTSVQKEHSRIPRSQ IQRARPVKMATLLVTYYGEEYAVQLTLQVLRAINQRLLAEELHR AAIQEYSTQENGTDDSAASSSLGENKPRSLKTPDHPEGNEGNGP RPYGGGAASLRCSQPEAGRGLSRKPLSKRREKASEGLDAQGKPR TRSPALPGGRSPGPCRALEGGQAEVRLRRNASSAGRLQGLAGGA PGQKECRPFEVYLPSGKMRPRSLEVTISTGEKAPANPEILLLTLE EKTAANLDSATEPRARPTPDGGASADLKEGPGNPEHSVTGREPD TAASPRCHAQEGDPVDGTCVRDSCSFPEAVSGHPQASGSRSPGC PRCQDSHERKSPGSLSPQPLPQCKRHLKQVQLLFCEDHDEPICL ICSLSQEHQGHRVRPIEEVALEHKKKIQKQLEHLKKLRKSGEEQ RSYGEEKAVSFLKQTEALKQRVQRKLEQVYYFLEQQEHFFVASL EDVGQMVGQIRKAYDTRVSQDIALLDALIGELEAKECQSEWELL QDIGDILHRAKTVPVPEKWTTPQEIKQKIQLLHQKSEFVEKSTK YFSETLRSEMEMENVPELIGAQAHAVNVILDAETAYPNLIFSDD LKSVRLGNKWERLPDGPQRFDSCIIVLGSPSFLSGRRYWEVEVG DKTAWILGACKTSISRKGNMTLSPENGYWVVIMMKENEYQASSV PPTRLLIKEPPKRVGIFVDYRVGSISFYNVTARSHIYTFASCSF SGPLQPIFSPGTRDGGKNTAPLTICPVGGQGPD SEQ ID NO: 96 | GACCACUCCUCAAGAGAUA SEQ ID NO: 97 GAGAAUGGCUACUGGGUGG SEQ ID NO: 98 GCCCGCAAAUUCCAGAAAUU SEQ ID NO: 99 GCAUAUGACACCCGCGUAU SEQ ID NO: 100 |
| TRIM21 | NM_003141 | MASAARLTMMWEEVTCPICLDPFVEPVSIECGHSFCQECISQVG KGGGSVCPVCRQRFLLKNLRPNRQLANMVNNLKEISQEAREGTQ GERCAVHGERLHLFCEKDGKALCWVCAQSRKHRDHAMVPLEEAA QEYQEKLQVALGELRRKQELAEKLEVEIAIKRADWKKTVETQKS RIHAEFVQQKNFLVEEEQRQLQELEKDEREQLRILGEKEAKLAQ QSQALQELISELDRRCHSSALELLQEVIIVLERSESWNLKDLDI TSPELRSVCHVPGLKKMLRTCAVHITLDPDTANPWLILSEDRRQ VRLGDTQQSIPGNEERFDSYPMVLGAQHFHSGKHYWEVDVTGKE AWDLGVCRDSVRRKGHFLLSSKSGFWTIWLWNKQKYEAGTYPQT PLHLQVPPCQVGIFLDYEAGMVSFYNITDHGSLIYSFSECAFTG PLRPFESPGFNDGGKNTAPLTLCPLNIGSQGSTDY SEQ ID NO: 101 | UCUCAGAGCUAGAUCGAAG SEQ ID NO: 102 GAGCAUACCUGGAAAUGAA SEQ ID NO: 103 GGUGAUAAUUGUCCUGGAA SEQ ID NO: 104 AAGAGUGGCUUCUGGACAA SEQ ID NO: 105 |

| TRIM # | Accession # | Sequence | SiRNA |
|---|---|---|---|
| TRIM22 | NM_006074 | MDFSVKVDIEKEVTCPICLELLTEPLSLDCGHSFCQACITAKIK ESVIISRGESSCPVCQTRFQPGNLRPNRHLANIVERVKEVKMSP QEGQKRDVCEHHGKKLQIFCKEDGKVICWVCELSQEHQGHQTFR INEVVKECQEKLQVALQRLIKEDEAEKLEDDIRQERTAWKNYI QIERQKILKGFNEMRVILDNEEQRELQKLEEGEVNVLDNLAAAT DQLVQQRQDASTLISDLQRRLGSSVEMLQDVIDVMKRSESWTL KKPKSVSKKLKSVFRVPDLSGMLQVLKELTDVQYYWVDVMLNPG SATSNVAISVDQRQVKTVRTCTFKNSNPCDFSAFGVFGCQYFSS GKYYWEVDVSGKIAWILGVHSKISSLNKRKSSGFAFDPSVNYSK VYSRYRPQYGYWVIGLQNTCEYNAFEDSSSSDPKVLTLFMAVPP CRIGVFLDYEAGIVSFFNVTNHGALIYKFSGCRFSRPAYPYFNP WNCLVPMTVCPPSS SEQ ID NO: 106 | GUACGCACCUGCACAUUUA SEQ ID NO: 107 CACCAAACAUUCCGCAUAA SEQ ID NO: 108 CCAGAUAUAGACCUCAAUA SEQ ID NO: 109 AGAAUUAUAUCCAGAUCGA SEQ ID NO: 110 |
| TRIM23 | NM_001656 | MATLVVNKLGAGVDSGRQGSRGTAVVKVLECGVCEDVFSLQGDK VPRLLLCGHTVCHDCLTRLPLHGRAIRCPFDRQVTDLGDSGVWG LKKNFALLELLERLQNGPIGQYGAAEESIGISGESIIRCDEDEA HLASVYCTVCATHLCSECSQVTHSTKTLAKHRRVPLADKPHEKT MCSQHQVHAIEFVCLEEGCQTSPLMCCVCKEYGKHQGHKHSVLE PEANQIRASILDMAHCIRTFTEEISDYSRKLVGIVQHIEGGEQI VEDGIGMAHTEHVPGTAENARSCIRAYFYDLHETLCRQEEMALS VVDAHVREKLIWLRQQQEDMTILLSEVSAACLHCEKTLQQDDCR VVLAKQEITRLLETLQKQQQQFTEVADHIQLDASIPVTFTKDNR VHIGPKMEIRVVTLGLDGAGKTTILFKLKQDEFMQPIPTIGFNV ETVEYKNLKFTIWDVGGKHKLRPLWKHYYLNTQAVVFVVDSSHR DRISEAHSELAKLLTEKELRDALLLIFANKQDVAGALSVEEITE LLSLHKLCCGRSWYIQGCDARSGMGLYEGLDWLSRQLVAAGVLD VA SEQ ID NO: 111 | GAAGAAGGUUGUCAAACUA SEQ ID NO: 112 UCACAAGCAUUCAGUAUUG SEQ ID NO: 113 GCAAAGUUGUUAACGAAA SEQ ID NO: 114 GGGAGAGCAUCAUUCGUU SEQ ID NO: 115 |
| TRIM24 | NM_003852 | MEVAVEKAVAAAAAASAAASGGPSAAPSGENEAESRQGPDSERG GEAARLNLLDTCAVCHQNIQSRAPKLLPCLHSFCQRCLPAPQRY LMLPAPMLGSAETPPPVPAPGSPVSGSSPFATQVGVIRCPVCSQ ECAERHIIDNFFVKDTTEVPSSTVEKSNQVCTSCEDNAEANGFC VECVEWLCKTCIRAHQRVKFTKDHTVRQKEEVSPEAVGVTSQRP VFCPPHKKEQLKLYCETCDKLTCRDCQLLEHKEHRYQFIEEAFQ NQKVIIDTLITKLMEKTKYIKFTGNQIQNRIIEVNQNQKQVEQD IKVAIFTLMVEINKKGKALLHQLESLAKDHRMKLMQQQQEVAGL SKQLEHVMHFSKWAVSSGSSTALLYSKRLITYRLRHLLRARCDA SPVTNNTIQFHCDPSFWAQNIINLGSLVIEDKESQPQMPKQNPV VEQNSQPPSGLSSNQLSKETTQISLAQLRLQHMQQQQPPPRLIN FQNHSPKPNGPVLPPHPQQLRYPPNQNIPRQAIKPNPLQMAFLA QQAIKQWQISSGQGTPSTTNSTSSTPSSPTITSAAGYDGKAFGS PMIDLSSPVGGSYNLPSLPDIDCSSTIMLDNIVRKDTNIDHGQP RPPSNRTVQSPNSSVPSPGLAGPVTMTSVHPPIRSPSASSVGSR GSSGSSSKPAGADSTHKVPVVMLEPIRIKQENSGPPENYDFPVV IVKQESDEESRPQNANYPRSILTSLLLNSSQSSTSEETVLRSDA PDSTGDQPGLHQDNSSNGKSEWLDPSQKSPLHVGETRKEDDPNE DWCAVCQNGGELLCCEKCPKVFHLSCHVPTLTNFPSGEWICTFC RDLSKPEVEYDCDAPSHNSEKKKTEGLVKLTPIDKRKCERLLLF LYCHEMSLAFQDPVPLTVPDYYKIIKNPMDLSTIKKRLQEDYSM YSKPEDFVADFRLIFQNCAEFNEPDSEVANAGIKLENYFEELLK NLYPEKREPKPEFRNESEDNKFSDDSDDDFVQPRKKRLKSIEER QLLK SEQ ID NO: 116 | GAACAUACCACGACAAGCA SEQ ID NO: 117 AGACUUAUCUAAACCAGAA SEQ ID NO: 118 CUUUAGUAAUCGAGGAUAA SEQ ID NO: 119 CUUUAUAGCAAACGACUGA SEQ ID NO: 120 |
| TRIM25 | NM_005082 | MAELCPLAEELSCSICLEPFKEPVTTPCGHNFCGSCLNETWAVQ GSPYLCPQCRAVYQARPQLHKNTVLCNVVEQFLQADLAREPPAD VWTPPARASAPSPNAQVACDHCLKEAAVKTCLVCMASFCQEHLQ PHFDSPAFQDHPLQPPVRDLLRRKCSQHNRLREFFCPERSECIC HIOLVEHKTCSPASLSQASADLEATLRHKLTVMYSQINGASRAL DDVRNRQQDVRMTANRKVEQLQQEYTEMKALLDASETTSTRKIK EEEKRVNSKFDTIYQILLKKKSEIQTLKEEIEQSLTKRDEFEFL EKASKLRGISTKPVYIPEVELNHKLIKGIHQSTIDLKNELKQCI GRLQEPTPSSGDPGEHDPASTHKSTRPVKKVSKEEKKSKKPPPV PALPSKLPTFGAPEQLVDLKQAGLEAAAKATSSHPNSTSLKAKV LETFLAKSRPELLEYYIKVILDYNTAHNKVALSECYTVASVAEM PQNYRPHPQRFTYCSQVLGLHCYKKGIHYWEVELQKNNFCGVGI CYGSMNRQGPESRLGRNSASWCVEWFNTKISAWHNNVEKTLPST KATRVGVLLNCDHGFVIFFAVADKVHLMYKERVDFTEALYPAFW VESAGATLSICSPK SEQ ID NO: 121 | GACCGCAGCUGCACAAGAA SEQ ID NO: 122 CAAACUAACUGUCAUGUAC SEQ ID NO: 123 CAACAAGAAUACACGGAAA SEQ ID NO: 124 GCGGAUGACUGCAAACAGA SEQ ID NO: 125 |
| TRIM26 | NM_003449* *variant 1 | MATSAPLRSLEEEVTCSICLDYLRDPVTIDCGHVFCRSCTTDVR PISGSRPVCPLCKKPFKKENIRPVWQLASLVENIERLKVDKGRQ PGEVTREQQDAKLCERHREKLHYYCEDDGKLLCVMCRESREHRP HTAVLMEKAAQPHREKILNHLSTLRRDRDKIQGFQAKGEADILA | |

-continued

| TRIM # | Accession # | Sequence | SiRNA |
|---|---|---|---|
| | | ALKKLQDQRQYIVAEFEQGHQFLREREEHLLEQLAKLEQELTEG REKFKSRGVGELARLALVISELEGKAQQPAAELMQDTRDFLNRY PRKKFWVGKPIARVVKKKTGEFSDKLLSLQRGLREFQGKLLRDL EYKTVSVTLDPQSASGYLQLSEDWKCVTYTSLYKSAYLHPQQFD CEPGVLGSKGFTWGKVYWEVEVEREGWSEDEEEGDEEEEGEEEE EEEEAGYGDGYDDWETDEDEESLGDEEEEEEEEEEEVLESCMVG VARDSVKRKGDLSLRPEDGVWALRLSSSGIWANTSPEAELFPAL RPRRVGIALDYEGGTVTFTNAESQELIYTETATFTRRLVPFLWL KWPGTRLLLRP<br>SEQ ID NO: 348 | |
| TRIM27 | NM_006510 | MASGSVAECLQQETTCPVCLQYFAEPMMLDCGHNICCACLARCW GTAETNVSCPQCRETFPQRHMRPNRHLANVTQLVKQLRTERPSG PGGEMGVCEKHREPLKLYCEEDQMPICVVCDRSREHRGHSVLPL EEAVEGFKEQIQNQLDHLKRVKDLKKRRRAQGEQARAELLSLTQ MEREKIVWEFEQLYHSLKEHEYRLLARLEELDLAIYNSINGAIT QFSCNISHLSSLIAQLEEKQQQPTRELLQDIGDTLSRAERIRIP EPWITPPDLQEKIHIFAQKCLFLTESLKQFTEKMQSDMEKIQEL REAQLYSVDVTLDPDTAYPSLILSDNLRQVRYSYLQQDLPDNPE RFNLFPCVLGSPCFIAGRHYWEVEVGDKAKWTIGVCEDSVCRKG GVTSAPQNGFWAVSLWYGKEYWALTSPMTALPLRTPLQRVGIFL DYDAGEVSFYNVTERCHTFTFSHATFCGPVRPYFSLSYSGGKSA APLIICPMSGIDGFSGHVGNHGHSMETSP<br>SEQ ID NO: 126 | GAGCAGGGCUGAAAGAAUC SEQ ID NO: 127<br>UAAGAGAGGCUCAGUUAUA SEQ ID NO: 128<br>GCUGAACUCUUGAGCCAA SEQ ID NO: 129<br>GAAGAUUGUUUGGGAGUUU SEQ ID NO: 130 |
| TRIM28 | NM_005762 | MAASAAASAAAASAASGSPGPGEGSAGGEKRSTAPSAAASASA SAAASSPAGGGAEALELLEHCGVCRERLRPEREPRLLPCLHSAC SACLGPAAPAAANSSGDGGAAGDGTVVDCPVCKQQCFSKDIVEN YFMRDSGSKAATDAQDANQCCTSCEDNAPATSYCVECSEPLCET CVEAHQRVKYTKDHTVRSTGPAKSRDGERTVYCNVHKHEPLVLF CESCDTLTCRDCQLNAHKDHQYQFLEDAVRNQRKLLASLVKRLG DKHATLQKSTKEVRSSIRQVSDVQKRVQVDVKMAILQIMKELNK RGRVLVNDAQKVTEGQQERLERQHWTMTKIQKHQEHILRFASWA LESDNNTALLLSKKLIYFQLHRALKMIVDPVEPHGEMKFQWDLN AWTKSAEAFGKIVAERPGTNSTGPAPMAPPRAPGPLSKQGSGSS QPMEVQEGYGFGSGDDPYSSAEPHVSGVKRSRSGEGEVSGLMRK VPRVSLERLDLDLTADSQPPVFKVFPGSTTEDYNLIVIERGAAA AATGQPGTAPAGTPGAPPLAGMAIVKEEETEAAIGAPPTATEGP ETKPVLMALAEGPGAEGPRLASPSGSTSSGLEVVAPEGTSAPGG GPGTLDDSATICRVCQKPGDLVMCNQCEFCFHLDCHLPALQDVP GEEWSCSLCHVLPDLKEEDGSLSLDGADSTGVVAKLSPANQRKC ERVLLALFCHEPCRPLHQLATDSTFSLDQPGGTLDLTLIRARLQ EKLSPPYSSPQEFAQDVGRMFKQFNKLTEDKADVQSIIGLQRFF ETRMNEAFGDTKFSAVLVEPPPMSLPGAGLSSQELSGGPGDGP<br>SEQ ID NO: 131 | GACCAAACCUGUGCUUAUG SEQ ID NO: 132<br>GAUGAUCCCUACUCAAGUG SEQ ID NO: 133<br>GCGAUCUGGUUAUGUGCAA SEQ ID NO: 134<br>AGAAUUAUUUCAUGCGUGA SEQ ID NO: 135 |
| TRIM29 | NM_012101 | MEAADASRSNGSSPEARDARSPSGPSGSLENGTKADGKDAKTTN GHGGEAAEGKSLGSALKPGEGRSALFAGNEWRRPIIQFVESGDD KNSNYFSMDSMEGKRSPYAGLQLGAAKKPPVTFAEKGELRKSIF SESRKPTVSIMEPGETRRNSYPRADTGLFSRSKSGSEEVLCDSC IGNKQKAVKSCLVCQASFCELHLKPHLEGAAFRDHQLLEPIRDF EARKCPVHGKTMELFCQTDQTCICYLCMFQEHKNHSTVTVEEAK AEKETELSLQKEQLQLKIIEIEDEAEKWQKEKDRIKSFTTNEKA ILEQNFRDLVRDLEKQKEEVRAALEQREQDAVDQVKVIMDALDE RAKVLHEDKQTREQLHSISDSVLFLQEFGALMSNYSLPPPLPTY HVLLEGEGLGQSLGNFKDDLLNVCMRHVEKMCKADLSRNFIERN HMENGGDHRYVNNYTNSFGGEWSAPDTMKRYSMYLTPKGGVRTS YQPSSPGRFTKETTQKNFNNLYGTKGNYTSRVWEYSSSIQNSDN DLPVVQGSSSFSLKGYPSLMRSQSPKAQPQTWKSGKQTMLSHYR PFYVNKGNGIGSNEAP<br>SEQ ID NO: 136 | GCAGGAAUUUGGUGCAUUG SEQ ID NO: 137<br>GAUCAUGGAUGCUCUGGAU SEQ ID NO: 138<br>GAAGAGAUACUCCAUGUAC SEQ ID NO: 139<br>CCAGAAGAAUUUCAACAAU SEQ ID NO: 140 |
| TRIM31 | NM_007028 | MASGQFVNKLQEEVICPICLDILQKPVTIDCGHNFCLKCITQIG ETSCGFFKCPLCKTSVRKNAIRFNSLLRNLVEKIQALQASEVQS KRKEATCPRHQEMFHYFCEDDGKFLCFVCRESKDHKSHNVSLIE EAAQNYQGQIQEQIQVLQQKEKETVQVKAQGVHRVDVFTDQVEH EKQRILTEFELLHQVLEEEKNFLLSRIYWLGHEGTEAGKHYVAS TEPQLNDLKKLVDSLKTKQNMPPRQLLEDIKVVLCRSEEFQFLN PTPVPLELEKKLSEAKSRHDSITGSLKKFKDQLQADRKKDENRF FKSMNKNDMKSWGLLQKNNHKMNKTSEPGSSSAGGRTTSGPPNH HSSAPSHSLFRASSAGKVTFPVCLLASYDEISGQGASSQDTKTF DVALSEELHAALSEWLTAIRAWFCEVPSS<br>SEQ ID NO: 141 | CGAAGAAGCUGCCCAGAAU SEQ ID NO: 142<br>GGAGAAGAAUUUCCUGCUA SEQ ID NO: 143<br>GAUGAGAUUUCUGGUCAAG SEQ ID NO: 144<br>GAGCCACAGUUGAACGAUC SEQ ID NO: 145 |
| TRIM32 | NM_001099679 | MAAAAASHLNLDALREVLECPICMESFTEEQLRPKLLHCGHTIC RQCLEKLLASSINGVRCPFCSKITRITSLTQLTDNLTVLKIIDT AGLSEAVGLLMCRSCGRRLPRQFCRSCGLVLCEPCREADHQPPG | GAUCAGGGGUGGUCAAAUA SEQ ID NO: 147<br>GCAUAGCCCUAACUCCUAA |

| TRIM # | Accession # | Sequence | SiRNA |
|---|---|---|---|
| | | HCTLPVKEAAEERRRDFGEKLTRLRELMGELQRRKAALEGVSKD<br>LQARYKAVLQEYGHEERRVQDELARSRKFFTGSLAEVEKSNSQV<br>VEEQSYLLNIAEVQAVSRCDYFLAKIKQADVALLEETADEEEPE<br>LTASLPRELTLQDVELLKVGHVGPLQIGQAVKKPRTVNVEDSWA<br>MEATASAASTSVTFREMDMSPEEVVASPRASPAKQRGPEAASNI<br>QQCLFLKKMGAKGSTPGMFNLPVSLYVTSQGEVLVADRGNYRIQ<br>VFTRKGFLKEIRRSPSGIDSFVLSFLGADLPNLTPLSVAMNCQG<br>LIGVTDSYDNSLKVYTLDGHCVACHRSQLSKPWGITALPSGQFV<br>VTDVEGGKLWCFTVDRGSGVVKYSCLCSAVRPKFVTCDAEGTVY<br>FTQGLGLNLENRQNEHHLEGGFSIGSVGPDGQLGRQISHFFSEN<br>EDFRCIAGMCVDARGDLIVADSSRKEILHFPKGGGYSVLIREGL<br>TCPVGIALTPKGQLLVLDCWDHCIKIYSYHLRRYSTP<br>SEQ ID NO: 146 | SEQ ID NO: 148<br>GAGCUGUGGUUUGGUGUUA<br>SEQ ID NO: 149<br>GUGAAGUACUAGUCGCUGA<br>SEQ ID NO: 150 |
| TRIM33 | NM_033020 | MAENKGGGEAESGGGGSGSAPVTAGAAGPAAQEAEPPLTAVLVE<br>EEEEGGRAGAEGGAAGPDDGGVAAASSGSAQAASSPAASVGTG<br>VAGGAVSTPAPAPASAPAPGPSAGPPPGPPASLLDTCAVCQQSL<br>QSRREAEPKLLPCLHSFCLRCLPEPERQLSVPIPGGSNGDIQQV<br>GVIRCPVCRQECRQIDLVDNYFVKDTSEAPSSSDEKSEQVCTSC<br>EDNASAVGFCVECGEWLCKTCIEAHQRVKFTKDHLIRKKEDVSE<br>SVGASGQRPVFCPVHKQEQLKLFCETCDRLTCRDCQLLEHKEHR<br>YQFLEEEAFQNQKGAIENLLAKLLEKKNYVHFAATQVQNRIKEVN<br>ETNKRVEQEIKVAIFTLINEINKKGKSLLQQLENVTKERQMKLL<br>QQQNDITGLSRQVKHVMNFTNWAIASGSSTALLYSKRLITFQLR<br>HILKARCDPVPAANGAIRFHCDPTFWAKNVVNLGNLVIESKPAP<br>GYTPNVVVGQVPPGTNHISKTPGQINLAQLRLQHMQQQVYAQKH<br>QQLQQMRMQQPPAPVPTTTTTTQQHPRQAAPQMLQQQPPRLISV<br>QTMQRGNMNCGAFQAHQMRLAQNAARIPGIPRHSGPQYSMMQPH<br>LQRQHSNPGHAGPFPVVSVHNTTINPTSPTTATMANANRGPTSP<br>SVTAIELIPSVTNPENLPSLPDIPPIQLEDAGSSSLDNLLSRYI<br>SGSHLPPQPTSTMNPSPGPSALSPGSSGLSNSHTPVRPPSTSST<br>GSRGSCGSSGRTAEKTSLSFKSDQVKVKQEPGTEDEICSFSGGV<br>KQEKTEDGRRSACMLSSPESSLTPPLSTNLHLESELDALASLEN<br>HVKIEPADMNESCKQSGLSSLVNGKSPIRSLMHRSARIGGDGNN<br>KDDDPNEDWCAVCQNGGDLLCCEKCPKVEHLTCHVPTLLSFPSG<br>DWICTFCRDIGKPEVEYDCDNLQHSKKGKTAQGLSPVDQRKCER<br>LLLYLYCHELSIEFQEPVPASIPNYYKIIKKPMDLSTVKKKLQK<br>KHSQHYQIPDDEVADVRLIFKNCERFNEADSEVAQAGKAVALYF<br>EDKLTEIYSDRTFAPLPEFEQEEDDGEVTEDSDEDFIQPRRKRL<br>KSDERPVHIK<br>SEQ ID NO: 151 | GGACAAACCACAUUAGUAA<br>SEQ ID NO: 152<br>GCAAGCGACUGAUUACUUU<br>SEQ ID NO: 153<br>UGAAACAUGUGAUAGAUUG<br>SEQ ID NO: 154<br>GUGAUAAUUUGCAACAUAG<br>SEQ ID NO: 155 |
| TRIM34 | NM_130390 | MASKILLNVQEEVTCPICLELLTEPLSLDCGHSLCRACITVSNK<br>EAVTSMGGKSSCPVCGISYSFEHLQANQHLANIVERLKEVKLSP<br>DNGKKRDLCDHHGEKLLLLECKEDRKVICWLCERSQEHRGHHTVL<br>TEEVEKECQEKLQAVLKRLKKEEEEAEKLEADIREEKTSWKYQV<br>QTERQRIQTEFDQLRSILNNEEQRELQRLEEEEKKTLDKFAEAE<br>DELVQQKQLVRELISDVECRSQWSTMELLQDMSGIMKWCVWVAR<br>SGACEL<br>SEQ ID NO: 156 | GAAAAGAAGACGCUGGAUA<br>SEQ ID NO: 157<br>GGAGGAAGUAUUCAAGGAA<br>SEQ ID NO: 158<br>UGUCGGAGUCAGUGGUCAA<br>SEQ ID NO: 159<br>AAAUCUUGCUUAACGUACA<br>SEQ ID NO: 160 |
| TRIM35 | NM_171982 | MERSPDVSPGPSRSFKEELLCAVCYDPFRDAVTLRCGHNFCRGC<br>VSRCWEVQVSPTCPVCKDRASPADLRTNHTLNNLVEKLLREEAE<br>GARWTSYRFSRVCRLHRGQLSLFCLEDKELLCCSCQADPRHQGH<br>RVQPVKDTAHDFRAKCRNMEHALREKAKAFWAMRRSYEAIAKHN<br>QVEAAWLEGRIRQEFDKLREFLRVEEQAILDAMAEETRQKQLLA<br>DEKMKQLTEETEVLAHEIERLQMEMKEDDVSFLMKHKSRKRRLF<br>CTMEPEPVQPGMLIDVCKYLGSLQYRVWKKMLASVESVPFSFDP<br>NTAAGWLSVSDDLTSVTNHGYRVQVENPERFSSAPCLLGSRVFS<br>QGSHAWEVALGGLQSWRVGVVRVRQDSGAEGHSHSCYHDTRSGF<br>WYVCRTQGVEGDHCVTSDPATSPLVLAIPRRLRVELECEEGELS<br>FYDAERHCHLYTFHARFGEVRPYFYLGGARGAGPPPEPLRICPLH<br>ISVKEELDG<br>SEQ ID NO: 161 | GACCUGCGCACCAACCACA<br>SEQ ID NO: 162<br>ACAAGGAGCUGCUGUGCUG<br>SEQ ID NO: 163<br>CCACCUGCCCAGUGUGCAA<br>SEQ ID NO: 164<br>GUGCAGCCGGUGAAGGACA<br>SEQ ID NO: 165 |
| TRIM36 | NM_018700*<br>*variant 1 | MSESGEMSEFGYIMELIAKGKVTIKNIERELICPACKELFTHPL<br>ILPCQHSICHKCVKELLLTLDDSFNDVGSDNSNQSSPRLRLPSP<br>SMDKIDRINRPGWKRNSLTPRTTVFPCPGCEHDVDLGERGINGL<br>FRNFTLETIVERYRQAARAATAIMCDLCKPPPQESTKSCMDCSA<br>SYCNECFKIHHPWGTIKAQHEYVGPTTNFRPKILMCPEHETERI<br>NMYCELCRRPVCHLCKLGGNHANHRVTTMSSAYKTLKEKLSKDI<br>DYLIGKESQVKSQISELNLLMKETECNGERAKEEAITHFEKLFE<br>VLEERKSSVLKAIDSSKKLRLDKFQTQMEEYQGLLENNGLVGYA<br>QEVLKETDQSCFVQTAKQLHLRIQKATESLKSFRPAAQTSFEDY<br>VVNTSKQTELLGELSFESSGIDVPEINEEQSKVYNNALINWHHP<br>EKDKADSYVLEYRKINRDDEMSWNEIEVCGTSKIIQDLENSSTY<br>AFRVRAYKGSICSPCSRELILHTPPAPVFSFLFDEKCGYNNEHL | |

-continued

| TRIM # | Accession # | Sequence | SiRNA |
|---|---|---|---|
| | | LLNLKRDRVESRAGFNLLLAAERIQVGYYTSLDYIIGDTGITKG KHFWAFRVEPYSYLVKVGVASSDKLQEWLRSPRDAVSPRYEQDS GHDSGSEDACFDSSQPFTLVTIGMQKFFIPKSPTSSNEPENRVL PMPTSIGIFLDCDKGKVDFYDMDQMKCLYERQVDCSHTLYPAFA LMGSGGIQLEEPITAKYLEYQEDM SEQ ID NO: 166 | |
| TRIM37 | NM_001005207 | MDEQSVESIAEVERCFICMEKLRDARLCPHCSKLCCFSCIRRWL TEQRAQCPHCRAPLQLRELVNCRWAEEVTQQLDTLQLCSLTKHE ENEKDKCENHHEKLSVFCWTCKKCICHQCALWGGMHGGHTFKPL AEIYEQHVTKVNEEVAKLRRRLMELISLVQEVERNVEAVRNAKD ERVREIRNAVEMMIARLDTQLKNKLITLMGQKTSLTQETELLES LLQEVEHQLRSCSKSELISKSSEILMMFQQVHRKPMASFVTTPV PPDFTSELVPSYDSATFVLENFSTLRQRADPVYSPPLQVSGLCW RLKVYPDGNGVVRGYYLSVFLELSAGLPETSKYEYRVEMVHQSC NDPTKNIIREFASDFEVGECWGYNRFFRLDLLANEGYLNPQNDT VILRFQVRSPTFFQKSRDQHWYITQLEAAQTSYIQQINNLKERL TIELSRTQKSRDLSPPDNHLSPQNDDALETRAKKSACSDMLLEG GPTTASVREAKEDEEDEEKIQNEDYHHELSDGDLDLDLVYEDEV NQLDGSSSSASSTATSNTEENDIDEETMSGENDVEYNNMELEEG ELMEDAAAAGPAGSSHGYVGSSSRISRRTHLCSAATSSLLDIDP LILIHLLDLKDRSSIENLWGLQPRPPASLLQPTASYSRKDKDQR KQQAMWRVPSDLKMLKRLKTQMAEVRCMKTDVKNTLSEIKSSSA ASGDMQTSLFSADQAALAACGTENSGRLQDLGMELLAKSSVANC YIRNSTNKKSNSPKPARSSVAGSLSLRRAVDPGENSRSKGDCQT LSEGSPGSSQSGSRHSSPRALIHGSIGDILPKTEDRQCKALDSD AVVVAVFSGLPAVEKRRKMVTLGANAKGGHLEGLQMTDLENNSE TGELQPVLPEGASAAPEEGMSSDSDIECDTENEEQEEHTSVGGE HDSFMVMTQPPDEDTHSSFPDGEQIGPEDLSFNTDENSGR SEQ ID NO: 167 | GGACAUACCUUUAAACCUU SEQ ID NO: 168 ACACACAGCUGAAGAAUAA SEQ ID NO: 169 GCAGAUGACUGAUUUGGAA SEQ ID NO: 170 UACGAGAACUAGUAAAUUG SEQ ID NO: 171 |
| TRIM38 | NM_006355 | MASTTSTKKMMEEATCSICLSLMTNPVSINCGHSYCHLCITDFF KNPSQKQLRQETFCCPQCRAPFHMDSLRPNKQLGSLIEALKETD QEMSCEEHGEQFHLFCEDEGQLICWRCERAPQHKGTTALVEDV CQGYKEKLQKAVTKLKQLEDRCTEQKLSTAMRITKWKEKVQIQR QKIRSDFKNLQCFLHEEEKSYLWRLEKEEQQTLSRLRDYEAGLG LKSNELKSHILELEEKCQGSAQKLLQNVNDTLSRSWAVKLETSE AVSLELHTMCNVSKLYFDVKKMLRSHQVSVTLDPDTAHHELILS EDRRQVTRGYTQENQDTSSRRFTAFPCVLGCEGFTSGRRYFEVD VGEGTGWDLGVCMENVQRGTGMKQEPQSGFWTLRLCKKKGYVAL TSPPTSLHLHEQPLLVGIFLDYEAGVVSFYNGNTGCHIFTFPKA SFSDTLRPYFQVYQYSPLFLPPPGD SEQ ID NO: 172 | GCGAAUAACUAAAUGGAAA SEQ ID NO: 173 AGAAAUUGCUGCAGAAUGU SEQ ID NO: 174 CAACUUGAAGACAGAUGUA SEQ ID NO: 175 AGAUACAGCUCAUCACGAA SEQ ID NO: 175 |
| TRIM39 | NM_172016 | MAETSLLEAGASAASTAAALENLQVEASCSVCLEYLKEPVIIEC GHNFCKACITRWWEDLERDFPCPVCRKTSRYRSLRPNRQLGSMV EIAKQLQAVKRKIRDESLCPQHHEALSLFCYEDQEAVCLICAIS HTHRAHTVVPLDDATQEYKEKLQKCLEPLEQKLQEITRCKSSEE KKPGELKRLVESRRQQILREFEELHRRLDEEQQVLLSRLEEEEQ DILQRLRENAAHLGDKRRDLAHLAAEVEGKCLQSGFEMLKDVKS TLEKCEKVKTMEVTSVSIELEKNFSNFPRQYFALRKILKQLIAD VTLDPETAHPNLVLSEDRKSVKFVETRLRDLPDTPRRFTFYPCV LATEGFTSGRHYWEVEVGDKTHWAVGVCRDSVSRKGELTPLPET GYWRVRLWNGDKYAATTTPFTPLHIKVKPKRVGIFLDYEAGTLS FYNVTDRSHIYTFTDTFTEKLWPLFYPGIRAGRKNAAPLTIRPP TDWE SEQ ID NO: 177 | GAAGGAACCUGUCAUCAUU SEQ ID NO: 178 UGACUUCAGUAUCCAUAGA SEQ ID NO: 179 GCUUCGAGAUGCUUAAGGA SEQ ID NO: 180 AGGGUAAGGUUGCGAUUAU SEQ ID NO: 181 |
| TRIM40 | NM_138700 | MIPLQKDNQEEGVCPICQESLKEAVSTNCGHLFCRVCLTQHVEK ASASGVFCCPLCRKPCSEEVLGTGYICPNHQKRVCRFCEESRLL LCVECLVSPEHMSHHELTIENALSHYKERLNRRSRKLRKDIAEL QRLKAQQEKKLQALQQWLGQLEHMPAEAARILDISRAVTQLRSL VIDLERTAKELDTNTLKNAGDLLNRSAPQKLEVIYPQLEKGVSE LLLQPPQKL SEQ ID NO: 182 | CCACAGAAAUUAGAGGUUA SEQ ID NO: 183 GAGCAGACUUCUUCUAUGU SEQ ID NO: 184 UCAGAAGCCUGGUCAUUGA SEQ ID NO: 185 GGACGGCCAAGGAAUUAGA SEQ ID NO: 186 |
| TRIM41 | NM_201627 | MAAVAMTPNPVQTLQEEAVCAICLDYFTDPVSIGCGHNFCRVCV TQLWGGEDEEDRDELDREEEEEDGEEEEVEAVGAGAGWDTPMRD EDYEGDMEEEVEEEEEGVFWTSGMSRSSWDNMDYVWEEEEDEED LDYYLGDMEEEDLRGEDEEDEEEVLEEVEEEDLDPVTPLPPPPA PRRCFTCPQCRKSFPRRSFRPNLQLANMVQIRQMHPTPGRGSR VTDQGICPKHQEALKLFCEVDEEAICVVCRESRSHKQHSVVPLE EVVQEYKAKLQGHVEPLRKHLEAVQKMKAKEERRVTELKSQMKS ELAAVASEFGRLTRFLAEEQAGLERRLREMHEAQLGRAGAAASR LAEQAAQLSRLLAEAQERSQQGGLRLLQDIKETFNRCEEVQLQP PEVWSPDPCQPHSHDFLTDAIVRKMSRMFCQAARVDLTLDPDTA | CAAGGAGACUUUCAAUAGG SEQ ID NO: 188 CCAAUAUGGUCCAGGUGAU SEQ ID NO: 189 GAGAUGAGUUAGAUCGGGA SEQ ID NO: 190 GGAUGAAGACUACGAGGGU SEQ ID NO: 191 |

-continued

| TRIM # | Accession # | Sequence | SiRNA |
|---|---|---|---|
| | | HPALMLSPDRRGVRLAERRQEVADHPKRFSADCCVLGAQGFRSG<br>RHYWEEPKEPSWPPAQPSLTYYVCPTDRPEFSFT<br>SEQ ID NO: 187 | |
| TRIM42 | NM_152616 | METAMCVCCPCCTWQRCCPQLCSCLCCKFIFTSERNCTCFPCPY<br>KDERNCQFCHCTCSESPNCHWCCCSWANDPNCKCCCTASSNLNC<br>YYYESRCCRNTIITFHKGRLRSIHTSSKTALRTGSSDTQVFSIG<br>SIPANSHLVNHLNCPMCSRLRLHSFMLPCNHSLCEKCLRQLQKH<br>AEVTENFFILICPVCDRSHCMPYSNKMQLPENYLHGRLTKRYMQ<br>EHGYLKWRFDRSSGPILCQVCRNKRIAYKRCITCRLNLCNDCLK<br>AFHSDVAMQDHVFVDTSAEEQDEKICIHHPSSRIIEYCRNDNKL<br>LCTFCKFSFHNGHDTISLIDACSERAASLFSAIAKFKAVRYEID<br>NDLMEFNILKNSFKADKEAKRKEIRNGFLKLRSILQEKEKIIME<br>QIENLEVSRQKEIEKYVYVTTMKVNEMDGLIAYSKEALKETQV<br>AFLQSAKILVDQIEDGIQTTYRPDPQLRLHSINYVPLDFVELSS<br>AIHELFPIGPKKVRSSGDSLPSPYPVHSETMIARKVTFSTHSLG<br>NQHIYQRSSSMLSFSNTDKKAKVGLEACGRAQSATPAKPTDGLY<br>TYWSAGADSQSVQNSSSFHNWYSFNDGSVKTPGPIVIYQTLVYP<br>RAAKVYWTCPAEDVDSFEMEFYEVITSPPNNVQMELCGQIRDIM<br>QQNLELHNLTPNTEYVFKVRAINDNGPGQWSDICKVVTPDGHGK<br>NRAKWGLLKNIQSALQKHF<br>SEQ ID NO: 192 | GCAAUACCAUCAUCACUUU<br>SEQ ID NO: 193<br>CCAAUGAUCCCAACUGUAA<br>SEQ ID NO: 194<br>CAAGUUCUCUUUCCACAAU<br>SEQ ID NO: 195<br>CAGAAUACGUGUUUAAAGU<br>SEQ ID NO: 196 |
| TRIM43 | NM_138800 | MDSDFSHAFQKELTCVICLNYLVDPVTICCGHSFCRPCLCLSWE<br>EAQSPANCPACREPSPKMDFKTNILLKNLVTIARKASLWQFLSS<br>EKQICGTHRQTKKMFCDMDKSLLCLLCSNSQEHGAHKHHPIEEA<br>AEEHREKLLKQMRILWKKIQENQRNLEYEGRTAFLWRGNVVLRA<br>QMIRNEYRKLHPVLHKEEKQHLERLNKEYQEIFQQLQRSWVKMD<br>QKSKHLKEMYQELMEMCHKPDVELLQDLGDIVARSESVLLHMPQ<br>PVNPELTAGPITGLVYRLNRFRVEISFHFEVTNHNIRLFEDVRS<br>WMFRRGPLNSDRSDYFAAWGARVFSFGKHYWELDVDNSCDWALG<br>VCNNSWIRKNSTMVNSEDIFLLLCLKVDNHFNLLTTSPVFPHYI<br>EKPLGRVGVFLDFESGSVSFLNVTKSSLIWSYPAGSLTFPVRPF<br>FYTGHR<br>SEQ ID NO: 197 | CCAGAGAAGUUGGGUCAAA<br>SEQ ID NO: 198<br>GGACCCAUAGGCAAACAAA<br>SEQ ID NO: 199<br>UGUACAGGCUCAACCGCUU<br>SEQ ID NO: 200<br>CGGUUCUCCAUAAGGAAGA<br>SEQ ID NO: 201 |
| TRIM44 | NM_017583 | MASGVGAAFEELPHDGTCDECEPDEAPGAEEVCRECGFCYCRRH<br>AEAHRQKFLSHHLAEYVHGSQAWTPPADGEGAGKEEAEVKVEQE<br>REIESEAGEESESEEESEEEESETEEESEDESDEESEEDSEEE<br>MEDEQESEAEEDNQEEGESAEGETEAESEFDPEIEMEAERVAK<br>RKCPDHGLDLSTYCQEDRQLICVLCPVIGAHQGHQLSTLDEAFE<br>ELRSKDSGGLKAAMIELVERLKFKSSDPKVTRDQMKMFIQQEFK<br>KVQKVIADEEQKALHLVDIQEAMATAHVTEILADIQSHMDRLMT<br>QMAQAKEQLDTSNESAEPKAEGDEEGPSGASEEEDT<br>SEQ ID NO: 202 | GAGGAAGUGUGCCGAGAAU<br>SEQ ID NO: 203<br>GUCACCAUCUGGCCGAAUA<br>SEQ ID NO: 204<br>ACGAAGCCUUUGAAGAAUU<br>SEQ ID NO: 205<br>GCUUUGUGCUCCCAGUAA<br>SEQ ID NO: 206 |
| TRIM45 | NM_025188 | MSENRKPLLGFVSKLTSGTALGNSGKTHCPLCLGLFKAPRLLPC<br>LHTVCTTCLEQLEPFSVVDIRGGDSDTSSEGSIFQELKPRSLQS<br>QIGILCPVCDAQVDLPMGGVKALTIDHLAVNDVMLESLRGEGQG<br>LVCDLCNDREVEKRCQTCKANLCHFCCQAHRRQKKTTYHTMVDL<br>KDLKGYSRIGKPILCPVHPAEELRLFCEFCDRPVCQDCVVGEHR<br>EHPCDFTSNVIHKHGDSVWELLKGTQPHVEALEEALAQIHIINS<br>ALQKRVEAVAADVRTFSEGYIKAIEEHRDKLLKQLEDIRAQKEN<br>SLQLQKAQLEQLLADMRTGVEFTEHLLTSGSDLEILITKRVVVE<br>RLRKLNKVQYSTRPGVNDKIRFCPQEKAGQCRGYETYGTINTKE<br>VDPAKCVLQGEDLHRAREKQTASFTLLCKDAAGEIMGRGGDNVQ<br>VAVVPKDKKDSPVRTMVQDNKDGTYYISYTPKEPGVYTVWVCIK<br>EQHVQGSPFTVMVRRKHRPHSGVFHCCTFCSSGGQKTARCACGG<br>TMPGGYLGCGHGHKGHPGHPHWSCCGKFNEKSECTWTGGQSAPR<br>SLLRTVAL<br>SEQ ID NO: 207 | GCACCGAGGAGUCUACUUA<br>SEQ ID NO: 208<br>GGACAUACUACAGUUUCCUA<br>SEQ ID NO: 209<br>GUGCAGGGCUCGCCAUUCA<br>SEQ ID NO: 210<br>GGGAGGAGACAACGUUCAA<br>SEQ ID NO: 211 |
| TRIM46 | NM_025058 | MAEGEDMQTFTSIMDALVRISTSMKNMEKELLCPVCQEMYKQPL<br>VLPCTHNVCQACAREVLGQQGYIGHGGDPSSEPTSPASTPSTRS<br>PRLSRRTLPKPDRLDRLLKSGFGTYPGRKRGALHPQVIMFPCPA<br>CQGDVELGERGLAGLFRNLTLERVVERYRQSVSVGGAILCQLCK<br>PPPLEATKGCTECRATFCNECFKLFHPWGTQKAQHEPTLPTLSF<br>RPKGLMCPDHKEEVTHYCKTCQRLVCQLCRVRRTHSGHKITPVL<br>SAYQALKDKLTKSLTYILGNQDTVQTQICELEEAVRHTEVSGQQ<br>AKEEVSQLVRGLGAVLEEKRASLLQAIEECQQERLARLSAQIQE<br>HRSLLDGSGLVGYAQEVLKETDQPCFVQAAKQLHNRIARATEAL<br>QTFRPAASSSFRHCQLDVGREMKLLTELNFLRVPEAPVIDTQRT<br>FAYDQIFLCWRLPPHSPPAWHYTVEFRRTDVPAQPGPTRWQRRE<br>EVRGTSALLENPDTGSVYVLRVRGCNKAGYGEYSEDVHLHTPPA<br>PVLHFFLDSRWGASRERLAISKDQRAVRSVPGLPLLLAADRLLT<br>GCHLSVDVVLGDVAVTQGRSYWACAVDPASYLVKVGVGLESKLQ<br>ESFQGAPDVISPRYDPDSGHDSGAEDATVEASPPFAFLTIGMGK | UGACAUACAUCCUGGGAAA<br>SEQ ID NO: 213<br>GGACAUACCCUGGGAGGAA<br>SEQ ID NO: 214<br>GCGAAUACAGUGAAGAUGU<br>SEQ ID NO: 215<br>GUCAAGAGAUGUACAAGCA<br>SEQ ID NO: 216 |

-continued

| TRIM # | Accession # | Sequence | SiRNA |
|---|---|---|---|
| | | ILLGSGASSNAGLTGRDGPTAGCTVPLPPRLGICLDYERGRVSF<br>LDAVSFRGLLECPLDCSGPVCPAFCFIGGGAVQLQEPVGTKPER<br>KVTIGGFAKLD<br>SEQ ID NO: 212 | |
| TRIM47 | NM_033452 | MDGSGPFSCPICLEPLREPVTLPCGHNFCLACLGALWPHRGASG<br>AGGPGGAARCPLCQEPFPDGLQLRKNHTLSELLQLRQGSGPGSG<br>PGPAPALAPEPSAPSALPSVPEPSAPCAPEPWPAGEEPVRCDAC<br>PEGAALPAALSCLSCLASFCPAHLGPHERSPALRGHRLVPPLRR<br>LEESLCPRHLRPLERYCRAERVCLCEACAAQEHRGHELVPLEQE<br>RALQEAEQSKVLSAVEDRMDELGAGIAQSRRTVALIKSAAVAER<br>ERVSRLFADAAAALQGFQTQVLGFIEEGEAAMLGRSQGDLRRQE<br>EQRSRLSRARQNLSQVPEADSVSFLQELLALRLALEDGCGPGPG<br>PPRELSFTKSSQAVRAVRDMLAVACVNQWEQLRGPGGNEDGPQK<br>LDSEADAEPQDLESTNLLESEAPRDYFLKFAYIVDLDSDTADKF<br>LQLFGTKGVKRVLCPINYPLSPTRFTHCEQVLGEGALDRGTYYW<br>EVEIIEGWVSMGVMAEDFSPQEPYDRGRLGRNAHSCCLQWNGRS<br>FSVWFHGLEAPLPHPFSPTVGVCLEYADRALAFYAVRDFKMSLL<br>RRLKASRPRRGGIPASPIDPFQSRLDSHFAGLFTHRLKPAFFLE<br>SVDAHLQIGPLKKSCISVLKRR<br>SEQ ID NO: 217 | GUACGGGACGGCAAGAUGA<br>SEQ ID NO: 218<br>GAACCAAAGGUGUCAAGAG<br>SEQ ID NO: 219<br>GCAUAUCCGUGCUGAAGAG<br>SEQ ID NO: 220<br>CAUCAAGAGUGCAGCCGUA<br>SEQ ID NO: 221 |
| TRIM48 | NM_024114 | MSRRIIVGTLQRTQRNMNSGISQVFQRELTCPICMNYFIDPVTI<br>DCGHSFCRPCFYLNWQDIPILTQCFECIKTIQQRNLKTNIRLKK<br>MASLARKASLWLFLSSEEQMCGIHRETKKMFCEVDRSLLCLLCS<br>SSQEHRYHRHCPAEWAAEEHWEKLLLKKMQSLWEKACENQRNLNV<br>ETTRISHWKAFGDILYRSESVLLHMPQPLNLALRAGPITGLRDR<br>LNQF<br>SEQ ID NO: 222 | GCAUAAAGACAAUACAGCA<br>SEQ ID NO: 223<br>CAGAGAAACCUGAAUGUGG<br>SEQ ID NO: 224<br>UGCUUUGAAUGCAUAAAGA<br>SEQ ID NO: 225<br>GAAGGCUUUGGAGACAUA<br>SEQ ID NO: 226 |
| TRIM49 | NM_020358 | MNSGILQVFQGELICPLCMNYFIDPVTIDCGHSFCRPCFYLNWQ<br>DIPFLVQCSECTKSTEQINLKTNIHLKKMASLARKVSLWLFLSS<br>EEQMCGTHRETKKIFCEVDRSLLCLLCSSSQEHRYHRHPIEWA<br>AEEHREKLLQKMQSLWEKACENHRNLNVETTRTRCWKDYVNLRL<br>EAIRAEYQKMPAFHHEEEKHNLEMLKKKGKEIFHRLHLSKAKMA<br>HRMEILRGMYEELNEMCHKPDVELLQAFGDILHRSESVLLHMPQ<br>PLNPELSAGPITGLRDRLNQFRVHITLHHEEANNDIFLYEILRS<br>MCIGCDHQDVPYFTATPRSFLAWGVQTFTSGKYYWEVHVGDSWN<br>WAFGVCNMYRKEKNQNEKIDGKAGLFLLGCVKNDIQCSLFTTSP<br>LMLQYIPKPTSRVGLFLDCEAKTVSFVDVNQSSLIYTIPNCSFS<br>PPLRPIFCCIHF<br>SEQ ID NO: 227 | GAAGAAGCCAACAAUGAUA<br>SEQ ID NO: 228<br>GGAAGGAUUAUGUGAAUUU<br>SEQ ID NO: 229<br>GAACGAAAUGUGCCAUAAA<br>SEQ ID NO: 230<br>GAAUCAGAAUGAGAAGAUA<br>SEQ ID NO: 231 |
| TRIM50 | NM_178125 | MAWQVSLPELEDRLQCPICLEVFKEPLMLQCGHSYCKGCLVSLS<br>CHLDAELRCPVCRQAVDGSSSLPNVSLARVIEALRLPGDPEPKV<br>CVHHRNPLSLFCEKDQELICGLCGLLGSHQHHPVTPVSTVYSRM<br>KEELAALISELKQEQKKVDELIAKLVNNRTRIVNESDVESWVIR<br>REFQELHHLVDEEKARCLEGIGGHHTRGLVASLDMQLEQAQGTRE<br>RLAQAECVLEQEGNEDHHKEIRKFHSMASRAEMPQARPLEGAFS<br>PISFKPGLHQADIKLTVWKRLFRKVLPAPEPLKLDPATAHPLLE<br>LSKGNTVVQCGLLAQRRASQPERFDYSTCVLASRGFSCGRHYWE<br>VVVGSKSDWRLGVIKGTASRKGKLNRSPEHGVWLIGLKEGRVYE<br>AFACPRVPLPVAGHPHRIGLYLHYEQGELTFFDADRPDDLRPLY<br>TFQADFQGKLYPILDTCWHERGSNSLPMVLPPPSGPGPLSPEQP<br>TKL<br>SEQ ID NO: 232 | GGACCCGAAUCGUCAAUGA<br>SEQ ID NO: 233<br>GGCUCUACCUGCACUAUGA<br>SEQ ID NO: 234<br>GCAACUCGCUGCCCAUGGU<br>SEQ ID NO: 235<br>UCGCAGCCCUCAUCUCUGA<br>SEQ ID NO: 236 |
| TRIM51 | NM_032681 | MNSGILQVFQRALTCPICMNYFLDPVTIDCGHSFCRPCLYLNWQ<br>DTAVLAQCSECKKTTRQRNLNTDICLKNMAFIARKASLRQFLSS<br>EEQICGMHRETKKMFCEVDKSLLCLPCSNSQEHRNHIHCPIEWA<br>AEEERREELLKKMQSLWEKACENLRNLNMETTRTRCWKDYVSLRI<br>EAIRAEYQKMPAFLHEEEQHHLERLRKEGEDIFQQLNESKARME<br>HSRELLRGMYEDLKQMCHKADVELLQAFGDILHRYESLLLQVSE<br>PVNPELSAGPITGLLDSLSGERVDFTLQPERANSHIFLCGDLRS<br>MNVGCDPQDDPDITGKSECFLVWGAQAFTSGKYYWEVHMGDSWN<br>WAFGVCNNYWKEKRQNDKIDGEEGLFLLGCVKEDTHCSLFTTSP<br>LVVQYVPRPTSTVGLFLDCEGRTVSFVDVDQSSLIYTIPNCSFS<br>PPLRPIFCCSHF<br>SEQ ID NO: 237 | GGAAGGAUUAUGUGAGUUU<br>SEQ ID NO: 238<br>ACUUGGAAAGGCUGCGAAA<br>SEQ ID NO: 239<br>AAGCAGAUGGAGCUACU<br>SEQ ID NO: 240<br>GGACAGCCUCAGUGGAUUC<br>SEQ ID NO: 241 |
| TRIM52 | NM_032765 | MAGYATTPSPMQTLQEEAVCAICLDYFKDPVSISCGHNFCRCGV<br>TQLWSKEDEEDQNEEEDEWEEEEDEEAVGAMDGWDGSIREVLYR<br>GNADEELFQDQDDDELWLGDSGITNWDNVDYMWDEEEEEEEDQ<br>DYYLGGLRPDLRIDVYREEEILEAYDEDEDEELYPDIHPPPSLP<br>LPGQFTCPQCRKSFTRRSFRPNLQLANMVQIIRQMCPTPYRGNR<br>SNDQGMCFKHQEALKLFCEVDKEAICVVCRESRSHKQHSVLPLE | GACCUGACCUGAGAAUUGA<br>SEQ ID NO: 243<br>UGACCCAGCUGUGGAGUAA<br>SEQ ID NO: 244<br>GGGACAACUAGACUAUAU<br>SEQ ID NO: 245 |

-continued

| TRIM # | Accession # | Sequence | SiRNA |
|---|---|---|---|
| | | EVVQEYQEIKLETTLVGILQIEQESIHSKAYNQ<br>SEQ ID NO: 242 | ACGAAGAGUUGUUCCAAGA<br>SEQ ID NO: 246 |
| TRIM54 | NM_187841 | MNFTVGFKPLLGDAHSMDNLEKQLICPICLEMFSKPVVILPCQH<br>NLCRKCANDVFQASNPLWQSRGSTIVSSGGRFRCPSCRHEVVLD<br>RHGVYGLQRNLLVENIIDIYKQESSRPLHSKAEQHLMCEEHEEE<br>KINIYCLSCEVPTCSLCKVFGAHKDCEVAPLPTIYKRQKSELSD<br>GIAMLVAGNDRVQAVITQMEEVCQTIEDNSRRQKQLLNQRFESL<br>CAVLEERKGELLQALAREQEEKLQRVRGLIRQYGDHLEASSKLV<br>ESAIQSMEEPQMALYLQQAKELINKVGAMSKVELAGRPEPGYES<br>MEQFTVRVEHVAEMLRTIDFQPGASGEEEEVAPDGEEGSAGPEE<br>ERPDGP<br>SEQ ID NO: 247 | GAGGAGGUGUGCCAGACUA<br>SEQ ID NO: 248<br>GAACAUUAUCGACAUUUAC<br>SEQ ID NO: 249<br>UCUACGGCCUGCAGCGAAA<br>SEQ ID NO: 250<br>CAAUAAAGAACUCGAGCGU<br>SEQ ID NO: 251 |
| TRIM55 | NM_184087 | MSASLNYKSFSKEQQTMDNLEKQLICPICLEMFTKPVVILPCQH<br>NLCRKCASDIFQASNPYLPTRGGTTMASGGRFRCPSCRHEVVLD<br>RHGVYGLQRNLLVENIIDIYKQESTRPEKKSDQPMCEEHEEERI<br>NIYCLNCEVPTCSLCKVFGAHKDCQVAPLTHVFQRQKSELSDGI<br>AILVGSNDRVQGVISQLEDTCKTIEIGFEAPPLQGQAAAPASGS<br>GADSEPARHIFSFSWLNSLNE<br>SEQ ID NO: 252 | GCGCAUCUCUGAAUUACAA<br>SEQ ID NO: 253<br>GAAAUGUGCCAGUGAUAUU<br>SEQ ID NO: 254<br>GGUUGAACUCCCUAAAUGA<br>SEQ ID NO: 255<br>CAUGAAGAGGAGCGCAUCA<br>SEQ ID NO: 256 |
| TRIM56 | NM_030961 | MVSHGSSPSLLEALSSDFLACKICLEQLRAPKTLPCLHTYCQDC<br>LAQLADGGRVRCPECRETVPVPPEGVASFKTNFFVNGLLDLVKA<br>RACGDLRAGKPACALCPLVGGTSTGGPATARCLDCADDLCQACA<br>DGHRCTRQTHTHRVVDLVGYRAGWYDEEARERQAAQCPQHPGEA<br>LRFLCQPCSQLLCRECRLDPHLDHPCLPLAEAVRARRPGLEGLL<br>AGVDNNLVELEAARRVEKEALARLREQAARVGTQVEEAAEGVLR<br>ALLAQKQEVLGQLRAHVEAAEEAARERLAELEGREQVARAAAAF<br>ARRVLSLGREAEILSLEGAIAQRLRQLQGCPWAPGPAPCLLPQL<br>ELHPGLLDKNCHLLRLSFEEQQPQKDGGKDGAGTQGGEESQSRR<br>EDEPKTERQGGVQPQAGDGAQTPKEEKAQTTREEGAQTLEEDRA<br>QTPHEDGGPQPHRGGRPNKKKKFKGRLKSISREPSPALGPNLDG<br>SGLLPRPIFYCSFPTRMPGDKRSPRITGLCPFGPREILVADEQN<br>RALKRFSLNGDYKGTVPVPEGCSPCSVAALQSAVAFSASARLYL<br>INPNGEVQWRRALSLSQASHAVAALPSGDRVAVSVAGHVEVYNM<br>EGSLATRFIPGGKASRGLRALVFLTTSPQGHFVGSDWQQNSVVI<br>CDGLGQVVGEYKGPGLHGCQPGSVSVDKKGYIFLTLREVNKVVI<br>LDPKGSLLGDFLTAYHGLEKPRVTTMVDGRYLVVSLSNGTIHIF<br>RVRSPDS<br>SEQ ID NO: 257 | GGACUGUGCCGAUGACUUG<br>SEQ ID NO: 258<br>GGUGUGGCCUCCUUCAAGA<br>SEQ ID NO: 259<br>GCGGAUGCCUGGAGACAAG<br>SEQ ID NO: 260<br>GAUAAGAAGGGCUACAUCU<br>SEQ ID NO: 261 |
| TRIM58 | NM_015431 | MAWAPPGERLREDARCPVCLDFLQEPVSVDCGHSFCLRCISEFC<br>EKSDGAQGGVYACPQCRGPFFRPSGFRPNRQLAGLVESVRRLGLG<br>AGPGARRCARHGEDLSRFCEEDEAALCWVCDAGPEHRTHRTAPL<br>QEAAGSYQVKLQMALELMRKELEDALTQEANVGKKTVIWKEKVE<br>MQRQRFRLEFEKHRGFLAQEEQRQLRRLEAEERATLQRLRESKS<br>RLVQQSKALKELADELQERCQRPALGLLEGVRGVLSRSKAVTRL<br>EAENIPMELKTACCIPGRRELLRKFQVDVKLDPATAHPSLLLTA<br>DLRSVQDGEPWRDVPNNPERFDTWPCILGLQSFSSGRHYWEVLV<br>GEGAEWGLGVCQDTLPRKGETTPSPENGVWALWLLKGNEYMVLA<br>SPSVPLLQLESPRCIGIFLDYEAGEISFYNVTDGSYIYTFNQLF<br>SGLLRPYFFICDATPLILPPTTIAGSGNWASRDHLDPASDVRDD<br>HL<br>SEQ ID NO: 262 | GAAAGUCCUCGCUGCAUUG<br>SEQ ID NO: 263<br>CUAUGAAGCCGGUGAAAUU<br>SEQ ID NO: 264<br>GAUUGGAGUUUGAGAAGCA<br>SEQ ID NO: 265<br>GGAAAGAGUUGGAGGACGC<br>SEQ ID NO: 266 |
| TRIM59 | NM_173084 | MHNFEEELTCPICYSIFEDPRVLPCSHTFCRNCLENILQASGNF<br>YIWRPLRIPLKCPNCRSITEIAPTGIESLPVNFALRAIIEKYQQ<br>EDHPDIVTCPEHYRQPLNVYCLLDKKLVCGHCLTIGQHHGHPID<br>DLQSAYLKEKDTPQKLLEQLTDTHWTDLTHLIEKLKEQKSHSEK<br>MIQGDKEAVLQYFKELNDTLEQKKKSFLTALCDVGNLINQEYTP<br>QIERMKEIREQQLELMALTISLQEESPLKFLEKVDDVRQHVQIL<br>KQRPLPEVQPVEIYPRVSKILKEEWSRTEIGQIKNVLIPKMKIS<br>PKRMSCSWPGKDEKEVEFLKILNIVVVTLISVILMSILFFNQHI<br>ITFLSEITLIWFSEASLSVYQSLSNSLHKVKNILCHIFYLLKEF<br>VWKIVSH<br>SEQ ID NO: 267 | GUACAGAUCUUGAAACAAA<br>SEQ ID NO: 268<br>CAACUGGCAUUGAAUCUUU<br>SEQ ID NO: 269<br>GCACUAAGGGCUAUUAUUG<br>SEQ ID NO: 270<br>GAUGUUGGCAAUCUAAUUA<br>SEQ ID NO: 271 |
| TRIM60 | NM_152620 | MEFVTALVNLQEESSCPICLEYLKDPVTINCGHNFCRSCLSVSW<br>KDLDDTFPCPVCRFCFPYKSFRRNPQLRNLTEIAKQLQIRRSKR<br>KRQKENAMCEKHNQFLTLFCVKDLEILCTQCSFSTKHQKHYICP<br>IKKAASYHREILEGSLEPLRNNIERVEKVIILQGSKSVELKKKV<br>EYKREEINSEFEQIRLFLQNEQEMILRQIQDEEMNILAKLNENL<br>VELSDYVSTLKHLLREVEGKSVQSNLELLTQAKSMHHKYQNLKC<br>PELFSFRLTKYGFSLPPQYSGLDRIIKPFQVDVILDLNTAHPQL<br>LVSEDRKAVRYERKKRNICYDPRRFYVCPAVLGSQRFSSGRHYW | GAAAGAGAAUGCCAUGUGU<br>SEQ ID NO: 273<br>GGAUCUAGAUGAUACCUUU<br>SEQ ID NO: 274<br>GGUCUAUUCUCUAUACUUU<br>SEQ ID NO: 275<br>GCAAUUGGGCGAUACAUGA<br>SEQ ID NO: 276 |

| TRIM # | Accession # | Sequence | SiRNA |
|---|---|---|---|
| | | EVEVGNKPKWILGVCQDCLLRNWQDQPSVLGGFWAIGRYMKSGY VASGPKTTQLLPVVKPSKIGIFLDYELGDLSFYNMNDRSILYYF YTGTDSEPLKICSVSDSER SEQ ID NO: 272 | |
| TRIM61 | NM_001012414 | MEFVTALADLRAEASCPICLDYLKDPVTISCGHNFCLSCIIMSW KDLHDSFPCPFCHFCCPERKFISNPQLGSLTEIAKQLQIRSKKR KRQEEKHVCKKHNQVLTFECQKDLELLCPRCSLSTDHQHHCVWP IKKAASYHRKKLEEYNAPWKERVELIEKVITMQTRKSLELKKKM ESPSVTRLECSCTISAHFNLRLPGSSDSSASGS SEQ ID NO: 277 | UCAGAAAGACCUAGAGCUU SEQ ID NO: 278<br>CUGGGUAGUUUGACUGAAA SEQ ID NO: 279<br>UAAGAAGCAUAAUCAGGUU SEQ ID NO: 280<br>GAGAGAGUGGAACUAAUUG SEQ ID NO: 281 |
| TRIM62 | NM_018207 | MACSLKDELLCSICLSIYQDPVSLGCEHYFCRRCITEHWVRQEA QGARDCPECRRTFAEPALAPSLKLANIVERYSSFPLDAILNARR AARPCQAHDKVKLFCLTDRALLCFFCDEPALHEQHQVTGIDDAF DELQRELKDQLQALQDSEREHTEALQLLKRQLAETKSSTKSLRT TIGEAFERLHRLLRERQKAMLEELEADTARTLTDIEQKVQRYSQ QLRKVQEGAQILQERLAETDRHTFLAGVASLSERLKGKIHETNL TYEDEPTSKYTGPLQYTIWKSLFQDIHPVPAALTLDPGTAHQRL ILSDDCTIVAYGNLHPQPLQDSPKRFDVEVSVLGSEAFSSGVHY WEVVVAEKTQWVIGLAHEAASRKGSIQIQPSRGFYCIVMHDGNQ YSACTEPWTRLNVRDKLDKVGVFLDYDQGLLIFYNADDMSWLYT FREKFPGKLCSYFSPGQSHANGKNVQPLRINTVRI SEQ ID NO: 282 | CUACAAUGCUGAUGACAUG SEQ ID NO: 283<br>UCGGACGACUGCACCAUUG SEQ ID NO: 284<br>CGCCAAAGCGCUUCGAUGU SEQ ID NO: 285<br>GGAUCAACACCGUCCGCAU SEQ ID NO: 286 |
| TRIM63 | NM_032588 | MDYKSSLIQDGNPMENLEKQLICPICLEMFTKPVVILPCQHNLC RKCANDIFQAANPYWTSRGSSVSMSGGRFRCPTCRHEVIMDRHG VYGLQRNLLVENIIDIYKQECSSRPLQKGSHPMCKEHEDEKINI YCLTCEVPTCSMCKVEGIHKACEVAPLQSVFQGGQKTELNNCISM INAGNDRVQTIITQLEDSRRVTKENSHQVKEELSQKFDTLYAIL DEKKSELLQRITQEQEKKLSFIEALIQQYQEQLDKSTKLVETAI QSLDEPGGATFLLTAKQLIKSIVEASKGCQLGKTEQGFENMDFF TLDLEHIADALRAIDFGTDEEEEEFIEEEDQEEEESTEGKEEGH Q SEQ ID NO: 287 | GGAAGAAGGACACCAGUAA SEQ ID NO: 288<br>UCACUCAGCUGGAGGAUUC SEQ ID NO: 289<br>GAACAUGGACUUCUUUACU SEQ ID NO: 290<br>GGAAUCCCAUGGAGAACUU SEQ ID NO: 291 |
| TRIM64 | NM_001136486 | MDSDDLQVFQNELICCICVNYFIDPVTIDCGHSFCRPCLCLCSE EGRAPMRCPSCRKISEKPNFNTNVVLKKLSSLARQTRPQNINSS DNICVLHEETKELFCEADKRLLCGPCSESPEHMAHSHSPIGWAA EECREKLIKEMDYLWEINQETRNNLNQETRTFHSLKDYVSVRKR IITIQYQKMPIFLDEEEQRHLQALEREAEELFQQLQDSQVRMTQ HLERMKDMYRELWETCHVPDVELLQDVRNVSARTDLAQMQKPQP VNPELTSWCITGVLDMLNNPRVDSALSTEMIPCYISLSEDVRYV IFGDDHLSAPTDPQGVDSFAVWGAQAFTSGKHYWEVDVILSSNW ILGVCQDSRTADANFVIDSDERFFLISSKRSNHYSLSINSPPLI QYVQRPLGQVGVFLDYDNGSVSFFDVSKGSLIYGFPPSSFSSAA SEQ ID NO: 292 | UCAGUAAGGAAGAGGAUAA SEQ ID NO: 293<br>UGUGGUUAUGAAUGGGAUA SEQ ID NO: 294<br>AAAGUUGGUUUCACGAUGA SEQ ID NO: 295<br>AAGCAUUCACCUCCGGCAA SEQ ID NO: 296 |
| TRIM65 | NM_173547 | MAAQLLEEKLTCAICLGLYQDPVTLPCGHNFCGACIRDWWDRCG KACPECREPFPDGAELRRNVALSGVLEVVRAGPARDPGPDPGPG PDPAARCPRHGRPLELFCRTEGRCVCSVCTVRECRLHERALLDA ERLKREAQLRASLEVTQQQATQAEGQLLELRKQSSQIQNSACIL ASWVSGKFSSLLQALEIQHTTALRSIEVAKTQALAQARDEEQRL RVHLEAVARHGCRIRELLEQVDEQTFLQESQLLQPPGPLGPLTP LQWDEDQQLGDLKQLLSRLCGLLLEEGSHPGAPAKPVDLAPVEA PGPLAPVPSTVCPLRRKLWQNYRNLTFDPVSANRHFYLSRQDQQ VKHCRQSRGPGGPGSFELWQVQCAQSFQAGHHYWEVRASDHSVT LGVSYPQLPRCRLGPHIDNIGRGPCSWGLCVQEDSLQAWHNGEA QRLPGVSGRLLGMDLDLASGCLTFYSLEPQTQPLYTFHALFNQP LTPVFWLLEGRTLTLCHQPGAVFPLGPQEEVLS SEQ ID NO: 297 | GCAGCCAGAUCCAGAACUC SEQ ID NO: 298<br>AGCCAAGCCUGUGGGACUUA SEQ ID NO: 299<br>GUAGGACCCUGACCCUGUG SEQ ID NO: 300<br>UGGCAGAAUUAUCGCAAUC SEQ ID NO: 301 |
| TRIM66 | NM_014818 | MARNCSECKEKRAAHILCTYCNRWLCSSCTEEHRHSPVPGGPFF PRAQKGSPGVNGGPGDFTLYCPLHTQEVLKLFCETCDMLTCHSC LVVEHKEHRCRHVEEVLQNQRMLLEGVTTQVAHKKSSLQTSAKQ IEDRIFEVKHQHRKVENQIKMAKMVLMNELNKQANGLIEELEGI TNERKRKLEQQLQSIMVLNRQFEHVQNFINWAVCSKTSVPPFLFS KELIVFQMQRLLETSCNTDPGSPWSIRFTWEPNFWTKQLASLGC ITTEGGQMSRADAPAYGGLQGSSPFYQSHQSPVAQQEALSHPSH KEQSPAVCSSSVCCSHCSPVSPSLKGQVPPPSIHPAHSFRQPPE MVPQQLGSLQCSALLPREKELACSPHPPKLLQPWLETQPPVEQE STSQRLGQQLTSQPVCIVPPQDVQQGAHAQPTLQTPSIQVQFGH HQKLKLSHFQQQPQQQLPPPPPPLPHPPPPLPPPPQQHPPPLPP SQHLASSQHESPPGPACSQNMDIHHHKFELEEMQKDLELLLQAQ QPSLQLSQTKSPQHLQQTIVGQINYIVRQPAPVQSQSQEETLQA | CGGCAUUAUUACCAGAUUA SEQ ID NO: 303<br>GCACAGAGGAACACCGACA SEQ ID NO: 304<br>CCUUCAUAGUGAGCAUAA SEQ ID NO: 305<br>UGUUUCAGAUGCAGCGAUU SEQ ID NO: 306 |

| TRIM # | Accession # | Sequence | SiRNA |
|---|---|---|---|
| | | TDEPPASQGSKPALPLDKNTAAALPQASGEETPLSVPPVDSTIQ<br>HSSPNVVRKHSTSLSIMGFSNTLEMELSSTRLERPLEPQIQSVS<br>NLTAGAPQAVPSLLSAPPKMVSSLTSVQNQAMPSLTTSHLQTVP<br>SLVHSTFQSMPNLISDSPQAMASLASDHPQAGPSLMSGHTQAVP<br>SLATCPLQSIPPVSDMQPETGSSSSSGRTSGSLCPRDGADPSLE<br>NALCKVKLEEPINLSVKKPPLAPVVSTSTALQQYQNPKECENFE<br>QGALELDAKENQSIRAFNSEHKIPYVRLERLKICAASSGEMPVF<br>KLKPQKNDQDGSFLLIIECGTESSSMSIKVSQDRLSEATQAPGL<br>EGRKVTVTSLAGQRPPEVEGTSPEEHRLIPRTPGAKKGPPAPIE<br>NEDFCAVCLNGGELLCCDRCPKVFHLSCHVPALLSFPGGEWVCT<br>LCRSLTQPEMEYDCENACYNQPGMRASPGLSMYDQKKCEKLVLS<br>LCCNNLSLPFHEPVSPLARHYYQIIKRPMDLSIIRRKLQKKDPA<br>HYTTPEEVVSDVRLMEWNCAKENYPDSEVAEAGRCLEVFFEGWL<br>KEIYPEKRFAQPRQEDSDSEEVSSESGCSTPQGFPWPPYMQEGI<br>QPKRRRRHMENERAKRMSFRLANSISQV<br>SEQ ID NO: 302 | |
| TRIM67 | NM_001004342 | MEEELKCPVCGSLFREPIILPCSHNVCLPCARTIAVQTPDGEQH<br>LPQPLLLSRGSGLQAGAAAAASLEHDAAAGPACGGAGGSAAGGL<br>GGGAGGGGDHADKLSLYSETDSGYGSYTPSLKSPNGVRVLPMVP<br>APPGSSAAAARGAACSSLSSSSSSITCPQCHRSASLDHRGLRGF<br>QRNRLLEAIVQRYQQGRGAVPGTSAAAAVAICQLCDRTPPEPAA<br>TLCEQCDVLYCSACQLKCHPSRGPFAKHRLVQPPPPPPPPAEEA<br>SGPTGTAQGAPSGGGGCKSPGGAGAGATGGSTARKFPTCPEHEM<br>ENYSMYCVSCRTPVCYLCLEEGRHAKHEVKPLGAMWKQHKAQLS<br>QALNGVSDKAKEAKEFLVQLKNILQQIQENGLDYEACLVAQCDA<br>LVDALTRQKAKLLTKVTKEREHKLKMVWDQINHCTLKLRQSTGL<br>MEYCLEVIKENDPSGFLQISDALIKRVQVSQEQWVKGALEPKVS<br>AEFDLTLDSEPLLQAIHQLDFIQMKCRVPPVPLLQLEKCCTRNN<br>SVTLAWRMPPFTHSPVDGYILELDDGAGGQFREVYVGKETLCTI<br>DGLHFNSTYNARVKAFNSSGVGPYSKTVVLQTSDVAWFTFDPNS<br>GHRDIILSNDNQTATCSSYDDRVVLGTAAFSKGVHYWELHVDRY<br>DNHPDPAFGVARASVVKDMMLGKDDKAWAMYVDNNRSWFMHCNS<br>HTNRTEGGVCKGATVGVLLDLNKHTLTFFINGQQQGPTAFSHVD<br>GVFMPALSLNRNVQVTLHTGLEVPTNLGRPKLSGN<br>SEQ ID NO: 307 | GGUAAGGAGACUUUGUGUA<br>SEQ ID NO: 308<br>GCACAUUGAAGCUGCGUCA<br>SEQ ID NO: 309<br>GAAAGUGUCUGCGGAGUUU<br>SEQ ID NO: 310<br>GAGAAAUGCUGCACCCGUA<br>SEQ ID NO: 311 |
| TRIM68 | NM_018073 | MDPTALVEAIVEEVACPICMTFLREPMSIDCGHSFCHSCLSGLW<br>EIPGESQNWGYTCPLCRAPVQPRNLRPNWQLANVVEKVRLLRLH<br>PGMGLKGDLCERHGEKLKMFCKEDVLIMCEACSQSPEHEAHSVV<br>PMEDVAWEYKWELHEALEHLKKEQEEAWKLEVGERKRTATWKIQ<br>VETRKQSIVWEFEKYQRLLEKKQPPHRQLGAEVAAALASLQREA<br>AETMQKLELNHSELIQQSQVLWRMIAELKERSQRPVRWMLQDIQ<br>EVLNRSKSWSLQQPEPISLELKTDCRVLGLREILKTYAADVRLD<br>PDTAYSRLIVSEDRKRVHYGDTNQKLPDNPERFYRYNIVLGSQC<br>ISSGRHYWEVEVGDRSEWGLGVCKQNVDRKEVVYLSPHYGFWVI<br>RLRKGNEYRAGTDEYPILSLPVPPRRVGIFVDYEAHDISFYNVT<br>DCGSHIFTFPRYPFPGRLLPYFSPCYSIGTNNTAPLAICSLDGE<br>D<br>SEQ ID NO: 312 | GAGAGAUCCUGAAGACUUA<br>SEQ ID NO: 313<br>CAAGGAACCUGCGGCCUAA<br>SEQ ID NO: 314<br>GGGAAAAGCUGAAGAUGUU<br>SEQ ID NO: 315<br>GGAGGAUGAUUGCAGAGUU<br>SEQ ID NO: 316 |
| TRIM69 | NM_182985*<br>*variant a | MEVSTNPSSNIDPGDYVEMNDSITHLPSKVVIQDITMELHCPLC<br>NDWFRDPLMLSCGHNFCEACIQDFWRLQAKETFCPECKMLCGYN<br>NCTFNPVLDKLVEKIKKLPLLKGHPQCPEHGENLKLFSKPDGKL<br>ICFQCKDARLSVGQSKEFLQISDAVHFFTEELAIQQGQLETTLK<br>ELQTLRNMQKEAIAAHKENKLHLQQHVSMEFLKLHQFLHSKEKD<br>ILTELREEGKALNEEMELNLSQLQEQCLLAKDMLVSIQAKTEQQ<br>NSFDFLKDITTLLHSLEQGMKVLATRELISRKLNLGQYKGPIQY<br>MVWREMQDTLCPGLSPLTLDPKTAHPNLVLSKSQTSVWHGDIKK<br>IMPDDPERFDSSVAVLGSRGFTSGKWYWEVEVAKKTKWTVGVVR<br>ESIIRKGSCPLTPEQGFWLLRLRNQTDLKALDLPSFSLTLTNNL<br>DKVGIYLDYEGGQLSFYNAKTMTHIYTFSNTFMEKLYPYFCPCL<br>NDGGENKEPLHILHPQ<br>SEQ ID NO: 317 | |
| TRIM71 | NM_001039111 | MASFPETDFQICLLCKEMCGSPAPLSSNSSASSSSSQTSTSSGG<br>GGGGPGAAAARRLHVLPCLHAFCRPCLEAHRLPAAGGGAAGEPLK<br>LRCPVCDQKVVLAEAAGMDALPSSAFLLSNLLDAVVATADEPPP<br>KNGRAGAPAGAGGHSNHRHHAHHAHPRASASAPPLPQAPQPPAP<br>SRSAPGGPAASPSALLLRRPHGCSSCDEGNAASSRCLDCQEHLC<br>DNCVRAHQRVRLTKDHYIERGPPGPGAAAAAQQLGLGPPPPGPP<br>FSILSVFPERLGFCQHHDDEVLHLYCDTCSVPICRECTMGRHGG<br>hSFIYLQEALQDSRALTIQLLADAQQGRQAIQLSIEQAQTVAEQ<br>VEMKAKVVQSEVKAVTARHKKALEERECELLWKVEKIRQVKAKS<br>LYLQVEKLRQNLNKLESTISAVQQVLEEGRALDILLARDRMLAQ<br>VQELKTVRSLLQPEDDRVMFTPPDQALYLAIKSFGFVSSGAFA<br>PLTKATGDGLKRALQGKVASFTVIGYDHDGEPRLSGGDLMSAVV | GGAGGAGGGUAGAGCGCUA<br>SEQ ID NO: 319<br>AGAAAGUAGUGCUAGCCGA<br>SEQ ID NO: 320<br>CUUGGGAUGUGGCGGUGAA<br>SEQ ID NO: 321<br>CACCAAGGCCACAGGCGAU<br>SEQ ID NO: 322 |

| TRIM # | Accession # | Sequence | SiRNA |
|---|---|---|---|
| | | LGPDGNLFGAEVSDQQNGTYVVSYRPQLEGEHLVSVTLCNQHIE NSPFKVVVKSGRSYVGIGLPGLSFGSEGDSDGKLCRPWGVSVDK EGYIIVADRSNNRIQVFKPCGAFHHKFGTLGSRPGQFDRPAGVA CDASRRIVVADKDNHRIQIFTFEGQFLLKFGEKGTKNGQFNYPW DVAVNSEGKILVSDTRNHRIQLFGPDGVFLNKYGFEGALWKHFD SPRGVAFNHEGHLVVTDFNNHRLLVIHPDCQSARFLGSEGTGNG QFLRPQGVAVDQEGRIIVADSRNHRVQMFESNGSFLCKFGAQGS GFGQMDRPSGIAITPDGMIVVVDFGNNRILVF SEQ ID NO: 318 | |
| TRIM72 | NM_001008274 | MSAAPGLLHQELSCPLCLQLFDAPVTAECGHSFCRACLGRVAGE PAADGTVLCPCCQAPTRPQALSTNLQLARLVEGLAQVPQGHCEE HLDPLSIYCEQDRALVCGVCASLGSHRGHRLLPAAEAHARLKTQ LPQQKLQLQEACMRKEKSVAVLEHQLVEVEETVRQFRGAVGEQL GKMRVFLAALEGSLDREAERVRGEAGVALRRELGSLNSYLEQLR QMEKVLEEVADKPQTEFLMKYCLVTSRLQKILAESPPPARLDIQ LPIISDDFKFQVWRKMFRALMPALEELTFDPSSAHPSLVVSSSG RRVECSEQKAPPAGEDPRQFDKAVAVVAHQQLSEGEHYWEVDVG DKPRWALGVIAAEAPRRGRLHAVPSQGLWLLGLREGKILEAHVE AKEPRALRSPERRPTRIGLYLSFGDGVLSFYDASDADALVPLFA FHERLPRPVYPFFDVCWHDKGKNAQPLLLVGPEGAEA SEQ ID NO: 323 | CCACGCGCAUUGGCCUUUA SEQ ID NO: 324 UCUCCGAGGGCGAGCACUA SEQ ID NO: 325 GACAUCCAGCUGCCAAUUA SEQ ID NO: 326 CGGACAAGCCGCAGACUGA SEQ ID NO: 327 |
| TRIM73 | NM_198924 | MAWQVSLLELEDRLQCPICLEVFKESLMLQCGHSYCKGCLVSLS YHLDTKVRCPMCWQVVDGSSSLPNVSLAWVIEALRLPGDPEPKV CVHHRNPLSLFCEKDQELICGLCGLLGSHQHHPVTPVSTVCSRM KEELAALFSELKQEQKKVDELIAKLVKNRTRIVNESDVFSWVIR REFQELRHPVDEEKARCLEGIGGHTRGLVASLDMQLEQAQGTRE RLAQAECVLEQFGNEDHHEFIWKFHSMASR SEQ ID NO: 328 | GGACCCGAAUCGUCAAUGA SEQ ID NO: 329 CAAGGAGUCCCUAAUGCUA SEQ ID NO: 330 UCGCAGCCCUCUUCUCUGA SEQ ID NO: 331 AGUGUGUGCUGGAACAGUU SEQ ID NO: 332 |
| TRIM74 | NM_198853 | MAWQVSLLELEDWLQCPICLEVFKESLMLQCGHSYCKGCLVSLS YHLDTKVRCPMCWQVVDGSSSLPNVSLAWVIEALRLPGDPEPKV CVHHRNPLSLFCEKDQELICGLCGLLGSHQHHPVTPVSTVCSRM KEELAALFSELKQEQKKVDELIAKLVKNRTRIVNESDVFSWVIR REFQELRHPVDEEKARCLEGIGGHTRGLVASLDMQLEQAQGTRE RLAQAECVLEQFGNEDHHEFIWKFHSMASR SEQ ID NO: 333 | GAAAUGAGGACCACCAUGA SEQ ID NO: 334 GGACCCGAAUCGUCAAUGA SEQ ID NO: 335 CAAGGAGUCCCUAAUGCUA SEQ ID NO: 336 UCGCAGCCCUCUUCUCUGA SEQ ID NO: 337 |
| TRIM75 | A6NK02 | MAVAAALTGLQAEAKCSICLDYLSDPVTIECGHNFCRSCIQQSW LDLQELFPCPVCRHQCQEGHFRSNTQLGRMIEIAKLLQSTKSNK RKQEETTLCEKHNQPLSVFCKEDLMVLCPLCTQPPDHQGHHVRP IEKAAIHYRKRFCSYIQPLKKQLADLQKLISTQSKKPLELREMV ENQRQELSSEFEHLNQFLDREQQAVLSRLAEEEKDNQQKLSANI TAFSNYSATLKSQLSKVVELSELSELELLSQIKIFYESESESSP SIFSIHLKRDGCSFPPQYSALQRIIKKFKVEIILDPETAHPNLI VSEDKKRVRFTKRKQKVPGFPKRFTVKPVVLGFPYFHSGRHFWE IEVGDKSEWAIGICKDSLPTKARRPSSAQQECWRIELQDDGYHA PGAFPTPLLLEVKARAIGIFLDYEMGEISFYNMAEKSHICTFTD TFTGPLRPYFYVGPDSQPLRICTGTVCE SEQ ID NO: 338 | |
| TRIM76 | NM_153610 | MASRDSNHAGESFLGSDGDEEATRELETEEESEGEEDETAAESE EEPDSRLSDQDEEGKIKQEYIISDPSFSMVTVQREDSGITWETN SSRSSTPWASEESQTSGVCSREGSTVNSPPGNVSFIVDEVKKVR KRTHKSKHGSPSLRRKGNRKRNSFESQDVPTNKKGSPLTSASQV LTTEKEKSYTGIYDKARKKKTTSNTPPITGAIYKEHKPLVLRPV YIGTVQYKIKMFNSVKEELIPLQFYGTLPKGYVIKEIHYRKGKD ASISLEPDLDNSGSNTVSKTRKLVAQSIEDKVKEVFPPWRGALS KGSESLTLMFSHEDQKKIYADSPLNATSALEHTVPSYSSSGRAE QGIQLRHSQSVPQQPEDEAKPHEVEPPSVTPDTPATMFLRTTKE ECELASPGTAASENDSSVSPSFANEVKKEDVYSAHHSISLEAAS PGLAASTQDGLDPDQEQPDLTSIERAEPVSAKLTPTHPSVKGEK EENMLEPSISLSEPLMLEEPEKEEIETSLPIAITPEPEDSNLVE EEIVELDYPESPLVSEKPFPPHMSPEVEHKEEELILPLLAASSP EHVALSEEEREEIASVSTGSAFVSEYSVPQDLNHELQEQEGEPV PPSNVEAIAEHAVLSEEENEEFEAYSPAAAPTSESSLSPSTTEK TSENQSPLFSTVTPEYMVLSGDEASESGCYTPDSTSASEYSVPS LATKESLKKTIDRKSPLILKGVSEYMIPSEEKEDTGSFTPAVAP ASEPSLSPSTTEKTSECQSPLPSTATSEHVVPSEGEDLGSERFT PDSKLISKYAAPLNATQESQKKIINEASQFKPKGISEHTVLSVD GKEVIGPSSPDLVVASEHSFPPHTTEMTSECQAPPLSATPSEYV VLSDEEAVELERYTPSSTSASEFSVPPYATPEAQEEEIVHRSLN LKGASSPMNLSEEDQEDIGPFSPDSAFVSEFSFPPYATQEAEKR EFECDSPICLTSPSEHTILSDEDTEEAELFSPDSASQVSIPPFR | GCACAACAAUUGCAGUUUA SEQ ID NO: 344 GGAAAUCAAUGAAAGGUUG SEQ ID NO: 345 GGAAGGAGUUCUAUCACGA SEQ ID NO: 346 GAACUUCACUGGAUGUAGC SEQ ID NO: 347 |

-continued

| TRIM # | Accession # | Sequence | SiRNA |
|---|---|---|---|
| | | ISETEKNELEPDSLLTAVSASGYSCFSEADEEDIGSTAATPVSE | |
| | | QFSSSQKQKAETFPLMSPLEDLSLPPSTDKSEKAEIKPEIPTTS | |
| | | TSVSEYLILAQKQKTQAYLEPESEDLIPSHLTSEVEKGEREASS | |
| | | SVAAIPAALPAQSSIVKEETKPASPHSVLPDSVPAIKKEQEPTA | |
| | | ALTLKAADEQMALSKVRKEEIVPDSQEATAHVSQDQKMEPQPPN | |
| | | VPESEMKYSVLPDMVDEPKKGVKPKLVLNVTSELEQRKLSKNEP | |
| | | EVIKPYSPLKETSLSGPEALSAVKMEMKHDSKITTTPIVLHSAS | |
| | | SGVEKQVEHGPPALAFSALSEEIKKEIEPSSSTTTASVTKLDSN | |
| | | LTRAVKEEIPTDSSLITPVDRPVLTKVGKGELGSGLPPLVTSAD | |
| | | EHSVLAEEDKVAIKGASPIETSSKHLAWSEAEKEIKFDSLPSVS | |
| | | SIAEHSVLSEVEAKEVKAGLPVIKTSSSQHSDKSEEARVEDKQD | |
| | | LLFSTVCDSERLVSSQKKSLMSTSEVLEPEHELPLSLWGEIKKK | |
| | | ETELPSSQNVSPASKHIIPKGKDEETASSSPELENLASGLAPTL | |
| | | LLLSDDKNKPAVEVSSTAQGDFPSEKQDVALAELSLEPEKKDKP | |
| | | HQPLELPNAGSEFSSDLGRQSGSIGTKQAKSPITETEDSVLEKG | |
| | | PAELRSREGKEENRELCASSTMPAISELSSLLREESQNEEIKPF | |
| | | SPKIISLESKEPPASVAEGGNPEEFQPFTFSLKGLSEEVSHPAD | |
| | | FKKGGNQEIGPLPPTGNLKAQVMGDILDKLSEETGHPNSSQVLQ | |
| | | SITEPSKIAPSDLLVEQKKTEKALHSDQTVKLPDVSTSSEDKQD | |
| | | LGIKQFSLMRENLPLEQSKSFMTTKPADVKETKMEEFFISPKDE | |
| | | NWMLGKPENVASQHEQRIAGSVQLDSSSSNELRPGQLKAAVSSK | |
| | | DHTCEVRKQVLPHSAEESHLSSQEAVSALDTSSGNTETLSSKSY | |
| | | SSEEVKLAEEPKSLVLAGNVERNIAEGKEIHSLMESESLLLEKA | |
| | | NTELSWPSKEDSQEKIKLPPERFFQKPVSGLSVEQVKSETISSS | |
| | | VKTAHFPAEGVEPALGNEKEAHRSTPPFPEEKPLEESKMVQSKV | |
| | | IDDADEGKKPSPEVKIPTQRKPISSIHAREPQSPESPEVTQNPP | |
| | | TQPKVAKPDLPEEKGKKGISSFKSWMSSLFFGSSTPDNKVAEQE | |
| | | DLETQPSPSVEKAVTVIDPEGTIPTNFNVAEKPADHSLSEVKLK | |
| | | TADEPRGTLVKSGDGQNVKEKSMILSNVEDLQQPKFISEVSRED | |
| | | YGKKEISGDSEEMNINSVVTSADGENLEIQSYSLIGEKLVMEEA | |
| | | KTIVPPHVTDSKRVQKPAIAPPSKWNISIFKEEPRSDQKQKSLL | |
| | | SFDVVDKVPQQPKSASSNFASKNITKESEKPESIILPVEESKGS | |
| | | LIDFSEDRLKKEMQNPTSLKISEEETKLRSVSPTEKKDNLENRS | |
| | | YTLAEKKVLAEKQNSVAPLELRDSNEIGKTQITLGSRSTELEEK | |
| | | KESKADAMPQHFYQNEDYNERPKIIVGSEKEKGENQVYVLSEGK | |
| | | KQQEHQPYSVNVAESMSRESDISLGHSLGETQSFSLVKATSVTE | |
| | | KSEAMLAEAHPEIREAKAVGTQPHPLEESKVLVEKTKTFLPVAL | |
| | | SCRDEIENHSLSQEGNLVLEKSSRDMPDHSEEKEQFRESELSKG | |
| | | GSVDITKETVKCGFQEKAVGTQPRPLEESKVLVEKTFTFLPVVL | |
| | | SCHDEIENHSLSQEGNLVLEKSSRDMPDHSEEKEQFKESELWKG | |
| | | GSVDITKESMKEGFPSKESERTLARPFDETKSSETPPYLISPVK | |
| | | PQTLASGASPEINAVKKKEMPRSELTPERHTVHTIQTSKDDTSD | |
| | | VPKQSVLVSKHHLEAAEDTRVKEPLSSAKSNYAQFISNTSASNA | |
| | | DKMVSNKEMPKEPEDTYAKGEDFTVTSKPAGLSEDQKTAFSIIS | |
| | | EGCEILNIHAPAFISSIDQEESEQMQDKLEYLEEKASFKTIPLP | |
| | | DDSETVACHKTLKSRLEDEKVTPLKENKQKETHKTKEEISTDSE | |
| | | TDLSFIQPTIPSEEDYFEKYTLIDYNISPDPEKQKAPQKLNVEE | |
| | | KLSKEVTEETISFPVSSVESAIEHEYDLVKLDESFYGPEKGHNI | |
| | | LSHPETQSQNSADRNVSKDTKRDVDSKSPGMPLFEREEGVLSRT | |
| | | QIFPTTIKVIDPEFLEEPPALAFLYKDLYEEAVGEKKKEEETAS | |
| | | EGDSVNSEASFPSRNSDTDDGTGIYFEKYILKDDILHDTSLTQK | |
| | | DQGQGLEEKRVGKDDSYQPIAAEGEIWGKEGTICREKSLEEQKG | |
| | | VYGEGESVDHVETVGNVAMQKKAPITEDVRVATQKISYAVPFED | |
| | | THHVLERADEAGSHGNEVGNASPEVNLNVPVQVSFPEEEFASGA | |
| | | THVQETSLEEPKILVPPEPSEERLRNSPVQDEYEFTESLHNEVV | |
| | | PQDILSEELSSESTPEDVLSQGKESFEHISENEFASEAEQSTPA | |
| | | EQKELGSERKEEDQLSSEVVTEKAQKELKKSQIDTYCYTCKCPI | |
| | | SATDKVFGTHKDHEVSTLDTAISAVKVQLAEFLENLQEKSLRIE | |
| | | AFVSEIESFFNTIEENCSKNEKRLEEQNEEMMKKVLAQYDEKAQ | |
| | | SFEEVKKKKMEFLHECMVHFLQSMDTAKDTLETIVREAEELDEA | |
| | | VFLTSFEEINERLLSAMESTASLEKMPAAFSLFEHYDDSSARSD | |
| | | QMLKQVAVPQPPRLEPQEPNSATSTTIAVYWSMNKEDVIDSFQV | |
| | | YCMEEPQDDQEVNELVEEYRLTVKESYCIFEDLEPDRCYQVWVM | |
| | | AVNFTGCSLPSERAIFRTAPSTPVIRAEDCTVCWNTATIRWRPT | |
| | | TPEATETYTLEYCRQHSPEGEGLRSFSGIKGLQLKVNLQPNDNY | |
| | | FFYVRAINAFGTSEQSEAALISTRGTRFLLLRETAHPALHISSS | |
| | | GTVISFGERRRLTEIPSVLGEELPSCGQHYWETTVTDCPAYRLG | |
| | | ICSSSAVQAGALGQGETSWYMHCSEPQRYTFFYSGIVSDVHVTE | |
| | | RPARVGILLDYNNQRLIFINAESEQLLFIIRHRFNEGVHPAFAL | |
| | | EKPGKCTLHLGIEPPDSVRHK | |
| | | SEQ ID NO: 343 | |

The invention claimed is:

1. A method of treating Crohn's disease in a patient in need thereof comprising administering to said patient an effective amount of an IRGM modulator in combination with an autophagy modulator in an effective amount and a pharmaceutically-acceptable carrier, additive and/or excipient, wherein said IRGM modulator is N-acetyl muramyl-L-alanyl-D-isoglutamine (muramyl dipeptide) or a pharmaceutically acceptable salt thereof.

2. The method according to claim 1 wherein said autophagy modulator is bromhexine or a pharmaceutically acceptable salt thereof.

3. A method of treating Crohn's disease in a patient in need thereof comprising co-administering to said patient an effective amount of N-acetyl muramyl-L-alanyl-D-isoglutamine (muramyl dipeptide) or a pharmaceutically acceptable salt thereof in combination with an effective amount of bromhexine or a pharmaceutically acceptable salt thereof and a pharmaceutically-acceptable carrier, additive and/or excipient.

* * * * *